US011852637B2

(12) United States Patent
Hellinga et al.

(10) Patent No.: US 11,852,637 B2
(45) Date of Patent: Dec. 26, 2023

(54) BICARBONATE BIOSENSORS, CALCIUM BIOSENSORS, AND USES THEREOF

(71) Applicant: Duke University, Durham, NC (US)

(72) Inventors: Homme W. Hellinga, Durham, NC (US); Malin J. Allert, Raleigh, NC (US)

(73) Assignee: Duke University, Durham, NC (US)

( * ) Notice: Subject to any disclaimer, the term of this patent is extended or adjusted under 35 U.S.C. 154(b) by 1398 days.

(21) Appl. No.: 15/776,871

(22) PCT Filed: Nov. 19, 2016

(86) PCT No.: PCT/US2016/062963
§ 371 (c)(1),
(2) Date: May 17, 2018

(87) PCT Pub. No.: WO2017/087917
PCT Pub. Date: May 26, 2017

(65) Prior Publication Data

US 2020/0284811 A1 Sep. 10, 2020

Related U.S. Application Data

(60) Provisional application No. 62/257,817, filed on Nov. 20, 2015, provisional application No. 62/257,792, (Continued)

(51) Int. Cl.
*G01N 33/58* (2006.01)
*G01N 33/68* (2006.01)
(Continued)

(52) U.S. Cl.
CPC ............. *G01N 33/84* (2013.01); *G01N 33/06* (2013.01); *G01N 33/582* (2013.01); (Continued)

(58) Field of Classification Search
CPC ........... C07K 2319/20; G01N 21/6428; G01N 33/542; G01N 33/582; G01N 33/68; G01N 33/84; G01N 2021/6439; G01N 2333/195
See application file for complete search history.

(56) References Cited

U.S. PATENT DOCUMENTS

| | | | |
|---|---|---|---|
| 6,428,797 | B2 | 8/2002 | Fishman |
| 8,608,310 | B2 | 12/2013 | Otis et al. |

(Continued)

FOREIGN PATENT DOCUMENTS

| | | | | |
|---|---|---|---|---|
| GB | 1429740 A | 3/1976 | | |
| WO | WO-0206789 A2 * | 1/2002 | .......... | C07K 14/001 |
| WO | 2017087917 A2 | 5/2017 | | |

OTHER PUBLICATIONS

Abouhamad, et al., "Peptide Transport and Chemotaxis in *Escherichia coli* and *Salmonella typhimurium*: Characterization of the Dipeptide Permease (Dpp) and the Dipeptide-Binding Protein", Molecular Microbiology, Jun. 1991, 5(5):1035-1047.

(Continued)

*Primary Examiner* — Jeremy C Flinders
(74) *Attorney, Agent, or Firm* — Nutter McClennen & Fish LLP

(57) ABSTRACT

The present subject matter provides biosensors for bicarbonate and calcium as well as compositions, devices, and methods comprising such biosensors.

26 Claims, 139 Drawing Sheets

Specification includes a Sequence Listing.

Related U.S. Application Data filed on Nov. 20, 2015, provisional application No. 62/257,796, filed on Nov. 20, 2015.

(51) Int. Cl.
*G01N 21/64* (2006.01)
*G01N 33/542* (2006.01)
*G01N 33/84* (2006.01)
*G01N 33/06* (2006.01)

(52) U.S. Cl.
CPC ...... *C07K 2319/20* (2013.01); *G01N 21/6428* (2013.01); *G01N 33/542* (2013.01); *G01N 2021/6439* (2013.01); *G01N 2333/195* (2013.01)

(56) References Cited

U.S. PATENT DOCUMENTS

| | | | |
|---|---|---|---|
| 2002/0004217 | A1 | 1/2002 | Hellinga |
| 2003/0130167 | A1 | 7/2003 | Pitner et al. |
| 2004/0118681 | A1 | 6/2004 | Hellinga et al. |
| 2009/0325221 | A1 | 12/2009 | Long et al. |
| 2011/0171737 | A1 | 7/2011 | Hellinga et al. |
| 2012/0005773 | A1 | 1/2012 | Aasen et al. |
| 2014/0259212 | A1 | 9/2014 | Plesch et al. |
| 2016/0220686 | A1 | 8/2016 | Brudno et al. |

OTHER PUBLICATIONS

Adey, et al., "Characterization of Phage that Bind Plastic from Phage-Displayed Random Peptide Libraries", Gene, Apr. 14, 1995, 156(1):27-31.
Adhikari, et al., "Biochemical Characterization of a Haemophilus influenzae Periplasmic Iron Transport Operon", The Journal of Biological Chemistry, Oct. 20, 1995, 270(42):25142-25149.
Ahmed, et al., "Personalized Diagnostics and Biosensors: A Review of the Biology and Technology Needed for Personalized Medicine", Critical Reviews in Biotechnology, Apr. 22, 2013, 34(2):180-196.
Allert, et al., "Multifactorial Determinants of Protein Expression in Prokaryotic Open Reading Frames", Journal of Molecular Biology, Oct. 8, 2010, 402(5):905-918.
Altschul, et al., "Basic Local Alignment Search Tool", Journal of Molecular Biology, 1990, 215:403-410.
Andersen, et al., "Secondary Structure Assignment", Structural Bioinformatics, 2003, 341-363.
Anraku, Y., "Transport of Sugars and Amino Acids in Bacteria", Journal of Biological Chemistry, Jun. 10, 1968, 243 (11):3116-3122.
Arora, et al., "Latest Developments in Micro Total Analysis Systems", Analytical Chemistry, May 12, 2010, 82 (12):4830-4847.
Artimo, et al., "ExPASy: SIB Bioinformatics Resource Portal", Nucleic Acids Research, May 2012, 40:W597-W603.
Avvakumova, et al., "Biotechnological Approaches Toward Nanoparticle Biofunctionalization", Trends in Biotechnology, Jan. 2014, 32(1):11-20.
Badugu, et al., "A Glucose-Sensing Contact Lens: From Bench Top to Patient", Current Opinion in Biotechnology, Feb. 2005, 16(1):100-107.
Bandodkar, et al., "Tattoo-Based Noninvasive Glucose Monitoring: A Proof-of-Concept Study", Analytical Chemistry, Dec. 12, 2014, 87(1):394-398.
Baneyx, et al., "Selection and Analysis of Solid-Binding Peptides", Current Opinion in Biotechnology, Jul. 5, 2007, 18(4):312-317.
Barash, et al., "Purification and Properties of Glutamate Binding Protein from the Periplasmic Space of *Escherichia coli* K-12", Biochimica et Biophysica Acta (BBA)—Protein Structure, Mar. 28, 1975, 386(1):168-180.
Baskin, et al., "Copper-Free Click Chemistry for Dynamic in Vivo Imaging", PNAS, Oct. 23, 2007, 104 (43):16793-16797.
Benedetti, et al., "Synthesis and Photophysical Properties of a Series of Cyclopenta[b]naphthalene Solvatochromic Fluorophores", Journal of the American Chemical Society, Jul. 13, 2012, 134(30):12418-12421.
Berman, et al., "The Protein Data Bank", Nucleic Acids Research, 2000, 28(1):235-242.
Berntsson, et al., "A Structural Classification of Substrate-Binding Proteins", FEBS Letters, Jun. 18, 2010, 584 (12):2606-2617.
Biju, et al., "Chemical Modifications and Bioconjugate Reactions of Nanomaterials for Sensing, Imaging, Drug Delivery and Therapy", Chemical Society Reviews, Feb. 7, 2014, 43(3):744-764.
Bjorkman, et al., "Multiple Open Forms of Ribose-Binding Protein Trace the Path of its Conformational Change", Journal of Molecular Biology, Jun. 12, 1998, 279(3):651-664.
Borisov, et al., "Optical Biosensors", Chemical Reviews, Feb. 2008, 108(2):423-461.
Bruns, et al., "Crystallographic and Biochemical Analyses of the Metal-Free Haemophilus influenzae Fe3+-Binding Protein", Biochemistry, Dec. 25, 2001, 40(51):15631-15637.
Bruns, et al., "Structure of Haemophilus Infuenzae Fe+3-Binding Protein Reveals Convergent Evolution within a Superfamily", Nature Structural Biology, Nov. 1997, 4(11):919-924.
Care, et al., "Solid-Binding Peptides: Smart Tools for Nanobiotechnology", Trends in Biotechnology, May 2015, 33 (5):259-268.
Chen, et al., "Binding Analysis of Peptides That Recognize Preferentially Cis-Azobenzene Groups of Synthetic Polymers", Journal of Peptide Science, Feb. 2011, 17(2):163-168.
Chenna, et al., "Multiple Sequence Alignment with the Clustal Series of Programs", Nucleic Acids Research, Jul. 2003, 31(13):3497-3500.
Cheung, Herbert C., "Resonance Energy Transfer", Topics in Fluorescence Spectroscopy, 1991, 2:127-176.
Choleau, et al., "Calibration of a Subcutaneous Amperometric Glucose Sensor: Part 1. Effect of Measurement Uncertainties on the Determination of Sensor Sensitivity and Background Current", Biosensors and Bioelectronics, Aug. 2002, 17(8):641-646.
Chothia, et al., "The Relation Between the Divergence of Sequence and Structure in Proteins", The EMBO Journal, 1986, 5(4):823-826.
Clark, et al., "Proton Nuclear Magnetic Resonance Spectroscopy and Ligand Binding Dynamics of the *Escherichia coli* L-Arabinose Binding Protein", Biochemistry, Apr. 27, 1982, 21:2227-2233.
Clegg, Robert M, "Fluorescence Resonance Energy Transfer", Current Opinion in Biotechnology, Feb. 1995, 6(1):103-110.
Cox, et al., "Protein Fabrication Automation", Protein Science, Mar. 2007, 16(3):379-390.
Cuneo, et al., "Structural Analysis of Semi-specific Oligosaccharide Recognition by a Cellulose-binding Protein of Thermotoga maritima Reveals Adaptations for Functional Diversification of the Oligopeptide Periplasmic Binding Protein Fold", The Journal of Biological chemistry, Nov. 27, 2009, 284(48):33217-33223.
Database Genbank, "Anabaena Variabilis ATCC 29413, Complete Genome", NCBI Accession No. NC_007413.1, 2 pages.
Database Genbank, "Bicarbonate Transport System Substrate-Binding Protein [Thermosynechococcus elongatus BP-1]", NCBI Reference Sequence: NP_682790.1.
Database Genbank, "Calothrix Sp. PCC 6303, Complete Genome", NCBI Accession No. NC_019751.1, 2 pages.
Database Genbank, "Candidatus Nitrospira Defluvii Chromosome, Complete Genome", NCBI Accession No. NC_014355.1, 1 page.
Database Genbank, "Chamaesiphon Minutus PCC 6605, Complete Genome", NCBI Accession No. NC_019697.1, 2 pages.
Database Genbank, "Chroococcidiopsis Thermalis PCC 7203, Complete Genome", NCBI Accession No. NC_019695.1, 2 pages.
Database Genbank, "Exiguobacterium Sp. AT1b, Complete Genome", NCBI Accession No. NC_012673.1, 2 pages.
Database Genbank, "Halorubrum Lacusprofundi ATCC 49239 Chromosome 1, Complete Sequence", NCBI Accession No. NC_012029.1, 2 pages.
Database Genbank, "Meiothermus Silvanus DSM 9946, Complete Genome", NCBI Accession No. NC_014212.1, 2 pages.
Database Genbank, "Salinibacter Ruber M8 Chromosome, Complete Genome", NCBI Accession No. NC_014032.1, 1 page.

(56) References Cited

OTHER PUBLICATIONS

Database Genbank, "Synechocystis Sp. PCC 6803 Substr. Pcc-N Dna, Complete Genome", NCBI Accession No. NC_ 017052.1, 2 pages.
Database Genbank, "Thermosynechococcus Elongatus BP-1 Chromosome, Complete Genome", NCBI Accession No. NC_004113.1, 1 page.
Database Genbank, "Thermus Thermophilus HB8 Chromosome, Complete Genome", NCBI Accession No. NC_006461.1, 1 page.
Database Uniprot, "RecName: Fuii=Bicarbonate-binding protein CmpA; Flags: Precursor", EBI accession No. UNIPROT:Q55460, Jul. 1, 2008, 3 pages.
Database Uniprotkbtrembl, "SubName: Full=Bicarbonate transport system substrate-binding protein", Jan. 7, 2015.
Zeng et al. (2014) "Nanomaterials Enhanced Surface Plasmon Resonance for Biological and Chemical Sensing Applications", Chemical Society Reviews, 43(10):3426-3452.
Hall et al. (Jul. 1983) "The Enzymatic Determination of Bicarbonate and Co2 in Reagents and Buffer Solutions", Analytical Biochemistry, 132(1):152-157.
Matzeu et al. (May 2015) "Advances in Wearable Chemical Sensor Design for Monitoring Biological Fluids", Sensors and Actuators B: Chemical, 211:403-418.
McDonagh et al. (Jan. 30, 2008) "Optical Chemical Sensors", Chemical Reviews, 108(2):400-422.
Medintz et al. (Jun. 1, 2005) "Quantum Dot Bioconjugates for Imaging, Labelling and Sensing", Nature Materials, 4:435-446.
Medveczky et al. (Nov. 18, 1969) "The Binding and Release of Phosphate by a Protein Isolated from *Escherichia coli*", Biochimica et Biophysica Acta (BBA)—General Subjects, 192(2):369-371.
Meyerhoff et al. (1966) "Current Status of the Glucose Sensor", Endricon, 6(1):51-58.
Miller et al. (Nov. 25, 1983) "Rates of Ligand Binding to Periplasmic Proteins Involved in Bacterial Transport and Chemotaxis", The Journal of Biological Chemistry, 258(22)13665-13672.
Mohammed et al. (Feb. 2011) "Lab on-a-Chip Based Immunosensor Principles and Technologies for the Detection of Cardiac Biomarkers: A Review", Lab on a Chip, 11(4):569-595.
Mowbray et al. (May 5, 1992) "1.7 A X-Ray Structure of the Periplasmic Ribose Receptor from *Escherichia coli*", Journal of Molecular Biology, 225(1):155-175.
Nanavati et al. (Feb. 2006) "Several Archaeal Homologs of Putative Oligopeptide-Binding Proteins Encoded by Thermotoga maritima Bind Sugars", Applied and Environmental Biology, 72(2):1336-1345.
Neves et al. (Jun. 19, 2013) "Imaging Cell Surface Glycosylation in Vivo Using "Double Click" Chemistry", Bioconjugate chemistry, 24(6):934-941.
Nickitenko (Dec. 1995) "2 A Resolution Structure of DppA, a Periplasmic Dipeptide Transport/Chemosensory Receptor", Biochemistry, 34(51):16585-16595.
Niko et al. (Jul. 22, 2013) "Solvatochromic Pyrene Analogues of Prodan Exhibiting Extremely High Fluorescence Quantum Yields in Apolar and Polar Solvents", Chemistry, 19(30):9760-9765.
Nohno et al. (1986) "Cloning and Complete Nucleotide Sequence of the *Escherichia coli* Glutamine Permease Operon (Ginhpq)", Molecular Genetics and Genomics, 205:260-269.
Nwe et al. (2009) "Growing Applications of "Click Chemistry" for Bioconjugation in Contemporary Biomedical Research", Cancer Biotherapy and Radiopharmaceuticals, 24(3):289-302.
Okumoto et al. (Jun. 2012) "Quantitative Imaging with Fluorescent Biosensors", Annual Review of Plant Biology, 63:663-706.
Oliveira et al. (May-Aug. 2015) "Recombinant CBM-Fusion Technology—Applications Overview", Biotechnology Advances, 33(3-4):358-369.
Omata et al. (Dec. 1999) "dentification of an ATP-binding Cassette Transporter Involved in Bicarbonate Uptake In cyanobacterium *Synechococcus* sp. strain PCC 7942", PNAS, 96(23):13571-13576.
Oneto et al. (2014) "Implantable Biomaterial Based on Click Chemistry for Targeting Small Molecules", Acta Biomaterilia, 10:5099-5105.
Pflugrath et al. (Mar. 21, 1985) "Sulphate Sequestered in the Sulphate-Binding Protein of *Salmonella typhimurium* is Bound Solely by Hydrogen Bonds", Nature, 314:257-260.
Pickup (1993) "Developing Glucose Sensors for In Vivo Use", Tibtech, 11:285-291.
Price et al. (May 2008) "Advances in Understanding the Cyanobacterial CO2-Concentrating-Mechanism (CCM): Functional Components, Ci Transporters, Diversity, Genetic Regulation and Prospects for Engineering into Plants", Journal of Experimental Botany, 59(7):1441-1491.
Quiocho et al. (Aug. 15, 1997) "Extensive Features of Tight Oligosaccharide Binding Revealed in High-Resolution Structures of the Maltodextrin Transport/Chemosensory Receptor", Structure, 5(8):997-1015.
Quiocho et al. (Aug. 2, 1984) "Novel Stereospecificity of the L-Arabinose-Binding Protein", Nature, 310:381-386.
Resch-Genger et al. (Oct. 2008) "Quantum Dots Versus Organic Dyes as Fluorescent Labels", Nature Methods, 5(9):763-775.
Riklin et al. (Aug. 24, 1995) "Improving Enzyme-Electrode Contacts by Redox Modification of Cofactors", Nature, 376:672-675.
Robinson et al. (Aug. 2012) "Microfluidic Technology for Molecular Diagnostics", Advances in biochemical engineering/biotechnology, 133:89-114.
Rogers et al. (Jun. 2013) "Real-Time Clinical Monitoring of Biomolecules", 6:427-453.
Rossin et al. (Apr. 10, 2010) "In Vivo Chemistry for Pretargeted Tumor Imaging in Live Mice", Angewandte Chemie, 49(19):3375-3378.
Sanders et al. (Oct. 1994) "Identification of a Locus Involved in the Utilization of Iron by Haemophilus Influenzae", Infection and Immunity, 62(10):4515-4525.
Sapsford et al. (Jul. 10, 2006) "Materials for Fluorescence Resonance Energy Transfer Analysis: Beyond Traditional Donor—Acceptor Combinations", Angew Chern Int Ed Engl, 45(28):4562-4589.
Scholle et al. (Jun. 1987) "Sequence of the Mglb Gene from *Escherichia coli* K12: Comparison of Wild-Type and Mutant Galactose Chemoreceptors", Molecular and General Genetics MGG, 208(1-2):247-253.
Schwartz et al. (1976) "Further Studies on the Binding of Maltose to the Maltose-Binding Protein of *Escherichia coli*", European Journal of Biochemistry, 71:167-170.
Scripture et al. (Sep. 5, 1987) "High-Affinity L-Arabinose Transport Operon. Nucleotide Sequence and Analysis of Gene Products", Journal of Molecular Biology, 197(1):37-46.
Serizawa et al. (Sep. 15, 2005) "A Peptide Motif Recognizing a Polymer Stereoregularity", Journal of the American Chemical Society, 127(40):13780-13781.
Serizawa et al. (Oct. 23, 2007) "Highly Specific Affinities of Short Peptides Against Synthetic Polymers", angmuir, 23(22):11127-11133.
Serizawa et al. (Jun. 18, 2007) "Isolation of Peptides that Can Recognize Syndiotactic Polystyrene", Chembiochem, 3(9):989-993.
Serizawa et al. (2007) "Peptide Motifs that Recognize Differences in Polymer-Film Surfaces", Angew Chem Int Ed Engl, 46(5):723-726.
Sharff et al. (Nov. 10, 1992) "Crystallographic Evidence of a Large Ligand-Induced Hinge-Twist Motion between the two Domains of the Maltodextrin Binding Protein Involved in Active Transport and Chemotaxis", Biochemistry, 31(44):10657-10663.
Shen et al. (Dec. 21, 2015) "Fluorescence Enhancement on Silver Nanoplates at the Single- and Sub-Nanoparticle Level", Nanoscale, 7(47):20132-20141.
Shin et al. (2005) "Chemical Structure and Physical Properties of Cyclic Olefin Copolymers (IUPAC Technical Report)", Pure and Applied Chemistry, 77(5):801-814.
Shoseyov et al. (Jun. 2006) "Carbohydrate Binding Modules: Biochemical Properties and Novel Applications", Microbiology and Molecular Biology Reviews, 70(2):283-295.

(56) References Cited

OTHER PUBLICATIONS

Siburt et al. (Mar. 2012) "FbpA—A Bacterial Transferrin with More to Offer", Biochimica et Biophysica Acta (BBA)—General Subjects, 1820(3):379-392.
Smith et al. (2005) "Orthogonal Site-Specific Protein Modification by Engineering Reversible Thiol Protection Mechanisms", Protein Science, 14:64-73.
Smith et al. (1999) "Substrate Specificity of the Periplasmic Dipeptide-Binding Protein from *Escherichia coli*: Experimental Basis for the Design of Peptide Prodrugs", Microbiology, 145:2891-2901.
Spurlino et al. (Mar. 15, 1991) "The 2.3-A Resolution Structure of the Maltose- or Maltodextrinbinding Protein, A Primary Receptor of Bacterial Active Transport and Chemotaxis", Journal of Biological Chemistry, 266(8):5202-5219.
Suleiman et al. (Oct. 23, 1992) "Biosensors for Food Analysis", Biosensor Design and Application, 511:26-40.
Sun et al. (Nov. 17, 1998) "Synthesis of Novel Fluorinated Coumarins: Excellent UV-light Excitable Fluorescent Dyes", Bioorganic & Medicinal Chemistry Letters, 8(22):3107-3110.
Sun et al. (Apr. 24, 1998) "The Structure of Glutamine-Binding Protein Complexed With Glutamine at 1.94 A Resolution: Comparisons with other Amino Acid Binding Proteins", Journal of Molecular Biology, 278(1):219-229.
Tian et al. (Oct. 1, 2003) "How Well is Enzyme Function Conserved as a Function of Pairwise Sequence Identity?", Journal of Molecular Biology, 333(4):863-882.
Todd (Apr. 1, 2001) "Evolution of Function in Protein Superfamilies, from a Structural Perspective", Journal of Molecular Biology, 307(4):1113-1143.
A0A0D6UK3, UniProtKB/TrEMBL Accession No. A0A0D6KUK3, May 27, 2015 [online][Retrieved on Apr. 6, 2017], Retrieved from the internet: < URL: www.uniprot.org/uniprot/A0AOD6KUK3.txt?version=1 >.
Q3MED5, UniProtKB/TrEMBL Accession No. Q3MED5, Jan. 7, 2015 [online][Retrieved on Apr. 6, 2017], Retrieved from the internet: < URL: www.uniprot.org/uniprot/Q3MED5.txt?version=45 >.
Urbieta et al. (Nov. 1, 2015) "Thermophiles in the Genomic Era: Biodiversity, Science, and Applications", Biotechnology Advances, 33(6):633-647.
Vodnik et al. (May 15, 2012) "HWGMWSY, An Unanticipated Polystyrene Binding Peptide from Random Phage Display Libraries", Analytical Biochemistry, 424(2):83-86.
Vyas et al. (Apr. 26, 1994) "Crystallographic Analysis of the Epimeric and Anomeric Specificity of the Periplasmic Transport/Chemosensory Protein Receptor for D-Glucose and D-Galactose", Biochemistry, 33(16):4762-4768.
Vyas et al. (Dec. 2, 1988) "Sugar and Signal-Transducer Binding Sites of the Escherichia Coli Galactose Chemoreceptor Protein", Science, 242(4883):1290-1295.
Wang et al. (Nov. 2, 2009) "Recent Progress in Strategies for the Creation of Protein-Based Fluorescent Biosensors", ChemBioChem, 10(16):2560-2577.
Weidemaier et al. (Jun. 15, 2011) "Multi-Day Pre-Clinical Demonstration of Glucose/Galactose Binding Protein-Based Fiber Optic Sensor", Biosensors and Bioelectronics, 26(10):4117-4123.
Weiner et al. (1971) "A Binding Protein for L-Glutamine and its Relation to Active Transport in *E. coli*", Archives of Biochemistry and Biophysics, 124:715-717.
Wenner et al. (2001) "Genetically Designed Biosensing Systems for High-Throughput Screening of Pharmaceuticals, Clinical Diagnostics, and Environmental Monitoring", Visual Communications and Image Processing, 4252:59-70.
Wilkins et al. (Jun. 1996) "Glucose Monitoring: State of Art and Future Possibilities", Medical Engineering & Physics, 18:273-288.
Willis et al. (Apr. 10, 1975) "Purification and Properties of a Periplasmic Glutamate-Aspartate Binding Protein from *Escherichkz coli* K12 Strain W3092", The Journal of Biological Chemistry, 250(7):2574-2580.
Willis et al. (Nov. 10, 1974) "Purification and Properties of a Ribose-binding Protein from *Escherichia coli*", Journal of Biological Chemistry, 249(21):6926-6929.
Willner et al. (Oct. 23, 1996) "Electrical Wiring of Glucose Oxidase by Reconstitution of FAD-Modified Monolayers Assembled onto Au-Electrodes", Journal of the American Chemical Society, 118(42):10321-10322.
Yao et al. (Apr. 26, 1994) "Refined 1.89-A Structure of the Histidine-Binding Protein Complexed with Histidine and its Relationship with Many Other Active Transport/Chemosensory Proteins", Biochemistry, 33(16):4769-4779.
Database Uniprotkbtrembl (May 27, 2015) "SubName: Full=Putative Nitrate Transport Protein NrtA (EC0:00003131EMBL".
Date et al. (Feb. 2, 2011) "Polymer-Binding Peptides for the Noncovalent Modification of Polymer Surfaces: Effects of Peptide Density on the Subsequent Immobilization of Functional Proteins", ACS Applied Materials & Interfaces, 3(2):351-359.
De Lorimier et al. (2002,) "Construction of a Fluorescent Biosensor Family", Protein Science, 11:2655-2575.
Demchenko (Dec. 5, 2014) "Practical Aspects of Wavelength Ratiometry in the Studies of Intermolecular Interactions", Journal of Molecular Structure, 1077:51-67.
Demchenko (Sep. 2010) "The Concept of λ-Ratiometry in Fluorescence Sensing and Imaging", Journal of Fluorescence, 20(5):1099-1128.
Dunten (Nov. 1995) "Crystal Structure of the Dipeptide Binding Protein From *Escherichia coli* Involved in Active Transport and Chemotaxis", Protein Science, 4(11): 2327-2334.
Duplay et al. (Aug. 25, 1984) "Sequences of the malE Gene and of its Product, the Maltose-binding Protein of *Escherichia coli* K12", The Journal of Biological Chemistry, 259(16):10606-10613.
Dwyer et al. (2004) "Periplasmic Binding Proteins: A Versatile Superfamily for Protein Engineering", Current Opinion in Structural Biology, 14:495-504.
Ejima et al. (Oct. 15, 2010) "Biological Identification of Peptides that Specifically Bind to Poly(phenylene vinylene) Surfaces: Recognition of the Branched or Linear Structure of the Conjugated Polymer", Langmuir, 26 (22):17278-17285.
George et al. (Aug. 30, 2005) "Effective Function Annotation Through Catalytic Residue Conservation", PNAS, 102(35):12299-12304.
Gill et al. (Nov. 1, 1989) "Calculation of Protein Extinction Coefficients from Amino Acid Sequence Data", Analytical Biochemistry, 182(2):319-326.
Gough et al. (Sep. 1995) "Development of the Implantable Glucose Sensor: What Are the Prospects and Why Is It Taking So Long?", Diabetes, 44(9):1005-1009.
Grimley et al. (Oct. 9, 2013) "Visualization of Synaptic Inhibition with an Optogenetic Sensor Developed by Cell-Free Protein Engineering Automation", The Journal of Neuroscience, 33(41):16297-16309.
Groarke et al. (Nov. 1983) "The Amino Acid Sequence of D-Ribose-binding Protein from *Escherichia coli* K12", Journal of Biological Chemistry, 258(21):12952-12956.
Group (Sep. 30, 1993) "The Effect of Intensive Treatment of Diabetes on the Development and Progression of Long-Term Complications in Insulin-Dependent Diabetes Mellitus", The New England Journal of Medicine, 329:977-986.
Grunewald (Nov. 2013) "Periplasmic Binding Proteins in Biosensing Applications", Bioanalytical Reviews, 1:205-236.
Gubala et al. (Jan. 2012) "Point of Care Diagnostics: Status and Future", Analytical Chemistry, 84(2):487-515.
Gunay et al. (Oct. 21, 2015) "Identification of Soft Matter Binding Peptide Ligands Using Phage Display", Bioconjugate Chemistry, 26(10):2002-2015.
Guo et al. (Jun. 10, 2013) "Identification and Characterization of a Cellulose Binding Heptapeptide Revealed by Phage Display", Biomacromolecules, 14(6):1795-1805.
Guyer et al. (Nov. 1986) "Binding Specificity of the Periplasmic Oligopeptide-Binding Protein from *Escherichia coli*", Journal of Bacteriology, 168(2):775-779.

(56) References Cited

OTHER PUBLICATIONS

He et al. (1993) "Dominant Role of Local Dipoles in Stabilizing Uncompensated Charges on a Sulfate Sequestered in a Periplasmic Active Transport Protein", Protein Science, 2:1643-1647.
Hellinga et al. (Jul. 1985) "Nucleotide Sequence and High-Level Expression of the Major *Escherichia coli* Phosphofructokinase", European Journal of Biochemistry, 149(2)363-373.
Hengen (Jul. 1995) "Purification of His-Tag Fusion Proteins from *Escherichia coli*", 20(7):285-286.
Heo et al. (Jan. 2013) "Towards Smart Tattoos: Implantable Biosensors for Continuous Glucose Monitoring", Advanced Healthcare Materials, 2(1):43-56.
Hinilova et al. (2012) "Peptide-Directed Co-Assembly of Nanoprobes on Multimaterial Patterned Solid Surfaces", Soft Matter, 8(16):4327-4334.
Hsiao et al. (Sep. 20, 1996) "The Crystal Structure of Glutamine-binding Protein from *Escherichia coli*", Journal of Molecular Biology, 262(2):225-242.
Ispas et al. (Jan. 2012) "Review: Recent Developments in Enzyme-Based Biosensors for Biomedical Analysis", Analytical Letters, 45(2-3):168-186.
Jacobson et al. (Dec. 5, 1998) "Sulfate-Binding Protein Dislikes Protonated Oxyacids. a Molecular Explanation", Journal of Molecular Biology, 204(3):783-787.
Joshi et al. (Jan. 29, 1998) "*Escherichia coli* Lysine-Arginine-Ornithine(LAO)-Binding Periplasmic Protein Argt (Argt) Gene, Partial Cds, Histidine-Binding Periplasmic Protein Hisj (Hisj) And Histidine Transport System Permease Protein Hisq (Hisq) Genes, Complete Cds, And Histidine Tran", GenBank: U47027.1, 2 pages.
Judge et al. (Feb. 27, 2011) "Continuous Glucose Monitoring Using a Novel Glucose/Galactose Binding Protein: Results of a 12-Hour Feasibility Study with the Becton Dickinson Glucose/Galactose Binding Protein Sensor", Diabetes Technology & Therapeutics, 13(3):309-317.
Klymchenko et al. (Jan. 1, 2013) "Fluorescent Environment-Sensitive Dyes as Reporters of Biomolecular Interactions", Progress in Molecular Biology and Translational Science, 113:35-58.
Kolb et al. (Jun. 1, 2001) "Click Chemistry: Diverse Chemical Function from a Few Good Reactions", Angewandte Chemie International Edition, 40(11):2004-2021.
Koo et al. (Nov. 19, 2012) "Bioorthogonal Copper-Free Click Chemistry In Vivo for Tumor-Targeted Delivery of Nanoparticles", Angewandte Chemie, 51(47):11836-11840.
Koropatkin et al. (Jan. 26, 2007) "The Structure of a Cyanobacterial Bicarbonate Transport Protein, CmpA", Journal of Biological Chemistry, 282(4):2606-2614.
Kozma et al. (Sep. 15, 2013) "A Novel Handheld Fluorescent Microarray Reader for Point-of-Care Diagnostic", Biosensors and Bioelectronics, 47:415-420.
Kucherak et al. (Jan. 12, 2010) "Fluorene Analogues of Prodan with Superior Fluorescence Brightness and Solvatochromism", The Journal of Physical Chemistry Letters, 1(3):616-620.
Kumada et al. (Dec. 14, 2009) "Characterization of Polystyrene-Binding Peptides (PS-tags) for Site-Specific Immobilization of Proteins", Journal of Bioscience and Bioengineering, 109(6):583-587.
Kumada et al. (Aug. 31, 2012) "Screening of PC and PMMA-Binding Peptides for Site-Specific Immobilization of Proteins", Journal of Biotechnology, 160(3-4):222-228.
Kumada (Nov. 2014) "Site-Specific Immobilization of Recombinant Antibody Fragments Through Material- Binding Peptides for the Sensitive Detection of Antigens in Enzyme Immunoassays", Biochimica et Biophysica Acta (BBA)—Proteins and Proteomics, 1844(11):1960-1969.
Layton et al. (Nov. 4, 2010) "Thermodynamic Analysis of Ligand-Induced Changes in Protein Thermal Unfolding Applied to High-Throughput Determination of Ligand Affinities with Extrinsic Fluorescent Dyes", Biochemistry, 49(51):10831-10841.
Ledvina et al. (Jun. 1996) "Negative Electrostatic Surface Potential of Protein Sites Specific for Anionic Ligands", Proceedings of the National Academy of Sciences, 93:6786-6791.
Lee et al. (Jun. 2002) "Ordering of Quantum Dots Using Genetically Engineered Viruses", Science, 296 (5569):892-895.
Liu et al. (Sep. 2015) "Applications and Advances of Metabolite Biosensors for Metabolic Engineering", Metabolic Engineering, 31:35-43.
Lu et al. (Nov. 23, 2006) "Long-Wavelength Analogue of PRODAN: Synthesis and Properties of Anthradan, a Fluorophore with a 2,6-Donor-Acceptor Anthracene Structure", The Journal of Organic Chemistry, 71(26):9651-9657.
Luecke et al. (Sep. 27, 1990) "High Specificity of a Phosphate Transport Protein Determined by Hydrogen Bonds", Nature, 347:402-406.
Magota et al. (Mar. 1984) "Nucleotide Sequence of the phoS Gene, the Structural Gene for the Phosphate-Binding Protein of *Escherichia coli*", Journal of Bacteriology, 157(3):909-917.
Marvin et al. (1998) "Engineering Biosensors by Introducing Fluorescent Allosteric Signal Transducers: Construction of a Novel Glucose Sensor", Journal of the American Chemical Society, 120:7-11.
Marvin et al. (Sep. 2001) "Manipulation of Ligand Binding Affinity by Exploitation of Conformational Coupling", Nature Structural & Molecular Biology, 8(9):795-798.
Marvin et al. (Apr. 1997) "The Rational Design of Allosteric Interactions in a Monomeric Protein and its Applications to the Construction of Biosensors", Proceedings of the National Academy of Sciences, 94:4366-4371.
Matsuno et al. (May 24, 2008) "Biological Selection of Peptides for Poly(I-lactide) Substrates", Langmuir, 24 (13):6399-6403.

* cited by examiner $$CO_2 + H_2O \rightleftharpoons H_2CO_3 \rightleftharpoons HCO_3^- + H^+$$

FIG. 2

FIG. 3A
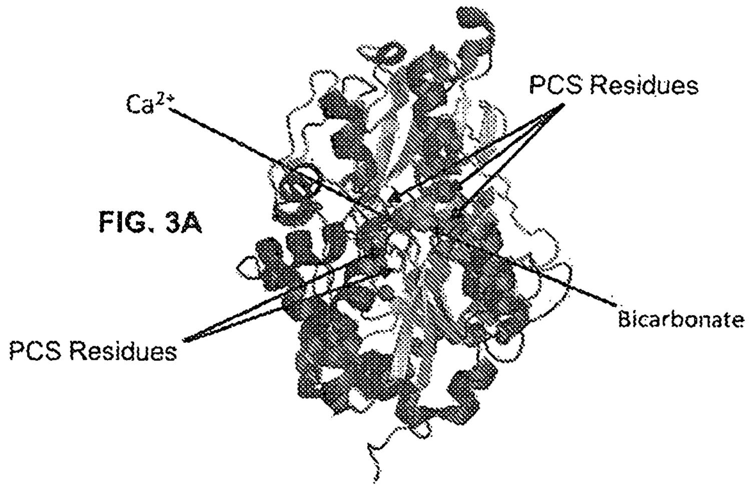
FIG. 3B
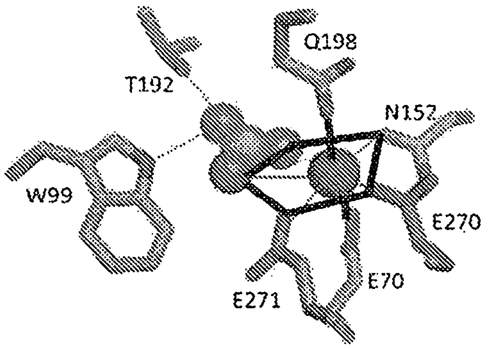
FIG. 3C
| Residue | Interaction | Allowed residues |
|---|---|---|
| E70 | $Ca^{2+}$ coordination | E |
| W99 | Indole hydrogen bond donor to bicarbonate | W |
| Q121 | Donor or acceptor hydrogen bond to bicarbonate | Q |
| N152 | $Ca^{2+}$ coordination | N |
| T192 | Hydrogen bond donor to bicarbonate | T |
| Q198 | $Ca^{2+}$ coordination | Q |
| E270 | $Ca^{2+}$ coordination | E |
| E271 | $Ca^{2+}$ coordination | E |

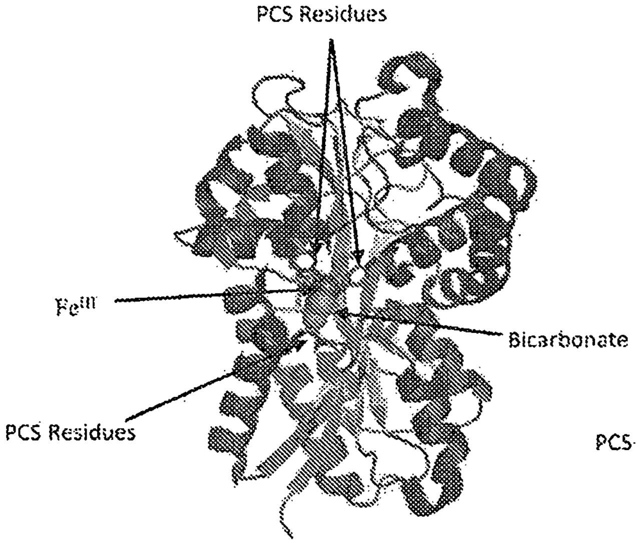
FIG. 4A
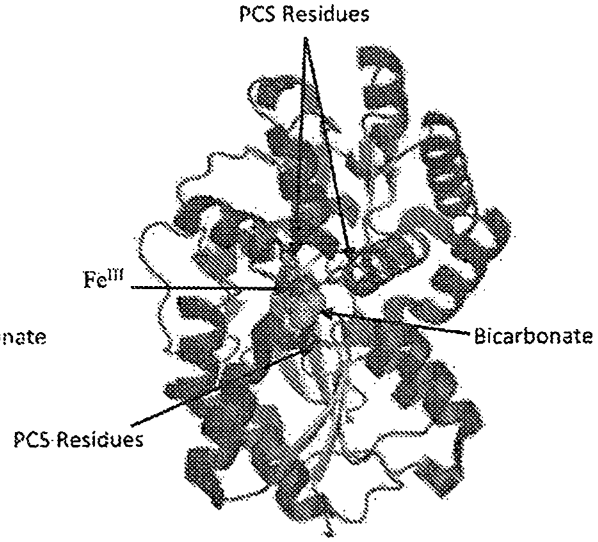
FIG. 4B
| Position | | Interaction | Allowed residues |
|---|---|---|---|
| mhFeBP1 | ttFeBP5 | | |
| R10 | R30 | Bidentate hydrogen bond to bicarbonate | R |
| R101 | R120 | Monodentate hydrogen bond to bicarbonate | R |
| Y142 | Y162 | Fe(III) coordination (Helix B) | Y |
| Y198 | Y219 | Fe(III) coordination (Helix A) | Y |
| Y199 | Y220 | Fe(III) coordination (Helix A) | Y |
FIG. 4C

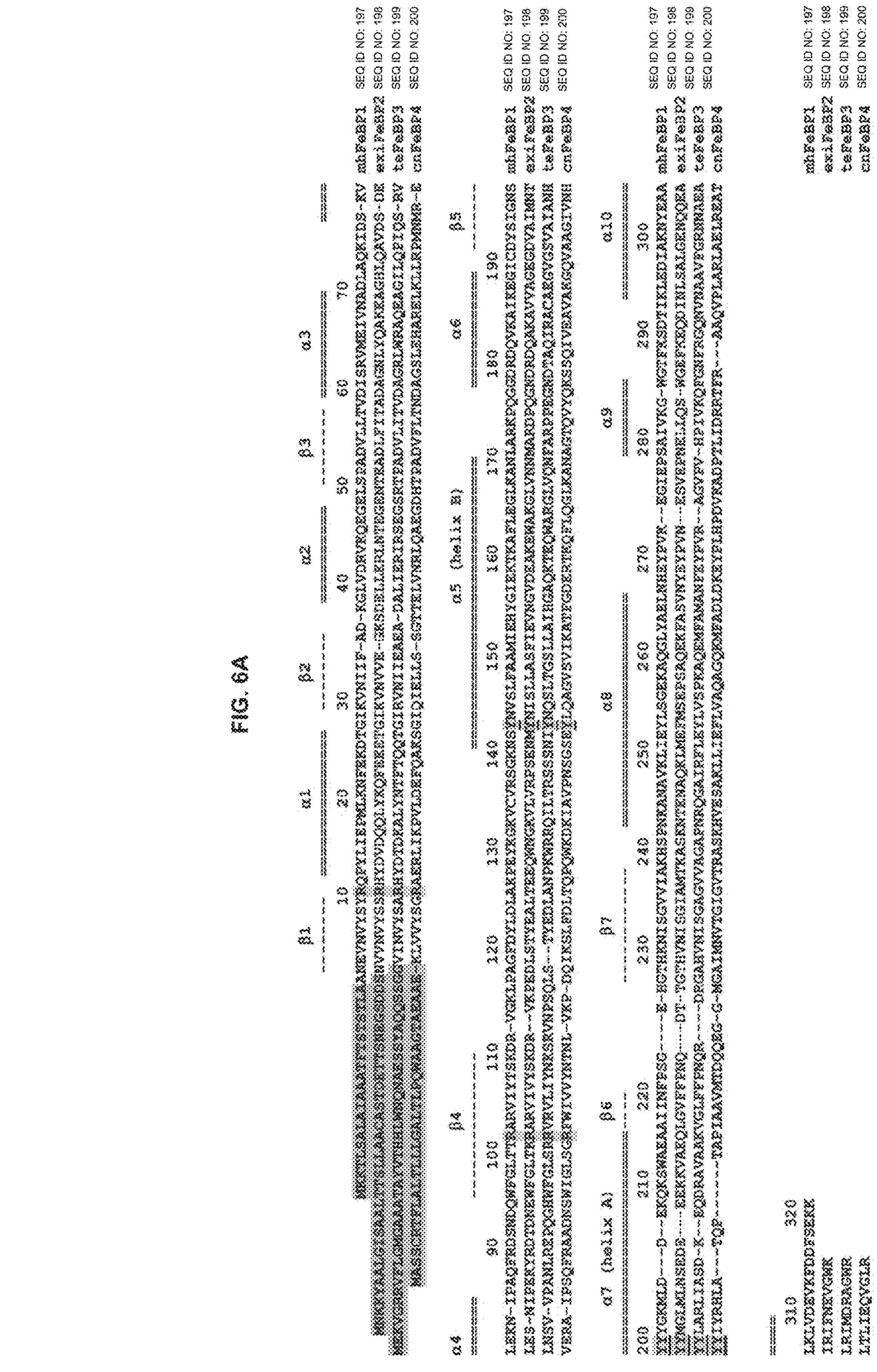

FIG. 6A

```
                        β1                         α1                                    β2                    β3             α3
                     ─────────                ─────────────                       ─────────               ─────         ───────────
                         10            20            30            40            50            60            70
MHTSLALAAARTGSTLLAREVAVYSTRQPYLIEDWLKNFEKDTGIKVNIIF-AD-KGLVDRVRQEGELSPADVLLTVDISRVMELTVNADLAQKIDS-RV    mhFeBP1    SEQ ID NO: 197
MHSSALAAATLILLAAAKVTLLIAACASTDMETFEMESSDDSRVPNPYSSSHYDVDQQLYKQFEKETGIKVNVVE--BKSDELLKRLNTEGENTEADLFITADAGNLYQAFKKAGHLQAVDS-DE    exiFeBP2    SEQ ID NO: 198
MSHYGHILLAAATALIFPAHLMEGQNESSATRAQQSBSGVTIKWYSAARHYDTDRALYNTFTQQTGIRVNIIEAKA-DALIERIRSEGSRTEADVLITVDAGRLWRAQEAGILQPIQS-RV      teFeBP3    SEQ ID NO: 199
MSSSCHFTLLILLGLLTFPGTAGTAAEG KLVVYSGRAERLIKPVLDEFQAKSGIQIELLS-SGTTELVNRLQAEGDHTPADVFTPADVLTNDAGSLEHARELKLLIRPMNMR-E              cnFeBP4    SEQ ID NO: 200

  α4                                                    β4                                             α5 (helix B)                                α6              β5
─────                                             ──────────                                       ──────────────────                          ─────────       ─────
         90           100           110           120           130           140           150           160           170           180           190
LEKN-IPAQFTRDSRDQWFGLTTBARVIYTSKDR-VGKLPAGSTIFLDLAKFELKGKVCVRSGKRSFRVSLFAAMIERHYGIEKTKAFLEGLKANLARKPQGGDRDQVKAIKEGICDYSIGNS   mhFeBP1    SEQ ID NO: 197
LES-NIFEKYRDTDKERFGLITBKARVIYIYSKDR--VKPEDLLSTYEALTEEQNNGGVLVRFSERMMNISLLASFIEVNGVDEAKEWARQGLYNMMARDPQGNRDQAKKAVVAGEGDVAIMNT   exiFeBP2    SEQ ID NO: 198
LRSV-VPAMLREPQGHRFGLSRHVRVLIYNRKSKVNPSQLS---TYEDLANPKWRRQILTRSSSNIYNQSLTGSLLAIRGAQKTEQWARGLVQNFARPFBGRDTAQIRACAEKGVSVIANH      teFeBP3    SEQ ID NO: 199
VERA-IFSQFRAADNSWIBLSGRFWTVVYNTNL-VKP-DQIKSLRDITQFQNRDKIAVFNSGGSEVLQAEGVSVIKATFGDERTKQFLQGLKANASTQYYQKSSQIVBAVAKGQVRAAGTYNH   cnFeBP4    SEQ ID NO: 200

  α7 (helix A)            β6                                                    β7                            α8                              α9                           α10
───────────────      ─────────                                             ─────────                    ────────────                     ────────                    ────────
    200           210           220           230           240           250           260           270           280           290           300
MIYGKKLD---D---EKQKSWAREAAIINFSG------E-HGTHKNISGVVIAKHSPNRAAVKLLIEYLSGEKAQGLYABLNHEYPVR---EGIEPSAIVKG--WGTFKSDTIKLEDIAKRYEAA  mhFeBP1    SEQ ID NO: 197
VMGLMLNSEDE----------DT--TGTHVNISGIAMTKASENTENAQKLMEFMSEPSAQEKFASVNYEYPVN--KSVEPNELLQS--WGEFKEQINLSALGENQEA                   exiFeBP2    SEQ ID NO: 198
TILARLIASD-K---EQDRAVARKVGLFFPWQR------DRGARYNISGAGVVRGAPKRQGSAIRFLYLVSPRADEMFAMAMEYFVR---AGYFV-HPIVKQFGNFFGQRVRAAVFGRMRAEA   teFeBP3    SEQ ID NO: 199
MIYRHLA----TQP----------TAPIAAVMTDQQEG-G-MGAIMNVTGIGVTRASEHVESAAKLLIEFLVAQAGQKMEADLDKEYFLHPDVKADPTLIDRRTER---AAQVFLARLAELREAI  cnFeBP4    SEQ ID NO: 200

──────
    310           320
LKLVDEVKFDDFSEKK    mhFeBP1    SEQ ID NO: 197
IRIFNKVGWR          exiFeBP2    SEQ ID NO: 198
LRIMDRAGWR          teFeBP3    SEQ ID NO: 199
LTLIEQVGLR          cnFeBP4    SEQ ID NO: 200
```

FIG. 12A
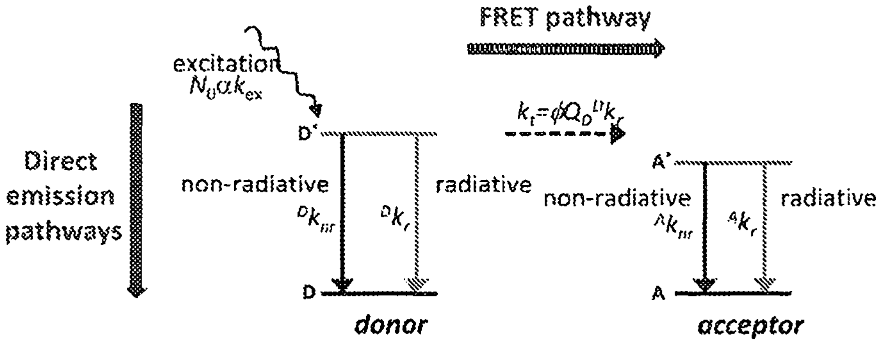
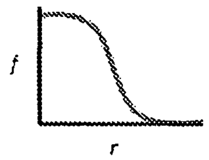
FIG. 12B
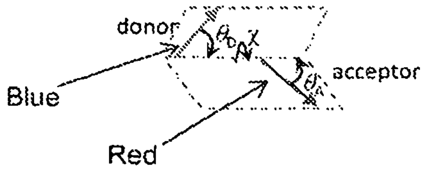
FIG. 12C
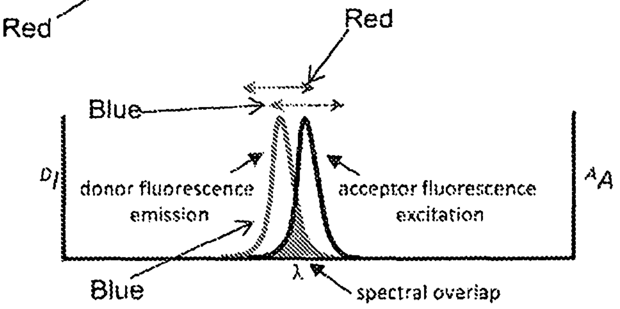
FIG. 12D
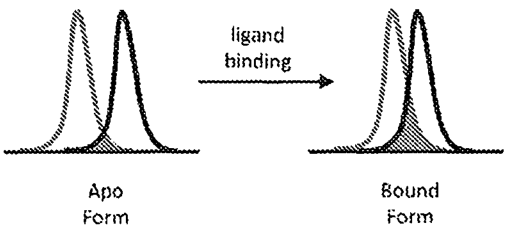

FIG. 13 - Exemplary Expression Construct for synBicarbBP1

SEQ ID NO: 95

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                              10
                                                                            M  P  E  M  M  P  E  T  A  N  I  K  L  G  Y  I  P  I  V  E
GGAGACCACAACGGTTTCCCTCTAGAAATAATTTTGTTTAACTTTAAGAAGGAGATATACCATGCCAGAAATGATGCCAGAAACAGCTAATATTAAGCTGGGTTATATCCCTATTGTTGA
CCTCTGGTGTTGCCAAAGGGAGATCTTTATTAAAACAAATTGAAATTCTTCCTCTATATGGTACGGTCTTTACTACGGTCTTTGTCGATTATAATTCGACCCAATATAGGGATAACAACT
       130       140       150       160       170       180       190       200       210       220       230       240

                                            30                            40                            50
A  A  P  L  I  I  A  Q  E  K  G  F  F  A  K  Y  G  M  T  G  V  E  V  S  K  Q  A  N  W  A  S  A  R  D  N  V  T  I  G  S
GGCAGCTCCTCTCATCATCGCCCAGGAAAAAGGGTTCTTCGCTAAATACGGGATGACGGGTGTGGAAGTCAGTAAACAAGCCAATTGGGCATCAGCACGTGATAATGTGACCATCGGCAG
CCGTCGAGGAGAGTAGTAGCGGGTCCTTTTTCCCAAGAAGCGATTTATGCCCTACTGCCCACACCTTCAGTCATTTGTTCGGTTAACCCGTAGTCGTGCACTATTACACTGGTAGCCGTC
       250       260       270       280       290       300       310       320       330       340       350       360

                                            70                            80                            90
Q  G  G  G  I  D  G  G  Q  W  Q  M  P  M  P  H  L  I  T  E  G  I  I  T  N  G  N  K  V  P  M  Y  V  L  A  Q  L  I  T  Q
TCAAGGCGGCGGGATTGACGGTGGCCAATGGCAAATGCCAATGCCTCACTTGATTACGGAAGGGATCATCACCAATGGCAACAAGGTACCAATGTACGTACTGGCACAGTTGATCACTCA
AGTTCCGCCGCCCTAACTGCCACCGGTTACCGTTTACGGTTACGGAGTGAACTAATGCCTTCCCTAGTAGTGGTTACCGTTGTTCCATGGTTACATGCATGACCGTGTCAACTAGTGAGT
       370       380       390       400       410       420       430       440       450       460       470       480

                                           110                           120                           130
G  N  G  I  A  V  A  P  M  H  E  G  K  G  V  N  L  D  I  T  K  A  A  D  Y  I  K  G  F  N  K  T  N  G  R  K  F  K  A  A
AGGTAACGGGATCGCAGTCGCGCCGATGCATGAAGGTAAAGGTGTAAACTTGGACATCACGAAAGCCGCCGACTACATTAAGGGTTTCAACAAGACAAACGGTCGTAAATTTAAAGCAGC
TCCATTGCCCTAGCGTCAGCGCGGCTACGTACTTCCATTTCCACATTTGAACCTGTAGTGCTTTCGGCGGCTGATGTAATTCCCAAAGTTGTTCTGTTTGCCAGCATTTAAATTTCGTCG
       490       500       510       520       530       540       550       560       570       580       590       600

                                           150                           160                           170
H  T  F  P  N  V  N  Q  D  F  W  I  R  Y  W  F  A  A  G  G  V  D  P  D  T  D  I  D  L  L  A  V  P  P  A  E  T  V  Q  G
GCACACCTTCCCAAATGTCAACCAAGACTTTTGGATTCGCTACTGGTTTGCAGCAGGCGGCGTCGACCCAGATACAGACATTGATTTATTGGCAGTGCCTCCAGCCGAGACAGTACAAGG
CGTGTGGAAGGGTTTACAGTTGGTTCTGAAAACCTAAGCGATGACCAAACGTCGTCCGCCGCAGCTGGGTCTATGTCTGTAACTAAATAACCGTCACGGAGGTCGGCTCTGTCATGTTCC
       610       620       630       640       650       660       670       680       690       700       710       720

                                           190                           200                           210
M  R  N  G  T  M  D  A  F  S  T  G  D  P  W  P  Y  R  I  V  T  E  N  I  G  Y  M  A  G  L  T  A  Q  I  W  P  Y  H  P  E
GATGCGGAATGGGACAATGGACGCCTTCTCGACCGGTGACCCATGGCCATACCGGATCGTAACTGAGAACATCGGGTATATGGCGGGTCTTACCGCGCAAATTTGGCCTTATCACCCTGA
CTACGCCTTACCCTGTTACCTGCGGAAGAGCTGGCCACTGGGTACCGGTATGGCCTAGCATTGACTCTTGTAGCCCATATACCGCCCAGAATGGCGCGTTTAAACCGGAATAGTGGGACT
       730       740       750       760       770       780       790       800       810       820       830       840

                                           230                           240                           250
E  Y  L  A  I  R  A  D  W  V  D  K  N  P  K  A  T  K  A  L  L  K  G  I  M  E  A  Q  Q  W  I  D  D  P  K  N  R  P  E  V
AGAATATTTAGCAATTCGTGCGGACTGGGTCGACAAGAATCCAAAGGCGACCAAAGCGTTACTCAAAGGTATTATGGAGGCTCAGCAGTGGATTGACGACCCAAAAAATCGTCCAGAGGT
TCTTATAAATCGTTAAGCACGCCTGACCCAGCTGTTCTTAGGTTTCCGCTGGTTTCGCAATGAGTTTCCATAATACCTCCGAGTCGTCACCTAACTGCTGGGTTTTTTAGCAGGTCTCCA
       850       860       870       880       890       900       910       920       930       940       950       960
```

```
                    270                           280                           290
V  Q  I  V  S  G  R  N  Y  F  N  V  P  T  T  I  L  E  S  P  F  K  G  Q  Y  T  M  G  D  G  Q  P  A  I  D  D  F  Q  K  G
TGTACAAATCGTCTCCGGTCGGAATTATTTTAACGTCCCAACTACTATCCTCGAGAGTCCATTCAAAGGTCAATATACTATGGGCGACGGTCAACCGGCCATCGATGACTTCCAAAAGGG
ACATGTTTAGCAGAGGCCAGCCTTAATAAAATTGCAGGGTTGATGATAGGAGCTCTCAGGTAAGTTTCCAGTTATATGATACCCGCTGCCAGTTGGCCGGTAGCTACTGAAGGTTTTCCC
       970       980       990      1000      1010      1020      1030      1040      1050      1060      1070      1080

                    310                           320                           330
P  L  Y  W  K  D  G  I  G  N  V  S  Y  P  Y  K  S  H  D  L  W  F  L  T  E  S  I  R  W  G  F  H  K  N  A  I  P  D  L  D
CCCATTGTACTGGAAAGATGGTATCGGGAACGTATCCTACCCATACAAATCTCACGATTTATGGTTTCTTACGGAATCCATCCGCTGGGGCTTCCATAAAAATGCTATTCCAGACTTAGA
GGGTAACATGACCTTTCTACCATAGCCCTTGCATAGGATGGGTATGTTTAGAGTGCTAAATACCAAAGAATGCCTTAGGTAGGCGACCCCGAAGGTATTTTTACGATAAGGTCTGAATCT
      1090      1100      1110      1120      1130      1140      1150      1160      1170      1180      1190      1200

                    350                           360                           370
T  A  Q  K  I  I  D  K  V  N  R  E  D  L  W  R  E  A  A  T  E  A  G  F  T  A  D  I  P  S  S  T  S  R  G  V  E  T  F  F
TACGGCGCAGAAGATTATCGATAAGGTCAACCGCGAAGATTTATGGCGGGAAGCGGCAACCGAGGCAGGCTTTACAGCTGACATTCCAAGTTCAACCTCACGTGGCGTAGAAACCTTTTT
ATGCCGCGTCTTCTAATAGCTATTCCAGTTGGCGCTTCTAAATACCGCCCTTCGCCGTTGGCTCCGTCCGAAATGTCGACTGTAAGGTTCAAGTTGGAGTGCACCGCATCTTTGGAAAAA
      1210      1220      1230      1240      1250      1260      1270      1280      1290      1300      1310      1320

                    390                           400                           410
D  G  I  T  F  D  P  A  N  P  S  A  Y  L  Q  S  L  A  I  K  K  V  G  G  S  H  H  H  H  H  H  *  *
CGATGGTATTACTTTCGACCCTGCAAACCCATCCGCATACTTACAGTCACTTGCAATTAAGAAAGTAGGTGGTTCACATCATCATCATCATCATTAATGAAAGGGCGATATCCAGCACAC
GCTACCATAATGAAAGCTGGGACGTTTGGGTAGGCGTATGAATGTCAGTGAACGTTAATTCTTTCATCCACCAAGTGTAGTAGTAGTAGTAGTAATTACTTTCCCGCTATAGGTCGTGTG
      1330      1340      1350      1360      1370      1380      1390      1400      1410      1420      1430      1440

TGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAACGGGTCTTGAGG
ACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTTGCCCAGAACTCC
      1450      1460      1470      1480      1490      1500      1510      1520      1530      1540      1550      1560

GGTTTTTTGCTGAAAGGAGGAACTATATCCGGAGCGACTCCCACGGCACGTTGGCAAGCTCGGAATTCGGCGTAATC
CCAAAAAACGACTTTCCTCCTTGATATAGGCCTCGCTGAGGGTGCCGTGCAACCGTTCGAGCCTTAAGCCGCATTAG
      1570      1580      1590      1600      1610      1620      1630
```

FIG. 13 (Continued)

FIG. 14 – Exemplary Expression Construct for teBicarbBP2

SEQ ID NO: 96

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                          10
                                                                         M  L  E  T  D  T  I  K  L  G  F  I  P  I  V  E  S  A  P  L
GGAGACCACAACGGTTTCCCTCTAGAAATAATTTTGTTTAACTTTAAGAAGGAGATATACCATGTTAGAAACAGATACCATTAAATTAGGTTTCATTCCGATTGTAGAGTCAGCCCCACT
CCTCTGGTGTTGCCAAAGGGAGATCTTTATTAAAACAAATTGAAATTCTTCCTCTATATGGTACAATCTTTGTCTATGGTAATTTAATCCAAAGTAAGGCTAACATCTCAGTCGGGGTGA
       130       140       150       160       170       180       190       200       210       220       230       240

                                      30                            40                            50
 I  I  A  K  E  K  G  F  F  A  K  H  G  L  T  N  A  E  L  S  K  Q  A  N  W  A  S  A  R  D  N  V  V  I  G  S  A  G  G  G
CATTATTGCCAAAGAAAAAGGCTTCTTCGCCAAACACGGGTTGACTAATGCGGAACTCTCCAAGCAGGCAAACTGGGCAAGTGCGCGTGACAACGTAGTAATCGGGTCGGCAGGTGGCGG
GTAATAACGGTTTCTTTTTCCGAAGAAGCGGTTTGTGCCCAACTGATTACGCCTTGAGAGGTTCGTCCGTTTGACCCGTTCACGCGCACTGTTGCATCATTAGCCCAGCCGTCCACCGCC
       250       260       270       280       290       300       310       320       330       340       350       360

                                      70                            80                            90
 I  D  G  G  Q  W  Q  M  P  M  P  Y  L  I  S  E  G  I  I  T  L  N  N  Q  K  L  P  M  Y  V  L  A  Q  L  N  T  Q  G  N  G
TATCGATGGTGGCCAGTGGCAAATGCCTATGCCTTATCTCATCTCAGAGGGGATCATTACACTCAATAACCAAAAACTCCCTATGTATGTCCTCGCACAGCTTAATACACAAGGCAACGG
ATAGCTACCACCGGTCACCGTTTACGGATACGGAATAGAGTAGAGTCTCCCCTAGTAATGTGAGTTATTGGTTTTTGAGGGATACATACAGGAGCGTGTCGAATTATGTGTTCCGTTGCC
       370       380       390       400       410       420       430       440       450       460       470       480

                                     110                           120                           130
 I  A  I  S  G  A  N  K  G  K  G  L  H  L  K  I  A  D  P  D  Y  I  K  G  F  A  A  K  N  G  R  K  F  K  A  A  H  T  F  P
TATCGCAATCTCCGGTGCAAATAAGGGGAAAGGTCTCCACTTAAAGATTGCCGACCCAGACTACATCAAGGGCTTCGCCGCCAAGAATGGTCGTAAATTTAAAGCAGCTCATACATTCCC
ATAGCGTTAGAGGCCACGTTTATTCCCCTTTCCAGAGGTGAATTTCTAACGGCTGGGTCTGATGTAGTTCCCGAAGCGGCGGTTCTTACCAGCATTTAAATTTCGTCGAGTATGTAAGGG
       490       500       510       520       530       540       550       560       570       580       590       600

                                     150                           160                           170
 H  V  N  Q  D  L  W  I  R  Y  W  F  A  A  N  G  I  D  P  D  R  D  I  E  L  L  A  V  P  P  A  E  T  V  A  G  M  R  N  G
TCACGTCAATCAAGATCTCTGGATTCGCTACTGGTTCGCAGCAAACGGCATTGACCCTGATCGCGACATTGAGTTATTAGCTGTTCCGCCAGCAGAGACTGTAGCGGGTATGCGCAATGG
AGTGCAGTTAGTTCTAGAGACCTAAGCGATGACCAAGCGTCGTTTGCCGTAACTGGGACTAGCGCTGTAACTCAATAATCGACAAGGCGGTCGTCTCTGACATCGCCCATACGCGTTACC
       610       620       630       640       650       660       670       680       690       700       710       720

                                     190                           200                           210
 T  M  D  A  F  S  T  G  D  P  W  P  F  R  I  V  S  D  D  I  G  Y  M  A  T  L  T  A  Q  I  W  P  Y  H  P  E  E  Y  L  A
TACAATGGACGCATTTTCAACCGGCGACCCATGGCCATTTCGTATCGTATCAGACGACATCGGTTACATGGCGACGTTAACAGCCCAGATCTGGCCATACCATCCTGAAGAATACCTCGC
ATGTTACCTGCGTAAAAGTTGGCCGCTGGGTACCGGTAAAGCATAGCATAGTCTGCTGTAGCCAATGTACCGCTGCAATTGTCGGGTCTAGACCGGTATGGTAGGACTTCTTATGGAGCG
       730       740       750       760       770       780       790       800       810       820       830       840

                                     230                           240                           250
 V  R  A  D  W  V  D  K  H  P  K  A  T  K  A  L  L  K  A  V  M  E  A  Q  Q  W  A  D  D  K  A  N  R  P  E  L  I  Q  I  A
AGTTCGTGCCGATTGGGTAGACAAACATCCTAAAGCTACTAAGGCGCTCCTCAAAGCAGTCATGGAGGCACAGCAGTGGGCAGACGACAAGGCCAATCGTCCAGAACTGATCCAGATCGC
TCAAGCACGGCTAACCCATCTGTTTGTAGGATTTCGATGATTCCGCGAGGAGTTTCGTCAGTACCTCCGTGTCGTCACCCGTCTGCTGTTCCGGTTAGCAGGTCTTGACTAGGTCTAGCG
       850       860       870       880       890       900       910       920       930       940       950       960
```

```
                 270                                     280                                     290
 S  R  R  E  Y  F  N  I  P  G  N  I  L  T  P  P  Y  E  G  T  Y  T  M  G  D  G  Q  P  N  F  N  D  F  N  I  G  P  L  Y  W
AAGTCGGCGCGAATACTTCAATATCCCTGGTAACATTTTGACCCCGCCATATGAGGGCACATATACAATGGGTGATGGCCAACCGAATTTCAACGATTTTAACATTGGTCCATTATACTG
TTCAGCCGCGCTTATGAAGTTATAGGGACCATTGTAAAACTGGGGCGGTATACTCCCGTGTATATGTTACCCACTACCGGTTGGCTTAAAGTTGCTAAAATTGTAACCAGGTAATATGAC
       970       980       990      1000      1010      1020      1030      1040      1050      1060      1070      1080

                 310                                     320                                     330
 R  D  P  N  G  N  S  I  S  Y  P  Y  K  S  H  D  L  W  F  L  T  E  N  L  R  W  G  F  N  A  D  K  L  K  D  F  D  N  I  K
GCGTGACCCGAACGGTAATTCTATCAGCTACCCGTATAAAAGCCACGACTTATGGTTCCTCACTGAGAATCTGCGCTGGGGCTTTAACGCCGACAAGCTGAAGGATTTTGACAATATTAA
CGCACTGGGCTTGCCATTAAGATAGTCGATGGGCATATTTTCGGTGCTGAATACCAAGGAGTGACTCTTAGACGCGACCCCGAAATTGCGGCTGTTCGACTTCCTAAAACTGTTATAATT
      1090      1100      1110      1120      1130      1140      1150      1160      1170      1180      1190      1200

                 350                                     360                                     370
 Q  M  I  G  R  V  N  R  S  D  L  W  Q  E  A  A  K  E  L  G  I  P  A  A  E  I  P  T  T  E  S  R  G  V  E  T  F  F  D  G
GCAGATGATTGGGCGGGTAAATCGCAGTGACCTCTGGCAGGAGGCAGCCAAGGAACTCGGTATCCCAGCAGCCGAAATCCCGACAACAGAATCACGCGGTGTAGAGACTTTCTTCGACGG
CGTCTACTAACCCGCCCATTTAGCGTCACTGGAGACCGTCCTCCGTCGGTTCCTTGAGCCATAGGGTCGTCGGCTTTAGGGCTGTTGTCTTAGTGCGCCACATCTCTGAAAGAAGCTGCC
      1210      1220      1230      1240      1250      1260      1270      1280      1290      1300      1310      1320

                 390                                     400                                     410
 I  K  F  D  P  D  N  P  Q  A  Y  L  D  S  L  K  I  K  V  K  S  G  G  S  H  H  H  H  H  H  *  *
GATTAAGTTCGACCCAGACAATCCACAAGCCTATCTCGATTCCTTAAAGATCAAAGTCAAGTCTGGCGGTTCTCATCATCATCATCATCATTAATGAAAGGGCGATATCCAGCACACTGG
CTAATTCAAGCTGGGTCTGTTAGGTGTTCGGATAGAGCTAAGGAATTTCTAGTTTCAGTTCAGACCGCCAAGAGTAGTAGTAGTAGTAGTAATTACTTTCCCGCTATAGGTCGTGTGACC
      1330      1340      1350      1360      1370      1380      1390      1400      1410      1420      1430      1440


CGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAACGGGTCTTGAGGGGT
GCCGGCAATGATCACCTAGGCCGACGATTGTTTCGGGCTTTCCTTCGACTCAACCGACGACGGTGGCGACTCGTTATTGATCGTATTGGGGAACCCCGGAGATTTGCCCAGAACTCCCCA
      1450      1460      1470      1480      1490      1500      1510      1520      1530      1540      1550      1560


TTTTTGCTGAAAGGAGGAACTATATCCGGAGCGACTCCCACGGCACGTTGGCAAGCTCGGAATTCGGCGTAATC
AAAAACGACTTTCCTCCTTGATATAGGCCTCGCTGAGGGTGCCGTGCAACCGTTCGAGCCTTAAGCCGCATTAG
      1570      1580      1590      1600      1610      1620      1630
```

FIG. 14 (Continued)

FIG. 15 – Exemplary Expression Construct for ctBicarbBP3

SEQ ID NO: 97

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                           10
                                                                               M  P  E  Q  A  P  E  T  T  R  V  K  L  G  Y  I  P  I  V  E
GGAGACCACAACGGTTTCCCTCTAGAAATAATTTTGTTTAACTTTAAGAAGGAGATATACCATGCCAGAACAAGCACCTGAAACAACACGTGTTAAGTTAGGCTATATCCCGATCGTTGA
CCTCTGGTGTTGCCAAAGGGAGATCTTTATTAAAACAAATTGAAATTCTTCCTCTATATGGTACGGTCTTGTTCGTGGACTTTGTTGTGCACAATTCAATCCGATATAGGGCTAGCAACT
       130       140       150       160       170       180       190       200       210       220       230       240

                         30                            40                            50
 A  A  P  I  I  I  A  K  E  K  G  F  F  A  K  Y  G  M  T  D  V  D  V  S  K  Q  A  S  W  G  S  M  R  D  N  T  E  I  G  A
AGCCGCACCGATCATCATTGCAAAAGAGAAAGGCTTCTTCGCTAAGTATGGCATGACCGATGTAGACGTAAGTAAGCAGGCTAGCTGGGGCTCGATGCGTGACAATACGGAGATCGGTGC
TCGGCGTGGCTAGTAGTAACGTTTTCTCTTTCCGAAGAAGCGATTCATACCGTACTGGCTACATCTGCATTCATTCGTCCGATCGACCCCGAGCTACGCACTGTTATGCCTCTAGCCACG
       250       260       270       280       290       300       310       320       330       340       350       360

                         70                            80                            90
 A  G  G  G  V  D  G  G  Q  Y  Q  M  P  M  P  H  L  I  T  E  G  R  I  T  K  G  N  K  P  I  P  M  Y  V  L  A  Q  L  N  T
AGCGGGCGGGGGGGTCGACGGGGGTCAATACCAAATGCCAATGCCACATCTGATCACTGAGGGCCGCATTACAAAGGGGAACAAACCAATCCCTATGTACGTCCTCGCCCAATTAAATAC
TCGCCCGCCCCCCCAGCTGCCCCCAGTTATGGTTTACGGTTACGGTGTAGACTAGTGACTCCCGGCGTAATGTTTCCCCTTGTTTGGTTAGGGATACATGCAGGAGCGGGTTAATTTATG
       370       380       390       400       410       420       430       440       450       460       470       480

                        110                           120                           130
 Q  G  N  G  I  A  I  A  E  K  H  R  G  K  G  I  E  L  E  L  A  K  G  G  K  N  L  F  G  Q  L  K  S  A  N  T  P  F  T  A
GCAGGGGAACGGCATTGCCATCGCCGAAAAACATCGGGGGAAAGGGATCGAACTGGAATTGGCAAAAGGTGGCAAAAACCTCTTTGGCCAGCTTAAGTCGGCTAATACTCCATTCACTGC
CGTCCCCTTGCCGTAACGGTAGCGGCTTTTTGTAGCCCCCTTTCCCTAGCTTGACCTTAACCGTTTTCCACCGTTTTTGGAGAAACCGGTCGAATTCAGCCGATTATGAGGTAAGTGACG
       490       500       510       520       530       540       550       560       570       580       590       600

                        150                           160                           170
 A  Y  T  F  A  Q  V  N  Q  D  F  W  I  R  Y  W  L  A  A  G  G  V  N  P  D  A  D  V  K  L  I  P  V  P  A  A  Q  T  V  A
CGCATACACATTCGCGCAAGTAAACCAAGACTTCTGGATCCGTTACTGGTTGGCTGCAGGGGGTGTAAACCCGGACGCGGATGTAAAACTGATTCCGGTTCCGGCGGCACAGACGGTAGC
GCGTATGTGTAAGCGCGTTCATTTGGTTCTGAAGACCTAGGCAATGACCAACCGACGTCCCCCACATTTGGGCCTGCGCCTACATTTTGACTAAGGCCAAGGCCGCCGTGTCTGCCATCG
       610       620       630       640       650       660       670       680       690       700       710       720

                        190                           200                           210
 N  M  K  T  G  T  M  D  A  F  S  T  G  D  P  W  P  Y  R  I  V  K  D  K  I  G  F  L  A  M  L  T  A  D  M  W  E  F  H  P
CAACATGAAGACAGGTACCATGGATGCATTCTCCACCGGTGACCCTTGGCCTTATCGTATCGTTAAAGACAAAATTGGCTTCTTAGCAATGCTCACCGCCGACATGTGGGAATTTCATCC
GTTGTACTTCTGTCCATGGTACCTACGTAAGAGGTGGCCACTGGGAACCGGAATAGCATAGCAATTTCTGTTTTAACCGAAGAATCGTTACGAGTGGCGGCTGTACACCCTTAAAGTAGG
       730       740       750       760       770       780       790       800       810       820       830       840

                        230                           240                           250
 E  E  Y  L  A  L  R  A  E  W  V  D  K  H  P  K  A  T  K  A  L  L  K  G  I  M  E  A  Q  Q  W  L  D  N  F  D  N  R  E  E
AGAGGAGTACTTAGCCTTGCGCGCGGAATGGGTCGACAAACACCCAAAAGCTACGAAAGCCTTGCTTAAAGGTATCATGGAGGCGCAACAATGGCTTGATAACTTTGATAACCGTGAAGA
TCTCCTCATGAATCGGAACGCGCGCCTTACCCAGCTGTTTGTGGGTTTTCGATGCTTTCGGAACGAATTTCCATAGTACCTCCGCGTTGTTACCGAACTATTGAAACTATTGGCACTTCT
       850       860       870       880       890       900       910       920       930       940       950       960
```

```
                      270                                     280                                     290
 A   A   K   I   L   G   G   R   N   Y   F   N   L   P   A   E   I   L   A   G   P   F   A   G   K   Y   D   M   G   E   G   R   T   V   D   D   R   N   K   A
GGCAGCCAAGATTCTCGGTGGCCGTAATTACTTCAATCTCCCAGCAGAAATCCTCGCAGGTCCATTCGCCGGGAAGTATGACATGGGGGAGGGTCGGACTGTAGATGACCGCAATAAGGC
CCGTCGGTTCTAAGAGCCACCGGCATTAATGAAGTTAGAGGGTCGTCTTTAGGAGCGTCCAGGTAAGCGGCCCTTCATACTGTACCCCCTCCCAGCCTGACATCTACTGGCGTTATTCCG
       970       980       990      1000      1010      1020      1030      1040      1050      1060      1070      1080

                      310                                     320                                     330
 V   L   Y   W   K   D   P   R   G   S   V   S   Y   P   Y   K   S   H   D   L   W   F   L   T   E   S   V   R   W   G   F   L   P   P   D   S   L   T   K   A
CGTACTCTACTGGAAGGATCCACGCGGCAGCGTCAGCTACCCATATAAATCACACGACTTATGGTTCTTAACTGAATCCGTCCGCTGGGGCTTTCTCCCACCGGATAGTTTAACTAAAGC
GCATGAGATGACCTTCCTAGGTGCGCCGTCGCAGTCGATGGGTATATTTAGTGTGCTGAATACCAAGAATTGACTTAGGCAGGCGACCCCGAAAGAGGGTGGCCTATCAAATTGATTTCG
      1090      1100      1110      1120      1130      1140      1150      1160      1170      1180      1190      1200

                      350                                     360                                     370
 Q   A   L   I   D   K   V   N   R   E   D   L   W   K   E   A   A   K   E   L   G   V   A   A   A   D   I   P   T   S   T   S   R   G   V   E   T   F   F   D
GCAGGCGCTGATTGACAAAGTGAACCGCGAAGATCTCTGGAAAGAAGCCGCAAAAGAATTAGGCGTAGCCGCAGCCGATATTCCAACCAGCACCAGTCGCGGCGTAGAAACCTTCTTTGA
CGTCCGCGACTAACTGTTTCACTTGGCGCTTCTAGAGACCTTTCTTCGGCGTTTTCTTAATCCGCATCGGCGTCGGCTATAAGGTTGGTCGTGGTCAGCGCCGCATCTTTGGAAGAAACT
      1210      1220      1230      1240      1250      1260      1270      1280      1290      1300      1310      1320

                      390                                     400                                     410
 G   V   K   F   D   P   E   N   P   A   A   Y   L   K   S   L   K   I   K   K   A   G   G   S   H   H   H   H   H   H   *   *
CGGTGTCAAGTTCGACCCGGAAAATCCTGCAGCGTATCTCAAGTCATTAAAGATTAAGAAAGCAGGCGGTAGTCATCATCATCATCATCATTAATGAAAGGGCGATATCCAGCACACTGG
GCCACAGTTCAAGCTGGGCCTTTTAGGACGTCGCATAGAGTTCAGTAATTTCTAATTCTTTCGTCCGCCATCAGTAGTAGTAGTAGTAGTAATTACTTTCCCGCTATAGGTCGTGTGACC
      1330      1340      1350      1360      1370      1380      1390      1400      1410      1420      1430      1440


CGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAACGGGTCTTGAGGGGT
GCCGGCAATGATCACCTAGGCCGACGATTGTTTCGGGCTTTCCTTCGACTCAACCGACGACGGTGGCGACTCGTTATTGATCGTATTGGGGAACCCCGGAGATTTGCCCAGAACTCCCCA
      1450      1460      1470      1480      1490      1500      1510      1520      1530      1540      1550      1560


TTTTTGCTGAAAGGAGGAACTATATCCGGAGCGACTCCCACGGCACGTTGGCAAGCTCGGAATTCGGCGTAATC
AAAAACGACTTTCCTCCTTGATATAGGCCTCGCTGAGGGTGCCGTGCAACCGTTCGAGCCTTAAGCCGCATTAG
      1570      1580      1590      1600      1610      1620      1630
```

FIG. 15 (Continued)

FIG. 16 - Exemplary Expression Construct for calBicarbBP4

SEQ ID NO: 98

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                          10
                                                                                M  P  E  Q  K  P  E  T  E  T  V  K  L  G  Y  I  P  I  V  E
GGAGACCACAACGGTTTCCCTCTAGAAATAATTTTGTTTAACTTTAAGAAGGAGATATACCATGCCTGAACAAAAACCTGAAACTGAAACAGTTAAACTCGGCTACATCCCAATCGTTGA
CCTCTGGTGTTGCCAAAGGGAGATCTTTATTAAAACAAATTGAAATTCTTCCTCTATATGGTACGGACTTGTTTTTGGACTTTGACTTTGTCAATTTGAGCCGATGTAGGGTTAGCAACT
       130       140       150       160       170       180       190       200       210       220       230       240

                              30                            40                            50
 S  A  P  L  I  I  A  K  E  K  G  L  F  A  K  Y  G  M  T  K  V  E  L  A  K  Q  A  S  W  G  A  A  R  D  N  V  E  I  G  S
ATCGGCGCCTCTCATCATTGCAAAGGAGAAAGGGTTGTTCGCAAAATACGGTATGACCAAGGTGGAGCTCGCAAAGCAGGCCAGCTGGGGTGCAGCACGGGATAACGTAGAAATTGGGTC
TAGCCGCGGAGAGTAGTAACGTTTCCTCTTTCCCAACAAGCGTTTTATGCCATACTGGTTCCACCTCGAGCGTTTCGTCCGGTCGACCCCACGTCGTGCCCTATTGCATCTTTAACCCAG
       250       260       270       280       290       300       310       320       330       340       350       360

                              70                            80                            90
 A  G  G  G  I  D  G  G  Q  W  Q  M  P  M  P  H  L  I  T  A  G  L  I  T  K  G  N  K  E  I  P  M  Y  V  L  A  Q  L  V  T
GGCAGGTGGCGGTATCGACGGCGGTCAGTGGCAAATGCCAATGCCTCATCTCATCACCGCAGGCCTGATTACAAAGGGTAATAAGGAGATCCCTATGTATGTACTCGCACAGTTAGTCAC
CCGTCCACCGCCATAGCTGCCGCCAGTCACCGTTTACGGTTACGGAGTAGAGTAGTGGCGTCCGGACTAATGTTTCCCATTATTCCTCTAGGGATACATACATGAGCGTGTCAATCAGTG
       370       380       390       400       410       420       430       440       450       460       470       480

                             110                           120                           130
 H  G  N  G  I  A  I  A  D  K  H  K  G  K  G  L  G  L  K  L  D  G  A  K  S  L  F  K  E  L  K  S  S  T  P  F  T  A  A  F
CCATGGCAACGGTATCGCCATTGCAGACAAACACAAAGGTAAGGGCCTCGGTTTAAAATTAGATGGTGCCAAATCCCTCTTCAAAGAACTGAAGTCAAGTACCCCTTTCACGGCAGCCTT
GGTACCGTTGCCATAGCGGTAACGTCTGTTTGTGTTTCCATTCCCGGAGCCAAATTTTAATCTACCACGGTTTAGGGAGAAGTTTCTTGACTTCAGTTCATGGGGAAAGTGCCGTCGGAA
       490       500       510       520       530       540       550       560       570       580       590       600

                             150                           160                           170
 T  F  P  H  V  N  Q  D  L  W  I  R  Y  W  L  A  A  S  G  L  D  P  D  A  D  V  K  L  L  T  V  P  A  A  Q  T  V  A  N  M
CACGTTCCCTCACGTCAACCAAGACTTATGGATCCGGTACTGGTTAGCGGCATCCGGTCTCGACCCTGACGCGGACGTCAAACTCTTGACAGTCCCAGCCGCACAAACAGTCGCCAACAT
GTGCAAGGGAGTGCAGTTGGTTCTGAATACCTAGGCCATGACCAATCGCCGTAGGCCAGAGCTGGGACTGCGCCTGCAGTTTGAGAACTGTCAGGGTCGGCGTGTTTGTCAGCGGTTGTA
       610       620       630       640       650       660       670       680       690       700       710       720

                             190                           200                           210
 K  T  G  T  M  D  A  F  S  T  G  D  P  W  P  F  R  I  V  N  D  K  I  G  F  M  A  L  L  T  A  E  M  W  K  N  H  P  E  E
GAAGACCGGCACCATGGATGCCTTTTCCACCGGCGACCCATGGCCATTTCGTATCGTAAATGATAAAATTGGTTTCATGGCATTGCTTACCGCGGAAATGTGGAAAAATCACCCTGAGGA
CTTCTGGCCGTGGTACCTACGGAAAAGGTGGCCGCTGGGTACCGGTAAAGCATAGCATTTACTATTTTAACCAAAGTACCGTAACGAATGGCGCCTTTACACCTTTTTAGTGGGACTCCT
       730       740       750       760       770       780       790       800       810       820       830       840

                             230                           240                           250
 Y  L  A  M  R  G  D  W  V  D  K  H  P  K  A  T  K  A  I  L  K  A  V  M  E  A  Q  Q  W  L  D  N  F  E  N  R  K  E  A  A
GTACTTAGCCATGCGTGGCGACTGGGTCGACAAGCACCCAAAGGCTACCAAAGCAATTTTAAAGGCGGTGATGGAAGCACAACAGTGGTTAGACAACTTTGAAAACCGGAAGGAGGCAGC
CATGAATCGGTACGCACCGCTGACCCAGCTGTTCGTGGGTTTCCGATGGTTTCGTTAAAATTTCCGCCACTACCTTCGTGTTGTCACCAATCTGTTGAAACTTTTGGCCTTCCTCCGTCG
       850       860       870       880       890       900       910       920       930       940       950       960
```

```
                        270                                     280                                     290
 T   I   L   A   G   R   K   Y   F   D   L   S   S   P   E   I   L   L   D   P   Y   Q   G   K   Y   D   M   G   D   G   R   K   I   D   D   K   L   M   A   P
AACGATTCTCGCAGGGCGTAAATATTTTGATCTCAGCTCACCAGAGATCCTCCTCGATCCATATCAAGGTAAATACGACATGGGCGATGGTCGTAAAATCGATGACAAACTGATGGCTCC
TTGCTAAGAGCGTCCCGCATTTATAAAACTAGAGTCGAGTGGTCTCTAGGAGGAGCTAGGTATAGTTCCATTTATGCTGTACCCGCTACCAGCATTTTAGCTACTGTTTGACTACCGAGG
       970       980       990      1000      1010      1020      1030      1040      1050      1060      1070      1080

                        310                                     320                                     330
 Y   Y   W   K   D   E   K   G   S   V   S   Y   P   Y   K   S   H   D   L   W   F   I   T   E   N   V   R   W   G   F   L   P   K   D   Y   L   A   N   N   A
ATACTACTGGAAAGACGAAAAGGGTTCCGTGTCCTATCCATACAAGAGTCACGATTTATGGTTCATCACCGAGAATGTACGTTGGGGCTTTTTACCAAAGGACTATCTCGCCAACAATGC
TATGATGACCTTTCTGCTTTTCCCAAGGCACAGGATAGGTATGTTCTCAGTGCTAAATACCAAGTAGTGGCTCTTACATGCAACCCCGAAAAATGGTTTCCTGATAGAGCGGTTGTTACG
      1090      1100      1110      1120      1130      1140      1150      1160      1170      1180      1190      1200

                        350                                     360                                     370
 A   K   A   K   E   L   I   N   K   V   N   R   E   D   I   W   K   E   A   A   K   D   L   G   I   A   A   A   D   I   P   T   S   T   S   R   G   V   E   E
CGCCAAAGCGAAAGAATTAATCAACAAAGTCAACCGTGAGGACATTTGGAAGGAGGCTGCCAAGGACCTGGGGATTGCAGCAGCAGACATCCCAACAAGTACGTCCCGCGGGGTAGAGGA
GCGGTTTCGCTTTCTTAATTAGTTGTTTCAGTTGGCACTCCTGTAAACCTTCCTCCGACGGTTCCTGGACCCCTAACGTCGTCGTCTGTAGGGTTGTTCATGCAGGGCGCCCCATCTCCT
      1210      1220      1230      1240      1250      1260      1270      1280      1290      1300      1310      1320

                        390                                     400                                     410
 F   F   D   G   V   K   F   D   P   E   K   P   E   E   Y   L   K   S   L   K   I   K   K   A   G   V   G   G   S   H   H   H   H   H   H   *   *
GTTCTTCGATGGCGTTAAGTTTGATCCAGAGAAGCCTGAAGAGTATCTCAAATCACTGAAAATTAAAAAAGCAGGGGTAGGTGGTTCTCATCATCATCATCATCATTAATGAAAGGGCGA
CAAGAAGCTACCGCAATTCAAACTAGGTCTCTTCGGACTTCTCATAGAGTTTAGTGACTTTTAATTTTTTCGTCCCCATCCACCAAGAGTAGTAGTAGTAGTAGTAATTACTTTCCCGCT
      1330      1340      1350      1360      1370      1380      1390      1400      1410      1420      1430      1440


TATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAA
ATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTT
      1450      1460      1470      1480      1490      1500      1510      1520      1530      1540      1550      1560


CGGGTCTTGAGGGGTTTTTTGCTGAAAGGAGGAACTATATCCGGAGCGACTCCCACGGCACGTTGGCAAGCTCGGAATTCGGCGTAATC
GCCCAGAACTCCCCAAAAAACGACTTTCCTCCTTGATATAGGCCTCGCTGAGGGTGCCGTGCAACCGTTCGAGCCTTAAGCCGCATTAG
      1570      1580      1590      1600      1610      1620      1630      1640
```

FIG. 16 (Continued)

FIG. 17 – Exemplary Expression Construct for avBicarbBP5

SEQ ID NO: 99

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                            10
                                                                M  A  E  Q  A  P  E  V  T  T  V  K  L  G  Y  I  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCTAACAGCT
       130       140       150       160       170       180       190       200       210       220       230       240

                             30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                             70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                            110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                            150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                            190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                            230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                    270                           280                           290
 Q  I  L  A  G  R  N  Y  F  N  L  N  N  P  E  I  L  A  D  P  Y  V  G  K  Y  D  M  G  D  G  R  K  I  D  D  K  S  M  A  A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
       970       980       990      1000      1010      1020      1030      1040      1050      1060      1070      1080

                    310                           320                           330
 Y  Y  W  K  D  E  K  G  S  V  S  Y  P  Y  K  S  H  D  L  W  F  I  T  E  N  V  R  W  G  F  L  P  K  D  Y  L  A  N  G  A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
      1090      1100      1110      1120      1130      1140      1150      1160      1170      1180      1190      1200

                    350                           360                           370
 A  K  A  K  E  L  I  D  K  V  N  R  E  D  I  W  K  E  A  A  K  E  A  G  I  A  A  A  D  I  P  T  S  T  S  R  G  V  E  E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
      1210      1220      1230      1240      1250      1260      1270      1280      1290      1300      1310      1320

                    390                           400                           410
 F  F  D  G  T  K  F  D  P  E  K  P  D  E  Y  L  K  S  L  K  I  K  K  V  S  V  G  G  S  H  H  H  H  H  H  *  *
GTTCTTCGACGGCACCAAATTCGACCCAGAAAAGCCAGACGAATATCTGAAATCGCTCAAAATCAAAAAAGTCAGCGTAGGTGGTTCACATCATCATCATCATCATTAATGAAAGGGCGA
CAAGAAGCTGCCGTGGTTTAAGCTGGGTCTTTTCGGTCTGCTTATAGACTTTAGCGAGTTTTAGTTTTTTCAGTCGCATCCACCAAGTGTAGTAGTAGTAGTAGTAATTACTTTCCCGCT
      1330      1340      1350      1360      1370      1380      1390      1400      1410      1420      1430      1440

TATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAA
ATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTT
      1450      1460      1470      1480      1490      1500      1510      1520      1530      1540      1550      1560

CGGGTCTTGAGGGGTTTTTTGCTGAAAGGAGGAACTATATCCGGAGCGACTCCCACGGCACGTTGGCAAGCTCGGAATTCGGCGTAATC
GCCCAGAACTCCCCAAAAAACGACTTTCCTCCTTGATATAGGCCTCGCTGAGGGTGCCGTGCAACCGTTCGAGCCTTAAGCCGCATTAG
      1570      1580      1590      1600      1610      1620      1630      1640
```

FIG. 17 (Continued)

FIG. 18 - Exemplary Expression Construct for cmBicarbBP6

SEQ ID NO: 100

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                         10
                                                                 M  S  S  A  T  T  P  E  T  T  A  V  K  L  G  Y  I  A  I  A
GGAGACCACAACGGTTTCCCTCTAGAAATAATTTTGTTTAACTTTAAGAAGGAGATATACCATGTCAAGTGCAACAACACCAGAAACAACAGCAGTTAAATTAGGTTACATCGCTATCGC
CCTCTGGTGTTGCCAAAGGGAGATCTTTATTAAAACAAATTGAAATTCTTCCTCTATATGGTACAGTTCACGTTGTTGTGGTCTTTGTTGTCGTCAATTTAATCCAATGTAGCGATAGCG
       130       140       150       160       170       180       190       200       210       220       230       240

                              30                            40                            50
 E  S  A  P  L  I  I  A  R  E  K  G  F  F  A  R  H  G  M  T  D  V  D  V  S  K  Q  A  S  W  G  S  A  R  D  N  I  E  I  G
CGAAAGCGCACCACTTATCATCGCGCGGGAGAAAGGCTTCTTCGCACGTCATGGTATGACCGATGTAGACGTCTCTAAGCAGGCCTCCTGGGGTAGCGCCCGCGATAACATTGAAATCGG
GCTTTCGCGTGGTGAATAGTAGCGCGCCCTCTTTCCGAAGAAGCGTGCAGTACCATACTGGCTACATCTGCAGAGATTCGTCCGGAGGACCCCATCGCGGGCGCTATTGTAACTTTAGCC
       250       260       270       280       290       300       310       320       330       340       350       360

                              70                            80                            90
 S  S  N  G  G  I  D  G  G  Q  W  Q  M  P  M  P  Q  L  I  S  E  G  I  I  T  K  G  N  R  K  I  P  M  L  S  L  A  Q  L  S
CTCGAGTAACGGTGGGATCGACGGGGGTCAGTGGCAGATGCCTATGCCGCAGTTAATTAGCGAAGGTATTATCACAAAGGGTAATCGTAAAATCCCAATGCTTAGTTTGGCCCAGCTCAG
GAGCTCATTGCCACCCTAGCTGCCCCCAGTCACCGTCTACGGATACGGCGTCAATTAATCGCTTCCATAATAGTGTTTCCCATTAGCATTTTAGGGTTACGAATCAAACCGGGTCGAGTC
       370       380       390       400       410       420       430       440       450       460       470       480

                             110                           120                           130
 T  Q  G  N  G  I  A  I  S  T  Q  H  A  G  K  G  F  G  L  D  V  S  G  A  A  E  Y  V  R  D  M  K  A  D  G  K  P  F  K  A
TACACAGGGTAACGGTATCGCCATCTCGACACAGCATGCAGGTAAGGGTTTTGGCCTGGACGTCTCCGGTGCCGCCGAATACGTACGCGACATGAAGGCAGACGGTAAACCATTTAAGGC
ATGTGTCCCATTGCCATAGCGGTAGAGCTGTGTCGTACGTCCATTCCCAAAACCGGACCTGCAGAGGCCACGGCGGCTTATGCATGCGCTGTACTTCCGTCTGCCATTTGGTAAATTCCG
       490       500       510       520       530       540       550       560       570       580       590       600

                             150                           160                           170
 A  Y  T  F  P  R  V  N  Q  D  F  W  I  R  Y  W  L  A  A  G  G  I  D  P  N  K  D  I  D  L  I  A  V  P  A  A  Q  T  V  A
AGCATACACATTCCCACGTGTCAATCAGGACTTTTGGATTCGGTACTGGCTCGCAGCAGGTGGGATCGACCCAAACAAGGACATCGACTTAATTGCAGTACCGGCCGCACAAACCGTAGC
TCGTATGTGTAAGGGTGCACAGTTAGTCCTGAAAACCTAAGCCATGACCGAGCGTCGTCCACCCTAGCTGGGTTTGTTCCTGTAGCTGAATTAACGTCATGGCCGGCGTGTTTGGCATCG
       610       620       630       640       650       660       670       680       690       700       710       720

                             190                           200                           210
 S  M  R  T  G  S  M  D  G  F  S  T  G  D  P  W  P  S  R  I  L  R  D  R  R  K  Y  G  F  L  A  V  L  T  A  Q  I  W  P  A
CTCCATGCGGACTGGCTCAATGGACGGGTTTAGTACAGGTGACCCTTGGCCATCCCGCATCCTGCGTGACCGGCGTAAGTACGGTTTCCTCGCCGTCCTCACGGCTCAGATTTGGCCTGC
GAGGTACGCCTGACCGAGTTACCTGCCCAAATCATGTCCACTGGGAACCGGTAGGGCGTAGGACGCACTGGCCGCATTCATGCCAAAGGAGCGGCAGGAGTGCCGAGTCTAAACCGGACG
       730       740       750       760       770       780       790       800       810       820       830       840

                             230                           240                           250
 H  P  E  E  Y  F  A  M  R  E  D  W  V  R  K  H  P  K  A  A  K  A  I  L  K  G  I  M  E  A  Q  M  W  A  D  D  P  K  N  R
TCATCCTGAAGAGTATTTTGCAATGCGTGAGGATTGGGTTCGTAAACACCCTAAGGCAGCGAAGGCCATCCTCAAAGGTATTATGGAAGCACAAATGTGGGCAGACGATCCAAAGAACCG
AGTAGGACTTCTCATAAAACGTTACGCACTCCTAACCCAAGCATTTGTGGGATTCCGTCGCTTCCGGTAGGAGTTTCCATAATACCTTCGTGTTTACACCCGTCTGCTAGGTTTCTTGGC
       850       860       870       880       890       900       910       920       930       940       950       960
```

```
                    270                           280                           290
A  E  M  A  A  I  L  A  Q  R  K  Y  F  N  V  P  S  D  L  L  I  G  P  Y  V  G  E  Y  I  L  G  A  D  R  K  T  V  K  D  E
TGCGGAAATGGCCGCCATCTTAGCCCAGCGTAAATATTTCAACGTCCCTAGCGACTTATTGATCGGTCCTTATGTCGGGGAATACATTTTGGGTGCGGACCGCAAGACAGTAAAGGACGA
ACGCCTTTACCGGCGGTAGAATCGGGTCGCATTTATAAAGTTGCAGGGATCGCTGAATAACTAGCCAGGAATACAGCCCCTTATGTAAAACCCACGCCTGGCGTTCTGTCATTTCCTGCT
      970       980       990      1000      1010      1020      1030      1040      1050      1060      1070      1080

                    310                           320                           330
K  L  A  I  R  Y  W  K  D  A  R  G  N  V  S  Y  P  Y  K  S  H  D  L  W  F  L  T  E  S  V  R  W  G  F  L  P  Q  G  A  L
GAAGCTCGCAATTCGCTATTGGAAAGATGCACGGGGTAATGTTTCTTACCCATACAAATCCCATGACTTATGGTTTCTTACAGAATCCGTCCGTTGGGGCTTCCTGCCACAAGGCGCGTT
CTTCGAGCGTTAAGCGATAACCTTTCTACGTGCCCCATTACAAAGAATGGGTATGTTTAGGGTACTGAATACCAAAGAATGTCTTAGGCAGGCAACCCCGAAGGACGGTGTTCCGCGCAA
     1090      1100      1110      1120      1130      1140      1150      1160      1170      1180      1190      1200

                    350                           360                           370
G  E  A  D  R  I  I  N  A  V  S  G  E  K  Y  W  R  E  A  A  Q  E  L  G  I  A  S  A  D  I  P  P  S  T  S  R  G  I  E  K
AGGTGAAGCCGATCGTATCATCAATGCCGTCTCAGGCGAAAAATACTGGCGGGAGGCAGCTCAAGAACTGGGTATCGCAAGTGCAGACATTCCACCGTCAACGTCACGTGGCATTGAGAA
TCCACTTCGGCTAGCATAGTAGTTACGGCAGAGTCCGCTTTTTATGACCGCCCTCCGTCGAGTTCTTGACCCATAGCGTTCACGTCTGTAAGGTGGCAGTTGCAGTGCACCGTAACTCTT
     1210      1220      1230      1240      1250      1260      1270      1280      1290      1300      1310      1320

                    390                           400                           410
F  F  D  G  A  E  F  N  P  E  K  P  K  A  Y  L  D  S  L  K  I  K  N  L  K  A  G  G  S  H  H  H  H  H  H  *  *
ATTCTTCGACGGCGCCGAGTTCAACCCGGAAAAACCAAAAGCATATTTAGACTCCTTAAAAATTAAGAATTTAAAAGCAGGTGGTTCACATCATCATCATCATCATTAATGAAAGGGCGA
TAAGAAGCTGCCGCGGCTCAAGTTGGGCCTTTTTGGTTTTCGTATAAATCTGAGGAATTTTTAATTCTTAAATTTTCGTCCACCAAGTGTAGTAGTAGTAGTAGTAATTACTTTCCCGCT
     1330      1340      1350      1360      1370      1380      1390      1400      1410      1420      1430      1440


TATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAA
ATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTT
     1450      1460      1470      1480      1490      1500      1510      1520      1530      1540      1550      1560


CGGGTCTTGAGGGGTTTTTTGCTGAAAGGAGGAACTATATCCGGAGCGACTCCCACGGCACGTTGGCAAGCTCGGAATTCGGCGTAATC
GCCCAGAACTCCCCAAAAAACGACTTTCCTCCTTGATATAGGCCTCGCTGAGGGTGCCGTGCAACCGTTCGAGCCTTAAGCCGCATTAG
     1570      1580      1590      1600      1610      1620      1630      1640
```

FIG. 18 (Continued)

FIG. 19 - Exemplary Expression Construct for mhFeBP1

SEQ ID NO: 101

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                   10                            20
                                                        M  A  N  E  V  N  V  Y  S  Y  R  Q  P  Y  L  I  E  P  M  L  K  N  F  E
GGTTTCCCTCTAGAAATAATTTTGTTTAACTTTAAGAAGGAGATATACCATGGCAAATGAAGTAAATGTATATAGTTATCGTCAACCGTACTTAATCGAGCCAATGCTCAAGAACTTCGA
CCAAAGGGAGATCTTTATTAAAACAAATTGAAATTCTTCCTCTATATGGTACCGTTTACTTCATTTACATATATCAATAGCAGTTGGCATGAATTAGCTCGGTTACGAGTTCTTGAAGCT
       130       140       150       160       170       180       190       200       210       220       230       240

            30                            40                            50                            60
 K  D  T  G  I  K  V  N  I  I  F  A  D  K  G  L  V  D  R  V  K  Q  E  G  E  L  S  P  A  D  V  L  L  T  V  D  I  S  R  V
GAAAGACACCGGTATCAAGGTCAACATTATCTTCGCAGACAAGGGCCTCGTCGACCGCGTCAAACAAGAGGGTGAATTGTCCCCAGCCGATGTATTATTAACCGTCGACATCAGTCGTGT
CTTTCTGTGGCCATAGTTCCAGTTGTAATAGAAGCGTCTGTTCCCGGAGCAGCTGGCGCAGTTTGTTCTCCCACTTAACAGGGGTCGGCTACATAATAATTGGCAGCTGTAGTCAGCACA
       250       260       270       280       290       300       310       320       330       340       350       360

            70                            80                            90                           100
 M  E  I  V  N  A  D  L  A  Q  K  I  D  S  K  V  L  E  K  N  I  P  A  Q  F  R  D  S  N  D  Q  W  F  G  L  T  T  R  A  R
CATGGAAATTGTAAACGCAGATCTCGCACAAAAGATCGACTCGAAGGTTCTGGAAAAGAACATCCCGGCGCAGTTTCGCGACAGTAACGATCAATGGTTCGGCTTAACGACACGTGCTCG
GTACCTTTAACATTTGCGTCTAGAGCGTGTTTTCTAGCTGAGCTTCCAAGACCTTTTCTTGTAGGGCCGCGTCAAAGCGCTGTCATTGCTAGTTACCAAGCCGAATTGCTGTGCACGAGC
       370       380       390       400       410       420       430       440       450       460       470       480

           110                           120                           130                           140
 V  I  Y  T  S  K  D  R  V  G  K  L  P  A  G  F  D  Y  L  D  L  A  K  P  E  Y  K  G  K  V  A  V  R  S  G  K  N  S  Y  N
TGTAATCTATACATCTAAAGACCGCGTCGGCAAACTCCCAGCGGGCTTCGACTATCTCGACTTGGCAAAGCCAGAATACAAGGGCAAAGTAGCGGTCCGTTCAGGGAAGAACTCCTATAA
ACATTAGATATGTAGATTTCTGGCGCAGCCGTTTGAGGGTCGCCCGAAGCTGATAGAGCTGAACCGTTTCGGTCTTATGTTCCCGTTTCATCGCCAGGCAAGTCCCTTCTTGAGGATATT
       490       500       510       520       530       540       550       560       570       580       590       600

           150                           160                           170                           180
 V  S  L  F  A  A  M  I  E  H  Y  G  I  E  K  T  K  A  F  L  E  G  L  K  A  N  L  A  R  K  P  Q  G  G  D  R  D  Q  V  K
CGTCAGTCTCTTCGCGGCCATGATCGAACATTACGGCATTGAAAAAACAAAAGCGTTTCTGGAAGGCCTCAAGGCGAACCTCGCACGCAAGCCACAGGGTGGTGACCGGGACCAGGTGAA
GCAGTCAGAGAAGCGCCGGTACTAGCTTGTAATGCCGTAACTTTTTTGTTTTCGCAAAGACCTTCCGGAGTTCCGCTTGGAGCGTGCGTTCGGTGTCCCACCACTGGCCCTGGTCCACTT
       610       620       630       640       650       660       670       680       690       700       710       720

           190                           200                           210                           220
 A  I  K  E  G  I  A  D  Y  S  I  G  N  S  Y  Y  Y  G  K  M  L  D  D  E  K  Q  K  S  W  A  E  A  A  I  I  N  F  P  S  G
AGCAATCAAGGAGGGCATCGCAGATTACTCTATCGGGAACTCATACTATTATGGCAAGATGCTTGACGATGAAAAGCAGAAAAGCTGGGCTGAGGCCGCGATCATCAATTTTCCATCAGG
TCGTTAGTTCCTCCCGTAGCGTCTAATGAGATAGCCCTTGAGTATGATAATACCGTTCTACGAACTGCTACTTTTCGTCTTTTCGACCCGACTCCGGCGCTAGTAGTTAAAAGGTAGTCC
       730       740       750       760       770       780       790       800       810       820       830       840

           230                           240                           250                           260
 E  H  G  T  H  K  N  I  S  G  V  V  I  A  K  H  S  P  N  K  A  N  A  V  K  L  I  E  Y  L  S  G  E  K  A  Q  G  L  Y  A
TGAACACGGTACCCACAAGAATATTTCAGGTGTAGTCATCGCCAAGCACTCTCCAAACAAAGCAAACGCCGTGAAGCTCATTGAGTACCTCTCTGGGGAGAAGGCACAAGGTCTGTATGC
ACTTGTGCCATGGGTGTTCTTATAAAGTCCACATCAGTAGCGGTTCGTGAGAGGTTTGTTTCGTTTGCGGCACTTCGAGTAACTCATGGAGAGACCCCTCTTCCGTGTTCCAGACATACG
       850       860       870       880       890       900       910       920       930       940       950       960
```

```
                270                                     280                                     290                                     300
 E   L   N   H   E   Y   P   V   K   E   G   I   E   P   S   A   I   V   K   G   W   G   T   F   K   S   D   T   I   K   L   E   D   I   A   K   N   Y   E   A
GGAACTCAACCACGAATACCCAGTCAAAGAGGGCATCGAGCCGTCGGCAATCGTAAAGGGCTGGGGTACATTTAAATCGGATACAATCAAGTTGGAAGATATTGCGAAGAACTACGAGGC
CCTTGAGTTGGTGCTTATGGGTCAGTTTCTCCCGTAGCTCGGCAGCCGTTAGCATTTCCCGACCCCATGTAAATTTAGCCTATGTTAGTTCAACCTTCTATAACGCTTCTTGATGCTCCG
        970       980       990      1000      1010      1020      1030      1040      1050      1060      1070      1080

                310                                     320
 A   L   K   L   V   D   E   V   K   F   D   D   F   G   G   S   H   H   H   H   H   H   *   *
GGCATTGAAATTAGTCGACGAGGTAAAATTCGACGACTTTGGGGGTTCTCATCATCATCATCATCATTAATGAAAGGGCGATATCCAGCACACTGGCGGCCGTTACTAGTGGATCCGGCT
CCGTAACTTTAATCAGCTGCTCCATTTTAAGCTGCTGAAACCCCCAAGAGTAGTAGTAGTAGTAGTAATTACTTTCCCGCTATAGGTCGTGTGACCGCCGGCAATGATCACCTAGGCCGA
       1090      1100      1110      1120      1130      1140      1150      1160      1170      1180      1190      1200

GCTAACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATA
CGATTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATAT
       1210      1220      1230      1240      1250      1260      1270      1280      1290      1300      1310      1320

TCCGGAGCGACTCCCACGGCACGTTGGCAAGCTCG
AGGCCTCGCTGAGGGTGCCGTGCAACCGTTCGAGC
       1330      1340      1350
```

FIG. 19 (Continued)

FIG. 20 - Exemplary Expression Construct for exiFeBP2

SEQ ID NO: 102

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                     10                            20
                                                    M  N  V  V  N  V  Y  S  S  R  H  Y  D  V  D  Q  Q  L  Y  K  Q  F  E  E
GGTTTCCCTCTAGAAATAATTTTGTTTAACTTTAAGAAGGAGATATACCATGAACGTAGTAAATGTGTATTCAAGTCGTCATTATGACGTGGACCAGCAGTTGTACAAACAGTTCGAGGA
CCAAAGGGAGATCTTTATTAAAACAAATTGAAATTCTTCCTCTATATGGTACTTGCATCATTTACACATAAGTTCAGCAGTAATACTGCACCTGGTCGTCAACATGTTTGTCAAGCTCCT
       130       140       150       160       170       180       190       200       210       220       230       240

             30                            40                            50                            60
 E  T  G  I  K  V  N  V  V  E  G  K  S  D  E  L  L  E  R  L  N  T  E  G  E  N  T  E  A  D  L  F  I  T  A  D  A  G  N  L
GGAAACAGGGATCAAGGTTAACGTCGTAGAGGGCAAATCAGATGAACTGCTCGAACGCCTTAACACCGAGGGCGAGAACACTGAGGCAGATCTCTTCATTACAGCAGATGCGGGGAATCT
CCTTTGTCCCTAGTTCCAATTGCAGCATCTCCCGTTTAGTCTACTTGACGAGCTTGCGGAATTGTGGCTCCCGCTCTTGTGACTCCGTCTAGAGAAGTAATGTCGTCTACGCCCCTTAGA
       250       260       270       280       290       300       310       320       330       340       350       360

             70                            80                            90                           100
 Y  Q  A  K  E  A  G  H  L  Q  A  V  D  S  D  E  L  E  S  N  I  P  E  K  Y  R  D  T  D  N  E  W  F  G  L  T  K  R  A  R
CTATCAAGCTAAAGAAGCTGGTCACTTACAGGCAGTAGATTCCGATGAATTAGAATCCAATATTCCAGAAAAATACCGCGACACTGACAACGAATGGTTCGGTCTTACCAAACGTGCGCG
GATAGTTCGATTTCTTCGACCAGTGAATGTCCGTCATCTAAGGCTACTTAATCTTAGGTTATAAGGTCTTTTTATGGCGCTGTGACTGTTGCTTACCAAGCCAGAATGGTTTGCACGCGC
       370       380       390       400       410       420       430       440       450       460       470       480

            110                           120                           130                           140
 V  I  V  Y  S  K  D  R  V  K  P  E  D  L  S  T  Y  E  A  L  T  E  E  Q  W  N  G  K  V  L  V  R  P  S  E  N  M  Y  N  I
TGTCATCGTCTATTCGAAAGACCGCGTGAAACCGGAAGATTTATCGACCTATGAGGCCCTGACAGAGGAGCAGTGGAACGGGAAAGTATTAGTCCGTCCGTCGGAAAACATGTATAACAT
ACAGTAGCAGATAAGCTTTCTGGCGCACTTTGGCCTTCTAAATAGCTGGATACTCCGGGACTGTCTCCTCGTCACCTTGCCCTTTCATAATCAGGCAGGCAGCCTTTTGTACATATTGTA
       490       500       510       520       530       540       550       560       570       580       590       600

            150                           160                           170                           180
 S  L  L  A  S  F  I  E  V  N  G  V  D  E  A  K  E  W  A  K  G  L  V  N  N  M  A  R  D  P  Q  G  N  D  R  D  Q  A  K  A
CAGTCTCCTGGCATCATTCATCGAGGTCAATGGCGTCGACGAAGCGAAAGAATGGGCAAAGGGTTTGGTCAACAATATGGCCCGTGATCCGCAGGGTAACGATCGGGATCAGGCAAAGGC
GTCAGAGGACCGTAGTAAGTAGCTCCAGTTACCGCAGCTGCTTCGCTTTCTTACCCGTTTCCCAAACCAGTTGTTATACCGGGCACTAGGCGTCCCATTGCTAGCCCTAGTCCGTTTCCG
       610       620       630       640       650       660       670       680       690       700       710       720

            190                           200                           210                           220
 V  V  A  G  E  G  D  V  A  I  M  N  T  Y  Y  M  G  L  M  L  N  S  E  D  E  E  E  K  K  V  A  E  Q  L  G  V  F  F  P  N
CGTAGTAGCAGGTGAGGGCGATGTAGCCATCATGAATACATACTACATGGGGTTGATGTTGAACTCAGAAGACGAAGAAGAAAAAAAAGTCGCCGAGCAGTTAGGCGTATTCTTTCCAAA
GCATCATCGTCCACTCCCGCTACATCGGTAGTACTTATGTATGATGTACCCCAACTACAACTTGAGTCTTCTGCTTCTTCTTTTTTTTCAGCGGCTCGTCAATCCGCATAAGAAAGGTTT
       730       740       750       760       770       780       790       800       810       820       830       840

            230                           240                           250                           260
 Q  D  T  T  G  T  H  V  N  I  S  G  I  A  M  T  K  A  S  K  N  T  E  N  A  Q  K  L  M  E  F  M  S  E  P  S  A  Q  E  K
TCAGGACACAACGGGGACTCATGTAAACATTTCCGGGATTGCCATGACGAAAGCCTCCAAGAACACGGAGAATGCACAGAAATTAATGGAGTTTATGTCGGAGCCATCAGCACAGGAAAA
AGTCCTGTGTTGCCCCTGAGTACATTTGTAAAGGCCCTAACGGTACTGCTTTCGGAGGTTCTTGTGCCTCTTACGTGTCTTTAATTACCTCAAATACAGCCTCGGTAGTCGTGTCCTTTT
       850       860       870       880       890       900       910       920       930       940       950       960
```

```
                   270                                     280                                     290                                     300
  F   A   S   V   N   Y   E   Y   P   V   N   E   S   V   E   P   N   E   L   L   Q   S   W   G   E   F   K   E   Q   D   I   N   L   S   A   L   G   E   N   Q
GTTCGCCTCTGTAAATTACGAATACCCAGTCAACGAATCGGTGGAACCGAACGAGTTACTTCAGTCGTGGGGCGAATTTAAAGAGCAGGATATTAACCTCAGCGCGCTCGGCGAAAACCA
CAAGCGGAGACATTTAATGCTTATGGGTCAGTTGCTTAGCCACCTTGGCTTGCTCAATGAAGTCAGCACCCCGCTTAAATTTCTCGTCCTATAATTGGAGTCGCGCGAGCCGCTTTTGGT
         970       980       990      1000      1010      1020      1030      1040      1050      1060      1070      1080

                   310                                     320
  Q   E   A   I   R   I   F   N   E   V   G   W   K   G   G   S   H   H   H   H   H   *   *
ACAGGAGGCAATCCGGATCTTCAACGAGGTGGGGTGGAAAGGTGGTTCACATCATCATCATCATCATTAATGAAAGGGCGATATCCAGCACACTGGCGGCCGTTACTAGTGGATCCGGCT
TGTCCTCCGTTAGGCCTAGAAGTTGCTCCACCCCACCTTTCCACCAAGTGTAGTAGTAGTAGTAGTAATTACTTTCCCGCTATAGGTCGTGTGACCGCCGGCAATGATCACCTAGGCCGA
        1090      1100      1110      1120      1130      1140      1150      1160      1170      1180      1190      1200


GCTAACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATA
CGATTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATAT
        1210      1220      1230      1240      1250      1260      1270      1280      1290      1300      1310      1320


TCCGGAGCGACTCCCACGGCACGTTGGCAAGCTCG
AGGCCTCGCTGAGGGTGCCGTGCAACCGTTCGAGC
        1330      1340      1350
```

FIG. 20 (Continued)

FIG. 21 – Exemplary Expression Construct for teFeBP3

SEQ ID NO: 103

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                              10                            20
                                                    M  V  I  N  V  Y  S  A  R  H  Y  D  T  D  K  A  L  Y  N  T  F  T  Q  Q
GGTTTCCCTCTAGAAATAATTTTGTTTAACTTTAAGAAGGAGATATACCATGGTAATTAATGTATATAGTGCACGTCATTACGACACTGACAAGGCTCTCTATAATACCTTCACCCAACA
CCAAAGGGAGATCTTTATTAAAACAAATTGAAATTCTTCCTCTATATGGTACCATTAATTACATATATCACGTGCAGTAATGCTGTGACTGTTCCGAGAGATATTATGGAAGTGGGTTGT
       130       140       150       160       170       180       190       200       210       220       230       240

              30                            40                            50                            60
 T  G  I  R  V  N  I  I  E  A  E  A  D  A  L  I  E  R  I  R  S  E  G  S  R  T  P  A  D  V  L  I  T  V  D  A  G  R  L  W
AACCGGGATTCGTGTAAACATCATTGAGGCTGAGGCAGATGCCCTCATTGAACGTATTCGTTCTGAAGGTTCGCGCACCCCAGCCGATGTACTCATTACAGTAGACGCGGGTCGCTTATG
TTGGCCCTAAGCACATTTGTAGTAACTCCGACTCCGTCTACGGGAGTAACTTGCATAAGCAAGACTTCCAAGCGCGTGGGGTCGGCTACATGAGTAATGTCATCTGCGCCCAGCGAATAC
       250       260       270       280       290       300       310       320       330       340       350       360

              70                            80                            90                           100
 R  A  Q  E  A  G  I  L  Q  P  I  Q  S  R  V  L  N  S  V  V  P  A  N  L  R  E  P  Q  G  H  W  F  G  L  S  R  R  V  R  V
GCGTGCGCAAGAAGCTGGCATCTTACAGCCGATTCAATCGCGTGTTTTAAACAGTGTAGTACCAGCCAACCTCCGGGAACCACAGGGTCACTGGTTCGGTCTCTCCCGTCGTGTTCGCGT
CGCACGCGTTCTTCGACCGTAGAATGTCGGCTAAGTTAGCGCACAAAATTTGTCACATCATGGTCGGTTGGAGGCCCTTGGTGTCCCAGTGACCAAGCCAGAGAGGGCAGCACAAGCGCA
       370       380       390       400       410       420       430       440       450       460       470       480

             110                           120                           130                           140
 L  I  Y  N  K  S  R  V  N  P  S  Q  L  S  T  Y  E  D  L  A  N  P  K  W  R  R  Q  I  L  T  R  S  S  S  N  I  Y  N  Q  S
TCTGATTTATAACAAGTCCCGTGTTAATCCATCTCAGCTTTCCACATACGAAGATTTAGCTAATCCGAAGTGGCGCCGTCAGATCCTGACACGTTCTTCAAGCAACATTTACAACCAATC
AGACTAAATATTGTTCAGGGCACAATTAGGTAGAGTCGAAAGGTGTATGCTTCTAAATCGATTAGGCTTCACCGCGGCAGTCTAGGACTGTGCAAGAAGTTCGTTGTAAATGTTGGTTAG
       490       500       510       520       530       540       550       560       570       580       590       600

             150                           160                           170                           180
 L  T  G  S  L  L  A  I  H  G  A  Q  K  T  E  Q  W  A  R  G  L  V  Q  N  F  A  R  P  P  E  G  N  D  T  A  Q  I  R  A  S
GTTGACAGGTTCCTTACTCGCCATTCACGGGGCACAGAAGACCGAACAATGGGCACGTGGCTTAGTACAGAACTTCGCACGTCCACCGGAGGGGAATGACACAGCTCAAATTCGTGCAAG
CAACTGTCCAAGGAATGAGCGGTAAGTGCCCCGTGTCTTCTGGCTTGTTACCCGTGCACCGAATCATGTCTTGAAGCGTGCAGGTGGCCTCCCCTTACTGTGTCGAGTTTAAGCACGTTC
       610       620       630       640       650       660       670       680       690       700       710       720

             190                           200                           210                           220
 A  E  G  V  G  S  V  A  I  A  N  H  Y  Y  L  A  R  L  I  A  S  D  K  E  Q  D  R  A  V  A  A  K  V  G  L  F  F  P  N  Q
TGCAGAGGGCGTTGGCTCAGTAGCGATCGCCAATCACTATTACCTCGCCCGTTTAATTGCCAGTGACAAGGAGCAAGACCGTGCGGTGGCCGCAAAGGTGGGCCTCTTTTTCCCGAACCA
ACGTCTCCCGCAACCGAGTCATCGCTAGCGGTTAGTGATAATGGAGCGGGCAAATTAACGGTCACTGTTCCTCGTTCTGGCACGCCACCGGCGTTTCCACCCGGAGAAAAAGGGCTTGGT
       730       740       750       760       770       780       790       800       810       820       830       840

             230                           240                           250                           260
 R  D  R  G  A  H  V  N  I  S  G  A  G  V  V  A  G  A  P  N  R  Q  G  A  I  R  F  L  E  Y  L  V  S  P  K  A  Q  E  M  F
ACGTGACCGCGGTGCACATGTCAATATCAGTGGGGCAGGTGTAGTCGCCGGCGCTCCTAACCGTCAAGGCGCAATTCGGTTCTTAGAGTACCTGGTCTCCCCAAAGGCCCAGGAAATGTT
TGCACTGGCGCCACGTGTACAGTTATAGTCACCCCGTCCACATCAGCGGCCGCGAGGATTGGCAGTTCCGCGTTAAGCCAAGAATCTCATGGACCAGAGGGGTTTCCGGGTCCTTTACAA
       850       860       870       880       890       900       910       920       930       940       950       960
```

```
            270                                     280                                     290                                     300
 A   M   A   N   F   E   Y   P   V   R   A   G   V   P   V   H   P   I   V   K   Q   F   G   N   F   R   G   Q   N   V   N   A   A   V   F   G   R   N   N   A
TGCTATGGCTAACTTTGAGTACCCGGTACGCGCAGGCGTCCCAGTCCACCCTATCGTCAAGCAATTCGGCAACTTTCGTGGTCAAAATGTCAACGCAGCAGTATTCGGGCGCAACAACGC
ACGATACCGATTGAAACTCATGGGCCATGCGCGTCCGCAGGGTCAGGTGGGATAGCAGTTCGTTAAGCCGTTGAAAGCACCAGTTTTACAGTTGCGTCGTCATAAGCCCGCGTTGTTGCG
        970         980         990        1000        1010        1020        1030        1040        1050        1060        1070        1080

            310                                     320
 E   A   L   R   I   M   D   R   A   G   W   R   G   G   S   H   H   H   H   H   H   *   *
AGAAGCACTTCGTATCATGGACCGGGCCGGTTGGCGTGGCGGTAGTCATCATCATCATCATCATTAATGAAAGGGCGATATCCAGCACACTGGCGGCCGTTACTAGTGGATCCGGCTGCT
TCTTCGTGAAGCATAGTACCTGGCCCGGCCAACCGCACCGCCATCAGTAGTAGTAGTAGTAGTAATTACTTTCCCGCTATAGGTCGTGTGACCGCCGGCAATGATCACCTAGGCCGACGA
       1090        1100        1110        1120        1130        1140        1150        1160        1170        1180        1190        1200

AACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCC
TTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGG
       1210        1220        1230        1240        1250        1260        1270        1280        1290        1300        1310        1320

GGAGCGACTCCCACGGCACGTTGGCAAGCTCG
CCTCGCTGAGGGTGCCGTGCAACCGTTCGAGC
       1330        1340        1350
```

FIG. 21 (Continued)

FIG. 22 - Exemplary Expression Construct for cnFeBP4

SEQ ID NO: 104

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                          10                            20
                                                  M  K  L  V  V  Y  S  G  R  A  E  R  L  I  K  P  V  L  D  E  F  Q  A  K
GGTTTCCCTCTAGAAATAATTTTGTTTAACTTTAAGAAGGAGATATACCATGAAATTAGTAGTATATTCAGGTCGTGCAGAACGTCTCATTAAACCAGTACTCGATGAATTTCAAGCAAA
CCAAAGGGAGATCTTTATTAAAACAAATTGAAATTCTTCCTCTATATGGTACTTTAATCATCATATAAGTCCAGCACGTCTTGCAGAGTAATTTGGTCATGAGCTACTTAAAGTTCGTTT
       130       140       150       160       170       180       190       200       210       220       230       240

          30                            40                            50                            60
S  G  I  Q  I  E  L  L  S  S  G  T  T  E  L  V  N  R  L  Q  A  E  G  D  H  T  P  A  D  V  F  L  T  N  D  A  G  S  L  E
GTCAGGCATTCAGATTGAACTGCTTTCCAGTGGGACGACCGAATTAGTAAACCGCCTCCAGGCAGAAGGCGATCATACTCCAGCCGATGTATTCTTAACAAACGACGCCGGTAGTCTCGA
CAGTCCGTAAGTCTAACTTGACGAAAGGTCACCCTGCTGGCTTAATCATTTGGCGGAGGTCCGTCTTCCGCTAGTATGAGGTCGGCTACATAAGAATTGTTTGCTGCGGCCATCAGAGCT
       250       260       270       280       290       300       310       320       330       340       350       360

          70                            80                            90                           100
H  A  R  E  L  K  L  L  R  P  M  N  M  R  E  V  E  R  A  I  P  S  Q  F  R  A  A  D  N  S  W  I  G  L  S  G  R  F  W  I
GCACGCGCGCGAATTGAAACTCCTTCGTCCGATGAACATGCGGGAAGTAGAGCGTGCGATCCCATCCCAGTTCCGGGCCGCGGACAATTCATGGATCGGGCTCTCTGGCCGTTTTTGGAT
CGTGCGCGCGCTTAACTTTGAGGAAGCAGGCTACTTGTACGCCCTTCATCTCGCACGCTAGGGTAGGGTCAAGGCCCGGCGCCTGTTAAGTACCTAGCCCGAGAGACCGGCAAAAACCTA
       370       380       390       400       410       420       430       440       450       460       470       480

         110                           120                           130                           140
V  V  Y  N  T  N  L  V  K  P  D  Q  I  K  S  L  F  D  L  T  Q  P  Q  W  K  D  K  I  A  V  P  N  S  G  S  E  Y  L  Q  A
CGTTGTCTACAACACAAACCTTGTAAAGCCAGATCAGATTAAATCGCTCTTCGACCTTACGCAGCCACAGTGGAAAGACAAGATCGCCGTCCCTAATTCAGGGTCAGAATACTTGCAGGC
GCAACAGATGTTGTGTTTGGAACATTTCGGTCTAGTCTAATTTAGCGAGAAGCTGGAATGCGTCGGTGTCACCTTTCTGTTCTAGCGGCAGGGATTAAGTCCCAGTCTTATGAACGTCCG
       490       500       510       520       530       540       550       560       570       580       590       600

         150                           160                           170                           180
G  V  S  V  I  K  A  T  F  G  D  E  R  T  K  Q  F  L  Q  G  L  K  A  N  A  G  T  Q  V  Y  Q  K  S  S  Q  I  V  E  A  V
TGGTGTCTCAGTGATTAAGGCTACTTTCGGCGACGAGCGTACCAAGCAGTTCCTCCAAGGGCTCAAGGCTAACGCAGGTACGCAAGTATATCAAAAATCAAGCCAGATTGTTGAAGCCGT
ACCACAGAGTCACTAATTCCGATGAAAGCCGCTGCTCGCATGGTTCGTCAAGGAGGTTCCCGAGTTCCGATTGCGTCCATGCGTTCATATAGTTTTTAGTTCGGTCTAACAACTTCGGCA
       610       620       630       640       650       660       670       680       690       700       710       720

         190                           200                           210                           220
A  K  G  Q  V  A  A  G  I  V  N  H  Y  Y  I  Y  R  H  L  A  T  Q  P  T  A  P  I  A  A  V  M  T  D  Q  Q  E  G  G  M  G
TGCTAAGGGTCAAGTTGCCGCTGGTATCGTAAACCACTACTATATCTACCGTCATCTCGCTACCCAACCTACTGCACCAATTGCAGCGGTCATGACAGACCAGCAAGAAGGTGGGATGGG
ACGATTCCCAGTTCAACGGCGACCATAGCATTTGGTGATGATATAGATGGCAGTAGAGCGATGGGTTGGATGACGTGGTTAACGTCGCCAGTACTGTCTGGTCGTTCTTCCACCCTACCC
       730       740       750       760       770       780       790       800       810       820       830       840

         230                           240                           250                           260
A  I  M  N  V  T  G  I  G  V  T  R  A  S  K  H  V  E  S  A  K  L  L  I  E  F  L  V  A  Q  A  G  Q  K  M  F  A  D  L  D
CGCAATTATGAATGTAACAGGTATCGGTGTAACCCGTGCAAGTAAACATGTAGAGAGCGCCAAATTACTGATTGAGTTTCTCGTGGCCCAGGCTGGCCAAAAGATGTTTGCCGATCTCGA
GCGTTAATACTTACATTGTCCATAGCCACATTGGGCACGTTCATTTGTACATCTCTCGCGGTTTAATGACTAACTCAAAGAGCACCGGGTCCGACCGGTTTTCTACAAACGGCTAGAGCT
       850       860       870       880       890       900       910       920       930       940       950       960
```

```
                270                                   280                                   290                                   300
 K   E   Y   P   L   H   P   D   V   K   A   D   P   T   L   I   D   R   R   T   F   R   A   A   Q   V   P   L   A   R   L   A   E   L   R   E   A   T   L   T
TAAAGAGTACCCGTTGCATCCAGACGTGAAAGCGGACCCAACTTTAATCGATCGCCGTACATTTCGTGCCGCTCAGGTGCCACTGGCCCGGTTAGCCGAATTGCGTGAGGCTACGCTCAC
ATTTCTCATGGGCAACGTAGGTCTGCACTTTCGCCTGGGTTGAAATTAGCTAGCGGCATGTAAAGCACGGCGAGTCCACGGTGACCGGGCCAATCGGCTTAACGCACTCCGATGCGAGTG
        970         980         990        1000        1010        1020        1030        1040        1050        1060        1070        1080

                310                                   320
 L   I   E   Q   V   G   L   R   G   G   S   H   H   H   H   H   H   *   *
ACTCATTGAGCAGGTCGGTTTACGTGGGGGTTCACATCATCATCATCATCATTAATGAAAGGGCGATATCCAGCACACTGGCGGCCGTTACTAGTGGATCCGGCTGCTAACAAAGCCCGA
TGAGTAACTCGTCCAGCCAAATGCACCCCCAAGTGTAGTAGTAGTAGTAGTAATTACTTTCCCGCTATAGGTCGTGTGACCGCCGGCAATGATCACCTAGGCCGACGATTGTTTCGGGCT
       1090        1100        1110        1120        1130        1140        1150        1160        1170        1180        1190        1200


AAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCC
TTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGG
       1210        1220        1230        1240        1250        1260        1270        1280        1290        1300        1310        1320


ACGGCACGTTGGCAAGCTCG
TGCCGTGCAACCGTTCGAGC
       1330        1340
```

FIG. 22 (Continued)

FIG. 23 - Exemplary Expression Construct for ttFeBP5

SEQ ID NO: 105

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                    10                            20
                                                           M  S  P  T  L  T  I  Y  S  G  R  G  Q  S  L  V  E  P  L  V  K  Q  F  E
GGTTTCCCTCTAGAAATAATTTTGTTTAACTTTAAGAAGGAGATATACCATGTCACCTACATTAACTATTTATTCAGGTCGTGGGCAGTCACTCGTAGAACCGTTAGTTAAGCAATTCGA
CCAAAGGGAGATCTTTATTAAAACAAATTGAAATTCTTCCTCTATATGGTACAGTGGATGTAATTGATAAATAAGTCCAGCACCCGTCAGTGAGCATCTTGGCAATCAATTCGTTAAGCT
       130       140       150       160       170       180       190       200       210       220       230       240

              30                            40                            50                            60
 A  E  T  G  I  R  V  Q  V  R  Y  S  T  D  A  Q  I  L  A  A  L  Q  E  E  G  S  R  S  P  A  D  L  F  W  A  N  T  A  G  A
AGCAGAGACAGGTATTCGTGTGCAAGTTCGGTACTCCACTGACGCACAGATTTTGGCCGCTTTGCAAGAGGAAGGGAGTCGTTCCCCAGCAGATCTGTTTTGGGCCAACACAGCCGGCGC
TCGTCTCTGTCCATAAGCACACGTTCAAGCCATGAGGTGACTGCGTGTCTAAAACCGGCGAAACGTTCTCCTTCCCTCAGCAAGGGGTCGTCTAGACAAAACCCGGTTGTGTCGGCCGCG
       250       260       270       280       290       300       310       320       330       340       350       360

              70                            80                            90                            100
 L  G  Q  A  S  A  K  G  L  L  R  P  L  G  E  T  L  L  E  K  P  I  A  F  V  P  A  S  R  T  W  V  P  V  T  V  R  L  R  V
GCTGGGCCAAGCCTCCGCCAAAGGCCTTTTACGTCCACTTGGCGAGACGTTGCTCGAGAAGCCAATTGCGTTCGTTCCAGCCTCACGGACCTGGGTCCCGGTCACTGTACGCCTCCGCGT
CGACCCGGTTCGGAGGCGGTTTCCGGAAAATGCAGGTGAACCGCTCTGCAACGAGCTCTTCGGTTAACGCAAGCAAGGTCGGAGTGCCTGGACCCAGGGCCAGTGACATGCGGAGGCGCA
       370       380       390       400       410       420       430       440       450       460       470       480

             110                           120                           130                           140
 L  A  Y  N  P  D  R  I  K  A  E  E  L  P  E  S  L  L  D  L  P  R  F  A  R  E  K  G  L  V  G  R  V  G  W  T  P  T  Y  S
CCTGGCATACAACCCAGATCGCATTAAGGCTGAAGAACTCCCAGAGTCACTGTTGGACTTACCTCGCTTCGCACGGGAAAAAGGGCTCGTAGGGCGTGTAGGGTGGACCCCAACATATTC
GGACCGTATGTTGGGTCTAGCGTAATTCCGACTTCTTGAGGGTCTCAGTGACAACCTGAATGGAGCGAAGCGTGCCCTTTTTCCCGAGCATCCCGCACATCCCACCTGGGGTTGTATAAG
       490       500       510       520       530       540       550       560       570       580       590       600

             150                           160                           170                           180
 S  F  Q  D  M  V  A  G  M  I  A  L  Y  G  E  E  K  T  R  E  W  L  L  A  M  K  A  L  A  P  K  A  Y  P  S  N  P  A  M  L
CAGTTTCCAGGACATGGTAGCTGGTATGATTGCCCTTTATGGTGAAGAAAAAACCCGGGAATGGCTCTTAGCGATGAAAGCCTTAGCACCAAAGGCGTACCCGTCCAATCCAGCGATGTT
GTCAAAGGTCCTGTACCATCGACCATACTAACGGGAAATACCACTTCTTTTTTGGGCCCTTACCGAGAATCGCTACTTTCGGAATCGTGGTTTCCGCATGGGCAGGTTAGGTCGCTACAA
       610       620       630       640       650       660       670       680       690       700       710       720

             190                           200                           210                           220
 D  A  I  R  A  G  E  V  D  L  G  S  T  N  H  Y  Y  V  V  R  F  R  R  A  G  Y  R  L  G  M  H  H  F  R  D  G  D  A  G  N
AGATGCAATCCGTGCCGGGGAAGTTGATTTAGGCAGTACTAATCACTACTACGTCGTCCGGTTCCGGCGCGCAGGGTACCGGCTCGGCATGCACCACTTTCGGGATGGTGACGCAGGCAA
TCTACGTTAGGCACGGCCCCTTCAACTAAATCCGTCATGATTAGTGATGATGCAGCAGGCCAAGGCCGCGCGTCCCATGGCCGAGCCGTACGTGGTGAAAGCCCTACCACTGCGTCCGTT
       730       740       750       760       770       780       790       800       810       820       830       840

             230                           240                           250                           260
 L  A  L  V  T  G  A  G  L  L  K  T  S  K  N  L  A  A  A  T  R  F  L  T  Y  L  L  S  P  Q  A  Q  Q  Y  F  V  G  N  I  G
TTTAGCACTCGTGACGGGCGCGGGTCTCTTGAAGACATCAAAAAATTTAGCCGCAGCGACGCGCTTCCTCACGTACTTACTGAGCCCTCAGGCCCAGCAATACTTTGTAGGCAATATTGG
AAATCGTGAGCACTGCCCGCGCCCAGAGAACTTCTGTAGTTTTTTAAATCGGCGTCGCTGCGCGAAGGAGTGCATGAATGACTCGGGAGTCCGGGTCGTTATGAAACATCCGTTATAACC
       850       860       870       880       890       900       910       920       930       940       950       960
```

```
                270                                280                                290                                300
 E   Y   P   L   V   K   G   V   A   L   D   P   N   L   L   P   L   E   E   A   L   A   K   S   P   K   L   D   L   E   K   L   P   L   D   R   A   L   R   L
TGAATACCCACTCGTAAAAGGCGTGGCCCTTGACCCAAATTTACTGCCGCTGGAGGAGGCCCTTGCAAAATCACCAAAATTAGACTTGGAAAAACTTCCATTGGATCGTGCATTACGCTT
ACTTATGGGTGAGCATTTTCCGCACCGGGAACTGGGTTTAAATGACGGCGACCTCCTCCGGGAACGTTTTAGTGGTTTTAATCTGAACCTTTTTGAAGGTAACCTAGCACGTAATGCGAA
        970       980       990      1000      1010      1020      1030      1040      1050      1060      1070      1080

                310                                320
 L   R   E   T   G   V   L   G   G   S   H   H   H   H   H   H   *   *
ATTACGTGAAACGGGGGTTTTAGGTGGTTCACATCATCATCATCATCATTAATGAAAGGGCGATATCCAGCACACTGGCGGCCGTTACTAGTGGATCCGGCTGCTAACAAAGCCCGAAAG
TAATGCACTTTGCCCCCAAAATCCACCAAGTGTAGTAGTAGTAGTAGTAATTACTTTCCCGCTATAGGTCGTGTGACCGCCGGCAATGATCACCTAGGCCGACGATTGTTTCGGGCTTTC
       1090      1100      1110      1120      1130      1140      1150      1160      1170      1180      1190      1200

GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1210      1220      1230      1240      1250      1260      1270      1280      1290      1300      1310      1320

GCACGTTGGCAAGCTCG
CGTGCAACCGTTCGAGC
       1330
```

FIG. 23 (Continued)

FIG. 24 - Exemplary Expression Construct for msFeBP6

SEQ ID NO: 106

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                           10                            20
                                                                   M  S  L  T  L  Y  T  G  R  S  Q  A  L  V  D  K  L  V  Q  Q  F  Q  K  D
GGTTTCCCTCTAGAAATAATTTTGTTTAACTTTAAGAAGGAGATATACCATGTCTTTAACATTATATACAGGTCGTAGTCAAGCATTGGTCGACAAACTCGTTCAACAGTTCCAGAAAGA
CCAAAGGGAGATCTTTATTAAAACAAATTGAAATTCTTCCTCTATATGGTACAGAAATTGTAATATATGTCCAGCATCAGTTCGTAACCAGCTGTTTGAGCAAGTTGTCAAGGTCTTTCT
       130       140       150       160       170       180       190       200       210       220       230       240

            30                            40                            50                            60
 T  G  I  K  V  N  V  R  Y  G  R  D  A  E  I  L  A  A  L  Q  E  E  G  S  R  S  P  A  D  V  F  W  A  N  T  S  G  A  L  E
TACGGGGATCAAGGTAAATGTACGTTACGGCCGGGACGCAGAAATCTTAGCCGCATTGCAGGAAGAAGGTAGCCGTTCTCCAGCCGATGTATTCTGGGCGAACACCTCTGGTGCTCTTGA
ATGCCCCTAGTTCCATTTACATGCAATGCCGGCCCTGCGTCTTTAGAATCGGCGTAACGTCCTTCTTCCATCGGCAAGAGGTCGGCTACATAAGACCCGCTTGTGGAGACCACGAGAACT
       250       260       270       280       290       300       310       320       330       340       350       360

            70                            80                            90                           100
 E  A  V  K  R  N  L  L  V  Q  L  P  A  S  L  T  R  Q  P  Q  E  F  V  P  S  H  G  R  W  V  P  V  S  V  R  F  R  V  A  A
AGAAGCAGTAAAGCGTAACCTCCTCGTACAACTTCCTGCATCCTTAACACGGCAGCCACAAGAGTTTGTACCAAGTCATGGGCGCTGGGTACCAGTATCAGTTCGCTTTCGCGTTGCCGC
TCTTCGTCATTTCGCATTGGAGGAGCATGTTGAAGGACGTAGGAATTGTGCCGTCGGTGTTCTCAAACATGGTTCAGTACCCGCGACCCATGGTCATAGTCAAGCGAAAGCGCAACGGCG
       370       380       390       400       410       420       430       440       450       460       470       480

           110                           120                           130                           140
 Y  N  P  T  K  V  K  D  S  D  F  P  A  S  V  M  D  L  P  K  V  A  K  F  K  G  R  I  G  W  T  P  T  Y  S  S  F  Q  D  F
CTACAACCCAACCAAGGTAAAAGATAGTGATTTTCCGGCATCCGTCATGGACTTGCCTAAAGTCGCCAAATTCAAAGGCCGTATTGGCTGGACGCCGACCTATTCCTCTTTCCAAGACTT
GATGTTGGGTTGGTTCCATTTTCTATCACTAAAAGGCCGTAGGCAGTACCTGAACGGATTTCAGCGGTTTAAGTTTCCGGCATAACCGACCTGCGGCTGGATAAGGAGAAAGGTTCTGAA
       490       500       510       520       530       540       550       560       570       580       590       600

           150                           160                           170                           180
 I  T  A  M  R  V  V  K  G  E  A  A  T  K  A  W  L  Q  A  M  I  A  A  G  A  K  A  Y  P  S  N  P  P  M  L  E  A  M  Q  A
CATTACAGCCATGCGCGTAGTAAAGGGCGAGGCCGCCACTAAAGCCTGGCTCCAAGCAATGATCGCTGCCGGTGCAAAGGCATATCCAAGCAACCCACCAATGTTAGAAGCGATGCAGGC
GTAATGTCGGTACGCGCATCATTTCCCGCTCCGGCGGTGATTTCGGACCGAGGTTCGTTACTAGCGACGGCCACGTTTCCGTATAGGTTCGTTGGGTGGTTACAATCTTCGCTACGTCCG
       610       620       630       640       650       660       670       680       690       700       710       720

           190                           200                           210                           220
 G  E  I  D  V  A  L  T  N  H  Y  Y  I  Q  R  I  L  A  G  V  G  E  G  E  Y  E  G  K  E  E  S  E  E  E  E  K  K  E  L  A
AGGTGAGATCGACGTGGCCTTAACTAACCACTATTATATCCAACGCATCTTGGCAGGCGTGGGTGAGGGCGAGTATGAAGGCAAGGAGGAATCCGAGGAGGAGGAGAAAAAAGAGCTGGC
TCCACTCTAGCTGCACCGGAATTGATTGGTGATAATATAGGTTGCGTAGAACCGTCCGCACCCACTCCCGCTCATACTTCCGTTCCTCCTTAGGCTCCTCCTCCTCTTTTTTCTCGACCG
       730       740       750       760       770       780       790       800       810       820       830       840

           230                           240                           250                           260
 A  R  E  A  K  A  G  V  A  T  H  Y  F  A  P  G  D  V  G  G  L  A  L  V  T  G  A  G  I  L  A  T  S  K  H  Q  T  N  A  T
GGCCCGGGAAGCCAAAGCCGGTGTAGCAACACATTACTTCGCTCCAGGCGACGTAGGCGGTTTAGCGCTCGTGACAGGCGCAGGTATTCTGGCTACATCAAAACATCAAACAAATGCAAC
CCGGGCCCTTCGGTTTCGGCCACATCGTTGTGTAATGAAGCGAGGTCCGCTGCATCCGCCAAATCGCGAGCACTGTCCGCGTCCATAAGACCGATGTAGTTTTGTAGTTTGTTTACGTTG
       850       860       870       880       890       900       910       920       930       940       950       960
```

```
                270                                    280                                    290                                    300
 R   F   L   N   Y   L   L   S   K   K   A   Q   P   Y   F   V   D   E   V   R   E   Y   P   V   I   A   G   V   R   V   A   K   G   M   L   P   F   A   N   A
CCGTTTTCTTAATTACTTGTTATCAAAAAAAGCTCAACCGTATTTCGTTGACGAAGTCCGTGAGTACCCAGTCATTGCCGGGGTTCGGGTAGCCAAGGGGATGTTACCTTTCGCAAACGC
GGCAAAAGAATTAATGAACAATAGTTTTTTTCGAGTTGGCATAAAGCAACTGCTTCAGGCACTCATGGGTCAGTAACGGCCCCAAGCCCATCGGTTCCCCTACAATGGAAAGCGTTTGCG
        970         980         990        1000        1010        1020        1030        1040        1050        1060        1070        1080

                310                                    320                                    330                                    340
 I   R   L   S   P   K   I   D   F   A   K   L   T   D   L   E   G   T   L   K   L   L   R   E   V   G   L   L   G   G   S   H   H   H   H   H   H   *   *
CATTCGCCTCTCCCCGAAAATTGACTTTGCCAAGCTCACGGATTTAGAAGGTACACTCAAATTGTTACGTGAAGTAGGCCTCTTAGGTGGTAGTCATCATCATCATCATCATTAATGAAA
GTAAGCGGAGAGGGGCTTTTAACTGAAACGGTTCGAGTGCCTAAATCTTCCATGTGAGTTTAACAATGCACTTCATCCGGAGAATCCACCATCAGTAGTAGTAGTAGTAGTAATTACTTT
       1090        1100        1110        1120        1130        1140        1150        1160        1170        1180        1190        1200


GGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCC
CCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGG
       1210        1220        1230        1240        1250        1260        1270        1280        1290        1300        1310        1320


TCTAAACGGGTCTTGAGGGGTTTTTTGCTGAAAGGAGGAACTATATCCGGAGCGACTCCCACGGCACGTTGGCAAGCTCG
AGATTTGCCCAGAACTCCCCAAAAAACGACTTTCCTCCTTGATATAGGCCTCGCTGAGGGTGCCGTGCAACCGTTCGAGC
       1330        1340        1350        1360        1370        1380        1390        1400
```

FIG. 24 (Continued)

FIG. 25 – Exemplary Expression Construct for srFeBP7

SEQ ID NO: 107

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                       10                            20
                                                    M  L  V  I  Y  S  G  R  S  K  A  L  V  D  S  L  V  Q  Q  Y  R  Q  Q  A
GGTTTCCCTCTAGAAATAATTTTGTTTAACTTTAAGAAGGAGATATACCATGTTAGTAATTTATTCAGGTCGTTCAAAAGCCTTGGTCGACTCCTTGGTACAACAGTATCGTCAACAGGC
CCAAAGGGAGATCTTTATTAAAACAAATTGAAATTCTTCCTCTATATGGTACAATCATTAAATAAGTCCAGCAAGTTTTCGGAACCAGCTGAGGAACCATGTTGTCATAGCAGTTGTCCG
       130       140       150       160       170       180       190       200       210       220       230       240

           30                            40                            50                            60
 D  V  P  V  R  V  R  Y  G  T  D  S  Q  L  L  A  A  L  Q  E  E  G  D  Q  S  P  A  D  V  F  W  A  N  T  T  G  A  L  G  N
AGATGTCCCAGTTCGCGTTCGGTACGGTACCGATTCGCAGCTCTTAGCAGCTTTACAAGAAGAGGGTGACCAATCGCCGGCAGACGTATTTTGGGCTAACACGACAGGCGCACTGGGTAA
TCTACAGGGTCAAGCGCAAGCCATGCCATGGCTAAGCGTCGAGAATCGTCGAAATGTTCTTCTCCCACTGGTTAGCGGCCGTCTGCATAAAACCCGATTGTGCTGTCCGCGTGACCCATT
       250       260       270       280       290       300       310       320       330       340       350       360

           70                            80                            90                           100
 A  V  N  N  G  L  L  T  E  L  P  D  T  L  A  N  R  A  A  R  F  T  P  S  N  Q  R  W  T  P  V  T  T  R  F  R  V  L  A  Y
CGCCGTCAACAATGGCTTACTGACTGAATTGCCGGATACTCTTGCGAACCGCGCTGCACGTTTTACCCCGTCGAACCAACGCTGGACTCCTGTAACAACACGTTTTCGGGTACTTGCTTA
GCGGCAGTTGTTACCGAATGACTGACTTAACGGCCTATGAGAACGCTTGGCGCGACGTGCAAAATGGGGCAGCTTGGTTGCGACCTGAGGACATTGTTGTGCAAAAGCCCATGAACGAAT
       370       380       390       400       410       420       430       440       450       460       470       480

          110                           120                           130                           140
 N  S  D  A  V  S  P  E  D  L  P  D  S  V  L  D  L  P  E  H  E  E  F  E  G  R  V  G  W  T  P  A  Y  S  S  F  Q  D  F  V
CAATTCAGACGCAGTATCACCGGAAGACCTCCCTGACAGTGTACTTGATTTACCTGAACACGAAGAGTTCGAAGGGCGTGTAGGCTGGACCCCAGCGTACTCGTCATTTCAGGATTTCGT
GTTAAGTCTGCGTCATAGTGGCCTTCTGGAGGGACTGTCACATGAACTAAATGGACTTGTGCTTCTCAAGCTTCCCGCACATCCGACCTGGGGTCGCATGAGCAGTAAAGTCCTAAAGCA
       490       500       510       520       530       540       550       560       570       580       590       600

          150                           160                           170                           180
 T  A  L  R  V  T  E  G  A  E  T  A  R  T  W  L  S  D  M  Q  A  L  N  P  N  S  Y  T  S  N  T  P  M  V  Q  A  L  E  A  G
CACCGCACTCCGGGTCACAGAAGGCGCCGAGACCGCTCGTACATGGTTGTCTGACATGCAAGCCCTCAATCCGAACTCCTACACAAGTAACACCCCAATGGTCCAAGCGCTGGAAGCAGG
GTGGCGTGAGGCCCAGTGTCTTCCGCGGCTCTGGCGAGCATGTACCAACAGACTGTACGTTCGGGAGTTAGGCTTGAGGATGTGTTCATTGTGGGGTTACCAGGTTCGCGACCTTCGTCC
       610       620       630       640       650       660       670       680       690       700       710       720

          190                           200                           210                           220
 E  I  D  V  A  L  T  N  H  Y  Y  V  L  R  L  K  H  G  G  A  E  G  E  Y  E  G  E  E  E  E  G  E  E  H  E  E  E  H  E  E
TGAAATTGATGTCGCGTTAACAAACCACTACTACGTACTGCGTCTCAAACATGGCGGCGCCGAAGGTGAATATGAGGGCGAGGAAGAAGAGGGTGAGGAGCATGAAGAAGAACACGAAGA
ACTTTAACTACAGCGCAATTGTTTGGTGATGATGCATGACGCAGAGTTTGTACCGCCGCGGCTTCCACTTATACTCCCGCTCCTTCTTCTCCCACTCCTCGTACTTCTTCTTGTGCTTCT
       730       740       750       760       770       780       790       800       810       820       830       840

          230                           240                           250                           260
 E  A  T  P  R  A  S  A  P  V  E  M  Y  H  F  A  D  G  D  L  G  N  L  A  L  V  T  G  A  G  A  L  Q  T  S  N  Q  P  D  A
GGAGGCCACACCACGCGCATCCGCACCAGTTGAAATGTACCACTTTGCAGACGGTGACTTAGGCAACCTGGCCCTTGTAACTGGCGCCGGCGCTCTTCAAACATCAAATCAGCCAGATGC
CCTCCGGTGTGGTGCGCGTAGGCGTGGTCAACTTTACATGGTGAAACGTCTGCCACTGAATCCGTTGGACCGGGAACATTGACCGCGGCCGCGAGAAGTTTGTAGTTTAGTCGGTCTACG
       850       860       870       880       890       900       910       920       930       940       950       960
```

```
                270                                     280                                     290                                     300
 A   N   R   F   L   R   F   L   L   S   E   Q   A   Q   S   F   A   A   T   R   V   N   E   Y   P   V   V   S   G   A   S   V   P   D   Y   L   M   P   A   D
CGCCAACCGCTTCTTACGGTTCTTATTGTCGGAACAGGCTCAGTCATTCGCGGCCACACGTGTCAACGAATACCCAGTCGTCTCGGGGGCAAGTGTACCTGACTATCTTATGCCAGCAGA
GCGGTTGGCGAAGAATGCCAAGAATAACAGCCTTGTCCGAGTCAGTAAGCGCCGGTGTGCACAGTTGCTTATGGGTCAGCAGAGCCCCCGTTCACATGGACTGATAGAATACGGTCGTCT
       970       980       990      1000      1010      1020      1030      1040      1050      1060      1070      1080

                310                                     320                                     330                                     340
 E   A   L   K   M   S   P   E   F   D   L   Q   K   L   Q   N   M   E   P   T   L   D   L   L   R   D   A   G   A   L   G   G   S   H   H   H   H   H   H   *
CGAGGCCCTCAAAATGTCACCAGAATTTGACTTACAGAAATTGCAAAATATGGAACCAACCTTAGATCTTTTACGGGACGCAGGGGCTTTAGGTGGTAGTCATCATCATCATCATCATTA
GCTCCGGGAGTTTTACAGTGGTCTTAAACTGAATGTCTTTAACGTTTTATACCTTGGTTGGAATCTAGAAAATGCCCTGCGTCCCCGAAATCCACCATCAGTAGTAGTAGTAGTAGTAAT
      1090      1100      1110      1120      1130      1140      1150      1160      1170      1180      1190      1200

 *
ATGAAAGGGCGATATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTT
TACTTTCCCGCTATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAA
      1210      1220      1230      1240      1250      1260      1270      1280      1290      1300      1310      1320

GGGGCCTCTAAACGGGTCTTGAGGGGTTTTTTGCTGAAAGGAGGAACTATATCCGGAGCGACTCCCACGGCACGTTGGCAAGCTCG
CCCCGGAGATTTGCCCAGAACTCCCCAAAAAACGACTTTCCTCCTTGATATAGGCCTCGCTGAGGGTGCCGTGCAACCGTTCGAGC
      1330      1340      1350      1360      1370      1380      1390      1400
```

FIG. 25 (Continued)

FIG. 26 – Exemplary Expression Construct for hlFeBP8

SEQ ID NO: 108

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10          20          30          40          50          60          70          80          90         100         110         120

                                                                                              10                                20
                                                       M  L  T  V  Y  S  G  R  G  E  F  L  V  G  E  L  V  E  Y  I  E  D  Q  Y
GGTTTCCCTCTAGAAATAATTTTGTTTAACTTTAAGAAGGAGATATACCATGTTAACTGTATATTCAGGTCGTGGCGAATTTCTCGTAGGTGAATTAGTAGAATACATTGAGGATCAGTA
CCAAAGGGAGATCTTTATTAAAACAAATTGAAATTCTTCCTCTATATGGTACAATTGACATATAAGTCCAGCACCGCTTAAAGAGCATCCACTTAATCATCTTATGTAACTCCTAGTCAT
       130         140         150         160         170         180         190         200         210         220         230         240

          30                                  40                                  50                                  60
 D  D  F  D  L  T  V  R  Y  A  G  S  T  D  L  V  N  Q  I  L  N  E  G  D  G  S  P  A  D  V  F  Y  S  V  N  A  G  S  L  G
TGACGACTTTGATTTAACCGTTCGCTACGCCGGTAGCACCGATCTCGTAAACCAAATTTTAAATGAAGGGGACGGCAGCCCAGCGGACGTATTCTACTCCGTTAATGCCGGCAGCTTAGG
ACTGCTGAAACTAAATTGGCAAGCGATGCGGCCATCGTGGCTAGAGCATTTGGTTTAAAATTTACTTCCCCTGCCGTCGGGTCGCCTGCATAAGATGAGGCAATTACGGCCGTCGAATCC
       250         260         270         280         290         300         310         320         330         340         350         360

          70                                  80                                  90                                 100
 T  L  A  G  E  G  R  S  Q  A  L  S  S  E  I  T  D  M  V  R  S  E  F  R  T  E  Q  W  I  G  T  S  G  R  A  R  T  V  P  Y
GACCCTCGCAGGTGAAGGTCGTTCACAGGCACTCAGCTCAGAGATCACGGATATGGTGCGTAGCGAGTTCCGCACAGAACAATGGATTGGTACCTCCGGGCGTGCACGCACAGTCCCTTA
CTGGGAGCGTCCACTTCCAGCAAGTGTCCGTGAGTCGAGTCTCTAGTGCCTATACCACGCATCGCTCAAGGCGTGTCTTGTTACCTAACCATGGAGGCCCGCACGTGCGTGTCAGGGAAT
       370         380         390         400         410         420         430         440         450         460         470         480

         110                                 120                                 130                                 140
 N  T  G  E  F  S  D  D  D  L  P  D  D  I  M  A  Y  P  E  E  F  A  G  S  L  G  W  A  P  S  Y  G  S  A  Q  A  F  I  T  A
TAATACTGGCGAGTTTAGCGATGACGACTTACCTGACGATATTATGGCCTACCCGGAGGAGTTTGCGGGGTCTCTCGGTTGGGCGCCGTCATATGGGTCAGCACAAGCCTTTATTACGGC
ATTATGACCGCTCAAATCGCTACTGCTGAATGGACTGCTATAATACCGGATGGGCCTCCTCAAACGCCCCAGAGAGCCAACCCGCGGCAGTATACCCAGTCGTGTTCGGAAATAATGCCG
       490         500         510         520         530         540         550         560         570         580         590         600

         150                                 160                                 170                                 180
 M  R  L  I  E  G  E  E  A  T  L  A  W  L  E  S  V  V  E  A  G  I  S  S  Y  P  D  E  F  A  A  A  Q  A  I  A  D  G  E  I
TATGCGTTTGATCGAAGGGGAAGAAGCCACATTGGCTTGGCTTGAATCGGTCGTAGAAGCAGGGATTAGCTCATATCCTGACGAATTTGCCGCGGCACAAGCTATCGCCGACGGTGAGAT
ATACGCAAACTAGCTTCCCCTTCTTCGGTGTAACCGAACCGAACTTAGCCAGCATCTTCGTCCCTAATCGAGTATAGGACTGCTTAAACGGCGCCGTGTTCGATAGCGGCTGCCACTCTA
       610         620         630         640         650         660         670         680         690         700         710         720

         190                                 200                                 210                                 220
 D  A  A  F  T  N  H  Y  Y  I  Q  R  V  L  D  G  N  P  D  A  S  I  G  T  A  F  T  S  G  D  A  G  A  V  F  N  V  A  G  A
CGACGCTGCCTTTACAAACCACTATTACATTCAGCGGGTCCTCGACGGGAACCCGGACGCCTCAATCGGGACAGCCTTCACGTCAGGCGACGCAGGTGCAGTGTTCAACGTAGCCGGGGC
GCTGCGACGGAAATGTTTGGTGATAATGTAAGTCGCCCAGGAGCTGCCCTTGGGCCTGCGGAGTTAGCCCTGTCGGAAGTGCAGTCCGCTGCGTCCACGTCACAAGTTGCATCGGCCCCG
       730         740         750         760         770         780         790         800         810         820         830         840

         230                                 240                                 250                                 260
 A  V  V  D  T  A  S  D  A  T  L  A  E  N  F  I  R  H  L  L  S  A  E  A  Q  D  Y  F  A  R  S  T  F  E  Y  P  L  I  P  D
GGCCGTCGTCGACACAGCCTCCGACGCTACTCTCGCAGAGAATTTTATCCGTCATTTGTTGTCGGCTGAGGCCCAAGACTATTTTGCACGCTCCACATTTGAGTACCCATTAATCCCTGA
CCGGCAGCAGCTGTGTCGGAGGCTGCGATGAGAGCGTCTCTTAAAATAGGCAGTAAACAACAGCCGACTCCGGGTTCTGATAAAACGTGCGAGGTGTAAACTCATGGGTAATTAGGGACT
       850         860         870         880         890         900         910         920         930         940         950         960
```

```
                 270                                     280                                     290                                     300
  V    E    P    I    G    D    L    P    T    I    D    E    L    D    V    P    D    I    D    L    T    E    L    S    D    L    E    P    T    I    D    L    M    R    E    A    G    V    E    V
TGTAGAGCCTATCGGTGATCTGCCAACTATTGACGAGCTCGACGTGCCTGACATCGACTTGACCGAACTTTCAGACTTAGAGCCGACTATTGATTTGATGCGCGAAGCAGGTGTAGAAGT
ACATCTCGGATAGCCACTAGACGGTTGATAACTGCTCGAGCTGCACGGACTGTAGCTGAACTGGCTTGAAAGTCTGAATCTCGGCTGATAACTAAACTACGCGCTTCGTCCACATCTTCA
        970          980          990         1000         1010         1020         1030         1040         1050         1060         1070         1080

                 310
  G    G    S    H    H    H    H    H    H    *    *
AGGTGGTAGTCATCATCATCATCATCATTAATGAAAGGGCGATATCCAGCACACTGGCGGCCGTTACTAGTGGATCCGGCTGCTAACAAAGCCCGAAAGGAAGCTGAGTTGGCTGCTGCC
TCCACCATCAGTAGTAGTAGTAGTAGTAATTACTTTCCCGCTATAGGTCGTGTGACCGCCGGCAATGATCACCTAGGCCGACGATTGTTTCGGGCTTTCCTTCGACTCAACCGACGACGG
       1090         1100         1110         1120         1130         1140         1150         1160         1170         1180         1190         1200


ACCGCTGAGCAATAACTAGCATAACCCCTTGGGGCCTCTAAACGGGTCTTGAGGGGTTTTTTGCTGAAAGGAGGAACTATATCCGGAGCGACTCCCACGGCACGTTGGCAAGCTCG
TGGCGACTCGTTATTGATCGTATTGGGGAACCCCGGAGATTTGCCCAGAACTCCCCAAAAAACGACTTTCCTCCTTGATATAGGCCTCGCTGAGGGTGCCGTGCAACCGTTCGAGC
       1210         1220         1230         1240         1250         1260         1270         1280         1290         1300         1310
```

FIG. 26 (Continued)

FIG. 27 - Exemplary Expression Construct for avBicarBP5_16C

SEQ ID NO: 109

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                          10
                                                                      M  A  E  Q  A  P  E  V  T  T  V  K  L  G  Y  C  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATTGCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATAACGGGCTAACAGCT
       130       140       150       160       170       180       190       200       210       220       230       240

                            30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                            70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                           110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                           150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                           190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                           230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                    270                                  280                                  290
 Q  I  L  A  G  R  N  Y  F  N  L  N  N  P  E  I  L  A  D  P  Y  V  G  K  Y  D  M  G  D  G  R  K  I  D  D  K  S  M  A  A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
       970       980       990      1000      1010      1020      1030      1040      1050      1060      1070      1080

                    310                                  320                                  330
 Y  Y  W  K  D  E  K  G  S  V  S  Y  P  Y  K  S  H  D  L  W  F  I  T  E  N  V  R  W  G  F  L  P  K  D  Y  L  A  N  G  A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
      1090      1100      1110      1120      1130      1140      1150      1160      1170      1180      1190      1200

                    350                                  360                                  370
 A  K  A  K  E  L  I  D  K  V  N  R  E  D  I  W  K  E  A  A  K  E  A  G  I  A  A  A  D  I  P  T  S  T  S  R  G  V  E  E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
      1210      1220      1230      1240      1250      1260      1270      1280      1290      1300      1310      1320

                    390                                  400                                  410
 F  F  D  G  T  K  F  D  P  E  K  P  D  E  Y  L  K  S  L  K  I  K  K  V  S  V  G  G  S  H  H  H  H  H  H  *  *
GTTCTTCGACGGCACCAAATTCGACCCAGAAAAGCCAGACGAATATCTGAAATCGCTCAAAATCAAAAAAGTCAGCGTAGGTGGTTCACATCATCATCATCATCATTAATGAAAGGGCGA
CAAGAAGCTGCCGTGGTTTAAGCTGGGTCTTTTCGGTCTGCTTATAGACTTTAGCGAGTTTTAGTTTTTTCAGTCGCATCCACCAAGTGTAGTAGTAGTAGTAGTAATTACTTTCCCGCT
      1330      1340      1350      1360      1370      1380      1390      1400      1410      1420      1430      1440


TATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAA
ATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTT
      1450      1460      1470      1480      1490      1500      1510      1520      1530      1540      1550      1560


CGGGTCTTGAGGGGTTTTTTGCTGAAAGGAGGAACTATATCCGGAGCGACTCCCACGGCACGTTGGCAAGCTCGGAATTCGGCGTAATC
GCCCAGAACTCCCCAAAAAACGACTTTCCTCCTTGATATAGGCCTCGCTGAGGGTGCCGTGCAACCGTTCGAGCCTTAAGCCGCATTAG
      1570      1580      1590      1600      1610      1620      1630      1640
```

FIG. 27 (Continued)

FIG. 28 - Exemplary Expression Construct for avBicarBP5_17C

SEQ ID NO: 110

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                           10
                                                                      M  A  E  Q  A  P  E  V  T  T  V  K  L  G  Y  I  C  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCTGCATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGACGTAACAGCT
       130       140       150       160       170       180       190       200       210       220       230       240

                                       30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                                       70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                                      110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                                      150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                                      190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                                      230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                      270                                     280                                     290
Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
        970         980         990        1000        1010        1020        1030        1040        1050        1060        1070        1080

                      310                                     320                                     330
Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
       1090        1100        1110        1120        1130        1140        1150        1160        1170        1180        1190        1200

                      350                                     360                                     370
A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
       1210        1220        1230        1240        1250        1260        1270        1280        1290        1300        1310        1320

                      390                                     400                                     410
F   F   D   G   T   K   F   D   P   E   K   P   D   E   Y   L   K   S   L   K   I   K   K   V   S   V   G   G   S   H   H   H   H   H   H   *   *
GTTCTTCGACGGCACCAAATTCGACCCAGAAAAGCCAGACGAATATCTGAAATCGCTCAAAATCAAAAAAGTCAGCGTAGGTGGTTCACATCATCATCATCATCATTAATGAAAGGGCGA
CAAGAAGCTGCCGTGGTTTAAGCTGGGTCTTTTCGGTCTGCTTATAGACTTTAGCGAGTTTTAGTTTTTTCAGTCGCATCCACCAAGTGTAGTAGTAGTAGTAGTAATTACTTTCCCGCT
       1330        1340        1350        1360        1370        1380        1390        1400        1410        1420        1430        1440


TATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAA
ATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTT
       1450        1460        1470        1480        1490        1500        1510        1520        1530        1540        1550        1560


CGGGTCTTGAGGGGTTTTTTGCTGAAAGGAGGAACTATATCCGGAGCGACTCCCACGGCACGTTGGCAAGCTCGGAATTCGGCGTAATC
GCCCAGAACTCCCCAAAAAACGACTTTCCTCCTTGATATAGGCCTCGCTGAGGGTGCCGTGCAACCGTTCGAGCCTTAAGCCGCATTAG
       1570        1580        1590        1600        1610        1620        1630        1640
```

FIG. 28 (Continued)

FIG. 29 - Exemplary Expression Construct for avBicarBP5_18C

SEQ ID NO: 111

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                              10
                                                                                M  A  E  Q  A  P  E  V  T  T  V  K  L  G  Y  I  P  C  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGTGCGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCACGCAGCT
       130       140       150       160       170       180       190       200       210       220       230       240

                             30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                             70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                            110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                            150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                            190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                            230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                    270                                     280                                     290
Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
       970       980       990      1000      1010      1020      1030      1040      1050      1060      1070      1080

                    310                                     320                                     330
Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
      1090      1100      1110      1120      1130      1140      1150      1160      1170      1180      1190      1200

                    350                                     360                                     370
A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
      1210      1220      1230      1240      1250      1260      1270      1280      1290      1300      1310      1320

                    390                                     400                                     410
F   F   D   G   T   K   F   D   P   E   K   P   D   E   Y   L   K   S   L   K   I   K   K   V   S   V   G   G   S   H   H   H   H   H   H   *   *
GTTCTTCGACGGCACCAAATTCGACCCAGAAAAGCCAGACGAATATCTGAAATCGCTCAAAATCAAAAAAGTCAGCGTAGGTGGTTCACATCATCATCATCATCATTAATGAAAGGGCGA
CAAGAAGCTGCCGTGGTTTAAGCTGGGTCTTTTCGGTCTGCTTATAGACTTTAGCGAGTTTTAGTTTTTTCAGTCGCATCCACCAAGTGTAGTAGTAGTAGTAGTAATTACTTTCCCGCT
      1330      1340      1350      1360      1370      1380      1390      1400      1410      1420      1430      1440

TATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAA
ATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTT
      1450      1460      1470      1480      1490      1500      1510      1520      1530      1540      1550      1560

CGGGTCTTGAGGGGTTTTTTGCTGAAAGGAGGAACTATATCCGGAGCGACTCCCACGGCACGTTGGCAAGCTCGGAATTCGGCGTAATC
GCCCAGAACTCCCCAAAAAACGACTTTCCTCCTTGATATAGGCCTCGCTGAGGGTGCCGTGCAACCGTTCGAGCCTTAAGCCGCATTAG
      1570      1580      1590      1600      1610      1620      1630      1640
```

FIG. 29 (Continued)

FIG. 30 – Exemplary Expression Construct for avBicarBP5_49C

SEQ ID NO: 112

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                            10
                                                                              M  A  E  Q  A  P  E  V  T  T  V  K  L  G  Y  I  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCTAACAGCT
       130       140       150       160       170       180       190       200       210       220       230       240

                                          30                            40                            50
S  A  P  L  I  I  A  K  E  K  G  F  F  A  K  Y  G  L  T  N  V  E  L  S  K  Q  A  S  C  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGCGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACGCCGTCACGGGCCCTATTACATCTCTAGCCATC
       250       260       270       280       290       300       310       320       330       340       350       360

                                          70                            80                            90
A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                                         110                           120                           130
H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                                         150                           160                           170
T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                                         190                           200                           210
K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                                         230                           240                           250
Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                      270                           280                           290
 Q  I  L  A  G  R  N  Y  F  N  L  N  N  P  E  I  L  A  D  P  Y  V  G  K  Y  D  M  G  D  G  R  K  I  D  D  K  S  M  A  A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
       970       980       990      1000      1010      1020      1030      1040      1050      1060      1070      1080

                      310                           320                           330
 Y  Y  W  K  D  E  K  G  S  V  S  Y  P  Y  K  S  H  D  L  W  F  I  T  E  N  V  R  W  G  F  L  P  K  D  Y  L  A  N  G  A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
      1090      1100      1110      1120      1130      1140      1150      1160      1170      1180      1190      1200

                      350                           360                           370
 A  K  A  K  E  L  I  D  K  V  N  R  E  D  I  W  K  E  A  A  K  E  A  G  I  A  A  A  D  I  P  T  S  T  S  R  G  V  E  E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
      1210      1220      1230      1240      1250      1260      1270      1280      1290      1300      1310      1320

                      390                           400                           410
 F  F  D  G  T  K  F  D  P  E  K  P  D  E  Y  L  K  S  L  K  I  K  K  V  S  V  G  G  S  H  H  H  H  H  H  *  *
GTTCTTCGACGGCACCAAATTCGACCCAGAAAAGCCAGACGAATATCTGAAATCGCTCAAAATCAAAAAAGTCAGCGTAGGTGGTTCACATCATCATCATCATCATTAATGAAAGGGCGA
CAAGAAGCTGCCGTGGTTTAAGCTGGGTCTTTTCGGTCTGCTTATAGACTTTAGCGAGTTTTAGTTTTTTCAGTCGCATCCACCAAGTGTAGTAGTAGTAGTAGTAATTACTTTCCCGCT
      1330      1340      1350      1360      1370      1380      1390      1400      1410      1420      1430      1440


TATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAA
ATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTT
      1450      1460      1470      1480      1490      1500      1510      1520      1530      1540      1550      1560


CGGGTCTTGAGGGGTTTTTTGCTGAAAGGAGGAACTATATCCGGAGCGACTCCCACGGCACGTTGGCAAGCTCGGAATTCGGCGTAATC
GCCCAGAACTCCCCAAAAAACGACTTTCCTCCTTGATATAGGCCTCGCTGAGGGTGCCGTGCAACCGTTCGAGCCTTAAGCCGCATTAG
      1570      1580      1590      1600      1610      1620      1630      1640
```

FIG. 30 (Continued)

FIG. 31 – Exemplary Expression Construct for avBicarBP5_71C

SEQ ID NO: 113

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                                   10
                                                                      M  A  E  Q  A  P  E  V  T  T  V  K  L  G  Y  I  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCTAACAGCT
       130       140       150       160       170       180       190       200       210       220       230       240

                                       30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                                       70                            80                            90
 A  G  G  G  I  D  G  G  Q  W  C  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGTGCATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCACGTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                                      110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                                      150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                                      190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                                      230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                270                                280                                290
Q  I  L  A  G  R  N  Y  F  N  L  N  N  P  E  I  L  A  D  P  Y  V  G  K  Y  D  M  G  D  G  R  K  I  D  D  K  S  M  A  A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
       970       980       990      1000      1010      1020      1030      1040      1050      1060      1070      1080

                310                                320                                330
Y  Y  W  K  D  E  K  G  S  V  S  Y  P  Y  K  S  H  D  L  W  F  I  T  E  N  V  R  W  G  F  L  P  K  D  Y  L  A  N  G  A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
      1090      1100      1110      1120      1130      1140      1150      1160      1170      1180      1190      1200

                350                                360                                370
A  K  A  K  E  L  I  D  K  V  N  R  E  D  I  W  K  E  A  A  K  E  A  G  I  A  A  A  D  I  P  T  S  T  S  R  G  V  E  E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
      1210      1220      1230      1240      1250      1260      1270      1280      1290      1300      1310      1320

                390                                400                                410
F  F  D  G  T  K  F  D  P  E  K  P  D  E  Y  L  K  S  L  K  I  K  K  V  S  V  G  G  S  H  H  H  H  H  H  *  *
GTTCTTCGACGGCACCAAATTCGACCCAGAAAAGCCAGACGAATATCTGAAATCGCTCAAAATCAAAAAAGTCAGCGTAGGTGGTTCACATCATCATCATCATCATTAATGAAAGGGCGA
CAAGAAGCTGCCGTGGTTTAAGCTGGGTCTTTTCGGTCTGCTTATAGACTTTAGCGAGTTTTAGTTTTTTCAGTCGCATCCACCAAGTGTAGTAGTAGTAGTAGTAATTACTTTCCCGCT
      1330      1340      1350      1360      1370      1380      1390      1400      1410      1420      1430      1440


TATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAA
ATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTT
      1450      1460      1470      1480      1490      1500      1510      1520      1530      1540      1550      1560


CGGGTCTTGAGGGGTTTTTTGCTGAAAGGAGGAACTATATCCGGAGCGACTCCCACGGCACGTTGGCAAGCTCGGAATTCGGCGTAATC
GCCCAGAACTCCCCAAAAAACGACTTTCCTCCTTGATATAGGCCTCGCTGAGGGTGCCGTGCAACCGTTCGAGCCTTAAGCCGCATTAG
      1570      1580      1590      1600      1610      1620      1630      1640
```

FIG. 31 (Continued)

FIG. 32 - Exemplary Expression Construct for avBicarBP5_140C

SEQ ID NO: 114

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                            10
                                                                               M  A  E  Q  A  P  E  V  T  T  V  K  L  G  Y  I  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCTAACAGCT
       130       140       150       160       170       180       190       200       210       220       230       240

                                            30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                                            70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                                           110                           120                           130
 H  G  N  G  I  A  I  A  N  K  H  Q  G  K  G  I  S  L  K  L  E  G  A  K  S  L  F  S  Q  L  K  S  S  T  P  F  T  A  A  C
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTG
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAC
       490       500       510       520       530       540       550       560       570       580       590       600

                                           150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                                           190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                                           230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                              270                                     280                                     290
 Q  I  L  A  G  R  N  Y  F  N  L  N  N  P  E  I  L  A  D  P  Y  V  G  K  Y  D  M  G  D  G  R  K  I  D  D  K  S  M  A  A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
        970       980       990      1000      1010      1020      1030      1040      1050      1060      1070      1080

                              310                                     320                                     330
 Y  Y  W  K  D  E  K  G  S  V  S  Y  P  Y  K  S  H  D  L  W  F  I  T  E  N  V  R  W  G  F  L  P  K  D  Y  L  A  N  G  A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
       1090      1100      1110      1120      1130      1140      1150      1160      1170      1180      1190      1200

                              350                                     360                                     370
 A  K  A  K  E  L  I  D  K  V  N  R  E  D  I  W  K  E  A  A  K  E  A  G  I  A  A  A  D  I  P  T  S  T  S  R  G  V  E  E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
       1210      1220      1230      1240      1250      1260      1270      1280      1290      1300      1310      1320

                              390                                     400                                     410
 F  F  D  G  T  K  F  D  P  E  K  P  D  E  Y  L  K  S  L  K  I  K  K  V  S  V  G  G  S  H  H  H  H  H  H  *  *
GTTCTTCGACGGCACCAAATTCGACCCAGAAAAGCCAGACGAATATCTGAAATCGCTCAAAATCAAAAAAGTCAGCGTAGGTGGTTCACATCATCATCATCATCATTAATGAAAGGGCGA
CAAGAAGCTGCCGTGGTTTAAGCTGGGTCTTTTCGGTCTGCTTATAGACTTTAGCGAGTTTTAGTTTTTTCAGTCGCATCCACCAAGTGTAGTAGTAGTAGTAGTAATTACTTTCCCGCT
       1330      1340      1350      1360      1370      1380      1390      1400      1410      1420      1430      1440

TATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAA
ATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTT
       1450      1460      1470      1480      1490      1500      1510      1520      1530      1540      1550      1560

CGGGTCTTGAGGGGTTTTTTGCTGAAAGGAGGAACTATATCCGGAGCGACTCCCACGGCACGTTGGCAAGCTCGGAATTCGGCGTAATC
GCCCAGAACTCCCCAAAAAACGACTTTCCTCCTTGATATAGGCCTCGCTGAGGGTGCCGTGCAACCGTTCGAGCCTTAAGCCGCATTAG
       1570      1580      1590      1600      1610      1620      1630      1640
```

FIG.32 (Continued)

FIG. 33 - Exemplary Expression Construct for avBicarBP5_141C

SEQ ID NO: 115

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                     10
                                                                          M  A  E  Q  A  P  E  V  T  T  V  K  L  G  Y  I  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCTAACAGCT
       130       140       150       160       170       180       190       200       210       220       230       240

                                       30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                                       70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                                      110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                                      150                           160                           170
 C  F  P  H  V  N  Q  D  L  W  I  R  Y  W  L  A  A  G  G  I  D  P  D  A  D  V  K  L  L  T  V  P  A  A  Q  T  V  A  N  M
CTGCTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GACGAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                                      190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                                      230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                    270                                     280                                     290
Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
       970       980       990      1000      1010      1020      1030      1040      1050      1060      1070      1080

                    310                                     320                                     330
Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
      1090      1100      1110      1120      1130      1140      1150      1160      1170      1180      1190      1200

                    350                                     360                                     370
A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
      1210      1220      1230      1240      1250      1260      1270      1280      1290      1300      1310      1320

                    390                                     400                                     410
F   F   D   G   T   K   F   D   P   E   K   P   D   E   Y   L   K   S   L   K   I   K   K   V   S   V   G   G   S   H   H   H   H   H   H   *   *
GTTCTTCGACGGCACCAAATTCGACCCAGAAAAGCCAGACGAATATCTGAAATCGCTCAAAATCAAAAAAGTCAGCGTAGGTGGTTCACATCATCATCATCATCATTAATGAAAGGGCGA
CAAGAAGCTGCCGTGGTTTAAGCTGGGTCTTTTCGGTCTGCTTATAGACTTTAGCGAGTTTTAGTTTTTTCAGTCGCATCCACCAAGTGTAGTAGTAGTAGTAGTAATTACTTTCCCGCT
      1330      1340      1350      1360      1370      1380      1390      1400      1410      1420      1430      1440


TATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAA
ATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTT
      1450      1460      1470      1480      1490      1500      1510      1520      1530      1540      1550      1560


CGGGTCTTGAGGGGTTTTTTGCTGAAAGGAGGAACTATATCCGGAGCGACTCCCACGGCACGTTGGCAAGCTCGGAATTCGGCGTAATC
GCCCAGAACTCCCCAAAAAACGACTTTCCTCCTTGATATAGGCCTCGCTGAGGGTGCCGTGCAACCGTTCGAGCCTTAAGCCGCATTAG
      1570      1580      1590      1600      1610      1620      1630      1640
```

FIG. 33 (Continued)

FIG. 34 - Exemplary Expression Construct for avBicarBP5_142C

SEQ ID NO: 116

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                         10
                                                           M  A  E  Q  A  P  E  V  T  T  V  K  L  G  Y  I  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCTAACAGCT
       130       140       150       160       170       180       190       200       210       220       230       240

                            30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                            70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                           110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                           150                           160                           170
 T  C  P  H  V  N  Q  D  L  W  I  R  Y  W  L  A  A  G  G  I  D  P  D  A  D  V  K  L  L  T  V  P  A  A  Q  T  V  A  N  M
CACTTGCCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAACGGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                           190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                           230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                       270                                     280                                     290
 Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
         970          980          990         1000         1010         1020         1030         1040         1050         1060         1070         1080

                       310                                     320                                     330
 Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
        1090         1100         1110         1120         1130         1140         1150         1160         1170         1180         1190         1200

                       350                                     360                                     370
 A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
        1210         1220         1230         1240         1250         1260         1270         1280         1290         1300         1310         1320

                       390                                     400                                     410
 F   F   D   G   T   K   F   D   P   E   K   P   D   E   Y   L   K   S   L   K   I   K   K   V   S   V   G   G   S   H   H   H   H   H   H   *   *
GTTCTTCGACGGCACCAAATTCGACCCAGAAAAGCCAGACGAATATCTGAAATCGCTCAAAATCAAAAAAGTCAGCGTAGGTGGTTCACATCATCATCATCATCATTAATGAAAGGGCGA
CAAGAAGCTGCCGTGGTTTAAGCTGGGTCTTTTCGGTCTGCTTATAGACTTTAGCGAGTTTTAGTTTTTTCAGTCGCATCCACCAAGTGTAGTAGTAGTAGTAGTAATTACTTTCCCGCT
        1330         1340         1350         1360         1370         1380         1390         1400         1410         1420         1430         1440


TATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAA
ATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTT
        1450         1460         1470         1480         1490         1500         1510         1520         1530         1540         1550         1560


CGGGTCTTGAGGGGTTTTTTGCTGAAAGGAGGAACTATATCCGGAGCGACTCCCACGGCACGTTGGCAAGCTCGGAATTCGGCGTAATC
GCCCAGAACTCCCCAAAAAACGACTTTCCTCCTTGATATAGGCCTCGCTGAGGGTGCCGTGCAACCGTTCGAGCCTTAAGCCGCATTAG
        1570         1580         1590         1600         1610         1620         1630         1640
```

FIG. 34 (Continued)

FIG. 35 - Exemplary Expression Construct for avBicarBP5_143C

SEQ ID NO: 117

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                           10
                                                                       M  A  E  Q  A  P  E  V  T  T  V  K  L  G  Y  I  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCTAACAGCT
       130       140       150       160       170       180       190       200       210       220       230       240

                         30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                         70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                        110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                        150                           160                           170
 T  F  C  H  V  N  Q  D  L  W  I  R  Y  W  L  A  A  G  G  I  D  P  D  A  D  V  K  L  L  T  V  P  A  A  Q  T  V  A  N  M
CACTTTTTGCCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAACGGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                        190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                        230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                        270                                     280                                     290
Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
        970       980       990      1000      1010      1020      1030      1040      1050      1060      1070      1080

                        310                                     320                                     330
Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
       1090      1100      1110      1120      1130      1140      1150      1160      1170      1180      1190      1200

                        350                                     360                                     370
A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
       1210      1220      1230      1240      1250      1260      1270      1280      1290      1300      1310      1320

                        390                                     400                                     410
F   F   D   G   T   K   F   D   P   E   K   P   D   E   Y   L   K   S   L   K   I   K   K   V   S   V   G   G   S   H   H   H   H   H   H   *   *
GTTCTTCGACGGCACCAAATTCGACCCAGAAAAGCCAGACGAATATCTGAAATCGCTCAAAATCAAAAAAGTCAGCGTAGGTGGTTCACATCATCATCATCATCATTAATGAAAGGGCGA
CAAGAAGCTGCCGTGGTTTAAGCTGGGTCTTTTCGGTCTGCTTATAGACTTTAGCGAGTTTTAGTTTTTTCAGTCGCATCCACCAAGTGTAGTAGTAGTAGTAGTAATTACTTTCCCGCT
       1330      1340      1350      1360      1370      1380      1390      1400      1410      1420      1430      1440


TATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAA
ATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTT
       1450      1460      1470      1480      1490      1500      1510      1520      1530      1540      1550      1560


CGGGTCTTGAGGGGTTTTTTGCTGAAAGGAGGAACTATATCCGGAGCGACTCCCACGGCACGTTGGCAAGCTCGGAATTCGGCGTAATC
GCCCAGAACTCCCCAAAAAACGACTTTCCTCCTTGATATAGGCCTCGCTGAGGGTGCCGTGCAACCGTTCGAGCCTTAAGCCGCATTAG
       1570      1580      1590      1600      1610      1620      1630      1640
```

FIG. 35 (Continued)

FIG. 36 - Exemplary Expression Construct for avBicarBP5_146C

SEQ ID NO: 118

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                       10
                                                                             M  A  E  Q  A  P  E  V  T  T  V  K  L  G  Y  I  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCTAACAGCT
       130       140       150       160       170       180       190       200       210       220       230       240

                                        30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                                        70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                                       110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                                       150                           160                           170
 T  F  P  H  V  C  Q  D  L  W  I  R  Y  W  L  A  A  G  G  I  D  P  D  A  D  V  K  L  L  T  V  P  A  A  Q  T  V  A  N  M
CACTTTTCCTCATGTATGCCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATACGGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                                       190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                                       230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                    270                                     280                                     290
 Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
        970       980       990      1000      1010      1020      1030      1040      1050      1060      1070      1080

                    310                                     320                                     330
 Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
       1090      1100      1110      1120      1130      1140      1150      1160      1170      1180      1190      1200

                    350                                     360                                     370
 A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
       1210      1220      1230      1240      1250      1260      1270      1280      1290      1300      1310      1320

                    390                                     400                                     410
 F   F   D   G   T   K   F   D   P   E   K   P   D   E   Y   L   K   S   L   K   I   K   K   V   S   V   G   G   S   H   H   H   H   H   H   *   *
GTTCTTCGACGGCACCAAATTCGACCCAGAAAAGCCAGACGAATATCTGAAATCGCTCAAAATCAAAAAAGTCAGCGTAGGTGGTTCACATCATCATCATCATCATTAATGAAAGGGCGA
CAAGAAGCTGCCGTGGTTTAAGCTGGGTCTTTTCGGTCTGCTTATAGACTTTAGCGAGTTTTAGTTTTTTCAGTCGCATCCACCAAGTGTAGTAGTAGTAGTAGTAATTACTTTCCCGCT
       1330      1340      1350      1360      1370      1380      1390      1400      1410      1420      1430      1440


TATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAA
ATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTT
       1450      1460      1470      1480      1490      1500      1510      1520      1530      1540      1550      1560


CGGGTCTTGAGGGGTTTTTTGCTGAAAGGAGGAACTATATCCGGAGCGACTCCCACGGCACGTTGGCAAGCTCGGAATTCGGCGTAATC
GCCCAGAACTCCCCAAAAAACGACTTTCCTCCTTGATATAGGCCTCGCTGAGGGTGCCGTGCAACCGTTCGAGCCTTAAGCCGCATTAG
       1570      1580      1590      1600      1610      1620      1630      1640
```

FIG. 36 (Continued)

FIG. 37 – Exemplary Expression Construct for avBicarBP5_190C

SEQ ID NO: 119

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                         10
                                                                               M  A  E  Q  A  P  E  V  T  T  V  K  L  G  Y  I  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCTAACAGCT
       130       140       150       160       170       180       190       200       210       220       230       240

                              30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                              70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                             110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                             150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                             190                           200                           210
 K  T  G  T  M  D  A  F  S  C  G  D  P  W  P  F  R  L  V  N  D  K  I  G  Y  M  A  A  L  T  A  E  I  W  K  N  H  P  E  E
GAAGACCGGCACAATGGACGCATTTTCCTGCGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGACGCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                             230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                    270                                     280                                     290
Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
        970         980         990        1000        1010        1020        1030        1040        1050        1060        1070        1080

                    310                                     320                                     330
Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
       1090        1100        1110        1120        1130        1140        1150        1160        1170        1180        1190        1200

                    350                                     360                                     370
A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
       1210        1220        1230        1240        1250        1260        1270        1280        1290        1300        1310        1320

                    390                                     400                                     410
F   F   D   G   T   K   F   D   P   E   K   P   D   E   Y   L   K   S   L   K   I   K   K   V   S   V   G   G   S   H   H   H   H   H   H   *   *
GTTCTTCGACGGCACCAAATTCGACCCAGAAAAGCCAGACGAATATCTGAAATCGCTCAAAATCAAAAAAGTCAGCGTAGGTGGTTCACATCATCATCATCATCATTAATGAAAGGGCGA
CAAGAAGCTGCCGTGGTTTAAGCTGGGTCTTTTCGGTCTGCTTATAGACTTTAGCGAGTTTTAGTTTTTTCAGTCGCATCCACCAAGTGTAGTAGTAGTAGTAGTAATTACTTTCCCGCT
       1330        1340        1350        1360        1370        1380        1390        1400        1410        1420        1430        1440

TATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAA
ATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTT
       1450        1460        1470        1480        1490        1500        1510        1520        1530        1540        1550        1560

CGGGTCTTGAGGGGTTTTTTGCTGAAAGGAGGAACTATATCCGGAGCGACTCCCACGGCACGTTGGCAAGCTCGGAATTCGGCGTAATC
GCCCAGAACTCCCCAAAAAACGACTTTCCTCCTTGATATAGGCCTCGCTGAGGGTGCCGTGCAACCGTTCGAGCCTTAAGCCGCATTAG
       1570        1580        1590        1600        1610        1620        1630        1640
```

FIG. 37 (Continued)

FIG. 38 - Exemplary Expression Construct for avBicarBP5_194C

SEQ ID NO: 120

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                           10
                                                                       M  A  E  Q  A  P  E  V  T  T  V  K  L  G  Y  I  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCTAACAGCT
       130       140       150       160       170       180       190       200       210       220       230       240

                            30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                            70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                           110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                           150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                           190                           200                           210
 K  T  G  T  M  D  A  F  S  T  G  D  P  C  P  F  R  L  V  N  D  K  I  G  Y  M  A  A  L  T  A  E  I  W  K  N  H  P  E  E
GAAGACCGGCACAATGGACGCATTTTCCACGGGCGACCCATGCCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACGGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                           230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                      270                                280                                290
 Q  I  L  A  G  R  N  Y  F  N  L  N  N  P  E  I  L  A  D  P  Y  V  G  K  Y  D  M  G  D  G  R  K  I  D  D  K  S  M  A  A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
      970       980       990      1000      1010      1020      1030      1040      1050      1060      1070      1080

                      310                                320                                330
 Y  Y  W  K  D  E  K  G  S  V  S  Y  P  Y  K  S  H  D  L  W  F  I  T  E  N  V  R  W  G  F  L  P  K  D  Y  L  A  N  G  A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
     1090      1100      1110      1120      1130      1140      1150      1160      1170      1180      1190      1200

                      350                                360                                370
 A  K  A  K  E  L  I  D  K  V  N  R  E  D  I  W  K  E  A  A  K  E  A  G  I  A  A  A  D  I  P  T  S  T  S  R  G  V  E  E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
     1210      1220      1230      1240      1250      1260      1270      1280      1290      1300      1310      1320

                      390                                400                                410
 F  F  D  G  T  K  F  D  P  E  K  P  D  E  Y  L  K  S  L  K  I  K  K  V  S  V  G  G  S  H  H  H  H  H  H  *  *
GTTCTTCGACGGCACCAAATTCGACCCAGAAAAGCCAGACGAATATCTGAAATCGCTCAAAATCAAAAAAGTCAGCGTAGGTGGTTCACATCATCATCATCATCATTAATGAAAGGGCGA
CAAGAAGCTGCCGTGGTTTAAGCTGGGTCTTTTCGGTCTGCTTATAGACTTTAGCGAGTTTTAGTTTTTTCAGTCGCATCCACCAAGTGTAGTAGTAGTAGTAGTAATTACTTTCCCGCT
     1330      1340      1350      1360      1370      1380      1390      1400      1410      1420      1430      1440


TATCCAGCACACTGGCGGCCGTTACTAGTGGATCCGGCTGCTAACAAAGCCCGAAAGGAAGCTGAGTTGGCTGCTGCCACCGCTGAGCAATAACTAGCATAACCCCTTGGGGCCTCTAAA
ATAGGTCGTGTGACCGCCGGCAATGATCACCTAGGCCGACGATTGTTTCGGGCTTTCCTTCGACTCAACCGACGACGGTGGCGACTCGTTATTGATCGTATTGGGGAACCCCGGAGATTT
     1450      1460      1470      1480      1490      1500      1510      1520      1530      1540      1550      1560


CGGGTCTTGAGGGGTTTTTTGCTGAAAGGAGGAACTATATCCGGAGCGACTCCCACGGCACGTTGGCAAGCTCGGAATTCGGCGTAATC
GCCCAGAACTCCCCAAAAAACGACTTTCCTCCTTGATATAGGCCTCGCTGAGGGTGCCGTGCAACCGTTCGAGCCTTAAGCCGCATTAG
     1570      1580      1590      1600      1610      1620      1630      1640
```

FIG. 38 (Continued)

FIG. 39 - Exemplary Expression Construct for teFeBP3_A8C

SEQ ID NO: 121

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                            10                  20
                                                   M  V  I  N  V  Y  S  C  R  H  Y  D  T  D  K  A  L  Y  N  T  F  T  Q  Q
GGTTTCCCTCTAGAAATAATTTTGTTTAACTTTAAGAAGGAGATATACCATGGTAATTAATGTATATAGTTGCCGTCATTACGACACTGACAAGGCTCTCTATAATACCTTCACCCAACA
CCAAAGGGAGATCTTTATTAAAACAAATTGAAATTCTTCCTCTATATGGTACCATTAATTACATATATCAACGGCAGTAATGCTGTGACTGTTCCGAGAGATATTATGGAAGTGGGTTGT
       130       140       150       160       170       180       190       200       210       220       230       240

              30                            40                            50                            60
 T  G  I  R  V  N  I  I  E  A  E  A  D  A  L  I  E  R  I  R  S  E  G  S  R  T  P  A  D  V  L  I  T  V  D  A  G  R  L  W
AACCGGGATTCGTGTAAACATCATTGAGGCTGAGGCAGATGCCCTCATTGAACGTATTCGTTCTGAAGGTTCGCGCACCCCAGCCGATGTACTCATTACAGTAGACGCGGGTCGCTTATG
TTGGCCCTAAGCACATTTGTAGTAACTCCGACTCCGTCTACGGGAGTAACTTGCATAAGCAAGACTTCCAAGCGCGTGGGGTCGGCTACATGAGTAATGTCATCTGCGCCCAGCGAATAC
       250       260       270       280       290       300       310       320       330       340       350       360

              70                            80                            90                           100
 R  A  Q  E  A  G  I  L  Q  P  I  Q  S  R  V  L  N  S  V  V  P  A  N  L  R  E  P  Q  G  H  W  F  G  L  S  R  R  V  R  V
GCGTGCGCAAGAAGCTGGCATCTTACAGCCGATTCAATCGCGTGTTTTAAACAGTGTAGTACCAGCCAACCTCCGGGAACCACAGGGTCACTGGTTCGGTCTCTCCCGTCGTGTTCGCGT
CGCACGCGTTCTTCGACCGTAGAATGTCGGCTAAGTTAGCGCACAAAATTTGTCACATCATGGTCGGTTGGAGGCCCTTGGTGTCCCAGTGACCAAGCCAGAGAGGGCAGCACAAGCGCA
       370       380       390       400       410       420       430       440       450       460       470       480

             110                           120                           130                           140
 L  I  Y  N  K  S  R  V  N  P  S  Q  L  S  T  Y  E  D  L  A  N  P  K  W  R  R  Q  I  L  T  R  S  S  S  N  I  Y  N  Q  S
TCTGATTTATAACAAGTCCCGTGTTAATCCATCTCAGCTTTCCACATACGAAGATTTAGCTAATCCGAAGTGGCGCCGTCAGATCCTGACACGTTCTTCAAGCAACATTTACAACCAATC
AGACTAAATATTGTTCAGGGCACAATTAGGTAGAGTCGAAAGGTGTATGCTTCTAAATCGATTAGGCTTCACCGCGGCAGTCTAGGACTGTGCAAGAAGTTCGTTGTAAATGTTGGTTAG
       490       500       510       520       530       540       550       560       570       580       590       600

             150                           160                           170                           180
 L  T  G  S  L  L  A  I  H  G  A  Q  K  T  E  Q  W  A  R  G  L  V  Q  N  F  A  R  P  P  E  G  N  D  T  A  Q  I  R  A  S
GTTGACAGGTTCCTTACTCGCCATTCACGGGGCACAGAAGACCGAACAATGGGCACGTGGCTTAGTACAGAACTTCGCACGTCCACCGGAGGGGAATGACACAGCTCAAATTCGTGCAAG
CAACTGTCCAAGGAATGAGCGGTAAGTGCCCCGTGTCTTCTGGCTTGTTACCCGTGCACCGAATCATGTCTTGAAGCGTGCAGGTGGCCTCCCCTTACTGTGTCGAGTTTAAGCACGTTC
       610       620       630       640       650       660       670       680       690       700       710       720

             190                           200                           210                           220
 A  E  G  V  G  S  V  A  I  A  N  H  Y  Y  L  A  R  L  I  A  S  D  K  E  Q  D  R  A  V  A  A  K  V  G  L  F  F  P  N  Q
TGCAGAGGGCGTTGGCTCAGTAGCGATCGCCAATCACTATTACCTCGCCCGTTTAATTGCCAGTGACAAGGAGCAAGACCGTGCGGTGGCCGCAAAGGTGGGCCTCTTTTTCCCGAACCA
ACGTCTCCCGCAACCGAGTCATCGCTAGCGGTTAGTGATAATGGAGCGGGCAAATTAACGGTCACTGTTCCTCGTTCTGGCACGCCACCGGCGTTTCCACCCGGAGAAAAAGGGCTTGGT
       730       740       750       760       770       780       790       800       810       820       830       840

             230                           240                           250                           260
 R  D  R  G  A  H  V  N  I  S  G  A  G  V  V  A  G  A  P  N  R  Q  G  A  I  R  F  L  E  Y  L  V  S  P  K  A  Q  E  M  F
ACGTGACCGCGGTGCACATGTCAATATCAGTGGGGCAGGTGTAGTCGCCGGCGCTCCTAACCGTCAAGGCGCAATTCGGTTCTTAGAGTACCTGGTCTCCCCAAAGGCCCAGGAAATGTT
TGCACTGGCGCCACGTGTACAGTTATAGTCACCCCGTCCACATCAGCGGCCGCGAGGATTGGCAGTTCCGCGTTAAGCCAAGAATCTCATGGACCAGAGGGGTTTCCGGGTCCTTTACAA
       850       860       870       880       890       900       910       920       930       940       950       960
```

```
                 270                                     280                                     290                                     300
 A   M   A   N   F   E   Y   P   V   R   A   G   V   P   V   H   P   I   V   K   Q   F   G   N   F   R   G   Q   N   V   N   A   A   V   F   G   R   N   N   A
TGCTATGGCTAACTTTGAGTACCCGGTACGCGCAGGCGTCCCAGTCCACCCTATCGTCAAGCAATTCGGCAACTTTCGTGGTCAAAATGTCAACGCAGCAGTATTCGGGCGCAACAACGC
ACGATACCGATTGAAACTCATGGGCCATGCGCGTCCGCAGGGTCAGGTGGGATAGCAGTTCGTTAAGCCGTTGAAAGCACCAGTTTTACAGTTGCGTCGTCATAAGCCCGCGTTGTTGCG
        970          980          990         1000         1010         1020         1030         1040         1050         1060         1070         1080

                 310                                     320
 E   A   L   R   I   M   D   R   A   G   W   R   G   G   S   H   H   H   H   H   H   *   *
AGAAGCACTTCGTATCATGGACCGGGCCGGTTGGCGTGGCGGTAGTCATCATCATCATCATCATTAATGAAAGGGCGATATCCAGCACACTGGCGGCCGTTACTAGTGGATCCGGCTGCT
TCTTCGTGAAGCATAGTACCTGGCCCGGCCAACCGCACCGCCATCAGTAGTAGTAGTAGTAGTAATTACTTTCCCGCTATAGGTCGTGTGACCGCCGGCAATGATCACCTAGGCCGACGA
       1090         1100         1110         1120         1130         1140         1150         1160         1170         1180         1190         1200


AACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCC
TTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGG
       1210         1220         1230         1240         1250         1260         1270         1280         1290         1300         1310         1320


GGAGCGACTCCCACGGCACGTTGGCAAGCTCG
CCTCGCTGAGGGTGCCGTGCAACCGTTCGAGC
       1330         1340         1350
```

FIG. 39 (Continued)

FIG. 40 – Exemplary Expression Construct for teFeBP3_H10C

SEQ ID NO: 122

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                       10                            20
                                                   M  V  I  N  V  Y  S  A  R  C  Y  D  T  D  K  A  L  Y  N  T  F  T  Q  Q
GGTTTCCCTCTAGAAATAATTTTGTTTAACTTTAAGAAGGAGATATACCATGGTAATTAATGTATATAGTGCACGTTGCTACGACACTGACAAGGCTCTCTATAATACCTTCACCCAACA
CCAAAGGGAGATCTTTATTAAAACAAATTGAAATTCTTCCTCTATATGGTACCATTAATTACATATATCACGTGCAACGATGCTGTGACTGTTCCGAGAGATATTATGGAAGTGGGTTGT
       130       140       150       160       170       180       190       200       210       220       230       240

             30                            40                            50                            60
 T  G  I  R  V  N  I  I  E  A  E  A  D  A  L  I  E  R  I  R  S  E  G  S  R  T  P  A  D  V  L  I  T  V  D  A  G  R  L  W
AACCGGGATTCGTGTAAACATCATTGAGGCTGAGGCAGATGCCCTCATTGAACGTATTCGTTCTGAAGGTTCGCGCACCCCAGCCGATGTACTCATTACAGTAGACGCGGGTCGCTTATG
TTGGCCCTAAGCACATTTGTAGTAACTCCGACTCCGTCTACGGGAGTAACTTGCATAAGCAAGACTTCCAAGCGCGTGGGGTCGGCTACATGAGTAATGTCATCTGCGCCCAGCGAATAC
       250       260       270       280       290       300       310       320       330       340       350       360

             70                            80                            90                           100
 R  A  Q  E  A  G  I  L  Q  P  I  Q  S  R  V  L  N  S  V  V  P  A  N  L  R  E  P  Q  G  H  W  F  G  L  S  R  R  V  R  V
GCGTGCGCAAGAAGCTGGCATCTTACAGCCGATTCAATCGCGTGTTTTAAACAGTGTAGTACCAGCCAACCTCCGGGAACCACAGGGTCACTGGTTCGGTCTCTCCCGTCGTGTTCGCGT
CGCACGCGTTCTTCGACCGTAGAATGTCGGCTAAGTTAGCGCACAAAATTTGTCACATCATGGTCGGTTGGAGGCCCTTGGTGTCCCAGTGACCAAGCCAGAGAGGGCAGCACAAGCGCA
       370       380       390       400       410       420       430       440       450       460       470       480

            110                           120                           130                           140
 L  I  Y  N  K  S  R  V  N  P  S  Q  L  S  T  Y  E  D  L  A  N  P  K  W  R  R  Q  I  L  T  R  S  S  S  N  I  Y  N  Q  S
TCTGATTTATAACAAGTCCCGTGTTAATCCATCTCAGCTTTCCACATACGAAGATTTAGCTAATCCGAAGTGGCGCCGTCAGATCCTGACACGTTCTTCAAGCAACATTTACAACCAATC
AGACTAAATATTGTTCAGGGCACAATTAGGTAGAGTCGAAAGGTGTATGCTTCTAAATCGATTAGGCTTCACCGCGGCAGTCTAGGACTGTGCAAGAAGTTCGTTGTAAATGTTGGTTAG
       490       500       510       520       530       540       550       560       570       580       590       600

            150                           160                           170                           180
 L  T  G  S  L  L  A  I  H  G  A  Q  K  T  E  Q  W  A  R  G  L  V  Q  N  F  A  R  P  P  E  G  N  D  T  A  Q  I  R  A  S
GTTGACAGGTTCCTTACTCGCCATTCACGGGGCACAGAAGACCGAACAATGGGCACGTGGCTTAGTACAGAACTTCGCACGTCCACCGGAGGGGAATGACACAGCTCAAATTCGTGCAAG
CAACTGTCCAAGGAATGAGCGGTAAGTGCCCCGTGTCTTCTGGCTTGTTACCCGTGCACCGAATCATGTCTTGAAGCGTGCAGGTGGCCTCCCCTTACTGTGTCGAGTTTAAGCACGTTC
       610       620       630       640       650       660       670       680       690       700       710       720

            190                           200                           210                           220
 A  E  G  V  G  S  V  A  I  A  N  H  Y  Y  L  A  R  L  I  A  S  D  K  E  Q  D  R  A  V  A  A  K  V  G  L  F  F  P  N  Q
TGCAGAGGGCGTTGGCTCAGTAGCGATCGCCAATCACTATTACCTCGCCCGTTTAATTGCCAGTGACAAGGAGCAAGACCGTGCGGTGGCCGCAAAGGTGGGCCTCTTTTTCCCGAACCA
ACGTCTCCCGCAACCGAGTCATCGCTAGCGGTTAGTGATAATGGAGCGGGCAAATTAACGGTCACTGTTCCTCGTTCTGGCACGCCACCGGCGTTTCCACCCGGAGAAAAAGGGCTTGGT
       730       740       750       760       770       780       790       800       810       820       830       840

            230                           240                           250                           260
 R  D  R  G  A  H  V  N  I  S  G  A  G  V  V  A  G  A  P  N  R  Q  G  A  I  R  F  L  E  Y  L  V  S  P  K  A  Q  E  M  F
ACGTGACCGCGGTGCACATGTCAATATCAGTGGGGCAGGTGTAGTCGCCGGCGCTCCTAACCGTCAAGGCGCAATTCGGTTCTTAGAGTACCTGGTCTCCCCAAAGGCCCAGGAAATGTT
TGCACTGGCGCCACGTGTACAGTTATAGTCACCCCGTCCACATCAGCGGCCGCGAGGATTGGCAGTTCCGCGTTAAGCCAAGAATCTCATGGACCAGAGGGGTTTCCGGGTCCTTTACAA
       850       860       870       880       890       900       910       920       930       940       950       960
```

```
                 270                                     280                                     290                                     300
 A   M   A   N   F   E   Y   P   V   R   A   G   V   P   V   H   P   I   V   K   Q   F   G   N   F   R   G   Q   N   V   N   A   A   V   F   G   R   N   N   A
TGCTATGGCTAACTTTGAGTACCCGGTACGCGCAGGCGTCCCAGTCCACCCTATCGTCAAGCAATTCGGCAACTTTCGTGGTCAAAATGTCAACGCAGCAGTATTCGGGCGCAACAACGC
ACGATACCGATTGAAACTCATGGGCCATGCGCGTCCGCAGGGTCAGGTGGGATAGCAGTTCGTTAAGCCGTTGAAAGCACCAGTTTTACAGTTGCGTCGTCATAAGCCCGCGTTGTTGCG
       970       980       990      1000      1010      1020      1030      1040      1050      1060      1070      1080

                 310                                     320
 E   A   L   R   I   M   D   R   A   G   W   R   G   G   S   H   H   H   H   H   H   *   *
AGAAGCACTTCGTATCATGGACCGGGCCGGTTGGCGTGGCGGTAGTCATCATCATCATCATCATTAATGAAAGGGCGATATCCAGCACACTGGCGGCCGTTACTAGTGGATCCGGCTGCT
TCTTCGTGAAGCATAGTACCTGGCCCGGCCAACCGCACCGCCATCAGTAGTAGTAGTAGTAGTAATTACTTTCCCGCTATAGGTCGTGTGACCGCCGGCAATGATCACCTAGGCCGACGA
      1090      1100      1110      1120      1130      1140      1150      1160      1170      1180      1190      1200


AACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCC
TTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGG
      1210      1220      1230      1240      1250      1260      1270      1280      1290      1300      1310      1320


GGAGCGACTCCCACGGCACGTTGGCAAGCTCG
CCTCGCTGAGGGTGCCGTGCAACCGTTCGAGC
      1330      1340      1350
```

FIG. 40 (Continued)

FIG. 41 – Exemplary Expression Construct for teFeBP3_D12C

SEQ ID NO: 123

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                       10                            20
                                                    M  V  I  N  V  Y  S  A  R  H  Y  C  T  D  K  A  L  Y  N  T  F  T  Q  Q
GGTTTCCCTCTAGAAATAATTTTGTTTAACTTTAAGAAGGAGATATACCATGGTAATTAATGTATATAGTGCACGTCATTACTGCACTGACAAGGCTCTCTATAATACCTTCACCCAACA
CCAAAGGGAGATCTTTATTAAAACAAATTGAAATTCTTCCTCTATATGGTACCATTAATTACATATATCACGTGCAGTAATGACGTGACTGTTCCGAGAGATATTATGGAAGTGGGTTGT
       130       140       150       160       170       180       190       200       210       220       230       240

            30                            40                            50                            60
 T  G  I  R  V  N  I  I  E  A  E  A  D  A  L  I  E  R  I  R  S  E  G  S  R  T  P  A  D  V  L  I  T  V  D  A  G  R  L  W
AACCGGGATTCGTGTAAACATCATTGAGGCTGAGGCAGATGCCCTCATTGAACGTATTCGTTCTGAAGGTTCGCGCACCCCAGCCGATGTACTCATTACAGTAGACGCGGGTCGCTTATG
TTGGCCCTAAGCACATTTGTAGTAACTCCGACTCCGTCTACGGGAGTAACTTGCATAAGCAAGACTTCCAAGCGCGTGGGGTCGGCTACATGAGTAATGTCATCTGCGCCCAGCGAATAC
       250       260       270       280       290       300       310       320       330       340       350       360

            70                            80                            90                           100
 R  A  Q  E  A  G  I  L  Q  P  I  Q  S  R  V  L  N  S  V  V  P  A  N  L  R  E  P  Q  G  H  W  F  G  L  S  R  R  V  R  V
GCGTGCGCAAGAAGCTGGCATCTTACAGCCGATTCAATCGCGTGTTTTAAACAGTGTAGTACCAGCCAACCTCCGGGAACCACAGGGTCACTGGTTCGGTCTCTCCCGTCGTGTTCGCGT
CGCACGCGTTCTTCGACCGTAGAATGTCGGCTAAGTTAGCGCACAAAATTTGTCACATCATGGTCGGTTGGAGGCCCTTGGTGTCCCAGTGACCAAGCCAGAGAGGGCAGCACAAGCGCA
       370       380       390       400       410       420       430       440       450       460       470       480

           110                           120                           130                           140
 L  I  Y  N  K  S  R  V  N  P  S  Q  L  S  T  Y  E  D  L  A  N  P  K  W  R  R  Q  I  L  T  R  S  S  S  N  I  Y  N  Q  S
TCTGATTTATAACAAGTCCCGTGTTAATCCATCTCAGCTTTCCACATACGAAGATTTAGCTAATCCGAAGTGGCGCCGTCAGATCCTGACACGTTCTTCAAGCAACATTTACAACCAATC
AGACTAAATATTGTTCAGGGCACAATTAGGTAGAGTCGAAAGGTGTATGCTTCTAAATCGATTAGGCTTCACCGCGGCAGTCTAGGACTGTGCAAGAAGTTCGTTGTAAATGTTGGTTAG
       490       500       510       520       530       540       550       560       570       580       590       600

           150                           160                           170                           180
 L  T  G  S  L  L  A  I  H  G  A  Q  K  T  E  Q  W  A  R  G  L  V  Q  N  F  A  R  P  P  E  G  N  D  T  A  Q  I  R  A  S
GTTGACAGGTTCCTTACTCGCCATTCACGGGGCACAGAAGACCGAACAATGGGCACGTGGCTTAGTACAGAACTTCGCACGTCCACCGGAGGGGAATGACACAGCTCAAATTCGTGCAAG
CAACTGTCCAAGGAATGAGCGGTAAGTGCCCCGTGTCTTCTGGCTTGTTACCCGTGCACCGAATCATGTCTTGAAGCGTGCAGGTGGCCTCCCCTTACTGTGTCGAGTTTAAGCACGTTC
       610       620       630       640       650       660       670       680       690       700       710       720

           190                           200                           210                           220
 A  E  G  V  G  S  V  A  I  A  N  H  Y  Y  L  A  R  L  I  A  S  D  K  E  Q  D  R  A  V  A  A  K  V  G  L  F  F  P  N  Q
TGCAGAGGGCGTTGGCTCAGTAGCGATCGCCAATCACTATTACCTCGCCCGTTTAATTGCCAGTGACAAGGAGCAAGACCGTGCGGTGGCCGCAAAGGTGGGCCTCTTTTTCCCGAACCA
ACGTCTCCCGCAACCGAGTCATCGCTAGCGGTTAGTGATAATGGAGCGGGCAAATTAACGGTCACTGTTCCTCGTTCTGGCACGCCACCGGCGTTTCCACCCGGAGAAAAAGGGCTTGGT
       730       740       750       760       770       780       790       800       810       820       830       840

           230                           240                           250                           260
 R  D  R  G  A  H  V  N  I  S  G  A  G  V  V  A  G  A  P  N  R  Q  G  A  I  R  F  L  E  Y  L  V  S  P  K  A  Q  E  M  F
ACGTGACCGCGGTGCACATGTCAATATCAGTGGGGCAGGTGTAGTCGCCGGCGCTCCTAACCGTCAAGGCGCAATTCGGTTCTTAGAGTACCTGGTCTCCCCAAAGGCCCAGGAAATGTT
TGCACTGGCGCCACGTGTACAGTTATAGTCACCCCGTCCACATCAGCGGCCGCGAGGATTGGCAGTTCCGCGTTAAGCCAAGAATCTCATGGACCAGAGGGGTTTCCGGGTCCTTTACAA
       850       860       870       880       890       900       910       920       930       940       950       960
```

```
                    270                                     280                                     290                                     300
 A   M   A   N   F   E   Y   P   V   R   A   G   V   P   V   H   P   I   V   K   Q   F   G   N   F   R   G   Q   N   V   N   A   A   V   F   G   R   N   N   A
TGCTATGGCTAACTTTGAGTACCCGGTACGCGCAGGCGTCCCAGTCCACCCTATCGTCAAGCAATTCGGCAACTTTCGTGGTCAAAATGTCAACGCAGCAGTATTCGGGCGCAACAACGC
ACGATACCGATTGAAACTCATGGGCCATGCGCGTCCGCAGGGTCAGGTGGGATAGCAGTTCGTTAAGCCGTTGAAAGCACCAGTTTTACAGTTGCGTCGTCATAAGCCCGCGTTGTTGCG
         970          980          990         1000         1010         1020         1030         1040         1050         1060         1070         1080

                    310                                     320
 E   A   L   R   I   M   D   R   A   G   W   R   G   G   S   H   H   H   H   H   H   *   *
AGAAGCACTTCGTATCATGGACCGGGCCGGTTGGCGTGGCGGTAGTCATCATCATCATCATCATTAATGAAAGGGCGATATCCAGCACACTGGCGGCCGTTACTAGTGGATCCGGCTGCT
TCTTCGTGAAGCATAGTACCTGGCCCGGCCAACCGCACCGCCATCAGTAGTAGTAGTAGTAGTAATTACTTTCCCGCTATAGGTCGTGTGACCGCCGGCAATGATCACCTAGGCCGACGA
        1090         1100         1110         1120         1130         1140         1150         1160         1170         1180         1190         1200

AACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCC
TTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGG
        1210         1220         1230         1240         1250         1260         1270         1280         1290         1300         1310         1320

GGAGCGACTCCCACGGCACGTTGGCAAGCTCG
CCTCGCTGAGGGTGCCGTGCAACCGTTCGAGC
        1330         1340         1350
```

FIG. 41 (Continued)

FIG. 42 - Exemplary Expression Construct for teFeBP3_T13C

SEQ ID NO: 124

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                           10                            20
                                                  M  V  I  N  V  Y  S  A  R  H  Y  D  C  D  K  A  L  Y  N  T  F  T  Q  Q
GGTTTCCCTCTAGAAATAATTTTGTTTAACTTTAAGAAGGAGATATACCATGGTAATTAATGTATATAGTGCACGTCATTACGACTGCGACAAGGCTCTCTATAATACCTTCACCCAACA
CCAAAGGGAGATCTTTATTAAAACAAATTGAAATTCTTCCTCTATATGGTACCATTAATTACATATATCACGTGCAGTAATGCTGACGCTGTTCCGAGAGATATTATGGAAGTGGGTTGT
       130       140       150       160       170       180       190       200       210       220       230       240

               30                            40                            50                            60
 T  G  I  R  V  N  I  I  E  A  E  A  D  A  L  I  E  R  I  R  S  E  G  S  R  T  P  A  D  V  L  I  T  V  D  A  G  R  L  W
AACCGGGATTCGTGTAAACATCATTGAGGCTGAGGCAGATGCCCTCATTGAACGTATTCGTTCTGAAGGTTCGCGCACCCCAGCCGATGTACTCATTACAGTAGACGCGGGTCGCTTATG
TTGGCCCTAAGCACATTTGTAGTAACTCCGACTCCGTCTACGGGAGTAACTTGCATAAGCAAGACTTCCAAGCGCGTGGGGTCGGCTACATGAGTAATGTCATCTGCGCCCAGCGAATAC
       250       260       270       280       290       300       310       320       330       340       350       360

               70                            80                            90                           100
 R  A  Q  E  A  G  I  L  Q  P  I  Q  S  R  V  L  N  S  V  V  P  A  N  L  R  E  P  Q  G  H  W  F  G  L  S  R  R  V  R  V
GCGTGCGCAAGAAGCTGGCATCTTACAGCCGATTCAATCGCGTGTTTTAAACAGTGTAGTACCAGCCAACCTCCGGGAACCACAGGGTCACTGGTTCGGTCTCTCCCGTCGTGTTCGCGT
CGCACGCGTTCTTCGACCGTAGAATGTCGGCTAAGTTAGCGCACAAAATTTGTCACATCATGGTCGGTTGGAGGCCCTTGGTGTCCCAGTGACCAAGCCAGAGAGGGCAGCACAAGCGCA
       370       380       390       400       410       420       430       440       450       460       470       480

              110                           120                           130                           140
 L  I  Y  N  K  S  R  V  N  P  S  Q  L  S  T  Y  E  D  L  A  N  P  K  W  R  R  Q  I  L  T  R  S  S  S  N  I  Y  N  Q  S
TCTGATTTATAACAAGTCCCGTGTTAATCCATCTCAGCTTTCCACATACGAAGATTTAGCTAATCCGAAGTGGCGCCGTCAGATCCTGACACGTTCTTCAAGCAACATTTACAACCAATC
AGACTAAATATTGTTCAGGGCACAATTAGGTAGAGTCGAAAGGTGTATGCTTCTAAATCGATTAGGCTTCACCGCGGCAGTCTAGGACTGTGCAAGAAGTTCGTTGTAAATGTTGGTTAG
       490       500       510       520       530       540       550       560       570       580       590       600

              150                           160                           170                           180
 L  T  G  S  L  L  A  I  H  G  A  Q  K  T  E  Q  W  A  R  G  L  V  Q  N  F  A  R  P  P  E  G  N  D  T  A  Q  I  R  A  S
GTTGACAGGTTCCTTACTCGCCATTCACGGGGCACAGAAGACCGAACAATGGGCACGTGGCTTAGTACAGAACTTCGCACGTCCACCGGAGGGGAATGACACAGCTCAAATTCGTGCAAG
CAACTGTCCAAGGAATGAGCGGTAAGTGCCCCGTGTCTTCTGGCTTGTTACCCGTGCACCGAATCATGTCTTGAAGCGTGCAGGTGGCCTCCCCTTACTGTGTCGAGTTTAAGCACGTTC
       610       620       630       640       650       660       670       680       690       700       710       720

              190                           200                           210                           220
 A  E  G  V  G  S  V  A  I  A  N  H  Y  Y  L  A  R  L  I  A  S  D  K  E  Q  D  R  A  V  A  A  K  V  G  L  F  F  P  N  Q
TGCAGAGGGCGTTGGCTCAGTAGCGATCGCCAATCACTATTACCTCGCCCGTTTAATTGCCAGTGACAAGGAGCAAGACCGTGCGGTGGCCGCAAAGGTGGGCCTCTTTTTCCCGAACCA
ACGTCTCCCGCAACCGAGTCATCGCTAGCGGTTAGTGATAATGGAGCGGGCAAATTAACGGTCACTGTTCCTCGTTCTGGCACGCCACCGGCGTTTCCACCCGGAGAAAAAGGGCTTGGT
       730       740       750       760       770       780       790       800       810       820       830       840

              230                           240                           250                           260
 R  D  R  G  A  H  V  N  I  S  G  A  G  V  V  A  G  A  P  N  R  Q  G  A  I  R  F  L  E  Y  L  V  S  P  K  A  Q  E  M  F
ACGTGACCGCGGTGCACATGTCAATATCAGTGGGGCAGGTGTAGTCGCCGGCGCTCCTAACCGTCAAGGCGCAATTCGGTTCTTAGAGTACCTGGTCTCCCCAAAGGCCCAGGAAATGTT
TGCACTGGCGCCACGTGTACAGTTATAGTCACCCCGTCCACATCAGCGGCCGCGAGGATTGGCAGTTCCGCGTTAAGCCAAGAATCTCATGGACCAGAGGGGTTTCCGGGTCCTTTACAA
       850       860       870       880       890       900       910       920       930       940       950       960
```

```
                 270                                     280                                     290                                     300
 A   M   A   N   F   E   Y   P   V   R   A   G   V   P   V   H   P   I   V   K   Q   F   G   N   F   R   G   Q   N   V   N   A   A   V   F   G   R   N   N   A
TGCTATGGCTAACTTTGAGTACCCGGTACGCGCAGGCGTCCCAGTCCACCCTATCGTCAAGCAATTCGGCAACTTTCGTGGTCAAAATGTCAACGCAGCAGTATTCGGGCGCAACAACGC
ACGATACCGATTGAAACTCATGGGCCATGCGCGTCCGCAGGGTCAGGTGGGATAGCAGTTCGTTAAGCCGTTGAAAGCACCAGTTTTACAGTTGCGTCGTCATAAGCCCGCGTTGTTGCG
        970       980       990      1000      1010      1020      1030      1040      1050      1060      1070      1080

                 310                                     320
 E   A   L   R   I   M   D   R   A   G   W   R   G   G   S   H   H   H   H   H   H   *   *
AGAAGCACTTCGTATCATGGACCGGGCCGGTTGGCGTGGCGGTAGTCATCATCATCATCATCATTAATGAAAGGGCGATATCCAGCACACTGGCGGCCGTTACTAGTGGATCCGGCTGCT
TCTTCGTGAAGCATAGTACCTGGCCCGGCCAACCGCACCGCCATCAGTAGTAGTAGTAGTAGTAATTACTTTCCCGCTATAGGTCGTGTGACCGCCGGCAATGATCACCTAGGCCGACGA
       1090      1100      1110      1120      1130      1140      1150      1160      1170      1180      1190      1200


AACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCC
TTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGG
       1210      1220      1230      1240      1250      1260      1270      1280      1290      1300      1310      1320


GGAGCGACTCCCACGGCACGTTGGCAAGCTCG
CCTCGCTGAGGGTGCCGTGCAACCGTTCGAGC
       1330      1340      1350
```

FIG. 42 (Continued)

FIG. 43 - Exemplary Expression Construct for teFeBP3_A36C

SEQ ID NO: 125

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                              10                            20
                                                           M  V  I  N  V  Y  S  A  R  H  Y  D  T  D  K  A  L  Y  N  T  F  T  Q  Q
GGTTTCCCTCTAGAAATAATTTTGTTTAACTTTAAGAAGGAGATATACCATGGTAATTAATGTATATAGTGCACGTCATTACGACACTGACAAGGCTCTCTATAATACCTTCACCCAACA
CCAAAGGGAGATCTTTATTAAAACAAATTGAAATTCTTCCTCTATATGGTACCATTAATTACATATATCACGTGCAGTAATGCTGTGACTGTTCCGAGAGATATTATGGAAGTGGGTTGT
       130       140       150       160       170       180       190       200       210       220       230       240

              30                            40                            50                            60
 T  G  I  R  V  N  I  I  E  A  E  C  D  A  L  I  E  R  I  R  S  E  G  S  R  T  P  A  D  V  L  I  T  V  D  A  G  R  L  W
AACCGGGATTCGTGTAAACATCATTGAGGCTGAGTGCGATGCCCTCATTGAACGTATTCGTTCTGAAGGTTCGCGCACCCCAGCCGATGTACTCATTACAGTAGACGCGGGTCGCTTATG
TTGGCCCTAAGCACATTTGTAGTAACTCCGACTCACGCTACGGGAGTAACTTGCATAAGCAAGACTTCCAAGCGCGTGGGGTCGGCTACATGAGTAATGTCATCTGCGCCCAGCGAATAC
       250       260       270       280       290       300       310       320       330       340       350       360

              70                            80                            90                           100
 R  A  Q  E  A  G  I  L  Q  P  I  Q  S  R  V  L  N  S  V  V  P  A  N  L  R  E  P  Q  G  H  W  F  G  L  S  R  R  V  R  V
GCGTGCGCAAGAAGCTGGCATCTTACAGCCGATTCAATCGCGTGTTTTAAACAGTGTAGTACCAGCCAACCTCCGGGAACCACAGGGTCACTGGTTCGGTCTCTCCCGTCGTGTTCGCGT
CGCACGCGTTCTTCGACCGTAGAATGTCGGCTAAGTTAGCGCACAAAATTTGTCACATCATGGTCGGTTGGAGGCCCTTGGTGTCCCAGTGACCAAGCCAGAGAGGGCAGCACAAGCGCA
       370       380       390       400       410       420       430       440       450       460       470       480

             110                           120                           130                           140
 L  I  Y  N  K  S  R  V  N  P  S  Q  L  S  T  Y  E  D  L  A  N  P  K  W  R  R  Q  I  L  T  R  S  S  S  N  I  Y  N  Q  S
TCTGATTTATAACAAGTCCCGTGTTAATCCATCTCAGCTTTCCACATACGAAGATTTAGCTAATCCGAAGTGGCGCCGTCAGATCCTGACACGTTCTTCAAGCAACATTTACAACCAATC
AGACTAAATATTGTTCAGGGCACAATTAGGTAGAGTCGAAAGGTGTATGCTTCTAAATCGATTAGGCTTCACCGCGGCAGTCTAGGACTGTGCAAGAAGTTCGTTGTAAATGTTGGTTAG
       490       500       510       520       530       540       550       560       570       580       590       600

             150                           160                           170                           180
 L  T  G  S  L  L  A  I  H  G  A  Q  K  T  E  Q  W  A  R  G  L  V  Q  N  F  A  R  P  P  E  G  N  D  T  A  Q  I  R  A  S
GTTGACAGGTTCCTTACTCGCCATTCACGGGGCACAGAAGACCGAACAATGGGCACGTGGCTTAGTACAGAACTTCGCACGTCCACCGGAGGGGAATGACACAGCTCAAATTCGTGCAAG
CAACTGTCCAAGGAATGAGCGGTAAGTGCCCCGTGTCTTCTGGCTTGTTACCCGTGCACCGAATCATGTCTTGAAGCGTGCAGGTGGCCTCCCCTTACTGTGTCGAGTTTAAGCACGTTC
       610       620       630       640       650       660       670       680       690       700       710       720

             190                           200                           210                           220
 A  E  G  V  G  S  V  A  I  A  N  H  Y  Y  L  A  R  L  I  A  S  D  K  E  Q  D  R  A  V  A  A  K  V  G  L  F  F  P  N  Q
TGCAGAGGGCGTTGGCTCAGTAGCGATCGCCAATCACTATTACCTCGCCCGTTTAATTGCCAGTGACAAGGAGCAAGACCGTGCGGTGGCCGCAAAGGTGGGCCTCTTTTTCCCGAACCA
ACGTCTCCCGCAACCGAGTCATCGCTAGCGGTTAGTGATAATGGAGCGGGCAAATTAACGGTCACTGTTCCTCGTTCTGGCACGCCACCGGCGTTTCCACCCGGAGAAAAAGGGCTTGGT
       730       740       750       760       770       780       790       800       810       820       830       840

             230                           240                           250                           260
 R  D  R  G  A  H  V  N  I  S  G  A  G  V  V  A  G  A  P  N  R  Q  G  A  I  R  F  L  E  Y  L  V  S  P  K  A  Q  E  M  F
ACGTGACCGCGGTGCACATGTCAATATCAGTGGGGCAGGTGTAGTCGCCGGCGCTCCTAACCGTCAAGGCGCAATTCGGTTCTTAGAGTACCTGGTCTCCCCAAAGGCCCAGGAAATGTT
TGCACTGGCGCCACGTGTACAGTTATAGTCACCCCGTCCACATCAGCGGCCGCGAGGATTGGCAGTTCCGCGTTAAGCCAAGAATCTCATGGACCAGAGGGGTTTCCGGGTCCTTTACAA
       850       860       870       880       890       900       910       920       930       940       950       960
```

```
                    270                                     280                                     290                                     300
  A   M   A   N   F   E   Y   P   V   R   A   G   V   P   V   H   P   I   V   K   Q   F   G   N   F   R   G   Q   N   V   N   A   A   V   F   G   R   N   N   A
TGCTATGGCTAACTTTGAGTACCCGGTACGCGCAGGCGTCCCAGTCCACCCTATCGTCAAGCAATTCGGCAACTTTCGTGGTCAAAATGTCAACGCAGCAGTATTCGGGCGCAACAACGC
ACGATACCGATTGAAACTCATGGGCCATGCGCGTCCGCAGGGTCAGGTGGGATAGCAGTTCGTTAAGCCGTTGAAAGCACCAGTTTTACAGTTGCGTCGTCATAAGCCCGCGTTGTTGCG
         970          980          990         1000         1010         1020         1030         1040         1050         1060         1070         1080

                    310                                     320
  E   A   L   R   I   M   D   R   A   G   W   R   G   G   S   H   H   H   H   H   H   *   *
AGAAGCACTTCGTATCATGGACCGGGCCGGTTGGCGTGGCGGTAGTCATCATCATCATCATCATTAATGAAAGGGCGATATCCAGCACACTGGCGGCCGTTACTAGTGGATCCGGCTGCT
TCTTCGTGAAGCATAGTACCTGGCCCGGCCAACCGCACCGCCATCAGTAGTAGTAGTAGTAGTAATTACTTTCCCGCTATAGGTCGTGTGACCGCCGGCAATGATCACCTAGGCCGACGA
        1090         1100         1110         1120         1130         1140         1150         1160         1170         1180         1190         1200

AACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCC
TTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGG
        1210         1220         1230         1240         1250         1260         1270         1280         1290         1300         1310         1320

GGAGCGACTCCCACGGCACGTTGGCAAGCTCG
CCTCGCTGAGGGTGCCGTGCAACCGTTCGAGC
        1330         1340         1350
```

FIG. 43 (Continued)

FIG. 44 - Exemplary Expression Construct for teFeBP3_V58C

SEQ ID NO: 126

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                           10                            20
                                                             M  V  I  N  V  Y  S  A  R  H  Y  D  T  D  K  A  L  Y  N  T  F  T  Q  Q
GGTTTCCCTCTAGAAATAATTTTGTTTAACTTTAAGAAGGAGATATACCATGGTAATTAATGTATATAGTGCACGTCATTACGACACTGACAAGGCTCTCTATAATACCTTCACCCAACA
CCAAAGGGAGATCTTTATTAAAACAAATTGAAATTCTTCCTCTATATGGTACCATTAATTACATATATCACGTGCAGTAATGCTGTGACTGTTCCGAGAGATATTATGGAAGTGGGTTGT
       130       140       150       160       170       180       190       200       210       220       230       240

             30                            40                            50                            60
 T  G  I  R  V  N  I  I  E  A  E  A  D  A  L  I  E  R  I  R  S  E  G  S  R  T  P  A  D  V  L  I  T  C  D  A  G  R  L  W
AACCGGGATTCGTGTAAACATCATTGAGGCTGAGGCAGATGCCCTCATTGAACGTATTCGTTCTGAAGGTTCGCGCACCCCAGCCGATGTACTCATTACATGCGACGCGGGTCGCTTATG
TTGGCCCTAAGCACATTTGTAGTAACTCCGACTCCGTCTACGGGAGTAACTTGCATAAGCAAGACTTCCAAGCGCGTGGGGTCGGCTACATGAGTAATGTACGCTGCGCCCAGCGAATAC
       250       260       270       280       290       300       310       320       330       340       350       360

             70                            80                            90                           100
 R  A  Q  E  A  G  I  L  Q  P  I  Q  S  R  V  L  N  S  V  V  P  A  N  L  R  E  P  Q  G  H  W  F  G  L  S  R  R  V  R  V
GCGTGCGCAAGAAGCTGGCATCTTACAGCCGATTCAATCGCGTGTTTTAAACAGTGTAGTACCAGCCAACCTCCGGGAACCACAGGGTCACTGGTTCGGTCTCTCCCGTCGTGTTCGCGT
CGCACGCGTTCTTCGACCGTAGAATGTCGGCTAAGTTAGCGCACAAAATTTGTCACATCATGGTCGGTTGGAGGCCCTTGGTGTCCCAGTGACCAAGCCAGAGAGGGCAGCACAAGCGCA
       370       380       390       400       410       420       430       440       450       460       470       480

            110                           120                           130                           140
 L  I  Y  N  K  S  R  V  N  P  S  Q  L  S  T  Y  E  D  L  A  N  P  K  W  R  R  Q  I  L  T  R  S  S  S  N  I  Y  N  Q  S
TCTGATTTATAACAAGTCCCGTGTTAATCCATCTCAGCTTTCCACATACGAAGATTTAGCTAATCCGAAGTGGCGCCGTCAGATCCTGACACGTTCTTCAAGCAACATTTACAACCAATC
AGACTAAATATTGTTCAGGGCACAATTAGGTAGAGTCGAAAGGTGTATGCTTCTAAATCGATTAGGCTTCACCGCGGCAGTCTAGGACTGTGCAAGAAGTTCGTTGTAAATGTTGGTTAG
       490       500       510       520       530       540       550       560       570       580       590       600

            150                           160                           170                           180
 L  T  G  S  L  L  A  I  H  G  A  Q  K  T  E  Q  W  A  R  G  L  V  Q  N  F  A  R  P  P  E  G  N  D  T  A  Q  I  R  A  S
GTTGACAGGTTCCTTACTCGCCATTCACGGGGCACAGAAGACCGAACAATGGGCACGTGGCTTAGTACAGAACTTCGCACGTCCACCGGAGGGGAATGACACAGCTCAAATTCGTGCAAG
CAACTGTCCAAGGAATGAGCGGTAAGTGCCCCGTGTCTTCTGGCTTGTTACCCGTGCACCGAATCATGTCTTGAAGCGTGCAGGTGGCCTCCCCTTACTGTGTCGAGTTTAAGCACGTTC
       610       620       630       640       650       660       670       680       690       700       710       720

            190                           200                           210                           220
 A  E  G  V  G  S  V  A  I  A  N  H  Y  Y  L  A  R  L  I  A  S  D  K  E  Q  D  R  A  V  A  A  K  V  G  L  F  F  P  N  Q
TGCAGAGGGCGTTGGCTCAGTAGCGATCGCCAATCACTATTACCTCGCCCGTTTAATTGCCAGTGACAAGGAGCAAGACCGTGCGGTGGCCGCAAAGGTGGGCCTCTTTTTCCCGAACCA
ACGTCTCCCGCAACCGAGTCATCGCTAGCGGTTAGTGATAATGGAGCGGGCAAATTAACGGTCACTGTTCCTCGTTCTGGCACGCCACCGGCGTTTCCACCCGGAGAAAAAGGGCTTGGT
       730       740       750       760       770       780       790       800       810       820       830       840

            230                           240                           250                           260
 R  D  R  G  A  H  V  N  I  S  G  A  G  V  V  A  G  A  P  N  R  Q  G  A  I  R  F  L  E  Y  L  V  S  P  K  A  Q  E  M  F
ACGTGACCGCGGTGCACATGTCAATATCAGTGGGGCAGGTGTAGTCGCCGGCGCTCCTAACCGTCAAGGCGCAATTCGGTTCTTAGAGTACCTGGTCTCCCCAAAGGCCCAGGAAATGTT
TGCACTGGCGCCACGTGTACAGTTATAGTCACCCCGTCCACATCAGCGGCCGCGAGGATTGGCAGTTCCGCGTTAAGCCAAGAATCTCATGGACCAGAGGGGTTTCCGGGTCCTTTACAA
       850       860       870       880       890       900       910       920       930       940       950       960
```

```
                 270                                     280                                     290                                     300
 A   M   A   N   F   E   Y   P   V   R   A   G   V   P   V   H   P   I   V   K   Q   F   G   N   F   R   G   Q   N   V   N   A   A   V   F   G   R   N   N   A
TGCTATGGCTAACTTTGAGTACCCGGTACGCGCAGGCGTCCCAGTCCACCCTATCGTCAAGCAATTCGGCAACTTTCGTGGTCAAAATGTCAACGCAGCAGTATTCGGGCGCAACAACGC
ACGATACCGATTGAAACTCATGGGCCATGCGCGTCCGCAGGGTCAGGTGGGATAGCAGTTCGTTAAGCCGTTGAAAGCACCAGTTTTACAGTTGCGTCGTCATAAGCCCGCGTTGTTGCG
         970       980       990      1000      1010      1020      1030      1040      1050      1060      1070      1080

                 310                                     320
 E   A   L   R   I   M   D   R   A   G   W   R   G   G   S   H   H   H   H   H   H   *   *
AGAAGCACTTCGTATCATGGACCGGGCCGGTTGGCGTGGCGGTAGTCATCATCATCATCATCATTAATGAAAGGGCGATATCCAGCACACTGGCGGCCGTTACTAGTGGATCCGGCTGCT
TCTTCGTGAAGCATAGTACCTGGCCCGGCCAACCGCACCGCCATCAGTAGTAGTAGTAGTAGTAATTACTTTCCCGCTATAGGTCGTGTGACCGCCGGCAATGATCACCTAGGCCGACGA
        1090      1100      1110      1120      1130      1140      1150      1160      1170      1180      1190      1200


AACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCC
TTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGG
        1210      1220      1230      1240      1250      1260      1270      1280      1290      1300      1310      1320


GGAGCGACTCCCACGGCACGTTGGCAAGCTCG
CCTCGCTGAGGGTGCCGTGCAACCGTTCGAGC
        1330      1340      1350
```

FIG. 44 (Continued)

FIG. 45 - Exemplary Expression Construct for teFeBP3_R135C

SEQ ID NO: 127

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                   10                            20
                                                 M  V  I  N  V  Y  S  A  R  H  Y  D  T  D  K  A  L  Y  N  T  F  T  Q  Q
GGTTTCCCTCTAGAAATAATTTTGTTTAACTTTAAGAAGGAGATATACCATGGTAATTAATGTATATAGTGCACGTCATTACGACACTGACAAGGCTCTCTATAATACCTTCACCCAACA
CCAAAGGGAGATCTTTATTAAAACAAATTGAAATTCTTCCTCTATATGGTACCATTAATTACATATATCACGTGCAGTAATGCTGTGACTGTTCCGAGAGATATTATGGAAGTGGGTTGT
       130       140       150       160       170       180       190       200       210       220       230       240

             30                            40                            50                            60
 T  G  I  R  V  N  I  I  E  A  E  A  D  A  L  I  E  R  I  R  S  E  G  S  R  T  P  A  D  V  L  I  T  V  D  A  G  R  L  W
AACCGGGATTCGTGTAAACATCATTGAGGCTGAGGCAGATGCCCTCATTGAACGTATTCGTTCTGAAGGTTCGCGCACCCCAGCCGATGTACTCATTACAGTAGACGCGGGTCGCTTATG
TTGGCCCTAAGCACATTTGTAGTAACTCCGACTCCGTCTACGGGAGTAACTTGCATAAGCAAGACTTCCAAGCGCGTGGGGTCGGCTACATGAGTAATGTCATCTGCGCCCAGCGAATAC
       250       260       270       280       290       300       310       320       330       340       350       360

             70                            80                            90                           100
 R  A  Q  E  A  G  I  L  Q  P  I  Q  S  R  V  L  N  S  V  V  P  A  N  L  R  E  P  Q  G  H  W  F  G  L  S  R  R  V  R  V
GCGTGCGCAAGAAGCTGGCATCTTACAGCCGATTCAATCGCGTGTTTTAAACAGTGTAGTACCAGCCAACCTCCGGGAACCACAGGGTCACTGGTTCGGTCTCTCCCGTCGTGTTCGCGT
CGCACGCGTTCTTCGACCGTAGAATGTCGGCTAAGTTAGCGCACAAAATTTGTCACATCATGGTCGGTTGGAGGCCCTTGGTGTCCCAGTGACCAAGCCAGAGAGGGCAGCACAAGCGCA
       370       380       390       400       410       420       430       440       450       460       470       480

            110                           120                           130                           140
 L  I  Y  N  K  S  R  V  N  P  S  Q  L  S  T  Y  E  D  L  A  N  P  K  W  R  R  Q  I  L  T  C  S  S  S  N  I  Y  N  Q  S
TCTGATTTATAACAAGTCCCGTGTTAATCCATCTCAGCTTTCCACATACGAAGATTTAGCTAATCCGAAGTGGCGCCGTCAGATCCTGACATGCTCTTCAAGCAACATTTACAACCAATC
AGACTAAATATTGTTCAGGGCACAATTAGGTAGAGTCGAAAGGTGTATGCTTCTAAATCGATTAGGCTTCACCGCGGCAGTCTAGGACTGTACGAGAAGTTCGTTGTAAATGTTGGTTAG
       490       500       510       520       530       540       550       560       570       580       590       600

            150                           160                           170                           180
 L  T  G  S  L  L  A  I  H  G  A  Q  K  T  E  Q  W  A  R  G  L  V  Q  N  F  A  R  P  P  E  G  N  D  T  A  Q  I  R  A  S
GTTGACAGGTTCCTTACTCGCCATTCACGGGGCACAGAAGACCGAACAATGGGCACGTGGCTTAGTACAGAACTTCGCACGTCCACCGGAGGGGAATGACACAGCTCAAATTCGTGCAAG
CAACTGTCCAAGGAATGAGCGGTAAGTGCCCCGTGTCTTCTGGCTTGTTACCCGTGCACCGAATCATGTCTTGAAGCGTGCAGGTGGCCTCCCCTTACTGTGTCGAGTTTAAGCACGTTC
       610       620       630       640       650       660       670       680       690       700       710       720

            190                           200                           210                           220
 A  E  G  V  G  S  V  A  I  A  N  H  Y  Y  L  A  R  L  I  A  S  D  K  E  Q  D  R  A  V  A  A  K  V  G  L  F  F  P  N  Q
TGCAGAGGGCGTTGGCTCAGTAGCGATCGCCAATCACTATTACCTCGCCCGTTTAATTGCCAGTGACAAGGAGCAAGACCGTGCGGTGGCCGCAAAGGTGGGCCTCTTTTTCCCGAACCA
ACGTCTCCCGCAACCGAGTCATCGCTAGCGGTTAGTGATAATGGAGCGGGCAAATTAACGGTCACTGTTCCTCGTTCTGGCACGCCACCGGCGTTTCCACCCGGAGAAAAAGGGCTTGGT
       730       740       750       760       770       780       790       800       810       820       830       840

            230                           240                           250                           260
 R  D  R  G  A  H  V  N  I  S  G  A  G  V  V  A  G  A  P  N  R  Q  G  A  I  R  F  L  E  Y  L  V  S  P  K  A  Q  E  M  F
ACGTGACCGCGGTGCACATGTCAATATCAGTGGGGCAGGTGTAGTCGCCGGCGCTCCTAACCGTCAAGGCGCAATTCGGTTCTTAGAGTACCTGGTCTCCCCAAAGGCCCAGGAAATGTT
TGCACTGGCGCCACGTGTACAGTTATAGTCACCCCGTCCACATCAGCGGCCGCGAGGATTGGCAGTTCCGCGTTAAGCCAAGAATCTCATGGACCAGAGGGGTTTCCGGGTCCTTTACAA
       850       860       870       880       890       900       910       920       930       940       950       960
```

```
                 270                                280                                290                                300
 A  M  A  N  F  E  Y  P  V  R  A  G  V  P  V  H  P  I  V  K  Q  F  G  N  F  R  G  Q  N  V  N  A  A  V  F  G  R  N  N  A
TGCTATGGCTAACTTTGAGTACCCGGTACGCGCAGGCGTCCCAGTCCACCCTATCGTCAAGCAATTCGGCAACTTTCGTGGTCAAAATGTCAACGCAGCAGTATTCGGGCGCAACAACGC
ACGATACCGATTGAAACTCATGGGCCATGCGCGTCCGCAGGGTCAGGTGGGATAGCAGTTCGTTAAGCCGTTGAAAGCACCAGTTTTACAGTTGCGTCGTCATAAGCCCGCGTTGTTGCG
        970         980         990        1000        1010        1020        1030        1040        1050        1060        1070        1080

                 310                                320
 E  A  L  R  I  M  D  R  A  G  W  R  G  G  S  H  H  H  H  H  H  *  *
AGAAGCACTTCGTATCATGGACCGGGCCGGTTGGCGTGGCGGTAGTCATCATCATCATCATCATTAATGAAAGGGCGATATCCAGCACACTGGCGGCCGTTACTAGTGGATCCGGCTGCT
TCTTCGTGAAGCATAGTACCTGGCCCGGCCAACCGCACCGCCATCAGTAGTAGTAGTAGTAGTAATTACTTTCCCGCTATAGGTCGTGTGACCGCCGGCAATGATCACCTAGGCCGACGA
       1090        1100        1110        1120        1130        1140        1150        1160        1170        1180        1190        1200


AACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCC
TTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGG
       1210        1220        1230        1240        1250        1260        1270        1280        1290        1300        1310        1320


GGAGCGACTCCCACGGCACGTTGGCAAGCTCG
CCTCGCTGAGGGTGCCGTGCAACCGTTCGAGC
       1330        1340        1350
```

FIG. 45 (Continued)

FIG. 46 - Exemplary Expression Construct for teFeBP3_N139C

SEQ ID NO: 128

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                       10                            20
                                                  M  V  I  N  V  Y  S  A  R  H  Y  D  T  D  K  A  L  Y  N  T  F  T  Q  Q
GGTTTCCCTCTAGAAATAATTTTGTTTAACTTTAAGAAGGAGATATACCATGGTAATTAATGTATATAGTGCACGTCATTACGACACTGACAAGGCTCTCTATAATACCTTCACCCAACA
CCAAAGGGAGATCTTTATTAAAACAAATTGAAATTCTTCCTCTATATGGTACCATTAATTACATATATCACGTGCAGTAATGCTGTGACTGTTCCGAGAGATATTATGGAAGTGGGTTGT
       130       140       150       160       170       180       190       200       210       220       230       240

             30                            40                            50                            60
 T  G  I  R  V  N  I  I  E  A  E  A  D  A  L  I  E  R  I  R  S  E  G  S  R  T  P  A  D  V  L  I  T  V  D  A  G  R  L  W
AACCGGGATTCGTGTAAACATCATTGAGGCTGAGGCAGATGCCCTCATTGAACGTATTCGTTCTGAAGGTTCGCGCACCCCAGCCGATGTACTCATTACAGTAGACGCGGGTCGCTTATG
TTGGCCCTAAGCACATTTGTAGTAACTCCGACTCCGTCTACGGGAGTAACTTGCATAAGCAAGACTTCCAAGCGCGTGGGGTCGGCTACATGAGTAATGTCATCTGCGCCCAGCGAATAC
       250       260       270       280       290       300       310       320       330       340       350       360

             70                            80                            90                           100
 R  A  Q  E  A  G  I  L  Q  P  I  Q  S  R  V  L  N  S  V  V  P  A  N  L  R  E  P  Q  G  H  W  F  G  L  S  R  R  V  R  V
GCGTGCGCAAGAAGCTGGCATCTTACAGCCGATTCAATCGCGTGTTTTAAACAGTGTAGTACCAGCCAACCTCCGGGAACCACAGGGTCACTGGTTCGGTCTCTCCCGTCGTGTTCGCGT
CGCACGCGTTCTTCGACCGTAGAATGTCGGCTAAGTTAGCGCACAAAATTTGTCACATCATGGTCGGTTGGAGGCCCTTGGTGTCCCAGTGACCAAGCCAGAGAGGGCAGCACAAGCGCA
       370       380       390       400       410       420       430       440       450       460       470       480

            110                           120                           130                           140
 L  I  Y  N  K  S  R  V  N  P  S  Q  L  S  T  Y  E  D  L  A  N  P  K  W  R  R  Q  I  L  T  R  S  S  S  C  I  Y  N  Q  S
TCTGATTTATAACAAGTCCCGTGTTAATCCATCTCAGCTTTCCACATACGAAGATTTAGCTAATCCGAAGTGGCGCCGTCAGATCCTGACACGTTCTTCAAGCTGCATTTACAACCAATC
AGACTAAATATTGTTCAGGGCACAATTAGGTAGAGTCGAAAGGTGTATGCTTCTAAATCGATTAGGCTTCACCGCGGCAGTCTAGGACTGTGCAAGAAGTTCGACGTAAATGTTGGTTAG
       490       500       510       520       530       540       550       560       570       580       590       600

            150                           160                           170                           180
 L  T  G  S  L  L  A  I  H  G  A  Q  K  T  E  Q  W  A  R  G  L  V  Q  N  F  A  R  P  P  E  G  N  D  T  A  Q  I  R  A  S
GTTGACAGGTTCCTTACTCGCCATTCACGGGGCACAGAAGACCGAACAATGGGCACGTGGCTTAGTACAGAACTTCGCACGTCCACCGGAGGGGAATGACACAGCTCAAATTCGTGCAAG
CAACTGTCCAAGGAATGAGCGGTAAGTGCCCCGTGTCTTCTGGCTTGTTACCCGTGCACCGAATCATGTCTTGAAGCGTGCAGGTGGCCTCCCCTTACTGTGTCGAGTTTAAGCACGTTC
       610       620       630       640       650       660       670       680       690       700       710       720

            190                           200                           210                           220
 A  E  G  V  G  S  V  A  I  A  N  H  Y  Y  L  A  R  L  I  A  S  D  K  E  Q  D  R  A  V  A  A  K  V  G  L  F  F  P  N  Q
TGCAGAGGGCGTTGGCTCAGTAGCGATCGCCAATCACTATTACCTCGCCCGTTTAATTGCCAGTGACAAGGAGCAAGACCGTGCGGTGGCCGCAAAGGTGGGCCTCTTTTTCCCGAACCA
ACGTCTCCCGCAACCGAGTCATCGCTAGCGGTTAGTGATAATGGAGCGGGCAAATTAACGGTCACTGTTCCTCGTTCTGGCACGCCACCGGCGTTTCCACCCGGAGAAAAAGGGCTTGGT
       730       740       750       760       770       780       790       800       810       820       830       840

            230                           240                           250                           260
 R  D  R  G  A  H  V  N  I  S  G  A  G  V  V  A  G  A  P  N  R  Q  G  A  I  R  F  L  E  Y  L  V  S  P  K  A  Q  E  M  F
ACGTGACCGCGGTGCACATGTCAATATCAGTGGGGCAGGTGTAGTCGCCGGCGCTCCTAACCGTCAAGGCGCAATTCGGTTCTTAGAGTACCTGGTCTCCCCAAAGGCCCAGGAAATGTT
TGCACTGGCGCCACGTGTACAGTTATAGTCACCCCGTCCACATCAGCGGCCGCGAGGATTGGCAGTTCCGCGTTAAGCCAAGAATCTCATGGACCAGAGGGGTTTCCGGGTCCTTTACAA
       850       860       870       880       890       900       910       920       930       940       950       960
```

```
                     270                                     280                                     290                                     300
 A   M   A   N   F   E   Y   P   V   R   A   G   V   P   V   H   P   I   V   K   Q   F   G   N   F   R   G   Q   N   V   N   A   A   V   F   G   R   N   N   A
TGCTATGGCTAACTTTGAGTACCCGGTACGCGCAGGCGTCCCAGTCCACCCTATCGTCAAGCAATTCGGCAACTTTCGTGGTCAAAATGTCAACGCAGCAGTATTCGGGCGCAACAACGC
ACGATACCGATTGAAACTCATGGGCCATGCGCGTCCGCAGGGTCAGGTGGGATAGCAGTTCGTTAAGCCGTTGAAAGCACCAGTTTTACAGTTGCGTCGTCATAAGCCCGCGTTGTTGCG
       970       980       990      1000      1010      1020      1030      1040      1050      1060      1070      1080

                     310                                     320
 E   A   L   R   I   M   D   R   A   G   W   R   G   G   S   H   H   H   H   H   H   *   *
AGAAGCACTTCGTATCATGGACCGGGCCGGTTGGCGTGGCGGTAGTCATCATCATCATCATCATTAATGAAAGGGCGATATCCAGCACACTGGCGGCCGTTACTAGTGGATCCGGCTGCT
TCTTCGTGAAGCATAGTACCTGGCCCGGCCAACCGCACCGCCATCAGTAGTAGTAGTAGTAGTAATTACTTTCCCGCTATAGGTCGTGTGACCGCCGGCAATGATCACCTAGGCCGACGA
      1090      1100      1110      1120      1130      1140      1150      1160      1170      1180      1190      1200


AACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCC
TTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGG
      1210      1220      1230      1240      1250      1260      1270      1280      1290      1300      1310      1320


GGAGCGACTCCCACGGCACGTTGGCAAGCTCG
CCTCGCTGAGGGTGCCGTGCAACCGTTCGAGC
      1330      1340      1350
```

FIG. 46 (Continued)

FIG. 47 - Exemplary Expression Construct for teFeBP3_I140C

SEQ ID NO: 129

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                10                            20
                                                    M  V  I  N  V  Y  S  A  R  H  Y  D  T  D  K  A  L  Y  N  T  F  T  Q  Q
GGTTTCCCTCTAGAAATAATTTTGTTTAACTTTAAGAAGGAGATATACCATGGTAATTAATGTATATAGTGCACGTCATTACGACACTGACAAGGCTCTCTATAATACCTTCACCCAACA
CCAAAGGGAGATCTTTATTAAAACAAATTGAAATTCTTCCTCTATATGGTACCATTAATTACATATATCACGTGCAGTAATGCTGTGACTGTTCCGAGAGATATTATGGAAGTGGGTTGT
       130       140       150       160       170       180       190       200       210       220       230       240

              30                            40                            50                            60
T  G  I  R  V  N  I  I  E  A  E  A  D  A  L  I  E  R  I  R  S  E  G  S  R  T  P  A  D  V  L  I  T  V  D  A  G  R  L  W
AACCGGGATTCGTGTAAACATCATTGAGGCTGAGGCAGATGCCCTCATTGAACGTATTCGTTCTGAAGGTTCGCGCACCCCAGCCGATGTACTCATTACAGTAGACGCGGGTCGCTTATG
TTGGCCCTAAGCACATTTGTAGTAACTCCGACTCCGTCTACGGGAGTAACTTGCATAAGCAAGACTTCCAAGCGCGTGGGGTCGGCTACATGAGTAATGTCATCTGCGCCCAGCGAATAC
       250       260       270       280       290       300       310       320       330       340       350       360

              70                            80                            90                           100
R  A  Q  E  A  G  I  L  Q  P  I  Q  S  R  V  L  N  S  V  V  P  A  N  L  R  E  P  Q  G  H  W  F  G  L  S  R  R  V  R  V
GCGTGCGCAAGAAGCTGGCATCTTACAGCCGATTCAATCGCGTGTTTTAAACAGTGTAGTACCAGCCAACCTCCGGGAACCACAGGGTCACTGGTTCGGTCTCTCCCGTCGTGTTCGCGT
CGCACGCGTTCTTCGACCGTAGAATGTCGGCTAAGTTAGCGCACAAAATTTGTCACATCATGGTCGGTTGGAGGCCCTTGGTGTCCCAGTGACCAAGCCAGAGAGGGCAGCACAAGCGCA
       370       380       390       400       410       420       430       440       450       460       470       480

             110                           120                           130                           140
L  I  Y  N  K  S  R  V  N  P  S  Q  L  S  T  Y  E  D  L  A  N  P  K  W  R  R  Q  I  L  T  R  S  S  S  N  C  Y  N  Q  S
TCTGATTTATAACAAGTCCCGTGTTAATCCATCTCAGCTTTCCACATACGAAGATTTAGCTAATCCGAAGTGGCGCCGTCAGATCCTGACACGTTCTTCAAGCAACTGCTACAACCAATC
AGACTAAATATTGTTCAGGGCACAATTAGGTAGAGTCGAAAGGTGTATGCTTCTAAATCGATTAGGCTTCACCGCGGCAGTCTAGGACTGTGCAAGAAGTTCGTTGACGATGTTGGTTAG
       490       500       510       520       530       540       550       560       570       580       590       600

             150                           160                           170                           180
L  T  G  S  L  L  A  I  H  G  A  Q  K  T  E  Q  W  A  R  G  L  V  Q  N  F  A  R  P  P  E  G  N  D  T  A  Q  I  R  A  S
GTTGACAGGTTCCTTACTCGCCATTCACGGGGCACAGAAGACCGAACAATGGGCACGTGGCTTAGTACAGAACTTCGCACGTCCACCGGAGGGGAATGACACAGCTCAAATTCGTGCAAG
CAACTGTCCAAGGAATGAGCGGTAAGTGCCCCGTGTCTTCTGGCTTGTTACCCGTGCACCGAATCATGTCTTGAAGCGTGCAGGTGGCCTCCCCTTACTGTGTCGAGTTTAAGCACGTTC
       610       620       630       640       650       660       670       680       690       700       710       720

             190                           200                           210                           220
A  E  G  V  G  S  V  A  I  A  N  H  Y  Y  L  A  R  L  I  A  S  D  K  E  Q  D  R  A  V  A  A  K  V  G  L  F  F  P  N  Q
TGCAGAGGGCGTTGGCTCAGTAGCGATCGCCAATCACTATTACCTCGCCCGTTTAATTGCCAGTGACAAGGAGCAAGACCGTGCGGTGGCCGCAAAGGTGGGCCTCTTTTTCCCGAACCA
ACGTCTCCCGCAACCGAGTCATCGCTAGCGGTTAGTGATAATGGAGCGGGCAAATTAACGGTCACTGTTCCTCGTTCTGGCACGCCACCGGCGTTTCCACCCGGAGAAAAAGGGCTTGGT
       730       740       750       760       770       780       790       800       810       820       830       840

             230                           240                           250                           260
R  D  R  G  A  H  V  N  I  S  G  A  G  V  V  A  G  A  P  N  R  Q  G  A  I  R  F  L  E  Y  L  V  S  P  K  A  Q  E  M  F
ACGTGACCGCGGTGCACATGTCAATATCAGTGGGGCAGGTGTAGTCGCCGGCGCTCCTAACCGTCAAGGCGCAATTCGGTTCTTAGAGTACCTGGTCTCCCCAAAGGCCCAGGAAATGTT
TGCACTGGCGCCACGTGTACAGTTATAGTCACCCCGTCCACATCAGCGGCCGCGAGGATTGGCAGTTCCGCGTTAAGCCAAGAATCTCATGGACCAGAGGGGTTTCCGGGTCCTTTACAA
       850       860       870       880       890       900       910       920       930       940       950       960
```

```
                270                                   280                                   290                                   300
 A   M   A   N   F   E   Y   P   V   R   A   G   V   P   V   H   P   I   V   K   Q   F   G   N   F   R   G   Q   N   V   N   A   A   V   F   G   R   N   N   A
TGCTATGGCTAACTTTGAGTACCCGGTACGCGCAGGCGTCCCAGTCCACCCTATCGTCAAGCAATTCGGCAACTTTCGTGGTCAAAATGTCAACGCAGCAGTATTCGGGCGCAACAACGC
ACGATACCGATTGAAACTCATGGGCCATGCGCGTCCGCAGGGTCAGGTGGGATAGCAGTTCGTTAAGCCGTTGAAAGCACCAGTTTTACAGTTGCGTCGTCATAAGCCCGCGTTGTTGCG
        970       980       990      1000      1010      1020      1030      1040      1050      1060      1070      1080

                310                                   320
 E   A   L   R   I   M   D   R   A   G   W   R   G   G   S   H   H   H   H   H   H   *   *
AGAAGCACTTCGTATCATGGACCGGGCCGGTTGGCGTGGCGGTAGTCATCATCATCATCATCATTAATGAAAGGGCGATATCCAGCACACTGGCGGCCGTTACTAGTGGATCCGGCTGCT
TCTTCGTGAAGCATAGTACCTGGCCCGGCCAACCGCACCGCCATCAGTAGTAGTAGTAGTAGTAATTACTTTCCCGCTATAGGTCGTGTGACCGCCGGCAATGATCACCTAGGCCGACGA
       1090      1100      1110      1120      1130      1140      1150      1160      1170      1180      1190      1200


AACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCC
TTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGG
       1210      1220      1230      1240      1250      1260      1270      1280      1290      1300      1310      1320


GGAGCGACTCCCACGGCACGTTGGCAAGCTCG
CCTCGCTGAGGGTGCCGTGCAACCGTTCGAGC
       1330      1340      1350
```

FIG. 47 (Continued)

FIG. 48 - Exemplary Expression Construct for teFeBP3_N176C

SEQ ID NO: 130

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                          10                            20
                                                                 M  V  I  N  V  Y  S  A  R  H  Y  D  T  D  K  A  L  Y  N  T  F  T  Q  Q
GGTTTCCCTCTAGAAATAATTTTGTTTAACTTTAAGAAGGAGATATACCATGGTAATTAATGTATATAGTGCACGTCATTACGACACTGACAAGGCTCTCTATAATACCTTCACCCAACA
CCAAAGGGAGATCTTTATTAAAACAAATTGAAATTCTTCCTCTATATGGTACCATTAATTACATATATCACGTGCAGTAATGCTGTGACTGTTCCGAGAGATATTATGGAAGTGGGTTGT
       130       140       150       160       170       180       190       200       210       220       230       240

             30                            40                            50                            60
 T  G  I  R  V  N  I  I  E  A  E  A  D  A  L  I  E  R  I  R  S  E  G  S  R  T  P  A  D  V  L  I  T  V  D  A  G  R  L  W
AACCGGGATTCGTGTAAACATCATTGAGGCTGAGGCAGATGCCCTCATTGAACGTATTCGTTCTGAAGGTTCGCGCACCCCAGCCGATGTACTCATTACAGTAGACGCGGGTCGCTTATG
TTGGCCCTAAGCACATTTGTAGTAACTCCGACTCCGTCTACGGGAGTAACTTGCATAAGCAAGACTTCCAAGCGCGTGGGGTCGGCTACATGAGTAATGTCATCTGCGCCCAGCGAATAC
       250       260       270       280       290       300       310       320       330       340       350       360

             70                            80                            90                           100
 R  A  Q  E  A  G  I  L  Q  P  I  Q  S  R  V  L  N  S  V  V  P  A  N  L  R  E  P  Q  G  H  W  F  G  L  S  R  R  V  R  V
GCGTGCGCAAGAAGCTGGCATCTTACAGCCGATTCAATCGCGTGTTTTAAACAGTGTAGTACCAGCCAACCTCCGGGAACCACAGGGTCACTGGTTCGGTCTCTCCCGTCGTGTTCGCGT
CGCACGCGTTCTTCGACCGTAGAATGTCGGCTAAGTTAGCGCACAAAATTTGTCACATCATGGTCGGTTGGAGGCCCTTGGTGTCCCAGTGACCAAGCCAGAGAGGGCAGCACAAGCGCA
       370       380       390       400       410       420       430       440       450       460       470       480

            110                           120                           130                           140
 L  I  Y  N  K  S  R  V  N  P  S  Q  L  S  T  Y  E  D  L  A  N  P  K  W  R  R  Q  I  L  T  R  S  S  S  N  I  Y  N  Q  S
TCTGATTTATAACAAGTCCCGTGTTAATCCATCTCAGCTTTCCACATACGAAGATTTAGCTAATCCGAAGTGGCGCCGTCAGATCCTGACACGTTCTTCAAGCAACATTTACAACCAATC
AGACTAAATATTGTTCAGGGCACAATTAGGTAGAGTCGAAAGGTGTATGCTTCTAAATCGATTAGGCTTCACCGCGGCAGTCTAGGACTGTGCAAGAAGTTCGTTGTAAATGTTGGTTAG
       490       500       510       520       530       540       550       560       570       580       590       600

            150                           160                           170                           180
 L  T  G  S  L  L  A  I  H  G  A  Q  K  T  E  Q  W  A  R  G  L  V  Q  N  F  A  R  P  P  E  G  C  D  T  A  Q  I  R  A  S
GTTGACAGGTTCCTTACTCGCCATTCACGGGGCACAGAAGACCGAACAATGGGCACGTGGCTTAGTACAGAACTTCGCACGTCCACCGGAGGGGTGCGACACAGCTCAAATTCGTGCAAG
CAACTGTCCAAGGAATGAGCGGTAAGTGCCCCGTGTCTTCTGGCTTGTTACCCGTGCACCGAATCATGTCTTGAAGCGTGCAGGTGGCCTCCCCACGCTGTGTCGAGTTTAAGCACGTTC
       610       620       630       640       650       660       670       680       690       700       710       720

            190                           200                           210                           220
 A  E  G  V  G  S  V  A  I  A  N  H  Y  Y  L  A  R  L  I  A  S  D  K  E  Q  D  R  A  V  A  A  K  V  G  L  F  F  P  N  Q
TGCAGAGGGCGTTGGCTCAGTAGCGATCGCCAATCACTATTACCTCGCCCGTTTAATTGCCAGTGACAAGGAGCAAGACCGTGCGGTGGCCGCAAAGGTGGGCCTCTTTTTCCCGAACCA
ACGTCTCCCGCAACCGAGTCATCGCTAGCGGTTAGTGATAATGGAGCGGGCAAATTAACGGTCACTGTTCCTCGTTCTGGCACGCCACCGGCGTTTCCACCCGGAGAAAAAGGGCTTGGT
       730       740       750       760       770       780       790       800       810       820       830       840

            230                           240                           250                           260
 R  D  R  G  A  H  V  N  I  S  G  A  G  V  V  A  G  A  P  N  R  Q  G  A  I  R  F  L  E  Y  L  V  S  P  K  A  Q  E  M  F
ACGTGACCGCGGTGCACATGTCAATATCAGTGGGGCAGGTGTAGTCGCCGGCGCTCCTAACCGTCAAGGCGCAATTCGGTTCTTAGAGTACCTGGTCTCCCCAAAGGCCCAGGAAATGTT
TGCACTGGCGCCACGTGTACAGTTATAGTCACCCCGTCCACATCAGCGGCCGCGAGGATTGGCAGTTCCGCGTTAAGCCAAGAATCTCATGGACCAGAGGGGTTTCCGGGTCCTTTACAA
       850       860       870       880       890       900       910       920       930       940       950       960
```

```
              270                                280                                290                                300
 A  M  A  N  F  E  Y  P  V  R  A  G  V  P  V  H  P  I  V  K  Q  F  G  N  F  R  G  Q  N  V  N  A  A  V  F  G  R  N  N  A
TGCTATGGCTAACTTTGAGTACCCGGTACGCGCAGGCGTCCCAGTCCACCCTATCGTCAAGCAATTCGGCAACTTTCGTGGTCAAAATGTCAACGCAGCAGTATTCGGGCGCAACAACGC
ACGATACCGATTGAAACTCATGGGCCATGCGCGTCCGCAGGGTCAGGTGGGATAGCAGTTCGTTAAGCCGTTGAAAGCACCAGTTTTACAGTTGCGTCGTCATAAGCCCGCGTTGTTGCG
       970       980       990      1000      1010      1020      1030      1040      1050      1060      1070      1080

              310                                320
 E  A  L  R  I  M  D  R  A  G  W  R  G  G  S  H  H  H  H  H  H  *  *
AGAAGCACTTCGTATCATGGACCGGGCCGGTTGGCGTGGCGGTAGTCATCATCATCATCATCATTAATGAAAGGGCGATATCCAGCACACTGGCGGCCGTTACTAGTGGATCCGGCTGCT
TCTTCGTGAAGCATAGTACCTGGCCCGGCCAACCGCACCGCCATCAGTAGTAGTAGTAGTAGTAATTACTTTCCCGCTATAGGTCGTGTGACCGCCGGCAATGATCACCTAGGCCGACGA
      1090      1100      1110      1120      1130      1140      1150      1160      1170      1180      1190      1200

AACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCC
TTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGG
      1210      1220      1230      1240      1250      1260      1270      1280      1290      1300      1310      1320

GGAGCGACTCCCACGGCACGTTGGCAAGCTCG
CCTCGCTGAGGGTGCCGTGCAACCGTTCGAGC
      1330      1340      1350
```

FIG. 48 (Continued)

FIG. 49 - Exemplary Expression Construct for teFeBP3_N195C

SEQ ID NO: 131

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                     10                            20
                                                     M  V  I  N  V  Y  S  A  R  H  Y  D  T  D  K  A  L  Y  N  T  F  T  Q  Q
GGTTTCCCTCTAGAAATAATTTTGTTTAACTTTAAGAAGGAGATATACCATGGTAATTAATGTATATAGTGCACGTCATTACGACACTGACAAGGCTCTCTATAATACCTTCACCCAACA
CCAAAGGGAGATCTTTATTAAAACAAATTGAAATTCTTCCTCTATATGGTACCATTAATTACATATATCACGTGCAGTAATGCTGTGACTGTTCCGAGAGATATTATGGAAGTGGGTTGT
       130       140       150       160       170       180       190       200       210       220       230       240

             30                            40                            50                            60
 T  G  I  R  V  N  I  I  E  A  E  A  D  A  L  I  E  R  I  R  S  E  G  S  R  T  P  A  D  V  L  I  T  V  D  A  G  R  L  W
AACCGGGATTCGTGTAAACATCATTGAGGCTGAGGCAGATGCCCTCATTGAACGTATTCGTTCTGAAGGTTCGCGCACCCCAGCCGATGTACTCATTACAGTAGACGCGGGTCGCTTATG
TTGGCCCTAAGCACATTTGTAGTAACTCCGACTCCGTCTACGGGAGTAACTTGCATAAGCAAGACTTCCAAGCGCGTGGGGTCGGCTACATGAGTAATGTCATCTGCGCCCAGCGAATAC
       250       260       270       280       290       300       310       320       330       340       350       360

             70                            80                            90                           100
 R  A  Q  E  A  G  I  L  Q  P  I  Q  S  R  V  L  N  S  V  V  P  A  N  L  R  E  P  Q  G  H  W  F  G  L  S  R  R  V  R  V
GCGTGCGCAAGAAGCTGGCATCTTACAGCCGATTCAATCGCGTGTTTTAAACAGTGTAGTACCAGCCAACCTCCGGGAACCACAGGGTCACTGGTTCGGTCTCTCCCGTCGTGTTCGCGT
CGCACGCGTTCTTCGACCGTAGAATGTCGGCTAAGTTAGCGCACAAAATTTGTCACATCATGGTCGGTTGGAGGCCCTTGGTGTCCCAGTGACCAAGCCAGAGAGGGCAGCACAAGCGCA
       370       380       390       400       410       420       430       440       450       460       470       480

            110                           120                           130                           140
 L  I  Y  N  K  S  R  V  N  P  S  Q  L  S  T  Y  E  D  L  A  N  P  K  W  R  R  Q  I  L  T  R  S  S  S  N  I  Y  N  Q  S
TCTGATTTATAACAAGTCCCGTGTTAATCCATCTCAGCTTTCCACATACGAAGATTTAGCTAATCCGAAGTGGCGCCGTCAGATCCTGACACGTTCTTCAAGCAACATTTACAACCAATC
AGACTAAATATTGTTCAGGGCACAATTAGGTAGAGTCGAAAGGTGTATGCTTCTAAATCGATTAGGCTTCACCGCGGCAGTCTAGGACTGTGCAAGAAGTTCGTTGTAAATGTTGGTTAG
       490       500       510       520       530       540       550       560       570       580       590       600

            150                           160                           170                           180
 L  T  G  S  L  L  A  I  H  G  A  Q  K  T  E  Q  W  A  R  G  L  V  Q  N  F  A  R  P  P  E  G  N  D  T  A  Q  I  R  A  S
GTTGACAGGTTCCTTACTCGCCATTCACGGGGCACAGAAGACCGAACAATGGGCACGTGGCTTAGTACAGAACTTCGCACGTCCACCGGAGGGGAATGACACAGCTCAAATTCGTGCAAG
CAACTGTCCAAGGAATGAGCGGTAAGTGCCCCGTGTCTTCTGGCTTGTTACCCGTGCACCGAATCATGTCTTGAAGCGTGCAGGTGGCCTCCCCTTACTGTGTCGAGTTTAAGCACGTTC
       610       620       630       640       650       660       670       680       690       700       710       720

            190                           200                           210                           220
 A  E  G  V  G  S  V  A  I  A  C  H  Y  Y  L  A  R  L  I  A  S  D  K  E  Q  D  R  A  V  A  A  K  V  G  L  F  F  P  N  Q
TGCAGAGGGCGTTGGCTCAGTAGCGATCGCCTGCCACTATTACCTCGCCCGTTTAATTGCCAGTGACAAGGAGCAAGACCGTGCGGTGGCCGCAAAGGTGGGCCTCTTTTTCCCGAACCA
ACGTCTCCCGCAACCGAGTCATCGCTAGCGGACGGTGATAATGGAGCGGGCAAATTAACGGTCACTGTTCCTCGTTCTGGCACGCCACCGGCGTTTCCACCCGGAGAAAAAGGGCTTGGT
       730       740       750       760       770       780       790       800       810       820       830       840

            230                           240                           250                           260
 R  D  R  G  A  H  V  N  I  S  G  A  G  V  V  A  G  A  P  N  R  Q  G  A  I  R  F  L  E  Y  L  V  S  P  K  A  Q  E  M  F
ACGTGACCGCGGTGCACATGTCAATATCAGTGGGGCAGGTGTAGTCGCCGGCGCTCCTAACCGTCAAGGCGCAATTCGGTTCTTAGAGTACCTGGTCTCCCCAAAGGCCCAGGAAATGTT
TGCACTGGCGCCACGTGTACAGTTATAGTCACCCCGTCCACATCAGCGGCCGCGAGGATTGGCAGTTCCGCGTTAAGCCAAGAATCTCATGGACCAGAGGGGTTTCCGGGTCCTTTACAA
       850       860       870       880       890       900       910       920       930       940       950       960
```

```
            270                                     280                                     290                                     300
 A  M  A  N  F  E  Y  P  V  R  A  G  V  P  V  H  P  I  V  K  Q  F  G  N  F  R  G  Q  N  V  N  A  A  V  F  G  R  N  N  A
TGCTATGGCTAACTTTGAGTACCCGGTACGCGCAGGCGTCCCAGTCCACCCTATCGTCAAGCAATTCGGCAACTTTCGTGGTCAAAATGTCAACGCAGCAGTATTCGGGCGCAACAACGC
ACGATACCGATTGAAACTCATGGGCCATGCGCGTCCGCAGGGTCAGGTGGGATAGCAGTTCGTTAAGCCGTTGAAAGCACCAGTTTTACAGTTGCGTCGTCATAAGCCCGCGTTGTTGCG
        970         980         990        1000        1010        1020        1030        1040        1050        1060        1070        1080

            310                                     320
 E  A  L  R  I  M  D  R  A  G  W  R  G  G  S  H  H  H  H  H  H  *  *
AGAAGCACTTCGTATCATGGACCGGGCCGGTTGGCGTGGCGGTAGTCATCATCATCATCATCATTAATGAAAGGGCGATATCCAGCACACTGGCGGCCGTTACTAGTGGATCCGGCTGCT
TCTTCGTGAAGCATAGTACCTGGCCCGGCCAACCGCACCGCCATCAGTAGTAGTAGTAGTAGTAATTACTTTCCCGCTATAGGTCGTGTGACCGCCGGCAATGATCACCTAGGCCGACGA
       1090        1100        1110        1120        1130        1140        1150        1160        1170        1180        1190        1200


AACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCC
TTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGG
       1210        1220        1230        1240        1250        1260        1270        1280        1290        1300        1310        1320


GGAGCGACTCCCACGGCACGTTGGCAAGCTCG
CCTCGCTGAGGGTGCCGTGCAACCGTTCGAGC
       1330        1340        1350
```

FIG. 49 (Continued)

FIG. 50 - Exemplary Expression Construct for teFeBP3_N268C

SEQ ID NO: 132

```
CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
        10        20        30        40        50        60        70        80        90       100       110       120

                                                                                     10                            20
                                                             M  V  I  N  V  Y  S  A  R  H  Y  D  T  D  K  A  L  Y  N  T  F  T  Q  Q
GGTTTCCCTCTAGAAATAATTTTGTTTAACTTTAAGAAGGAGATATACCATGGTAATTAATGTATATAGTGCACGTCATTACGACACTGACAAGGCTCTCTATAATACCTTCACCCAACA
CCAAAGGGAGATCTTTATTAAAACAAATTGAAATTCTTCCTCTATATGGTACCATTAATTACATATATCACGTGCAGTAATGCTGTGACTGTTCCGAGAGATATTATGGAAGTGGGTTGT
       130       140       150       160       170       180       190       200       210       220       230       240

               30                            40                            50                            60
 T  G  I  R  V  N  I  I  E  A  E  A  D  A  L  I  E  R  I  R  S  E  G  S  R  T  P  A  D  V  L  I  T  V  D  A  G  R  L  W
AACCGGGATTCGTGTAAACATCATTGAGGCTGAGGCAGATGCCCTCATTGAACGTATTCGTTCTGAAGGTTCGCGCACCCCAGCCGATGTACTCATTACAGTAGACGCGGGTCGCTTATG
TTGGCCCTAAGCACATTTGTAGTAACTCCGACTCCGTCTACGGGAGTAACTTGCATAAGCAAGACTTCCAAGCGCGTGGGGTCGGCTACATGAGTAATGTCATCTGCGCCCAGCGAATAC
       250       260       270       280       290       300       310       320       330       340       350       360

               70                            80                            90                           100
 R  A  Q  E  A  G  I  L  Q  P  I  Q  S  R  V  L  N  S  V  V  P  A  N  L  R  E  P  Q  G  H  W  F  G  L  S  R  R  V  R  V
GCGTGCGCAAGAAGCTGGCATCTTACAGCCGATTCAATCGCGTGTTTTAAACAGTGTAGTACCAGCCAACCTCCGGGAACCACAGGGTCACTGGTTCGGTCTCTCCCGTCGTGTTCGCGT
CGCACGCGTTCTTCGACCGTAGAATGTCGGCTAAGTTAGCGCACAAAATTTGTCACATCATGGTCGGTTGGAGGCCCTTGGTGTCCCAGTGACCAAGCCAGAGAGGGCAGCACAAGCGCA
       370       380       390       400       410       420       430       440       450       460       470       480

              110                           120                           130                           140
 L  I  Y  N  K  S  R  V  N  P  S  Q  L  S  T  Y  E  D  L  A  N  P  K  W  R  R  Q  I  L  T  R  S  S  S  N  I  Y  N  Q  S
TCTGATTTATAACAAGTCCCGTGTTAATCCATCTCAGCTTTCCACATACGAAGATTTAGCTAATCCGAAGTGGCGCCGTCAGATCCTGACACGTTCTTCAAGCAACATTTACAACCAATC
AGACTAAATATTGTTCAGGGCACAATTAGGTAGAGTCGAAAGGTGTATGCTTCTAAATCGATTAGGCTTCACCGCGGCAGTCTAGGACTGTGCAAGAAGTTCGTTGTAAATGTTGGTTAG
       490       500       510       520       530       540       550       560       570       580       590       600

              150                           160                           170                           180
 L  T  G  S  L  L  A  I  H  G  A  Q  K  T  E  Q  W  A  R  G  L  V  Q  N  F  A  R  P  P  E  G  N  D  T  A  Q  I  R  A  S
GTTGACAGGTTCCTTACTCGCCATTCACGGGGCACAGAAGACCGAACAATGGGCACGTGGCTTAGTACAGAACTTCGCACGTCCACCGGAGGGGAATGACACAGCTCAAATTCGTGCAAG
CAACTGTCCAAGGAATGAGCGGTAAGTGCCCCGTGTCTTCTGGCTTGTTACCCGTGCACCGAATCATGTCTTGAAGCGTGCAGGTGGCCTCCCCTTACTGTGTCGAGTTTAAGCACGTTC
       610       620       630       640       650       660       670       680       690       700       710       720

              190                           200                           210                           220
 A  E  G  V  G  S  V  A  I  A  N  H  Y  Y  L  A  R  L  I  A  S  D  K  E  Q  D  R  A  V  A  A  K  V  G  L  F  F  P  N  Q
TGCAGAGGGCGTTGGCTCAGTAGCGATCGCCAATCACTATTACCTCGCCCGTTTAATTGCCAGTGACAAGGAGCAAGACCGTGCGGTGGCCGCAAAGGTGGGCCTCTTTTTCCCGAACCA
ACGTCTCCCGCAACCGAGTCATCGCTAGCGGTTAGTGATAATGGAGCGGGCAAATTAACGGTCACTGTTCCTCGTTCTGGCACGCCACCGGCGTTTCCACCCGGAGAAAAAGGGCTTGGT
       730       740       750       760       770       780       790       800       810       820       830       840

              230                           240                           250                           260
 R  D  R  G  A  H  V  N  I  S  G  A  G  V  V  A  G  A  P  N  R  Q  G  A  I  R  F  L  E  Y  L  V  S  P  K  A  Q  E  M  F
ACGTGACCGCGGTGCACATGTCAATATCAGTGGGGCAGGTGTAGTCGCCGGCGCTCCTAACCGTCAAGGCGCAATTCGGTTCTTAGAGTACCTGGTCTCCCCAAAGGCCCAGGAAATGTT
TGCACTGGCGCCACGTGTACAGTTATAGTCACCCCGTCCACATCAGCGGCCGCGAGGATTGGCAGTTCCGCGTTAAGCCAAGAATCTCATGGACCAGAGGGGTTTCCGGGTCCTTTACAA
       850       860       870       880       890       900       910       920       930       940       950       960
```

```
                270                                     280                                     290                                     300
  A   M   A   C   F   E   Y   P   V   R   A   G   V   P   V   H   P   I   V   K   Q   F   G   N   F   R   G   Q   N   V   N   A   A   V   F   G   R   N   N   A
TGCTATGGCTTGCTTTGAGTACCCGGTACGCGCAGGCGTCCCAGTCCACCCTATCGTCAAGCAATTCGGCAACTTTCGTGGTCAAAATGTCAACGCAGCAGTATTCGGGCGCAACAACGC
ACGATACCGAACGAAACTCATGGGCCATGCGCGTCCGCAGGGTCAGGTGGGATAGCAGTTCGTTAAGCCGTTGAAAGCACCAGTTTTACAGTTGCGTCGTCATAAGCCCGCGTTGTTGCG
         970          980          990         1000         1010         1020         1030         1040         1050         1060         1070         1080

                310                                     320
  E   A   L   R   I   M   D   R   A   G   W   R   G   G   S   H   H   H   H   H   H   *   *
AGAAGCACTTCGTATCATGGACCGGGCCGGTTGGCGTGGCGGTAGTCATCATCATCATCATCATTAATGAAAGGGCGATATCCAGCACACTGGCGGCCGTTACTAGTGGATCCGGCTGCT
TCTTCGTGAAGCATAGTACCTGGCCCGGCCAACCGCACCGCCATCAGTAGTAGTAGTAGTAGTAATTACTTTCCCGCTATAGGTCGTGTGACCGCCGGCAATGATCACCTAGGCCGACGA
        1090         1100         1110         1120         1130         1140         1150         1160         1170         1180         1190         1200


AACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCC
TTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGG
        1210         1220         1230         1240         1250         1260         1270         1280         1290         1300         1310         1320


GGAGCGACTCCCACGGCACGTTGGCAAGCTCG
CCTCGCTGAGGGTGCCGTGCAACCGTTCGAGC
        1330         1340         1350
```

FIG. 50 (Continued)

FIG. 51 - Exemplary Expression Construct for teFeBP3_E270C

SEQ ID NO: 133

CGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAGGGAGACCACAAC
GCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATCCCTCTGGTGTTG
10 20 30 40 50 60 70 80 90 100 110 120

10 20
M V I N V Y S A R H Y D T D K A L Y N T F T Q Q
GGTTTCCCTCTAGAAATAATTTTGTTTAACTTTAAGAAGGAGATATACCATGGTAATTAATGTATATAGTGCACGTCATTACGACACTGACAAGGCTCTCTATAATACCTTCACCCAACA
CCAAAGGGAGATCTTTATTAAAACAAATTGAAATTCTTCCTCTATATGGTACCATTAATTACATATATCACGTGCAGTAATGCTGTGACTGTTCCGAGAGATATTATGGAAGTGGGTTGT
130 140 150 160 170 180 190 200 210 220 230 240

30 40 50 60
T G I R V N I I E A E A D A L I E R I R S E G S R T P A D V L I T V D A G R L W
AACCGGGATTCGTGTAAACATCATTGAGGCTGAGGCAGATGCCCTCATTGAACGTATTCGTTCTGAAGGTTCGCGCACCCCAGCCGATGTACTCATTACAGTAGACGCGGGTCGCTTATG
TTGGCCCTAAGCACATTTGTAGTAACTCCGACTCCGTCTACGGGAGTAACTTGCATAAGCAAGACTTCCAAGCGCGTGGGGTCGGCTACATGAGTAATGTCATCTGCGCCCAGCGAATAC
250 260 270 280 290 300 310 320 330 340 350 360

70 80 90 100
R A Q E A G I L Q P I Q S R V L N S V V P A N L R E P Q G H W F G L S R R V R V
GCGTGCGCAAGAAGCTGGCATCTTACAGCCGATTCAATCGCGTGTTTTAAACAGTGTAGTACCAGCCAACCTCCGGGAACCACAGGGTCACTGGTTCGGTCTCTCCCGTCGTGTTCGCGT
CGCACGCGTTCTTCGACCGTAGAATGTCGGCTAAGTTAGCGCACAAAATTTGTCACATCATGGTCGGTTGGAGGCCCTTGGTGTCCCAGTGACCAAGCCAGAGAGGGCAGCACAAGCGCA
370 380 390 400 410 420 430 440 450 460 470 480

110 120 130 140
L I Y N K S R V N P S Q L S T Y E D L A N P K W R R Q I L T R S S S N I Y N Q S
TCTGATTTATAACAAGTCCCGTGTTAATCCATCTCAGCTTTCCACATACGAAGATTTAGCTAATCCGAAGTGGCGCCGTCAGATCCTGACACGTTCTTCAAGCAACATTTACAACCAATC
AGACTAAATATTGTTCAGGGCACAATTAGGTAGAGTCGAAAGGTGTATGCTTCTAAATCGATTAGGCTTCACCGCGGCAGTCTAGGACTGTGCAAGAAGTTCGTTGTAAATGTTGGTTAG
490 500 510 520 530 540 550 560 570 580 590 600

150 160 170 180
L T G S L L A I H G A Q K T E Q W A R G L V Q N F A R P P E G N D T A Q I R A S
GTTGACAGGTTCCTTACTCGCCATTCACGGGGCACAGAAGACCGAACAATGGGCACGTGGCTTAGTACAGAACTTCGCACGTCCACCGGAGGGGAATGACACAGCTCAAATTCGTGCAAG
CAACTGTCCAAGGAATGAGCGGTAAGTGCCCCGTGTCTTCTGGCTTGTTACCCGTGCACCGAATCATGTCTTGAAGCGTGCAGGTGGCCTCCCCTTACTGTGTCGAGTTTAAGCACGTTC
610 620 630 640 650 660 670 680 690 700 710 720

190 200 210 220
A E G V G S V A I A N H Y Y L A R L I A S D K E Q D R A V A A K V G L F F P N Q
TGCAGAGGGCGTTGGCTCAGTAGCGATCGCCAATCACTATTACCTCGCCCGTTTAATTGCCAGTGACAAGGAGCAAGACCGTGCGGTGGCCGCAAAGGTGGGCCTCTTTTTCCCGAACCA
ACGTCTCCCGCAACCGAGTCATCGCTAGCGGTTAGTGATAATGGAGCGGGCAAATTAACGGTCACTGTTCCTCGTTCTGGCACGCCACCGGCGTTTCCACCCGGAGAAAAAGGGCTTGGT
730 740 750 760 770 780 790 800 810 820 830 840

230 240 250 260
R D R G A H V N I S G A G V V A G A P N R Q G A I R F L E Y L V S P K A Q E M F
ACGTGACCGCGGTGCACATGTCAATATCAGTGGGGCAGGTGTAGTCGCCGGCGCTCCTAACCGTCAAGGCGCAATTCGGTTCTTAGAGTACCTGGTCTCCCCAAAGGCCCAGGAAATGTT
TGCACTGGCGCCACGTGTACAGTTATAGTCACCCCGTCCACATCAGCGGCCGCGAGGATTGGCAGTTCCGCGTTAAGCCAAGAATCTCATGGACCAGAGGGGTTTCCGGGTCCTTTACAA
850 860 870 880 890 900 910 920 930 940 950 960

```
                270                                     280                                     290                                     300
 A   M   A   N   F   C   Y   P   V   R   A   G   V   P   V   H   P   I   V   K   Q   F   G   N   F   R   G   Q   N   V   N   A   A   V   F   G   R   N   N   A
TGCTATGGCTAACTTTTGCTACCCGGTACGCGCAGGCGTCCCAGTCCACCCTATCGTCAAGCAATTCGGCAACTTTCGTGGTCAAAATGTCAACGCAGCAGTATTCGGGCGCAACAACGC
ACGATACCGATTGAAAACGATGGGCCATGCGCGTCCGCAGGGTCAGGTGGGATAGCAGTTCGTTAAGCCGTTGAAAGCACCAGTTTTACAGTTGCGTCGTCATAAGCCCGCGTTGTTGCG
         970          980          990         1000         1010         1020         1030         1040         1050         1060         1070         1080

                310                                     320
 E   A   L   R   I   M   D   R   A   G   W   R   G   G   S   H   H   H   H   H   H   *   *
AGAAGCACTTCGTATCATGGACCGGGCCGGTTGGCGTGGCGGTAGTCATCATCATCATCATCATTAATGAAAGGGCGATATCCAGCACACTGGCGGCCGTTACTAGTGGATCCGGCTGCT
TCTTCGTGAAGCATAGTACCTGGCCCGGCCAACCGCACCGCCATCAGTAGTAGTAGTAGTAGTAATTACTTTCCCGCTATAGGTCGTGTGACCGCCGGCAATGATCACCTAGGCCGACGA
        1090         1100         1110         1120         1130         1140         1150         1160         1170         1180         1190         1200


AACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCC
TTGTTTCGGGCTTTCCTTCGACTCAACCGACGACGGTGGCGACTCGTTATTGATCGTATTGGGGAACCCCGGAGATTTGCCCAGAACTCCCCAAAAAACGACTTTCCTCCTTGATATAGG
        1210         1220         1230         1240         1250         1260         1270         1280         1290         1300         1310         1320


GGAGCGACTCCCACGGCACGTTGGCAAGCTCG
CCTCGCTGAGGGTGCCGTGCAACCGTTCGAGC
        1330         1340         1350
```

FIG. 51 (Continued)

FIG. 52 – Exemplary Expression Construct for avBicarbBP5_16C_bZif

SEQ ID NO: 134

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                          10
                                                                          M  A  E  Q  A  P  E  V  T  T  V  K  L  G  Y  C  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATTGCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATAACGGGCTAACAGCT
       130       140       150       160       170       180       190       200       210       220       230       240

                                          30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                                          70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                                         110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                                         150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                                         190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                                         230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                                   270                                 280                                 290
 Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
        970         980         990        1000        1010        1020        1030        1040        1050        1060        1070        1080

                                   310                                 320                                 330
 Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
       1090        1100        1110        1120        1130        1140        1150        1160        1170        1180        1190        1200

                                   350                                 360                                 370
 A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
       1210        1220        1230        1240        1250        1260        1270        1280        1290        1300        1310        1320

                                   390                                 400                                 410
 F   F   D   G   T   K   F   D   P   E   K   P   D   E   Y   L   K   S   L   K   I   K   K   V   S   V   G   G   S   T   G   E   K   P   Y   K   C   P   E   C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
       1330        1340        1350        1360        1370        1380        1390        1400        1410        1420        1430        1440

                                   430
 G   K   S   F   S   R   S   G   G   S   H   H   H   H   H   H   *   *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
       1450        1460        1470        1480        1490        1500        1510        1520        1530        1540        1550        1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1570        1580        1590        1600        1610        1620        1630        1640        1650        1660        1670        1680


GCACGTTGGCAAGCTCGGAATTCGGCGTAATC
CGTGCAACCGTTCGAGCCTTAAGCCGCATTAG
       1690        1700        1710
```

FIG. 52 (Continued)

FIG. 53 - Exemplary Expression Construct for avBicarbBP5_17C_bZif

SEQ ID NO: 135

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                             10
                                                                        M  A  E  Q  A  P  E  V  T  T  V  K  L  G  Y  I  C  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCTGCATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGACGTAACAGCT
       130       140       150       160       170       180       190       200       210       220       230       240

                             30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                             70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                            110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                            150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                            190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                            230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                                  270                                280                                290
 Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
       970       980       990      1000      1010      1020      1030      1040      1050      1060      1070      1080

                                  310                                320                                330
 Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
      1090      1100      1110      1120      1130      1140      1150      1160      1170      1180      1190      1200

                                  350                                360                                370
 A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
      1210      1220      1230      1240      1250      1260      1270      1280      1290      1300      1310      1320

                                  390                                400                                410
 F   F   D   G   T   K   F   D   P   E   K   P   D   E   Y   L   K   S   L   K   I   K   K   V   S   V   G   G   S   T   G   E   K   P   Y   K   C   P   E   C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
      1330      1340      1350      1360      1370      1380      1390      1400      1410      1420      1430      1440

                                  430
 G   K   S   F   S   R   S   G   G   S   H   H   H   H   H   H   *   *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
      1450      1460      1470      1480      1490      1500      1510      1520      1530      1540      1550      1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1570      1580      1590      1600      1610      1620      1630      1640      1650      1660      1670      1680


GCACGTTGGCAAGCTCGGAATTCGGCGTAATC
CGTGCAACCGTTCGAGCCTTAAGCCGCATTAG
      1690      1700      1710
```

FIG. 53 (Continued)

FIG. 54 – Exemplary Expression Construct for avBicarbBP5_18C_bZif

SEQ ID NO: 136

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                       10
                                                                M  A  E  Q  A  P  E  V  T  T  V  K  L  G  Y  I  P  C  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGTGCGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCACGCAGCT
       130       140       150       160       170       180       190       200       210       220       230       240

                          30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                          70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                         110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                         150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                         190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                         230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                          270                                  280                                  290
 Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
        970         980         990        1000        1010        1020        1030        1040        1050        1060        1070        1080

                          310                                  320                                  330
 Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
       1090        1100        1110        1120        1130        1140        1150        1160        1170        1180        1190        1200

                          350                                  360                                  370
 A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
       1210        1220        1230        1240        1250        1260        1270        1280        1290        1300        1310        1320

                          390                                  400                                  410
 F   F   D   G   T   K   F   D   P   E   K   P   D   E   Y   L   K   S   L   K   I   K   K   V   S   V   G   G   S   T   G   E   K   P   Y   K   C   P   E   C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
       1330        1340        1350        1360        1370        1380        1390        1400        1410        1420        1430        1440

                          430
 G   K   S   F   S   R   S   G   G   S   H   H   H   H   H   H   *   *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
       1450        1460        1470        1480        1490        1500        1510        1520        1530        1540        1550        1560

GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1570        1580        1590        1600        1610        1620        1630        1640        1650        1660        1670        1680

GCACGTTGGCAAGCTCGGAATTCGGCGTAATC
CGTGCAACCGTTCGAGCCTTAAGCCGCATTAG
       1690        1700        1710
```

FIG. 54 (Continued)

FIG. 55 – Exemplary Expression Construct for avBicarbBP5_190C_bZif

SEQ ID NO: 137

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                           10
                                                                              M  A  E  Q  A  P  E  V  T  T  V  K  L  G  Y  I  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCTAACAGCT
       130       140       150       160       170       180       190       200       210       220       230       240

                                       30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                                       70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                                      110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                                      150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                                      190                           200                           210
 K  T  G  T  M  D  A  F  S  C  G  D  P  W  P  F  R  L  V  N  D  K  I  G  Y  M  A  A  L  T  A  E  I  W  K  N  H  P  E  E
GAAGACCGGCACAATGGACGCATTTTCCTGCGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGACGCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                                      230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                   270                           280                           290
 Q  I  L  A  G  R  N  Y  F  N  L  N  N  P  E  I  L  A  D  P  Y  V  G  K  Y  D  M  G  D  G  R  K  I  D  D  K  S  M  A  A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
       970       980       990      1000      1010      1020      1030      1040      1050      1060      1070      1080

                   310                           320                           330
 Y  Y  W  K  D  E  K  G  S  V  S  Y  P  Y  K  S  H  D  L  W  F  I  T  E  N  V  R  W  G  F  L  P  K  D  Y  L  A  N  G  A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
      1090      1100      1110      1120      1130      1140      1150      1160      1170      1180      1190      1200

                   350                           360                           370
 A  K  A  K  E  L  I  D  K  V  N  R  E  D  I  W  K  E  A  A  K  E  A  G  I  A  A  A  D  I  P  T  S  T  S  R  G  V  E  E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
      1210      1220      1230      1240      1250      1260      1270      1280      1290      1300      1310      1320

                   390                           400                           410
 F  F  D  G  T  K  F  D  P  E  K  P  D  E  Y  L  K  S  L  K  I  K  K  V  S  V  G  G  S  T  G  E  K  P  Y  K  C  P  E  C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
      1330      1340      1350      1360      1370      1380      1390      1400      1410      1420      1430      1440

                   430
 G  K  S  F  S  R  S  G  G  S  H  H  H  H  H  H  *  *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
      1450      1460      1470      1480      1490      1500      1510      1520      1530      1540      1550      1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1570      1580      1590      1600      1610      1620      1630      1640      1650      1660      1670      1680


GCACGTTGGCAAGCTCGGAATTCGGCGTAATC
CGTGCAACCGTTCGAGCCTTAAGCCGCATTAG
      1690      1700      1710
```

FIG. 55 (Continued)

FIG. 56 - Exemplary Expression Construct for avBicarbBP5_194C_bZif

SEQ ID NO: 138

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                       10
                                                                  M  A  E  Q  A  P  E  V  T  T  V  K  L  G  Y  I  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCTAACAGCT
       130       140       150       160       170       180       190       200       210       220       230       240

                             30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                             70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                            110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                            150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                            190                           200                           210
 K  T  G  T  M  D  A  F  S  T  G  D  P  C  P  F  R  L  V  N  D  K  I  G  Y  M  A  A  L  T  A  E  I  W  K  N  H  P  E  E
GAAGACCGGCACAATGGACGCATTTTCCACGGGCGACCCATGCCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACGGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                            230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                            270                                     280                                     290
 Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
        970       980       990      1000      1010      1020      1030      1040      1050      1060      1070      1080

                            310                                     320                                     330
 Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
       1090      1100      1110      1120      1130      1140      1150      1160      1170      1180      1190      1200

                            350                                     360                                     370
 A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
       1210      1220      1230      1240      1250      1260      1270      1280      1290      1300      1310      1320

                            390                                     400                                     410
 F   F   D   G   T   K   F   D   P   E   K   P   D   E   Y   L   K   S   L   K   I   K   K   V   S   V   G   G   S   T   G   E   K   P   Y   K   C   P   E   C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
       1330      1340      1350      1360      1370      1380      1390      1400      1410      1420      1430      1440

                            430
 G   K   S   F   S   R   S   G   G   S   H   H   H   H   H   H   *   *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
       1450      1460      1470      1480      1490      1500      1510      1520      1530      1540      1550      1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1570      1580      1590      1600      1610      1620      1630      1640      1650      1660      1670      1680


GCACGTTGGCAAGCTCGGAATTCGGCGTAATC
CGTGCAACCGTTCGAGCCTTAAGCCGCATTAG
       1690      1700      1710
```

FIG. 56 (Continued)

FIG. 57 – Exemplary Expression Construct for avBicarbBP5_16C_71D_bZif

SEQ ID NO: 139

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10          20          30          40          50          60          70          80          90         100         110         120

                                                                                                                     10
                                                                              M  A  E  Q  A  P  E  V  T  T  V  K  L  G  Y  C  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATTGCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATAACGGGCTAACAGCT
       130         140         150         160         170         180         190         200         210         220         230         240

                                             30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250         260         270         280         290         300         310         320         330         340         350         360

                                             70                            80                            90
 A  G  G  G  I  D  G  G  Q  W  D  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGGATATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCCTATACGGATACGGTGTAGAGTAGTGACTTCCGAATTAATGCTTCCCGTTAGTCTTTTAGGGTTACATGCAGAATCGTGTCAACTAGTG
       370         380         390         400         410         420         430         440         450         460         470         480

                                            110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490         500         510         520         530         540         550         560         570         580         590         600

                                            150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610         620         630         640         650         660         670         680         690         700         710         720

                                            190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730         740         750         760         770         780         790         800         810         820         830         840

                                            230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850         860         870         880         890         900         910         920         930         940         950         960
```

```
                    270                           280                           290
 Q  I  L  A  G  R  N  Y  F  N  L  N  N  P  E  I  L  A  D  P  Y  V  G  K  Y  D  M  G  D  G  R  K  I  D  D  K  S  M  A  A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
      970       980       990      1000      1010      1020      1030      1040      1050      1060      1070      1080

                    310                           320                           330
 Y  Y  W  K  D  E  K  G  S  V  S  Y  P  Y  K  S  H  D  L  W  F  I  T  E  N  V  R  W  G  F  L  P  K  D  Y  L  A  N  G  A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
     1090      1100      1110      1120      1130      1140      1150      1160      1170      1180      1190      1200

                    350                           360                           370
 A  K  A  K  E  L  I  D  K  V  N  R  E  D  I  W  K  E  A  A  K  E  A  G  I  A  A  A  D  I  P  T  S  T  S  R  G  V  E  E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
     1210      1220      1230      1240      1250      1260      1270      1280      1290      1300      1310      1320

                    390                           400                           410
 F  F  D  G  T  K  F  D  P  E  K  P  D  E  Y  L  K  S  L  K  I  K  K  V  S  V  G  G  S  T  G  E  K  P  Y  K  C  P  E  C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
     1330      1340      1350      1360      1370      1380      1390      1400      1410      1420      1430      1440

                    430
 G  K  S  F  S  R  S  G  G  S  H  H  H  H  H  H  *  *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
     1450      1460      1470      1480      1490      1500      1510      1520      1530      1540      1550      1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
     1570      1580      1590      1600      1610      1620      1630      1640      1650      1660      1670      1680


GCACGTTGGCAAGCTCGGAATTCGGCGTAATC
CGTGCAACCGTTCGAGCCTTAAGCCGCATTAG
     1690      1700      1710
```

FIG. 57 (Continued)

FIG. 58 - Exemplary Expression Construct for avBicarbBP5_16C_71N_bZif

SEQ ID NO: 140

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                                  10
                                                                               M  A  E  Q  A  P  E  V  T  T  V  K  L  G  Y  C  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATTGCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATAACGGGCTAACAGCT
       130       140       150       160       170       180       190       200       210       220       230       240

                                            30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                                            70                            80                            90
 A  G  G  G  I  D  G  G  Q  W  N  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGAACATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCTTGTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                                           110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                                           150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                                           190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                                           230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                    270                           280                           290
 Q  I  L  A  G  R  N  Y  F  N  L  N  N  P  E  I  L  A  D  P  Y  V  G  K  Y  D  M  G  D  G  R  K  I  D  D  K  S  M  A  A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
       970       980       990      1000      1010      1020      1030      1040      1050      1060      1070      1080

                    310                           320                           330
 Y  Y  W  K  D  E  K  G  S  V  S  Y  P  Y  K  S  H  D  L  W  F  I  T  E  N  V  R  W  G  F  L  P  K  D  Y  L  A  N  G  A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
      1090      1100      1110      1120      1130      1140      1150      1160      1170      1180      1190      1200

                    350                           360                           370
 A  K  A  K  E  L  I  D  K  V  N  R  E  D  I  W  K  E  A  A  K  E  A  G  I  A  A  A  D  I  P  T  S  T  S  R  G  V  E  E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
      1210      1220      1230      1240      1250      1260      1270      1280      1290      1300      1310      1320

                    390                           400                           410
 F  F  D  G  T  K  F  D  P  E  K  P  D  E  Y  L  K  S  L  K  I  K  K  V  S  V  G  G  S  T  G  E  K  P  Y  K  C  P  E  C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
      1330      1340      1350      1360      1370      1380      1390      1400      1410      1420      1430      1440

                    430
 G  K  S  F  S  R  S  G  G  S  H  H  H  H  H  H  *  *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
      1450      1460      1470      1480      1490      1500      1510      1520      1530      1540      1550      1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1570      1580      1590      1600      1610      1620      1630      1640      1650      1660      1670      1680


GCACGTTGGCAAGCTCGGAATTCGGCGTAATC
CGTGCAACCGTTCGAGCCTTAAGCCGCATTAG
      1690      1700      1710
```

FIG. 58 (Continued)

FIG. 59 - Exemplary Expression Construct for avBicarbBP5_16C_71E_bZif

SEQ ID NO: 141

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                         10
                                                                      M  A  E  Q  A  P  E  V  T  T  V  K  L  G  Y  C  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATTGCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATAACGGGCTAACAGCT
       130       140       150       160       170       180       190       200       210       220       230       240

                             30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                             70                            80                            90
 A  G  G  G  I  D  G  G  Q  W  E  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGGAAATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCCTTTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                             110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                             150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                             190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                             230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                         270                                     280                                     290
 Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
        970       980       990      1000      1010      1020      1030      1040      1050      1060      1070      1080

                         310                                     320                                     330
 Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
       1090      1100      1110      1120      1130      1140      1150      1160      1170      1180      1190      1200

                         350                                     360                                     370
 A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
       1210      1220      1230      1240      1250      1260      1270      1280      1290      1300      1310      1320

                         390                                     400                                     410
 F   F   D   G   T   K   F   D   P   E   K   P   D   E   Y   L   K   S   L   K   I   K   K   V   S   V   G   G   S   T   G   E   K   P   Y   K   C   P   E   C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
       1330      1340      1350      1360      1370      1380      1390      1400      1410      1420      1430      1440

                         430
 G   K   S   F   S   R   S   G   G   S   H   H   H   H   H   H   *   *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
       1450      1460      1470      1480      1490      1500      1510      1520      1530      1540      1550      1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1570      1580      1590      1600      1610      1620      1630      1640      1650      1660      1670      1680


GCACGTTGGCAAGCTCGGAATTCGGCGTAATC
CGTGCAACCGTTCGAGCCTTAAGCCGCATTAG
       1690      1700      1710
```

FIG. 59 (Continued)

FIG. 60 – Exemplary Expression Construct for avBicarbBP5_16C_71M_bZif

SEQ ID NO: 142

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                                 10
                                                                              M  A  E  Q  A  P  E  V  T  T  V  K  L  G  Y  C  P  I  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATTGCCCGATTGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATAACGGGCTAACAGCT
       130       140       150       160       170       180       190       200       210       220       230       240

                                             30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                                             70                            80                            90
 A  G  G  G  I  D  G  G  Q  W  M  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGATGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCTACTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                                            110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                                            150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                                            190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                                            230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                          270                                     280                                     290
Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
         970          980          990         1000         1010         1020         1030         1040         1050         1060         1070         1080

                          310                                     320                                     330
Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
        1090         1100         1110         1120         1130         1140         1150         1160         1170         1180         1190         1200

                          350                                     360                                     370
A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
        1210         1220         1230         1240         1250         1260         1270         1280         1290         1300         1310         1320

                          390                                     400                                     410
F   F   D   G   T   K   F   D   P   E   K   P   D   E   Y   L   K   S   L   K   I   K   K   V   S   V   G   G   S   T   G   E   K   P   Y   K   C   P   E   C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
        1330         1340         1350         1360         1370         1380         1390         1400         1410         1420         1430         1440

                          430
G   K   S   F   S   R   S   G   G   S   H   H   H   H   H   H   *   *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
        1450         1460         1470         1480         1490         1500         1510         1520         1530         1540         1550         1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
        1570         1580         1590         1600         1610         1620         1630         1640         1650         1660         1670         1680


GCACGTTGGCAAGCTCGGAATTCGGCGTAATC
CGTGCAACCGTTCGAGCCTTAAGCCGCATTAG
        1690         1700         1710
```

FIG. 60 (Continued)

FIG. 61 – Exemplary Expression Construct for avBicarbBP5_18C_16M_bZif

SEQ ID NO: 143

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                                 10
                                                                              M  A  E  Q  A  P  E  V  T  T  V  K  L  G  Y  M  P  C  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATGCCGTGCGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATACGGCACGCAGCT
       130       140       150       160       170       180       190       200       210       220       230       240

                                             30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                                             70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                                            110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                                            150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                                            190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                                            230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                                  270                                     280                                     290
 Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
        970          980          990         1000         1010         1020         1030         1040         1050         1060         1070         1080

                                  310                                     320                                     330
 Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
       1090         1100         1110         1120         1130         1140         1150         1160         1170         1180         1190         1200

                                  350                                     360                                     370
 A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
       1210         1220         1230         1240         1250         1260         1270         1280         1290         1300         1310         1320

                                  390                                     400                                     410
 F   F   D   G   T   K   F   D   P   E   K   P   D   E   Y   L   K   S   L   K   I   K   K   V   S   V   G   G   S   T   G   E   K   P   Y   K   C   P   E   C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
       1330         1340         1350         1360         1370         1380         1390         1400         1410         1420         1430         1440

                                  430
 G   K   S   F   S   R   S   G   G   S   H   H   H   H   H   H   *   *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
       1450         1460         1470         1480         1490         1500         1510         1520         1530         1540         1550         1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1570         1580         1590         1600         1610         1620         1630         1640         1650         1660         1670         1680


GCACGTTGGCAAGCTCGGAATTCGGCGTAATC
CGTGCAACCGTTCGAGCCTTAAGCCGCATTAG
       1690         1700         1710
```

FIG. 61 (Continued)

FIG. 62 - Exemplary Expression Construct for avBicarbBP5_18C_16F_bZif

SEQ ID NO: 144

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                           10
                                                                       M  A  E  Q  A  P  E  V  T  T  V  K  L  G  Y  F  P  C  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATTTTCCGTGCGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATAAAAGGCACGCAGCT
       130       140       150       160       170       180       190       200       210       220       230       240

                               30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                               70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                              110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                              150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                              190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                              230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                                270                                          280                                          290
 Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
       970       980       990      1000      1010      1020      1030      1040      1050      1060      1070      1080

                                310                                          320                                          330
 Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
      1090      1100      1110      1120      1130      1140      1150      1160      1170      1180      1190      1200

                                350                                          360                                          370
 A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
      1210      1220      1230      1240      1250      1260      1270      1280      1290      1300      1310      1320

                                390                                          400                                          410
 F   F   D   G   T   K   F   D   P   E   K   P   D   E   Y   L   K   S   L   K   I   K   K   V   S   V   G   G   S   T   G   E   K   P   Y   K   C   P   E   C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
      1330      1340      1350      1360      1370      1380      1390      1400      1410      1420      1430      1440

                                430
 G   K   S   F   S   R   S   G   G   S   H   H   H   H   H   H   *   *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
      1450      1460      1470      1480      1490      1500      1510      1520      1530      1540      1550      1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1570      1580      1590      1600      1610      1620      1630      1640      1650      1660      1670      1680


GCACGTTGGCAAGCTCGGAATTCGGCGTAATC
CGTGCAACCGTTCGAGCCTTAAGCCGCATTAG
      1690      1700      1710
```

FIG. 62 (Continued)

FIG. 63 - Exemplary Expression Construct for avBicarbBP5_18C_16Y_bZif

SEQ ID NO: 145

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                         10
                                                                      M  A  E  Q  A  P  E  V  T  T  V  K  L  G  Y  Y  P  C  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATTATCCGTGCGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATAATAGGCACGCAGCT
       130       140       150       160       170       180       190       200       210       220       230       240

                              30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                              70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                             110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                             150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                             190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                             230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                    270                           280                           290
 Q  I  L  A  G  R  N  Y  F  N  L  N  N  P  E  I  L  A  D  P  Y  V  G  K  Y  D  M  G  D  G  R  K  I  D  D  K  S  M  A  A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
       970       980       990      1000      1010      1020      1030      1040      1050      1060      1070      1080

                    310                           320                           330
 Y  Y  W  K  D  E  K  G  S  V  S  Y  P  Y  K  S  H  D  L  W  F  I  T  E  N  V  R  W  G  F  L  P  K  D  Y  L  A  N  G  A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
      1090      1100      1110      1120      1130      1140      1150      1160      1170      1180      1190      1200

                    350                           360                           370
 A  K  A  K  E  L  I  D  K  V  N  R  E  D  I  W  K  E  A  A  K  E  A  G  I  A  A  A  D  I  P  T  S  T  S  R  G  V  E  E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
      1210      1220      1230      1240      1250      1260      1270      1280      1290      1300      1310      1320

                    390                           400                           410
 F  F  D  G  T  K  F  D  P  E  K  P  D  E  Y  L  K  S  L  K  I  K  K  V  S  V  G  G  S  T  G  E  K  P  Y  K  C  P  E  C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
      1330      1340      1350      1360      1370      1380      1390      1400      1410      1420      1430      1440

                    430
 G  K  S  F  S  R  S  G  G  S  H  H  H  H  H  H  *  *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
      1450      1460      1470      1480      1490      1500      1510      1520      1530      1540      1550      1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
      1570      1580      1590      1600      1610      1620      1630      1640      1650      1660      1670      1680


GCACGTTGGCAAGCTCGGAATTCGGCGTAATC
CGTGCAACCGTTCGAGCCTTAAGCCGCATTAG
      1690      1700      1710
```

FIG. 63 (Continued)

FIG. 64 - Exemplary Expression Construct for avBicarbBP5_18C_16W_bZif

SEQ ID NO: 146

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                           10
                                                                              M  A  E  Q  A  P  E  V  T  T  V  K  L  G  Y  W  P  C  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATTGGCCGTGCGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATAACCGGCACGCAGCT
       130       140       150       160       170       180       190       200       210       220       230       240

                                       30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                                       70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                                      110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                                      150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                                      190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                                      230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                        270                                     280                                     290
 Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
        970         980         990        1000        1010        1020        1030        1040        1050        1060        1070        1080

                        310                                     320                                     330
 Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
       1090        1100        1110        1120        1130        1140        1150        1160        1170        1180        1190        1200

                        350                                     360                                     370
 A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
       1210        1220        1230        1240        1250        1260        1270        1280        1290        1300        1310        1320

                        390                                     400                                     410
 F   F   D   G   T   K   F   D   P   E   K   P   D   E   Y   L   K   S   L   K   I   K   K   V   S   V   G   G   S   T   G   E   K   P   Y   K   C   P   E   C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
       1330        1340        1350        1360        1370        1380        1390        1400        1410        1420        1430        1440

                        430
 G   K   S   F   S   R   S   G   G   S   H   H   H   H   H   H   *   *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
       1450        1460        1470        1480        1490        1500        1510        1520        1530        1540        1550        1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1570        1580        1590        1600        1610        1620        1630        1640        1650        1660        1670        1680


GCACGTTGGCAAGCTCGGAATTCGGCGTAATC
CGTGCAACCGTTCGAGCCTTAAGCCGCATTAG
       1690        1700        1710
```

FIG. 64 (Continued)

FIG. 65 - Exemplary Expression Construct for avBicarbBP5_18C_16E_bZif

SEQ ID NO: 147

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                           10
                                                                       M  A  E  Q  A  P  E  V  T  T  V  K  L  G  Y  E  P  C  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATGAACCGTGCGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATACTTGGCACGCAGCT
       130       140       150       160       170       180       190       200       210       220       230       240

                                        30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                                        70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                                       110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                                       150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                                       190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                                       230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                              270                                     280                                     290
 Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
        970          980          990         1000         1010         1020         1030         1040         1050         1060         1070         1080

                              310                                     320                                     330
 Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
       1090         1100         1110         1120         1130         1140         1150         1160         1170         1180         1190         1200

                              350                                     360                                     370
 A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
       1210         1220         1230         1240         1250         1260         1270         1280         1290         1300         1310         1320

                              390                                     400                                     410
 F   F   D   G   T   K   F   D   P   E   K   P   D   E   Y   L   K   S   L   K   I   K   K   V   S   V   G   G   S   T   G   E   K   P   Y   K   C   P   E   C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
       1330         1340         1350         1360         1370         1380         1390         1400         1410         1420         1430         1440

                              430
 G   K   S   F   S   R   S   G   G   S   H   H   H   H   H   H   *   *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
       1450         1460         1470         1480         1490         1500         1510         1520         1530         1540         1550         1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1570         1580         1590         1600         1610         1620         1630         1640         1650         1660         1670         1680


GCACGTTGGCAAGCTCGGAATTCGGCGTAATC
CGTGCAACCGTTCGAGCCTTAAGCCGCATTAG
       1690         1700         1710
```

FIG. 65 (Continued)

FIG. 66 - Exemplary Expression Construct for avBicarbBP5_18C_49F_bZif

SEQ ID NO: 148

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10          20          30          40          50          60          70          80          90         100         110         120

                                                                                                        10
                                                                                    M  A  E  Q  A  P  E  V  T  T  V  K  L  G  Y  I  P  C  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGTGCGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCACGCAGCT
       130         140         150         160         170         180         190         200         210         220         230         240

                                    30                            40                            50
 S  A  P  L  I  I  A  K  E  K  G  F  F  A  K  Y  G  L  T  N  V  E  L  S  K  Q  A  S  F  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTTTGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCAAACCGTCACGGGCCCTATTACATCTCTAGCCATC
       250         260         270         280         290         300         310         320         330         340         350         360

                                    70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370         380         390         400         410         420         430         440         450         460         470         480

                                   110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490         500         510         520         530         540         550         560         570         580         590         600

                                   150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610         620         630         640         650         660         670         680         690         700         710         720

                                   190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730         740         750         760         770         780         790         800         810         820         830         840

                                   230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850         860         870         880         890         900         910         920         930         940         950         960
```

```
                                270                                     280                                     290
 Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
         970          980          990         1000         1010         1020         1030         1040         1050         1060         1070         1080

                                310                                     320                                     330
 Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
        1090         1100         1110         1120         1130         1140         1150         1160         1170         1180         1190         1200

                                350                                     360                                     370
 A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
        1210         1220         1230         1240         1250         1260         1270         1280         1290         1300         1310         1320

                                390                                     400                                     410
 F   F   D   G   T   K   F   D   P   E   K   P   D   E   Y   L   K   S   L   K   I   K   K   V   S   V   G   G   S   T   G   E   K   P   Y   K   C   P   E   C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
        1330         1340         1350         1360         1370         1380         1390         1400         1410         1420         1430         1440

                                430
 G   K   S   F   S   R   S   G   G   S   H   H   H   H   H   H   *   *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
        1450         1460         1470         1480         1490         1500         1510         1520         1530         1540         1550         1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
        1570         1580         1590         1600         1610         1620         1630         1640         1650         1660         1670         1680


GCACGTTGGCAAGCTCGGAATTCGGCGTAATC
CGTGCAACCGTTCGAGCCTTAAGCCGCATTAG
        1690         1700         1710
```

FIG. 66 (Continued)

FIG. 67 – Exemplary Expression Construct for avBicarbBP5_18C_49Y_bZif

SEQ ID NO: 149

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                     10
                                                                    M  A  E  Q  A  P  E  V  T  T  V  K  L  G  Y  I  P  C  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGTGCGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCACGCAGCT
       130       140       150       160       170       180       190       200       210       220       230       240

                          30                            40                            50
 S  A  P  L  I  I  A  K  E  K  G  F  F  A  K  Y  G  L  T  N  V  E  L  S  K  Q  A  S  Y  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTATGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCATACCGTCACGGGCCCTATTACATCTCTAGCCATC
       250       260       270       280       290       300       310       320       330       340       350       360

                          70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                         110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                         150                           160                           170
 T  F  P  H  V  N  Q  D  L  W  I  R  Y  W  L  A  A  G  G  I  D  P  D  A  D  V  K  L  L  T  V  P  A  A  Q  T  V  A  N  M
CACTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GTGAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                         190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                         230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                               270                                      280                                      290
Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
         970         980         990        1000        1010        1020        1030        1040        1050        1060        1070        1080

                               310                                      320                                      330
Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
        1090        1100        1110        1120        1130        1140        1150        1160        1170        1180        1190        1200

                               350                                      360                                      370
A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
        1210        1220        1230        1240        1250        1260        1270        1280        1290        1300        1310        1320

                               390                                      400                                      410
F   F   D   G   T   K   F   D   P   E   K   P   D   E   Y   L   K   S   L   K   I   K   K   V   S   V   G   G   S   T   G   E   K   P   Y   K   C   P   E   C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
        1330        1340        1350        1360        1370        1380        1390        1400        1410        1420        1430        1440

                               430
G   K   S   F   S   R   S   G   G   S   H   H   H   H   H   H   *   *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
        1450        1460        1470        1480        1490        1500        1510        1520        1530        1540        1550        1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
        1570        1580        1590        1600        1610        1620        1630        1640        1650        1660        1670        1680


GCACGTTGGCAAGCTCGGAATTCGGCGTAATC
CGTGCAACCGTTCGAGCCTTAAGCCGCATTAG
        1690        1700        1710
```

FIG. 67 (Continued)

FIG. 68 - Exemplary Expression Construct for avBicarbBP5_18C_141V_bZif

SEQ ID NO: 150

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                   10
                                                                              M  A  E  Q  A  P  E  V  T  T  V  K  L  G  Y  I  P  C  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGTGCGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCACGCAGCT
       130       140       150       160       170       180       190       200       210       220       230       240

                       30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                       70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                      110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                      150                           160                           170
 V  F  P  H  V  N  Q  D  L  W  I  R  Y  W  L  A  A  G  G  I  D  P  D  A  D  V  K  L  L  T  V  P  A  A  Q  T  V  A  N  M
CGTGTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GCACAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                      190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                      230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                          270                                     280                                     290
 Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
        970       980       990      1000      1010      1020      1030      1040      1050      1060      1070      1080

                          310                                     320                                     330
 Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
       1090      1100      1110      1120      1130      1140      1150      1160      1170      1180      1190      1200

                          350                                     360                                     370
 A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
       1210      1220      1230      1240      1250      1260      1270      1280      1290      1300      1310      1320

                          390                                     400                                     410
 F   F   D   G   T   K   F   D   P   E   K   P   D   E   Y   L   K   S   L   K   I   K   K   V   S   V   G   G   S   T   G   E   K   P   Y   K   C   P   E   C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
       1330      1340      1350      1360      1370      1380      1390      1400      1410      1420      1430      1440

                          430
 G   K   S   F   S   R   S   G   G   S   H   H   H   H   H   H   *   *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
       1450      1460      1470      1480      1490      1500      1510      1520      1530      1540      1550      1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1570      1580      1590      1600      1610      1620      1630      1640      1650      1660      1670      1680


GCACGTTGGCAAGCTCGGAATTCGGCGTAATC
CGTGCAACCGTTCGAGCCTTAAGCCGCATTAG
       1690      1700      1710
```

FIG. 68 (Continued)

FIG. 69 – Exemplary Expression Construct for avBicarbBP5_18C_141F_bZif

SEQ ID NO: 151

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10         20         30         40         50         60         70         80         90        100        110        120

                                                                                                           10
                                                                               M  A  E  Q  A  P  E  V  T  T  V  K  L  G  Y  I  P  C  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGTGCGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCACGCAGCT
       130        140        150        160        170        180        190        200        210        220        230        240

                                             30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250        260        270        280        290        300        310        320        330        340        350        360

                                             70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370        380        390        400        410        420        430        440        450        460        470        480

                                            110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490        500        510        520        530        540        550        560        570        580        590        600

                                            150                           160                           170
 F  F  P  H  V  N  Q  D  L  W  I  R  Y  W  L  A  A  G  G  I  D  P  D  A  D  V  K  L  L  T  V  P  A  A  Q  T  V  A  N  M
CTTTTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GAAAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610        620        630        640        650        660        670        680        690        700        710        720

                                            190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730        740        750        760        770        780        790        800        810        820        830        840

                                            230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850        860        870        880        890        900        910        920        930        940        950        960
```

```
                                270                                     280                                     290
 Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
        970       980       990      1000      1010      1020      1030      1040      1050      1060      1070      1080

                                310                                     320                                     330
 Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
       1090      1100      1110      1120      1130      1140      1150      1160      1170      1180      1190      1200

                                350                                     360                                     370
 A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
       1210      1220      1230      1240      1250      1260      1270      1280      1290      1300      1310      1320

                                390                                     400                                     410
 F   F   D   G   T   K   F   D   P   E   K   P   D   E   Y   L   K   S   L   K   I   K   K   V   S   V   G   G   S   T   G   E   K   P   Y   K   C   P   E   C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
       1330      1340      1350      1360      1370      1380      1390      1400      1410      1420      1430      1440

                                430
 G   K   S   F   S   R   S   G   G   S   H   H   H   H   H   H   *   *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
       1450      1460      1470      1480      1490      1500      1510      1520      1530      1540      1550      1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1570      1580      1590      1600      1610      1620      1630      1640      1650      1660      1670      1680


GCACGTTGGCAAGCTCGGAATTCGGCGTAATC
CGTGCAACCGTTCGAGCCTTAAGCCGCATTAG
       1690      1700      1710
```

FIG. 69 (Continued)

FIG. 70 - Exemplary Expression Construct for avBicarbBP5_18C_141Y_bZif

SEQ ID NO: 152

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                           10
                                                                    M  A  E  Q  A  P  E  V  T  T  V  K  L  G  Y  I  P  C  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGTGCGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCACGCAGCT
       130       140       150       160       170       180       190       200       210       220       230       240

                             30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                             70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                             110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                             150                           160                           170
 Y  F  P  H  V  N  Q  D  L  W  I  R  Y  W  L  A  A  G  G  I  D  P  D  A  D  V  K  L  L  T  V  P  A  A  Q  T  V  A  N  M
CTATTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GATAAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                             190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                             230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                               270                                                 280                                                 290
 Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
         970       980       990      1000      1010      1020      1030      1040      1050      1060      1070      1080

                               310                                                 320                                                 330
 Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
        1090      1100      1110      1120      1130      1140      1150      1160      1170      1180      1190      1200

                               350                                                 360                                                 370
 A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
        1210      1220      1230      1240      1250      1260      1270      1280      1290      1300      1310      1320

                               390                                                 400                                                 410
 F   F   D   G   T   K   F   D   P   E   K   P   D   E   Y   L   K   S   L   K   I   K   K   V   S   V   G   G   S   T   G   E   K   P   Y   K   C   P   E   C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
        1330      1340      1350      1360      1370      1380      1390      1400      1410      1420      1430      1440

                               430
 G   K   S   F   S   R   S   G   G   S   H   H   H   H   H   H   *   *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
        1450      1460      1470      1480      1490      1500      1510      1520      1530      1540      1550      1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
        1570      1580      1590      1600      1610      1620      1630      1640      1650      1660      1670      1680


GCACGTTGGCAAGCTCGGAATTCGGCGTAATC
CGTGCAACCGTTCGAGCCTTAAGCCGCATTAG
        1690      1700      1710
```

FIG. 70 (Continued)

FIG. 71 - Exemplary Expression Construct for avBicarbBP5_18C_141W_bZif

SEQ ID NO: 153

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                          10
                                                                              M  A  E  Q  A  P  E  V  T  T  V  K  L  G  Y  I  P  C  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGTGCGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCACGCAGCT
       130       140       150       160       170       180       190       200       210       220       230       240

                             30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                             70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                            110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                            150                           160                           170
 W  F  P  H  V  N  Q  D  L  W  I  R  Y  W  L  A  A  G  G  I  D  P  D  A  D  V  K  L  L  T  V  P  A  A  Q  T  V  A  N  M
CTGGTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GACCAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                            190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                            230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                                 270                                     280                                     290
 Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
        970          980          990         1000         1010         1020         1030         1040         1050         1060         1070         1080

                                 310                                     320                                     330
 Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
       1090         1100         1110         1120         1130         1140         1150         1160         1170         1180         1190         1200

                                 350                                     360                                     370
 A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
       1210         1220         1230         1240         1250         1260         1270         1280         1290         1300         1310         1320

                                 390                                     400                                     410
 F   F   D   G   T   K   F   D   P   E   K   P   D   E   Y   L   K   S   L   K   I   K   K   V   S   V   G   G   S   T   G   E   K   P   Y   K   C   P   E   C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
       1330         1340         1350         1360         1370         1380         1390         1400         1410         1420         1430         1440

                                 430
 G   K   S   F   S   R   S   G   G   S   H   H   H   H   H   H   *   *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
       1450         1460         1470         1480         1490         1500         1510         1520         1530         1540         1550         1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1570         1580         1590         1600         1610         1620         1630         1640         1650         1660         1670         1680


GCACGTTGGCAAGCTCGGAATTCGGCGTAATC
CGTGCAACCGTTCGAGCCTTAAGCCGCATTAG
       1690         1700         1710
```

FIG. 71 (Continued)

FIG. 72 - Exemplary Expression Construct for avBicarbBP5_18C_141Q_bZif

SEQ ID NO: 154

```
GCCAGTAAGCTTCGGTCACGCTTGGGACTGCCATAGGCTGGCCCGGTGATGCCGGCCACGATGCGTCCGGCGTAGAGGATCGAGATCTCGATCCCGCGAAATTAATACGACTCACTATAG
CGGTCATTCGAAGCCAGTGCGAACCCTGACGGTATCCGACCGGGCCACTACGGCCGGTGCTACGCAGGCCGCATCTCCTAGCTCTAGAGCTAGGGCGCTTTAATTATGCTGAGTGATATC
        10        20        30        40        50        60        70        80        90       100       110       120

                                                                                           10
                                                                        M  A  E  Q  A  P  E  V  T  T  V  K  L  G  Y  I  P  C  V  E
GGAGACCACAACGGTTTCCCTCTAGAAATAATTTTGTTTAACTTTAAGAAGGAGATATACCATGGCTGAACAAGCACCAGAAGTTACAACAGTAAAGCTCGGGTATATCCCGTGCGTCGA
CCTCTGGTGTTGCCAAAGGGAGATCTTTATTAAAACAAATTGAAATTCTTCCTCTATATGGTACCGACTTGTTCGTGGTCTTCAATGTTGTCATTTCGAGCCCATATAGGGCACGCAGCT
       130       140       150       160       170       180       190       200       210       220       230       240

                             30                            40                            50
 S  A  P  L  I  I  A  K  E  K  G  F  F  A  K  Y  G  L  T  N  V  E  L  S  K  Q  A  S  W  G  S  A  R  D  N  V  E  I  G  S
ATCCGCTCCTCTCATCATTGCTAAAGAAAAGGGGTTTTTCGCCAAGTATGGTCTGACAAATGTAGAATTATCGAAACAGGCATCGTGGGGCAGTGCCCGGGATAATGTAGAGATCGGTAG
TAGGCGAGGAGAGTAGTAACGATTTCTTTTCCCCAAAAAGCGGTTCATACCAGACTGTTTACATCTTAATAGCTTTGTCCGTAGCACCCCGTCACGGGCCCTATTACATCTCTAGCCATC
       250       260       270       280       290       300       310       320       330       340       350       360

                             70                            80                            90
 A  G  G  G  I  D  G  G  Q  W  Q  M  P  M  P  H  L  I  T  E  G  L  I  T  K  G  N  Q  K  I  P  M  Y  V  L  A  Q  L  I  T
CGCCGGGGGCGGGATCGACGGTGGTCAATGGCAGATGCCTATGCCACATCTCATCACTGAAGGCTTAATTACGAAGGGCAATCAGAAAATCCCAATGTACGTCTTAGCACAGTTGATCAC
GCGGCCCCCGCCCTAGCTGCCACCAGTTACCGTCTACGGATACGGTGTAGAGTAGTGACTTCCGAATTAATGCTTCCCGTTAGTCTTTTAGGGTTACATGCAGAATCGTGTCAACTAGTG
       370       380       390       400       410       420       430       440       450       460       470       480

                            110                           120                           130
 H  G  N  G  I  A  I  A  N  K  H  Q  G  K  G  I  S  L  K  L  E  G  A  K  S  L  F  S  Q  L  K  S  S  T  P  F  T  A  A  F
CCACGGGAACGGGATTGCCATTGCAAACAAACATCAAGGGAAGGGGATCAGTTTGAAGCTCGAGGGTGCTAAGAGCCTGTTCAGTCAGCTCAAGAGCTCCACGCCATTCACAGCCGCTTT
GGTGCCCTTGCCCTAACGGTAACGTTTGTTTGTAGTTCCCTTCCCCTAGTCAAACTTCGAGCTCCCACGATTCTCGGACAAGTCAGTCGAGTTCTCGAGGTGCGGTAAGTGTCGGCGAAA
       490       500       510       520       530       540       550       560       570       580       590       600

                            150                           160                           170
 Q  F  P  H  V  N  Q  D  L  W  I  R  Y  W  L  A  A  G  G  I  D  P  D  A  D  V  K  L  L  T  V  P  A  A  Q  T  V  A  N  M
CCAGTTTCCTCATGTAAATCAAGACTTATGGATTCGCTACTGGTTGGCTGCAGGGGGTATTGACCCTGATGCAGATGTAAAATTGTTAACGGTCCCAGCAGCCCAAACCGTAGCCAATAT
GGTCAAAGGAGTACATTTAGTTCTGAATACCTAAGCGATGACCAACCGACGTCCCCCATAACTGGGACTACGTCTACATTTTAACAATTGCCAGGGTCGTCGGGTTTGGCATCGGTTATA
       610       620       630       640       650       660       670       680       690       700       710       720

                            190                           200                           210
 K  T  G  T  M  D  A  F  S  T  G  D  P  W  P  F  R  L  V  N  D  K  I  G  Y  M  A  A  L  T  A  E  I  W  K  N  H  P  E  E
GAAGACCGGCACAATGGACGCATTTTCCACGGGCGACCCATGGCCATTCCGTCTCGTAAACGACAAAATCGGTTACATGGCGGCCTTGACAGCGGAGATCTGGAAAAACCACCCTGAGGA
CTTCTGGCCGTGTTACCTGCGTAAAAGGTGCCCGCTGGGTACCGGTAAGGCAGAGCATTTGCTGTTTTAGCCAATGTACCGCCGGAACTGTCGCCTCTAGACCTTTTTGGTGGGACTCCT
       730       740       750       760       770       780       790       800       810       820       830       840

                            230                           240                           250
 Y  L  A  M  R  A  D  W  V  D  K  Y  P  K  A  T  K  A  L  L  K  G  I  M  E  A  Q  Q  W  L  D  N  F  D  N  R  K  E  A  A
ATACCTCGCAATGCGTGCAGATTGGGTCGACAAGTATCCAAAAGCAACTAAGGCATTATTAAAAGGCATCATGGAGGCCCAACAATGGTTGGACAACTTTGACAATCGCAAGGAGGCGGC
TATGGAGCGTTACGCACGTCTAACCCAGCTGTTCATAGGTTTTCGTTGATTCCGTAATAATTTTCCGTAGTACCTCCGGGTTGTTACCAACCTGTTGAAACTGTTAGCGTTCCTCCGCCG
       850       860       870       880       890       900       910       920       930       940       950       960
```

```
                                  270                                     280                                     290
 Q   I   L   A   G   R   N   Y   F   N   L   N   N   P   E   I   L   A   D   P   Y   V   G   K   Y   D   M   G   D   G   R   K   I   D   D   K   S   M   A   A
ACAGATTTTGGCTGGCCGCAACTACTTTAACCTCAACAACCCGGAAATCCTGGCGGATCCTTACGTAGGTAAGTACGATATGGGTGATGGTCGCAAGATTGACGATAAAAGCATGGCTGC
TGTCTAAAACCGACCGGCGTTGATGAAATTGGAGTTGTTGGGCCTTTAGGACCGCCTAGGAATGCATCCATTCATGCTATACCCACTACCAGCGTTCTAACTGCTATTTTCGTACCGACG
        970       980       990      1000      1010      1020      1030      1040      1050      1060      1070      1080

                                  310                                     320                                     330
 Y   Y   W   K   D   E   K   G   S   V   S   Y   P   Y   K   S   H   D   L   W   F   I   T   E   N   V   R   W   G   F   L   P   K   D   Y   L   A   N   G   A
GTATTACTGGAAGGATGAAAAAGGGTCAGTTTCTTACCCATACAAATCGCACGACTTATGGTTCATCACTGAAAACGTCCGTTGGGGGTTTCTGCCGAAGGATTATCTGGCAAACGGTGC
CATAATGACCTTCCTACTTTTTCCCAGTCAAAGAATGGGTATGTTTAGCGTGCTGAATACCAAGTAGTGACTTTTGCAGGCAACCCCCAAAGACGGCTTCCTAATAGACCGTTTGCCACG
       1090      1100      1110      1120      1130      1140      1150      1160      1170      1180      1190      1200

                                  350                                     360                                     370
 A   K   A   K   E   L   I   D   K   V   N   R   E   D   I   W   K   E   A   A   K   E   A   G   I   A   A   A   D   I   P   T   S   T   S   R   G   V   E   E
AGCCAAAGCTAAGGAGTTAATCGACAAGGTCAATCGGGAGGACATCTGGAAAGAAGCAGCTAAAGAAGCCGGTATTGCAGCGGCCGACATTCCAACCAGCACGTCCCGTGGGGTAGAAGA
TCGGTTTCGATTCCTCAATTAGCTGTTCCAGTTAGCCCTCCTGTAGACCTTTCTTCGTCGATTTCTTCGGCCATAACGTCGCCGGCTGTAAGGTTGGTCGTGCAGGGCACCCCATCTTCT
       1210      1220      1230      1240      1250      1260      1270      1280      1290      1300      1310      1320

                                  390                                     400                                     410
 F   F   D   G   T   K   F   D   P   E   K   P   D   E   Y   L   K   S   L   K   I   K   K   V   S   V   G   G   S   T   G   E   K   P   Y   K   C   P   E   C
GTTCTTCGACGGCACCAAATTCGACCCAGAAAAGCCAGACGAATATCTGAAATCGCTCAAAATCAAAAAAGTCAGCGTAGGCGGCAGCACCGGCGAAAAACCGTATAAATGCCCGGAATG
CAAGAAGCTGCCGTGGTTTAAGCTGGGTCTTTTCGGTCTGCTTATAGACTTTAGCGAGTTTTAGTTTTTTCAGTCGCATCCGCCGTCGTGGCCGCTTTTTGGCATATTTACGGGCCTTAC
       1330      1340      1350      1360      1370      1380      1390      1400      1410      1420      1430      1440

                                  430
 G   K   S   F   S   R   S   G   G   S   H   H   H   H   H   H   *   *
CGGCAAAAGCTTTAGCCGCAGCGGTGGTTCACATCATCATCATCATCATTAATGAAAGGGCGATATCCAGCACACTGGCGGCCGTTACTAGTGGATCCGGCTGCTAACAAAGCCCGAAAG
GCCGTTTTCGAAATCGGCGTCGCCACCAAGTGTAGTAGTAGTAGTAGTAATTACTTTCCCGCTATAGGTCGTGTGACCGCCGGCAATGATCACCTAGGCCGACGATTGTTTCGGGCTTTC
       1450      1460      1470      1480      1490      1500      1510      1520      1530      1540      1550      1560


GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTATATCCGGAGCGACTCCCACG
CTTCGACTCAACCGACGACGGTGGCGACTCGTTATTGATCGTATTGGGGAACCCCGGAGATTTGCCCAGAACTCCCCAAAAAACGACTTTCCTCCTTGATATAGGCCTCGCTGAGGGTGC
       1570      1580      1590      1600      1610      1620      1630      1640      1650      1660      1670      1680


GCACGTTGGCAAGCTCGGAATTCGGCGTAATC
CGTGCAACCGTTCGAGCCTTAAGCCGCATTAG
       1690      1700      1710
```

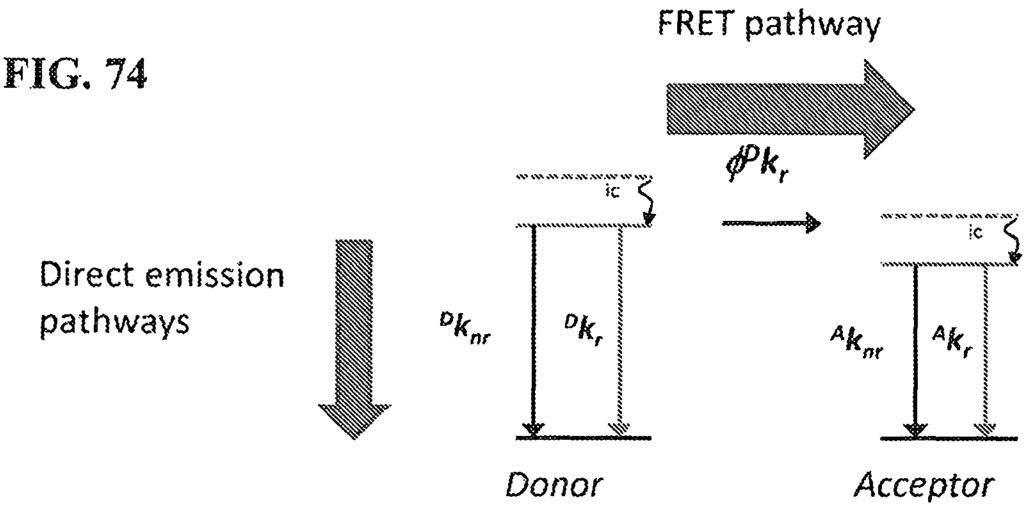

*Directly responsive partner*

- Responds directly to ligand-induced protein conformational changes
- Binds ligand (chemosensor)

Changes due to balance on photon flow in FRET and/or direct emission pathways

*Indirectly responsive partner*

No interactions with ligand of protein conformational changes
Changes only due photon flow in FRET pathway

Effects depend on role of directly responsive partner

*Donor:* Photon flow through competing output pathways
*Outputs*: Direct emission pathway (quenching) and FRET (spectral overlap) pathway

*Acceptor*
Balance of photon flow through input and output pathways
*Input:* FRET pathway (spectral overlap only)
*Output:* Direct emission pathway (quenching)

SEQUENCE LISTING

```
<160> NUMBER OF SEQ ID NOS: 204

<210> SEQ ID NO 1
<211> LENGTH: 452
<212> TYPE: PRT
<213> ORGANISM: Synechocystis sp. PCC 6803

<400> SEQUENCE: 1

Met Gly Ser Phe Asn Arg Arg Lys Phe Leu Leu Thr Ser Ala Ala Thr
1               5                   10                  15

Ala Thr Gly Ala Leu Phe Leu Lys Gly Cys Ala Gly Asn Pro Pro Asp
            20                  25                  30

Pro Asn Ala Ala Ser Thr Gly Thr Asn Pro Ser Pro Gln Ala Ala Gly
        35                  40                  45

Asp Ile Ser Pro Glu Met Met Pro Glu Thr Ala Asn Ile Lys Leu Gly
    50                  55                  60

Tyr Ile Pro Ile Val Glu Ala Ala Pro Leu Ile Ile Ala Gln Glu Lys
65                  70                  75                  80

Gly Phe Phe Ala Lys Tyr Gly Met Thr Gly Val Glu Val Ser Lys Gln
                85                  90                  95

Ala Asn Trp Ala Ser Ala Arg Asp Asn Val Thr Ile Gly Ser Gln Gly
            100                 105                 110

Gly Gly Ile Asp Gly Gly Gln Trp Gln Met Pro Met Pro His Leu Ile
        115                 120                 125

Thr Glu Gly Ile Ile Thr Asn Gly Asn Lys Val Pro Met Tyr Val Leu
    130                 135                 140
```

Ala Gln Leu Ile Thr Gln Gly Asn Gly Ile Ala Val Ala Pro Met His
145 150 155 160

Glu Gly Lys Gly Val Asn Leu Asp Ile Thr Lys Ala Ala Asp Tyr Ile
165 170 175

Lys Gly Phe Asn Lys Thr Asn Gly Arg Lys Phe Lys Ala Ala His Thr
180 185 190

Phe Pro Asn Val Asn Gln Asp Phe Trp Ile Arg Tyr Trp Phe Ala Ala
195 200 205

Gly Gly Val Asp Pro Asp Thr Asp Ile Asp Leu Leu Ala Val Pro Pro
210 215 220

Ala Glu Thr Val Gln Gly Met Arg Asn Gly Thr Met Asp Ala Phe Ser
225 230 235 240

Thr Gly Asp Pro Trp Pro Tyr Arg Ile Val Thr Glu Asn Ile Gly Tyr
245 250 255

Met Ala Gly Leu Thr Ala Gln Ile Trp Pro Tyr His Pro Glu Glu Tyr
260 265 270

Leu Ala Ile Arg Ala Asp Trp Val Asp Lys Asn Pro Lys Ala Thr Lys
275 280 285

Ala Leu Leu Lys Gly Ile Met Glu Ala Gln Gln Trp Ile Asp Asp Pro
290 295 300

Lys Asn Arg Pro Glu Val Val Gln Ile Val Ser Gly Arg Asn Tyr Phe
305 310 315 320

Asn Val Pro Thr Thr Ile Leu Glu Ser Pro Phe Lys Gly Gln Tyr Thr
325 330 335

Met Gly Asp Gly Gln Pro Ala Ile Asp Asp Phe Gln Lys Gly Pro Leu
340 345 350

Tyr Trp Lys Asp Gly Ile Gly Asn Val Ser Tyr Pro Tyr Lys Ser His
355 360 365

Asp Leu Trp Phe Leu Thr Glu Ser Ile Arg Trp Gly Phe His Lys Asn
370 375 380

Ala Ile Pro Asp Leu Asp Thr Ala Gln Lys Ile Ile Asp Lys Val Asn
385 390 395 400

Arg Glu Asp Leu Trp Arg Glu Ala Ala Thr Glu Ala Gly Phe Thr Ala
405 410 415

Asp Ile Pro Ser Ser Thr Ser Arg Gly Val Glu Thr Phe Phe Asp Gly
420 425 430

Ile Thr Phe Asp Pro Ala Asn Pro Ser Ala Tyr Leu Gln Ser Leu Ala
435 440 445

Ile Lys Lys Val
450

<210> SEQ ID NO 2
<211> LENGTH: 444
<212> TYPE: PRT
<213> ORGANISM: hermosynechococcus elongatus BP-1

<400> SEQUENCE: 2

Met Ser Gln Leu Ser Arg Arg Arg Phe Leu Met Thr Ala Thr Ala Thr
1 5 10 15

Ala Val Gly Ala Ile Ala Leu Lys Gly Cys Ala Pro Ala Glu Thr Pro
20 25 30

Gln Gly Gln Gln Gln Gly Gly Thr Thr Thr Gly Gly Leu Glu Thr Asp
35 40 45

Thr Ile Lys Leu Gly Phe Ile Pro Ile Val Glu Ser Ala Pro Leu Ile

```
    50                  55                  60

Ile Ala Lys Glu Lys Gly Phe Phe Ala Lys His Gly Leu Thr Asn Ala
65                  70                  75                  80

Glu Leu Ser Lys Gln Ala Asn Trp Ala Ser Ala Arg Asp Asn Val Val
                85                  90                  95

Ile Gly Ser Ala Gly Gly Gly Ile Asp Gly Gly Gln Trp Gln Met Pro
            100                 105                 110

Met Pro Tyr Leu Ile Ser Glu Gly Ile Ile Thr Leu Asn Asn Gln Lys
        115                 120                 125

Leu Pro Met Tyr Val Leu Ala Gln Leu Asn Thr Gln Gly Asn Gly Ile
    130                 135                 140

Ala Ile Ser Gly Ala Asn Lys Gly Lys Gly Leu His Leu Lys Ile Ala
145                 150                 155                 160

Asp Pro Asp Tyr Ile Lys Gly Phe Ala Ala Lys Asn Gly Arg Lys Phe
                165                 170                 175

Lys Ala Ala His Thr Phe Pro His Val Asn Gln Asp Leu Trp Ile Arg
            180                 185                 190

Tyr Trp Phe Ala Ala Asn Gly Ile Asp Pro Asp Arg Asp Ile Glu Leu
        195                 200                 205

Leu Ala Val Pro Pro Ala Glu Thr Val Ala Gly Met Arg Asn Gly Thr
    210                 215                 220

Met Asp Ala Phe Ser Thr Gly Asp Pro Trp Pro Phe Arg Ile Val Ser
225                 230                 235                 240

Asp Asp Ile Gly Tyr Met Ala Thr Leu Thr Ala Gln Ile Trp Pro Tyr
                245                 250                 255

His Pro Glu Glu Tyr Leu Ala Val Arg Ala Asp Trp Val Asp Lys His
            260                 265                 270

Pro Lys Ala Thr Lys Ala Leu Leu Lys Ala Val Met Glu Ala Gln Gln
        275                 280                 285

Trp Cys Asp Asp Lys Ala Asn Arg Pro Glu Leu Ile Gln Ile Cys Ser
    290                 295                 300

Arg Arg Glu Tyr Phe Asn Ile Pro Gly Asn Ile Leu Thr Pro Pro Tyr
305                 310                 315                 320

Glu Gly Thr Tyr Thr Met Gly Asp Gly Gln Pro Asn Phe Asn Asp Phe
                325                 330                 335

Asn Ile Gly Pro Leu Tyr Trp Arg Asp Pro Asn Gly Asn Ser Ile Ser
            340                 345                 350

Tyr Pro Tyr Lys Ser His Asp Leu Trp Phe Leu Thr Glu Asn Leu Arg
        355                 360                 365

Trp Gly Phe Asn Ala Asp Lys Leu Lys Asp Phe Asp Asn Ile Lys Gln
    370                 375                 380

Met Ile Gly Arg Val Asn Arg Ser Asp Leu Trp Gln Glu Ala Ala Lys
385                 390                 395                 400

Glu Leu Gly Ile Pro Ala Ala Glu Ile Pro Thr Thr Glu Ser Arg Gly
                405                 410                 415

Val Glu Thr Phe Phe Asp Gly Ile Lys Phe Asp Pro Asp Asn Pro Gln
            420                 425                 430

Ala Tyr Leu Asp Ser Leu Lys Ile Lys Val Lys Ser
        435                 440
```

<210> SEQ ID NO 3
<211> LENGTH: 448
<212> TYPE: PRT
<213> ORGANISM: Chroococcidiopsis thermalis

<400> SEQUENCE: 3

Met Thr Glu Phe Ser Arg Arg Lys Phe Ile Ile Thr Ala Gly Ala Ser
1               5                   10                  15

Ala Val Gly Ser Val Phe Leu Lys Gly Cys Leu Gly Asn Pro Pro Asp
            20                  25                  30

Ser Val Thr Gly Thr Gln Thr Gln Gln Val Ala Ala Val Asn Val Ser
        35                  40                  45

Pro Glu Gln Ala Pro Glu Thr Thr Arg Val Lys Leu Gly Tyr Ile Pro
    50                  55                  60

Ile Val Glu Ala Ala Pro Ile Ile Ile Ala Lys Glu Lys Gly Phe Phe
65                  70                  75                  80

Ala Lys Tyr Gly Met Thr Asp Val Asp Val Ser Lys Gln Ala Ser Trp
                85                  90                  95

Gly Ser Met Arg Asp Asn Thr Glu Ile Gly Ala Ala Gly Gly Gly Val
            100                 105                 110

Asp Gly Gly Gln Tyr Gln Met Pro Met Pro His Leu Ile Thr Glu Gly
        115                 120                 125

Arg Ile Thr Lys Gly Asn Lys Pro Ile Pro Met Tyr Val Leu Ala Gln
    130                 135                 140

Leu Asn Thr Gln Gly Asn Gly Ile Ala Ile Ala Glu Lys His Arg Gly
145                 150                 155                 160

Lys Gly Ile Glu Leu Glu Leu Ala Lys Gly Gly Lys Asn Leu Phe Gly
                165                 170                 175

Gln Leu Lys Ser Ala Asn Thr Pro Phe Thr Ala Ala Tyr Thr Phe Ala
            180                 185                 190

Gln Val Asn Gln Asp Phe Trp Ile Arg Tyr Trp Leu Ala Ala Gly Gly
        195                 200                 205

Val Asn Pro Asp Ala Asp Val Lys Leu Ile Pro Val Pro Ala Ala Gln
    210                 215                 220

Thr Val Ala Asn Met Lys Thr Gly Thr Met Asp Ala Phe Ser Thr Gly
225                 230                 235                 240

Asp Pro Trp Pro Tyr Arg Ile Val Lys Asp Lys Ile Gly Phe Leu Ala
                245                 250                 255

Met Leu Thr Ala Asp Met Trp Glu Phe His Pro Glu Glu Tyr Leu Ala
            260                 265                 270

Leu Arg Ala Glu Trp Val Asp Lys His Pro Lys Ala Thr Lys Ala Leu
        275                 280                 285

Leu Lys Gly Ile Met Glu Ala Gln Gln Trp Leu Asp Asn Phe Asp Asn
    290                 295                 300

Arg Glu Glu Ala Ala Lys Ile Leu Gly Gly Arg Asn Tyr Phe Asn Leu
305                 310                 315                 320

Pro Ala Glu Ile Leu Ala Gly Pro Phe Ala Gly Lys Tyr Asp Met Gly
                325                 330                 335

Glu Gly Arg Thr Val Asp Asp Arg Asn Lys Ala Val Leu Tyr Trp Lys
            340                 345                 350

Asp Pro Arg Gly Ser Val Ser Tyr Pro Tyr Lys Ser His Asp Leu Trp
        355                 360                 365

Phe Leu Thr Glu Ser Val Arg Trp Gly Phe Leu Pro Pro Asp Ser Leu
    370                 375                 380

Thr Lys Ala Gln Ala Leu Ile Asp Lys Val Asn Arg Glu Asp Leu Trp
385                 390                 395                 400

Lys Glu Ala Ala Lys Glu Leu Gly Val Ala Ala Ala Asp Ile Pro Thr

```
                405                 410                 415

Ser Thr Ser Arg Gly Val Glu Thr Phe Phe Asp Gly Val Lys Phe Asp
            420                 425                 430

Pro Glu Asn Pro Ala Ala Tyr Leu Lys Ser Leu Lys Ile Lys Lys Ala
        435                 440                 445


<210> SEQ ID NO 4
<211> LENGTH: 459
<212> TYPE: PRT
<213> ORGANISM: Calothrix parietina

<400> SEQUENCE: 4

Met Ser Asp Phe Leu Asn Gln Ile Asn Arg Arg Lys Phe Ile Leu Thr
1               5                   10                  15

Ala Gly Ala Ser Ala Gly Ala Ile Phe Leu Lys Gly Cys Leu Gly Asn
            20                  25                  30

Pro Pro Asp Ser Thr Gly Gly Asn Ser Gln Ala Ile Pro Thr Ala Gln
        35                  40                  45

Gln Val Ala Asn Leu Thr Pro Glu Gln Lys Pro Glu Thr Glu Thr Val
    50                  55                  60

Lys Leu Gly Tyr Ile Pro Ile Val Glu Ser Ala Pro Leu Ile Ile Ala
65                  70                  75                  80

Lys Glu Lys Gly Leu Phe Ala Lys Tyr Gly Met Thr Lys Val Glu Leu
                85                  90                  95

Ala Lys Gln Ala Ser Trp Gly Ala Ala Arg Asp Asn Val Glu Ile Gly
            100                 105                 110

Ser Ala Gly Gly Gly Ile Asp Gly Gly Gln Trp Gln Met Pro Met Pro
        115                 120                 125

His Leu Ile Thr Ala Gly Leu Ile Thr Lys Gly Asn Lys Glu Ile Pro
    130                 135                 140

Met Tyr Val Leu Ala Gln Leu Val Thr His Gly Asn Gly Ile Ala Ile
145                 150                 155                 160

Ala Asp Lys His Lys Gly Lys Gly Leu Gly Leu Lys Leu Asp Gly Ala
                165                 170                 175

Lys Ser Leu Phe Lys Glu Leu Lys Ser Ser Thr Pro Phe Thr Ala Ala
            180                 185                 190

Phe Thr Phe Pro His Val Asn Gln Asp Leu Trp Ile Arg Tyr Trp Leu
        195                 200                 205

Ala Ala Ser Gly Leu Asp Pro Asp Ala Asp Val Lys Leu Leu Thr Val
    210                 215                 220

Pro Ala Ala Gln Thr Val Ala Asn Met Lys Thr Gly Thr Met Asp Ala
225                 230                 235                 240

Phe Ser Thr Gly Asp Pro Trp Pro Phe Arg Ile Val Asn Asp Lys Ile
                245                 250                 255

Gly Phe Met Ala Leu Leu Thr Ala Glu Met Trp Lys Asn His Pro Glu
            260                 265                 270

Glu Tyr Leu Ala Met Arg Gly Asp Trp Val Asp Lys His Pro Lys Ala
        275                 280                 285

Thr Lys Ala Ile Leu Lys Ala Val Met Glu Ala Gln Gln Trp Leu Asp
    290                 295                 300

Asn Phe Glu Asn Arg Lys Glu Ala Ala Thr Ile Leu Ala Gly Arg Lys
305                 310                 315                 320

Tyr Phe Asp Leu Ser Ser Pro Glu Ile Leu Leu Asp Pro Tyr Gln Gly
                325                 330                 335
```

```
Lys Tyr Asp Met Gly Asp Gly Arg Lys Ile Asp Asp Lys Leu Met Ala
            340                 345                 350

Pro Tyr Tyr Trp Lys Asp Glu Lys Gly Ser Val Ser Tyr Pro Tyr Lys
        355                 360                 365

Ser His Asp Leu Trp Phe Ile Thr Glu Asn Val Arg Trp Gly Phe Leu
    370                 375                 380

Pro Lys Asp Tyr Leu Ala Asn Asn Ala Ala Lys Ala Lys Glu Leu Ile
385                 390                 395                 400

Asn Lys Val Asn Arg Glu Asp Ile Trp Lys Glu Ala Ala Lys Asp Leu
                405                 410                 415

Gly Ile Ala Ala Ala Asp Ile Pro Thr Ser Thr Ser Arg Gly Val Glu
            420                 425                 430

Glu Phe Phe Asp Gly Val Lys Phe Asp Pro Glu Lys Pro Glu Glu Tyr
        435                 440                 445

Leu Lys Ser Leu Lys Ile Lys Lys Ala Gly Val
    450                 455


<210> SEQ ID NO 5
<211> LENGTH: 458
<212> TYPE: PRT
<213> ORGANISM: Anabaena variabilis

<400> SEQUENCE: 5

Met Thr Glu Phe Phe Asn Gln Phe Ser Arg Arg Lys Phe Ile Val Thr
1               5                   10                  15

Ala Gly Ala Ser Ala Gly Ala Val Phe Leu Lys Gly Cys Leu Gly Asn
            20                  25                  30

Pro Pro Glu Thr Thr Gly Gly Thr Gln Ser Ala Pro Thr Ala Gln Pro
        35                  40                  45

Ala Ala Asn Val Ser Ala Glu Gln Ala Pro Glu Val Thr Thr Val Lys
    50                  55                  60

Leu Gly Tyr Ile Pro Ile Val Glu Ser Ala Pro Leu Ile Ile Ala Lys
65                  70                  75                  80

Glu Lys Gly Phe Phe Ala Lys Tyr Gly Leu Thr Asn Val Glu Leu Ser
                85                  90                  95

Lys Gln Ala Ser Trp Gly Ser Ala Arg Asp Asn Val Glu Ile Gly Ser
            100                 105                 110

Ala Gly Gly Gly Ile Asp Gly Gly Gln Trp Gln Met Pro Met Pro His
        115                 120                 125

Leu Ile Thr Glu Gly Leu Ile Thr Lys Gly Asn Gln Lys Ile Pro Met
    130                 135                 140

Tyr Val Leu Cys Gln Leu Ile Thr His Gly Asn Gly Ile Ala Ile Ala
145                 150                 155                 160

Asn Lys His Gln Gly Lys Gly Ile Ser Leu Lys Leu Glu Gly Ala Lys
                165                 170                 175

Ser Leu Phe Ser Gln Leu Lys Ser Ser Thr Pro Phe Thr Ala Ala Phe
            180                 185                 190

Thr Phe Pro His Val Asn Gln Asp Leu Trp Ile Arg Tyr Trp Leu Ala
        195                 200                 205

Ala Gly Gly Ile Asp Pro Asp Ala Asp Val Lys Leu Leu Thr Val Pro
    210                 215                 220

Ala Ala Gln Thr Val Ala Asn Met Lys Thr Gly Thr Met Asp Ala Phe
225                 230                 235                 240

Ser Thr Gly Asp Pro Trp Pro Phe Arg Leu Val Asn Asp Lys Ile Gly
                245                 250                 255
```

```
Tyr Met Ala Ala Leu Thr Ala Glu Ile Trp Lys Asn His Pro Glu Glu
            260                 265                 270

Tyr Leu Ala Met Arg Ala Asp Trp Val Asp Lys Tyr Pro Lys Ala Thr
        275                 280                 285

Lys Ala Leu Leu Lys Gly Ile Met Glu Ala Gln Gln Trp Leu Asp Asn
    290                 295                 300

Phe Asp Asn Arg Lys Glu Ala Ala Gln Ile Leu Ala Gly Arg Asn Tyr
305                 310                 315                 320

Phe Asn Leu Asn Asn Pro Glu Ile Leu Ala Asp Pro Tyr Val Gly Lys
                325                 330                 335

Tyr Asp Met Gly Asp Gly Arg Lys Ile Asp Asp Lys Ser Met Ala Ala
            340                 345                 350

Tyr Tyr Trp Lys Asp Glu Lys Gly Ser Val Ser Tyr Pro Tyr Lys Ser
        355                 360                 365

His Asp Leu Trp Phe Ile Thr Glu Asn Val Arg Trp Gly Phe Leu Pro
    370                 375                 380

Lys Asp Tyr Leu Ala Asn Gly Ala Ala Lys Ala Lys Glu Leu Ile Asp
385                 390                 395                 400

Lys Val Asn Arg Glu Asp Ile Trp Lys Glu Ala Ala Lys Glu Ala Gly
                405                 410                 415

Ile Ala Ala Ala Asp Ile Pro Thr Ser Thr Ser Arg Gly Val Glu Glu
            420                 425                 430

Phe Phe Asp Gly Thr Lys Phe Asp Pro Glu Lys Pro Asp Glu Tyr Leu
        435                 440                 445

Lys Ser Leu Lys Ile Lys Lys Val Ser Val
    450                 455


<210> SEQ ID NO 6
<211> LENGTH: 449
<212> TYPE: PRT
<213> ORGANISM: Chamaesiphon minutus

<400> SEQUENCE: 6

Met Gln His Leu Ser Arg Arg His Phe Leu Leu Ala Ala Gly Ala Ala
1               5                   10                  15

Gly Gly Ala Thr Leu Leu Lys Gly Cys Ala Ile Asn Pro Pro Ser Pro
            20                  25                  30

Asp Ala Leu Ser Pro Lys Ala Gln Ala Leu Thr Leu Ser Ser Ala Thr
        35                  40                  45

Thr Pro Glu Thr Thr Ala Val Lys Leu Gly Tyr Ile Ala Ile Ala Glu
    50                  55                  60

Ser Ala Pro Leu Ile Ile Ala Arg Glu Lys Gly Phe Phe Ala Arg His
65                  70                  75                  80

Gly Met Thr Asp Val Asp Val Ser Lys Gln Ala Ser Trp Gly Ser Ala
                85                  90                  95

Arg Asp Asn Ile Glu Ile Gly Ser Ser Asn Gly Gly Ile Asp Gly Gly
            100                 105                 110

Gln Trp Gln Met Pro Met Pro Gln Leu Ile Ser Glu Gly Ile Ile Thr
        115                 120                 125

Lys Gly Asn Arg Lys Ile Pro Met Leu Ser Leu Ala Gln Leu Ser Thr
    130                 135                 140

Gln Gly Asn Gly Ile Ala Ile Ser Thr Gln His Ala Gly Lys Gly Phe
145                 150                 155                 160

Gly Leu Asp Val Ser Gly Ala Ala Glu Tyr Val Arg Asp Met Lys Ala
```

```
                165                 170                 175

Asp Gly Lys Pro Phe Lys Ala Ala Tyr Thr Phe Pro Arg Val Asn Gln
            180                 185                 190

Asp Phe Trp Ile Arg Tyr Trp Leu Ala Ala Gly Gly Ile Asp Pro Asn
        195                 200                 205

Lys Asp Ile Asp Leu Ile Ala Val Pro Ala Ala Gln Thr Val Ala Ser
    210                 215                 220

Met Arg Thr Gly Ser Met Asp Gly Phe Ser Thr Gly Asp Pro Trp Pro
225                 230                 235                 240

Ser Arg Ile Leu Arg Asp Arg Arg Lys Tyr Gly Phe Leu Ala Val Leu
                245                 250                 255

Thr Ala Gln Ile Trp Pro Ala His Pro Glu Glu Tyr Phe Ala Met Arg
            260                 265                 270

Glu Asp Trp Val Arg Lys His Pro Lys Ala Ala Lys Ala Ile Leu Lys
        275                 280                 285

Gly Ile Met Glu Ala Gln Met Trp Cys Asp Asp Pro Lys Asn Arg Ala
    290                 295                 300

Glu Met Ala Ala Ile Leu Ala Gln Arg Lys Tyr Phe Asn Val Pro Ser
305                 310                 315                 320

Asp Leu Leu Ile Gly Pro Tyr Val Gly Glu Tyr Ile Leu Gly Ala Asp
                325                 330                 335

Arg Lys Thr Val Lys Asp Glu Lys Leu Ala Ile Arg Tyr Trp Lys Asp
            340                 345                 350

Ala Arg Gly Asn Val Ser Tyr Pro Tyr Lys Ser His Asp Leu Trp Phe
        355                 360                 365

Leu Thr Glu Ser Val Arg Trp Gly Phe Leu Pro Gln Gly Ala Leu Gly
    370                 375                 380

Glu Ala Asp Arg Ile Ile Asn Ala Val Ser Gly Glu Lys Tyr Trp Arg
385                 390                 395                 400

Glu Ala Ala Gln Glu Leu Gly Ile Ala Ser Ala Asp Ile Pro Pro Ser
                405                 410                 415

Thr Ser Arg Gly Ile Glu Lys Phe Phe Asp Gly Ala Glu Phe Asn Pro
            420                 425                 430

Glu Lys Pro Lys Ala Tyr Leu Asp Ser Leu Lys Ile Lys Asn Leu Lys
        435                 440                 445

Ala


<210> SEQ ID NO 7
<211> LENGTH: 342
<212> TYPE: PRT
<213> ORGANISM: Mannheimia haemolytica

<400> SEQUENCE: 7

Met Lys Lys Thr Leu Ser Ala Leu Ala Ile Ala Ala Ala Thr Phe Thr
1               5                   10                  15

Ser Thr Ser Thr Leu Ala Ala Asn Glu Val Asn Val Tyr Ser Tyr Arg
            20                  25                  30

Gln Pro Tyr Leu Ile Glu Pro Met Leu Lys Asn Phe Glu Lys Asp Thr
        35                  40                  45

Gly Ile Lys Val Asn Ile Ile Phe Ala Asp Lys Gly Leu Val Asp Arg
    50                  55                  60

Val Lys Gln Glu Gly Glu Leu Ser Pro Ala Asp Val Leu Leu Thr Val
65                  70                  75                  80

Asp Ile Ser Arg Val Met Glu Ile Val Asn Ala Asp Leu Ala Gln Lys
```

-continued

```
                85                  90                  95

Ile Asp Ser Lys Val Leu Glu Lys Asn Ile Pro Ala Gln Phe Arg Asp
            100                 105                 110

Ser Asn Asp Gln Trp Phe Gly Leu Thr Thr Arg Ala Arg Val Ile Tyr
        115                 120                 125

Thr Ser Lys Asp Arg Val Gly Lys Leu Pro Ala Gly Phe Asp Tyr Leu
    130                 135                 140

Asp Leu Ala Lys Pro Glu Tyr Lys Gly Lys Val Cys Val Arg Ser Gly
145                 150                 155                 160

Lys Asn Ser Tyr Asn Val Ser Leu Phe Ala Ala Met Ile Glu His Tyr
                165                 170                 175

Gly Ile Glu Lys Thr Lys Ala Phe Leu Glu Gly Leu Lys Ala Asn Leu
            180                 185                 190

Ala Arg Lys Pro Gln Gly Gly Asp Arg Asp Gln Val Lys Ala Ile Lys
        195                 200                 205

Glu Gly Ile Cys Asp Tyr Ser Ile Gly Asn Ser Tyr Tyr Tyr Gly Lys
    210                 215                 220

Met Leu Asp Asp Glu Lys Gln Lys Ser Trp Ala Glu Ala Ala Ile Ile
225                 230                 235                 240

Asn Phe Pro Ser Gly Glu His Gly Thr His Lys Asn Ile Ser Gly Val
                245                 250                 255

Val Ile Ala Lys His Ser Pro Asn Lys Ala Asn Ala Val Lys Leu Ile
            260                 265                 270

Glu Tyr Leu Ser Gly Glu Lys Ala Gln Gly Leu Tyr Ala Glu Leu Asn
        275                 280                 285

His Glu Tyr Pro Val Lys Glu Gly Ile Glu Pro Ser Ala Ile Val Lys
    290                 295                 300

Gly Trp Gly Thr Phe Lys Ser Asp Thr Ile Lys Leu Glu Asp Ile Ala
305                 310                 315                 320

Lys Asn Tyr Glu Ala Ala Leu Lys Leu Val Asp Glu Val Lys Phe Asp
                325                 330                 335

Asp Phe Ser Glu Lys Lys
            340


<210> SEQ ID NO 8
<211> LENGTH: 353
<212> TYPE: PRT
<213> ORGANISM: Exiguobacterium

<400> SEQUENCE: 8

Met Asn Lys Lys Tyr Ala Ala Leu Gly Ile Ser Ala Ala Leu Thr Thr
1               5                   10                  15

Ser Leu Leu Ala Ala Cys Ala Ser Thr Asp Glu Thr Thr Ser Asn Glu
            20                  25                  30

Gly Ser Asp Asp Ser Asn Val Val Asn Val Tyr Ser Ser Arg His Tyr
        35                  40                  45

Asp Val Asp Gln Gln Leu Tyr Lys Gln Phe Glu Glu Glu Thr Gly Ile
    50                  55                  60

Lys Val Asn Val Val Glu Gly Lys Ser Asp Glu Leu Leu Glu Arg Leu
65                  70                  75                  80

Asn Thr Glu Gly Glu Asn Thr Glu Ala Asp Leu Phe Ile Thr Ala Asp
                85                  90                  95

Ala Gly Asn Leu Tyr Gln Ala Lys Glu Ala Gly His Leu Gln Ala Val
            100                 105                 110
```

-continued

```
Asp Ser Asp Glu Leu Glu Ser Asn Ile Pro Glu Lys Tyr Arg Asp Thr
        115                 120                 125

Asp Asn Glu Trp Phe Gly Leu Thr Lys Arg Ala Arg Val Ile Val Tyr
    130                 135                 140

Ser Lys Asp Arg Val Lys Pro Glu Asp Leu Ser Thr Tyr Glu Ala Leu
145                 150                 155                 160

Thr Glu Glu Gln Trp Asn Gly Lys Val Leu Val Arg Pro Ser Glu Asn
                165                 170                 175

Met Tyr Asn Ile Ser Leu Leu Ala Ser Phe Ile Glu Val Asn Gly Val
            180                 185                 190

Asp Glu Ala Lys Glu Trp Ala Lys Gly Leu Val Asn Asn Met Ala Arg
        195                 200                 205

Asp Pro Gln Gly Asn Asp Arg Asp Gln Ala Lys Ala Val Val Ala Gly
    210                 215                 220

Glu Gly Asp Val Ala Ile Met Asn Thr Tyr Tyr Met Gly Leu Met Leu
225                 230                 235                 240

Asn Ser Glu Asp Glu Glu Glu Lys Lys Val Ala Glu Gln Leu Gly Val
                245                 250                 255

Phe Phe Pro Asn Gln Asp Thr Thr Gly Thr His Val Asn Ile Ser Gly
            260                 265                 270

Ile Ala Met Thr Lys Ala Ser Lys Asn Thr Glu Asn Ala Gln Lys Leu
        275                 280                 285

Met Glu Phe Met Ser Glu Pro Ser Ala Gln Glu Lys Phe Ala Ser Val
    290                 295                 300

Asn Tyr Glu Tyr Pro Val Asn Glu Ser Val Glu Pro Asn Glu Leu Leu
305                 310                 315                 320

Gln Ser Trp Gly Glu Phe Lys Glu Gln Asp Ile Asn Leu Ser Ala Leu
                325                 330                 335

Gly Glu Asn Gln Gln Glu Ala Ile Arg Ile Phe Asn Glu Val Gly Trp
            340                 345                 350

Lys


<210> SEQ ID NO 9
<211> LENGTH: 355
<212> TYPE: PRT
<213> ORGANISM: Thermosynechococcus elongatus BP-1

<400> SEQUENCE: 9

Met Glu Lys Val Gly Arg Arg Val Phe Leu Gly Met Gly Ala Ala Ala
1               5                   10                  15

Thr Ala Tyr Val Thr His His Leu Trp Asn Gln Asn Ala Glu Ser Ser
            20                  25                  30

Tyr Ala Gln Gln Ser Ser Gly Gly Val Ile Asn Val Tyr Ser Ala Arg
        35                  40                  45

His Tyr Asp Thr Asp Lys Ala Leu Tyr Asn Thr Phe Thr Gln Gln Thr
    50                  55                  60

Gly Ile Arg Val Asn Ile Ile Glu Ala Glu Ala Asp Ala Leu Ile Glu
65                  70                  75                  80

Arg Ile Arg Ser Glu Gly Ser Arg Thr Pro Ala Asp Val Leu Ile Thr
                85                  90                  95

Val Asp Ala Gly Arg Leu Trp Arg Ala Gln Glu Ala Gly Ile Leu Gln
            100                 105                 110

Pro Ile Gln Ser Arg Val Leu Asn Ser Val Val Pro Ala Asn Leu Arg
        115                 120                 125
```

Glu Pro Gln Gly His Trp Phe Gly Leu Ser Arg Arg Val Arg Val Leu
130 135 140

Ile Tyr Asn Lys Ser Arg Val Asn Pro Ser Gln Leu Ser Thr Tyr Glu
145 150 155 160

Asp Leu Ala Asn Pro Lys Trp Arg Arg Gln Ile Leu Thr Arg Ser Ser
165 170 175

Ser Asn Ile Tyr Asn Gln Ser Leu Thr Gly Ser Leu Leu Ala Ile His
180 185 190

Gly Ala Gln Lys Thr Glu Gln Trp Ala Arg Gly Leu Val Gln Asn Phe
195 200 205

Ala Arg Pro Pro Glu Gly Asn Asp Thr Ala Gln Ile Arg Ala Cys Ala
210 215 220

Glu Gly Val Gly Ser Val Ala Ile Ala Asn His Tyr Tyr Leu Ala Arg
225 230 235 240

Leu Ile Ala Ser Asp Lys Glu Gln Asp Arg Ala Val Ala Ala Lys Val
245 250 255

Gly Leu Phe Phe Pro Asn Gln Arg Asp Arg Gly Ala His Val Asn Ile
260 265 270

Ser Gly Ala Gly Val Val Ala Gly Ala Pro Asn Arg Gln Gly Ala Ile
275 280 285

Arg Phe Leu Glu Tyr Leu Val Ser Pro Lys Ala Gln Glu Met Phe Ala
290 295 300

Met Ala Asn Phe Glu Tyr Pro Val Arg Ala Gly Val Pro Val His Pro
305 310 315 320

Ile Val Lys Gln Phe Gly Asn Phe Arg Gly Gln Asn Val Asn Ala Ala
325 330 335

Val Phe Gly Arg Asn Asn Ala Glu Ala Leu Arg Ile Met Asp Arg Ala
340 345 350

Gly Trp Arg
355

<210> SEQ ID NO 10
<211> LENGTH: 343
<212> TYPE: PRT
<213> ORGANISM: Nitrospira defluvii

<400> SEQUENCE: 10

Met Ala Ser Ser Cys Arg Thr Phe Leu Ala Leu Thr Leu Leu Leu Gly
1 5 10 15

Ala Leu Thr Leu Pro Gln Trp Ala Ala Gly Thr Ala Glu Ala Ala Glu
20 25 30

Lys Leu Val Val Tyr Ser Gly Arg Ala Glu Arg Leu Ile Lys Pro Val
35 40 45

Leu Asp Glu Phe Gln Ala Lys Ser Gly Ile Gln Ile Glu Leu Leu Ser
50 55 60

Ser Gly Thr Thr Glu Leu Val Asn Arg Leu Gln Ala Glu Gly Asp His
65 70 75 80

Thr Pro Ala Asp Val Phe Leu Thr Asn Asp Ala Gly Ser Leu Glu His
85 90 95

Ala Arg Glu Leu Lys Leu Leu Arg Pro Met Asn Met Arg Glu Val Glu
100 105 110

Arg Ala Ile Pro Ser Gln Phe Arg Ala Ala Asp Asn Ser Trp Ile Gly
115 120 125

Leu Ser Gly Arg Phe Trp Ile Val Val Tyr Asn Thr Asn Leu Val Lys
130 135 140

```
Pro Asp Gln Ile Lys Ser Leu Phe Asp Leu Thr Gln Pro Gln Trp Lys
145                 150                 155                 160

Asp Lys Ile Ala Val Pro Asn Ser Gly Ser Glu Tyr Leu Gln Ala Gly
                165                 170                 175

Val Ser Val Ile Lys Ala Thr Phe Gly Asp Glu Arg Thr Lys Gln Phe
            180                 185                 190

Leu Gln Gly Leu Lys Ala Asn Ala Gly Thr Gln Val Tyr Gln Lys Ser
        195                 200                 205

Ser Gln Ile Val Glu Ala Val Ala Lys Gly Gln Val Ala Ala Gly Ile
    210                 215                 220

Val Asn His Tyr Tyr Ile Tyr Arg His Leu Ala Thr Gln Pro Thr Ala
225                 230                 235                 240

Pro Ile Ala Ala Val Met Thr Asp Gln Gln Glu Gly Gly Met Gly Ala
                245                 250                 255

Ile Met Asn Val Thr Gly Ile Gly Val Thr Arg Ala Ser Lys His Val
            260                 265                 270

Glu Ser Ala Lys Leu Leu Ile Glu Phe Leu Val Ala Gln Ala Gly Gln
        275                 280                 285

Lys Met Phe Ala Asp Leu Asp Lys Glu Tyr Pro Leu His Pro Asp Val
    290                 295                 300

Lys Ala Asp Pro Thr Leu Ile Asp Arg Arg Thr Phe Arg Ala Ala Gln
305                 310                 315                 320

Val Pro Leu Ala Arg Leu Ala Glu Leu Arg Glu Ala Thr Leu Thr Leu
                325                 330                 335

Ile Glu Gln Val Gly Leu Arg
            340


<210> SEQ ID NO 11
<211> LENGTH: 330
<212> TYPE: PRT
<213> ORGANISM: Thermus thermophilus HB8

<400> SEQUENCE: 11

Met Met Lys Arg Tyr Leu Leu Thr Leu Ala Ala Phe Ala Ala Leu Gly
1               5                   10                  15

Ala Leu Ala Gln Ser Pro Thr Leu Thr Ile Tyr Ser Gly Arg Gly Gln
            20                  25                  30

Ser Leu Val Glu Pro Leu Val Lys Gln Phe Glu Ala Glu Thr Gly Ile
        35                  40                  45

Arg Val Gln Val Arg Tyr Ser Thr Asp Ala Gln Ile Leu Ala Ala Leu
    50                  55                  60

Gln Glu Glu Gly Ser Arg Ser Pro Ala Asp Leu Phe Trp Ala Asn Thr
65                  70                  75                  80

Ala Gly Ala Leu Gly Gln Ala Ser Ala Lys Gly Leu Leu Arg Pro Leu
                85                  90                  95

Gly Glu Thr Leu Leu Glu Lys Pro Ile Ala Phe Val Pro Ala Ser Arg
            100                 105                 110

Thr Trp Val Pro Val Thr Val Arg Leu Arg Val Leu Ala Tyr Asn Pro
        115                 120                 125

Asp Arg Ile Lys Ala Glu Glu Leu Pro Glu Ser Leu Leu Asp Leu Pro
    130                 135                 140

Arg Phe Ala Arg Glu Lys Gly Leu Val Gly Arg Val Gly Trp Thr Pro
145                 150                 155                 160

Thr Tyr Ser Ser Phe Gln Asp Met Val Ala Gly Met Ile Ala Leu Tyr
```

```
                165                 170                 175

Gly Glu Glu Lys Thr Arg Glu Trp Leu Leu Ala Met Lys Ala Leu Ala
            180                 185                 190

Pro Lys Ala Tyr Pro Ser Asn Pro Ala Met Leu Asp Ala Ile Arg Ala
        195                 200                 205

Gly Glu Val Asp Leu Gly Ser Thr Asn His Tyr Tyr Val Val Arg Phe
    210                 215                 220

Arg Arg Ala Gly Tyr Arg Leu Gly Met His His Phe Arg Asp Gly Asp
225                 230                 235                 240

Ala Gly Asn Leu Ala Leu Val Thr Gly Ala Gly Leu Leu Lys Thr Ser
                245                 250                 255

Lys Asn Leu Ala Ala Ala Thr Arg Phe Leu Thr Tyr Leu Leu Ser Pro
            260                 265                 270

Gln Ala Gln Gln Tyr Phe Val Gly Asn Ile Gly Glu Tyr Pro Leu Val
        275                 280                 285

Lys Gly Val Ala Leu Asp Pro Asn Leu Leu Pro Leu Glu Glu Ala Leu
    290                 295                 300

Ala Lys Ser Pro Lys Leu Asp Leu Glu Lys Leu Pro Leu Asp Arg Ala
305                 310                 315                 320

Leu Arg Leu Leu Arg Glu Thr Gly Val Leu
                325                 330


<210> SEQ ID NO 12
<211> LENGTH: 353
<212> TYPE: PRT
<213> ORGANISM: Meiothermus silvanus

<400> SEQUENCE: 12

Met Lys Lys Val Phe Ser Val Leu Leu Ala Ser Ala Leu Ala Leu Gly
1               5                   10                  15

Val Ala Gln Ala Gln Gln Ser Leu Thr Leu Tyr Thr Gly Arg Ser Gln
            20                  25                  30

Ala Leu Val Asp Lys Leu Val Gln Gln Phe Gln Lys Asp Thr Gly Ile
        35                  40                  45

Lys Val Asn Val Arg Tyr Gly Arg Asp Ala Glu Ile Leu Ala Ala Leu
    50                  55                  60

Gln Glu Glu Gly Ser Arg Ser Pro Ala Asp Val Phe Trp Ala Asn Thr
65                  70                  75                  80

Ser Gly Ala Leu Glu Glu Ala Val Lys Arg Asn Leu Leu Val Gln Leu
                85                  90                  95

Pro Ala Ser Leu Thr Arg Gln Pro Gln Glu Phe Val Pro Ser His Gly
            100                 105                 110

Arg Trp Val Pro Val Ser Val Arg Phe Arg Val Ala Ala Tyr Asn Pro
        115                 120                 125

Thr Lys Val Lys Asp Ser Asp Phe Pro Ala Ser Val Met Asp Leu Pro
    130                 135                 140

Lys Val Ala Lys Phe Lys Gly Arg Ile Gly Trp Thr Pro Thr Tyr Ser
145                 150                 155                 160

Ser Phe Gln Asp Phe Ile Thr Ala Met Arg Val Val Lys Gly Glu Ala
                165                 170                 175

Ala Thr Lys Ala Trp Leu Gln Ala Met Ile Ala Ala Gly Ala Lys Ala
            180                 185                 190

Tyr Pro Ser Asn Pro Pro Met Leu Glu Ala Met Gln Ala Gly Glu Ile
        195                 200                 205
```

```
Asp Val Ala Leu Thr Asn His Tyr Tyr Ile Gln Arg Ile Leu Ala Gly
    210                 215                 220

Val Gly Glu Gly Glu Tyr Glu Gly Lys Glu Glu Ser Glu Glu Glu Glu
225                 230                 235                 240

Lys Lys Glu Leu Ala Ala Arg Glu Ala Lys Ala Gly Val Ala Thr His
                245                 250                 255

Tyr Phe Ala Pro Gly Asp Val Gly Gly Leu Ala Leu Val Thr Gly Ala
            260                 265                 270

Gly Ile Leu Ala Thr Ser Lys His Gln Thr Asn Ala Thr Arg Phe Leu
        275                 280                 285

Asn Tyr Leu Leu Ser Lys Lys Ala Gln Pro Tyr Phe Val Asp Glu Val
    290                 295                 300

Arg Glu Tyr Pro Val Ile Ala Gly Val Arg Val Ala Lys Gly Met Leu
305                 310                 315                 320

Pro Phe Ala Asn Ala Ile Arg Leu Ser Pro Lys Ile Asp Phe Ala Lys
                325                 330                 335

Leu Thr Asp Leu Glu Gly Thr Leu Lys Leu Leu Arg Glu Val Gly Leu
            340                 345                 350

Leu


<210> SEQ ID NO 13
<211> LENGTH: 360
<212> TYPE: PRT
<213> ORGANISM: Salinibacter ruber

<400> SEQUENCE: 13

Met Lys Arg Leu Leu Ser Leu Ser Leu Val Val Thr Leu Val Leu Ser
1               5                   10                  15

Leu Leu Gly Cys Gly Gly Glu Gln Gln Asp Glu Leu Val Ile Tyr Ser
            20                  25                  30

Gly Arg Ser Lys Ala Leu Val Asp Ser Leu Val Gln Gln Tyr Arg Gln
        35                  40                  45

Gln Ala Asp Val Pro Val Arg Val Arg Tyr Gly Thr Asp Ser Gln Leu
    50                  55                  60

Leu Ala Ala Leu Gln Glu Glu Gly Asp Gln Ser Pro Ala Asp Val Phe
65                  70                  75                  80

Trp Ala Asn Thr Thr Gly Ala Leu Gly Asn Ala Val Asn Asn Gly Leu
                85                  90                  95

Leu Thr Glu Leu Pro Asp Thr Leu Ala Asn Arg Ala Ala Arg Phe Thr
            100                 105                 110

Pro Ser Asn Gln Arg Trp Thr Pro Val Thr Thr Arg Phe Arg Val Leu
        115                 120                 125

Ala Tyr Asn Ser Asp Ala Val Ser Pro Glu Asp Leu Pro Asp Ser Val
    130                 135                 140

Leu Asp Leu Pro Glu His Glu Glu Phe Glu Gly Arg Val Gly Trp Thr
145                 150                 155                 160

Pro Ala Tyr Ser Ser Phe Gln Asp Phe Val Thr Ala Leu Arg Val Thr
                165                 170                 175

Glu Gly Ala Glu Thr Ala Arg Thr Trp Leu Ser Asp Met Gln Ala Leu
            180                 185                 190

Asn Pro Asn Ser Tyr Thr Ser Asn Thr Pro Met Val Gln Ala Leu Glu
        195                 200                 205

Ala Gly Glu Ile Asp Val Ala Leu Thr Asn His Tyr Tyr Val Leu Arg
    210                 215                 220
```

Leu Lys His Gly Gly Ala Glu Gly Glu Tyr Glu Gly Glu Glu Glu Glu
225 230 235 240

Gly Glu Glu His Glu Glu Glu His Glu Glu Glu Ala Thr Pro Arg Ala
245 250 255

Ser Ala Pro Val Glu Met Tyr His Phe Ala Asp Gly Asp Leu Gly Asn
260 265 270

Leu Ala Leu Val Thr Gly Ala Gly Ala Leu Gln Thr Ser Asn Gln Pro
275 280 285

Asp Ala Ala Asn Arg Phe Leu Arg Phe Leu Leu Ser Glu Gln Ala Gln
290 295 300

Ser Phe Ala Ala Thr Arg Val Asn Glu Tyr Pro Val Val Ser Gly Ala
305 310 315 320

Ser Val Pro Asp Tyr Leu Met Pro Ala Asp Glu Ala Leu Lys Met Ser
325 330 335

Pro Glu Phe Asp Leu Gln Lys Leu Gln Asn Met Glu Pro Thr Leu Asp
340 345 350

Leu Leu Arg Asp Ala Gly Ala Leu
355 360

<210> SEQ ID NO 14
<211> LENGTH: 385
<212> TYPE: PRT
<213> ORGANISM: Halorubrum lacusprofundi

<400> SEQUENCE: 14

Met Thr Asn Tyr Leu Pro Asp Gly Val Asp Arg Arg Gln Phe Leu Ala
1 5 10 15

Ala Thr Gly Ala Leu Gly Val Ala Gly Leu Ala Gly Cys Thr Gly Asp
20 25 30

Asp Thr Asp Gly Gly Ser Gly Asn Ser Ser Asp Gly Gly Asp Gly Gly
35 40 45

Asp Gly Gly Asp Gly Ser Ile Gly Gln Ile Gly Ser Gly Arg Glu Gly
50 55 60

Arg Gly Ala Pro Gly Gly Ile Pro Met Ala Glu Met Pro Asp Leu Glu
65 70 75 80

Gly Glu Leu Thr Val Tyr Ser Gly Arg Gly Glu Phe Leu Val Gly Glu
85 90 95

Leu Val Glu Tyr Ile Glu Asp Gln Tyr Asp Asp Phe Asp Leu Thr Val
100 105 110

Arg Tyr Ala Gly Ser Thr Asp Leu Val Asn Gln Ile Leu Asn Glu Gly
115 120 125

Asp Gly Ser Pro Ala Asp Val Phe Tyr Ser Val Asn Ala Gly Ser Leu
130 135 140

Gly Thr Leu Ala Gly Glu Gly Arg Ser Gln Ala Leu Ser Ser Glu Ile
145 150 155 160

Thr Asp Met Val Arg Ser Glu Phe Arg Thr Glu Gln Trp Ile Gly Thr
165 170 175

Ser Gly Arg Ala Arg Thr Val Pro Tyr Asn Thr Gly Glu Phe Ser Asp
180 185 190

Asp Asp Leu Pro Asp Asp Ile Met Ala Tyr Pro Glu Glu Phe Ala Gly
195 200 205

Ser Leu Gly Trp Ala Pro Ser Tyr Gly Ser Cys Gln Ala Phe Ile Thr
210 215 220

Ala Met Arg Leu Ile Glu Gly Glu Glu Ala Thr Leu Ala Trp Leu Glu
225 230 235 240

Ser Val Val Glu Ala Gly Ile Ser Ser Tyr Pro Asp Glu Phe Ala Ala
245 250 255

Cys Gln Ala Ile Ala Asp Gly Glu Ile Asp Ala Ala Phe Thr Asn His
260 265 270

Tyr Tyr Ile Gln Arg Val Leu Asp Gly Asn Pro Asp Ala Ser Ile Gly
275 280 285

Thr Ala Phe Thr Ser Gly Asp Ala Gly Ala Val Phe Asn Val Ala Gly
290 295 300

Ala Ala Val Val Asp Thr Ala Ser Asp Ala Thr Leu Ala Glu Asn Phe
305 310 315 320

Ile Arg His Leu Leu Ser Ala Glu Ala Gln Asp Tyr Phe Ala Arg Ser
325 330 335

Thr Phe Glu Tyr Pro Leu Ile Pro Asp Val Glu Pro Ile Gly Asp Leu
340 345 350

Pro Thr Ile Asp Glu Leu Asp Val Pro Asp Ile Asp Leu Thr Glu Leu
355 360 365

Ser Asp Leu Glu Pro Thr Ile Asp Leu Met Arg Glu Ala Gly Val Glu
370 375 380

Val
385

<210> SEQ ID NO 15
<211> LENGTH: 411
<212> TYPE: PRT
<213> ORGANISM: Artificial Sequence
<220> FEATURE:
<223> OTHER INFORMATION: synBicarbBP1 (with signal peptide replaced with M and a GGSHHHHHH at C-terminus)

<400> SEQUENCE: 15

Met Pro Glu Met Met Pro Glu Thr Ala Asn Ile Lys Leu Gly Tyr Ile
1 5 10 15

Pro Ile Val Glu Ala Ala Pro Leu Ile Ile Ala Gln Glu Lys Gly Phe
20 25 30

Phe Ala Lys Tyr Gly Met Thr Gly Val Glu Val Ser Lys Gln Ala Asn
35 40 45

Trp Ala Ser Ala Arg Asp Asn Val Thr Ile Gly Ser Gln Gly Gly Gly
50 55 60

Ile Asp Gly Gly Gln Trp Gln Met Pro Met Pro His Leu Ile Thr Glu
65 70 75 80

Gly Ile Ile Thr Asn Gly Asn Lys Val Pro Met Tyr Val Leu Ala Gln
85 90 95

Leu Ile Thr Gln Gly Asn Gly Ile Ala Val Ala Pro Met His Glu Gly
100 105 110

Lys Gly Val Asn Leu Asp Ile Thr Lys Ala Ala Asp Tyr Ile Lys Gly
115 120 125

Phe Asn Lys Thr Asn Gly Arg Lys Phe Lys Ala Ala His Thr Phe Pro
130 135 140

Asn Val Asn Gln Asp Phe Trp Ile Arg Tyr Trp Phe Ala Ala Gly Gly
145 150 155 160

Val Asp Pro Asp Thr Asp Ile Asp Leu Leu Ala Val Pro Pro Ala Glu
165 170 175

Thr Val Gln Gly Met Arg Asn Gly Thr Met Asp Ala Phe Ser Thr Gly
180 185 190

Asp Pro Trp Pro Tyr Arg Ile Val Thr Glu Asn Ile Gly Tyr Met Ala

```
        195                 200                 205

Gly Leu Thr Ala Gln Ile Trp Pro Tyr His Pro Glu Glu Tyr Leu Ala
    210                 215                 220

Ile Arg Ala Asp Trp Val Asp Lys Asn Pro Lys Ala Thr Lys Ala Leu
225                 230                 235                 240

Leu Lys Gly Ile Met Glu Ala Gln Gln Trp Ile Asp Asp Pro Lys Asn
                245                 250                 255

Arg Pro Glu Val Val Gln Ile Val Ser Gly Arg Asn Tyr Phe Asn Val
            260                 265                 270

Pro Thr Thr Ile Leu Glu Ser Pro Phe Lys Gly Gln Tyr Thr Met Gly
        275                 280                 285

Asp Gly Gln Pro Ala Ile Asp Asp Phe Gln Lys Gly Pro Leu Tyr Trp
    290                 295                 300

Lys Asp Gly Ile Gly Asn Val Ser Tyr Pro Tyr Lys Ser His Asp Leu
305                 310                 315                 320

Trp Phe Leu Thr Glu Ser Ile Arg Trp Gly Phe His Lys Asn Ala Ile
                325                 330                 335

Pro Asp Leu Asp Thr Ala Gln Lys Ile Ile Asp Lys Val Asn Arg Glu
            340                 345                 350

Asp Leu Trp Arg Glu Ala Ala Thr Glu Ala Gly Phe Thr Ala Asp Ile
        355                 360                 365

Pro Ser Ser Thr Ser Arg Gly Val Glu Thr Phe Phe Asp Gly Ile Thr
    370                 375                 380

Phe Asp Pro Ala Asn Pro Ser Ala Tyr Leu Gln Ser Leu Ala Ile Lys
385                 390                 395                 400

Lys Val Gly Gly Ser His His His His His His
                405                 410


<210> SEQ ID NO 16
<211> LENGTH: 410
<212> TYPE: PRT
<213> ORGANISM: Artificial Sequence
<220> FEATURE:
<223> OTHER INFORMATION: teBicarbBP2 (with C247A and C260A substitution
      mutations, the signal peptide replaced with M, and a GGSHHHHHH at
      C-terminus)

<400> SEQUENCE: 16

Met Leu Glu Thr Asp Thr Ile Lys Leu Gly Phe Ile Pro Ile Val Glu
1               5                   10                  15

Ser Ala Pro Leu Ile Ile Ala Lys Glu Lys Gly Phe Phe Ala Lys His
            20                  25                  30

Gly Leu Thr Asn Ala Glu Leu Ser Lys Gln Ala Asn Trp Ala Ser Ala
        35                  40                  45

Arg Asp Asn Val Val Ile Gly Ser Ala Gly Gly Gly Ile Asp Gly Gly
    50                  55                  60

Gln Trp Gln Met Pro Met Pro Tyr Leu Ile Ser Glu Gly Ile Ile Thr
65                  70                  75                  80

Leu Asn Asn Gln Lys Leu Pro Met Tyr Val Leu Ala Gln Leu Asn Thr
                85                  90                  95

Gln Gly Asn Gly Ile Ala Ile Ser Gly Ala Asn Lys Gly Lys Gly Leu
            100                 105                 110

His Leu Lys Ile Ala Asp Pro Asp Tyr Ile Lys Gly Phe Ala Ala Lys
        115                 120                 125

Asn Gly Arg Lys Phe Lys Ala Ala His Thr Phe Pro His Val Asn Gln
    130                 135                 140
```

```
Asp Leu Trp Ile Arg Tyr Trp Phe Ala Ala Asn Gly Ile Asp Pro Asp
145                 150                 155                 160

Arg Asp Ile Glu Leu Leu Ala Val Pro Pro Ala Glu Thr Val Ala Gly
                165                 170                 175

Met Arg Asn Gly Thr Met Asp Ala Phe Ser Thr Gly Asp Pro Trp Pro
            180                 185                 190

Phe Arg Ile Val Ser Asp Asp Ile Gly Tyr Met Ala Thr Leu Thr Ala
        195                 200                 205

Gln Ile Trp Pro Tyr His Pro Glu Glu Tyr Leu Ala Val Arg Ala Asp
    210                 215                 220

Trp Val Asp Lys His Pro Lys Ala Thr Lys Ala Leu Leu Lys Ala Val
225                 230                 235                 240

Met Glu Ala Gln Gln Trp Ala Asp Asp Lys Ala Asn Arg Pro Glu Leu
                245                 250                 255

Ile Gln Ile Ala Ser Arg Arg Glu Tyr Phe Asn Ile Pro Gly Asn Ile
            260                 265                 270

Leu Thr Pro Pro Tyr Glu Gly Thr Tyr Thr Met Gly Asp Gly Gln Pro
        275                 280                 285

Asn Phe Asn Asp Phe Asn Ile Gly Pro Leu Tyr Trp Arg Asp Pro Asn
    290                 295                 300

Gly Asn Ser Ile Ser Tyr Pro Tyr Lys Ser His Asp Leu Trp Phe Leu
305                 310                 315                 320

Thr Glu Asn Leu Arg Trp Gly Phe Asn Ala Asp Lys Leu Lys Asp Phe
                325                 330                 335

Asp Asn Ile Lys Gln Met Ile Gly Arg Val Asn Arg Ser Asp Leu Trp
            340                 345                 350

Gln Glu Ala Ala Lys Glu Leu Gly Ile Pro Ala Ala Glu Ile Pro Thr
        355                 360                 365

Thr Glu Ser Arg Gly Val Glu Thr Phe Phe Asp Gly Ile Lys Phe Asp
    370                 375                 380

Pro Asp Asn Pro Gln Ala Tyr Leu Asp Ser Leu Lys Ile Lys Val Lys
385                 390                 395                 400

Ser Gly Gly Ser His His His His His His
                405                 410


<210> SEQ ID NO 17
<211> LENGTH: 410
<212> TYPE: PRT
<213> ORGANISM: Artificial Sequence
<220> FEATURE:
<223> OTHER INFORMATION: ctBicarbBP3 (with signal peptide replaced with
      M and a GGSHHHHHH at C-terminus)

<400> SEQUENCE: 17

Met Pro Glu Gln Ala Pro Glu Thr Thr Arg Val Lys Leu Gly Tyr Ile
1               5                   10                  15

Pro Ile Val Glu Ala Ala Pro Ile Ile Ile Ala Lys Glu Lys Gly Phe
            20                  25                  30

Phe Ala Lys Tyr Gly Met Thr Asp Val Asp Val Ser Lys Gln Ala Ser
        35                  40                  45

Trp Gly Ser Met Arg Asp Asn Thr Glu Ile Gly Ala Ala Gly Gly Gly
    50                  55                  60

Val Asp Gly Gly Gln Tyr Gln Met Pro Met Pro His Leu Ile Thr Glu
65                  70                  75                  80

Gly Arg Ile Thr Lys Gly Asn Lys Pro Ile Pro Met Tyr Val Leu Ala
```

```
                85                  90                  95

Gln Leu Asn Thr Gln Gly Asn Gly Ile Ala Ile Ala Glu Lys His Arg
            100                 105                 110

Gly Lys Gly Ile Glu Leu Glu Leu Ala Lys Gly Gly Lys Asn Leu Phe
        115                 120                 125

Gly Gln Leu Lys Ser Ala Asn Thr Pro Phe Thr Ala Ala Tyr Thr Phe
    130                 135                 140

Ala Gln Val Asn Gln Asp Phe Trp Ile Arg Tyr Trp Leu Ala Ala Gly
145                 150                 155                 160

Gly Val Asn Pro Asp Ala Asp Val Lys Leu Ile Pro Val Pro Ala Ala
                165                 170                 175

Gln Thr Val Ala Asn Met Lys Thr Gly Thr Met Asp Ala Phe Ser Thr
            180                 185                 190

Gly Asp Pro Trp Pro Tyr Arg Ile Val Lys Asp Lys Ile Gly Phe Leu
        195                 200                 205

Ala Met Leu Thr Ala Asp Met Trp Glu Phe His Pro Glu Glu Tyr Leu
    210                 215                 220

Ala Leu Arg Ala Glu Trp Val Asp Lys His Pro Lys Ala Thr Lys Ala
225                 230                 235                 240

Leu Leu Lys Gly Ile Met Glu Ala Gln Gln Trp Leu Asp Asn Phe Asp
                245                 250                 255

Asn Arg Glu Glu Ala Ala Lys Ile Leu Gly Gly Arg Asn Tyr Phe Asn
            260                 265                 270

Leu Pro Ala Glu Ile Leu Ala Gly Pro Phe Ala Gly Lys Tyr Asp Met
        275                 280                 285

Gly Glu Gly Arg Thr Val Asp Asp Arg Asn Lys Ala Val Leu Tyr Trp
    290                 295                 300

Lys Asp Pro Arg Gly Ser Val Ser Tyr Pro Tyr Lys Ser His Asp Leu
305                 310                 315                 320

Trp Phe Leu Thr Glu Ser Val Arg Trp Gly Phe Leu Pro Pro Asp Ser
                325                 330                 335

Leu Thr Lys Ala Gln Ala Leu Ile Asp Lys Val Asn Arg Glu Asp Leu
            340                 345                 350

Trp Lys Glu Ala Ala Lys Glu Leu Gly Val Ala Ala Ala Asp Ile Pro
        355                 360                 365

Thr Ser Thr Ser Arg Gly Val Glu Thr Phe Phe Asp Gly Val Lys Phe
    370                 375                 380

Asp Pro Glu Asn Pro Ala Ala Tyr Leu Lys Ser Leu Lys Ile Lys Lys
385                 390                 395                 400

Ala Gly Gly Ser His His His His His His
                405                 410


<210> SEQ ID NO 18
<211> LENGTH: 415
<212> TYPE: PRT
<213> ORGANISM: Artificial Sequence
<220> FEATURE:
<223> OTHER INFORMATION: calBicarbBP4 (with signal peptide replaced with
      M and a GGSHHHHHH at C-terminus)

<400> SEQUENCE: 18

Met Pro Glu Gln Lys Pro Glu Thr Glu Thr Val Lys Leu Gly Tyr Ile
1               5                   10                  15

Pro Ile Val Glu Ser Ala Pro Leu Ile Ile Ala Lys Glu Lys Gly Leu
            20                  25                  30
```

```
Phe Ala Lys Tyr Gly Met Thr Lys Val Glu Leu Ala Lys Gln Ala Ser
        35                  40                  45

Trp Gly Ala Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Ala
65                  70                  75                  80

Gly Leu Ile Thr Lys Gly Asn Lys Glu Ile Pro Met Tyr Val Leu Ala
                85                  90                  95

Gln Leu Val Thr His Gly Asn Gly Ile Ala Ile Ala Asp Lys His Lys
            100                 105                 110

Gly Lys Gly Leu Gly Leu Lys Leu Asp Gly Ala Lys Ser Leu Phe Lys
        115                 120                 125

Glu Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Ser Gly Leu
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Ile Val Asn Asp Lys Ile Gly Phe Met Ala Leu
        195                 200                 205

Leu Thr Ala Glu Met Trp Lys Asn His Pro Glu Glu Tyr Leu Ala Met
    210                 215                 220

Arg Gly Asp Trp Val Asp Lys His Pro Lys Ala Thr Lys Ala Ile Leu
225                 230                 235                 240

Lys Ala Val Met Glu Ala Gln Gln Trp Leu Asp Asn Phe Glu Asn Arg
                245                 250                 255

Lys Glu Ala Ala Thr Ile Leu Ala Gly Arg Lys Tyr Phe Asp Leu Ser
            260                 265                 270

Ser Pro Glu Ile Leu Leu Asp Pro Tyr Gln Gly Lys Tyr Asp Met Gly
        275                 280                 285

Asp Gly Arg Lys Ile Asp Asp Lys Leu Met Ala Pro Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Asn Ala Ala Lys Ala Lys Glu Leu Ile Asn Lys Val Asn Arg
            340                 345                 350

Glu Asp Ile Trp Lys Glu Ala Ala Lys Asp Leu Gly Ile Ala Ala Ala
        355                 360                 365

Asp Ile Pro Thr Ser Thr Ser Arg Gly Val Glu Glu Phe Phe Asp Gly
    370                 375                 380

Val Lys Phe Asp Pro Glu Lys Pro Glu Glu Tyr Leu Lys Ser Leu Lys
385                 390                 395                 400

Ile Lys Lys Ala Gly Val Gly Gly Ser His His His His His His
                405                 410                 415
```

<210> SEQ ID NO 19
<211> LENGTH: 415
<212> TYPE: PRT
<213> ORGANISM: Artificial Sequence
<220> FEATURE:
<223> OTHER INFORMATION: avBicarbBP5 (with C96A substitution mutation, signal peptide replaced with M, and a GGSHHHHHH at C-terminus)

<400> SEQUENCE: 19

```
Met Ala Glu Gln Ala Pro Glu Val Thr Thr Val Lys Leu Gly Tyr Ile
1               5                   10                  15

Pro Ile Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400
```

```
Ile Lys Lys Val Ser Val Gly Gly Ser His His His His His His
                405                 410                 415


<210> SEQ ID NO 20
<211> LENGTH: 415
<212> TYPE: PRT
<213> ORGANISM: Artificial Sequence
<220> FEATURE:
<223> OTHER INFORMATION: cmBicarbBP6 (with C254A substitution mutation,
      signal peptide replaced with M, and a GGSHHHHHH at C-terminus)

<400> SEQUENCE: 20

Met Ser Ser Ala Thr Thr Pro Glu Thr Thr Ala Val Lys Leu Gly Tyr
1               5                   10                  15

Ile Ala Ile Ala Glu Ser Ala Pro Leu Ile Ile Ala Arg Glu Lys Gly
            20                  25                  30

Phe Phe Ala Arg His Gly Met Thr Asp Val Asp Val Ser Lys Gln Ala
        35                  40                  45

Ser Trp Gly Ser Ala Arg Asp Asn Ile Glu Ile Gly Ser Ser Asn Gly
    50                  55                  60

Gly Ile Asp Gly Gly Gln Trp Gln Met Pro Met Pro Gln Leu Ile Ser
65                  70                  75                  80

Glu Gly Ile Ile Thr Lys Gly Asn Arg Lys Ile Pro Met Leu Ser Leu
                85                  90                  95

Ala Gln Leu Ser Thr Gln Gly Asn Gly Ile Ala Ile Ser Thr Gln His
            100                 105                 110

Ala Gly Lys Gly Phe Gly Leu Asp Val Ser Gly Ala Ala Glu Tyr Val
        115                 120                 125

Arg Asp Met Lys Ala Asp Gly Lys Pro Phe Lys Ala Ala Tyr Thr Phe
    130                 135                 140

Pro Arg Val Asn Gln Asp Phe Trp Ile Arg Tyr Trp Leu Ala Ala Gly
145                 150                 155                 160

Gly Ile Asp Pro Asn Lys Asp Ile Asp Leu Ile Ala Val Pro Ala Ala
                165                 170                 175

Gln Thr Val Ala Ser Met Arg Thr Gly Ser Met Asp Gly Phe Ser Thr
            180                 185                 190

Gly Asp Pro Trp Pro Ser Arg Ile Leu Arg Asp Arg Arg Lys Tyr Gly
        195                 200                 205

Phe Leu Ala Val Leu Thr Ala Gln Ile Trp Pro Ala His Pro Glu Glu
    210                 215                 220

Tyr Phe Ala Met Arg Glu Asp Trp Val Arg Lys His Pro Lys Ala Ala
225                 230                 235                 240

Lys Ala Ile Leu Lys Gly Ile Met Glu Ala Gln Met Trp Ala Asp Asp
                245                 250                 255

Pro Lys Asn Arg Ala Glu Met Ala Ala Ile Leu Ala Gln Arg Lys Tyr
            260                 265                 270

Phe Asn Val Pro Ser Asp Leu Leu Ile Gly Pro Tyr Val Gly Glu Tyr
        275                 280                 285

Ile Leu Gly Ala Asp Arg Lys Thr Val Lys Asp Glu Lys Leu Ala Ile
    290                 295                 300

Arg Tyr Trp Lys Asp Ala Arg Gly Asn Val Ser Tyr Pro Tyr Lys Ser
305                 310                 315                 320

His Asp Leu Trp Phe Leu Thr Glu Ser Val Arg Trp Gly Phe Leu Pro
                325                 330                 335

Gln Gly Ala Leu Gly Glu Ala Asp Arg Ile Ile Asn Ala Val Ser Gly
            340                 345                 350
```

Glu Lys Tyr Trp Arg Glu Ala Ala Gln Glu Leu Gly Ile Ala Ser Ala
355 360 365

Asp Ile Pro Pro Ser Thr Ser Arg Gly Ile Glu Lys Phe Phe Asp Gly
370 375 380

Ala Glu Phe Asn Pro Glu Lys Pro Lys Ala Tyr Leu Asp Ser Leu Lys
385 390 395 400

Ile Lys Asn Leu Lys Ala Gly Gly Ser His His His His His His
405 410 415

<210> SEQ ID NO 21
<211> LENGTH: 326
<212> TYPE: PRT
<213> ORGANISM: Artificial Sequence
<220> FEATURE:
<223> OTHER INFORMATION: mhFeBP1 (with C135A and C191A substitution mutations, the signal peptide replaced with M, and a GGSHHHHHH at C-terminus)

<400> SEQUENCE: 21

Met Ala Asn Glu Val Asn Val Tyr Ser Tyr Arg Gln Pro Tyr Leu Ile
1 5 10 15

Glu Pro Met Leu Lys Asn Phe Glu Lys Asp Thr Gly Ile Lys Val Asn
20 25 30

Ile Ile Phe Ala Asp Lys Gly Leu Val Asp Arg Val Lys Gln Glu Gly
35 40 45

Glu Leu Ser Pro Ala Asp Val Leu Leu Thr Val Asp Ile Ser Arg Val
50 55 60

Met Glu Ile Val Asn Ala Asp Leu Ala Gln Lys Ile Asp Ser Lys Val
65 70 75 80

Leu Glu Lys Asn Ile Pro Ala Gln Phe Arg Asp Ser Asn Asp Gln Trp
85 90 95

Phe Gly Leu Thr Thr Arg Ala Arg Val Ile Tyr Thr Ser Lys Asp Arg
100 105 110

Val Gly Lys Leu Pro Ala Gly Phe Asp Tyr Leu Asp Leu Ala Lys Pro
115 120 125

Glu Tyr Lys Gly Lys Val Ala Val Arg Ser Gly Lys Asn Ser Tyr Asn
130 135 140

Val Ser Leu Phe Ala Ala Met Ile Glu His Tyr Gly Ile Glu Lys Thr
145 150 155 160

Lys Ala Phe Leu Glu Gly Leu Lys Ala Asn Leu Ala Arg Lys Pro Gln
165 170 175

Gly Gly Asp Arg Asp Gln Val Lys Ala Ile Lys Glu Gly Ile Ala Asp
180 185 190

Tyr Ser Ile Gly Asn Ser Tyr Tyr Tyr Gly Lys Met Leu Asp Asp Glu
195 200 205

Lys Gln Lys Ser Trp Ala Glu Ala Ala Ile Ile Asn Phe Pro Ser Gly
210 215 220

Glu His Gly Thr His Lys Asn Ile Ser Gly Val Val Ile Ala Lys His
225 230 235 240

Ser Pro Asn Lys Ala Asn Ala Val Lys Leu Ile Glu Tyr Leu Ser Gly
245 250 255

Glu Lys Ala Gln Gly Leu Tyr Ala Glu Leu Asn His Glu Tyr Pro Val
260 265 270

Lys Glu Gly Ile Glu Pro Ser Ala Ile Val Lys Gly Trp Gly Thr Phe
275 280 285

-continued

```
Lys Ser Asp Thr Ile Lys Leu Glu Asp Ile Ala Lys Asn Tyr Glu Ala
    290                 295                 300

Ala Leu Lys Leu Val Asp Glu Val Lys Phe Asp Asp Phe Gly Gly Ser
305                 310                 315                 320

His His His His His His
                325


<210> SEQ ID NO 22
<211> LENGTH: 326
<212> TYPE: PRT
<213> ORGANISM: Artificial Sequence
<220> FEATURE:
<223> OTHER INFORMATION: exiFeBP2 (with signal peptide replaced with M
      and a GGSHHHHHH at C-terminus)

<400> SEQUENCE: 22

Met Asn Val Val Asn Val Tyr Ser Ser Arg His Tyr Asp Val Asp Gln
1               5                   10                  15

Gln Leu Tyr Lys Gln Phe Glu Glu Glu Thr Gly Ile Lys Val Asn Val
            20                  25                  30

Val Glu Gly Lys Ser Asp Glu Leu Leu Glu Arg Leu Asn Thr Glu Gly
        35                  40                  45

Glu Asn Thr Glu Ala Asp Leu Phe Ile Thr Ala Asp Ala Gly Asn Leu
    50                  55                  60

Tyr Gln Ala Lys Glu Ala Gly His Leu Gln Ala Val Asp Ser Asp Glu
65                  70                  75                  80

Leu Glu Ser Asn Ile Pro Glu Lys Tyr Arg Asp Thr Asp Asn Glu Trp
                85                  90                  95

Phe Gly Leu Thr Lys Arg Ala Arg Val Ile Val Tyr Ser Lys Asp Arg
            100                 105                 110

Val Lys Pro Glu Asp Leu Ser Thr Tyr Glu Ala Leu Thr Glu Glu Gln
        115                 120                 125

Trp Asn Gly Lys Val Leu Val Arg Pro Ser Glu Asn Met Tyr Asn Ile
    130                 135                 140

Ser Leu Leu Ala Ser Phe Ile Glu Val Asn Gly Val Asp Glu Ala Lys
145                 150                 155                 160

Glu Trp Ala Lys Gly Leu Val Asn Asn Met Ala Arg Asp Pro Gln Gly
                165                 170                 175

Asn Asp Arg Asp Gln Ala Lys Ala Val Val Ala Gly Glu Gly Asp Val
            180                 185                 190

Ala Ile Met Asn Thr Tyr Tyr Met Gly Leu Met Leu Asn Ser Glu Asp
        195                 200                 205

Glu Glu Glu Lys Lys Val Ala Glu Gln Leu Gly Val Phe Phe Pro Asn
    210                 215                 220

Gln Asp Thr Thr Gly Thr His Val Asn Ile Ser Gly Ile Ala Met Thr
225                 230                 235                 240

Lys Ala Ser Lys Asn Thr Glu Asn Ala Gln Lys Leu Met Glu Phe Met
                245                 250                 255

Ser Glu Pro Ser Ala Gln Glu Lys Phe Ala Ser Val Asn Tyr Glu Tyr
            260                 265                 270

Pro Val Asn Glu Ser Val Glu Pro Asn Glu Leu Leu Gln Ser Trp Gly
        275                 280                 285

Glu Phe Lys Glu Gln Asp Ile Asn Leu Ser Ala Leu Gly Glu Asn Gln
    290                 295                 300

Gln Glu Ala Ile Arg Ile Phe Asn Glu Val Gly Trp Lys Gly Gly Ser
305                 310                 315                 320
```

His His His His His His
325

<210> SEQ ID NO 23
<211> LENGTH: 325
<212> TYPE: PRT
<213> ORGANISM: Artificial Sequence
<220> FEATURE:
<223> OTHER INFORMATION: teFeBP3 (with C184S substitution mutation, the signal peptide replaced with M, and a GGSHHHHHH at C-terminus)

<400> SEQUENCE: 23

Met Val Ile Asn Val Tyr Ser Ala Arg His Tyr Asp Thr Asp Lys Ala
1 5 10 15

Leu Tyr Asn Thr Phe Thr Gln Gln Thr Gly Ile Arg Val Asn Ile Ile
20 25 30

Glu Ala Glu Ala Asp Ala Leu Ile Glu Arg Ile Arg Ser Glu Gly Ser
35 40 45

Arg Thr Pro Ala Asp Val Leu Ile Thr Val Asp Ala Gly Arg Leu Trp
50 55 60

Arg Ala Gln Glu Ala Gly Ile Leu Gln Pro Ile Gln Ser Arg Val Leu
65 70 75 80

Asn Ser Val Val Pro Ala Asn Leu Arg Glu Pro Gln Gly His Trp Phe
85 90 95

Gly Leu Ser Arg Arg Val Arg Val Leu Ile Tyr Asn Lys Ser Arg Val
100 105 110

Asn Pro Ser Gln Leu Ser Thr Tyr Glu Asp Leu Ala Asn Pro Lys Trp
115 120 125

Arg Arg Gln Ile Leu Thr Arg Ser Ser Ser Asn Ile Tyr Asn Gln Ser
130 135 140

Leu Thr Gly Ser Leu Leu Ala Ile His Gly Ala Gln Lys Thr Glu Gln
145 150 155 160

Trp Ala Arg Gly Leu Val Gln Asn Phe Ala Arg Pro Pro Glu Gly Asn
165 170 175

Asp Thr Ala Gln Ile Arg Ala Ser Ala Glu Gly Val Gly Ser Val Ala
180 185 190

Ile Ala Asn His Tyr Tyr Leu Ala Arg Leu Ile Ala Ser Asp Lys Glu
195 200 205

Gln Asp Arg Ala Val Ala Ala Lys Val Gly Leu Phe Phe Pro Asn Gln
210 215 220

Arg Asp Arg Gly Ala His Val Asn Ile Ser Gly Ala Gly Val Val Ala
225 230 235 240

Gly Ala Pro Asn Arg Gln Gly Ala Ile Arg Phe Leu Glu Tyr Leu Val
245 250 255

Ser Pro Lys Ala Gln Glu Met Phe Ala Met Ala Asn Phe Glu Tyr Pro
260 265 270

Val Arg Ala Gly Val Pro Val His Pro Ile Val Lys Gln Phe Gly Asn
275 280 285

Phe Arg Gly Gln Asn Val Asn Ala Ala Val Phe Gly Arg Asn Asn Ala
290 295 300

Glu Ala Leu Arg Ile Met Asp Arg Ala Gly Trp Arg Gly Gly Ser His
305 310 315 320

His His His His His
325

<210> SEQ ID NO 24
<211> LENGTH: 321
<212> TYPE: PRT
<213> ORGANISM: Artificial Sequence
<220> FEATURE:
<223> OTHER INFORMATION: cnFeBP4 (with signal peptide replaced with M and a GGSHHHHHH at C-terminus)

<400> SEQUENCE: 24

```
Met Lys Leu Val Val Tyr Ser Gly Arg Ala Glu Arg Leu Ile Lys Pro
1               5                   10                  15

Val Leu Asp Glu Phe Gln Ala Lys Ser Gly Ile Gln Ile Glu Leu Leu
            20                  25                  30

Ser Ser Gly Thr Thr Glu Leu Val Asn Arg Leu Gln Ala Glu Gly Asp
        35                  40                  45

His Thr Pro Ala Asp Val Phe Leu Thr Asn Asp Ala Gly Ser Leu Glu
    50                  55                  60

His Ala Arg Glu Leu Lys Leu Leu Arg Pro Met Asn Met Arg Glu Val
65                  70                  75                  80

Glu Arg Ala Ile Pro Ser Gln Phe Arg Ala Ala Asp Asn Ser Trp Ile
                85                  90                  95

Gly Leu Ser Gly Arg Phe Trp Ile Val Val Tyr Asn Thr Asn Leu Val
            100                 105                 110

Lys Pro Asp Gln Ile Lys Ser Leu Phe Asp Leu Thr Gln Pro Gln Trp
        115                 120                 125

Lys Asp Lys Ile Ala Val Pro Asn Ser Gly Ser Glu Tyr Leu Gln Ala
    130                 135                 140

Gly Val Ser Val Ile Lys Ala Thr Phe Gly Asp Glu Arg Thr Lys Gln
145                 150                 155                 160

Phe Leu Gln Gly Leu Lys Ala Asn Ala Gly Thr Gln Val Tyr Gln Lys
                165                 170                 175

Ser Ser Gln Ile Val Glu Ala Val Ala Lys Gly Gln Val Ala Ala Gly
            180                 185                 190

Ile Val Asn His Tyr Tyr Ile Tyr Arg His Leu Ala Thr Gln Pro Thr
        195                 200                 205

Ala Pro Ile Ala Ala Val Met Thr Asp Gln Gln Glu Gly Gly Met Gly
    210                 215                 220

Ala Ile Met Asn Val Thr Gly Ile Gly Val Thr Arg Ala Ser Lys His
225                 230                 235                 240

Val Glu Ser Ala Lys Leu Leu Ile Glu Phe Leu Val Ala Gln Ala Gly
                245                 250                 255

Gln Lys Met Phe Ala Asp Leu Asp Lys Glu Tyr Pro Leu His Pro Asp
            260                 265                 270

Val Lys Ala Asp Pro Thr Leu Ile Asp Arg Arg Thr Phe Arg Ala Ala
        275                 280                 285

Gln Val Pro Leu Ala Arg Leu Ala Glu Leu Arg Glu Ala Thr Leu Thr
    290                 295                 300

Leu Ile Glu Gln Val Gly Leu Arg Gly Gly Ser His His His His His
305                 310                 315                 320

His
```

<210> SEQ ID NO 25
<211> LENGTH: 320
<212> TYPE: PRT
<213> ORGANISM: Artificial Sequence
<220> FEATURE:
<223> OTHER INFORMATION: ttFeBP5 (with signal peptide replaced with M and a GGSHHHHHH at C-terminus)

<400> SEQUENCE: 25

Met Ser Pro Thr Leu Thr Ile Tyr Ser Gly Arg Gly Gln Ser Leu Val
1 5 10 15

Glu Pro Leu Val Lys Gln Phe Glu Ala Glu Thr Gly Ile Arg Val Gln
20 25 30

Val Arg Tyr Ser Thr Asp Ala Gln Ile Leu Ala Ala Leu Gln Glu Glu
35 40 45

Gly Ser Arg Ser Pro Ala Asp Leu Phe Trp Ala Asn Thr Ala Gly Ala
50 55 60

Leu Gly Gln Ala Ser Ala Lys Gly Leu Leu Arg Pro Leu Gly Glu Thr
65 70 75 80

Leu Leu Glu Lys Pro Ile Ala Phe Val Pro Ala Ser Arg Thr Trp Val
85 90 95

Pro Val Thr Val Arg Leu Arg Val Leu Ala Tyr Asn Pro Asp Arg Ile
100 105 110

Lys Ala Glu Glu Leu Pro Glu Ser Leu Leu Asp Leu Pro Arg Phe Ala
115 120 125

Arg Glu Lys Gly Leu Val Gly Arg Val Gly Trp Thr Pro Thr Tyr Ser
130 135 140

Ser Phe Gln Asp Met Val Ala Gly Met Ile Ala Leu Tyr Gly Glu Glu
145 150 155 160

Lys Thr Arg Glu Trp Leu Leu Ala Met Lys Ala Leu Ala Pro Lys Ala
165 170 175

Tyr Pro Ser Asn Pro Ala Met Leu Asp Ala Ile Arg Ala Gly Glu Val
180 185 190

Asp Leu Gly Ser Thr Asn His Tyr Tyr Val Val Arg Phe Arg Arg Ala
195 200 205

Gly Tyr Arg Leu Gly Met His His Phe Arg Asp Gly Asp Ala Gly Asn
210 215 220

Leu Ala Leu Val Thr Gly Ala Gly Leu Leu Lys Thr Ser Lys Asn Leu
225 230 235 240

Ala Ala Ala Thr Arg Phe Leu Thr Tyr Leu Leu Ser Pro Gln Ala Gln
245 250 255

Gln Tyr Phe Val Gly Asn Ile Gly Glu Tyr Pro Leu Val Lys Gly Val
260 265 270

Ala Leu Asp Pro Asn Leu Leu Pro Leu Glu Glu Ala Leu Ala Lys Ser
275 280 285

Pro Lys Leu Asp Leu Glu Lys Leu Pro Leu Asp Arg Ala Leu Arg Leu
290 295 300

Leu Arg Glu Thr Gly Val Leu Gly Gly Ser His His His His His His
305 310 315 320

<210> SEQ ID NO 26
<211> LENGTH: 341
<212> TYPE: PRT
<213> ORGANISM: Artificial Sequence
<220> FEATURE:
<223> OTHER INFORMATION: msFeBP6 (with signal peptide replaced with M
and a GGSHHHHHH at C-terminus)

<400> SEQUENCE: 26

Met Ser Leu Thr Leu Tyr Thr Gly Arg Ser Gln Ala Leu Val Asp Lys
1 5 10 15

Leu Val Gln Gln Phe Gln Lys Asp Thr Gly Ile Lys Val Asn Val Arg

```
            20                  25                  30

Tyr Gly Arg Asp Ala Glu Ile Leu Ala Ala Leu Gln Glu Glu Gly Ser
        35                  40                  45

Arg Ser Pro Ala Asp Val Phe Trp Ala Asn Thr Ser Gly Ala Leu Glu
    50                  55                  60

Glu Ala Val Lys Arg Asn Leu Leu Val Gln Leu Pro Ala Ser Leu Thr
65                  70                  75                  80

Arg Gln Pro Gln Glu Phe Val Pro Ser His Gly Arg Trp Val Pro Val
                85                  90                  95

Ser Val Arg Phe Arg Val Ala Ala Tyr Asn Pro Thr Lys Val Lys Asp
            100                 105                 110

Ser Asp Phe Pro Ala Ser Val Met Asp Leu Pro Lys Val Ala Lys Phe
        115                 120                 125

Lys Gly Arg Ile Gly Trp Thr Pro Thr Tyr Ser Ser Phe Gln Asp Phe
    130                 135                 140

Ile Thr Ala Met Arg Val Val Lys Gly Glu Ala Ala Thr Lys Ala Trp
145                 150                 155                 160

Leu Gln Ala Met Ile Ala Ala Gly Ala Lys Ala Tyr Pro Ser Asn Pro
                165                 170                 175

Pro Met Leu Glu Ala Met Gln Ala Gly Glu Ile Asp Val Ala Leu Thr
            180                 185                 190

Asn His Tyr Tyr Ile Gln Arg Ile Leu Ala Gly Val Gly Glu Gly Glu
        195                 200                 205

Tyr Glu Gly Lys Glu Glu Ser Glu Glu Glu Glu Lys Lys Glu Leu Ala
    210                 215                 220

Ala Arg Glu Ala Lys Ala Gly Val Ala Thr His Tyr Phe Ala Pro Gly
225                 230                 235                 240

Asp Val Gly Gly Leu Ala Leu Val Thr Gly Ala Gly Ile Leu Ala Thr
                245                 250                 255

Ser Lys His Gln Thr Asn Ala Thr Arg Phe Leu Asn Tyr Leu Leu Ser
            260                 265                 270

Lys Lys Ala Gln Pro Tyr Phe Val Asp Glu Val Arg Glu Tyr Pro Val
        275                 280                 285

Ile Ala Gly Val Arg Val Ala Lys Gly Met Leu Pro Phe Ala Asn Ala
    290                 295                 300

Ile Arg Leu Ser Pro Lys Ile Asp Phe Ala Lys Leu Thr Asp Leu Glu
305                 310                 315                 320

Gly Thr Leu Lys Leu Leu Arg Glu Val Gly Leu Leu Gly Gly Ser His
                325                 330                 335

His His His His His
            340


<210> SEQ ID NO 27
<211> LENGTH: 343
<212> TYPE: PRT
<213> ORGANISM: Artificial Sequence
<220> FEATURE:
<223> OTHER INFORMATION: srFeBP7 (with signal peptide replaced with M
      and a GGSHHHHHH at C-terminus)

<400> SEQUENCE: 27

Met Leu Val Ile Tyr Ser Gly Arg Ser Lys Ala Leu Val Asp Ser Leu
1               5                   10                  15

Val Gln Gln Tyr Arg Gln Gln Ala Asp Val Pro Val Arg Val Arg Tyr
            20                  25                  30
```

```
Gly Thr Asp Ser Gln Leu Leu Ala Ala Leu Gln Glu Glu Gly Asp Gln
        35                  40                  45

Ser Pro Ala Asp Val Phe Trp Ala Asn Thr Thr Gly Ala Leu Gly Asn
    50                  55                  60

Ala Val Asn Asn Gly Leu Leu Thr Glu Leu Pro Asp Thr Leu Ala Asn
65                  70                  75                  80

Arg Ala Ala Arg Phe Thr Pro Ser Asn Gln Arg Trp Thr Pro Val Thr
                85                  90                  95

Thr Arg Phe Arg Val Leu Ala Tyr Asn Ser Asp Ala Val Ser Pro Glu
            100                 105                 110

Asp Leu Pro Asp Ser Val Leu Asp Leu Pro Glu His Glu Glu Phe Glu
        115                 120                 125

Gly Arg Val Gly Trp Thr Pro Ala Tyr Ser Ser Phe Gln Asp Phe Val
    130                 135                 140

Thr Ala Leu Arg Val Thr Glu Gly Ala Glu Thr Ala Arg Thr Trp Leu
145                 150                 155                 160

Ser Asp Met Gln Ala Leu Asn Pro Asn Ser Tyr Thr Ser Asn Thr Pro
                165                 170                 175

Met Val Gln Ala Leu Glu Ala Gly Glu Ile Asp Val Ala Leu Thr Asn
            180                 185                 190

His Tyr Tyr Val Leu Arg Leu Lys His Gly Gly Ala Glu Gly Glu Tyr
        195                 200                 205

Glu Gly Glu Glu Glu Glu Gly Glu Glu His Glu Glu Glu His Glu Glu
    210                 215                 220

Glu Ala Thr Pro Arg Ala Ser Ala Pro Val Glu Met Tyr His Phe Ala
225                 230                 235                 240

Asp Gly Asp Leu Gly Asn Leu Ala Leu Val Thr Gly Ala Gly Ala Leu
                245                 250                 255

Gln Thr Ser Asn Gln Pro Asp Ala Ala Asn Arg Phe Leu Arg Phe Leu
            260                 265                 270

Leu Ser Glu Gln Ala Gln Ser Phe Ala Ala Thr Arg Val Asn Glu Tyr
        275                 280                 285

Pro Val Val Ser Gly Ala Ser Val Pro Asp Tyr Leu Met Pro Ala Asp
    290                 295                 300

Glu Ala Leu Lys Met Ser Pro Glu Phe Asp Leu Gln Lys Leu Gln Asn
305                 310                 315                 320

Met Glu Pro Thr Leu Asp Leu Leu Arg Asp Ala Gly Ala Leu Gly Gly
                325                 330                 335

Ser His His His His His His
            340
```

<210> SEQ ID NO 28
<211> LENGTH: 313
<212> TYPE: PRT
<213> ORGANISM: Artificial Sequence
<220> FEATURE:
<223> OTHER INFORMATION: hlFeBP8 (with C138A and C176A substitution mutations, the signal peptide replaced with M, and a GGSHHHHHH at C-terminus)

<400> SEQUENCE: 28

```
Met Leu Thr Val Tyr Ser Gly Arg Gly Glu Phe Leu Val Gly Glu Leu
1               5                   10                  15

Val Glu Tyr Ile Glu Asp Gln Tyr Asp Asp Phe Asp Leu Thr Val Arg
            20                  25                  30

Tyr Ala Gly Ser Thr Asp Leu Val Asn Gln Ile Leu Asn Glu Gly Asp
```

35 40 45

Gly Ser Pro Ala Asp Val Phe Tyr Ser Val Asn Ala Gly Ser Leu Gly
50 55 60

Thr Leu Ala Gly Glu Gly Arg Ser Gln Ala Leu Ser Ser Glu Ile Thr
65 70 75 80

Asp Met Val Arg Ser Glu Phe Arg Thr Glu Gln Trp Ile Gly Thr Ser
85 90 95

Gly Arg Ala Arg Thr Val Pro Tyr Asn Thr Gly Glu Phe Ser Asp Asp
100 105 110

Asp Leu Pro Asp Asp Ile Met Ala Tyr Pro Glu Glu Phe Ala Gly Ser
115 120 125

Leu Gly Trp Ala Pro Ser Tyr Gly Ser Ala Gln Ala Phe Ile Thr Ala
130 135 140

Met Arg Leu Ile Glu Gly Glu Glu Ala Thr Leu Ala Trp Leu Glu Ser
145 150 155 160

Val Val Glu Ala Gly Ile Ser Ser Tyr Pro Asp Glu Phe Ala Ala Ala
165 170 175

Gln Ala Ile Ala Asp Gly Glu Ile Asp Ala Ala Phe Thr Asn His Tyr
180 185 190

Tyr Ile Gln Arg Val Leu Asp Gly Asn Pro Asp Ala Ser Ile Gly Thr
195 200 205

Ala Phe Thr Ser Gly Asp Ala Gly Ala Val Phe Asn Val Ala Gly Ala
210 215 220

Ala Val Val Asp Thr Ala Ser Asp Ala Thr Leu Ala Glu Asn Phe Ile
225 230 235 240

Arg His Leu Leu Ser Ala Glu Ala Gln Asp Tyr Phe Ala Arg Ser Thr
245 250 255

Phe Glu Tyr Pro Leu Ile Pro Asp Val Glu Pro Ile Gly Asp Leu Pro
260 265 270

Thr Ile Asp Glu Leu Asp Val Pro Asp Ile Asp Leu Thr Glu Leu Ser
275 280 285

Asp Leu Glu Pro Thr Ile Asp Leu Met Arg Glu Ala Gly Val Glu Val
290 295 300

Gly Gly Ser His His His His His His
305 310

<210> SEQ ID NO 29
<211> LENGTH: 415
<212> TYPE: PRT
<213> ORGANISM: Artificial Sequence
<220> FEATURE:
<223> OTHER INFORMATION: avBicarBP5_16C (with I16C and C96A substitution mutations, signal peptide replaced with M, and a GGSHHHHHH at C-terminus)

<400> SEQUENCE: 29

Met Ala Glu Gln Ala Pro Glu Val Thr Thr Val Lys Leu Gly Tyr Cys
1 5 10 15

Pro Ile Val Glu Ser Ala Pro Leu Ile Ile Ala Lys Glu Lys Gly Phe
20 25 30

Phe Ala Lys Tyr Gly Leu Thr Asn Val Glu Leu Ser Lys Gln Ala Ser
35 40 45

Trp Gly Ser Ala Arg Asp Asn Val Glu Ile Gly Ser Ala Gly Gly Gly
50 55 60

Ile Asp Gly Gly Gln Trp Gln Met Pro Met Pro His Leu Ile Thr Glu
65 70 75 80

Gly Leu Ile Thr Lys Gly Asn Gln Lys Ile Pro Met Tyr Val Leu Ala
85 90 95

Gln Leu Ile Thr His Gly Asn Gly Ile Ala Ile Ala Asn Lys His Gln
100 105 110

Gly Lys Gly Ile Ser Leu Lys Leu Glu Gly Ala Lys Ser Leu Phe Ser
115 120 125

Gln Leu Lys Ser Ser Thr Pro Phe Thr Ala Ala Phe Thr Phe Pro His
130 135 140

Val Asn Gln Asp Leu Trp Ile Arg Tyr Trp Leu Ala Ala Gly Gly Ile
145 150 155 160

Asp Pro Asp Ala Asp Val Lys Leu Leu Thr Val Pro Ala Ala Gln Thr
165 170 175

Val Ala Asn Met Lys Thr Gly Thr Met Asp Ala Phe Ser Thr Gly Asp
180 185 190

Pro Trp Pro Phe Arg Leu Val Asn Asp Lys Ile Gly Tyr Met Ala Ala
195 200 205

Leu Thr Ala Glu Ile Trp Lys Asn His Pro Glu Glu Tyr Leu Ala Met
210 215 220

Arg Ala Asp Trp Val Asp Lys Tyr Pro Lys Ala Thr Lys Ala Leu Leu
225 230 235 240

Lys Gly Ile Met Glu Ala Gln Gln Trp Leu Asp Asn Phe Asp Asn Arg
245 250 255

Lys Glu Ala Ala Gln Ile Leu Ala Gly Arg Asn Tyr Phe Asn Leu Asn
260 265 270

Asn Pro Glu Ile Leu Ala Asp Pro Tyr Val Gly Lys Tyr Asp Met Gly
275 280 285

Asp Gly Arg Lys Ile Asp Asp Lys Ser Met Ala Ala Tyr Tyr Trp Lys
290 295 300

Asp Glu Lys Gly Ser Val Ser Tyr Pro Tyr Lys Ser His Asp Leu Trp
305 310 315 320

Phe Ile Thr Glu Asn Val Arg Trp Gly Phe Leu Pro Lys Asp Tyr Leu
325 330 335

Ala Asn Gly Ala Ala Lys Ala Lys Glu Leu Ile Asp Lys Val Asn Arg
340 345 350

Glu Asp Ile Trp Lys Glu Ala Ala Lys Glu Ala Gly Ile Ala Ala Ala
355 360 365

Asp Ile Pro Thr Ser Thr Ser Arg Gly Val Glu Glu Phe Phe Asp Gly
370 375 380

Thr Lys Phe Asp Pro Glu Lys Pro Asp Glu Tyr Leu Lys Ser Leu Lys
385 390 395 400

Ile Lys Lys Val Ser Val Gly Gly Ser His His His His His His
405 410 415

<210> SEQ ID NO 30
<211> LENGTH: 415
<212> TYPE: PRT
<213> ORGANISM: Artificial Sequence
<220> FEATURE:
<223> OTHER INFORMATION: avBicarBP5_17C (with P17C and C96A substitution mutations, signal peptide replaced with M, and a GGSHHHHHH at C-terminus)

<400> SEQUENCE: 30

Met Ala Glu Gln Ala Pro Glu Val Thr Thr Val Lys Leu Gly Tyr Ile
1 5 10 15

```
Cys Ile Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser His His His His His His
                405                 410                 415
```

<210> SEQ ID NO 31
<211> LENGTH: 415
<212> TYPE: PRT

<213> ORGANISM: Artificial Sequence
<220> FEATURE:
<223> OTHER INFORMATION: avBicarBP5_18C (with I18C and C96A substitution mutations, signal peptide replaced with M, and a GGSHHHHHH at C-terminus)

<400> SEQUENCE: 31

```
Met Ala Glu Gln Ala Pro Glu Val Thr Thr Val Lys Leu Gly Tyr Ile
1               5                   10                  15

Pro Cys Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380
```

Thr Lys Phe Asp Pro Glu Lys Pro Asp Glu Tyr Leu Lys Ser Leu Lys
385 390 395 400

Ile Lys Lys Val Ser Val Gly Gly Ser His His His His His His
405 410 415

<210> SEQ ID NO 32
<211> LENGTH: 415
<212> TYPE: PRT
<213> ORGANISM: Artificial Sequence
<220> FEATURE:
<223> OTHER INFORMATION: avBicarBP5_49C (with W49C and C96A substitution mutations, signal peptide replaced with M, and a GGSHHHHHH at C-terminus)

<400> SEQUENCE: 32

Met Ala Glu Gln Ala Pro Glu Val Thr Thr Val Lys Leu Gly Tyr Ile
1 5 10 15

Pro Ile Val Glu Ser Ala Pro Leu Ile Ile Ala Lys Glu Lys Gly Phe
20 25 30

Phe Ala Lys Tyr Gly Leu Thr Asn Val Glu Leu Ser Lys Gln Ala Ser
35 40 45

Cys Gly Ser Ala Arg Asp Asn Val Glu Ile Gly Ser Ala Gly Gly Gly
50 55 60

Ile Asp Gly Gly Gln Trp Gln Met Pro Met Pro His Leu Ile Thr Glu
65 70 75 80

Gly Leu Ile Thr Lys Gly Asn Gln Lys Ile Pro Met Tyr Val Leu Ala
85 90 95

Gln Leu Ile Thr His Gly Asn Gly Ile Ala Ile Ala Asn Lys His Gln
100 105 110

Gly Lys Gly Ile Ser Leu Lys Leu Glu Gly Ala Lys Ser Leu Phe Ser
115 120 125

Gln Leu Lys Ser Ser Thr Pro Phe Thr Ala Ala Phe Thr Phe Pro His
130 135 140

Val Asn Gln Asp Leu Trp Ile Arg Tyr Trp Leu Ala Ala Gly Gly Ile
145 150 155 160

Asp Pro Asp Ala Asp Val Lys Leu Leu Thr Val Pro Ala Ala Gln Thr
165 170 175

Val Ala Asn Met Lys Thr Gly Thr Met Asp Ala Phe Ser Thr Gly Asp
180 185 190

Pro Trp Pro Phe Arg Leu Val Asn Asp Lys Ile Gly Tyr Met Ala Ala
195 200 205

Leu Thr Ala Glu Ile Trp Lys Asn His Pro Glu Glu Tyr Leu Ala Met
210 215 220

Arg Ala Asp Trp Val Asp Lys Tyr Pro Lys Ala Thr Lys Ala Leu Leu
225 230 235 240

Lys Gly Ile Met Glu Ala Gln Gln Trp Leu Asp Asn Phe Asp Asn Arg
245 250 255

Lys Glu Ala Ala Gln Ile Leu Ala Gly Arg Asn Tyr Phe Asn Leu Asn
260 265 270

Asn Pro Glu Ile Leu Ala Asp Pro Tyr Val Gly Lys Tyr Asp Met Gly
275 280 285

Asp Gly Arg Lys Ile Asp Asp Lys Ser Met Ala Ala Tyr Tyr Trp Lys
290 295 300

Asp Glu Lys Gly Ser Val Ser Tyr Pro Tyr Lys Ser His Asp Leu Trp
305 310 315 320

```
Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser His His His His His His
                405                 410                 415


<210> SEQ ID NO 33
<211> LENGTH: 415
<212> TYPE: PRT
<213> ORGANISM: Artificial Sequence
<220> FEATURE:
<223> OTHER INFORMATION: avBicarBP5_71C (with Q71C and C96A substitution
      mutations, signal peptide replaced with M, and a GGSHHHHHH at
      C-terminus)

<400> SEQUENCE: 33

Met Ala Glu Gln Ala Pro Glu Val Thr Thr Val Lys Leu Gly Tyr Ile
1               5                   10                  15

Pro Ile Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Cys Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
```

```
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser His His His His His His
                405                 410                 415


<210> SEQ ID NO 34
<211> LENGTH: 415
<212> TYPE: PRT
<213> ORGANISM: Artificial Sequence
<220> FEATURE:
<223> OTHER INFORMATION: avBicarBP5_140C (with F140C and C96A
      substitution mutations, signal peptide replaced with M, and a
      GGSHHHHHH at C-terminus)

<400> SEQUENCE: 34

Met Ala Glu Gln Ala Pro Glu Val Thr Thr Val Lys Leu Gly Tyr Ile
1               5                   10                  15

Pro Ile Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Cys Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205
```

```
Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser His His His His His His
                405                 410                 415
```

<210> SEQ ID NO 35
<211> LENGTH: 415
<212> TYPE: PRT
<213> ORGANISM: Artificial Sequence
<220> FEATURE:
<223> OTHER INFORMATION: avBicarBP5_141C (with T141C and C96A substitution mutations, signal peptide replaced with M, and a GGSHHHHHH at C-terminus)

<400> SEQUENCE: 35

```
Met Ala Glu Gln Ala Pro Glu Val Thr Thr Val Lys Leu Gly Tyr Ile
1               5                   10                  15

Pro Ile Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Cys Phe Pro His
    130                 135                 140
```

```
Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser His His His His His His
                405                 410                 415


<210> SEQ ID NO 36
<211> LENGTH: 415
<212> TYPE: PRT
<213> ORGANISM: Artificial Sequence
<220> FEATURE:
<223> OTHER INFORMATION: avBicarBP5_142C (with F142C and C96A
      substitution mutations, signal peptide replaced with M, and a
      GGSHHHHHH at C-terminus)

<400> SEQUENCE: 36

Met Ala Glu Gln Ala Pro Glu Val Thr Thr Val Lys Leu Gly Tyr Ile
1               5                   10                  15

Pro Ile Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
```

```
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Cys Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser His His His His His His
                405                 410                 415
```

```
<210> SEQ ID NO 37
<211> LENGTH: 415
<212> TYPE: PRT
<213> ORGANISM: Artificial Sequence
<220> FEATURE:
<223> OTHER INFORMATION: avBicarBP5_143C (with P143C and C96A
      substitution mutations, signal peptide replaced with M, and a
      GGSHHHHHH at C-terminus)

<400> SEQUENCE: 37

Met Ala Glu Gln Ala Pro Glu Val Thr Thr Val Lys Leu Gly Tyr Ile
1               5                   10                  15

Pro Ile Val Glu Ser Ala Pro Leu Ile Ile Ala Lys Glu Lys Gly Phe
            20                  25                  30
```

```
Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Cys His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser His His His His His His
                405                 410                 415
```

<210> SEQ ID NO 38
<211> LENGTH: 415
<212> TYPE: PRT
<213> ORGANISM: Artificial Sequence
<220> FEATURE:

<223> OTHER INFORMATION: avBicarBP5_146C (with N146C and C96A substitution mutations, signal peptide replaced with M, and a GGSHHHHHH at C-terminus)

<400> SEQUENCE: 38

```
Met Ala Glu Gln Ala Pro Glu Val Thr Thr Val Lys Leu Gly Tyr Ile
1               5                   10                  15

Pro Ile Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Cys Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
```

385 390 395 400

Ile Lys Lys Val Ser Val Gly Gly Ser His His His His His His
405 410 415

<210> SEQ ID NO 39
<211> LENGTH: 415
<212> TYPE: PRT
<213> ORGANISM: Artificial Sequence
<220> FEATURE:
<223> OTHER INFORMATION: avBicarBP5_190C (with T190C and C96A substitution mutations, signal peptide replaced with M, and a GGSHHHHHH at C-terminus)

<400> SEQUENCE: 39

Met Ala Glu Gln Ala Pro Glu Val Thr Thr Val Lys Leu Gly Tyr Ile
1 5 10 15

Pro Ile Val Glu Ser Ala Pro Leu Ile Ile Ala Lys Glu Lys Gly Phe
20 25 30

Phe Ala Lys Tyr Gly Leu Thr Asn Val Glu Leu Ser Lys Gln Ala Ser
35 40 45

Trp Gly Ser Ala Arg Asp Asn Val Glu Ile Gly Ser Ala Gly Gly Gly
50 55 60

Ile Asp Gly Gly Gln Trp Gln Met Pro Met Pro His Leu Ile Thr Glu
65 70 75 80

Gly Leu Ile Thr Lys Gly Asn Gln Lys Ile Pro Met Tyr Val Leu Ala
85 90 95

Gln Leu Ile Thr His Gly Asn Gly Ile Ala Ile Ala Asn Lys His Gln
100 105 110

Gly Lys Gly Ile Ser Leu Lys Leu Glu Gly Ala Lys Ser Leu Phe Ser
115 120 125

Gln Leu Lys Ser Ser Thr Pro Phe Thr Ala Ala Phe Thr Phe Pro His
130 135 140

Val Asn Gln Asp Leu Trp Ile Arg Tyr Trp Leu Ala Ala Gly Gly Ile
145 150 155 160

Asp Pro Asp Ala Asp Val Lys Leu Leu Thr Val Pro Ala Ala Gln Thr
165 170 175

Val Ala Asn Met Lys Thr Gly Thr Met Asp Ala Phe Ser Cys Gly Asp
180 185 190

Pro Trp Pro Phe Arg Leu Val Asn Asp Lys Ile Gly Tyr Met Ala Ala
195 200 205

Leu Thr Ala Glu Ile Trp Lys Asn His Pro Glu Glu Tyr Leu Ala Met
210 215 220

Arg Ala Asp Trp Val Asp Lys Tyr Pro Lys Ala Thr Lys Ala Leu Leu
225 230 235 240

Lys Gly Ile Met Glu Ala Gln Gln Trp Leu Asp Asn Phe Asp Asn Arg
245 250 255

Lys Glu Ala Ala Gln Ile Leu Ala Gly Arg Asn Tyr Phe Asn Leu Asn
260 265 270

Asn Pro Glu Ile Leu Ala Asp Pro Tyr Val Gly Lys Tyr Asp Met Gly
275 280 285

Asp Gly Arg Lys Ile Asp Asp Lys Ser Met Ala Ala Tyr Tyr Trp Lys
290 295 300

Asp Glu Lys Gly Ser Val Ser Tyr Pro Tyr Lys Ser His Asp Leu Trp
305 310 315 320

Phe Ile Thr Glu Asn Val Arg Trp Gly Phe Leu Pro Lys Asp Tyr Leu
325 330 335

```
Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser His His His His His His
                405                 410                 415


<210> SEQ ID NO 40
<211> LENGTH: 415
<212> TYPE: PRT
<213> ORGANISM: Artificial Sequence
<220> FEATURE:
<223> OTHER INFORMATION: avBicarBP5_194C (with W194C and C96A
      substitution mutations, signal peptide replaced with M, and a
      GGSHHHHHH at C-terminus)

<400> SEQUENCE: 40

Met Ala Glu Gln Ala Pro Glu Val Thr Thr Val Lys Leu Gly Tyr Ile
1               5                   10                  15

Pro Ile Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Cys Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270
```

```
Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser His His His His His His
                405                 410                 415


<210> SEQ ID NO 41
<211> LENGTH: 325
<212> TYPE: PRT
<213> ORGANISM: Artificial Sequence
<220> FEATURE:
<223> OTHER INFORMATION: teFeBP3_A8C (with A8C and C184S substitution
      mutations, the signal peptide replaced with M, and a GGSHHHHHH at
      C-terminus)

<400> SEQUENCE: 41

Met Val Ile Asn Val Tyr Ser Cys Arg His Tyr Asp Thr Asp Lys Ala
1               5                   10                  15

Leu Tyr Asn Thr Phe Thr Gln Gln Thr Gly Ile Arg Val Asn Ile Ile
            20                  25                  30

Glu Ala Glu Ala Asp Ala Leu Ile Glu Arg Ile Arg Ser Glu Gly Ser
        35                  40                  45

Arg Thr Pro Ala Asp Val Leu Ile Thr Val Asp Ala Gly Arg Leu Trp
    50                  55                  60

Arg Ala Gln Glu Ala Gly Ile Leu Gln Pro Ile Gln Ser Arg Val Leu
65                  70                  75                  80

Asn Ser Val Val Pro Ala Asn Leu Arg Glu Pro Gln Gly His Trp Phe
                85                  90                  95

Gly Leu Ser Arg Arg Val Arg Val Leu Ile Tyr Asn Lys Ser Arg Val
            100                 105                 110

Asn Pro Ser Gln Leu Ser Thr Tyr Glu Asp Leu Ala Asn Pro Lys Trp
        115                 120                 125

Arg Arg Gln Ile Leu Thr Arg Ser Ser Ser Asn Ile Tyr Asn Gln Ser
    130                 135                 140

Leu Thr Gly Ser Leu Leu Ala Ile His Gly Ala Gln Lys Thr Glu Gln
145                 150                 155                 160

Trp Ala Arg Gly Leu Val Gln Asn Phe Ala Arg Pro Pro Glu Gly Asn
                165                 170                 175

Asp Thr Ala Gln Ile Arg Ala Ser Ala Glu Gly Val Gly Ser Val Ala
            180                 185                 190

Ile Ala Asn His Tyr Tyr Leu Ala Arg Leu Ile Ala Ser Asp Lys Glu
        195                 200                 205

Gln Asp Arg Ala Val Ala Ala Lys Val Gly Leu Phe Phe Pro Asn Gln
```

```
    210                 215                 220

Arg Asp Arg Gly Ala His Val Asn Ile Ser Gly Ala Gly Val Val Ala
225                 230                 235                 240

Gly Ala Pro Asn Arg Gln Gly Ala Ile Arg Phe Leu Glu Tyr Leu Val
                245                 250                 255

Ser Pro Lys Ala Gln Glu Met Phe Ala Met Ala Asn Phe Glu Tyr Pro
            260                 265                 270

Val Arg Ala Gly Val Pro Val His Pro Ile Val Lys Gln Phe Gly Asn
        275                 280                 285

Phe Arg Gly Gln Asn Val Asn Ala Ala Val Phe Gly Arg Asn Asn Ala
    290                 295                 300

Glu Ala Leu Arg Ile Met Asp Arg Ala Gly Trp Arg Gly Gly Ser His
305                 310                 315                 320

His His His His His
                325


<210> SEQ ID NO 42
<211> LENGTH: 325
<212> TYPE: PRT
<213> ORGANISM: Artificial Sequence
<220> FEATURE:
<223> OTHER INFORMATION: teFeBP3_H10C (with H10C and C184S substitution
      mutations, the signal peptide replaced with M, and a GGSHHHHHH at
      C-terminus)

<400> SEQUENCE: 42

Met Val Ile Asn Val Tyr Ser Ala Arg Cys Tyr Asp Thr Asp Lys Ala
1               5                   10                  15

Leu Tyr Asn Thr Phe Thr Gln Gln Thr Gly Ile Arg Val Asn Ile Ile
            20                  25                  30

Glu Ala Glu Ala Asp Ala Leu Ile Glu Arg Ile Arg Ser Glu Gly Ser
        35                  40                  45

Arg Thr Pro Ala Asp Val Leu Ile Thr Val Asp Ala Gly Arg Leu Trp
    50                  55                  60

Arg Ala Gln Glu Ala Gly Ile Leu Gln Pro Ile Gln Ser Arg Val Leu
65                  70                  75                  80

Asn Ser Val Val Pro Ala Asn Leu Arg Glu Pro Gln Gly His Trp Phe
                85                  90                  95

Gly Leu Ser Arg Arg Val Arg Val Leu Ile Tyr Asn Lys Ser Arg Val
            100                 105                 110

Asn Pro Ser Gln Leu Ser Thr Tyr Glu Asp Leu Ala Asn Pro Lys Trp
        115                 120                 125

Arg Arg Gln Ile Leu Thr Arg Ser Ser Ser Asn Ile Tyr Asn Gln Ser
    130                 135                 140

Leu Thr Gly Ser Leu Leu Ala Ile His Gly Ala Gln Lys Thr Glu Gln
145                 150                 155                 160

Trp Ala Arg Gly Leu Val Gln Asn Phe Ala Arg Pro Pro Glu Gly Asn
                165                 170                 175

Asp Thr Ala Gln Ile Arg Ala Ser Ala Glu Gly Val Gly Ser Val Ala
            180                 185                 190

Ile Ala Asn His Tyr Tyr Leu Ala Arg Leu Ile Ala Ser Asp Lys Glu
        195                 200                 205

Gln Asp Arg Ala Val Ala Ala Lys Val Gly Leu Phe Phe Pro Asn Gln
    210                 215                 220

Arg Asp Arg Gly Ala His Val Asn Ile Ser Gly Ala Gly Val Val Ala
225                 230                 235                 240
```

```
Gly Ala Pro Asn Arg Gln Gly Ala Ile Arg Phe Leu Glu Tyr Leu Val
                245                 250                 255

Ser Pro Lys Ala Gln Glu Met Phe Ala Met Ala Asn Phe Glu Tyr Pro
            260                 265                 270

Val Arg Ala Gly Val Pro Val His Pro Ile Val Lys Gln Phe Gly Asn
        275                 280                 285

Phe Arg Gly Gln Asn Val Asn Ala Ala Val Phe Gly Arg Asn Asn Ala
    290                 295                 300

Glu Ala Leu Arg Ile Met Asp Arg Ala Gly Trp Arg Gly Gly Ser His
305                 310                 315                 320

His His His His His
                325


<210> SEQ ID NO 43
<211> LENGTH: 325
<212> TYPE: PRT
<213> ORGANISM: Artificial Sequence
<220> FEATURE:
<223> OTHER INFORMATION: teFeBP3_D12C (with D12C and C184S substitution
      mutations, the signal peptide replaced with M, and a GGSHHHHHH at
      C-terminus)

<400> SEQUENCE: 43

Met Val Ile Asn Val Tyr Ser Ala Arg His Tyr Cys Thr Asp Lys Ala
1               5                   10                  15

Leu Tyr Asn Thr Phe Thr Gln Gln Thr Gly Ile Arg Val Asn Ile Ile
            20                  25                  30

Glu Ala Glu Ala Asp Ala Leu Ile Glu Arg Ile Arg Ser Glu Gly Ser
        35                  40                  45

Arg Thr Pro Ala Asp Val Leu Ile Thr Val Asp Ala Gly Arg Leu Trp
    50                  55                  60

Arg Ala Gln Glu Ala Gly Ile Leu Gln Pro Ile Gln Ser Arg Val Leu
65                  70                  75                  80

Asn Ser Val Val Pro Ala Asn Leu Arg Glu Pro Gln Gly His Trp Phe
                85                  90                  95

Gly Leu Ser Arg Arg Val Arg Val Leu Ile Tyr Asn Lys Ser Arg Val
            100                 105                 110

Asn Pro Ser Gln Leu Ser Thr Tyr Glu Asp Leu Ala Asn Pro Lys Trp
        115                 120                 125

Arg Arg Gln Ile Leu Thr Arg Ser Ser Ser Asn Ile Tyr Asn Gln Ser
    130                 135                 140

Leu Thr Gly Ser Leu Leu Ala Ile His Gly Ala Gln Lys Thr Glu Gln
145                 150                 155                 160

Trp Ala Arg Gly Leu Val Gln Asn Phe Ala Arg Pro Pro Glu Gly Asn
                165                 170                 175

Asp Thr Ala Gln Ile Arg Ala Ser Ala Glu Gly Val Gly Ser Val Ala
            180                 185                 190

Ile Ala Asn His Tyr Tyr Leu Ala Arg Leu Ile Ala Ser Asp Lys Glu
        195                 200                 205

Gln Asp Arg Ala Val Ala Ala Lys Val Gly Leu Phe Phe Pro Asn Gln
    210                 215                 220

Arg Asp Arg Gly Ala His Val Asn Ile Ser Gly Ala Gly Val Val Ala
225                 230                 235                 240

Gly Ala Pro Asn Arg Gln Gly Ala Ile Arg Phe Leu Glu Tyr Leu Val
                245                 250                 255
```

```
Ser Pro Lys Ala Gln Glu Met Phe Ala Met Ala Asn Phe Glu Tyr Pro
            260                 265                 270

Val Arg Ala Gly Val Pro Val His Pro Ile Val Lys Gln Phe Gly Asn
        275                 280                 285

Phe Arg Gly Gln Asn Val Asn Ala Ala Val Phe Gly Arg Asn Asn Ala
    290                 295                 300

Glu Ala Leu Arg Ile Met Asp Arg Ala Gly Trp Arg Gly Gly Ser His
305                 310                 315                 320

His His His His His
                325


<210> SEQ ID NO 44
<211> LENGTH: 325
<212> TYPE: PRT
<213> ORGANISM: Artificial Sequence
<220> FEATURE:
<223> OTHER INFORMATION: teFeBP3_T13C (with T13C and C184S substitution
      mutations, the signal peptide replaced with M, and a GGSHHHHHH at
      C-terminus)

<400> SEQUENCE: 44

Met Val Ile Asn Val Tyr Ser Ala Arg His Tyr Asp Cys Asp Lys Ala
1               5                   10                  15

Leu Tyr Asn Thr Phe Thr Gln Gln Thr Gly Ile Arg Val Asn Ile Ile
            20                  25                  30

Glu Ala Glu Ala Asp Ala Leu Ile Glu Arg Ile Arg Ser Glu Gly Ser
        35                  40                  45

Arg Thr Pro Ala Asp Val Leu Ile Thr Val Asp Ala Gly Arg Leu Trp
    50                  55                  60

Arg Ala Gln Glu Ala Gly Ile Leu Gln Pro Ile Gln Ser Arg Val Leu
65                  70                  75                  80

Asn Ser Val Val Pro Ala Asn Leu Arg Glu Pro Gln Gly His Trp Phe
                85                  90                  95

Gly Leu Ser Arg Arg Val Arg Val Leu Ile Tyr Asn Lys Ser Arg Val
            100                 105                 110

Asn Pro Ser Gln Leu Ser Thr Tyr Glu Asp Leu Ala Asn Pro Lys Trp
        115                 120                 125

Arg Arg Gln Ile Leu Thr Arg Ser Ser Ser Asn Ile Tyr Asn Gln Ser
    130                 135                 140

Leu Thr Gly Ser Leu Leu Ala Ile His Gly Ala Gln Lys Thr Glu Gln
145                 150                 155                 160

Trp Ala Arg Gly Leu Val Gln Asn Phe Ala Arg Pro Pro Glu Gly Asn
                165                 170                 175

Asp Thr Ala Gln Ile Arg Ala Ser Ala Glu Gly Val Gly Ser Val Ala
            180                 185                 190

Ile Ala Asn His Tyr Tyr Leu Ala Arg Leu Ile Ala Ser Asp Lys Glu
        195                 200                 205

Gln Asp Arg Ala Val Ala Ala Lys Val Gly Leu Phe Phe Pro Asn Gln
    210                 215                 220

Arg Asp Arg Gly Ala His Val Asn Ile Ser Gly Ala Gly Val Val Ala
225                 230                 235                 240

Gly Ala Pro Asn Arg Gln Gly Ala Ile Arg Phe Leu Glu Tyr Leu Val
                245                 250                 255

Ser Pro Lys Ala Gln Glu Met Phe Ala Met Ala Asn Phe Glu Tyr Pro
            260                 265                 270

Val Arg Ala Gly Val Pro Val His Pro Ile Val Lys Gln Phe Gly Asn
```

```
        275                 280                 285

Phe Arg Gly Gln Asn Val Asn Ala Ala Val Phe Gly Arg Asn Asn Ala
    290                 295                 300

Glu Ala Leu Arg Ile Met Asp Arg Ala Gly Trp Arg Gly Gly Ser His
305                 310                 315                 320

His His His His His
                325


<210> SEQ ID NO 45
<211> LENGTH: 325
<212> TYPE: PRT
<213> ORGANISM: Artificial Sequence
<220> FEATURE:
<223> OTHER INFORMATION: teFeBP3_A36C (with A36C and C184S substitution
      mutations, the signal peptide replaced with M, and a GGSHHHHHH at
      C-terminus)

<400> SEQUENCE: 45

Met Val Ile Asn Val Tyr Ser Ala Arg His Tyr Asp Thr Asp Lys Ala
1               5                   10                  15

Leu Tyr Asn Thr Phe Thr Gln Gln Thr Gly Ile Arg Val Asn Ile Ile
            20                  25                  30

Glu Ala Glu Cys Asp Ala Leu Ile Glu Arg Ile Arg Ser Glu Gly Ser
        35                  40                  45

Arg Thr Pro Ala Asp Val Leu Ile Thr Val Asp Ala Gly Arg Leu Trp
    50                  55                  60

Arg Ala Gln Glu Ala Gly Ile Leu Gln Pro Ile Gln Ser Arg Val Leu
65                  70                  75                  80

Asn Ser Val Val Pro Ala Asn Leu Arg Glu Pro Gln Gly His Trp Phe
                85                  90                  95

Gly Leu Ser Arg Arg Val Arg Val Leu Ile Tyr Asn Lys Ser Arg Val
            100                 105                 110

Asn Pro Ser Gln Leu Ser Thr Tyr Glu Asp Leu Ala Asn Pro Lys Trp
        115                 120                 125

Arg Arg Gln Ile Leu Thr Arg Ser Ser Ser Asn Ile Tyr Asn Gln Ser
    130                 135                 140

Leu Thr Gly Ser Leu Leu Ala Ile His Gly Ala Gln Lys Thr Glu Gln
145                 150                 155                 160

Trp Ala Arg Gly Leu Val Gln Asn Phe Ala Arg Pro Pro Glu Gly Asn
                165                 170                 175

Asp Thr Ala Gln Ile Arg Ala Ser Ala Glu Gly Val Gly Ser Val Ala
            180                 185                 190

Ile Ala Asn His Tyr Tyr Leu Ala Arg Leu Ile Ala Ser Asp Lys Glu
        195                 200                 205

Gln Asp Arg Ala Val Ala Ala Lys Val Gly Leu Phe Phe Pro Asn Gln
    210                 215                 220

Arg Asp Arg Gly Ala His Val Asn Ile Ser Gly Ala Gly Val Val Ala
225                 230                 235                 240

Gly Ala Pro Asn Arg Gln Gly Ala Ile Arg Phe Leu Glu Tyr Leu Val
                245                 250                 255

Ser Pro Lys Ala Gln Glu Met Phe Ala Met Ala Asn Phe Glu Tyr Pro
            260                 265                 270

Val Arg Ala Gly Val Pro Val His Pro Ile Val Lys Gln Phe Gly Asn
        275                 280                 285

Phe Arg Gly Gln Asn Val Asn Ala Ala Val Phe Gly Arg Asn Asn Ala
    290                 295                 300
```

```
Glu Ala Leu Arg Ile Met Asp Arg Ala Gly Trp Arg Gly Gly Ser His
305                 310                 315                 320

His His His His His
                325


<210> SEQ ID NO 46
<211> LENGTH: 325
<212> TYPE: PRT
<213> ORGANISM: Artificial Sequence
<220> FEATURE:
<223> OTHER INFORMATION: teFeBP3_V58C (with V58C and C184S substitution
      mutations, the signal peptide replaced with M, and a GGSHHHHHH at
      C-terminus)

<400> SEQUENCE: 46

Met Val Ile Asn Val Tyr Ser Ala Arg His Tyr Asp Thr Asp Lys Ala
1               5                   10                  15

Leu Tyr Asn Thr Phe Thr Gln Gln Thr Gly Ile Arg Val Asn Ile Ile
            20                  25                  30

Glu Ala Glu Ala Asp Ala Leu Ile Glu Arg Ile Arg Ser Glu Gly Ser
        35                  40                  45

Arg Thr Pro Ala Asp Val Leu Ile Thr Cys Asp Ala Gly Arg Leu Trp
    50                  55                  60

Arg Ala Gln Glu Ala Gly Ile Leu Gln Pro Ile Gln Ser Arg Val Leu
65                  70                  75                  80

Asn Ser Val Val Pro Ala Asn Leu Arg Glu Pro Gln Gly His Trp Phe
                85                  90                  95

Gly Leu Ser Arg Arg Val Arg Val Leu Ile Tyr Asn Lys Ser Arg Val
            100                 105                 110

Asn Pro Ser Gln Leu Ser Thr Tyr Glu Asp Leu Ala Asn Pro Lys Trp
        115                 120                 125

Arg Arg Gln Ile Leu Thr Arg Ser Ser Ser Asn Ile Tyr Asn Gln Ser
    130                 135                 140

Leu Thr Gly Ser Leu Leu Ala Ile His Gly Ala Gln Lys Thr Glu Gln
145                 150                 155                 160

Trp Ala Arg Gly Leu Val Gln Asn Phe Ala Arg Pro Pro Glu Gly Asn
                165                 170                 175

Asp Thr Ala Gln Ile Arg Ala Ser Ala Glu Gly Val Gly Ser Val Ala
            180                 185                 190

Ile Ala Asn His Tyr Tyr Leu Ala Arg Leu Ile Ala Ser Asp Lys Glu
        195                 200                 205

Gln Asp Arg Ala Val Ala Ala Lys Val Gly Leu Phe Phe Pro Asn Gln
    210                 215                 220

Arg Asp Arg Gly Ala His Val Asn Ile Ser Gly Ala Gly Val Val Ala
225                 230                 235                 240

Gly Ala Pro Asn Arg Gln Gly Ala Ile Arg Phe Leu Glu Tyr Leu Val
                245                 250                 255

Ser Pro Lys Ala Gln Glu Met Phe Ala Met Ala Asn Phe Glu Tyr Pro
            260                 265                 270

Val Arg Ala Gly Val Pro Val His Pro Ile Val Lys Gln Phe Gly Asn
        275                 280                 285

Phe Arg Gly Gln Asn Val Asn Ala Ala Val Phe Gly Arg Asn Asn Ala
    290                 295                 300

Glu Ala Leu Arg Ile Met Asp Arg Ala Gly Trp Arg Gly Gly Ser His
305                 310                 315                 320
```

His His His His His
325

<210> SEQ ID NO 47
<211> LENGTH: 325
<212> TYPE: PRT
<213> ORGANISM: Artificial Sequence
<220> FEATURE:
<223> OTHER INFORMATION: teFeBP3_R135C (with R135C and C184S substitution mutations, the signal peptide replaced with M, and a GGSHHHHHH at C-terminus)

<400> SEQUENCE: 47

```
Met Val Ile Asn Val Tyr Ser Ala Arg His Tyr Asp Thr Asp Lys Ala
1               5                   10                  15

Leu Tyr Asn Thr Phe Thr Gln Gln Thr Gly Ile Arg Val Asn Ile Ile
            20                  25                  30

Glu Ala Glu Ala Asp Ala Leu Ile Glu Arg Ile Arg Ser Glu Gly Ser
        35                  40                  45

Arg Thr Pro Ala Asp Val Leu Ile Thr Val Asp Ala Gly Arg Leu Trp
    50                  55                  60

Arg Ala Gln Glu Ala Gly Ile Leu Gln Pro Ile Gln Ser Arg Val Leu
65                  70                  75                  80

Asn Ser Val Val Pro Ala Asn Leu Arg Glu Pro Gln Gly His Trp Phe
                85                  90                  95

Gly Leu Ser Arg Arg Val Arg Val Leu Ile Tyr Asn Lys Ser Arg Val
            100                 105                 110

Asn Pro Ser Gln Leu Ser Thr Tyr Glu Asp Leu Ala Asn Pro Lys Trp
        115                 120                 125

Arg Arg Gln Ile Leu Thr Cys Ser Ser Ser Asn Ile Tyr Asn Gln Ser
    130                 135                 140

Leu Thr Gly Ser Leu Leu Ala Ile His Gly Ala Gln Lys Thr Glu Gln
145                 150                 155                 160

Trp Ala Arg Gly Leu Val Gln Asn Phe Ala Arg Pro Pro Glu Gly Asn
                165                 170                 175

Asp Thr Ala Gln Ile Arg Ala Ser Ala Glu Gly Val Gly Ser Val Ala
            180                 185                 190

Ile Ala Asn His Tyr Tyr Leu Ala Arg Leu Ile Ala Ser Asp Lys Glu
        195                 200                 205

Gln Asp Arg Ala Val Ala Ala Lys Val Gly Leu Phe Phe Pro Asn Gln
    210                 215                 220

Arg Asp Arg Gly Ala His Val Asn Ile Ser Gly Ala Gly Val Val Ala
225                 230                 235                 240

Gly Ala Pro Asn Arg Gln Gly Ala Ile Arg Phe Leu Glu Tyr Leu Val
                245                 250                 255

Ser Pro Lys Ala Gln Glu Met Phe Ala Met Ala Asn Phe Glu Tyr Pro
            260                 265                 270

Val Arg Ala Gly Val Pro Val His Pro Ile Val Lys Gln Phe Gly Asn
        275                 280                 285

Phe Arg Gly Gln Asn Val Asn Ala Ala Val Phe Gly Arg Asn Asn Ala
    290                 295                 300

Glu Ala Leu Arg Ile Met Asp Arg Ala Gly Trp Arg Gly Gly Ser His
305                 310                 315                 320

His His His His His
                325
```

<210> SEQ ID NO 48
<211> LENGTH: 325
<212> TYPE: PRT
<213> ORGANISM: Artificial Sequence
<220> FEATURE:
<223> OTHER INFORMATION: teFeBP3_N139C (with N139C and C184S substitution mutations, the signal peptide replaced with M, and a GGSHHHHHH at C-terminus)

<400> SEQUENCE: 48

```
Met Val Ile Asn Val Tyr Ser Ala Arg His Tyr Asp Thr Asp Lys Ala
1               5                   10                  15

Leu Tyr Asn Thr Phe Thr Gln Gln Thr Gly Ile Arg Val Asn Ile Ile
            20                  25                  30

Glu Ala Glu Ala Asp Ala Leu Ile Glu Arg Ile Arg Ser Glu Gly Ser
        35                  40                  45

Arg Thr Pro Ala Asp Val Leu Ile Thr Val Asp Ala Gly Arg Leu Trp
    50                  55                  60

Arg Ala Gln Glu Ala Gly Ile Leu Gln Pro Ile Gln Ser Arg Val Leu
65                  70                  75                  80

Asn Ser Val Val Pro Ala Asn Leu Arg Glu Pro Gln Gly His Trp Phe
                85                  90                  95

Gly Leu Ser Arg Arg Val Arg Val Leu Ile Tyr Asn Lys Ser Arg Val
            100                 105                 110

Asn Pro Ser Gln Leu Ser Thr Tyr Glu Asp Leu Ala Asn Pro Lys Trp
        115                 120                 125

Arg Arg Gln Ile Leu Thr Arg Ser Ser Ser Cys Ile Tyr Asn Gln Ser
    130                 135                 140

Leu Thr Gly Ser Leu Leu Ala Ile His Gly Ala Gln Lys Thr Glu Gln
145                 150                 155                 160

Trp Ala Arg Gly Leu Val Gln Asn Phe Ala Arg Pro Pro Glu Gly Asn
                165                 170                 175

Asp Thr Ala Gln Ile Arg Ala Ser Ala Glu Gly Val Gly Ser Val Ala
            180                 185                 190

Ile Ala Asn His Tyr Tyr Leu Ala Arg Leu Ile Ala Ser Asp Lys Glu
        195                 200                 205

Gln Asp Arg Ala Val Ala Ala Lys Val Gly Leu Phe Phe Pro Asn Gln
    210                 215                 220

Arg Asp Arg Gly Ala His Val Asn Ile Ser Gly Ala Gly Val Val Ala
225                 230                 235                 240

Gly Ala Pro Asn Arg Gln Gly Ala Ile Arg Phe Leu Glu Tyr Leu Val
                245                 250                 255

Ser Pro Lys Ala Gln Glu Met Phe Ala Met Ala Asn Phe Glu Tyr Pro
            260                 265                 270

Val Arg Ala Gly Val Pro Val His Pro Ile Val Lys Gln Phe Gly Asn
        275                 280                 285

Phe Arg Gly Gln Asn Val Asn Ala Ala Val Phe Gly Arg Asn Asn Ala
    290                 295                 300

Glu Ala Leu Arg Ile Met Asp Arg Ala Gly Trp Arg Gly Gly Ser His
305                 310                 315                 320

His His His His His
                325
```

<210> SEQ ID NO 49
<211> LENGTH: 325
<212> TYPE: PRT
<213> ORGANISM: Artificial Sequence
<220> FEATURE:
<223> OTHER INFORMATION: teFeBP3_I140C (with I140C and C184S substitution mutations, the signal peptide replaced with M, and a GGSHHHHHH at C-terminus)

<400> SEQUENCE: 49

```
Met Val Ile Asn Val Tyr Ser Ala Arg His Tyr Asp Thr Asp Lys Ala
1               5                   10                  15

Leu Tyr Asn Thr Phe Thr Gln Gln Thr Gly Ile Arg Val Asn Ile Ile
            20                  25                  30

Glu Ala Glu Ala Asp Ala Leu Ile Glu Arg Ile Arg Ser Glu Gly Ser
        35                  40                  45

Arg Thr Pro Ala Asp Val Leu Ile Thr Val Asp Ala Gly Arg Leu Trp
    50                  55                  60

Arg Ala Gln Glu Ala Gly Ile Leu Gln Pro Ile Gln Ser Arg Val Leu
65                  70                  75                  80

Asn Ser Val Val Pro Ala Asn Leu Arg Glu Pro Gln Gly His Trp Phe
                85                  90                  95

Gly Leu Ser Arg Arg Val Arg Val Leu Ile Tyr Asn Lys Ser Arg Val
            100                 105                 110

Asn Pro Ser Gln Leu Ser Thr Tyr Glu Asp Leu Ala Asn Pro Lys Trp
        115                 120                 125

Arg Arg Gln Ile Leu Thr Arg Ser Ser Ser Asn Cys Tyr Asn Gln Ser
    130                 135                 140

Leu Thr Gly Ser Leu Leu Ala Ile His Gly Ala Gln Lys Thr Glu Gln
145                 150                 155                 160

Trp Ala Arg Gly Leu Val Gln Asn Phe Ala Arg Pro Pro Glu Gly Asn
                165                 170                 175

Asp Thr Ala Gln Ile Arg Ala Ser Ala Glu Gly Val Gly Ser Val Ala
            180                 185                 190

Ile Ala Asn His Tyr Tyr Leu Ala Arg Leu Ile Ala Ser Asp Lys Glu
        195                 200                 205

Gln Asp Arg Ala Val Ala Ala Lys Val Gly Leu Phe Phe Pro Asn Gln
    210                 215                 220

Arg Asp Arg Gly Ala His Val Asn Ile Ser Gly Ala Gly Val Val Ala
225                 230                 235                 240

Gly Ala Pro Asn Arg Gln Gly Ala Ile Arg Phe Leu Glu Tyr Leu Val
                245                 250                 255

Ser Pro Lys Ala Gln Glu Met Phe Ala Met Ala Asn Phe Glu Tyr Pro
            260                 265                 270

Val Arg Ala Gly Val Pro Val His Pro Ile Val Lys Gln Phe Gly Asn
        275                 280                 285

Phe Arg Gly Gln Asn Val Asn Ala Ala Val Phe Gly Arg Asn Asn Ala
    290                 295                 300

Glu Ala Leu Arg Ile Met Asp Arg Ala Gly Trp Arg Gly Gly Ser His
305                 310                 315                 320

His His His His His
                325
```

<210> SEQ ID NO 50
<211> LENGTH: 325
<212> TYPE: PRT
<213> ORGANISM: Artificial Sequence
<220> FEATURE:
<223> OTHER INFORMATION: teFeBP3_N176C (with N176C and C184S substitution mutations, the signal peptide replaced with M, and a GGSHHHHHH at C-terminus)

<400> SEQUENCE: 50

Met Val Ile Asn Val Tyr Ser Ala Arg His Tyr Asp Thr Asp Lys Ala
1               5                   10                  15

Leu Tyr Asn Thr Phe Thr Gln Gln Thr Gly Ile Arg Val Asn Ile Ile
            20                  25                  30

Glu Ala Glu Ala Asp Ala Leu Ile Glu Arg Ile Arg Ser Glu Gly Ser
        35                  40                  45

Arg Thr Pro Ala Asp Val Leu Ile Thr Val Asp Ala Gly Arg Leu Trp
    50                  55                  60

Arg Ala Gln Glu Ala Gly Ile Leu Gln Pro Ile Gln Ser Arg Val Leu
65                  70                  75                  80

Asn Ser Val Val Pro Ala Asn Leu Arg Glu Pro Gln Gly His Trp Phe
                85                  90                  95

Gly Leu Ser Arg Arg Val Arg Val Leu Ile Tyr Asn Lys Ser Arg Val
            100                 105                 110

Asn Pro Ser Gln Leu Ser Thr Tyr Glu Asp Leu Ala Asn Pro Lys Trp
        115                 120                 125

Arg Arg Gln Ile Leu Thr Arg Ser Ser Ser Asn Ile Tyr Asn Gln Ser
    130                 135                 140

Leu Thr Gly Ser Leu Leu Ala Ile His Gly Ala Gln Lys Thr Glu Gln
145                 150                 155                 160

Trp Ala Arg Gly Leu Val Gln Asn Phe Ala Arg Pro Pro Glu Gly Cys
                165                 170                 175

Asp Thr Ala Gln Ile Arg Ala Ser Ala Glu Gly Val Gly Ser Val Ala
            180                 185                 190

Ile Ala Asn His Tyr Tyr Leu Ala Arg Leu Ile Ala Ser Asp Lys Glu
        195                 200                 205

Gln Asp Arg Ala Val Ala Ala Lys Val Gly Leu Phe Phe Pro Asn Gln
    210                 215                 220

Arg Asp Arg Gly Ala His Val Asn Ile Ser Gly Ala Gly Val Val Ala
225                 230                 235                 240

Gly Ala Pro Asn Arg Gln Gly Ala Ile Arg Phe Leu Glu Tyr Leu Val
                245                 250                 255

Ser Pro Lys Ala Gln Glu Met Phe Ala Met Ala Asn Phe Glu Tyr Pro
            260                 265                 270

Val Arg Ala Gly Val Pro Val His Pro Ile Val Lys Gln Phe Gly Asn
        275                 280                 285

Phe Arg Gly Gln Asn Val Asn Ala Ala Val Phe Gly Arg Asn Asn Ala
    290                 295                 300

Glu Ala Leu Arg Ile Met Asp Arg Ala Gly Trp Arg Gly Gly Ser His
305                 310                 315                 320

His His His His His
                325

<210> SEQ ID NO 51
<211> LENGTH: 325
<212> TYPE: PRT
<213> ORGANISM: Artificial Sequence
<220> FEATURE:
<223> OTHER INFORMATION: teFeBP3_N195C (with N195C and C184S substitution mutations, the signal peptide replaced with M, and a GGSHHHHHH at C-terminus)

<400> SEQUENCE: 51

Met Val Ile Asn Val Tyr Ser Ala Arg His Tyr Asp Thr Asp Lys Ala

-continued

```
1               5                   10                  15

Leu Tyr Asn Thr Phe Thr Gln Gln Thr Gly Ile Arg Val Asn Ile Ile
            20                  25                  30

Glu Ala Glu Ala Asp Ala Leu Ile Glu Arg Ile Arg Ser Glu Gly Ser
        35                  40                  45

Arg Thr Pro Ala Asp Val Leu Ile Thr Val Asp Ala Gly Arg Leu Trp
    50                  55                  60

Arg Ala Gln Glu Ala Gly Ile Leu Gln Pro Ile Gln Ser Arg Val Leu
65                  70                  75                  80

Asn Ser Val Val Pro Ala Asn Leu Arg Glu Pro Gln Gly His Trp Phe
                85                  90                  95

Gly Leu Ser Arg Arg Val Arg Val Leu Ile Tyr Asn Lys Ser Arg Val
            100                 105                 110

Asn Pro Ser Gln Leu Ser Thr Tyr Glu Asp Leu Ala Asn Pro Lys Trp
        115                 120                 125

Arg Arg Gln Ile Leu Thr Arg Ser Ser Ser Asn Ile Tyr Asn Gln Ser
    130                 135                 140

Leu Thr Gly Ser Leu Leu Ala Ile His Gly Ala Gln Lys Thr Glu Gln
145                 150                 155                 160

Trp Ala Arg Gly Leu Val Gln Asn Phe Ala Arg Pro Pro Glu Gly Asn
                165                 170                 175

Asp Thr Ala Gln Ile Arg Ala Ser Ala Glu Gly Val Gly Ser Val Ala
            180                 185                 190

Ile Ala Cys His Tyr Tyr Leu Ala Arg Leu Ile Ala Ser Asp Lys Glu
        195                 200                 205

Gln Asp Arg Ala Val Ala Ala Lys Val Gly Leu Phe Phe Pro Asn Gln
    210                 215                 220

Arg Asp Arg Gly Ala His Val Asn Ile Ser Gly Ala Gly Val Val Ala
225                 230                 235                 240

Gly Ala Pro Asn Arg Gln Gly Ala Ile Arg Phe Leu Glu Tyr Leu Val
                245                 250                 255

Ser Pro Lys Ala Gln Glu Met Phe Ala Met Ala Asn Phe Glu Tyr Pro
            260                 265                 270

Val Arg Ala Gly Val Pro Val His Pro Ile Val Lys Gln Phe Gly Asn
        275                 280                 285

Phe Arg Gly Gln Asn Val Asn Ala Ala Val Phe Gly Arg Asn Asn Ala
    290                 295                 300

Glu Ala Leu Arg Ile Met Asp Arg Ala Gly Trp Arg Gly Gly Ser His
305                 310                 315                 320

His His His His His
                325


<210> SEQ ID NO 52
<211> LENGTH: 325
<212> TYPE: PRT
<213> ORGANISM: Artificial Sequence
<220> FEATURE:
<223> OTHER INFORMATION: teFeBP3_N268C (with N268C and C184S
      substitution mutations, the signal peptide replaced with M, and a
      GGSHHHHHH at C-terminus)

<400> SEQUENCE: 52

Met Val Ile Asn Val Tyr Ser Ala Arg His Tyr Asp Thr Asp Lys Ala
1               5                   10                  15

Leu Tyr Asn Thr Phe Thr Gln Gln Thr Gly Ile Arg Val Asn Ile Ile
            20                  25                  30
```

```
Glu Ala Glu Ala Asp Ala Leu Ile Glu Arg Ile Arg Ser Glu Gly Ser
        35                  40                  45

Arg Thr Pro Ala Asp Val Leu Ile Thr Val Asp Ala Gly Arg Leu Trp
    50                  55                  60

Arg Ala Gln Glu Ala Gly Ile Leu Gln Pro Ile Gln Ser Arg Val Leu
65                  70                  75                  80

Asn Ser Val Val Pro Ala Asn Leu Arg Glu Pro Gln Gly His Trp Phe
                85                  90                  95

Gly Leu Ser Arg Arg Val Arg Val Leu Ile Tyr Asn Lys Ser Arg Val
            100                 105                 110

Asn Pro Ser Gln Leu Ser Thr Tyr Glu Asp Leu Ala Asn Pro Lys Trp
        115                 120                 125

Arg Arg Gln Ile Leu Thr Arg Ser Ser Ser Asn Ile Tyr Asn Gln Ser
    130                 135                 140

Leu Thr Gly Ser Leu Leu Ala Ile His Gly Ala Gln Lys Thr Glu Gln
145                 150                 155                 160

Trp Ala Arg Gly Leu Val Gln Asn Phe Ala Arg Pro Pro Glu Gly Asn
                165                 170                 175

Asp Thr Ala Gln Ile Arg Ala Ser Ala Glu Gly Val Gly Ser Val Ala
            180                 185                 190

Ile Ala Asn His Tyr Tyr Leu Ala Arg Leu Ile Ala Ser Asp Lys Glu
        195                 200                 205

Gln Asp Arg Ala Val Ala Ala Lys Val Gly Leu Phe Phe Pro Asn Gln
    210                 215                 220

Arg Asp Arg Gly Ala His Val Asn Ile Ser Gly Ala Gly Val Val Ala
225                 230                 235                 240

Gly Ala Pro Asn Arg Gln Gly Ala Ile Arg Phe Leu Glu Tyr Leu Val
                245                 250                 255

Ser Pro Lys Ala Gln Glu Met Phe Ala Met Ala Cys Phe Glu Tyr Pro
            260                 265                 270

Val Arg Ala Gly Val Pro Val His Pro Ile Val Lys Gln Phe Gly Asn
        275                 280                 285

Phe Arg Gly Gln Asn Val Asn Ala Ala Val Phe Gly Arg Asn Asn Ala
    290                 295                 300

Glu Ala Leu Arg Ile Met Asp Arg Ala Gly Trp Arg Gly Gly Ser His
305                 310                 315                 320

His His His His His
                325


<210> SEQ ID NO 53
<211> LENGTH: 325
<212> TYPE: PRT
<213> ORGANISM: Artificial Sequence
<220> FEATURE:
<223> OTHER INFORMATION: teFeBP3_E270C (with E270C and C184S
      substitution mutations, the signal peptide replaced with M, and a
      GGSHHHHHH at C-terminus)

<400> SEQUENCE: 53

Met Val Ile Asn Val Tyr Ser Ala Arg His Tyr Asp Thr Asp Lys Ala
1               5                   10                  15

Leu Tyr Asn Thr Phe Thr Gln Gln Thr Gly Ile Arg Val Asn Ile Ile
            20                  25                  30

Glu Ala Glu Ala Asp Ala Leu Ile Glu Arg Ile Arg Ser Glu Gly Ser
        35                  40                  45
```

```
Arg Thr Pro Ala Asp Val Leu Ile Thr Val Asp Ala Gly Arg Leu Trp
    50                  55                  60

Arg Ala Gln Glu Ala Gly Ile Leu Gln Pro Ile Gln Ser Arg Val Leu
65                  70                  75                  80

Asn Ser Val Val Pro Ala Asn Leu Arg Glu Pro Gln Gly His Trp Phe
                85                  90                  95

Gly Leu Ser Arg Arg Val Arg Val Leu Ile Tyr Asn Lys Ser Arg Val
            100                 105                 110

Asn Pro Ser Gln Leu Ser Thr Tyr Glu Asp Leu Ala Asn Pro Lys Trp
        115                 120                 125

Arg Arg Gln Ile Leu Thr Arg Ser Ser Ser Asn Ile Tyr Asn Gln Ser
    130                 135                 140

Leu Thr Gly Ser Leu Leu Ala Ile His Gly Ala Gln Lys Thr Glu Gln
145                 150                 155                 160

Trp Ala Arg Gly Leu Val Gln Asn Phe Ala Arg Pro Pro Glu Gly Asn
                165                 170                 175

Asp Thr Ala Gln Ile Arg Ala Ser Ala Glu Gly Val Gly Ser Val Ala
            180                 185                 190

Ile Ala Asn His Tyr Tyr Leu Ala Arg Leu Ile Ala Ser Asp Lys Glu
        195                 200                 205

Gln Asp Arg Ala Val Ala Ala Lys Val Gly Leu Phe Phe Pro Asn Gln
    210                 215                 220

Arg Asp Arg Gly Ala His Val Asn Ile Ser Gly Ala Gly Val Val Ala
225                 230                 235                 240

Gly Ala Pro Asn Arg Gln Gly Ala Ile Arg Phe Leu Glu Tyr Leu Val
                245                 250                 255

Ser Pro Lys Ala Gln Glu Met Phe Ala Met Ala Asn Phe Cys Tyr Pro
            260                 265                 270

Val Arg Ala Gly Val Pro Val His Pro Ile Val Lys Gln Phe Gly Asn
        275                 280                 285

Phe Arg Gly Gln Asn Val Asn Ala Ala Val Phe Gly Arg Asn Asn Ala
    290                 295                 300

Glu Ala Leu Arg Ile Met Asp Arg Ala Gly Trp Arg Gly Gly Ser His
305                 310                 315                 320

His His His His His
                325
```

<210> SEQ ID NO 54
<211> LENGTH: 436
<212> TYPE: PRT
<213> ORGANISM: Artificial Sequence
<220> FEATURE:
<223> OTHER INFORMATION: avBicarbBP5_16C_bZif (with I16C substitution mutation, signal peptide replaced with M, a bZif fusion, and a GGSHHHHHH at C-terminus)

<400> SEQUENCE: 54

```
Met Ala Glu Gln Ala Pro Glu Val Thr Thr Val Lys Leu Gly Tyr Cys
1               5                   10                  15

Pro Ile Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
```

-continued

```
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser Thr Gly Glu Lys Pro Tyr Lys
                405                 410                 415

Cys Pro Glu Cys Gly Lys Ser Phe Ser Arg Ser Gly Gly Ser His His
            420                 425                 430

His His His His
        435
```

<210> SEQ ID NO 55
<211> LENGTH: 436
<212> TYPE: PRT
<213> ORGANISM: Artificial Sequence
<220> FEATURE:
<223> OTHER INFORMATION: avBicarbBP5_17C_bZif (with P17C substitution mutation, signal peptide replaced with M, a bZif fusion, and a GGSHHHHHH at C-terminus)

<400> SEQUENCE: 55

Met Ala Glu Gln Ala Pro Glu Val Thr Thr Val Lys Leu Gly Tyr Ile
1 5 10 15

Cys Ile Val Glu Ser Ala Pro Leu Ile Ile Ala Lys Glu Lys Gly Phe
20 25 30

Phe Ala Lys Tyr Gly Leu Thr Asn Val Glu Leu Ser Lys Gln Ala Ser
35 40 45

Trp Gly Ser Ala Arg Asp Asn Val Glu Ile Gly Ser Ala Gly Gly Gly
50 55 60

Ile Asp Gly Gly Gln Trp Gln Met Pro Met Pro His Leu Ile Thr Glu
65 70 75 80

Gly Leu Ile Thr Lys Gly Asn Gln Lys Ile Pro Met Tyr Val Leu Ala
85 90 95

Gln Leu Ile Thr His Gly Asn Gly Ile Ala Ile Ala Asn Lys His Gln
100 105 110

Gly Lys Gly Ile Ser Leu Lys Leu Glu Gly Ala Lys Ser Leu Phe Ser
115 120 125

Gln Leu Lys Ser Ser Thr Pro Phe Thr Ala Ala Phe Thr Phe Pro His
130 135 140

Val Asn Gln Asp Leu Trp Ile Arg Tyr Trp Leu Ala Ala Gly Gly Ile
145 150 155 160

Asp Pro Asp Ala Asp Val Lys Leu Leu Thr Val Pro Ala Ala Gln Thr
165 170 175

Val Ala Asn Met Lys Thr Gly Thr Met Asp Ala Phe Ser Thr Gly Asp
180 185 190

Pro Trp Pro Phe Arg Leu Val Asn Asp Lys Ile Gly Tyr Met Ala Ala
195 200 205

Leu Thr Ala Glu Ile Trp Lys Asn His Pro Glu Glu Tyr Leu Ala Met
210 215 220

Arg Ala Asp Trp Val Asp Lys Tyr Pro Lys Ala Thr Lys Ala Leu Leu
225 230 235 240

Lys Gly Ile Met Glu Ala Gln Gln Trp Leu Asp Asn Phe Asp Asn Arg
245 250 255

Lys Glu Ala Ala Gln Ile Leu Ala Gly Arg Asn Tyr Phe Asn Leu Asn
260 265 270

Asn Pro Glu Ile Leu Ala Asp Pro Tyr Val Gly Lys Tyr Asp Met Gly
275 280 285

Asp Gly Arg Lys Ile Asp Asp Lys Ser Met Ala Ala Tyr Tyr Trp Lys
290 295 300

Asp Glu Lys Gly Ser Val Ser Tyr Pro Tyr Lys Ser His Asp Leu Trp
305 310 315 320

Phe Ile Thr Glu Asn Val Arg Trp Gly Phe Leu Pro Lys Asp Tyr Leu
325 330 335

Ala Asn Gly Ala Ala Lys Ala Lys Glu Leu Ile Asp Lys Val Asn Arg
340 345 350

Glu Asp Ile Trp Lys Glu Ala Ala Lys Glu Ala Gly Ile Ala Ala Ala
355 360 365

Asp Ile Pro Thr Ser Thr Ser Arg Gly Val Glu Glu Phe Phe Asp Gly
370 375 380

Thr Lys Phe Asp Pro Glu Lys Pro Asp Glu Tyr Leu Lys Ser Leu Lys
385 390 395 400

```
Ile Lys Lys Val Ser Val Gly Gly Ser Thr Gly Glu Lys Pro Tyr Lys
                405                 410                 415

Cys Pro Glu Cys Gly Lys Ser Phe Ser Arg Ser Gly Gly Ser His His
            420                 425                 430

His His His His
        435


<210> SEQ ID NO 56
<211> LENGTH: 436
<212> TYPE: PRT
<213> ORGANISM: Artificial Sequence
<220> FEATURE:
<223> OTHER INFORMATION: avBicarbBP5_18C_bZif (with I18C substitution
      mutation, signal peptide replaced with M, a bZif fusion, and a
      GGSHHHHHH at C-terminus)

<400> SEQUENCE: 56

Met Ala Glu Gln Ala Pro Glu Val Thr Thr Val Lys Leu Gly Tyr Ile
1               5                   10                  15

Pro Cys Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
```

```
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser Thr Gly Glu Lys Pro Tyr Lys
                405                 410                 415

Cys Pro Glu Cys Gly Lys Ser Phe Ser Arg Ser Gly Gly Ser His His
            420                 425                 430

His His His His
        435


<210> SEQ ID NO 57
<211> LENGTH: 436
<212> TYPE: PRT
<213> ORGANISM: Artificial Sequence
<220> FEATURE:
<223> OTHER INFORMATION: avBicarbBP5_190C_bZif (with T190C substitution
      mutation, signal peptide replaced with M, a bZif fusion, and a
      GGSHHHHHH at C-terminus)

<400> SEQUENCE: 57

Met Ala Glu Gln Ala Pro Glu Val Thr Thr Val Lys Leu Gly Tyr Ile
1               5                   10                  15

Pro Ile Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Cys Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220
```

```
Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser Thr Gly Glu Lys Pro Tyr Lys
                405                 410                 415

Cys Pro Glu Cys Gly Lys Ser Phe Ser Arg Ser Gly Gly Ser His His
            420                 425                 430

His His His His
        435
```

<210> SEQ ID NO 58
<211> LENGTH: 436
<212> TYPE: PRT
<213> ORGANISM: Artificial Sequence
<220> FEATURE:
<223> OTHER INFORMATION: avBicarbBP5_194C_bZif (with W194C substitution mutation, signal peptide replaced with M, a bZif fusion, and a GGSHHHHHH at C-terminus)

<400> SEQUENCE: 58

```
Met Ala Glu Gln Ala Pro Glu Val Thr Thr Val Lys Leu Gly Tyr Ile
1               5                   10                  15

Pro Ile Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125
```

```
Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Cys Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser Thr Gly Glu Lys Pro Tyr Lys
                405                 410                 415

Cys Pro Glu Cys Gly Lys Ser Phe Ser Arg Ser Gly Gly Ser His His
            420                 425                 430

His His His His
        435
```

<210> SEQ ID NO 59
<211> LENGTH: 436
<212> TYPE: PRT
<213> ORGANISM: Artificial Sequence
<220> FEATURE:
<223> OTHER INFORMATION: avBicarbBP5_16C_71D_bZif (with I16C and Q71D substitution mutations, signal peptide replaced with M, a bZif fusion, and a GGSHHHHHH at C-terminus)

<400> SEQUENCE: 59

```
Met Ala Glu Gln Ala Pro Glu Val Thr Thr Val Lys Leu Gly Tyr Cys
1               5                   10                  15

Pro Ile Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
```

-continued 35 40 45

Trp Gly Ser Ala Arg Asp Asn Val Glu Ile Gly Ser Ala Gly Gly Gly
50 55 60

Ile Asp Gly Gly Gln Trp Asp Met Pro Met Pro His Leu Ile Thr Glu
65 70 75 80

Gly Leu Ile Thr Lys Gly Asn Gln Lys Ile Pro Met Tyr Val Leu Ala
85 90 95

Gln Leu Ile Thr His Gly Asn Gly Ile Ala Ile Ala Asn Lys His Gln
100 105 110

Gly Lys Gly Ile Ser Leu Lys Leu Glu Gly Ala Lys Ser Leu Phe Ser
115 120 125

Gln Leu Lys Ser Ser Thr Pro Phe Thr Ala Ala Phe Thr Phe Pro His
130 135 140

Val Asn Gln Asp Leu Trp Ile Arg Tyr Trp Leu Ala Ala Gly Gly Ile
145 150 155 160

Asp Pro Asp Ala Asp Val Lys Leu Leu Thr Val Pro Ala Ala Gln Thr
165 170 175

Val Ala Asn Met Lys Thr Gly Thr Met Asp Ala Phe Ser Thr Gly Asp
180 185 190

Pro Trp Pro Phe Arg Leu Val Asn Asp Lys Ile Gly Tyr Met Ala Ala
195 200 205

Leu Thr Ala Glu Ile Trp Lys Asn His Pro Glu Glu Tyr Leu Ala Met
210 215 220

Arg Ala Asp Trp Val Asp Lys Tyr Pro Lys Ala Thr Lys Ala Leu Leu
225 230 235 240

Lys Gly Ile Met Glu Ala Gln Gln Trp Leu Asp Asn Phe Asp Asn Arg
245 250 255

Lys Glu Ala Ala Gln Ile Leu Ala Gly Arg Asn Tyr Phe Asn Leu Asn
260 265 270

Asn Pro Glu Ile Leu Ala Asp Pro Tyr Val Gly Lys Tyr Asp Met Gly
275 280 285

Asp Gly Arg Lys Ile Asp Asp Lys Ser Met Ala Ala Tyr Tyr Trp Lys
290 295 300

Asp Glu Lys Gly Ser Val Ser Tyr Pro Tyr Lys Ser His Asp Leu Trp
305 310 315 320

Phe Ile Thr Glu Asn Val Arg Trp Gly Phe Leu Pro Lys Asp Tyr Leu
325 330 335

Ala Asn Gly Ala Ala Lys Ala Lys Glu Leu Ile Asp Lys Val Asn Arg
340 345 350

Glu Asp Ile Trp Lys Glu Ala Ala Lys Glu Ala Gly Ile Ala Ala Ala
355 360 365

Asp Ile Pro Thr Ser Thr Ser Arg Gly Val Glu Glu Phe Phe Asp Gly
370 375 380

Thr Lys Phe Asp Pro Glu Lys Pro Asp Glu Tyr Leu Lys Ser Leu Lys
385 390 395 400

Ile Lys Lys Val Ser Val Gly Gly Ser Thr Gly Glu Lys Pro Tyr Lys
405 410 415

Cys Pro Glu Cys Gly Lys Ser Phe Ser Arg Ser Gly Gly Ser His His
420 425 430

His His His His
435

<210> SEQ ID NO 60

<211> LENGTH: 436
<212> TYPE: PRT
<213> ORGANISM: Artificial Sequence
<220> FEATURE:
<223> OTHER INFORMATION: avBicarbBP5_16C_71N_bZif (with I16C and Q71N substitution mutations, signal peptide replaced with M, a bZif fusion, and a GGSHHHHHH at C-terminus)

<400> SEQUENCE: 60

```
Met Ala Glu Gln Ala Pro Glu Val Thr Thr Val Lys Leu Gly Tyr Cys
1               5                   10                  15

Pro Ile Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Asn Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365
```

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser Thr Gly Glu Lys Pro Tyr Lys
                405                 410                 415

Cys Pro Glu Cys Gly Lys Ser Phe Ser Arg Ser Gly Gly Ser His His
            420                 425                 430

His His His His
        435

<210> SEQ ID NO 61
<211> LENGTH: 436
<212> TYPE: PRT
<213> ORGANISM: Artificial Sequence
<220> FEATURE:
<223> OTHER INFORMATION: avBicarbBP5_16C_71E_bZif (with I16C and Q71E substitution mutations, signal peptide replaced with M, a bZif fusion, and a GGSHHHHHH at C-terminus)

<400> SEQUENCE: 61

Met Ala Glu Gln Ala Pro Glu Val Thr Thr Val Lys Leu Gly Tyr Cys
1               5                   10                  15

Pro Ile Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Glu Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly 275 280 285

Asp Gly Arg Lys Ile Asp Asp Lys Ser Met Ala Ala Tyr Tyr Trp Lys
290 295 300

Asp Glu Lys Gly Ser Val Ser Tyr Pro Tyr Lys Ser His Asp Leu Trp
305 310 315 320

Phe Ile Thr Glu Asn Val Arg Trp Gly Phe Leu Pro Lys Asp Tyr Leu
325 330 335

Ala Asn Gly Ala Ala Lys Ala Lys Glu Leu Ile Asp Lys Val Asn Arg
340 345 350

Glu Asp Ile Trp Lys Glu Ala Ala Lys Glu Ala Gly Ile Ala Ala Ala
355 360 365

Asp Ile Pro Thr Ser Thr Ser Arg Gly Val Glu Glu Phe Phe Asp Gly
370 375 380

Thr Lys Phe Asp Pro Glu Lys Pro Asp Glu Tyr Leu Lys Ser Leu Lys
385 390 395 400

Ile Lys Lys Val Ser Val Gly Gly Ser Thr Gly Glu Lys Pro Tyr Lys
405 410 415

Cys Pro Glu Cys Gly Lys Ser Phe Ser Arg Ser Gly Gly Ser His His
420 425 430

His His His His
435

<210> SEQ ID NO 62
<211> LENGTH: 436
<212> TYPE: PRT
<213> ORGANISM: Artificial Sequence
<220> FEATURE:
<223> OTHER INFORMATION: avBicarbBP5_16C_71M_bZif (with I16C and Q71M substitution mutations, signal peptide replaced with M, a bZif fusion, and a GGSHHHHHH at C-terminus)

<400> SEQUENCE: 62

Met Ala Glu Gln Ala Pro Glu Val Thr Thr Val Lys Leu Gly Tyr Cys
1 5 10 15

Pro Ile Val Glu Ser Ala Pro Leu Ile Ile Ala Lys Glu Lys Gly Phe
20 25 30

Phe Ala Lys Tyr Gly Leu Thr Asn Val Glu Leu Ser Lys Gln Ala Ser
35 40 45

Trp Gly Ser Ala Arg Asp Asn Val Glu Ile Gly Ser Ala Gly Gly Gly
50 55 60

Ile Asp Gly Gly Gln Trp Met Met Pro Met Pro His Leu Ile Thr Glu
65 70 75 80

Gly Leu Ile Thr Lys Gly Asn Gln Lys Ile Pro Met Tyr Val Leu Ala
85 90 95

Gln Leu Ile Thr His Gly Asn Gly Ile Ala Ile Ala Asn Lys His Gln
100 105 110

Gly Lys Gly Ile Ser Leu Lys Leu Glu Gly Ala Lys Ser Leu Phe Ser
115 120 125

Gln Leu Lys Ser Ser Thr Pro Phe Thr Ala Ala Phe Thr Phe Pro His
130 135 140

Val Asn Gln Asp Leu Trp Ile Arg Tyr Trp Leu Ala Ala Gly Gly Ile
145 150 155 160

Asp Pro Asp Ala Asp Val Lys Leu Leu Thr Val Pro Ala Ala Gln Thr
165 170 175

Val Ala Asn Met Lys Thr Gly Thr Met Asp Ala Phe Ser Thr Gly Asp
180 185 190

Pro Trp Pro Phe Arg Leu Val Asn Asp Lys Ile Gly Tyr Met Ala Ala
195 200 205

Leu Thr Ala Glu Ile Trp Lys Asn His Pro Glu Glu Tyr Leu Ala Met
210 215 220

Arg Ala Asp Trp Val Asp Lys Tyr Pro Lys Ala Thr Lys Ala Leu Leu
225 230 235 240

Lys Gly Ile Met Glu Ala Gln Gln Trp Leu Asp Asn Phe Asp Asn Arg
245 250 255

Lys Glu Ala Ala Gln Ile Leu Ala Gly Arg Asn Tyr Phe Asn Leu Asn
260 265 270

Asn Pro Glu Ile Leu Ala Asp Pro Tyr Val Gly Lys Tyr Asp Met Gly
275 280 285

Asp Gly Arg Lys Ile Asp Asp Lys Ser Met Ala Ala Tyr Tyr Trp Lys
290 295 300

Asp Glu Lys Gly Ser Val Ser Tyr Pro Tyr Lys Ser His Asp Leu Trp
305 310 315 320

Phe Ile Thr Glu Asn Val Arg Trp Gly Phe Leu Pro Lys Asp Tyr Leu
325 330 335

Ala Asn Gly Ala Ala Lys Ala Lys Glu Leu Ile Asp Lys Val Asn Arg
340 345 350

Glu Asp Ile Trp Lys Glu Ala Ala Lys Glu Ala Gly Ile Ala Ala Ala
355 360 365

Asp Ile Pro Thr Ser Thr Ser Arg Gly Val Glu Glu Phe Phe Asp Gly
370 375 380

Thr Lys Phe Asp Pro Glu Lys Pro Asp Glu Tyr Leu Lys Ser Leu Lys
385 390 395 400

Ile Lys Lys Val Ser Val Gly Gly Ser Thr Gly Glu Lys Pro Tyr Lys
405 410 415

Cys Pro Glu Cys Gly Lys Ser Phe Ser Arg Ser Gly Gly Ser His His
420 425 430

His His His His
435

<210> SEQ ID NO 63
<211> LENGTH: 436
<212> TYPE: PRT
<213> ORGANISM: Artificial Sequence
<220> FEATURE:
<223> OTHER INFORMATION: avBicarbBP5_18C_16M_bZif (with I18C and I16M substitution mutations, signal peptide replaced with M, a bZif fusion, and a GGSHHHHHH at C-terminus)

<400> SEQUENCE: 63

Met Ala Glu Gln Ala Pro Glu Val Thr Thr Val Lys Leu Gly Tyr Met
1 5 10 15

Pro Cys Val Glu Ser Ala Pro Leu Ile Ile Ala Lys Glu Lys Gly Phe
20 25 30

Phe Ala Lys Tyr Gly Leu Thr Asn Val Glu Leu Ser Lys Gln Ala Ser
35 40 45

Trp Gly Ser Ala Arg Asp Asn Val Glu Ile Gly Ser Ala Gly Gly Gly
50 55 60

Ile Asp Gly Gly Gln Trp Gln Met Pro Met Pro His Leu Ile Thr Glu
65 70 75 80

Gly Leu Ile Thr Lys Gly Asn Gln Lys Ile Pro Met Tyr Val Leu Ala
85 90 95

```
Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser Thr Gly Glu Lys Pro Tyr Lys
                405                 410                 415

Cys Pro Glu Cys Gly Lys Ser Phe Ser Arg Ser Gly Gly Ser His His
            420                 425                 430

His His His His
        435
```

<210> SEQ ID NO 64
<211> LENGTH: 436
<212> TYPE: PRT
<213> ORGANISM: Artificial Sequence
<220> FEATURE:
<223> OTHER INFORMATION: avBicarbBP5_18C_16F_bZif (with I18C and I16F substitution mutations, signal peptide replaced with M, a bZif fusion, and a GGSHHHHHH at C-terminus)

<400> SEQUENCE: 64

```
Met Ala Glu Gln Ala Pro Glu Val Thr Thr Val Lys Leu Gly Tyr Phe
```

-continued

```
1               5                   10                  15

Pro Cys Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser Thr Gly Glu Lys Pro Tyr Lys
                405                 410                 415

Cys Pro Glu Cys Gly Lys Ser Phe Ser Arg Ser Gly Gly Ser His His
            420                 425                 430
```

His His His His
        435

<210> SEQ ID NO 65
<211> LENGTH: 436
<212> TYPE: PRT
<213> ORGANISM: Artificial Sequence
<220> FEATURE:
<223> OTHER INFORMATION: avBicarbBP5_18C_16Y_bZif (with I18C and I16Y substitution mutations, signal peptide replaced with M, a bZif fusion, and a GGSHHHHHH at C-terminus)

<400> SEQUENCE: 65

```
Met Ala Glu Gln Ala Pro Glu Val Thr Thr Val Lys Leu Gly Tyr Tyr
1               5                   10                  15

Pro Cys Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335
```

Ala Asn Gly Ala Ala Lys Ala Lys Glu Leu Ile Asp Lys Val Asn Arg
340 345 350

Glu Asp Ile Trp Lys Glu Ala Ala Lys Glu Ala Gly Ile Ala Ala Ala
355 360 365

Asp Ile Pro Thr Ser Thr Ser Arg Gly Val Glu Glu Phe Phe Asp Gly
370 375 380

Thr Lys Phe Asp Pro Glu Lys Pro Asp Glu Tyr Leu Lys Ser Leu Lys
385 390 395 400

Ile Lys Lys Val Ser Val Gly Gly Ser Thr Gly Glu Lys Pro Tyr Lys
405 410 415

Cys Pro Glu Cys Gly Lys Ser Phe Ser Arg Ser Gly Gly Ser His His
420 425 430

His His His His
435

<210> SEQ ID NO 66
<211> LENGTH: 436
<212> TYPE: PRT
<213> ORGANISM: Artificial Sequence
<220> FEATURE:
<223> OTHER INFORMATION: avBicarbBP5_18C_16W_bZif (with I18C and I16W substitution mutations, signal peptide replaced with M, a bZif fusion, and a GGSHHHHHH at C-terminus)

<400> SEQUENCE: 66

Met Ala Glu Gln Ala Pro Glu Val Thr Thr Val Lys Leu Gly Tyr Trp
1 5 10 15

Pro Cys Val Glu Ser Ala Pro Leu Ile Ile Ala Lys Glu Lys Gly Phe
20 25 30

Phe Ala Lys Tyr Gly Leu Thr Asn Val Glu Leu Ser Lys Gln Ala Ser
35 40 45

Trp Gly Ser Ala Arg Asp Asn Val Glu Ile Gly Ser Ala Gly Gly Gly
50 55 60

Ile Asp Gly Gly Gln Trp Gln Met Pro Met Pro His Leu Ile Thr Glu
65 70 75 80

Gly Leu Ile Thr Lys Gly Asn Gln Lys Ile Pro Met Tyr Val Leu Ala
85 90 95

Gln Leu Ile Thr His Gly Asn Gly Ile Ala Ile Ala Asn Lys His Gln
100 105 110

Gly Lys Gly Ile Ser Leu Lys Leu Glu Gly Ala Lys Ser Leu Phe Ser
115 120 125

Gln Leu Lys Ser Ser Thr Pro Phe Thr Ala Ala Phe Thr Phe Pro His
130 135 140

Val Asn Gln Asp Leu Trp Ile Arg Tyr Trp Leu Ala Ala Gly Gly Ile
145 150 155 160

Asp Pro Asp Ala Asp Val Lys Leu Leu Thr Val Pro Ala Ala Gln Thr
165 170 175

Val Ala Asn Met Lys Thr Gly Thr Met Asp Ala Phe Ser Thr Gly Asp
180 185 190

Pro Trp Pro Phe Arg Leu Val Asn Asp Lys Ile Gly Tyr Met Ala Ala
195 200 205

Leu Thr Ala Glu Ile Trp Lys Asn His Pro Glu Glu Tyr Leu Ala Met
210 215 220

Arg Ala Asp Trp Val Asp Lys Tyr Pro Lys Ala Thr Lys Ala Leu Leu
225 230 235 240

Lys Gly Ile Met Glu Ala Gln Gln Trp Leu Asp Asn Phe Asp Asn Arg

```
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser Thr Gly Glu Lys Pro Tyr Lys
                405                 410                 415

Cys Pro Glu Cys Gly Lys Ser Phe Ser Arg Ser Gly Gly Ser His His
            420                 425                 430

His His His His
        435


<210> SEQ ID NO 67
<211> LENGTH: 436
<212> TYPE: PRT
<213> ORGANISM: Artificial Sequence
<220> FEATURE:
<223> OTHER INFORMATION: avBicarbBP5_18C_16E_bZif (with I18C and I16E
      substitution mutations, signal peptide replaced with M, a bZif
      fusion, and a GGSHHHHHH at C-terminus)

<400> SEQUENCE: 67

Met Ala Glu Gln Ala Pro Glu Val Thr Thr Val Lys Leu Gly Tyr Glu
1               5                   10                  15

Pro Cys Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160
```

```
Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser Thr Gly Glu Lys Pro Tyr Lys
                405                 410                 415

Cys Pro Glu Cys Gly Lys Ser Phe Ser Arg Ser Gly Gly Ser His His
            420                 425                 430

His His His His
        435
```

<210> SEQ ID NO 68
<211> LENGTH: 436
<212> TYPE: PRT
<213> ORGANISM: Artificial Sequence
<220> FEATURE:
<223> OTHER INFORMATION: avBicarbBP5_18C_49F_bZif (with I18C and W49F substitution mutations, signal peptide replaced with M, a bZif fusion, and a GGSHHHHHH at C-terminus)

<400> SEQUENCE: 68

```
Met Ala Glu Gln Ala Pro Glu Val Thr Thr Val Lys Leu Gly Tyr Ile
1               5                   10                  15

Pro Cys Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Phe Gly Ser Ala Arg Asp Asn Val Glu Ile Gly Ser Ala Gly Gly Gly
    50                  55                  60
```

```
Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser Thr Gly Glu Lys Pro Tyr Lys
                405                 410                 415

Cys Pro Glu Cys Gly Lys Ser Phe Ser Arg Ser Gly Gly Ser His His
            420                 425                 430

His His His His
        435
```

<210> SEQ ID NO 69
<211> LENGTH: 436
<212> TYPE: PRT
<213> ORGANISM: Artificial Sequence
<220> FEATURE:
<223> OTHER INFORMATION: avBicarbBP5_18C_49Y_bZif (with I18C and W49Y substitution mutations, signal peptide replaced with M, a bZif fusion, and a GGSHHHHHH at C-terminus)

<400> SEQUENCE: 69

Met Ala Glu Gln Ala Pro Glu Val Thr Thr Val Lys Leu Gly Tyr Ile
1               5                   10                  15

Pro Cys Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Tyr Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

```
Ile Lys Lys Val Ser Val Gly Gly Ser Thr Gly Glu Lys Pro Tyr Lys
                405                 410                 415

Cys Pro Glu Cys Gly Lys Ser Phe Ser Arg Ser Gly Gly Ser His His
            420                 425                 430

His His His His
        435


<210> SEQ ID NO 70
<211> LENGTH: 436
<212> TYPE: PRT
<213> ORGANISM: Artificial Sequence
<220> FEATURE:
<223> OTHER INFORMATION: avBicarbBP5_18C_141V_bZif (with I18C and T141V
      substitution mutations, signal peptide replaced with M, a bZif
      fusion, and a GGSHHHHHH at C-terminus)

<400> SEQUENCE: 70

Met Ala Glu Gln Ala Pro Glu Val Thr Thr Val Lys Leu Gly Tyr Ile
1               5                   10                  15

Pro Cys Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Val Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300
```

```
Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser Thr Gly Glu Lys Pro Tyr Lys
                405                 410                 415

Cys Pro Glu Cys Gly Lys Ser Phe Ser Arg Ser Gly Gly Ser His His
            420                 425                 430

His His His His
        435


<210> SEQ ID NO 71
<211> LENGTH: 436
<212> TYPE: PRT
<213> ORGANISM: Artificial Sequence
<220> FEATURE:
<223> OTHER INFORMATION: avBicarbBP5_18C_141F_bZif (with I18C and T141F
      substitution mutations, signal peptide replaced with M, a bZif
      fusion, and a GGSHHHHHH at C-terminus)

<400> SEQUENCE: 71

Met Ala Glu Gln Ala Pro Glu Val Thr Thr Val Lys Leu Gly Tyr Ile
1               5                   10                  15

Pro Cys Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Phe Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
```

```
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser Thr Gly Glu Lys Pro Tyr Lys
                405                 410                 415

Cys Pro Glu Cys Gly Lys Ser Phe Ser Arg Ser Gly Gly Ser His His
            420                 425                 430

His His His His
        435


<210> SEQ ID NO 72
<211> LENGTH: 436
<212> TYPE: PRT
<213> ORGANISM: Artificial Sequence
<220> FEATURE:
<223> OTHER INFORMATION: avBicarbBP5_18C_141Y_bZif (with I18C and T141Y
      substitution mutations, signal peptide replaced with M, a bZif
      fusion, and a GGSHHHHHH at C-terminus)

<400> SEQUENCE: 72

Met Ala Glu Gln Ala Pro Glu Val Thr Thr Val Lys Leu Gly Tyr Ile
1               5                   10                  15

Pro Cys Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125
```

```
Gln Leu Lys Ser Ser Thr Pro Phe Thr Ala Ala Phe Tyr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser Thr Gly Glu Lys Pro Tyr Lys
                405                 410                 415

Cys Pro Glu Cys Gly Lys Ser Phe Ser Arg Ser Gly Gly Ser His His
            420                 425                 430

His His His His
        435


<210> SEQ ID NO 73
<211> LENGTH: 436
<212> TYPE: PRT
<213> ORGANISM: Artificial Sequence
<220> FEATURE:
<223> OTHER INFORMATION: avBicarbBP5_18C_141W_bZif (with I18C and T141W
      substitution mutations, signal peptide replaced with M, a bZif
      fusion, and a GGSHHHHHH at C-terminus)

<400> SEQUENCE: 73

Met Ala Glu Gln Ala Pro Glu Val Thr Thr Val Lys Leu Gly Tyr Ile
1               5                   10                  15

Pro Cys Val Glu Ser Ala Pro Leu Ile Ile Ala Lys Glu Lys Gly Phe
            20                  25                  30
```

-continued

```
Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Trp Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser Thr Gly Glu Lys Pro Tyr Lys
                405                 410                 415

Cys Pro Glu Cys Gly Lys Ser Phe Ser Arg Ser Gly Gly Ser His His
            420                 425                 430

His His His His
        435
```

<210> SEQ ID NO 74
<211> LENGTH: 436
<212> TYPE: PRT
<213> ORGANISM: Artificial Sequence
<220> FEATURE:
<223> OTHER INFORMATION: avBicarbBP5_18C_141Q_bZif (with I18C and T141Q substitution mutations, signal peptide replaced with M, a bZif fusion, and a GGSHHHHHH at C-terminus)

<400> SEQUENCE: 74

```
Met Ala Glu Gln Ala Pro Glu Val Thr Thr Val Lys Leu Gly Tyr Ile
1               5                   10                  15

Pro Cys Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80

Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Gln Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365
```

```
Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val Gly Gly Ser Thr Gly Glu Lys Pro Tyr Lys
                405                 410                 415

Cys Pro Glu Cys Gly Lys Ser Phe Ser Arg Ser Gly Gly Ser His His
            420                 425                 430

His His His His
        435


<210> SEQ ID NO 75
<211> LENGTH: 402
<212> TYPE: PRT
<213> ORGANISM: Artificial Sequence
<220> FEATURE:
<223> OTHER INFORMATION: synBicarbBP1 (with signal peptide replaced with
      M)

<400> SEQUENCE: 75

Met Pro Glu Met Met Pro Glu Thr Ala Asn Ile Lys Leu Gly Tyr Ile
1               5                   10                  15

Pro Ile Val Glu Ala Ala Pro Leu Ile Ile Ala Gln Glu Lys Gly Phe
            20                  25                  30

Phe Ala Lys Tyr Gly Met Thr Gly Val Glu Val Ser Lys Gln Ala Asn
        35                  40                  45

Trp Ala Ser Ala Arg Asp Asn Val Thr Ile Gly Ser Gln Gly Gly Gly
    50                  55                  60

Ile Asp Gly Gly Gln Trp Gln Met Pro Met Pro His Leu Ile Thr Glu
65                  70                  75                  80

Gly Ile Ile Thr Asn Gly Asn Lys Val Pro Met Tyr Val Leu Ala Gln
                85                  90                  95

Leu Ile Thr Gln Gly Asn Gly Ile Ala Val Ala Pro Met His Glu Gly
            100                 105                 110

Lys Gly Val Asn Leu Asp Ile Thr Lys Ala Ala Asp Tyr Ile Lys Gly
        115                 120                 125

Phe Asn Lys Thr Asn Gly Arg Lys Phe Lys Ala Ala His Thr Phe Pro
    130                 135                 140

Asn Val Asn Gln Asp Phe Trp Ile Arg Tyr Trp Phe Ala Ala Gly Gly
145                 150                 155                 160

Val Asp Pro Asp Thr Asp Ile Asp Leu Leu Ala Val Pro Pro Ala Glu
                165                 170                 175

Thr Val Gln Gly Met Arg Asn Gly Thr Met Asp Ala Phe Ser Thr Gly
            180                 185                 190

Asp Pro Trp Pro Tyr Arg Ile Val Thr Glu Asn Ile Gly Tyr Met Ala
        195                 200                 205

Gly Leu Thr Ala Gln Ile Trp Pro Tyr His Pro Glu Glu Tyr Leu Ala
    210                 215                 220

Ile Arg Ala Asp Trp Val Asp Lys Asn Pro Lys Ala Thr Lys Ala Leu
225                 230                 235                 240

Leu Lys Gly Ile Met Glu Ala Gln Gln Trp Ile Asp Asp Pro Lys Asn
                245                 250                 255

Arg Pro Glu Val Val Gln Ile Val Ser Gly Arg Asn Tyr Phe Asn Val
            260                 265                 270

Pro Thr Thr Ile Leu Glu Ser Pro Phe Lys Gly Gln Tyr Thr Met Gly
```

```
        275                 280                 285

Asp Gly Gln Pro Ala Ile Asp Asp Phe Gln Lys Gly Pro Leu Tyr Trp
    290                 295                 300

Lys Asp Gly Ile Gly Asn Val Ser Tyr Pro Tyr Lys Ser His Asp Leu
305                 310                 315                 320

Trp Phe Leu Thr Glu Ser Ile Arg Trp Gly Phe His Lys Asn Ala Ile
                325                 330                 335

Pro Asp Leu Asp Thr Ala Gln Lys Ile Ile Asp Lys Val Asn Arg Glu
            340                 345                 350

Asp Leu Trp Arg Glu Ala Ala Thr Glu Ala Gly Phe Thr Ala Asp Ile
        355                 360                 365

Pro Ser Ser Thr Ser Arg Gly Val Glu Thr Phe Phe Asp Gly Ile Thr
    370                 375                 380

Phe Asp Pro Ala Asn Pro Ser Ala Tyr Leu Gln Ser Leu Ala Ile Lys
385                 390                 395                 400

Lys Val


<210> SEQ ID NO 76
<211> LENGTH: 401
<212> TYPE: PRT
<213> ORGANISM: Artificial Sequence
<220> FEATURE:
<223> OTHER INFORMATION: teBicarbBP2 (with C247A and C260A substitution
      mutations and signal peptide replaced with M)

<400> SEQUENCE: 76

Met Leu Glu Thr Asp Thr Ile Lys Leu Gly Phe Ile Pro Ile Val Glu
1               5                   10                  15

Ser Ala Pro Leu Ile Ile Ala Lys Glu Lys Gly Phe Phe Ala Lys His
            20                  25                  30

Gly Leu Thr Asn Ala Glu Leu Ser Lys Gln Ala Asn Trp Ala Ser Ala
        35                  40                  45

Arg Asp Asn Val Val Ile Gly Ser Ala Gly Gly Gly Ile Asp Gly Gly
    50                  55                  60

Gln Trp Gln Met Pro Met Pro Tyr Leu Ile Ser Glu Gly Ile Ile Thr
65                  70                  75                  80

Leu Asn Asn Gln Lys Leu Pro Met Tyr Val Leu Ala Gln Leu Asn Thr
                85                  90                  95

Gln Gly Asn Gly Ile Ala Ile Ser Gly Ala Asn Lys Gly Lys Gly Leu
            100                 105                 110

His Leu Lys Ile Ala Asp Pro Asp Tyr Ile Lys Gly Phe Ala Ala Lys
        115                 120                 125

Asn Gly Arg Lys Phe Lys Ala Ala His Thr Phe Pro His Val Asn Gln
    130                 135                 140

Asp Leu Trp Ile Arg Tyr Trp Phe Ala Ala Asn Gly Ile Asp Pro Asp
145                 150                 155                 160

Arg Asp Ile Glu Leu Leu Ala Val Pro Pro Ala Glu Thr Val Ala Gly
                165                 170                 175

Met Arg Asn Gly Thr Met Asp Ala Phe Ser Thr Gly Asp Pro Trp Pro
            180                 185                 190

Phe Arg Ile Val Ser Asp Asp Ile Gly Tyr Met Ala Thr Leu Thr Ala
        195                 200                 205

Gln Ile Trp Pro Tyr His Pro Glu Glu Tyr Leu Ala Val Arg Ala Asp
    210                 215                 220

Trp Val Asp Lys His Pro Lys Ala Thr Lys Ala Leu Leu Lys Ala Val
```

```
225                 230                 235                 240

Met Glu Ala Gln Gln Trp Ala Asp Asp Lys Ala Asn Arg Pro Glu Leu
                245                 250                 255

Ile Gln Ile Ala Ser Arg Arg Glu Tyr Phe Asn Ile Pro Gly Asn Ile
            260                 265                 270

Leu Thr Pro Pro Tyr Glu Gly Thr Tyr Thr Met Gly Asp Gly Gln Pro
        275                 280                 285

Asn Phe Asn Asp Phe Asn Ile Gly Pro Leu Tyr Trp Arg Asp Pro Asn
    290                 295                 300

Gly Asn Ser Ile Ser Tyr Pro Tyr Lys Ser His Asp Leu Trp Phe Leu
305                 310                 315                 320

Thr Glu Asn Leu Arg Trp Gly Phe Asn Ala Asp Lys Leu Lys Asp Phe
                325                 330                 335

Asp Asn Ile Lys Gln Met Ile Gly Arg Val Asn Arg Ser Asp Leu Trp
            340                 345                 350

Gln Glu Ala Ala Lys Glu Leu Gly Ile Pro Ala Ala Glu Ile Pro Thr
        355                 360                 365

Thr Glu Ser Arg Gly Val Glu Thr Phe Phe Asp Gly Ile Lys Phe Asp
    370                 375                 380

Pro Asp Asn Pro Gln Ala Tyr Leu Asp Ser Leu Lys Ile Lys Val Lys
385                 390                 395                 400

Ser
```

<210> SEQ ID NO 77
<211> LENGTH: 401
<212> TYPE: PRT
<213> ORGANISM: Artificial Sequence
<220> FEATURE:
<223> OTHER INFORMATION: ctBicarbBP3 (with signal peptide replaced with M)

<400> SEQUENCE: 77

```
Met Pro Glu Gln Ala Pro Glu Thr Thr Arg Val Lys Leu Gly Tyr Ile
1               5                   10                  15

Pro Ile Val Glu Ala Ala Pro Ile Ile Ile Ala Lys Glu Lys Gly Phe
            20                  25                  30

Phe Ala Lys Tyr Gly Met Thr Asp Val Asp Val Ser Lys Gln Ala Ser
        35                  40                  45

Trp Gly Ser Met Arg Asp Asn Thr Glu Ile Gly Ala Ala Gly Gly Gly
    50                  55                  60

Val Asp Gly Gly Gln Tyr Gln Met Pro Met Pro His Leu Ile Thr Glu
65                  70                  75                  80

Gly Arg Ile Thr Lys Gly Asn Lys Pro Ile Pro Met Tyr Val Leu Ala
                85                  90                  95

Gln Leu Asn Thr Gln Gly Asn Gly Ile Ala Ile Ala Glu Lys His Arg
            100                 105                 110

Gly Lys Gly Ile Glu Leu Glu Leu Ala Lys Gly Gly Lys Asn Leu Phe
        115                 120                 125

Gly Gln Leu Lys Ser Ala Asn Thr Pro Phe Thr Ala Ala Tyr Thr Phe
    130                 135                 140

Ala Gln Val Asn Gln Asp Phe Trp Ile Arg Tyr Trp Leu Ala Ala Gly
145                 150                 155                 160

Gly Val Asn Pro Asp Ala Asp Val Lys Leu Ile Pro Val Pro Ala Ala
                165                 170                 175

Gln Thr Val Ala Asn Met Lys Thr Gly Thr Met Asp Ala Phe Ser Thr
```

```
            180                 185                 190

Gly Asp Pro Trp Pro Tyr Arg Ile Val Lys Asp Lys Ile Gly Phe Leu
        195                 200                 205

Ala Met Leu Thr Ala Asp Met Trp Glu Phe His Pro Glu Glu Tyr Leu
    210                 215                 220

Ala Leu Arg Ala Glu Trp Val Asp Lys His Pro Lys Ala Thr Lys Ala
225                 230                 235                 240

Leu Leu Lys Gly Ile Met Glu Ala Gln Gln Trp Leu Asp Asn Phe Asp
                245                 250                 255

Asn Arg Glu Glu Ala Ala Lys Ile Leu Gly Gly Arg Asn Tyr Phe Asn
            260                 265                 270

Leu Pro Ala Glu Ile Leu Ala Gly Pro Phe Ala Gly Lys Tyr Asp Met
        275                 280                 285

Gly Glu Gly Arg Thr Val Asp Asp Arg Asn Lys Ala Val Leu Tyr Trp
    290                 295                 300

Lys Asp Pro Arg Gly Ser Val Ser Tyr Pro Tyr Lys Ser His Asp Leu
305                 310                 315                 320

Trp Phe Leu Thr Glu Ser Val Arg Trp Gly Phe Leu Pro Pro Asp Ser
                325                 330                 335

Leu Thr Lys Ala Gln Ala Leu Ile Asp Lys Val Asn Arg Glu Asp Leu
            340                 345                 350

Trp Lys Glu Ala Ala Lys Glu Leu Gly Val Ala Ala Ala Asp Ile Pro
        355                 360                 365

Thr Ser Thr Ser Arg Gly Val Glu Thr Phe Phe Asp Gly Val Lys Phe
    370                 375                 380

Asp Pro Glu Asn Pro Ala Ala Tyr Leu Lys Ser Leu Lys Ile Lys Lys
385                 390                 395                 400

Ala


<210> SEQ ID NO 78
<211> LENGTH: 406
<212> TYPE: PRT
<213> ORGANISM: Artificial Sequence
<220> FEATURE:
<223> OTHER INFORMATION: calBicarbBP4 (with signal peptide replaced with
      M)

<400> SEQUENCE: 78

Met Pro Glu Gln Lys Pro Glu Thr Glu Thr Val Lys Leu Gly Tyr Ile
1               5                   10                  15

Pro Ile Val Glu Ser Ala Pro Leu Ile Ile Ala Lys Glu Lys Gly Leu
            20                  25                  30

Phe Ala Lys Tyr Gly Met Thr Lys Val Glu Leu Ala Lys Gln Ala Ser
        35                  40                  45

Trp Gly Ala Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Ala
65                  70                  75                  80

Gly Leu Ile Thr Lys Gly Asn Lys Glu Ile Pro Met Tyr Val Leu Ala
                85                  90                  95

Gln Leu Val Thr His Gly Asn Gly Ile Ala Ile Ala Asp Lys His Lys
            100                 105                 110

Gly Lys Gly Leu Gly Leu Lys Leu Asp Gly Ala Lys Ser Leu Phe Lys
        115                 120                 125

Glu Leu Lys Ser Ser Thr Pro Phe Thr Ala Ala Phe Thr Phe Pro His
```

```
    130                 135                 140

Val Asn Gln Asp Leu Trp Ile Arg Tyr Trp Leu Ala Ala Ser Gly Leu
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Ile Val Asn Asp Lys Ile Gly Phe Met Ala Leu
        195                 200                 205

Leu Thr Ala Glu Met Trp Lys Asn His Pro Glu Glu Tyr Leu Ala Met
    210                 215                 220

Arg Gly Asp Trp Val Asp Lys His Pro Lys Ala Thr Lys Ala Ile Leu
225                 230                 235                 240

Lys Ala Val Met Glu Ala Gln Gln Trp Leu Asp Asn Phe Glu Asn Arg
                245                 250                 255

Lys Glu Ala Ala Thr Ile Leu Ala Gly Arg Lys Tyr Phe Asp Leu Ser
            260                 265                 270

Ser Pro Glu Ile Leu Leu Asp Pro Tyr Gln Gly Lys Tyr Asp Met Gly
        275                 280                 285

Asp Gly Arg Lys Ile Asp Asp Lys Leu Met Ala Pro Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Asn Ala Ala Lys Ala Lys Glu Leu Ile Asn Lys Val Asn Arg
            340                 345                 350

Glu Asp Ile Trp Lys Glu Ala Ala Lys Asp Leu Gly Ile Ala Ala Ala
        355                 360                 365

Asp Ile Pro Thr Ser Thr Ser Arg Gly Val Glu Glu Phe Phe Asp Gly
    370                 375                 380

Val Lys Phe Asp Pro Glu Lys Pro Glu Glu Tyr Leu Lys Ser Leu Lys
385                 390                 395                 400

Ile Lys Lys Ala Gly Val
                405


<210> SEQ ID NO 79
<211> LENGTH: 406
<212> TYPE: PRT
<213> ORGANISM: Artificial Sequence
<220> FEATURE:
<223> OTHER INFORMATION: avBicarbBP5 (with C96A substitution mutation
      and signal peptide replaced with M)

<400> SEQUENCE: 79

Met Ala Glu Gln Ala Pro Glu Val Thr Thr Val Lys Leu Gly Tyr Ile
1               5                   10                  15

Pro Ile Val Glu Ser Ala Pro Leu Ile Ile Ala Lys Glu Lys Gly Phe
            20                  25                  30

Phe Ala Lys Tyr Gly Leu Thr Asn Val Glu Leu Ser Lys Gln Ala Ser
        35                  40                  45

Trp Gly Ser Ala Arg Asp Asn Val Glu Ile Gly Ser Ala Gly Gly Gly
    50                  55                  60

Ile Asp Gly Gly Gln Trp Gln Met Pro Met Pro His Leu Ile Thr Glu
65                  70                  75                  80
```

```
Gly Leu Ile Thr Lys Gly Asn Gln Lys Ile Pro Met Tyr Val Leu Ala
                85                  90                  95

Gln Leu Ile Thr His Gly Asn Gly Ile Ala Ile Ala Asn Lys His Gln
            100                 105                 110

Gly Lys Gly Ile Ser Leu Lys Leu Glu Gly Ala Lys Ser Leu Phe Ser
        115                 120                 125

Gln Leu Lys Ser Ser Thr Pro Phe Thr Ala Ala Phe Thr Phe Pro His
    130                 135                 140

Val Asn Gln Asp Leu Trp Ile Arg Tyr Trp Leu Ala Ala Gly Gly Ile
145                 150                 155                 160

Asp Pro Asp Ala Asp Val Lys Leu Leu Thr Val Pro Ala Ala Gln Thr
                165                 170                 175

Val Ala Asn Met Lys Thr Gly Thr Met Asp Ala Phe Ser Thr Gly Asp
            180                 185                 190

Pro Trp Pro Phe Arg Leu Val Asn Asp Lys Ile Gly Tyr Met Ala Ala
        195                 200                 205

Leu Thr Ala Glu Ile Trp Lys Asn His Pro Glu Glu Tyr Leu Ala Met
    210                 215                 220

Arg Ala Asp Trp Val Asp Lys Tyr Pro Lys Ala Thr Lys Ala Leu Leu
225                 230                 235                 240

Lys Gly Ile Met Glu Ala Gln Gln Trp Leu Asp Asn Phe Asp Asn Arg
                245                 250                 255

Lys Glu Ala Ala Gln Ile Leu Ala Gly Arg Asn Tyr Phe Asn Leu Asn
            260                 265                 270

Asn Pro Glu Ile Leu Ala Asp Pro Tyr Val Gly Lys Tyr Asp Met Gly
        275                 280                 285

Asp Gly Arg Lys Ile Asp Asp Lys Ser Met Ala Ala Tyr Tyr Trp Lys
    290                 295                 300

Asp Glu Lys Gly Ser Val Ser Tyr Pro Tyr Lys Ser His Asp Leu Trp
305                 310                 315                 320

Phe Ile Thr Glu Asn Val Arg Trp Gly Phe Leu Pro Lys Asp Tyr Leu
                325                 330                 335

Ala Asn Gly Ala Ala Lys Ala Lys Glu Leu Ile Asp Lys Val Asn Arg
            340                 345                 350

Glu Asp Ile Trp Lys Glu Ala Ala Lys Glu Ala Gly Ile Ala Ala Ala
        355                 360                 365

Asp Ile Pro Thr Ser Thr Ser Arg Gly Val Glu Glu Phe Phe Asp Gly
    370                 375                 380

Thr Lys Phe Asp Pro Glu Lys Pro Asp Glu Tyr Leu Lys Ser Leu Lys
385                 390                 395                 400

Ile Lys Lys Val Ser Val
                405
```

<210> SEQ ID NO 80
<211> LENGTH: 406
<212> TYPE: PRT
<213> ORGANISM: Artificial Sequence
<220> FEATURE:
<223> OTHER INFORMATION: cmBicarbBP6 (with C254A substitution mutation and signal peptide replaced with M)

<400> SEQUENCE: 80

```
Met Ser Ser Ala Thr Thr Pro Glu Thr Thr Ala Val Lys Leu Gly Tyr
1               5                   10                  15

Ile Ala Ile Ala Glu Ser Ala Pro Leu Ile Ile Ala Arg Glu Lys Gly
            20                  25                  30
```

-continued

```
Phe Phe Ala Arg His Gly Met Thr Asp Val Asp Val Ser Lys Gln Ala
        35                  40                  45

Ser Trp Gly Ser Ala Arg Asp Asn Ile Glu Ile Gly Ser Ser Asn Gly
    50                  55                  60

Gly Ile Asp Gly Gly Gln Trp Gln Met Pro Met Pro Gln Leu Ile Ser
65                  70                  75                  80

Glu Gly Ile Ile Thr Lys Gly Asn Arg Lys Ile Pro Met Leu Ser Leu
                85                  90                  95

Ala Gln Leu Ser Thr Gln Gly Asn Gly Ile Ala Ile Ser Thr Gln His
            100                 105                 110

Ala Gly Lys Gly Phe Gly Leu Asp Val Ser Gly Ala Ala Glu Tyr Val
        115                 120                 125

Arg Asp Met Lys Ala Asp Gly Lys Pro Phe Lys Ala Ala Tyr Thr Phe
    130                 135                 140

Pro Arg Val Asn Gln Asp Phe Trp Ile Arg Tyr Trp Leu Ala Ala Gly
145                 150                 155                 160

Gly Ile Asp Pro Asn Lys Asp Ile Asp Leu Ile Ala Val Pro Ala Ala
                165                 170                 175

Gln Thr Val Ala Ser Met Arg Thr Gly Ser Met Asp Gly Phe Ser Thr
            180                 185                 190

Gly Asp Pro Trp Pro Ser Arg Ile Leu Arg Asp Arg Arg Lys Tyr Gly
        195                 200                 205

Phe Leu Ala Val Leu Thr Ala Gln Ile Trp Pro Ala His Pro Glu Glu
    210                 215                 220

Tyr Phe Ala Met Arg Glu Asp Trp Val Arg Lys His Pro Lys Ala Ala
225                 230                 235                 240

Lys Ala Ile Leu Lys Gly Ile Met Glu Ala Gln Met Trp Ala Asp Asp
                245                 250                 255

Pro Lys Asn Arg Ala Glu Met Ala Ala Ile Leu Ala Gln Arg Lys Tyr
            260                 265                 270

Phe Asn Val Pro Ser Asp Leu Leu Ile Gly Pro Tyr Val Gly Glu Tyr
        275                 280                 285

Ile Leu Gly Ala Asp Arg Lys Thr Val Lys Asp Glu Lys Leu Ala Ile
    290                 295                 300

Arg Tyr Trp Lys Asp Ala Arg Gly Asn Val Ser Tyr Pro Tyr Lys Ser
305                 310                 315                 320

His Asp Leu Trp Phe Leu Thr Glu Ser Val Arg Trp Gly Phe Leu Pro
                325                 330                 335

Gln Gly Ala Leu Gly Glu Ala Asp Arg Ile Ile Asn Ala Val Ser Gly
            340                 345                 350

Glu Lys Tyr Trp Arg Glu Ala Ala Gln Glu Leu Gly Ile Ala Ser Ala
        355                 360                 365

Asp Ile Pro Pro Ser Thr Ser Arg Gly Ile Glu Lys Phe Phe Asp Gly
    370                 375                 380

Ala Glu Phe Asn Pro Glu Lys Pro Lys Ala Tyr Leu Asp Ser Leu Lys
385                 390                 395                 400

Ile Lys Asn Leu Lys Ala
                405
```

<210> SEQ ID NO 81
<211> LENGTH: 317
<212> TYPE: PRT
<213> ORGANISM: Artificial Sequence
<220> FEATURE:

<223> OTHER INFORMATION: mhFeBP1 (with C135A and C191A substitution
      mutations and signal peptide replaced with M)

<400> SEQUENCE: 81

```
Met Ala Asn Glu Val Asn Val Tyr Ser Tyr Arg Gln Pro Tyr Leu Ile
1               5                   10                  15

Glu Pro Met Leu Lys Asn Phe Glu Lys Asp Thr Gly Ile Lys Val Asn
            20                  25                  30

Ile Ile Phe Ala Asp Lys Gly Leu Val Asp Arg Val Lys Gln Glu Gly
        35                  40                  45

Glu Leu Ser Pro Ala Asp Val Leu Leu Thr Val Asp Ile Ser Arg Val
    50                  55                  60

Met Glu Ile Val Asn Ala Asp Leu Ala Gln Lys Ile Asp Ser Lys Val
65                  70                  75                  80

Leu Glu Lys Asn Ile Pro Ala Gln Phe Arg Asp Ser Asn Asp Gln Trp
                85                  90                  95

Phe Gly Leu Thr Thr Arg Ala Arg Val Ile Tyr Thr Ser Lys Asp Arg
            100                 105                 110

Val Gly Lys Leu Pro Ala Gly Phe Asp Tyr Leu Asp Leu Ala Lys Pro
        115                 120                 125

Glu Tyr Lys Gly Lys Val Ala Val Arg Ser Gly Lys Asn Ser Tyr Asn
    130                 135                 140

Val Ser Leu Phe Ala Ala Met Ile Glu His Tyr Gly Ile Glu Lys Thr
145                 150                 155                 160

Lys Ala Phe Leu Glu Gly Leu Lys Ala Asn Leu Ala Arg Lys Pro Gln
                165                 170                 175

Gly Gly Asp Arg Asp Gln Val Lys Ala Ile Lys Glu Gly Ile Ala Asp
            180                 185                 190

Tyr Ser Ile Gly Asn Ser Tyr Tyr Tyr Gly Lys Met Leu Asp Asp Glu
        195                 200                 205

Lys Gln Lys Ser Trp Ala Glu Ala Ala Ile Ile Asn Phe Pro Ser Gly
    210                 215                 220

Glu His Gly Thr His Lys Asn Ile Ser Gly Val Val Ile Ala Lys His
225                 230                 235                 240

Ser Pro Asn Lys Ala Asn Ala Val Lys Leu Ile Glu Tyr Leu Ser Gly
                245                 250                 255

Glu Lys Ala Gln Gly Leu Tyr Ala Glu Leu Asn His Glu Tyr Pro Val
            260                 265                 270

Lys Glu Gly Ile Glu Pro Ser Ala Ile Val Lys Gly Trp Gly Thr Phe
        275                 280                 285

Lys Ser Asp Thr Ile Lys Leu Glu Asp Ile Ala Lys Asn Tyr Glu Ala
    290                 295                 300

Ala Leu Lys Leu Val Asp Glu Val Lys Phe Asp Asp Phe
305                 310                 315
```

<210> SEQ ID NO 82
<211> LENGTH: 317
<212> TYPE: PRT
<213> ORGANISM: Artificial Sequence
<220> FEATURE:
<223> OTHER INFORMATION: exiFeBP2 (with signal peptide replaced with M)

<400> SEQUENCE: 82

```
Met Asn Val Val Asn Val Tyr Ser Ser Arg His Tyr Asp Val Asp Gln
1               5                   10                  15

Gln Leu Tyr Lys Gln Phe Glu Glu Glu Thr Gly Ile Lys Val Asn Val
```

```
            20                  25                  30

Val Glu Gly Lys Ser Asp Glu Leu Leu Glu Arg Leu Asn Thr Glu Gly
        35                  40                  45

Glu Asn Thr Glu Ala Asp Leu Phe Ile Thr Ala Asp Ala Gly Asn Leu
    50                  55                  60

Tyr Gln Ala Lys Glu Ala Gly His Leu Gln Ala Val Asp Ser Asp Glu
65                  70                  75                  80

Leu Glu Ser Asn Ile Pro Glu Lys Tyr Arg Asp Thr Asp Asn Glu Trp
                85                  90                  95

Phe Gly Leu Thr Lys Arg Ala Arg Val Ile Val Tyr Ser Lys Asp Arg
            100                 105                 110

Val Lys Pro Glu Asp Leu Ser Thr Tyr Glu Ala Leu Thr Glu Glu Gln
        115                 120                 125

Trp Asn Gly Lys Val Leu Val Arg Pro Ser Glu Asn Met Tyr Asn Ile
    130                 135                 140

Ser Leu Leu Ala Ser Phe Ile Glu Val Asn Gly Val Asp Glu Ala Lys
145                 150                 155                 160

Glu Trp Ala Lys Gly Leu Val Asn Asn Met Ala Arg Asp Pro Gln Gly
                165                 170                 175

Asn Asp Arg Asp Gln Ala Lys Ala Val Val Ala Gly Glu Gly Asp Val
            180                 185                 190

Ala Ile Met Asn Thr Tyr Tyr Met Gly Leu Met Leu Asn Ser Glu Asp
        195                 200                 205

Glu Glu Glu Lys Lys Val Ala Glu Gln Leu Gly Val Phe Phe Pro Asn
    210                 215                 220

Gln Asp Thr Thr Gly Thr His Val Asn Ile Ser Gly Ile Ala Met Thr
225                 230                 235                 240

Lys Ala Ser Lys Asn Thr Glu Asn Ala Gln Lys Leu Met Glu Phe Met
                245                 250                 255

Ser Glu Pro Ser Ala Gln Glu Lys Phe Ala Ser Val Asn Tyr Glu Tyr
            260                 265                 270

Pro Val Asn Glu Ser Val Glu Pro Asn Glu Leu Leu Gln Ser Trp Gly
        275                 280                 285

Glu Phe Lys Glu Gln Asp Ile Asn Leu Ser Ala Leu Gly Glu Asn Gln
    290                 295                 300

Gln Glu Ala Ile Arg Ile Phe Asn Glu Val Gly Trp Lys
305                 310                 315


<210> SEQ ID NO 83
<211> LENGTH: 316
<212> TYPE: PRT
<213> ORGANISM: Artificial Sequence
<220> FEATURE:
<223> OTHER INFORMATION: teFeBP3 (with C184S substitution mutation and
      signal peptide replaced with M)

<400> SEQUENCE: 83

Met Val Ile Asn Val Tyr Ser Ala Arg His Tyr Asp Thr Asp Lys Ala
1               5                   10                  15

Leu Tyr Asn Thr Phe Thr Gln Gln Thr Gly Ile Arg Val Asn Ile Ile
            20                  25                  30

Glu Ala Glu Ala Asp Ala Leu Ile Glu Arg Ile Arg Ser Glu Gly Ser
        35                  40                  45

Arg Thr Pro Ala Asp Val Leu Ile Thr Val Asp Ala Gly Arg Leu Trp
    50                  55                  60
```

-continued

```
Arg Ala Gln Glu Ala Gly Ile Leu Gln Pro Ile Gln Ser Arg Val Leu
65                  70                  75                  80

Asn Ser Val Val Pro Ala Asn Leu Arg Glu Pro Gln Gly His Trp Phe
                85                  90                  95

Gly Leu Ser Arg Arg Val Arg Val Leu Ile Tyr Asn Lys Ser Arg Val
            100                 105                 110

Asn Pro Ser Gln Leu Ser Thr Tyr Glu Asp Leu Ala Asn Pro Lys Trp
        115                 120                 125

Arg Arg Gln Ile Leu Thr Arg Ser Ser Ser Asn Ile Tyr Asn Gln Ser
    130                 135                 140

Leu Thr Gly Ser Leu Leu Ala Ile His Gly Ala Gln Lys Thr Glu Gln
145                 150                 155                 160

Trp Ala Arg Gly Leu Val Gln Asn Phe Ala Arg Pro Pro Glu Gly Asn
                165                 170                 175

Asp Thr Ala Gln Ile Arg Ala Ser Ala Glu Gly Val Gly Ser Val Ala
            180                 185                 190

Ile Ala Asn His Tyr Tyr Leu Ala Arg Leu Ile Ala Ser Asp Lys Glu
        195                 200                 205

Gln Asp Arg Ala Val Ala Ala Lys Val Gly Leu Phe Phe Pro Asn Gln
    210                 215                 220

Arg Asp Arg Gly Ala His Val Asn Ile Ser Gly Ala Gly Val Val Ala
225                 230                 235                 240

Gly Ala Pro Asn Arg Gln Gly Ala Ile Arg Phe Leu Glu Tyr Leu Val
                245                 250                 255

Ser Pro Lys Ala Gln Glu Met Phe Ala Met Ala Asn Phe Glu Tyr Pro
            260                 265                 270

Val Arg Ala Gly Val Pro Val His Pro Ile Val Lys Gln Phe Gly Asn
        275                 280                 285

Phe Arg Gly Gln Asn Val Asn Ala Ala Val Phe Gly Arg Asn Asn Ala
    290                 295                 300

Glu Ala Leu Arg Ile Met Asp Arg Ala Gly Trp Arg
305                 310                 315
```

<210> SEQ ID NO 84
<211> LENGTH: 312
<212> TYPE: PRT
<213> ORGANISM: Artificial Sequence
<220> FEATURE:
<223> OTHER INFORMATION: cnFeBP4 (with signal peptide replaced with M)

<400> SEQUENCE: 84

```
Met Lys Leu Val Val Tyr Ser Gly Arg Ala Glu Arg Leu Ile Lys Pro
1               5                   10                  15

Val Leu Asp Glu Phe Gln Ala Lys Ser Gly Ile Gln Ile Glu Leu Leu
            20                  25                  30

Ser Ser Gly Thr Thr Glu Leu Val Asn Arg Leu Gln Ala Glu Gly Asp
        35                  40                  45

His Thr Pro Ala Asp Val Phe Leu Thr Asn Asp Ala Gly Ser Leu Glu
    50                  55                  60

His Ala Arg Glu Leu Lys Leu Leu Arg Pro Met Asn Met Arg Glu Val
65                  70                  75                  80

Glu Arg Ala Ile Pro Ser Gln Phe Arg Ala Ala Asp Asn Ser Trp Ile
                85                  90                  95

Gly Leu Ser Gly Arg Phe Trp Ile Val Val Tyr Asn Thr Asn Leu Val
            100                 105                 110
```

Lys Pro Asp Gln Ile Lys Ser Leu Phe Asp Leu Thr Gln Pro Gln Trp
115 120 125

Lys Asp Lys Ile Ala Val Pro Asn Ser Gly Ser Glu Tyr Leu Gln Ala
130 135 140

Gly Val Ser Val Ile Lys Ala Thr Phe Gly Asp Glu Arg Thr Lys Gln
145 150 155 160

Phe Leu Gln Gly Leu Lys Ala Asn Ala Gly Thr Gln Val Tyr Gln Lys
165 170 175

Ser Ser Gln Ile Val Glu Ala Val Ala Lys Gly Gln Val Ala Ala Gly
180 185 190

Ile Val Asn His Tyr Tyr Ile Tyr Arg His Leu Ala Thr Gln Pro Thr
195 200 205

Ala Pro Ile Ala Ala Val Met Thr Asp Gln Gln Glu Gly Gly Met Gly
210 215 220

Ala Ile Met Asn Val Thr Gly Ile Gly Val Thr Arg Ala Ser Lys His
225 230 235 240

Val Glu Ser Ala Lys Leu Leu Ile Glu Phe Leu Val Ala Gln Ala Gly
245 250 255

Gln Lys Met Phe Ala Asp Leu Asp Lys Glu Tyr Pro Leu His Pro Asp
260 265 270

Val Lys Ala Asp Pro Thr Leu Ile Asp Arg Arg Thr Phe Arg Ala Ala
275 280 285

Gln Val Pro Leu Ala Arg Leu Ala Glu Leu Arg Glu Ala Thr Leu Thr
290 295 300

Leu Ile Glu Gln Val Gly Leu Arg
305 310

<210> SEQ ID NO 85
<211> LENGTH: 311
<212> TYPE: PRT
<213> ORGANISM: Artificial Sequence
<220> FEATURE:
<223> OTHER INFORMATION: ttFeBP5 (with signal peptide replaced with M)

<400> SEQUENCE: 85

Met Ser Pro Thr Leu Thr Ile Tyr Ser Gly Arg Gly Gln Ser Leu Val
1 5 10 15

Glu Pro Leu Val Lys Gln Phe Glu Ala Glu Thr Gly Ile Arg Val Gln
20 25 30

Val Arg Tyr Ser Thr Asp Ala Gln Ile Leu Ala Ala Leu Gln Glu Glu
35 40 45

Gly Ser Arg Ser Pro Ala Asp Leu Phe Trp Ala Asn Thr Ala Gly Ala
50 55 60

Leu Gly Gln Ala Ser Ala Lys Gly Leu Leu Arg Pro Leu Gly Glu Thr
65 70 75 80

Leu Leu Glu Lys Pro Ile Ala Phe Val Pro Ala Ser Arg Thr Trp Val
85 90 95

Pro Val Thr Val Arg Leu Arg Val Leu Ala Tyr Asn Pro Asp Arg Ile
100 105 110

Lys Ala Glu Glu Leu Pro Glu Ser Leu Leu Asp Leu Pro Arg Phe Ala
115 120 125

Arg Glu Lys Gly Leu Val Gly Arg Val Gly Trp Thr Pro Thr Tyr Ser
130 135 140

Ser Phe Gln Asp Met Val Ala Gly Met Ile Ala Leu Tyr Gly Glu Glu
145 150 155 160

```
Lys Thr Arg Glu Trp Leu Leu Ala Met Lys Ala Leu Ala Pro Lys Ala
                165                 170                 175

Tyr Pro Ser Asn Pro Ala Met Leu Asp Ala Ile Arg Ala Gly Glu Val
            180                 185                 190

Asp Leu Gly Ser Thr Asn His Tyr Tyr Val Val Arg Phe Arg Arg Ala
        195                 200                 205

Gly Tyr Arg Leu Gly Met His His Phe Arg Asp Gly Asp Ala Gly Asn
    210                 215                 220

Leu Ala Leu Val Thr Gly Ala Gly Leu Leu Lys Thr Ser Lys Asn Leu
225                 230                 235                 240

Ala Ala Ala Thr Arg Phe Leu Thr Tyr Leu Leu Ser Pro Gln Ala Gln
                245                 250                 255

Gln Tyr Phe Val Gly Asn Ile Gly Glu Tyr Pro Leu Val Lys Gly Val
            260                 265                 270

Ala Leu Asp Pro Asn Leu Leu Pro Leu Glu Glu Ala Leu Ala Lys Ser
        275                 280                 285

Pro Lys Leu Asp Leu Glu Lys Leu Pro Leu Asp Arg Ala Leu Arg Leu
    290                 295                 300

Leu Arg Glu Thr Gly Val Leu
305                 310


<210> SEQ ID NO 86
<211> LENGTH: 332
<212> TYPE: PRT
<213> ORGANISM: Artificial Sequence
<220> FEATURE:
<223> OTHER INFORMATION: msFeBP6 (with signal peptide replaced with M)

<400> SEQUENCE: 86

Met Ser Leu Thr Leu Tyr Thr Gly Arg Ser Gln Ala Leu Val Asp Lys
1               5                   10                  15

Leu Val Gln Gln Phe Gln Lys Asp Thr Gly Ile Lys Val Asn Val Arg
            20                  25                  30

Tyr Gly Arg Asp Ala Glu Ile Leu Ala Ala Leu Gln Glu Glu Gly Ser
        35                  40                  45

Arg Ser Pro Ala Asp Val Phe Trp Ala Asn Thr Ser Gly Ala Leu Glu
    50                  55                  60

Glu Ala Val Lys Arg Asn Leu Leu Val Gln Leu Pro Ala Ser Leu Thr
65                  70                  75                  80

Arg Gln Pro Gln Glu Phe Val Pro Ser His Gly Arg Trp Val Pro Val
                85                  90                  95

Ser Val Arg Phe Arg Val Ala Ala Tyr Asn Pro Thr Lys Val Lys Asp
            100                 105                 110

Ser Asp Phe Pro Ala Ser Val Met Asp Leu Pro Lys Val Ala Lys Phe
        115                 120                 125

Lys Gly Arg Ile Gly Trp Thr Pro Thr Tyr Ser Ser Phe Gln Asp Phe
    130                 135                 140

Ile Thr Ala Met Arg Val Val Lys Gly Glu Ala Ala Thr Lys Ala Trp
145                 150                 155                 160

Leu Gln Ala Met Ile Ala Ala Gly Ala Lys Ala Tyr Pro Ser Asn Pro
                165                 170                 175

Pro Met Leu Glu Ala Met Gln Ala Gly Glu Ile Asp Val Ala Leu Thr
            180                 185                 190

Asn His Tyr Tyr Ile Gln Arg Ile Leu Ala Gly Val Gly Glu Gly Glu
        195                 200                 205
```

Tyr Glu Gly Lys Glu Glu Ser Glu Glu Glu Glu Lys Lys Glu Leu Ala
    210                 215                 220

Ala Arg Glu Ala Lys Ala Gly Val Ala Thr His Tyr Phe Ala Pro Gly
225                 230                 235                 240

Asp Val Gly Gly Leu Ala Leu Val Thr Gly Ala Gly Ile Leu Ala Thr
                245                 250                 255

Ser Lys His Gln Thr Asn Ala Thr Arg Phe Leu Asn Tyr Leu Leu Ser
            260                 265                 270

Lys Lys Ala Gln Pro Tyr Phe Val Asp Glu Val Arg Glu Tyr Pro Val
        275                 280                 285

Ile Ala Gly Val Arg Val Ala Lys Gly Met Leu Pro Phe Ala Asn Ala
    290                 295                 300

Ile Arg Leu Ser Pro Lys Ile Asp Phe Ala Lys Leu Thr Asp Leu Glu
305                 310                 315                 320

Gly Thr Leu Lys Leu Leu Arg Glu Val Gly Leu Leu
                325                 330

<210> SEQ ID NO 87
<211> LENGTH: 334
<212> TYPE: PRT
<213> ORGANISM: Artificial Sequence
<220> FEATURE:
<223> OTHER INFORMATION: srFeBP7 (with signal peptide replaced with M)

<400> SEQUENCE: 87

Met Leu Val Ile Tyr Ser Gly Arg Ser Lys Ala Leu Val Asp Ser Leu
1               5                   10                  15

Val Gln Gln Tyr Arg Gln Gln Ala Asp Val Pro Val Arg Val Arg Tyr
            20                  25                  30

Gly Thr Asp Ser Gln Leu Leu Ala Ala Leu Gln Glu Glu Gly Asp Gln
        35                  40                  45

Ser Pro Ala Asp Val Phe Trp Ala Asn Thr Thr Gly Ala Leu Gly Asn
    50                  55                  60

Ala Val Asn Asn Gly Leu Leu Thr Glu Leu Pro Asp Thr Leu Ala Asn
65                  70                  75                  80

Arg Ala Ala Arg Phe Thr Pro Ser Asn Gln Arg Trp Thr Pro Val Thr
                85                  90                  95

Thr Arg Phe Arg Val Leu Ala Tyr Asn Ser Asp Ala Val Ser Pro Glu
            100                 105                 110

Asp Leu Pro Asp Ser Val Leu Asp Leu Pro Glu His Glu Glu Phe Glu
        115                 120                 125

Gly Arg Val Gly Trp Thr Pro Ala Tyr Ser Ser Phe Gln Asp Phe Val
    130                 135                 140

Thr Ala Leu Arg Val Thr Glu Gly Ala Glu Thr Ala Arg Thr Trp Leu
145                 150                 155                 160

Ser Asp Met Gln Ala Leu Asn Pro Asn Ser Tyr Thr Ser Asn Thr Pro
                165                 170                 175

Met Val Gln Ala Leu Glu Ala Gly Glu Ile Asp Val Ala Leu Thr Asn
            180                 185                 190

His Tyr Tyr Val Leu Arg Leu Lys His Gly Gly Ala Glu Gly Glu Tyr
        195                 200                 205

Glu Gly Glu Glu Glu Glu Gly Glu Glu His Glu Glu Glu His Glu Glu
    210                 215                 220

Glu Ala Thr Pro Arg Ala Ser Ala Pro Val Glu Met Tyr His Phe Ala
225                 230                 235                 240

```
Asp Gly Asp Leu Gly Asn Leu Ala Leu Val Thr Gly Ala Gly Ala Leu
                245                 250                 255

Gln Thr Ser Asn Gln Pro Asp Ala Ala Asn Arg Phe Leu Arg Phe Leu
            260                 265                 270

Leu Ser Glu Gln Ala Gln Ser Phe Ala Ala Thr Arg Val Asn Glu Tyr
        275                 280                 285

Pro Val Val Ser Gly Ala Ser Val Pro Asp Tyr Leu Met Pro Ala Asp
    290                 295                 300

Glu Ala Leu Lys Met Ser Pro Glu Phe Asp Leu Gln Lys Leu Gln Asn
305                 310                 315                 320

Met Glu Pro Thr Leu Asp Leu Leu Arg Asp Ala Gly Ala Leu
                325                 330


<210> SEQ ID NO 88
<211> LENGTH: 304
<212> TYPE: PRT
<213> ORGANISM: Artificial Sequence
<220> FEATURE:
<223> OTHER INFORMATION: hlFeBP8 (with C138A and C176A substitution
      mutations and signal peptide replaced with M)

<400> SEQUENCE: 88

Met Leu Thr Val Tyr Ser Gly Arg Gly Glu Phe Leu Val Gly Glu Leu
1               5                   10                  15

Val Glu Tyr Ile Glu Asp Gln Tyr Asp Asp Phe Asp Leu Thr Val Arg
            20                  25                  30

Tyr Ala Gly Ser Thr Asp Leu Val Asn Gln Ile Leu Asn Glu Gly Asp
        35                  40                  45

Gly Ser Pro Ala Asp Val Phe Tyr Ser Val Asn Ala Gly Ser Leu Gly
    50                  55                  60

Thr Leu Ala Gly Glu Gly Arg Ser Gln Ala Leu Ser Ser Glu Ile Thr
65                  70                  75                  80

Asp Met Val Arg Ser Glu Phe Arg Thr Glu Gln Trp Ile Gly Thr Ser
                85                  90                  95

Gly Arg Ala Arg Thr Val Pro Tyr Asn Thr Gly Glu Phe Ser Asp Asp
            100                 105                 110

Asp Leu Pro Asp Asp Ile Met Ala Tyr Pro Glu Glu Phe Ala Gly Ser
        115                 120                 125

Leu Gly Trp Ala Pro Ser Tyr Gly Ser Ala Gln Ala Phe Ile Thr Ala
    130                 135                 140

Met Arg Leu Ile Glu Gly Glu Glu Ala Thr Leu Ala Trp Leu Glu Ser
145                 150                 155                 160

Val Val Glu Ala Gly Ile Ser Ser Tyr Pro Asp Glu Phe Ala Ala Ala
                165                 170                 175

Gln Ala Ile Ala Asp Gly Glu Ile Asp Ala Ala Phe Thr Asn His Tyr
            180                 185                 190

Tyr Ile Gln Arg Val Leu Asp Gly Asn Pro Asp Ala Ser Ile Gly Thr
        195                 200                 205

Ala Phe Thr Ser Gly Asp Ala Gly Ala Val Phe Asn Val Ala Gly Ala
    210                 215                 220

Ala Val Val Asp Thr Ala Ser Asp Ala Thr Leu Ala Glu Asn Phe Ile
225                 230                 235                 240

Arg His Leu Leu Ser Ala Glu Ala Gln Asp Tyr Phe Ala Arg Ser Thr
                245                 250                 255

Phe Glu Tyr Pro Leu Ile Pro Asp Val Glu Pro Ile Gly Asp Leu Pro
            260                 265                 270
```

```
Thr Ile Asp Glu Leu Asp Val Pro Asp Ile Asp Leu Thr Glu Leu Ser
        275                 280                 285

Asp Leu Glu Pro Thr Ile Asp Leu Met Arg Glu Ala Gly Val Glu Val
    290                 295                 300


<210> SEQ ID NO 89
<211> LENGTH: 9
<212> TYPE: PRT
<213> ORGANISM: Artificial Sequence
<220> FEATURE:
<223> OTHER INFORMATION: GGSHHHHHH Sequence

<400> SEQUENCE: 89

Gly Gly Ser His His His His His His
1               5


<210> SEQ ID NO 90
<211> LENGTH: 18
<212> TYPE: PRT
<213> ORGANISM: Artificial Sequence
<220> FEATURE:
<223> OTHER INFORMATION: bZif

<400> SEQUENCE: 90

Thr Gly Glu Lys Pro Tyr Lys Cys Pro Glu Cys Gly Lys Ser Phe Ser
1               5                   10                  15

Arg Ser


<210> SEQ ID NO 91
<211> LENGTH: 32
<212> TYPE: PRT
<213> ORGANISM: Artificial Sequence
<220> FEATURE:
<223> OTHER INFORMATION: ZF-QNK

<400> SEQUENCE: 91

Thr Gly Glu Lys Pro Tyr Lys Cys Pro Glu Cys Gly Lys Ser Phe Ser
1               5                   10                  15

Arg Ser Asp His Leu Ser Arg His Gln Arg Thr His Gln Asn Lys Lys
            20                  25                  30


<210> SEQ ID NO 92
<211> LENGTH: 6
<212> TYPE: PRT
<213> ORGANISM: Artificial Sequence
<220> FEATURE:
<223> OTHER INFORMATION: Hexahistidine Tag

<400> SEQUENCE: 92

His His His His His His
1               5


<210> SEQ ID NO 93
<211> LENGTH: 6
<212> TYPE: PRT
<213> ORGANISM: Artificial Sequence
<220> FEATURE:
<223> OTHER INFORMATION: Hexalysine Tag

<400> SEQUENCE: 93

Lys Lys Lys Lys Lys Lys
1               5


<210> SEQ ID NO 94
```

<211> LENGTH: 309
<212> TYPE: PRT
<213> ORGANISM: Artificial Sequence
<220> FEATURE:
<223> OTHER INFORMATION: ecGGBP (with signal peptide removed)

<400> SEQUENCE: 94

```
Ala Asp Thr Arg Ile Gly Val Thr Ile Tyr Lys Tyr Asp Asp Asn Phe
1               5                   10                  15

Met Ser Val Val Arg Lys Ala Ile Glu Gln Asp Ala Lys Ala Ala Pro
            20                  25                  30

Asp Val Gln Leu Leu Met Asn Asp Ser Gln Asn Asp Gln Ser Lys Gln
        35                  40                  45

Asn Asp Gln Ile Asp Val Leu Leu Ala Lys Gly Val Lys Ala Leu Ala
    50                  55                  60

Ile Asn Leu Val Asp Pro Ala Ala Ala Gly Thr Val Ile Glu Lys Ala
65                  70                  75                  80

Arg Gly Gln Asn Val Pro Val Val Phe Phe Asn Lys Glu Pro Ser Arg
                85                  90                  95

Lys Ala Leu Asp Ser Tyr Asp Lys Ala Tyr Tyr Val Gly Thr Asp Ser
            100                 105                 110

Lys Glu Ser Gly Ile Ile Gln Gly Asp Leu Ile Ala Lys His Trp Ala
        115                 120                 125

Ala Asn Gln Gly Trp Asp Leu Asn Lys Asp Gly Gln Ile Gln Phe Val
    130                 135                 140

Leu Leu Lys Gly Glu Pro Gly His Pro Asp Ala Glu Ala Arg Thr Thr
145                 150                 155                 160

Tyr Val Ile Lys Glu Leu Asn Asp Lys Gly Ile Lys Thr Glu Gln Leu
                165                 170                 175

Gln Leu Asp Thr Ala Met Trp Asp Thr Ala Gln Ala Lys Asp Lys Met
            180                 185                 190

Asp Ala Trp Leu Ser Gly Pro Asn Ala Asn Lys Ile Glu Val Val Ile
        195                 200                 205

Ala Asn Asn Asp Ala Met Ala Met Gly Ala Val Glu Ala Leu Lys Ala
    210                 215                 220

His Asn Lys Ser Ser Ile Pro Val Phe Gly Val Asp Ala Leu Pro Glu
225                 230                 235                 240

Ala Leu Ala Leu Val Lys Ser Gly Ala Leu Ala Gly Thr Val Leu Asn
                245                 250                 255

Asp Ala Asn Asn Gln Ala Lys Ala Thr Phe Asp Leu Ala Lys Asn Gln
            260                 265                 270

Ala Asp Gly Lys Gly Ala Ala Asp Gly Thr Asn Trp Lys Ile Asp Asn
        275                 280                 285

Lys Val Val Arg Val Pro Tyr Val Gly Val Asp Lys Asp Asn Leu Ala
    290                 295                 300

Glu Phe Ser Lys Lys
305
```

<210> SEQ ID NO 95
<211> LENGTH: 1637
<212> TYPE: DNA
<213> ORGANISM: Artificial Sequence
<220> FEATURE:
<223> OTHER INFORMATION: Exemplary Expression Construct for synBicarbBP1

<400> SEQUENCE: 95

```
gccagtaagc ttcggtcacg cttgggactg ccataggctg gcccggtgat gccggccacg     60
```

atgcgtccgg cgtagaggat cgagatctcg atcccgcgaa attaatacga ctcactatag 120
ggagaccaca acggtttccc tctagaaata attttgttta actttaagaa ggagatatac 180
catgccagaa atgatgccag aaacagctaa tattaagctg ggttatatcc ctattgttga 240
ggcagctcct ctcatcatcg cccaggaaaa agggttcttc gctaaatacg ggatgacggg 300
tgtggaagtc agtaaacaag ccaattgggc atcagcacgt gataatgtga ccatcggcag 360
tcaaggcggc gggattgacg gtggccaatg gcaaatgcca atgcctcact tgattacgga 420
agggatcatc accaatggca acaaggtacc aatgtacgta ctggcacagt tgatcactca 480
aggtaacggg atcgcagtcg cgccgatgca tgaaggtaaa ggtgtaaact tggacatcac 540
gaaagccgcc gactacatta agggtttcaa caagacaaac ggtcgtaaat ttaaagcagc 600
gcacaccttc ccaaatgtca accaagactt ttggattcgc tactggtttg cagcaggcgg 660
cgtcgaccca gatacagaca ttgatttatt ggcagtgcct ccagccgaga cagtacaagg 720
gatgcggaat gggacaatgg acgccttctc gaccggtgac ccatggccat accggatcgt 780
aactgagaac atcgggtata tggcgggtct taccgcgcaa atttggcctt atcaccctga 840
agaatattta gcaattcgtg cggactgggt cgacaagaat ccaaaggcga ccaaagcgtt 900
actcaaaggt attatggagg ctcagcagtg gattgacgac ccaaaaaatc gtccagaggt 960
tgtacaaatc gtctccggtc ggaattattt taacgtccca actactatcc tcgagagtcc 1020
attcaaaggt caatatacta tgggcgacgg tcaaccggcc atcgatgact tccaaaaggg 1080
cccattgtac tggaaagatg gtatcgggaa cgtatcctac ccatacaaat ctcacgattt 1140
atggtttctt acggaatcca tccgctgggg cttccataaa aatgctattc cagacttaga 1200
tacggcgcag aagattatcg ataaggtcaa ccgcgaagat ttatggcggg aagcggcaac 1260
cgaggcaggc tttacagctg acattccaag ttcaacctca cgtggcgtag aaaccttttt 1320
cgatggtatt actttcgacc ctgcaaaccc atccgcatac ttacagtcac ttgcaattaa 1380
gaaagtaggt ggttcacatc atcatcatca tcattaatga aagggcgata tccagcacac 1440
tggcggccgt tactagtgga tccggctgct aacaaagccc gaaaggaagc tgagttggct 1500
gctgccaccg ctgagcaata actagcataa ccccttgggg cctctaaacg ggtcttgagg 1560 ggtttttttgc tgaaaggagg aactatatcc ggagcgactc ccacggcacg ttggcaagct 1620
cggaattcgg cgtaatc 1637

<210> SEQ ID NO 96
<211> LENGTH: 1634
<212> TYPE: DNA
<213> ORGANISM: Artificial Sequence
<220> FEATURE:
<223> OTHER INFORMATION: Exemplary Expression Construct for teBicarbBP2

<400> SEQUENCE: 96
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catgttagaa acagatacca ttaaattagg tttcattccg attgtagagt cagccccact 240
cattattgcc aaagaaaaag gcttcttcgc caaacacggg ttgactaatg cggaactctc 300
caagcaggca aactgggcaa gtgcgcgtga caacgtagta atcgggtcgg caggtggcgg 360
tatcgatggt ggccagtggc aaatgcctat gccttatctc atctcagagg ggatcattac 420

-continued

```
actcaataac caaaaactcc ctatgtatgt cctcgcacag cttaatacac aaggcaacgg    480

tatcgcaatc tccggtgcaa ataaggggaa aggtctccac ttaaagattg ccgacccaga    540

ctacatcaag ggcttcgccg ccaagaatgg tcgtaaattt aaagcagctc atacattccc    600

tcacgtcaat caagatctct ggattcgcta ctggttcgca gcaaacggca ttgaccctga    660

tcgcgacatt gagttattag ctgttccgcc agcagagact gtagcgggta tgcgcaatgg    720

tacaatggac gcattttcaa ccggcgaccc atggccattt cgtatcgtat cagacgacat    780

cggttacatg gcgacgttaa cagcccagat ctggccatac catcctgaag aatacctcgc    840

agttcgtgcc gattgggtag acaaacatcc taaagctact aaggcgctcc tcaaagcagt    900

catggaggca cagcagtggg cagacgacaa ggccaatcgt ccagaactga tccagatcgc    960

aagtcggcgc gaatacttca atatccctgg taacattttg accccgccat atgagggcac   1020

atatacaatg ggtgatggcc aaccgaattt caacgatttt aacattggtc cattatactg   1080

gcgtgacccg aacggtaatt ctatcagcta cccgtataaa agccacgact tatggttcct   1140

cactgagaat ctgcgctggg gctttaacgc cgacaagctg aaggattttg acaatattaa   1200

gcagatgatt gggcgggtaa atcgcagtga cctctggcag gaggcagcca aggaactcgg   1260

tatcccagca gccgaaatcc cgacaacaga atcacgcggt gtagagactt tcttcgacgg   1320

gattaagttc gacccagaca atccacaagc ctatctcgat tccttaaaga tcaaagtcaa   1380

gtctggcggt tctcatcatc atcatcatca ttaatgaaag ggcgatatcc agcacactgg   1440

cggccgttac tagtggatcc ggctgctaac aaagcccgaa aggaagctga gttggctgct   1500

gccaccgctg agcaataact agcataaccc cttggggcct ctaaacgggt cttgaggggt   1560

tttttgctga aaggaggaac tatatccgga gcgactccca cggcacgttg gcaagctcgg   1620

aattcggcgt aatc                                                     1634
```

<210> SEQ ID NO 97
<211> LENGTH: 1634
<212> TYPE: DNA
<213> ORGANISM: Artificial Sequence
<220> FEATURE:
<223> OTHER INFORMATION: Exemplary Expression Construct for ctBicarbBP3

<400> SEQUENCE: 97

```
gccagtaagc ttcggtcacg cttgggactg ccataggctg gcccggtgat gccggccacg     60

atgcgtccgg cgtagaggat cgagatctcg atcccgcgaa attaatacga ctcactatag    120

ggagaccaca acggtttccc tctagaaata attttgttta actttaagaa ggagatatac    180

catgccagaa caagcacctg aaacaacacg tgttaagtta ggctatatcc cgatcgttga    240

agccgcaccg atcatcattg caaaagagaa aggcttcttc gctaagtatg gcatgaccga    300

tgtagacgta agtaagcagg ctagctgggg ctcgatgcgt gacaatacgg agatcggtgc    360

agcgggcggg ggggtcgacg gggtcaata ccaaatgcca atgccacatc tgatcactga     420

gggccgcatt acaaagggga acaaaccaat ccctatgtac gtcctcgccc aattaaatac    480

gcaggggaac ggcattgcca tcgccgaaaa acatcggggg aaagggatcg aactggaatt    540

ggcaaaaggt ggcaaaaacc tctttggcca gcttaagtcg gctaatactc cattcactgc    600

cgcatacaca ttcgcgcaag taaaccaaga cttctggatc cgttactggt tggctgcagg    660

gggtgtaaac ccggacgcgg atgtaaaact gattccggtt ccggcggcac agacggtagc    720

caacatgaag acaggtacca tggatgcatt ctccaccggt gacccttggc cttatcgtat    780

cgttaaagac aaaattggct tcttagcaat gctcaccgcc gacatgtggg aatttcatcc    840
```

```
agaggagtac ttagccttgc gcgcggaatg ggtcgacaaa cacccaaaag ctacgaaagc    900

cttgcttaaa ggtatcatgg aggcgcaaca atggcttgat aactttgata accgtgaaga    960

ggcagccaag attctcggtg gccgtaatta cttcaatctc ccagcagaaa tcctcgcagg   1020

tccattcgcc gggaagtatg acatgggggga gggtcggact gtagatgacc gcaataaggc   1080

cgtactctac tggaaggatc cacgcggcag cgtcagctac ccatataaat cacacgactt   1140

atggttctta actgaatccg tccgctgggg ctttctccca ccggatagtt taactaaagc   1200

gcaggcgctg attgacaaag tgaaccgcga agatctctgg aaagaagccg caaaagaatt   1260

aggcgtagcc gcagccgata ttccaaccag caccagtcgc ggcgtagaaa ccttctttga   1320

cggtgtcaag ttcgacccgg aaaatcctgc agcgtatctc aagtcattaa agattaagaa   1380

agcaggcggt agtcatcatc atcatcatca ttaatgaaag ggcgatatcc agcacactgg   1440

cggccgttac tagtggatcc ggctgctaac aaagcccgaa aggaagctga gttggctgct   1500

gccaccgctg agcaataact agcataaccc cttggggcct ctaaacgggt cttgaggggt   1560

tttttgctga aaggaggaac tatatccgga gcgactccca cggcacgttg gcaagctcgg   1620

aattcggcgt aatc                                                     1634


<210> SEQ ID NO 98
<211> LENGTH: 1649
<212> TYPE: DNA
<213> ORGANISM: Artificial Sequence
<220> FEATURE:
<223> OTHER INFORMATION: Exemplary Expression Construct for calBicarbBP4

<400> SEQUENCE: 98

gccagtaagc ttcggtcacg cttgggactg ccataggctg gcccggtgat gccggccacg     60

atgcgtccgg cgtagaggat cgagatctcg atcccgcgaa attaatacga ctcactatag    120

ggagaccaca acggtttccc tctagaaata attttgttta actttaagaa ggagatatac    180

catgcctgaa caaaaacctg aaactgaaac agttaaactc ggctacatcc caatcgttga    240

atcggcgcct ctcatcattg caaaggagaa agggttgttc gcaaaaatacg gtatgaccaa   300

ggtggagctc gcaaagcagg ccagctgggg tgcagcacgg gataacgtag aaattgggtc    360

ggcaggtggc ggtatcgacg gcggtcagtg gcaaatgcca atgcctcatc tcatcaccgc    420

aggcctgatt acaaagggta ataaggagat ccctatgtat gtactcgcac agttagtcac    480

ccatggcaac ggtatcgcca ttgcagacaa acacaaaggt aagggcctcg gtttaaaatt    540

agatggtgcc aaatccctct tcaaagaact gaagtcaagt accccctttca cggcagcctt   600

cacgttccct cacgtcaacc aagacttatg gatccggtac tggttagcgg catccggtct    660

cgaccctgac gcggacgtca aactcttgac agtcccagcc gcacaaacag tcgccaacat    720

gaagaccggc accatggatg ccttttccac cggcgaccca tggccatttc gtatcgtaaa    780

tgataaaatt ggtttcatgg cattgcttac cgcggaaatg tggaaaaatc accctgagga    840

gtacttagcc atgcgtggcg actgggtcga caagcaccca aaggctacca aagcaatttt    900

aaaggcggtg atggaagcac aacagtggtt agacaacttt gaaaaccgga aggaggcagc    960

aacgattctc gcagggcgta aatattttga tctcagctca ccagagatcc tcctcgatcc   1020

atatcaaggt aaatacgaca tgggcgatgg tcgtaaaatc gatgacaaac tgatggctcc   1080

atactactgg aaagacgaaa agggttccgt gtcctatcca tacaagagtc acgatttatg   1140

gttcatcacc gagaatgtac gttggggctt tttaccaaag gactatctcg ccaacaatgc   1200
```

```
cgccaaagcg aaagaattaa tcaacaaagt caaccgtgag gacatttgga aggaggctgc   1260

caaggacctg ggattgcag cagcagacat cccaacaagt acgtcccgcg ggtagagga   1320

gttcttcgat ggcgttaagt ttgatccaga gaagcctgaa gagtatctca aatcactgaa   1380

aattaaaaaa gcaggggtag gtggttctca tcatcatcat catcattaat gaaagggcga   1440

tatccagcac actggcggcc gttactagtg gatccggctg ctaacaaagc ccgaaaggaa   1500

gctgagttgg ctgctgccac cgctgagcaa taactagcat aaccccttgg ggcctctaaa   1560

cgggtcttga ggggtttttt gctgaaagga ggaactatat ccggagcgac tcccacggca   1620

cgttggcaag ctcggaattc ggcgtaatc                                      1649
```

<210> SEQ ID NO 99
<211> LENGTH: 1649
<212> TYPE: DNA
<213> ORGANISM: Artificial Sequence
<220> FEATURE:
<223> OTHER INFORMATION: Exemplary Expression Construct for avBicarbBP5

<400> SEQUENCE: 99

```
gccagtaagc ttcggtcacg cttgggactg ccataggctg gcccggtgat gccggccacg     60

atgcgtccgg cgtagaggat cgagatctcg atcccgcgaa attaatacga ctcactatag    120

ggagaccaca acggtttccc tctagaaata attttgttta actttaagaa ggagatatac    180

catggctgaa caagcaccag aagttacaac agtaaagctc gggtatatcc cgattgtcga    240

atccgctcct ctcatcattg ctaaagaaaa ggggtttttc gccaagtatg gtctgacaaa    300

tgtagaatta tcgaaacagg catcgtgggg cagtgcccgg gataatgtag agatcggtag    360

cgccgggggc gggatcgacg gtggtcaatg gcagatgcct atgccacatc tcatcactga    420

aggcttaatt acgaagggca atcagaaaat cccaatgtac gtcttagcac agttgatcac    480

ccacgggaac gggattgcca ttgcaaacaa acatcaaggg aaggggatca gtttgaagct    540

cgagggtgct aagagcctgt tcagtcagct caagagctcc acgccattca cagccgcttt    600

cacttttcct catgtaaatc aagacttatg gattcgctac tggttggctg caggggggtat   660

tgaccctgat gcagatgtaa aattgttaac ggtcccagca gcccaaaccg tagccaatat    720

gaagaccggc acaatggacg cattttccac gggcgaccca tggccattcc gtctcgtaaa    780

cgacaaaatc ggttacatgg cggccttgac agcggagatc tggaaaaacc accctgagga    840

atacctcgca atgcgtgcag attgggtcga caagtatcca aaagcaacta aggcattatt    900

aaaaggcatc atggaggccc aacaatggtt ggacaacttt gacaatcgca aggaggcggc    960

acagattttg gctggccgca actactttaa cctcaacaac ccggaaatcc tggcggatcc   1020

ttacgtaggt aagtacgata tgggtgatgg tcgcaagatt gacgataaaa gcatggctgc   1080

gtattactgg aaggatgaaa aagggtcagt ttcttaccca tacaaatcgc acgacttatg   1140

gttcatcact gaaaacgtcc gttggggggtt tctgccgaag gattatctgg caaacggtgc   1200

agccaaagct aaggagttaa tcgacaaggt caatcgggag gacatctgga aagaagcagc   1260

taaagaagcc ggtattgcag cggccgacat tccaaccagc acgtcccgtg gggtagaaga   1320

gttcttcgac ggcaccaaat tcgacccaga aaagccagac gaatatctga aatcgctcaa   1380

aatcaaaaaa gtcagcgtag gtggttcaca tcatcatcat catcattaat gaaagggcga   1440

tatccagcac actggcggcc gttactagtg gatccggctg ctaacaaagc ccgaaaggaa   1500

gctgagttgg ctgctgccac cgctgagcaa taactagcat aaccccttgg ggcctctaaa   1560

cgggtcttga ggggtttttt gctgaaagga ggaactatat ccggagcgac tcccacggca   1620
```

cgttggcaag ctcggaattc ggcgtaatc 1649

<210> SEQ ID NO 100
<211> LENGTH: 1649
<212> TYPE: DNA
<213> ORGANISM: Artificial Sequence
<220> FEATURE:
<223> OTHER INFORMATION: Exemplary Expression Construct for cmBicarbBP6

<400> SEQUENCE: 100
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catgtcaagt gcaacaacac cagaaacaac agcagttaaa ttaggttaca tcgctatcgc 240
cgaaagcgca ccacttatca tcgcgcggga gaaaggcttc ttcgcacgtc atggtatgac 300
cgatgtagac gtctctaagc aggcctcctg ggtagcgcc cgcgataaca ttgaaatcgg 360
ctcgagtaac ggtgggatcg acgggggtca gtggcagatg cctatgccgc agttaattag 420
cgaaggtatt atcacaaagg gtaatcgtaa aatcccaatg cttagtttgg cccagctcag 480
tacacagggt aacggtatcg ccatctcgac acagcatgca ggtaagggtt ttggcctgga 540
cgtctccggt gccgccgaat acgtacgcga catgaaggca gacggtaaac catttaaggc 600
agcatacaca ttcccacgtg tcaatcagga cttttggatt cggtactggc tcgcagcagg 660
tgggatcgac ccaaacaagg acatcgactt aattgcagta ccggccgcac aaaccgtagc 720
ctccatgcgg actggctcaa tggacgggtt tagtacaggt gacccttggc catcccgcat 780
cctgcgtgac cggcgtaagt acggtttcct cgccgtcctc acggctcaga tttggcctgc 840
tcatcctgaa gagtattttg caatgcgtga ggattgggtt cgtaaacacc ctaaggcagc 900
gaaggccatc ctcaaaggta ttatggaagc acaaatgtgg gcagacgatc caaagaaccg 960
tgcggaaatg gccgccatct tagcccagcg taaatatttc aacgtcccta gcgacttatt 1020
gatcggtcct tatgtcgggg aatacatttt gggtgcggac cgcaagacag taaaggacga 1080
gaagctcgca attcgctatt ggaaagatgc acggggtaat gtttcttacc catacaaatc 1140
ccatgactta tggtttctta cagaatccgt ccgttggggc ttcctgccac aaggcgcgtt 1200
aggtgaagcc gatcgtatca tcaatgccgt ctcaggcgaa aaatactggc gggaggcagc 1260
tcaagaactg ggtatcgcaa gtgcagacat tccaccgtca acgtcacgtg gcattgagaa 1320
attcttcgac ggcgccgagt tcaacccgga aaaaccaaaa gcatatttag actccttaaa 1380
aattaagaat ttaaaagcag gtggttcaca tcatcatcat catcattaat gaaagggcga 1440
tatccagcac actggcggcc gttactagtg gatccggctg ctaacaaagc ccgaaaggaa 1500
gctgagttgg ctgctgccac cgctgagcaa taactagcat aaccccttgg ggcctctaaa 1560
cgggtcttga ggggtttttt gctgaaagga ggaactatat ccggagcgac tcccacggca 1620
cgttggcaag ctcggaattc ggcgtaatc 1649

<210> SEQ ID NO 101
<211> LENGTH: 1355
<212> TYPE: DNA
<213> ORGANISM: Artificial Sequence
<220> FEATURE:
<223> OTHER INFORMATION: Exemplary Expression Construct for mhFeBP1

<400> SEQUENCE: 101

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggcaaatga    180

agtaaatgta tatagttatc gtcaaccgta cttaatcgag ccaatgctca agaacttcga    240

gaaagacacc ggtatcaagg tcaacattat cttcgcagac aagggcctcg tcgaccgcgt    300

caaacaagag ggtgaattgt ccccagccga tgtattatta accgtcgaca tcagtcgtgt    360

catggaaatt gtaaacgcag atctcgcaca aaagatcgac tcgaaggttc tggaaaagaa    420

catcccggcg cagtttcgcg acagtaacga tcaatggttc ggcttaacga cacgtgctcg    480

tgtaatctat acatctaaag accgcgtcgg caaactccca gcgggcttcg actatctcga    540

cttggcaaag ccagaataca agggcaaagt agcggtccgt tcagggaaga actcctataa    600

cgtcagtctc ttcgcggcca tgatcgaaca ttacggcatt gaaaaaacaa aagcgtttct    660

ggaaggcctc aaggcgaacc tcgcacgcaa gccacagggt ggtgaccggg accaggtgaa    720

agcaatcaag gagggcatcg cagattactc tatcgggaac tcatactatt atggcaagat    780

gcttgacgat gaaaagcaga aaagctgggc tgaggccgcg atcatcaatt ttccatcagg    840

tgaacacggt acccacaaga atatttcagg tgtagtcatc gccaagcact ctccaaacaa    900

agcaaacgcc gtgaagctca ttgagtacct ctctggggag aaggcacaag gtctgtatgc    960

ggaactcaac cacgaatacc cagtcaaaga gggcatcgag ccgtcggcaa tcgtaaaggg   1020

ctggggtaca tttaaatcgg atacaatcaa gttggaagat attgcgaaga actacgaggc   1080

ggcattgaaa ttagtcgacg aggtaaaatt cgacgacttt gggggttctc atcatcatca   1140

tcatcattaa tgaaagggcg atatccagca cactggcggc cgttactagt ggatccggct   1200

gctaacaaag cccgaaagga agctgagttg gctgctgcca ccgctgagca ataactagca   1260

taaccccttg gggcctctaa acgggtcttg aggggttttt tgctgaaagg aggaactata   1320

tccggagcga ctcccacggc acgttggcaa gctcg                              1355
```

<210> SEQ ID NO 102
<211> LENGTH: 1355
<212> TYPE: DNA
<213> ORGANISM: Artificial Sequence
<220> FEATURE:
<223> OTHER INFORMATION: Exemplary Expression Construct for exiFeBP2

<400> SEQUENCE: 102

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgaacgtagt    180

aaatgtgtat tcaagtcgtc attatgacgt ggaccagcag ttgtacaaac agttcgagga    240

ggaaacaggg atcaaggtta acgtcgtaga gggcaaatca gatgaactgc tcgaacgcct    300

taacaccgag ggcgagaaca ctgaggcaga tctcttcatt acagcagatg cggggaatct    360

ctatcaagct aaagaagctg gtcacttaca ggcagtagat tccgatgaat tagaatccaa    420

tattccagaa aaataccgcg acactgacaa cgaatggttc ggtcttacca aacgtgcgcg    480

tgtcatcgtc tattcgaaag accgcgtgaa accggaagat ttatcgacct atgaggccct    540

gacagaggag cagtggaacg ggaaagtatt agtccgtccg tcggaaaaca tgtataacat    600

cagtctcctg gcatcattca tcgaggtcaa tggcgtcgac gaagcgaaag aatgggcaaa    660

gggtttggtc aacaatatgg cccgtgatcc gcagggtaac gatcgggatc aggcaaaggc    720
```

cgtagtagca ggtgagggcg atgtagccat catgaataca tactacatgg ggttgatgtt 780
gaactcagaa gacgaagaag aaaaaaaagt cgccgagcag ttaggcgtat tctttccaaa 840
tcaggacaca acggggactc atgtaaacat ttccgggatt gccatgacga aagcctccaa 900
gaacacggag aatgcacaga aattaatgga gtttatgtcg gagccatcag cacaggaaaa 960
gttcgcctct gtaaattacg aatacccagt caacgaatcg gtggaaccga acgagttact 1020
tcagtcgtgg ggcgaattta aagagcagga tattaacctc agcgcgctcg gcgaaaacca 1080
acaggaggca atccggatct tcaacgaggt ggggtggaaa ggtggttcac atcatcatca 1140
tcatcattaa tgaaagggcg atatccagca cactggcggc cgttactagt ggatccggct 1200
gctaacaaag cccgaaagga agctgagttg gctgctgcca ccgctgagca ataactagca 1260
taaccccttg gggcctctaa acgggtcttg aggggttttt tgctgaaagg aggaactata 1320
tccggagcga ctcccacggc acgttggcaa gctcg 1355

<210> SEQ ID NO 103
<211> LENGTH: 1352
<212> TYPE: DNA
<213> ORGANISM: Artificial Sequence
<220> FEATURE:
<223> OTHER INFORMATION: Exemplary Expression Construct for teFeBP3

<400> SEQUENCE: 103
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggtaattaa 180
tgtatatagt gcacgtcatt acgacactga caaggctctc tataatacct tcacccaaca 240
aaccgggatt cgtgtaaaca tcattgaggc tgaggcagat gccctcattg aacgtattcg 300
ttctgaaggt tcgcgcaccc cagccgatgt actcattaca gtagacgcgg gtcgcttatg 360
gcgtgcgcaa gaagctggca tcttacagcc gattcaatcg cgtgttttaa acagtgtagt 420
accagccaac ctccgggaac cacagggtca ctggttcggt ctctcccgtc gtgttcgcgt 480
tctgatttat aacaagtccc gtgttaatcc atctcagctt tccacatacg aagatttagc 540
taatccgaag tggcgccgtc agatcctgac acgttcttca agcaacattt acaaccaatc 600
gttgacaggt tccttactcg ccattcacgg ggcacagaag accgaacaat gggcacgtgg 660
cttagtacag aacttcgcac gtccaccgga ggggaatgac acagctcaaa ttcgtgcaag 720
tgcagagggc gttggctcag tagcgatcgc caatcactat tacctcgccc gtttaattgc 780
cagtgacaag gagcaagacc gtgcggtggc cgcaaaggtg ggcctctttt tcccgaacca 840
acgtgaccgc ggtgcacatg tcaatatcag tggggcaggt gtagtcgccg gcgctcctaa 900
ccgtcaaggc gcaattcggt tcttagagta cctggtctcc ccaaaggccc aggaaatgtt 960
tgctatggct aactttgagt acccggtacg cgcaggcgtc ccagtccacc ctatcgtcaa 1020
gcaattcggc aactttcgtg gtcaaaatgt caacgcagca gtattcgggc gcaacaacgc 1080
agaagcactt cgtatcatgg accgggccgg ttggcgtggc ggtagtcatc atcatcatca 1140
tcattaatga aagggcgata tccagcacac tggcggccgt tactagtgga tccggctgct 1200
aacaaagccc gaaaggaagc tgagttggct gctgccaccg ctgagcaata actagcataa 1260
ccccttgggg cctctaaacg ggtcttgagg ggttttttgc tgaaaggagg aactatatcc 1320
ggagcgactc ccacggcacg ttggcaagct cg 1352

<210> SEQ ID NO 104
<211> LENGTH: 1340
<212> TYPE: DNA
<213> ORGANISM: Artificial Sequence
<220> FEATURE:
<223> OTHER INFORMATION: Exemplary Expression Construct for cnFeBP4

<400> SEQUENCE: 104
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgaaattagt 180
agtatattca ggtcgtgcag aacgtctcat taaaccagta ctcgatgaat ttcaagcaaa 240
gtcaggcatt cagattgaac tgctttccag tgggacgacc gaattagtaa accgcctcca 300
ggcagaaggc gatcatactc cagccgatgt attcttaaca aacgacgccg gtagtctcga 360
gcacgcgcgc gaattgaaac tccttcgtcc gatgaacatg cgggaagtag agcgtgcgat 420
cccatcccag ttccgggccg cggacaattc atggatcggg ctctctggcc gtttttggat 480
cgttgtctac aacacaaacc ttgtaaagcc agatcagatt aaatcgctct tcgaccttac 540
gcagccacag tggaaagaca agatcgccgt ccctaattca gggtcagaat acttgcaggc 600
tggtgtctca gtgattaagg ctactttcgg cgacgagcgt accaagcagt tcctccaagg 660
gctcaaggct aacgcaggta cgcaagtata tcaaaaatca agccagattg ttgaagccgt 720
tgctaagggt caagttgccg ctggtatcgt aaaccactac tatatctacc gtcatctcgc 780
tacccaacct actgcaccaa ttgcagcggt catgacagac cagcaagaag gtgggatggg 840
cgcaattatg aatgtaacag gtatcggtgt aacccgtgca agtaaacatg tagagagcgc 900
caaattactg attgagtttc tcgtggccca ggctggccaa aagatgtttg ccgatctcga 960
taaagagtac ccgttgcatc cagacgtgaa agcggaccca actttaatcg atcgccgtac 1020
atttcgtgcc gctcaggtgc cactggcccg gttagccgaa ttgcgtgagg ctacgctcac 1080
actcattgag caggtcggtt tacgtggggg ttcacatcat catcatcatc attaatgaaa 1140
gggcgatatc cagcacactg gcggccgtta ctagtggatc cggctgctaa caaagcccga 1200
aaggaagctg agttggctgc tgccaccgct gagcaataac tagcataacc ccttggggcc 1260
tctaaacggg tcttgagggg ttttttgctg aaaggaggaa ctatatccgg agcgactccc 1320
acggcacgtt ggcaagctcg 1340

<210> SEQ ID NO 105
<211> LENGTH: 1337
<212> TYPE: DNA
<213> ORGANISM: Artificial Sequence
<220> FEATURE:
<223> OTHER INFORMATION: Exemplary Expression Construct for ttFeBP5

<400> SEQUENCE: 105
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgtcacctac 180
attaactatt tattcaggtc gtgggcagtc actcgtagaa ccgttagtta agcaattcga 240
agcagagaca ggtattcgtg tgcaagttcg gtactccact gacgcacaga ttttggccgc 300
tttgcaagag gaagggagtc gttccccagc agatctgttt tgggccaaca cagccggcgc 360
gctgggccaa gcctccgcca aaggcctttt acgtccactt ggcgagacgt tgctcgagaa 420
gccaattgcg ttcgttccag cctcacggac ctgggtcccg gtcactgtac gcctccgcgt 480
cctggcatac aacccagatc gcattaaggc tgaagaactc ccagagtcac tgttggactt 540
acctcgcttc gcacgggaaa aagggctcgt agggcgtgta gggtggaccc caacatattc 600
cagtttccag gacatggtag ctggtatgat tgccctttat ggtgaagaaa aaacccggga 660
atggctctta gcgatgaaag ccttagcacc aaaggcgtac ccgtccaatc cagcgatgtt 720
agatgcaatc cgtgccgggg aagttgattt aggcagtact aatcactact acgtcgtccg 780
gttccggcgc gcagggtacc ggctcggcat gcaccacttt cgggatggtg acgcaggcaa 840
tttagcactc gtgacgggcg cgggtctctt gaagacatca aaaaatttag ccgcagcgac 900
gcgcttcctc acgtacttac tgagccctca ggcccagcaa tactttgtag gcaatattgg 960
tgaataccca ctcgtaaaag gcgtggccct tgacccaaat ttactgccgc tggaggaggc 1020
ccttgcaaaa tcaccaaaat tagacttgga aaaacttcca ttggatcgtg cattacgctt 1080
attacgtgaa acgggggttt taggtggttc acatcatcat catcatcatt aatgaaaggg 1140
cgatatccag cacactggcg gccgttacta gtggatccgg ctgctaacaa agcccgaaag 1200
gaagctgagt tggctgctgc caccgctgag caataactag cataacccct tggggcctct 1260
aaacgggtct tgaggggttt tttgctgaaa ggaggaacta tatccggagc gactcccacg 1320
gcacgttggc aagctcg 1337

<210> SEQ ID NO 106
<211> LENGTH: 1400
<212> TYPE: DNA
<213> ORGANISM: Artificial Sequence
<220> FEATURE:
<223> OTHER INFORMATION: Exemplary Expression Construct for msFeBP6

<400> SEQUENCE: 106
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgtctttaac 180
attatataca ggtcgtagtc aagcattggt cgacaaactc gttcaacagt tccagaaaga 240
tacggggatc aaggtaaatg tacgttacgg ccgggacgca gaaatcttag ccgcattgca 300
ggaagaaggt agccgttctc cagccgatgt attctgggcg aacacctctg gtgctcttga 360
agaagcagta aagcgtaacc tcctcgtaca acttcctgca tccttaacac ggcagccaca 420
agagtttgta ccaagtcatg ggcgctgggt accagtatca gttcgctttc gcgttgccgc 480
ctacaaccca accaaggtaa aagatagtga ttttccggca tccgtcatgg acttgcctaa 540
agtcgccaaa ttcaaaggcc gtattggctg gacgccgacc tattcctctt tccaagactt 600
cattacagcc atgcgcgtag taaagggcga ggccgccact aaagcctggc tccaagcaat 660
gatcgctgcc ggtgcaaagg catatccaag caacccacca atgttagaag cgatgcaggc 720
aggtgagatc gacgtggcct taactaacca ctattatatc caacgcatct tggcaggcgt 780
gggtgagggc gagtatgaag gcaaggagga atccgaggag gaggagaaaa aagagctggc 840
ggcccgggaa gccaaagccg gtgtagcaac acattacttc gctccaggcg acgtaggcgg 900
tttagcgctc gtgacaggcg caggtattct ggctacatca aaacatcaaa caaatgcaac 960
ccgttttctt aattacttgt tatcaaaaaa agctcaaccg tatttcgttg acgaagtccg 1020
tgagtaccca gtcattgccg ggttcgggt agccaagggg atgttacctt tcgcaaacgc 1080
cattcgcctc tccccgaaaa ttgactttgc caagctcacg gatttagaag gtacactcaa 1140
attgttacgt gaagtaggcc tcttaggtgg tagtcatcat catcatcatc attaatgaaa 1200
gggcgatatc cagcacactg gcggccgtta ctagtggatc cggctgctaa caaagcccga 1260
aaggaagctg agttggctgc tgccaccgct gagcaataac tagcataacc ccttggggcc 1320
tctaaacggg tcttgagggg ttttttgctg aaaggaggaa ctatatccgg agcgactccc 1380
acggcacgtt ggcaagctcg 1400

<210> SEQ ID NO 107
<211> LENGTH: 1406
<212> TYPE: DNA
<213> ORGANISM: Artificial Sequence
<220> FEATURE:
<223> OTHER INFORMATION: Exemplary Expression Construct for srFeBP7

<400> SEQUENCE: 107
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tgttagtaat 180
ttattcaggt cgttcaaaag ccttggtcga ctccttggta caacagtatc gtcaacaggc 240
agatgtccca gttcgcgttc ggtacggtac cgattcgcag ctcttagcag ctttacaaga 300
agagggtgac caatcgccgg cagacgtatt ttgggctaac acgacaggcg cactgggtaa 360
cgccgtcaac aatggcttac tgactgaatt gccggatact cttgcgaacc gcgctgcacg 420
ttttaccccg tcgaaccaac gctggactcc tgtaacaaca cgttttcggg tacttgctta 480
caattcagac gcagtatcac cggaagacct ccctgacagt gtacttgatt tacctgaaca 540
cgaagagttc gaagggcgtg taggctggac cccagcgtac tcgtcatttc aggatttcgt 600
caccgcactc cgggtcacag aaggcgccga gaccgctcgt acatggttgt ctgacatgca 660
agccctcaat ccgaactcct acacaagtaa caccccaatg gtccaagcgc tggaagcagg 720
tgaaattgat gtcgcgttaa caaaccacta ctacgtactg cgtctcaaac atggcggcgc 780
cgaaggtgaa tatgagggcg aggaagaaga gggtgaggag catgaagaag aacacgaaga 840
ggaggccaca ccacgcgcat ccgcaccagt tgaaatgtac cactttgcag acggtgactt 900
aggcaacctg gcccttgtaa ctggcgccgg cgctcttcaa acatcaaatc agccagatgc 960
cgccaaccgc ttcttacggt tcttattgtc ggaacaggct cagtcattcg cggccacacg 1020
tgtcaacgaa tacccagtcg tctcgggggc aagtgtacct gactatctta tgccagcaga 1080
cgaggccctc aaaatgtcac cagaatttga cttacagaaa ttgcaaaata tggaaccaac 1140
cttagatctt ttacgggacg caggggcttt aggtggtagt catcatcatc atcatcatta 1200
atgaaagggc gatatccagc acactggcgg ccgttactag tggatccggc tgctaacaaa 1260
gcccgaaagg aagctgagtt ggctgctgcc accgctgagc aataactagc ataacccctt 1320
ggggcctcta aacgggtctt gaggggtttt ttgctgaaag gaggaactat atccggagcg 1380
actcccacgg cacgttggca agctcg 1406

<210> SEQ ID NO 108
<211> LENGTH: 1316
<212> TYPE: DNA
<213> ORGANISM: Artificial Sequence
<220> FEATURE:
<223> OTHER INFORMATION: Exemplary Expression Construct for hlFeBP8

<400> SEQUENCE: 108

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tgttaactgt    180

atattcaggt cgtggcgaat ttctcgtagg tgaattagta gaatacattg aggatcagta    240

tgacgacttt gatttaaccg ttcgctacgc cggtagcacc gatctcgtaa accaaatttt    300

aaatgaaggg gacggcagcc cagcggacgt attctactcc gttaatgccg gcagcttagg    360

gaccctcgca ggtgaaggtc gttcacaggc actcagctca gagatcacgg atatggtgcg    420

tagcgagttc cgcacagaac aatggattgg tacctccggg cgtgcacgca cagtccctta    480

taatactggc gagtttagcg atgacgactt acctgacgat attatggcct acccggagga    540

gtttgcgggg tctctcggtt gggcgccgtc atatgggtca gcacaagcct ttattacggc    600

tatgcgtttg atcgaagggg aagaagccac attggcttgg cttgaatcgg tcgtagaagc    660

agggattagc tcatatcctg acgaatttgc cgcggcacaa gctatcgccg acggtgagat    720

cgacgctgcc tttacaaacc actattacat tcagcgggtc ctcgacggga acccggacgc    780

ctcaatcggg acagccttca cgtcaggcga cgcaggtgca gtgttcaacg tagccggggc    840

ggccgtcgtc gacacagcct ccgacgctac tctcgcagag aattttatcc gtcatttgtt    900

gtcggctgag gcccaagact attttgcacg ctccacattt gagtacccat taatccctga    960

tgtagagcct atcggtgatc tgccaactat tgacgagctc gacgtgcctg acatcgactt   1020

gaccgaactt tcagacttag agccgactat tgatttgatg cgcgaagcag gtgtagaagt   1080

aggtggtagt catcatcatc atcatcatta atgaaagggc gatatccagc acactggcgg   1140

ccgttactag tggatccggc tgctaacaaa gcccgaaagg aagctgagtt ggctgctgcc   1200

accgctgagc aataactagc ataacccctt ggggcctcta aacgggtctt gaggggtttt   1260

ttgctgaaag gaggaactat atccggagcg actcccacgg cacgttggca agctcg       1316
```

<210> SEQ ID NO 109
<211> LENGTH: 1649
<212> TYPE: DNA
<213> ORGANISM: Artificial Sequence
<220> FEATURE:
<223> OTHER INFORMATION: Exemplary Expression Construct for avBicarBP5_16C

<400> SEQUENCE: 109

```
gccagtaagc ttcggtcacg cttgggactg ccataggctg gcccggtgat gccggccacg     60

atgcgtccgg cgtagaggat cgagatctcg atcccgcgaa attaatacga ctcactatag    120

ggagaccaca acggtttccc tctagaaata attttgttta actttaagaa ggagatatac    180

catggctgaa caagcaccag aagttacaac agtaaagctc gggtattgcc cgattgtcga    240

atccgctcct ctcatcattg ctaaagaaaa ggggtttttc gccaagtatg gtctgacaaa    300

tgtagaatta tcgaaacagg catcgtgggg cagtgcccgg gataatgtag agatcggtag    360

cgccgggggc gggatcgacg gtggtcaatg gcagatgcct atgccacatc tcatcactga    420

aggcttaatt acgaagggca atcagaaaat cccaatgtac gtcttagcac agttgatcac    480

ccacgggaac gggattgcca ttgcaaacaa acatcaaggg aaggggatca gtttgaagct    540

cgagggtgct aagagcctgt tcagtcagct caagagctcc acgccattca cagccgcttt    600

cacttttcct catgtaaatc aagacttatg gattcgctac tggttggctg caggggggtat    660

tgaccctgat gcagatgtaa aattgttaac ggtcccagca gcccaaaccg tagccaatat    720
```

-continued gaagaccggc acaatggacg cattttccac gggcgaccca tggccattcc gtctcgtaaa 780
cgacaaaatc ggttacatgg cggccttgac agcggagatc tggaaaaacc accctgagga 840
atacctcgca atgcgtgcag attgggtcga caagtatcca aaagcaacta aggcattatt 900
aaaaggcatc atggaggccc aacaatggtt ggacaacttt gacaatcgca aggaggcggc 960
acagattttg gctggccgca actactttaa cctcaacaac ccggaaatcc tggcggatcc 1020
ttacgtaggt aagtacgata tgggtgatgg tcgcaagatt gacgataaaa gcatggctgc 1080
gtattactgg aaggatgaaa aagggtcagt ttcttaccca tacaaatcgc acgacttatg 1140
gttcatcact gaaaacgtcc gttggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg ggtagaaga 1320 gttcttcgac ggcaccaaat tcgacccaga aaagccagac gaatatctga aatcgctcaa 1380
aatcaaaaaa gtcagcgtag gtggttcaca tcatcatcat catcattaat gaaagggcga 1440
tatccagcac actggcggcc gttactagtg gatccggctg ctaacaaagc ccgaaaggaa 1500
gctgagttgg ctgctgccac cgctgagcaa taactagcat aaccccttgg ggcctctaaa 1560
cgggtcttga ggggtttttt gctgaaagga ggaactatat ccggagcgac tcccacggca 1620
cgttggcaag ctcggaattc ggcgtaatc 1649

<210> SEQ ID NO 110
<211> LENGTH: 1649
<212> TYPE: DNA
<213> ORGANISM: Artificial Sequence
<220> FEATURE:
<223> OTHER INFORMATION: Exemplary Expression Construct for avBicarBP5_17C

<400> SEQUENCE: 110
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catggctgaa caagcaccag aagttacaac agtaaagctc gggtatatct gcattgtcga 240
atccgctcct ctcatcattg ctaaagaaaa ggggtttttc gccaagtatg gtctgacaaa 300
tgtagaatta tcgaaacagg catcgtgggg cagtgcccgg gataatgtag agatcggtag 360
cgccgggggc gggatcgacg gtggtcaatg gcagatgcct atgccacatc tcatcactga 420
aggcttaatt acgaagggca atcagaaaat cccaatgtac gtcttagcac agttgatcac 480
ccacgggaac gggattgcca ttgcaaacaa acatcaaggg aaggggatca gtttgaagct 540
cgagggtgct aagagcctgt tcagtcagct caagagctcc acgccattca cagccgcttt 600
cacttttcct catgtaaatc aagacttatg gattcgctac tggttggctg caggggggtat 660 tgaccctgat gcagatgtaa aattgttaac ggtcccagca gcccaaaccg tagccaatat 720
gaagaccggc acaatggacg cattttccac gggcgaccca tggccattcc gtctcgtaaa 780
cgacaaaatc ggttacatgg cggccttgac agcggagatc tggaaaaacc accctgagga 840
atacctcgca atgcgtgcag attgggtcga caagtatcca aaagcaacta aggcattatt 900
aaaaggcatc atggaggccc aacaatggtt ggacaacttt gacaatcgca aggaggcggc 960
acagattttg gctggccgca actactttaa cctcaacaac ccggaaatcc tggcggatcc 1020
ttacgtaggt aagtacgata tgggtgatgg tcgcaagatt gacgataaaa gcatggctgc 1080
gtattactgg aaggatgaaa aagggtcagt ttcttaccca tacaaatcgc acgacttatg 1140
gttcatcact gaaaacgtcc gttgggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg gggtagaaga 1320
gttcttcgac ggcaccaaat tcgacccaga aaagccagac gaatatctga aatcgctcaa 1380
aatcaaaaaa gtcagcgtag gtggttcaca tcatcatcat catcattaat gaaagggcga 1440
tatccagcac actggcggcc gttactagtg gatccggctg ctaacaaagc ccgaaaggaa 1500
gctgagttgg ctgctgccac cgctgagcaa taactagcat aaccccttgg ggcctctaaa 1560
cgggtcttga ggggtttttt gctgaaagga ggaactatat ccggagcgac tcccacggca 1620
cgttggcaag ctcggaattc ggcgtaatc 1649

<210> SEQ ID NO 111
<211> LENGTH: 1649
<212> TYPE: DNA
<213> ORGANISM: Artificial Sequence
<220> FEATURE:
<223> OTHER INFORMATION: Exemplary Expression Construct for avBicarBP5_18C

<400> SEQUENCE: 111
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catggctgaa caagcaccag aagttacaac agtaaagctc gggtatatcc cgtgcgtcga 240
atccgctcct ctcatcattg ctaaagaaaa ggggtttttc gccaagtatg gtctgacaaa 300
tgtagaatta tcgaaacagg catcgtgggg cagtgcccgg gataatgtag agatcggtag 360
cgccgggggc gggatcgacg gtggtcaatg gcagatgcct atgccacatc tcatcactga 420
aggcttaatt acgaagggca atcagaaaat cccaatgtac gtcttagcac agttgatcac 480
ccacgggaac gggattgcca ttgcaaacaa acatcaaggg aaggggatca gtttgaagct 540
cgagggtgct aagagcctgt tcagtcagct caagagctcc acgccattca cagccgcttt 600
cacttttcct catgtaaatc aagacttatg gattcgctac tggttggctg caggggggtat 660 tgaccctgat gcagatgtaa aattgttaac ggtcccagca gcccaaaccg tagccaatat 720
gaagaccggc acaatggacg cattttccac gggcgaccca tggccattcc gtctcgtaaa 780
cgacaaaatc ggttacatgg cggccttgac agcggagatc tggaaaaacc accctgagga 840
atacctcgca atgcgtgcag attgggtcga caagtatcca aaagcaacta aggcattatt 900
aaaaggcatc atggaggccc aacaatggtt ggacaacttt gacaatcgca aggaggcggc 960
acagattttg gctggccgca actactttaa cctcaacaac ccggaaatcc tggcggatcc 1020
ttacgtaggt aagtacgata tgggtgatgg tcgcaagatt gacgataaaa gcatggctgc 1080
gtattactgg aaggatgaaa aagggtcagt ttcttaccca tacaaatcgc acgacttatg 1140
gttcatcact gaaaacgtcc gttgggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg gggtagaaga 1320
gttcttcgac ggcaccaaat tcgacccaga aaagccagac gaatatctga aatcgctcaa 1380
aatcaaaaaa gtcagcgtag gtggttcaca tcatcatcat catcattaat gaaagggcga 1440
tatccagcac actggcggcc gttactagtg gatccggctg ctaacaaagc ccgaaaggaa 1500
gctgagttgg ctgctgccac cgctgagcaa taactagcat aaccccttgg ggcctctaaa 1560
cgggtcttga ggggtttttt gctgaaagga ggaactatat ccggagcgac tcccacggca 1620
cgttggcaag ctcggaattc ggcgtaatc 1649

<210> SEQ ID NO 112
<211> LENGTH: 1649
<212> TYPE: DNA
<213> ORGANISM: Artificial Sequence
<220> FEATURE:
<223> OTHER INFORMATION: Exemplary Expression Construct for avBicarBP5_49C

<400> SEQUENCE: 112
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catggctgaa caagcaccag aagttacaac agtaaagctc gggtatatcc cgattgtcga 240
atccgctcct ctcatcattg ctaaagaaaa ggggtttttc gccaagtatg gtctgacaaa 300
tgtagaatta tcgaaacagg catcgtgcgg cagtgcccgg gataatgtag agatcggtag 360
cgccgggggc gggatcgacg gtggtcaatg gcagatgcct atgccacatc tcatcactga 420
aggcttaatt acgaagggca atcagaaaat cccaatgtac gtcttagcac agttgatcac 480
ccacgggaac gggattgcca ttgcaaacaa acatcaaggg aaggggatca gtttgaagct 540
cgagggtgct aagagcctgt tcagtcagct caagagctcc acgccattca cagccgcttt 600
cacttttcct catgtaaatc aagacttatg gattcgctac tggttggctg caggggggtat 660 tgaccctgat gcagatgtaa aattgttaac ggtcccagca gcccaaaccg tagccaatat 720
gaagaccggc acaatggacg cattttccac gggcgaccca tggccattcc gtctcgtaaa 780
cgacaaaatc ggttacatgg cggccttgac agcggagatc tggaaaaacc accctgagga 840
atacctcgca atgcgtgcag attgggtcga caagtatcca aaagcaacta aggcattatt 900
aaaaggcatc atggaggccc aacaatggtt ggacaacttt gacaatcgca aggaggcggc 960
acagattttg gctggccgca actactttaa cctcaacaac ccggaaatcc tggcggatcc 1020
ttacgtaggt aagtacgata tgggtgatgg tcgcaagatt gacgataaaa gcatggctgc 1080
gtattactgg aaggatgaaa aagggtcagt ttcttaccca tacaaatcgc acgacttatg 1140
gttcatcact gaaaacgtcc gttggggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg gggtagaaga 1320
gttcttcgac ggcaccaaat tcgacccaga aaagccagac gaatatctga aatcgctcaa 1380
aatcaaaaaa gtcagcgtag gtggttcaca tcatcatcat catcattaat gaaagggcga 1440
tatccagcac actggcggcc gttactagtg gatccggctg ctaacaaagc ccgaaaggaa 1500
gctgagttgg ctgctgccac cgctgagcaa taactagcat aaccccttgg ggcctctaaa 1560
cgggtcttga ggggtttttt gctgaaagga ggaactatat ccggagcgac tcccacggca 1620
cgttggcaag ctcggaattc ggcgtaatc 1649

<210> SEQ ID NO 113
<211> LENGTH: 1649

<212> TYPE: DNA
<213> ORGANISM: Artificial Sequence
<220> FEATURE:
<223> OTHER INFORMATION: Exemplary Expression Construct for avBicarBP5_71C

<400> SEQUENCE: 113
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catggctgaa caagcaccag aagttacaac agtaaagctc gggtatatcc cgattgtcga 240
atccgctcct ctcatcattg ctaaagaaaa ggggtttttc gccaagtatg gtctgacaaa 300
tgtagaatta tcgaaacagg catcgtgggg cagtgcccgg gataatgtag agatcggtag 360
cgccgggggc gggatcgacg gtggtcaatg gtgcatgcct atgccacatc tcatcactga 420
aggcttaatt acgaagggca atcagaaaat cccaatgtac gtcttagcac agttgatcac 480
ccacgggaac gggattgcca ttgcaaacaa acatcaaggg aaggggatca gtttgaagct 540
cgagggtgct aagagcctgt tcagtcagct caagagctcc acgccattca cagccgcttt 600
cacttttcct catgtaaatc aagacttatg gattcgctac tggttggctg caggggggtat 660 tgaccctgat gcagatgtaa aattgttaac ggtcccagca gcccaaaccg tagccaatat 720
gaagaccggc acaatggacg cattttccac gggcgaccca tggccattcc gtctcgtaaa 780
cgacaaaatc ggttacatgg cggccttgac agcggagatc tggaaaaacc accctgagga 840
atacctcgca atgcgtgcag attgggtcga caagtatcca aaagcaacta aggcattatt 900
aaaaggcatc atggaggccc aacaatggtt ggacaacttt gacaatcgca aggaggcggc 960
acagattttg gctggccgca actactttaa cctcaacaac ccggaaatcc tggcggatcc 1020
ttacgtaggt aagtacgata tgggtgatgg tcgcaagatt gacgataaaa gcatggctgc 1080
gtattactgg aaggatgaaa aagggtcagt ttcttaccca tacaaatcgc acgacttatg 1140
gttcatcact gaaaacgtcc gttgggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg ggtagaaga 1320 gttcttcgac ggcaccaaat tcgacccaga aaagccagac gaatatctga aatcgctcaa 1380
aatcaaaaaa gtcagcgtag gtggttcaca tcatcatcat catcattaat gaaagggcga 1440
tatccagcac actggcggcc gttactagtg gatccggctg ctaacaaagc ccgaaaggaa 1500
gctgagttgg ctgctgccac cgctgagcaa taactagcat aaccccttgg ggcctctaaa 1560
cgggtcttga ggggtttttt gctgaaagga ggaactatat ccggagcgac tcccacggca 1620
cgttggcaag ctcggaattc ggcgtaatc 1649

<210> SEQ ID NO 114
<211> LENGTH: 1649
<212> TYPE: DNA
<213> ORGANISM: Artificial Sequence
<220> FEATURE:
<223> OTHER INFORMATION: Exemplary Expression Construct for avBicarBP5_140C

<400> SEQUENCE: 114
gccagtaagc ttcggtcacg cttgggactg ccataggctg gcccggtgat gccggccacg 60
atgcgtccgg cgtagaggat cgagatctcg atcccgcgaa attaatacga ctcactatag 120

```
ggagaccaca acggtttccc tctagaaata attttgttta actttaagaa ggagatatac    180
catggctgaa caagcaccag aagttacaac agtaaagctc gggtatatcc cgattgtcga    240
atccgctcct ctcatcattg ctaaagaaaa ggggtttttc gccaagtatg gtctgacaaa    300
tgtagaatta tcgaaacagg catcgtgggg cagtgcccgg gataatgtag agatcggtag    360
cgccgggggc gggatcgacg gtggtcaatg gcagatgcct atgccacatc tcatcactga    420
aggcttaatt acgaagggca atcagaaaat cccaatgtac gtcttagcac agttgatcac    480
ccacgggaac gggattgcca ttgcaaacaa acatcaaggg aaggggatca gtttgaagct    540
cgagggtgct aagagcctgt tcagtcagct caagagctcc acgccattca cagccgcttg    600
cacttttcct catgtaaatc aagacttatg gattcgctac tggttggctg caggggggtat    660
tgaccctgat gcagatgtaa aattgttaac ggtcccagca gcccaaaccg tagccaatat    720
gaagaccggc acaatggacg cattttccac gggcgaccca tggccattcc gtctcgtaaa    780
cgacaaaatc ggttacatgg cggccttgac agcggagatc tggaaaaacc accctgagga    840
atacctcgca atgcgtgcag attgggtcga caagtatcca aaagcaacta aggcattatt    900
aaaaggcatc atggaggccc aacaatggtt ggacaacttt gacaatcgca aggaggcggc    960
acagattttg gctggccgca actactttaa cctcaacaac ccggaaatcc tggcggatcc   1020
ttacgtaggt aagtacgata tgggtgatgg tcgcaagatt gacgataaaa gcatggctgc   1080
gtattactgg aaggatgaaa aagggtcagt ttcttaccca tacaaatcgc acgacttatg   1140
gttcatcact gaaaacgtcc gttgggggtt tctgccgaag gattatctgg caaacggtgc   1200
agccaaagct aaggagttaa tcgacaaggt caatcgggag gacatctgga aagaagcagc   1260
taaagaagcc ggtattgcag cggccgacat tccaaccagc acgtcccgtg ggtagaaga   1320
gttcttcgac ggcaccaaat tcgacccaga aaagccagac gaatatctga aatcgctcaa   1380
aatcaaaaaa gtcagcgtag gtggttcaca tcatcatcat catcattaat gaaagggcga   1440
tatccagcac actggcggcc gttactagtg gatccggctg ctaacaaagc ccgaaaggaa   1500
gctgagttgg ctgctgccac cgctgagcaa taactagcat aaccccttgg ggcctctaaa   1560
cgggtcttga ggggtttttt gctgaaagga ggaactatat ccggagcgac tcccacggca   1620
cgttggcaag ctcggaattc ggcgtaatc                                     1649
```

<210> SEQ ID NO 115
<211> LENGTH: 1649
<212> TYPE: DNA
<213> ORGANISM: Artificial Sequence
<220> FEATURE:
<223> OTHER INFORMATION: Exemplary Expression Construct for avBicarBP5_141C

<400> SEQUENCE: 115

```
gccagtaagc ttcggtcacg cttgggactg ccataggctg gcccggtgat gccggccacg     60
atgcgtccgg cgtagaggat cgagatctcg atcccgcgaa attaatacga ctcactatag    120
ggagaccaca acggtttccc tctagaaata attttgttta actttaagaa ggagatatac    180
catggctgaa caagcaccag aagttacaac agtaaagctc gggtatatcc cgattgtcga    240
atccgctcct ctcatcattg ctaaagaaaa ggggtttttc gccaagtatg gtctgacaaa    300
tgtagaatta tcgaaacagg catcgtgggg cagtgcccgg gataatgtag agatcggtag    360
cgccgggggc gggatcgacg gtggtcaatg gcagatgcct atgccacatc tcatcactga    420
aggcttaatt acgaagggca atcagaaaat cccaatgtac gtcttagcac agttgatcac    480
```

ccacgggaac gggattgcca ttgcaaacaa acatcaaggg aaggggatca gtttgaagct 540
cgagggtgct aagagcctgt tcagtcagct caagagctcc acgccattca cagccgcttt 600
ctgctttcct catgtaaatc aagacttatg gattcgctac tggttggctg caggggggtat 660 tgaccctgat gcagatgtaa aattgttaac ggtcccagca gcccaaaccg tagccaatat 720
gaagaccggc acaatggacg cattttccac gggcgaccca tggccattcc gtctcgtaaa 780
cgacaaaatc ggttacatgg cggccttgac agcggagatc tggaaaaacc accctgagga 840
atacctcgca atgcgtgcag attgggtcga caagtatcca aaagcaacta aggcattatt 900
aaaaggcatc atggaggccc aacaatggtt ggacaacttt gacaatcgca aggaggcggc 960
acagattttg gctggccgca actactttaa cctcaacaac ccggaaatcc tggcggatcc 1020
ttacgtaggt aagtacgata tgggtgatgg tcgcaagatt gacgataaaa gcatggctgc 1080
gtattactgg aaggatgaaa aagggtcagt ttcttaccca tacaaatcgc acgacttatg 1140
gttcatcact gaaaacgtcc gttggggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg gggtagaaga 1320
gttcttcgac ggcaccaaat tcgacccaga aaagccagac gaatatctga aatcgctcaa 1380
aatcaaaaaa gtcagcgtag gtggttcaca tcatcatcat catcattaat gaaagggcga 1440
tatccagcac actggcggcc gttactagtg gatccggctg ctaacaaagc ccgaaaggaa 1500
gctgagttgg ctgctgccac cgctgagcaa taactagcat aaccccttgg ggcctctaaa 1560
cgggtcttga ggggtttttt gctgaaagga ggaactatat ccggagcgac tcccacggca 1620
cgttggcaag ctcggaattc ggcgtaatc 1649

<210> SEQ ID NO 116
<211> LENGTH: 1649
<212> TYPE: DNA
<213> ORGANISM: Artificial Sequence
<220> FEATURE:
<223> OTHER INFORMATION: Exemplary Expression Construct for avBicarBP5_142C

<400> SEQUENCE: 116
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catggctgaa caagcaccag aagttacaac agtaaagctc gggtatatcc cgattgtcga 240
atccgctcct ctcatcattg ctaaagaaaa ggggtttttc gccaagtatg gtctgacaaa 300
tgtagaatta tcgaaacagg catcgtgggg cagtgcccgg gataatgtag agatcggtag 360
cgccgggggc gggatcgacg gtggtcaatg gcagatgcct atgccacatc tcatcactga 420
aggcttaatt acgaagggca atcagaaaat cccaatgtac gtcttagcac agttgatcac 480
ccacgggaac gggattgcca ttgcaaacaa acatcaaggg aaggggatca gtttgaagct 540
cgagggtgct aagagcctgt tcagtcagct caagagctcc acgccattca cagccgcttt 600
cacttgccct catgtaaatc aagacttatg gattcgctac tggttggctg caggggggtat 660 tgaccctgat gcagatgtaa aattgttaac ggtcccagca gcccaaaccg tagccaatat 720
gaagaccggc acaatggacg cattttccac gggcgaccca tggccattcc gtctcgtaaa 780
cgacaaaatc ggttacatgg cggccttgac agcggagatc tggaaaaacc accctgagga 840
atacctcgca atgcgtgcag attgggtcga caagtatcca aaagcaacta aggcattatt 900
aaaaggcatc atggaggccc aacaatggtt ggacaacttt gacaatcgca aggaggcggc 960
acagattttg gctggccgca actactttaa cctcaacaac ccggaaatcc tggcggatcc 1020
ttacgtaggt aagtacgata tgggtgatgg tcgcaagatt gacgataaaa gcatggctgc 1080
gtattactgg aaggatgaaa aagggtcagt ttcttaccca tacaaatcgc acgacttatg 1140
gttcatcact gaaaacgtcc gttgggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg ggtagaaga 1320 gttcttcgac ggcaccaaat tcgacccaga aaagccagac gaatatctga aatcgctcaa 1380
aatcaaaaaa gtcagcgtag gtggttcaca tcatcatcat catcattaat gaaagggcga 1440
tatccagcac actggcggcc gttactagtg gatccggctg ctaacaaagc ccgaaaggaa 1500
gctgagttgg ctgctgccac cgctgagcaa taactagcat aaccccttgg ggcctctaaa 1560
cgggtcttga ggggtttttt gctgaaagga ggaactatat ccggagcgac tcccacggca 1620
cgttggcaag ctcggaattc ggcgtaatc 1649

<210> SEQ ID NO 117
<211> LENGTH: 1649
<212> TYPE: DNA
<213> ORGANISM: Artificial Sequence
<220> FEATURE:
<223> OTHER INFORMATION: Exemplary Expression Construct for avBicarBP5_143C

<400> SEQUENCE: 117
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catggctgaa caagcaccag aagttacaac agtaaagctc gggtatatcc cgattgtcga 240
atccgctcct ctcatcattg ctaaagaaaa ggggtttttc gccaagtatg gtctgacaaa 300
tgtagaatta tcgaaacagg catcgtgggg cagtgcccgg gataatgtag agatcggtag 360
cgccgggggc gggatcgacg gtggtcaatg gcagatgcct atgccacatc tcatcactga 420
aggcttaatt acgaagggca atcagaaaat cccaatgtac gtcttagcac agttgatcac 480
ccacgggaac gggattgcca ttgcaaacaa acatcaaggg aaggggatca gtttgaagct 540
cgagggtgct aagagcctgt tcagtcagct caagagctcc acgccattca cagccgcttt 600
cactttttgc catgtaaatc aagacttatg gattcgctac tggttggctg caggggggtat 660 tgaccctgat gcagatgtaa aattgttaac ggtcccagca gcccaaaccg tagccaatat 720
gaagaccggc acaatggacg cattttccac gggcgaccca tggccattcc gtctcgtaaa 780
cgacaaaatc ggttacatgg cggccttgac agcggagatc tggaaaaacc accctgagga 840
atacctcgca atgcgtgcag attgggtcga caagtatcca aaagcaacta aggcattatt 900
aaaaggcatc atggaggccc aacaatggtt ggacaacttt gacaatcgca aggaggcggc 960
acagattttg gctggccgca actactttaa cctcaacaac ccggaaatcc tggcggatcc 1020
ttacgtaggt aagtacgata tgggtgatgg tcgcaagatt gacgataaaa gcatggctgc 1080
gtattactgg aaggatgaaa aagggtcagt ttcttaccca tacaaatcgc acgacttatg 1140
gttcatcact gaaaacgtcc gttgggggtt tctgccgaag gattatctgg caaacggtgc 1200

```
agccaaagct aaggagttaa tcgacaaggt caatcgggag gacatctgga aagaagcagc   1260

taaagaagcc ggtattgcag cggccgacat tccaaccagc acgtcccgtg ggtagaaga   1320

gttcttcgac ggcaccaaat tcgacccaga aaagccagac gaatatctga aatcgctcaa   1380

aatcaaaaaa gtcagcgtag gtggttcaca tcatcatcat catcattaat gaaagggcga   1440

tatccagcac actggcggcc gttactagtg gatccggctg ctaacaaagc ccgaaaggaa   1500

gctgagttgg ctgctgccac cgctgagcaa taactagcat aaccccttgg ggcctctaaa   1560

cgggtcttga ggggtttttt gctgaaagga ggaactatat ccggagcgac tcccacggca   1620

cgttggcaag ctcggaattc ggcgtaatc                                     1649
```

```
<210> SEQ ID NO 118
<211> LENGTH: 1649
<212> TYPE: DNA
<213> ORGANISM: Artificial Sequence
<220> FEATURE:
<223> OTHER INFORMATION: Exemplary Expression Construct for
      avBicarBP5_146C

<400> SEQUENCE: 118

gccagtaagc ttcggtcacg cttgggactg ccataggctg gcccggtgat gccggccacg     60

atgcgtccgg cgtagaggat cgagatctcg atcccgcgaa attaatacga ctcactatag    120

ggagaccaca acggtttccc tctagaaata attttgttta actttaagaa ggagatatac    180

catggctgaa caagcaccag aagttacaac agtaaagctc gggtatatcc cgattgtcga    240

atccgctcct ctcatcattg ctaaagaaaa ggggtttttc gccaagtatg gtctgacaaa    300

tgtagaatta tcgaaacagg catcgtgggg cagtgcccgg gataatgtag agatcggtag    360

cgccgggggc gggatcgacg gtggtcaatg gcagatgcct atgccacatc tcatcactga    420

aggcttaatt acgaagggca atcagaaaat cccaatgtac gtcttagcac agttgatcac    480

ccacgggaac gggattgcca ttgcaaacaa acatcaaggg aaggggatca gtttgaagct    540

cgagggtgct aagagcctgt tcagtcagct caagagctcc acgccattca cagccgcttt    600

cacttttcct catgtatgcc aagacttatg gattcgctac tggttggctg caggggggtat    660

tgaccctgat gcagatgtaa aattgttaac ggtcccagca gcccaaaccg tagccaatat    720

gaagaccggc acaatggacg cattttccac gggcgaccca tggccattcc gtctcgtaaa    780

cgacaaaatc ggttacatgg cggccttgac agcggagatc tggaaaaacc accctgagga    840

atacctcgca atgcgtgcag attgggtcga caagtatcca aaagcaacta aggcattatt    900

aaaaggcatc atggaggccc aacaatggtt ggacaacttt gacaatcgca aggaggcggc    960

acagattttg gctggccgca actactttaa cctcaacaac ccggaaatcc tggcggatcc   1020

ttacgtaggt aagtacgata tgggtgatgg tcgcaagatt gacgataaaa gcatggctgc   1080

gtattactgg aaggatgaaa aagggtcagt ttcttaccca tacaaatcgc acgacttatg   1140

gttcatcact gaaaacgtcc gttgggggtt tctgccgaag gattatctgg caaacggtgc   1200

agccaaagct aaggagttaa tcgacaaggt caatcgggag gacatctgga aagaagcagc   1260

taaagaagcc ggtattgcag cggccgacat tccaaccagc acgtcccgtg ggtagaaga   1320

gttcttcgac ggcaccaaat tcgacccaga aaagccagac gaatatctga aatcgctcaa   1380

aatcaaaaaa gtcagcgtag gtggttcaca tcatcatcat catcattaat gaaagggcga   1440

tatccagcac actggcggcc gttactagtg gatccggctg ctaacaaagc ccgaaaggaa   1500

gctgagttgg ctgctgccac cgctgagcaa taactagcat aaccccttgg ggcctctaaa   1560
```

```
cgggtcttga ggggtttttt gctgaaagga ggaactatat ccggagcgac tcccacggca   1620

cgttggcaag ctcggaattc ggcgtaatc                                     1649


<210> SEQ ID NO 119
<211> LENGTH: 1649
<212> TYPE: DNA
<213> ORGANISM: Artificial Sequence
<220> FEATURE:
<223> OTHER INFORMATION: Exemplary Expression Construct for
      avBicarBP5_190C

<400> SEQUENCE: 119

gccagtaagc ttcggtcacg cttgggactg ccataggctg gcccggtgat gccggccacg     60

atgcgtccgg cgtagaggat cgagatctcg atcccgcgaa attaatacga ctcactatag    120

ggagaccaca acggtttccc tctagaaata attttgttta actttaagaa ggagatatac    180

catggctgaa caagcaccag aagttacaac agtaaagctc gggtatatcc cgattgtcga    240

atccgctcct ctcatcattg ctaaagaaaa ggggtttttc gccaagtatg gtctgacaaa    300

tgtagaatta tcgaaacagg catcgtgggg cagtgcccgg gataatgtag agatcggtag    360

cgccgggggc gggatcgacg gtggtcaatg gcagatgcct atgccacatc tcatcactga    420

aggcttaatt acgaagggca atcagaaaat cccaatgtac gtcttagcac agttgatcac    480

ccacgggaac gggattgcca ttgcaaacaa acatcaaggg aaggggatca gtttgaagct    540

cgagggtgct aagagcctgt tcagtcagct caagagctcc acgccattca cagccgcttt    600

cacttttcct catgtaaatc aagacttatg gattcgctac tggttggctg caggggggtat    660

tgaccctgat gcagatgtaa aattgttaac ggtcccagca gcccaaaccg tagccaatat    720

gaagaccggc acaatggacg cattttcctg cggcgaccca tggccattcc gtctcgtaaa    780

cgacaaaatc ggttacatgg cggccttgac agcggagatc tggaaaaacc accctgagga    840

atacctcgca atgcgtgcag attgggtcga caagtatcca aaagcaacta aggcattatt    900

aaaaggcatc atggaggccc aacaatggtt ggacaacttt gacaatcgca aggaggcggc    960

acagattttg gctggccgca actactttaa cctcaacaac ccggaaatcc tggcggatcc   1020

ttacgtaggt aagtacgata tgggtgatgg tcgcaagatt gacgataaaa gcatggctgc   1080

gtattactgg aaggatgaaa aagggtcagt ttcttaccca tacaaatcgc acgacttatg   1140

gttcatcact gaaaacgtcc gttggggggtt tctgccgaag gattatctgg caaacggtgc   1200

agccaaagct aaggagttaa tcgacaaggt caatcgggag gacatctgga aagaagcagc   1260

taaagaagcc ggtattgcag cggccgacat tccaaccagc acgtcccgtg gggtagaaga   1320

gttcttcgac ggcaccaaat tcgacccaga aaagccagac gaatatctga aatcgctcaa   1380

aatcaaaaaa gtcagcgtag gtggttcaca tcatcatcat catcattaat gaaagggcga   1440

tatccagcac actggcggcc gttactagtg gatccggctg ctaacaaagc ccgaaaggaa   1500

gctgagttgg ctgctgccac cgctgagcaa taactagcat aaccccttgg ggcctctaaa   1560

cgggtcttga ggggtttttt gctgaaagga ggaactatat ccggagcgac tcccacggca   1620

cgttggcaag ctcggaattc ggcgtaatc                                     1649


<210> SEQ ID NO 120
<211> LENGTH: 1649
<212> TYPE: DNA
<213> ORGANISM: Artificial Sequence
<220> FEATURE:
<223> OTHER INFORMATION: Exemplary Expression Construct for
      avBicarBP5_194C
```

<400> SEQUENCE: 120
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catggctgaa caagcaccag aagttacaac agtaaagctc gggtatatcc cgattgtcga 240
atccgctcct ctcatcattg ctaaagaaaa ggggtttttc gccaagtatg gtctgacaaa 300
tgtagaatta tcgaaacagg catcgtgggg cagtgcccgg gataatgtag agatcggtag 360
cgccgggggc gggatcgacg gtggtcaatg gcagatgcct atgccacatc tcatcactga 420
aggcttaatt acgaagggca atcagaaaat cccaatgtac gtcttagcac agttgatcac 480
ccacgggaac gggattgcca ttgcaaacaa acatcaaggg aaggggatca gtttgaagct 540
cgagggtgct aagagcctgt tcagtcagct caagagctcc acgccattca cagccgcttt 600
cacttttcct catgtaaatc aagacttatg gattcgctac tggttggctg caggggggtat 660 tgaccctgat gcagatgtaa aattgttaac ggtcccagca gcccaaaccg tagccaatat 720
gaagaccggc acaatggacg cattttccac gggcgaccca tgcccattcc gtctcgtaaa 780
cgacaaaatc ggttacatgg cggccttgac agcggagatc tggaaaaacc accctgagga 840
atacctcgca atgcgtgcag attgggtcga caagtatcca aaagcaacta aggcattatt 900
aaaaggcatc atggaggccc aacaatggtt ggacaacttt gacaatcgca aggaggcggc 960
acagattttg gctggccgca actactttaa cctcaacaac ccggaaatcc tggcggatcc 1020
ttacgtaggt aagtacgata tgggtgatgg tcgcaagatt gacgataaaa gcatggctgc 1080
gtattactgg aaggatgaaa aagggtcagt ttcttaccca tacaaatcgc acgacttatg 1140
gttcatcact gaaaacgtcc gttgggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg gggtagaaga 1320
gttcttcgac ggcaccaaat tcgacccaga aaagccagac gaatatctga aatcgctcaa 1380
aatcaaaaaa gtcagcgtag gtggttcaca tcatcatcat catcattaat gaaagggcga 1440
tatccagcac actggcggcc gttactagtg gatccggctg ctaacaaagc ccgaaaggaa 1500
gctgagttgg ctgctgccac cgctgagcaa taactagcat aaccccttgg ggcctctaaa 1560
cgggtcttga ggggtttttt gctgaaagga ggaactatat ccggagcgac tcccacggca 1620
cgttggcaag ctcggaattc ggcgtaatc 1649

<210> SEQ ID NO 121
<211> LENGTH: 1352
<212> TYPE: DNA
<213> ORGANISM: Artificial Sequence
<220> FEATURE:
<223> OTHER INFORMATION: Exemplary Expression Construct for teFeBP3_A8C

<400> SEQUENCE: 121
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggtaattaa 180
tgtatatagt tgccgtcatt acgacactga caaggctctc tataatacct tcacccaaca 240
aaccgggatt cgtgtaaaca tcattgaggc tgaggcagat gccctcattg aacgtattcg 300

```
ttctgaaggt tcgcgcaccc cagccgatgt actcattaca gtagacgcgg gtcgcttatg    360

gcgtgcgcaa gaagctggca tcttacagcc gattcaatcg cgtgttttaa acagtgtagt    420

accagccaac ctccgggaac cacagggtca ctggttcggt ctctcccgtc gtgttcgcgt    480

tctgatttat aacaagtccc gtgttaatcc atctcagctt tccacatacg aagatttagc    540

taatccgaag tggcgccgtc agatcctgac acgttcttca agcaacattt acaaccaatc    600

gttgacaggt tccttactcg ccattcacgg ggcacagaag accgaacaat gggcacgtgg    660

cttagtacag aacttcgcac gtccaccgga ggggaatgac acagctcaaa ttcgtgcaag    720

tgcagagggc gttggctcag tagcgatcgc caatcactat tacctcgccc gtttaattgc    780

cagtgacaag gagcaagacc gtgcggtggc cgcaaaggtg ggcctctttt tcccgaacca    840

acgtgaccgc ggtgcacatg tcaatatcag tggggcaggt gtagtcgccg gcgctcctaa    900

ccgtcaaggc gcaattcggt tcttagagta cctggtctcc ccaaaggccc aggaaatgtt    960

tgctatggct aactttgagt acccggtacg cgcaggcgtc ccagtccacc ctatcgtcaa   1020

gcaattcggc aactttcgtg gtcaaaatgt caacgcagca gtattcgggc gcaacaacgc   1080

agaagcactt cgtatcatgg accgggccgg ttggcgtggc ggtagtcatc atcatcatca   1140

tcattaatga aagggcgata tccagcacac tggcggccgt tactagtgga tccggctgct   1200

aacaaagccc gaaaggaagc tgagttggct gctgccaccg ctgagcaata actagcataa   1260

ccccttgggg cctctaaacg ggtcttgagg ggtttttttgc tgaaaggagg aactatatcc   1320

ggagcgactc ccacggcacg ttggcaagct cg                                 1352
```

<210> SEQ ID NO 122
<211> LENGTH: 1352
<212> TYPE: DNA
<213> ORGANISM: Artificial Sequence
<220> FEATURE:
<223> OTHER INFORMATION: Exemplary Expression Construct for teFeBP3_H10C

<400> SEQUENCE: 122

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggtaattaa    180

tgtatatagt gcacgttgct acgacactga caaggctctc tataatacct tcacccaaca    240

aaccgggatt cgtgtaaaca tcattgaggc tgaggcagat gccctcattg aacgtattcg    300

ttctgaaggt tcgcgcaccc cagccgatgt actcattaca gtagacgcgg gtcgcttatg    360

gcgtgcgcaa gaagctggca tcttacagcc gattcaatcg cgtgttttaa acagtgtagt    420

accagccaac ctccgggaac cacagggtca ctggttcggt ctctcccgtc gtgttcgcgt    480

tctgatttat aacaagtccc gtgttaatcc atctcagctt tccacatacg aagatttagc    540

taatccgaag tggcgccgtc agatcctgac acgttcttca agcaacattt acaaccaatc    600

gttgacaggt tccttactcg ccattcacgg ggcacagaag accgaacaat gggcacgtgg    660

cttagtacag aacttcgcac gtccaccgga ggggaatgac acagctcaaa ttcgtgcaag    720

tgcagagggc gttggctcag tagcgatcgc caatcactat tacctcgccc gtttaattgc    780

cagtgacaag gagcaagacc gtgcggtggc cgcaaaggtg ggcctctttt tcccgaacca    840

acgtgaccgc ggtgcacatg tcaatatcag tggggcaggt gtagtcgccg gcgctcctaa    900

ccgtcaaggc gcaattcggt tcttagagta cctggtctcc ccaaaggccc aggaaatgtt    960

tgctatggct aactttgagt acccggtacg cgcaggcgtc ccagtccacc ctatcgtcaa   1020
```

gcaattcggc aactttcgtg gtcaaaatgt caacgcagca gtattcgggc gcaacaacgc 1080
agaagcactt cgtatcatgg accgggccgg ttggcgtggc ggtagtcatc atcatcatca 1140
tcattaatga aagggcgata tccagcacac tggcggccgt tactagtgga tccggctgct 1200
aacaaagccc gaaaggaagc tgagttggct gctgccaccg ctgagcaata actagcataa 1260
ccccttgggg cctctaaacg ggtcttgagg ggttttttgc tgaaaggagg aactatatcc 1320
ggagcgactc ccacggcacg ttggcaagct cg 1352

<210> SEQ ID NO 123
<211> LENGTH: 1352
<212> TYPE: DNA
<213> ORGANISM: Artificial Sequence
<220> FEATURE:
<223> OTHER INFORMATION: Exemplary Expression Construct for teFeBP3_D12C

<400> SEQUENCE: 123
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggtaattaa 180
tgtatatagt gcacgtcatt actgcactga caaggctctc tataatacct tcacccaaca 240
aaccgggatt cgtgtaaaca tcattgaggc tgaggcagat gccctcattg aacgtattcg 300
ttctgaaggt tcgcgcaccc cagccgatgt actcattaca gtagacgcgg gtcgcttatg 360
gcgtgcgcaa gaagctggca tcttacagcc gattcaatcg cgtgttttaa acagtgtagt 420
accagccaac ctccgggaac cacagggtca ctggttcggt ctctcccgtc gtgttcgcgt 480
tctgatttat aacaagtccc gtgttaatcc atctcagctt tccacatacg aagatttagc 540
taatccgaag tggcgccgtc agatcctgac acgttcttca agcaacattt acaaccaatc 600
gttgacaggt tccttactcg ccattcacgg ggcacagaag accgaacaat gggcacgtgg 660
cttagtacag aacttcgcac gtccaccgga ggggaatgac acagctcaaa ttcgtgcaag 720
tgcagagggc gttggctcag tagcgatcgc caatcactat tacctcgccc gtttaattgc 780
cagtgacaag gagcaagacc gtgcggtggc cgcaaaggtg ggcctctttt tcccgaacca 840
acgtgaccgc ggtgcacatg tcaatatcag tggggcaggt gtagtcgccg gcgctcctaa 900
ccgtcaaggc gcaattcggt tcttagagta cctggtctcc ccaaaggccc aggaaatgtt 960
tgctatggct aactttgagt acccggtacg cgcaggcgtc ccagtccacc ctatcgtcaa 1020
gcaattcggc aactttcgtg gtcaaaatgt caacgcagca gtattcgggc gcaacaacgc 1080
agaagcactt cgtatcatgg accgggccgg ttggcgtggc ggtagtcatc atcatcatca 1140
tcattaatga aagggcgata tccagcacac tggcggccgt tactagtgga tccggctgct 1200
aacaaagccc gaaaggaagc tgagttggct gctgccaccg ctgagcaata actagcataa 1260
ccccttgggg cctctaaacg ggtcttgagg ggttttttgc tgaaaggagg aactatatcc 1320
ggagcgactc ccacggcacg ttggcaagct cg 1352

<210> SEQ ID NO 124
<211> LENGTH: 1352
<212> TYPE: DNA
<213> ORGANISM: Artificial Sequence
<220> FEATURE:
<223> OTHER INFORMATION: Exemplary Expression Construct for teFeBP3_T13C

<400> SEQUENCE: 124

```
cggtcacgct tgggactgcc ataggctggc ccggtgatgc cggccacgat gcgtccggcg      60
tagaggatcg agatctcgat cccgcgaaat taatacgact cactataggg agaccacaac     120
ggtttccctc tagaaataat tttgtttaac tttaagaagg agatatacca tggtaattaa     180
tgtatatagt gcacgtcatt acgactgcga caaggctctc tataatacct tcacccaaca     240
aaccgggatt cgtgtaaaca tcattgaggc tgaggcagat gccctcattg aacgtattcg     300
ttctgaaggt tcgcgcaccc cagccgatgt actcattaca gtagacgcgg gtcgcttatg     360
gcgtgcgcaa gaagctggca tcttacagcc gattcaatcg cgtgttttaa acagtgtagt     420
accagccaac ctccgggaac cacagggtca ctggttcggt ctctcccgtc gtgttcgcgt     480
tctgatttat aacaagtccc gtgttaatcc atctcagctt tccacatacg aagatttagc     540
taatccgaag tggcgccgtc agatcctgac acgttcttca agcaacattt acaaccaatc     600
gttgacaggt tccttactcg ccattcacgg ggcacagaag accgaacaat gggcacgtgg     660
cttagtacag aacttcgcac gtccaccgga ggggaatgac acagctcaaa ttcgtgcaag     720
tgcagagggc gttggctcag tagcgatcgc caatcactat tacctcgccc gtttaattgc     780
cagtgacaag gagcaagacc gtgcggtggc cgcaaaggtg ggcctctttt tcccgaacca     840
acgtgaccgc ggtgcacatg tcaatatcag tggggcaggt gtagtcgccg gcgctcctaa     900
ccgtcaaggc gcaattcggt tcttagagta cctggtctcc ccaaaggccc aggaaatgtt     960
tgctatggct aactttgagt acccggtacg cgcaggcgtc ccagtccacc ctatcgtcaa    1020
gcaattcggc aactttcgtg gtcaaaatgt caacgcagca gtattcgggc gcaacaacgc    1080
agaagcactt cgtatcatgg accgggccgg ttggcgtggc ggtagtcatc atcatcatca    1140
tcattaatga aagggcgata tccagcacac tggcggccgt tactagtgga tccggctgct    1200
aacaaagccc gaaaggaagc tgagttggct gctgccaccg ctgagcaata actagcataa    1260
ccccttgggg cctctaaacg ggtcttgagg ggtttttttgc tgaaaggagg aactatatcc  1320
ggagcgactc ccacggcacg ttggcaagct cg                                 1352
```

<210> SEQ ID NO 125
<211> LENGTH: 1352
<212> TYPE: DNA
<213> ORGANISM: Artificial Sequence
<220> FEATURE:
<223> OTHER INFORMATION: Exemplary Expression Construct for teFeBP3_A36C

<400> SEQUENCE: 125

```
cggtcacgct tgggactgcc ataggctggc ccggtgatgc cggccacgat gcgtccggcg      60
tagaggatcg agatctcgat cccgcgaaat taatacgact cactataggg agaccacaac     120
ggtttccctc tagaaataat tttgtttaac tttaagaagg agatatacca tggtaattaa     180
tgtatatagt gcacgtcatt acgacactga caaggctctc tataatacct tcacccaaca     240
aaccgggatt cgtgtaaaca tcattgaggc tgagtgcgat gccctcattg aacgtattcg     300
ttctgaaggt tcgcgcaccc cagccgatgt actcattaca gtagacgcgg gtcgcttatg     360
gcgtgcgcaa gaagctggca tcttacagcc gattcaatcg cgtgttttaa acagtgtagt     420
accagccaac ctccgggaac cacagggtca ctggttcggt ctctcccgtc gtgttcgcgt     480
tctgatttat aacaagtccc gtgttaatcc atctcagctt tccacatacg aagatttagc     540
taatccgaag tggcgccgtc agatcctgac acgttcttca agcaacattt acaaccaatc     600
gttgacaggt tccttactcg ccattcacgg ggcacagaag accgaacaat gggcacgtgg     660
cttagtacag aacttcgcac gtccaccgga ggggaatgac acagctcaaa ttcgtgcaag     720
```

tgcagagggc gttggctcag tagcgatcgc caatcactat tacctcgccc gtttaattgc 780
cagtgacaag gagcaagacc gtgcggtggc cgcaaaggtg ggcctctttt tcccgaacca 840
acgtgaccgc ggtgcacatg tcaatatcag tggggcaggt gtagtcgccg gcgctcctaa 900
ccgtcaaggc gcaattcggt tcttagagta cctggtctcc ccaaaggccc aggaaatgtt 960
tgctatggct aactttgagt acccggtacg cgcaggcgtc ccagtccacc ctatcgtcaa 1020
gcaattcggc aactttcgtg gtcaaaatgt caacgcagca gtattcgggc gcaacaacgc 1080
agaagcactt cgtatcatgg accgggccgg ttggcgtggc ggtagtcatc atcatcatca 1140
tcattaatga aagggcgata tccagcacac tggcggccgt tactagtgga tccggctgct 1200
aacaaagccc gaaaggaagc tgagttggct gctgccaccg ctgagcaata actagcataa 1260
ccccttgggg cctctaaacg ggtcttgagg ggttttttgc tgaaaggagg aactatatcc 1320
ggagcgactc ccacggcacg ttggcaagct cg 1352

<210> SEQ ID NO 126
<211> LENGTH: 1352
<212> TYPE: DNA
<213> ORGANISM: Artificial Sequence
<220> FEATURE:
<223> OTHER INFORMATION: Exemplary Expression Construct for teFeBP3_V58C

<400> SEQUENCE: 126
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggtaattaa 180
tgtatatagt gcacgtcatt acgacactga caaggctctc tataatacct tcacccaaca 240
aaccgggatt cgtgtaaaca tcattgaggc tgaggcagat gccctcattg aacgtattcg 300
ttctgaaggt tcgcgcaccc cagccgatgt actcattaca tgcgacgcgg gtcgcttatg 360
gcgtgcgcaa gaagctggca tcttacagcc gattcaatcg cgtgttttaa acagtgtagt 420
accagccaac ctccgggaac cacagggtca ctggttcggt ctctcccgtc gtgttcgcgt 480
tctgatttat aacaagtccc gtgttaatcc atctcagctt tccacatacg aagatttagc 540
taatccgaag tggcgccgtc agatcctgac acgttcttca agcaacattt acaaccaatc 600
gttgacaggt tccttactcg ccattcacgg ggcacagaag accgaacaat gggcacgtgg 660
cttagtacag aacttcgcac gtccaccgga ggggaatgac acagctcaaa ttcgtgcaag 720
tgcagagggc gttggctcag tagcgatcgc caatcactat tacctcgccc gtttaattgc 780
cagtgacaag gagcaagacc gtgcggtggc cgcaaaggtg ggcctctttt tcccgaacca 840
acgtgaccgc ggtgcacatg tcaatatcag tggggcaggt gtagtcgccg gcgctcctaa 900
ccgtcaaggc gcaattcggt tcttagagta cctggtctcc ccaaaggccc aggaaatgtt 960
tgctatggct aactttgagt acccggtacg cgcaggcgtc ccagtccacc ctatcgtcaa 1020
gcaattcggc aactttcgtg gtcaaaatgt caacgcagca gtattcgggc gcaacaacgc 1080
agaagcactt cgtatcatgg accgggccgg ttggcgtggc ggtagtcatc atcatcatca 1140
tcattaatga aagggcgata tccagcacac tggcggccgt tactagtgga tccggctgct 1200
aacaaagccc gaaaggaagc tgagttggct gctgccaccg ctgagcaata actagcataa 1260
ccccttgggg cctctaaacg ggtcttgagg ggttttttgc tgaaaggagg aactatatcc 1320
ggagcgactc ccacggcacg ttggcaagct cg 1352

<210> SEQ ID NO 127
<211> LENGTH: 1352
<212> TYPE: DNA
<213> ORGANISM: Artificial Sequence
<220> FEATURE:
<223> OTHER INFORMATION: Exemplary Expression Construct for teFeBP3_R135C

<400> SEQUENCE: 127

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggtaattaa    180

tgtatatagt gcacgtcatt acgacactga caaggctctc tataatacct tcacccaaca    240

aaccgggatt cgtgtaaaca tcattgaggc tgaggcagat gccctcattg aacgtattcg    300

ttctgaaggt tcgcgcaccc cagccgatgt actcattaca gtagacgcgg gtcgcttatg    360

gcgtgcgcaa gaagctggca tcttacagcc gattcaatcg cgtgttttaa acagtgtagt    420

accagccaac ctccgggaac cacagggtca ctggttcggt ctctcccgtc gtgttcgcgt    480

tctgatttat aacaagtccc gtgttaatcc atctcagctt tccacatacg aagatttagc    540

taatccgaag tggcgccgtc agatcctgac atgctcttca agcaacattt acaaccaatc    600

gttgacaggt tccttactcg ccattcacgg ggcacagaag accgaacaat gggcacgtgg    660

cttagtacag aacttcgcac gtccaccgga ggggaatgac acagctcaaa ttcgtgcaag    720

tgcagagggc gttggctcag tagcgatcgc caatcactat tacctcgccc gtttaattgc    780

cagtgacaag gagcaagacc gtgcggtggc cgcaaaggtg ggcctctttt tcccgaacca    840

acgtgaccgc ggtgcacatg tcaatatcag tggggcaggt gtagtcgccg gcgctcctaa    900

ccgtcaaggc gcaattcggt tcttagagta cctggtctcc ccaaaggccc aggaaatgtt    960

tgctatggct aactttgagt acccggtacg cgcaggcgtc ccagtccacc ctatcgtcaa   1020

gcaattcggc aactttcgtg gtcaaaatgt caacgcagca gtattcgggc gcaacaacgc   1080

agaagcactt cgtatcatgg accgggccgg ttggcgtggc ggtagtcatc atcatcatca   1140

tcattaatga aagggcgata tccagcacac tggcggccgt tactagtgga tccggctgct   1200

aacaaagccc gaaaggaagc tgagttggct gctgccaccg ctgagcaata actagcataa   1260

ccccttgggg cctctaaacg ggtcttgagg ggttttttgc tgaaaggagg aactatatcc   1320

ggagcgactc ccacggcacg ttggcaagct cg                                 1352
```

<210> SEQ ID NO 128
<211> LENGTH: 1352
<212> TYPE: DNA
<213> ORGANISM: Artificial Sequence
<220> FEATURE:
<223> OTHER INFORMATION: Exemplary Expression Construct for teFeBP3_N139C

<400> SEQUENCE: 128

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggtaattaa    180

tgtatatagt gcacgtcatt acgacactga caaggctctc tataatacct tcacccaaca    240

aaccgggatt cgtgtaaaca tcattgaggc tgaggcagat gccctcattg aacgtattcg    300

ttctgaaggt tcgcgcaccc cagccgatgt actcattaca gtagacgcgg gtcgcttatg    360
```

gcgtgcgcaa gaagctggca tcttacagcc gattcaatcg cgtgttttaa acagtgtagt 420
accagccaac ctccgggaac cacagggtca ctggttcggt ctctcccgtc gtgttcgcgt 480
tctgatttat aacaagtccc gtgttaatcc atctcagctt tccacatacg aagatttagc 540
taatccgaag tggcgccgtc agatcctgac acgttcttca agctgcattt acaaccaatc 600
gttgacaggt tccttactcg ccattcacgg ggcacagaag accgaacaat gggcacgtgg 660
cttagtacag aacttcgcac gtccaccgga ggggaatgac acagctcaaa ttcgtgcaag 720
tgcagagggc gttggctcag tagcgatcgc caatcactat tacctcgccc gtttaattgc 780
cagtgacaag gagcaagacc gtgcggtggc cgcaaaggtg ggcctctttt tcccgaacca 840
acgtgaccgc ggtgcacatg tcaatatcag tggggcaggt gtagtcgccg gcgctcctaa 900
ccgtcaaggc gcaattcggt tcttagagta cctggtctcc ccaaaggccc aggaaatgtt 960
tgctatggct aactttgagt acccggtacg cgcaggcgtc ccagtccacc ctatcgtcaa 1020
gcaattcggc aactttcgtg gtcaaaatgt caacgcagca gtattcgggc gcaacaacgc 1080
agaagcactt cgtatcatgg accgggccgg ttggcgtggc ggtagtcatc atcatcatca 1140
tcattaatga aagggcgata tccagcacac tggcggccgt tactagtgga tccggctgct 1200
aacaaagccc gaaaggaagc tgagttggct gctgccaccg ctgagcaata actagcataa 1260
ccccttgggg cctctaaacg ggtcttgagg ggttttttgc tgaaaggagg aactatatcc 1320
ggagcgactc ccacggcacg ttggcaagct cg 1352

<210> SEQ ID NO 129
<211> LENGTH: 1352
<212> TYPE: DNA
<213> ORGANISM: Artificial Sequence
<220> FEATURE:
<223> OTHER INFORMATION: Exemplary Expression Construct for teFeBP3_I140C

<400> SEQUENCE: 129
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggtaattaa 180
tgtatatagt gcacgtcatt acgacactga caaggctctc tataatacct tcacccaaca 240
aaccgggatt cgtgtaaaca tcattgaggc tgaggcagat gccctcattg aacgtattcg 300
ttctgaaggt tcgcgcaccc cagccgatgt actcattaca gtagacgcgg gtcgcttatg 360
gcgtgcgcaa gaagctggca tcttacagcc gattcaatcg cgtgttttaa acagtgtagt 420
accagccaac ctccgggaac cacagggtca ctggttcggt ctctcccgtc gtgttcgcgt 480
tctgatttat aacaagtccc gtgttaatcc atctcagctt tccacatacg aagatttagc 540
taatccgaag tggcgccgtc agatcctgac acgttcttca agcaactgct acaaccaatc 600
gttgacaggt tccttactcg ccattcacgg ggcacagaag accgaacaat gggcacgtgg 660
cttagtacag aacttcgcac gtccaccgga ggggaatgac acagctcaaa ttcgtgcaag 720
tgcagagggc gttggctcag tagcgatcgc caatcactat tacctcgccc gtttaattgc 780
cagtgacaag gagcaagacc gtgcggtggc cgcaaaggtg ggcctctttt tcccgaacca 840
acgtgaccgc ggtgcacatg tcaatatcag tggggcaggt gtagtcgccg gcgctcctaa 900
ccgtcaaggc gcaattcggt tcttagagta cctggtctcc ccaaaggccc aggaaatgtt 960
tgctatggct aactttgagt acccggtacg cgcaggcgtc ccagtccacc ctatcgtcaa 1020

```
gcaattcggc aactttcgtg gtcaaaatgt caacgcagca gtattcgggc gcaacaacgc   1080

agaagcactt cgtatcatgg accgggccgg ttggcgtggc ggtagtcatc atcatcatca   1140

tcattaatga aagggcgata tccagcacac tggcggccgt tactagtgga tccggctgct   1200

aacaaagccc gaaaggaagc tgagttggct gctgccaccg ctgagcaata actagcataa   1260

ccccttgggg cctctaaacg ggtcttgagg ggttttttgc tgaaaggagg aactatatcc   1320

ggagcgactc ccacggcacg ttggcaagct cg                                 1352
```

<210> SEQ ID NO 130
<211> LENGTH: 1352
<212> TYPE: DNA
<213> ORGANISM: Artificial Sequence
<220> FEATURE:
<223> OTHER INFORMATION: Exemplary Expression Construct for teFeBP3_N176C

<400> SEQUENCE: 130

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggtaattaa    180

tgtatatagt gcacgtcatt acgacactga caaggctctc tataatacct tcacccaaca    240

aaccgggatt cgtgtaaaca tcattgaggc tgaggcagat gccctcattg aacgtattcg    300

ttctgaaggt tcgcgcaccc cagccgatgt actcattaca gtagacgcgg gtcgcttatg    360

gcgtgcgcaa gaagctggca tcttacagcc gattcaatcg cgtgttttaa acagtgtagt    420

accagccaac ctccgggaac cacagggtca ctggttcggt ctctcccgtc gtgttcgcgt    480

tctgatttat aacaagtccc gtgttaatcc atctcagctt tccacatacg aagatttagc    540

taatccgaag tggcgccgtc agatcctgac acgttcttca agcaacattt acaaccaatc    600

gttgacaggt tccttactcg ccattcacgg ggcacagaag accgaacaat gggcacgtgg    660

cttagtacag aacttcgcac gtccaccgga ggggtgcgac acagctcaaa ttcgtgcaag    720

tgcagagggc gttggctcag tagcgatcgc caatcactat tacctcgccc gtttaattgc    780

cagtgacaag gagcaagacc gtgcggtggc cgcaaaggtg ggcctctttt tcccgaacca    840

acgtgaccgc ggtgcacatg tcaatatcag tggggcaggt gtagtcgccg gcgctcctaa    900

ccgtcaaggc gcaattcggt tcttagagta cctggtctcc ccaaaggccc aggaaatgtt    960

tgctatggct aactttgagt acccggtacg cgcaggcgtc ccagtccacc ctatcgtcaa   1020

gcaattcggc aactttcgtg gtcaaaatgt caacgcagca gtattcgggc gcaacaacgc   1080

agaagcactt cgtatcatgg accgggccgg ttggcgtggc ggtagtcatc atcatcatca   1140

tcattaatga aagggcgata tccagcacac tggcggccgt tactagtgga tccggctgct   1200

aacaaagccc gaaaggaagc tgagttggct gctgccaccg ctgagcaata actagcataa   1260

ccccttgggg cctctaaacg ggtcttgagg ggttttttgc tgaaaggagg aactatatcc   1320

ggagcgactc ccacggcacg ttggcaagct cg                                 1352
```

<210> SEQ ID NO 131
<211> LENGTH: 1352
<212> TYPE: DNA
<213> ORGANISM: Artificial Sequence
<220> FEATURE:
<223> OTHER INFORMATION: Exemplary Expression Construct for teFeBP3_N195C

<400> SEQUENCE: 131
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggtaattaa 180
tgtatatagt gcacgtcatt acgacactga caaggctctc tataatacct tcacccaaca 240
aaccgggatt cgtgtaaaca tcattgaggc tgaggcagat gccctcattg aacgtattcg 300
ttctgaaggt tcgcgcaccc cagccgatgt actcattaca gtagacgcgg gtcgcttatg 360
gcgtgcgcaa gaagctggca tcttacagcc gattcaatcg cgtgttttaa acagtgtagt 420
accagccaac ctccgggaac cacagggtca ctggttcggt ctctcccgtc gtgttcgcgt 480
tctgatttat aacaagtccc gtgttaatcc atctcagctt tccacatacg aagatttagc 540
taatccgaag tggcgccgtc agatcctgac acgttcttca agcaacattt acaaccaatc 600
gttgacaggt tccttactcg ccattcacgg ggcacagaag accgaacaat gggcacgtgg 660
cttagtacag aacttcgcac gtccaccgga ggggaatgac acagctcaaa ttcgtgcaag 720
tgcagagggc gttggctcag tagcgatcgc ctgccactat tacctcgccc gtttaattgc 780
cagtgacaag gagcaagacc gtgcggtggc cgcaaaggtg ggcctctttt tcccgaacca 840
acgtgaccgc ggtgcacatg tcaatatcag tggggcaggt gtagtcgccg gcgctcctaa 900
ccgtcaaggc gcaattcggt tcttagagta cctggtctcc ccaaaggccc aggaaatgtt 960
tgctatggct aactttgagt acccggtacg cgcaggcgtc ccagtccacc ctatcgtcaa 1020
gcaattcggc aactttcgtg gtcaaaatgt caacgcagca gtattcgggc gcaacaacgc 1080
agaagcactt cgtatcatgg accgggccgg ttggcgtggc ggtagtcatc atcatcatca 1140
tcattaatga aagggcgata tccagcacac tggcggccgt tactagtgga tccggctgct 1200
aacaaagccc gaaaggaagc tgagttggct gctgccaccg ctgagcaata actagcataa 1260
ccccttgggg cctctaaacg ggtcttgagg ggttttttgc tgaaaggagg aactatatcc 1320
ggagcgactc ccacggcacg ttggcaagct cg 1352

<210> SEQ ID NO 132
<211> LENGTH: 1352
<212> TYPE: DNA
<213> ORGANISM: Artificial Sequence
<220> FEATURE:
<223> OTHER INFORMATION: Exemplary Expression Construct for teFeBP3_N268C

<400> SEQUENCE: 132
cggtcacgct tgggactgcc ataggctggc ccggtgatgc cggccacgat gcgtccggcg 60
tagaggatcg agatctcgat cccgcgaaat taatacgact cactataggg agaccacaac 120
ggtttccctc tagaaataat tttgtttaac tttaagaagg agatatacca tggtaattaa 180
tgtatatagt gcacgtcatt acgacactga caaggctctc tataatacct tcacccaaca 240
aaccgggatt cgtgtaaaca tcattgaggc tgaggcagat gccctcattg aacgtattcg 300
ttctgaaggt tcgcgcaccc cagccgatgt actcattaca gtagacgcgg gtcgcttatg 360
gcgtgcgcaa gaagctggca tcttacagcc gattcaatcg cgtgttttaa acagtgtagt 420
accagccaac ctccgggaac cacagggtca ctggttcggt ctctcccgtc gtgttcgcgt 480
tctgatttat aacaagtccc gtgttaatcc atctcagctt tccacatacg aagatttagc 540
taatccgaag tggcgccgtc agatcctgac acgttcttca agcaacattt acaaccaatc 600

```
gttgacaggt tccttactcg ccattcacgg ggcacagaag accgaacaat gggcacgtgg    660

cttagtacag aacttcgcac gtccaccgga ggggaatgac acagctcaaa ttcgtgcaag    720

tgcagagggc gttggctcag tagcgatcgc caatcactat tacctcgccc gtttaattgc    780

cagtgacaag gagcaagacc gtgcggtggc cgcaaaggtg ggcctctttt tcccgaacca    840

acgtgaccgc ggtgcacatg tcaatatcag tggggcaggt gtagtcgccg gcgctcctaa    900

ccgtcaaggc gcaattcggt tcttagagta cctggtctcc ccaaaggccc aggaaatgtt    960

tgctatggct tgctttgagt acccggtacg cgcaggcgtc ccagtccacc ctatcgtcaa   1020

gcaattcggc aactttcgtg gtcaaaatgt caacgcagca gtattcgggc gcaacaacgc   1080

agaagcactt cgtatcatgg accgggccgg ttggcgtggc ggtagtcatc atcatcatca   1140

tcattaatga aagggcgata tccagcacac tggcggccgt tactagtgga tccggctgct   1200

aacaaagccc gaaaggaagc tgagttggct gctgccaccg ctgagcaata actagcataa   1260

ccccttgggg cctctaaacg ggtcttgagg ggttttttgc tgaaaggagg aactatatcc   1320

ggagcgactc ccacggcacg ttggcaagct cg                                 1352
```

<210> SEQ ID NO 133
<211> LENGTH: 1352
<212> TYPE: DNA
<213> ORGANISM: Artificial Sequence
<220> FEATURE:
<223> OTHER INFORMATION: Exemplary Expression Construct for teFeBP3_E270C

<400> SEQUENCE: 133

```
cggtcacgct tgggactgcc ataggctggc ccggtgatgc cggccacgat gcgtccggcg     60

tagaggatcg agatctcgat cccgcgaaat taatacgact cactataggg agaccacaac    120

ggtttccctc tagaaataat tttgtttaac tttaagaagg agatatacca tggtaattaa    180

tgtatatagt gcacgtcatt acgacactga caaggctctc tataatacct tcacccaaca    240

aaccgggatt cgtgtaaaca tcattgaggc tgaggcagat gccctcattg aacgtattcg    300

ttctgaaggt tcgcgcaccc cagccgatgt actcattaca gtagacgcgg gtcgcttatg    360

gcgtgcgcaa gaagctggca tcttacagcc gattcaatcg cgtgttttaa acagtgtagt    420

accagccaac ctccgggaac cacagggtca ctggttcggt ctctcccgtc gtgttcgcgt    480

tctgatttat aacaagtccc gtgttaatcc atctcagctt tccacatacg aagatttagc    540

taatccgaag tggcgccgtc agatcctgac acgttcttca agcaacattt acaaccaatc    600

gttgacaggt tccttactcg ccattcacgg ggcacagaag accgaacaat gggcacgtgg    660

cttagtacag aacttcgcac gtccaccgga ggggaatgac acagctcaaa ttcgtgcaag    720

tgcagagggc gttggctcag tagcgatcgc caatcactat tacctcgccc gtttaattgc    780

cagtgacaag gagcaagacc gtgcggtggc cgcaaaggtg ggcctctttt tcccgaacca    840

acgtgaccgc ggtgcacatg tcaatatcag tggggcaggt gtagtcgccg gcgctcctaa    900

ccgtcaaggc gcaattcggt tcttagagta cctggtctcc ccaaaggccc aggaaatgtt    960

tgctatggct aacttttgct acccggtacg cgcaggcgtc ccagtccacc ctatcgtcaa   1020

gcaattcggc aactttcgtg gtcaaaatgt caacgcagca gtattcgggc gcaacaacgc   1080

agaagcactt cgtatcatgg accgggccgg ttggcgtggc ggtagtcatc atcatcatca   1140

tcattaatga aagggcgata tccagcacac tggcggccgt tactagtgga tccggctgct   1200

aacaaagccc gaaaggaagc tgagttggct gctgccaccg ctgagcaata actagcataa   1260
```

```
ccccttgggg cctctaaacg ggtcttgagg ggttttttgc tgaaaggagg aactatatcc   1320

ggagcgactc ccacggcacg ttggcaagct cg                                 1352
```

<210> SEQ ID NO 134
<211> LENGTH: 1712
<212> TYPE: DNA
<213> ORGANISM: Artificial Sequence
<220> FEATURE:
<223> OTHER INFORMATION: Exemplary Expression Construct for avBicarbBP5_16C_bZif

<400> SEQUENCE: 134

```
gccagtaagc ttcggtcacg cttgggactg ccataggctg gcccggtgat gccggccacg     60

atgcgtccgg cgtagaggat cgagatctcg atcccgcgaa attaatacga ctcactatag    120

ggagaccaca acggtttccc tctagaaata attttgttta actttaagaa ggagatatac    180

catggctgaa caagcaccag aagttacaac agtaaagctc gggtattgcc cgattgtcga    240

atccgctcct ctcatcattg ctaaagaaaa ggggtttttc gccaagtatg gtctgacaaa    300

tgtagaatta tcgaaacagg catcgtgggg cagtgcccgg gataatgtag agatcggtag    360

cgccgggggc gggatcgacg gtggtcaatg gcagatgcct atgccacatc tcatcactga    420

aggcttaatt acgaagggca atcagaaaat cccaatgtac gtcttagcac agttgatcac    480

ccacgggaac gggattgcca ttgcaaacaa acatcaaggg aaggggatca gtttgaagct    540

cgagggtgct aagagcctgt tcagtcagct caagagctcc acgccattca cagccgcttt    600

cacttttcct catgtaaatc aagacttatg gattcgctac tggttggctg caggggggtat    660

tgaccctgat gcagatgtaa aattgttaac ggtcccagca gcccaaaccg tagccaatat    720

gaagaccggc acaatggacg cattttccac gggcgaccca tggccattcc gtctcgtaaa    780

cgacaaaatc ggttacatgg cggccttgac agcggagatc tggaaaaacc accctgagga    840

atacctcgca atgcgtgcag attgggtcga caagtatcca aaagcaacta aggcattatt    900

aaaaggcatc atggaggccc aacaatggtt ggacaacttt gacaatcgca aggaggcggc    960

acagattttg gctggccgca actactttaa cctcaacaac ccggaaatcc tggcggatcc   1020

ttacgtaggt aagtacgata tgggtgatgg tcgcaagatt gacgataaaa gcatggctgc   1080

gtattactgg aaggatgaaa aagggtcagt ttcttaccca tacaaatcgc acgacttatg   1140

gttcatcact gaaaacgtcc gttggggggtt tctgccgaag gattatctgg caaacggtgc   1200

agccaaagct aaggagttaa tcgacaaggt caatcgggag gacatctgga aagaagcagc   1260

taaagaagcc ggtattgcag cggccgacat tccaaccagc acgtcccgtg gggtagaaga   1320

gttcttcgac ggcaccaaat tcgacccaga aaagccagac gaatatctga aatcgctcaa   1380

aatcaaaaaa gtcagcgtag gcggcagcac cggcgaaaaa ccgtataaat gcccggaatg   1440

cggcaaaagc tttagccgca gcggtggttc acatcatcat catcatcatt aatgaaaggg   1500

cgatatccag cacactggcg gccgttacta gtggatccgg ctgctaacaa agcccgaaag   1560

gaagctgagt tggctgctgc caccgctgag caataactag cataacccct tggggcctct   1620

aaacgggtct tgaggggttt tttgctgaaa ggaggaacta tatccggagc gactcccacg   1680

gcacgttggc aagctcggaa ttcggcgtaa tc                                 1712
```

<210> SEQ ID NO 135
<211> LENGTH: 1712
<212> TYPE: DNA
<213> ORGANISM: Artificial Sequence
<220> FEATURE:

<223> OTHER INFORMATION: Exemplary Expression Construct for avBicarbBP5_17C_bZif

<400> SEQUENCE: 135

```
gccagtaagc ttcggtcacg cttgggactg ccataggctg gcccggtgat gccggccacg     60
atgcgtccgg cgtagaggat cgagatctcg atcccgcgaa attaatacga ctcactatag    120
ggagaccaca acggtttccc tctagaaata attttgttta actttaagaa ggagatatac    180
catggctgaa caagcaccag aagttacaac agtaaagctc gggtatatct gcattgtcga    240
atccgctcct ctcatcattg ctaaagaaaa ggggtttttc gccaagtatg gtctgacaaa    300
tgtagaatta tcgaaacagg catcgtgggg cagtgcccgg gataatgtag agatcggtag    360
cgccgggggc gggatcgacg gtggtcaatg gcagatgcct atgccacatc tcatcactga    420
aggcttaatt acgaagggca atcagaaaat cccaatgtac gtcttagcac agttgatcac    480
ccacgggaac gggattgcca ttgcaaacaa acatcaaggg aaggggatca gtttgaagct    540
cgagggtgct aagagcctgt tcagtcagct caagagctcc acgccattca cagccgcttt    600
cacttttcct catgtaaatc aagacttatg gattcgctac tggttggctg caggggggtat    660
tgaccctgat gcagatgtaa aattgttaac ggtcccagca gcccaaaccg tagccaatat    720
gaagaccggc acaatggacg cattttccac gggcgaccca tggccattcc gtctcgtaaa    780
cgacaaaatc ggttacatgg cggccttgac agcggagatc tggaaaaacc accctgagga    840
atacctcgca atgcgtgcag attgggtcga caagtatcca aaagcaacta aggcattatt    900
aaaaggcatc atggaggccc aacaatggtt ggacaacttt gacaatcgca aggaggcggc    960
acagattttg gctggccgca actactttaa cctcaacaac ccggaaatcc tggcggatcc   1020
ttacgtaggt aagtacgata tgggtgatgg tcgcaagatt gacgataaaa gcatggctgc   1080
gtattactgg aaggatgaaa aagggtcagt ttcttaccca tacaaatcgc acgacttatg   1140
gttcatcact gaaaacgtcc gttgggggtt tctgccgaag gattatctgg caaacggtgc   1200
agccaaagct aaggagttaa tcgacaaggt caatcgggag gacatctgga aagaagcagc   1260
taaagaagcc ggtattgcag cggccgacat tccaaccagc acgtcccgtg gggtagaaga   1320
gttcttcgac ggcaccaaat tcgacccaga aaagccagac gaatatctga aatcgctcaa   1380
aatcaaaaaa gtcagcgtag gcggcagcac cggcgaaaaa ccgtataaat gcccggaatg   1440
cggcaaaagc tttagccgca gcggtggttc acatcatcat catcatcatt aatgaaaggg   1500
cgatatccag cacactggcg gccgttacta gtggatccgg ctgctaacaa agcccgaaag   1560
gaagctgagt tggctgctgc caccgctgag caataactag cataacccct tggggcctct   1620
aaacgggtct tgaggggttt tttgctgaaa ggaggaacta tatccggagc gactcccacg   1680
gcacgttggc aagctcggaa ttcggcgtaa tc                                 1712
```

<210> SEQ ID NO 136
<211> LENGTH: 1712
<212> TYPE: DNA
<213> ORGANISM: Artificial Sequence
<220> FEATURE:
<223> OTHER INFORMATION: Exemplary Expression Construct for avBicarbBP5_18C_bZif

<400> SEQUENCE: 136

```
gccagtaagc ttcggtcacg cttgggactg ccataggctg gcccggtgat gccggccacg     60
atgcgtccgg cgtagaggat cgagatctcg atcccgcgaa attaatacga ctcactatag    120
ggagaccaca acggtttccc tctagaaata attttgttta actttaagaa ggagatatac    180
```

```
catggctgaa caagcaccag aagttacaac agtaaagctc gggtatatcc cgtgcgtcga    240

atccgctcct ctcatcattg ctaaagaaaa ggggtttttc gccaagtatg gtctgacaaa    300

tgtagaatta tcgaaacagg catcgtgggg cagtgcccgg gataatgtag agatcggtag    360

cgccgggggc gggatcgacg gtggtcaatg gcagatgcct atgccacatc tcatcactga    420

aggcttaatt acgaagggca atcagaaaat cccaatgtac gtcttagcac agttgatcac    480

ccacgggaac gggattgcca ttgcaaacaa acatcaaggg aaggggatca gtttgaagct    540

cgagggtgct aagagcctgt tcagtcagct caagagctcc acgccattca cagccgcttt    600

cacttttcct catgtaaatc aagacttatg gattcgctac tggttggctg caggggggtat    660

tgaccctgat gcagatgtaa aattgttaac ggtcccagca gcccaaaccg tagccaatat    720

gaagaccggc acaatggacg cattttccac gggcgaccca tggccattcc gtctcgtaaa    780

cgacaaaatc ggttacatgg cggccttgac agcggagatc tggaaaaacc accctgagga    840

atacctcgca atgcgtgcag attgggtcga caagtatcca aaagcaacta aggcattatt    900

aaaaggcatc atggaggccc aacaatggtt ggacaacttt gacaatcgca aggaggcggc    960

acagattttg gctggccgca actactttaa cctcaacaac ccggaaatcc tggcggatcc   1020

ttacgtaggt aagtacgata tgggtgatgg tcgcaagatt gacgataaaa gcatggctgc   1080

gtattactgg aaggatgaaa aagggtcagt ttcttaccca tacaaatcgc acgacttatg   1140

gttcatcact gaaaacgtcc gttgggggtt tctgccgaag gattatctgg caaacggtgc   1200

agccaaagct aaggagttaa tcgacaaggt caatcgggag gacatctgga aagaagcagc   1260

taaagaagcc ggtattgcag cggccgacat tccaaccagc acgtcccgtg ggtagaaga    1320

gttcttcgac ggcaccaaat tcgacccaga aaagccagac gaatatctga aatcgctcaa   1380

aatcaaaaaa gtcagcgtag gcggcagcac cggcgaaaaa ccgtataaat gcccggaatg   1440

cggcaaaagc tttagccgca gcggtggttc acatcatcat catcatcatt aatgaaaggg   1500

cgatatccag cacactggcg gccgttacta gtggatccgg ctgctaacaa agcccgaaag   1560

gaagctgagt tggctgctgc caccgctgag caataactag cataacccct tggggcctct   1620

aaacgggtct tgaggggttt tttgctgaaa ggaggaacta tatccggagc gactcccacg   1680

gcacgttggc aagctcggaa ttcggcgtaa tc                                 1712
```

<210> SEQ ID NO 137
<211> LENGTH: 1712
<212> TYPE: DNA
<213> ORGANISM: Artificial Sequence
<220> FEATURE:
<223> OTHER INFORMATION: Exemplary Expression Construct for avBicarbBP5_190C_bZif

<400> SEQUENCE: 137

```
gccagtaagc ttcggtcacg cttgggactg ccataggctg gcccggtgat gccggccacg     60

atgcgtccgg cgtagaggat cgagatctcg atcccgcgaa attaatacga ctcactatag    120

ggagaccaca acggtttccc tctagaaata attttgttta actttaagaa ggagatatac    180

catggctgaa caagcaccag aagttacaac agtaaagctc gggtatatcc cgattgtcga    240

atccgctcct ctcatcattg ctaaagaaaa ggggtttttc gccaagtatg gtctgacaaa    300

tgtagaatta tcgaaacagg catcgtgggg cagtgcccgg gataatgtag agatcggtag    360

cgccgggggc gggatcgacg gtggtcaatg gcagatgcct atgccacatc tcatcactga    420

aggcttaatt acgaagggca atcagaaaat cccaatgtac gtcttagcac agttgatcac    480
```

```
ccacgggaac gggattgcca ttgcaaacaa acatcaaggg aaggggatca gtttgaagct    540
cgagggtgct aagagcctgt tcagtcagct caagagctcc acgccattca cagccgcttt    600
cacttttcct catgtaaatc aagacttatg gattcgctac tggttggctg caggggggtat    660
tgaccctgat gcagatgtaa aattgttaac ggtcccagca gcccaaaccg tagccaatat    720
gaagaccggc acaatggacg cattttcctg cggcgaccca tggccattcc gtctcgtaaa    780
cgacaaaatc ggttacatgg cggccttgac agcggagatc tggaaaaacc accctgagga    840
atacctcgca atgcgtgcag attgggtcga caagtatcca aaagcaacta aggcattatt    900
aaaaggcatc atggaggccc aacaatggtt ggacaacttt gacaatcgca aggaggcggc    960
acagattttg gctggccgca actactttaa cctcaacaac ccggaaatcc tggcggatcc   1020
ttacgtaggt aagtacgata tgggtgatgg tcgcaagatt gacgataaaa gcatggctgc   1080
gtattactgg aaggatgaaa aagggtcagt ttcttaccca tacaaatcgc acgacttatg   1140
gttcatcact gaaaacgtcc gttggggggtt tctgccgaag gattatctgg caaacggtgc   1200
agccaaagct aaggagttaa tcgacaaggt caatcgggag gacatctgga aagaagcagc   1260
taaagaagcc ggtattgcag cggccgacat tccaaccagc acgtcccgtg ggtagaaga   1320
gttcttcgac ggcaccaaat tcgacccaga aaagccagac gaatatctga aatcgctcaa   1380
aatcaaaaaa gtcagcgtag gcggcagcac cggcgaaaaa ccgtataaat gcccggaatg   1440
cggcaaaagc tttagccgca gcggtggttc acatcatcat catcatcatt aatgaaaggg   1500
cgatatccag cacactggcg gccgttacta gtggatccgg ctgctaacaa agcccgaaag   1560
gaagctgagt tggctgctgc caccgctgag caataactag cataacccct tggggcctct   1620
aaacgggtct tgaggggttt tttgctgaaa ggaggaacta tatccggagc gactcccacg   1680
gcacgttggc aagctcggaa ttcggcgtaa tc                                 1712
```

<210> SEQ ID NO 138
<211> LENGTH: 1712
<212> TYPE: DNA
<213> ORGANISM: Artificial Sequence
<220> FEATURE:
<223> OTHER INFORMATION: Exemplary Expression Construct for avBicarbBP5_194C_bZif

<400> SEQUENCE: 138

```
gccagtaagc ttcggtcacg cttgggactg ccataggctg gcccggtgat gccggccacg     60
atgcgtccgg cgtagaggat cgagatctcg atcccgcgaa attaatacga ctcactatag    120
ggagaccaca acggtttccc tctagaaata attttgttta actttaagaa ggagatatac    180
catggctgaa caagcaccag aagttacaac agtaaagctc gggtatatcc cgattgtcga    240
atccgctcct ctcatcattg ctaaagaaaa ggggtttttc gccaagtatg gtctgacaaa    300
tgtagaatta tcgaaacagg catcgtgggg cagtgcccgg gataatgtag agatcggtag    360
cgccgggggc gggatcgacg gtggtcaatg gcagatgcct atgccacatc tcatcactga    420
aggcttaatt acgaagggca atcagaaaat cccaatgtac gtcttagcac agttgatcac    480
ccacgggaac gggattgcca ttgcaaacaa acatcaaggg aaggggatca gtttgaagct    540
cgagggtgct aagagcctgt tcagtcagct caagagctcc acgccattca cagccgcttt    600
cacttttcct catgtaaatc aagacttatg gattcgctac tggttggctg caggggggtat    660
tgaccctgat gcagatgtaa aattgttaac ggtcccagca gcccaaaccg tagccaatat    720
gaagaccggc acaatggacg cattttccac gggcgaccca tgcccattcc gtctcgtaaa    780
```

```
cgacaaaatc ggttacatgg cggccttgac agcggagatc tggaaaaacc accctgagga    840

atacctcgca atgcgtgcag attgggtcga caagtatcca aaagcaacta aggcattatt    900

aaaaggcatc atggaggccc aacaatggtt ggacaacttt gacaatcgca aggaggcggc    960

acagattttg gctggccgca actactttaa cctcaacaac ccggaaatcc tggcggatcc   1020

ttacgtaggt aagtacgata tgggtgatgg tcgcaagatt gacgataaaa gcatggctgc   1080

gtattactgg aaggatgaaa aagggtcagt ttcttaccca tacaaatcgc acgacttatg   1140

gttcatcact gaaaacgtcc gttgggggtt tctgccgaag gattatctgg caaacggtgc   1200

agccaaagct aaggagttaa tcgacaaggt caatcgggag gacatctgga aagaagcagc   1260

taaagaagcc ggtattgcag cggccgacat tccaaccagc acgtcccgtg gggtagaaga   1320

gttcttcgac ggcaccaaat tcgacccaga aaagccagac gaatatctga aatcgctcaa   1380

aatcaaaaaa gtcagcgtag gcggcagcac cggcgaaaaa ccgtataaat gcccggaatg   1440

cggcaaaagc tttagccgca gcggtggttc acatcatcat catcatcatt aatgaaaggg   1500

cgatatccag cacactggcg gccgttacta gtggatccgg ctgctaacaa agcccgaaag   1560

gaagctgagt tggctgctgc caccgctgag caataactag cataacccct tggggcctct   1620

aaacgggtct tgaggggttt tttgctgaaa ggaggaacta tatccggagc gactcccacg   1680

gcacgttggc aagctcggaa ttcggcgtaa tc                                 1712
```

```
<210> SEQ ID NO 139
<211> LENGTH: 1712
<212> TYPE: DNA
<213> ORGANISM: Artificial Sequence
<220> FEATURE:
<223> OTHER INFORMATION: Exemplary Expression Construct for
      avBicarbBP5_16C_71D_bZif

<400> SEQUENCE: 139
```

```
gccagtaagc ttcggtcacg cttgggactg ccataggctg gcccggtgat gccggccacg     60

atgcgtccgg cgtagaggat cgagatctcg atcccgcgaa attaatacga ctcactatag    120

ggagaccaca acggtttccc tctagaaata attttgttta actttaagaa ggagatatac    180

catggctgaa caagcaccag aagttacaac agtaaagctc gggtattgcc cgattgtcga    240

atccgctcct ctcatcattg ctaaagaaaa ggggtttttc gccaagtatg gtctgacaaa    300

tgtagaatta tcgaaacagg catcgtgggg cagtgcccgg gataatgtag agatcggtag    360

cgccgggggc gggatcgacg gtggtcaatg ggatatgcct atgccacatc tcatcactga    420

aggcttaatt acgaagggca atcagaaaat cccaatgtac gtcttagcac agttgatcac    480

ccacgggaac gggattgcca ttgcaaacaa acatcaaggg aaggggatca gtttgaagct    540

cgagggtgct aagagcctgt tcagtcagct caagagctcc acgccattca cagccgcttt    600

cacttttcct catgtaaatc aagacttatg gattcgctac tggttggctg caggggggtat    660

tgaccctgat gcagatgtaa aattgttaac ggtcccagca gcccaaaccg tagccaatat    720

gaagaccggc acaatggacg cattttccac gggcgaccca tggccattcc gtctcgtaaa    780

cgacaaaatc ggttacatgg cggccttgac agcggagatc tggaaaaacc accctgagga    840

atacctcgca atgcgtgcag attgggtcga caagtatcca aaagcaacta aggcattatt    900

aaaaggcatc atggaggccc aacaatggtt ggacaacttt gacaatcgca aggaggcggc    960

acagattttg gctggccgca actactttaa cctcaacaac ccggaaatcc tggcggatcc   1020

ttacgtaggt aagtacgata tgggtgatgg tcgcaagatt gacgataaaa gcatggctgc   1080
```

gtattactgg aaggatgaaa aagggtcagt ttcttaccca tacaaatcgc acgacttatg 1140
gttcatcact gaaaacgtcc gttgggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg ggtagaaga 1320 gttcttcgac ggcaccaaat tcgacccaga aaagccagac gaatatctga aatcgctcaa 1380
aatcaaaaaa gtcagcgtag gcggcagcac cggcgaaaaa ccgtataaat gcccggaatg 1440
cggcaaaagc tttagccgca gcggtggttc acatcatcat catcatcatt aatgaaaggg 1500
cgatatccag cacactggcg gccgttacta gtggatccgg ctgctaacaa agcccgaaag 1560
gaagctgagt tggctgctgc caccgctgag caataactag cataacccct tggggcctct 1620
aaacgggtct tgaggggttt tttgctgaaa ggaggaacta tatccggagc gactcccacg 1680
gcacgttggc aagctcggaa ttcggcgtaa tc 1712

<210> SEQ ID NO 140
<211> LENGTH: 1712
<212> TYPE: DNA
<213> ORGANISM: Artificial Sequence
<220> FEATURE:
<223> OTHER INFORMATION: Exemplary Expression Construct for avBicarbBP5_16C_71N_bZif

<400> SEQUENCE: 140
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catggctgaa caagcaccag aagttacaac agtaaagctc gggtattgcc cgattgtcga 240
atccgctcct ctcatcattg ctaaagaaaa ggggtttttc gccaagtatg gtctgacaaa 300
tgtagaatta tcgaaacagg catcgtgggg cagtgcccgg gataatgtag agatcggtag 360
cgccgggggc gggatcgacg gtggtcaatg gaacatgcct atgccacatc tcatcactga 420
aggcttaatt acgaagggca atcagaaaat cccaatgtac gtcttagcac agttgatcac 480
ccacgggaac gggattgcca ttgcaaacaa acatcaaggg aaggggatca gtttgaagct 540
cgagggtgct aagagcctgt tcagtcagct caagagctcc acgccattca cagccgcttt 600
cacttttcct catgtaaatc aagacttatg gattcgctac tggttggctg caggggggtat 660 tgaccctgat gcagatgtaa aattgttaac ggtcccagca gcccaaaccg tagccaatat 720
gaagaccggc acaatggacg cattttccac gggcgaccca tggccattcc gtctcgtaaa 780
cgacaaaatc ggttacatgg cggccttgac agcggagatc tggaaaaacc accctgagga 840
atacctcgca atgcgtgcag attgggtcga caagtatcca aaagcaacta aggcattatt 900
aaaaggcatc atggaggccc aacaatggtt ggacaacttt gacaatcgca aggaggcggc 960
acagattttg gctggccgca actactttaa cctcaacaac ccggaaatcc tggcggatcc 1020
ttacgtaggt aagtacgata tgggtgatgg tcgcaagatt gacgataaaa gcatggctgc 1080
gtattactgg aaggatgaaa aagggtcagt ttcttaccca tacaaatcgc acgacttatg 1140
gttcatcact gaaaacgtcc gttgggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg ggtagaaga 1320 gttcttcgac ggcaccaaat tcgacccaga aaagccagac gaatatctga aatcgctcaa 1380
aatcaaaaaa gtcagcgtag gcggcagcac cggcgaaaaa ccgtataaat gcccggaatg 1440
cggcaaaagc tttagccgca gcggtggttc acatcatcat catcatcatt aatgaaaggg 1500
cgatatccag cacactggcg gccgttacta gtggatccgg ctgctaacaa agcccgaaag 1560
gaagctgagt tggctgctgc caccgctgag caataactag cataacccct tggggcctct 1620
aaacgggtct tgaggggttt tttgctgaaa ggaggaacta tatccggagc gactcccacg 1680
gcacgttggc aagctcggaa ttcggcgtaa tc 1712

<210> SEQ ID NO 141
<211> LENGTH: 1712
<212> TYPE: DNA
<213> ORGANISM: Artificial Sequence
<220> FEATURE:
<223> OTHER INFORMATION: Exemplary Expression Construct for avBicarbBP5_16C_71E_bZif

<400> SEQUENCE: 141
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catggctgaa caagcaccag aagttacaac agtaaagctc gggtattgcc cgattgtcga 240
atccgctcct ctcatcattg ctaaagaaaa ggggtttttc gccaagtatg gtctgacaaa 300
tgtagaatta tcgaaacagg catcgtgggg cagtgcccgg gataatgtag agatcggtag 360
cgccgggggc gggatcgacg gtggtcaatg ggaaatgcct atgccacatc tcatcactga 420
aggcttaatt acgaagggca atcagaaaat cccaatgtac gtcttagcac agttgatcac 480
ccacgggaac gggattgcca ttgcaaacaa acatcaaggg aaggggatca gtttgaagct 540
cgagggtgct aagagcctgt tcagtcagct caagagctcc acgccattca cagccgcttt 600
cacttttcct catgtaaatc aagacttatg gattcgctac tggttggctg caggggggtat 660 tgaccctgat gcagatgtaa aattgttaac ggtcccagca gcccaaaccg tagccaatat 720
gaagaccggc acaatggacg cattttccac gggcgaccca tggccattcc gtctcgtaaa 780
cgacaaaatc ggttacatgg cggccttgac agcggagatc tggaaaaacc accctgagga 840
atacctcgca atgcgtgcag attgggtcga caagtatcca aaagcaacta aggcattatt 900
aaaaggcatc atggaggccc aacaatggtt ggacaacttt gacaatcgca aggaggcggc 960
acagattttg gctggccgca actactttaa cctcaacaac ccggaaatcc tggcggatcc 1020
ttacgtaggt aagtacgata tgggtgatgg tcgcaagatt gacgataaaa gcatggctgc 1080
gtattactgg aaggatgaaa aagggtcagt ttcttaccca tacaaatcgc acgacttatg 1140
gttcatcact gaaaacgtcc gttgggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg gggtagaaga 1320
gttcttcgac ggcaccaaat tcgacccaga aaagccagac gaatatctga aatcgctcaa 1380
aatcaaaaaa gtcagcgtag gcggcagcac cggcgaaaaa ccgtataaat gcccggaatg 1440
cggcaaaagc tttagccgca gcggtggttc acatcatcat catcatcatt aatgaaaggg 1500
cgatatccag cacactggcg gccgttacta gtggatccgg ctgctaacaa agcccgaaag 1560
gaagctgagt tggctgctgc caccgctgag caataactag cataacccct tggggcctct 1620
aaacgggtct tgaggggttt tttgctgaaa ggaggaacta tatccggagc gactcccacg 1680
gcacgttggc aagctcggaa ttcggcgtaa tc 1712

<210> SEQ ID NO 142
<211> LENGTH: 1712
<212> TYPE: DNA
<213> ORGANISM: Artificial Sequence
<220> FEATURE:
<223> OTHER INFORMATION: Exemplary Expression Construct for
avBicarbBP5_16C_71M_bZif

<400> SEQUENCE: 142
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catggctgaa caagcaccag aagttacaac agtaaagctc gggtattgcc cgattgtcga 240
atccgctcct ctcatcattg ctaaagaaaa ggggtttttc gccaagtatg gtctgacaaa 300
tgtagaatta tcgaaacagg catcgtgggg cagtgcccgg gataatgtag agatcggtag 360
cgccgggggc gggatcgacg gtggtcaatg gatgatgcct atgccacatc tcatcactga 420
aggcttaatt acgaagggca atcagaaaat cccaatgtac gtcttagcac agttgatcac 480
ccacgggaac gggattgcca ttgcaaacaa acatcaaggg aaggggatca gtttgaagct 540
cgagggtgct aagagcctgt tcagtcagct caagagctcc acgccattca cagccgcttt 600
cacttttcct catgtaaatc aagacttatg gattcgctac tggttggctg caggggggtat 660 tgaccctgat gcagatgtaa aattgttaac ggtcccagca gcccaaaccg tagccaatat 720
gaagaccggc acaatggacg cattttccac gggcgaccca tggccattcc gtctcgtaaa 780
cgacaaaatc ggttacatgg cggccttgac agcggagatc tggaaaaacc accctgagga 840
atacctcgca atgcgtgcag attgggtcga caagtatcca aaagcaacta aggcattatt 900
aaaaggcatc atggaggccc aacaatggtt ggacaacttt gacaatcgca aggaggcggc 960
acagattttg gctggccgca actactttaa cctcaacaac ccggaaatcc tggcggatcc 1020
ttacgtaggt aagtacgata tgggtgatgg tcgcaagatt gacgataaaa gcatggctgc 1080
gtattactgg aaggatgaaa aagggtcagt ttcttaccca tacaaatcgc acgacttatg 1140
gttcatcact gaaaacgtcc gttgggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg ggtagaaga 1320 gttcttcgac ggcaccaaat tcgacccaga aaagccagac gaatatctga aatcgctcaa 1380
aatcaaaaaa gtcagcgtag gcggcagcac cggcgaaaaa ccgtataaat gcccggaatg 1440
cggcaaaagc tttagccgca gcggtggttc acatcatcat catcatcatt aatgaaaggg 1500
cgatatccag cacactggcg gccgttacta gtggatccgg ctgctaacaa agcccgaaag 1560
gaagctgagt tggctgctgc caccgctgag caataactag cataacccct tggggcctct 1620
aaacgggtct tgaggggttt tttgctgaaa ggaggaacta tatccggagc gactcccacg 1680
gcacgttggc aagctcggaa ttcggcgtaa tc 1712

<210> SEQ ID NO 143
<211> LENGTH: 1712
<212> TYPE: DNA
<213> ORGANISM: Artificial Sequence
<220> FEATURE:
<223> OTHER INFORMATION: Exemplary Expression Construct for avBicarbBP5_18C_16M_bZif

<400> SEQUENCE: 143

```
gccagtaagc ttcggtcacg cttgggactg ccataggctg gcccggtgat gccggccacg     60
atgcgtccgg cgtagaggat cgagatctcg atcccgcgaa attaatacga ctcactatag    120
ggagaccaca acggtttccc tctagaaata attttgttta actttaagaa ggagatatac    180
catggctgaa caagcaccag aagttacaac agtaaagctc gggtatatgc cgtgcgtcga    240
atccgctcct ctcatcattg ctaaagaaaa ggggtttttc gccaagtatg gtctgacaaa    300
tgtagaatta tcgaaacagg catcgtgggg cagtgcccgg gataatgtag agatcggtag    360
cgccgggggc gggatcgacg gtggtcaatg gcagatgcct atgccacatc tcatcactga    420
aggcttaatt acgaagggca atcagaaaat cccaatgtac gtcttagcac agttgatcac    480
ccacgggaac gggattgcca ttgcaaacaa acatcaaggg aaggggatca gtttgaagct    540
cgagggtgct aagagcctgt tcagtcagct caagagctcc acgccattca cagccgcttt    600
cacttttcct catgtaaatc aagacttatg gattcgctac tggttggctg caggggggtat    660
tgaccctgat gcagatgtaa aattgttaac ggtcccagca gcccaaaccg tagccaatat    720
gaagaccggc acaatggacg cattttccac gggcgaccca tggccattcc gtctcgtaaa    780
cgacaaaatc ggttacatgg cggccttgac agcggagatc tggaaaaacc accctgagga    840
atacctcgca atgcgtgcag attgggtcga caagtatcca aaagcaacta aggcattatt    900
aaaaggcatc atggaggccc aacaatggtt ggacaacttt gacaatcgca aggaggcggc    960
acagattttg gctggccgca actactttaa cctcaacaac ccggaaatcc tggcggatcc   1020
ttacgtaggt aagtacgata tgggtgatgg tcgcaagatt gacgataaaa gcatggctgc   1080
gtattactgg aaggatgaaa aagggtcagt ttcttaccca tacaaatcgc acgacttatg   1140
gttcatcact gaaaacgtcc gttgggggtt tctgccgaag gattatctgg caaacggtgc   1200
agccaaagct aaggagttaa tcgacaaggt caatcgggag gacatctgga aagaagcagc   1260
taaagaagcc ggtattgcag cggccgacat tccaaccagc acgtcccgtg ggtagaaga   1320
gttcttcgac ggcaccaaat tcgacccaga aaagccagac gaatatctga aatcgctcaa   1380
aatcaaaaaa gtcagcgtag gcggcagcac cggcgaaaaa ccgtataaat gcccggaatg   1440
cggcaaaagc tttagccgca gcggtggttc acatcatcat catcatcatt aatgaaaggg   1500
cgatatccag cacactggcg gccgttacta gtggatccgg ctgctaacaa agcccgaaag   1560
gaagctgagt tggctgctgc caccgctgag caataactag cataacccct tggggcctct   1620
aaacgggtct tgaggggttt tttgctgaaa ggaggaacta tatccggagc gactcccacg   1680
gcacgttggc aagctcggaa ttcggcgtaa tc                                 1712
```

<210> SEQ ID NO 144
<211> LENGTH: 1712
<212> TYPE: DNA
<213> ORGANISM: Artificial Sequence
<220> FEATURE:
<223> OTHER INFORMATION: Exemplary Expression Construct for
avBicarbBP5_18C_16F_bZif

<400> SEQUENCE: 144

```
gccagtaagc ttcggtcacg cttgggactg ccataggctg gcccggtgat gccggccacg     60
atgcgtccgg cgtagaggat cgagatctcg atcccgcgaa attaatacga ctcactatag    120
ggagaccaca acggtttccc tctagaaata attttgttta actttaagaa ggagatatac    180
```

```
catggctgaa caagcaccag aagttacaac agtaaagctc gggtattttc cgtgcgtcga    240

atccgctcct ctcatcattg ctaaagaaaa ggggtttttc gccaagtatg gtctgacaaa    300

tgtagaatta tcgaaacagg catcgtgggg cagtgcccgg gataatgtag agatcggtag    360

cgccgggggc gggatcgacg gtggtcaatg gcagatgcct atgccacatc tcatcactga    420

aggcttaatt acgaagggca atcagaaaat cccaatgtac gtcttagcac agttgatcac    480

ccacgggaac gggattgcca ttgcaaacaa acatcaaggg aaggggatca gtttgaagct    540

cgagggtgct aagagcctgt tcagtcagct caagagctcc acgccattca cagccgcttt    600

cacttttcct catgtaaatc aagacttatg gattcgctac tggttggctg caggggggtat    660

tgaccctgat gcagatgtaa aattgttaac ggtcccagca gcccaaaccg tagccaatat    720

gaagaccggc acaatggacg cattttccac gggcgaccca tggccattcc gtctcgtaaa    780

cgacaaaatc ggttacatgg cggccttgac agcggagatc tggaaaaacc accctgagga    840

atacctcgca atgcgtgcag attgggtcga caagtatcca aaagcaacta aggcattatt    900

aaaaggcatc atggaggccc aacaatggtt ggacaacttt gacaatcgca aggaggcggc    960

acagattttg gctggccgca actactttaa cctcaacaac ccggaaatcc tggcggatcc   1020

ttacgtaggt aagtacgata tgggtgatgg tcgcaagatt gacgataaaa gcatggctgc   1080

gtattactgg aaggatgaaa aagggtcagt ttcttaccca tacaaatcgc acgacttatg   1140

gttcatcact gaaaacgtcc gttgggggtt tctgccgaag gattatctgg caaacggtgc   1200

agccaaagct aaggagttaa tcgacaaggt caatcgggag gacatctgga aagaagcagc   1260

taaagaagcc ggtattgcag cggccgacat tccaaccagc acgtcccgtg gggtagaaga   1320

gttcttcgac ggcaccaaat tcgacccaga aaagccagac gaatatctga aatcgctcaa   1380

aatcaaaaaa gtcagcgtag gcggcagcac cggcgaaaaa ccgtataaat gcccggaatg   1440

cggcaaaagc tttagccgca gcggtggttc acatcatcat catcatcatt aatgaaaggg   1500

cgatatccag cacactggcg gccgttacta gtggatccgg ctgctaacaa agcccgaaag   1560

gaagctgagt tggctgctgc caccgctgag caataactag cataacccct tggggcctct   1620

aaacgggtct tgaggggttt tttgctgaaa ggaggaacta tatccggagc gactcccacg   1680

gcacgttggc aagctcggaa ttcggcgtaa tc                                 1712
```

```
<210> SEQ ID NO 145
<211> LENGTH: 1712
<212> TYPE: DNA
<213> ORGANISM: Artificial Sequence
<220> FEATURE:
<223> OTHER INFORMATION: Exemplary Expression Construct for
      avBicarbBP5_18C_16Y_bZif

<400> SEQUENCE: 145
```

```
gccagtaagc ttcggtcacg cttgggactg ccataggctg gcccggtgat gccggccacg     60

atgcgtccgg cgtagaggat cgagatctcg atcccgcgaa attaatacga ctcactatag    120

ggagaccaca acggtttccc tctagaaata attttgttta actttaagaa ggagatatac    180

catggctgaa caagcaccag aagttacaac agtaaagctc gggtattatc cgtgcgtcga    240

atccgctcct ctcatcattg ctaaagaaaa ggggtttttc gccaagtatg gtctgacaaa    300

tgtagaatta tcgaaacagg catcgtgggg cagtgcccgg gataatgtag agatcggtag    360

cgccgggggc gggatcgacg gtggtcaatg gcagatgcct atgccacatc tcatcactga    420

aggcttaatt acgaagggca atcagaaaat cccaatgtac gtcttagcac agttgatcac    480
```

```
ccacgggaac gggattgcca ttgcaaacaa acatcaaggg aaggggatca gtttgaagct    540

cgagggtgct aagagcctgt tcagtcagct caagagctcc acgccattca cagccgcttt    600

cacttttcct catgtaaatc aagacttatg gattcgctac tggttggctg caggggggtat    660

tgaccctgat gcagatgtaa aattgttaac ggtcccagca gcccaaaccg tagccaatat    720

gaagaccggc acaatggacg cattttccac gggcgaccca tggccattcc gtctcgtaaa    780

cgacaaaatc ggttacatgg cggccttgac agcggagatc tggaaaaacc accctgagga    840

atacctcgca atgcgtgcag attgggtcga caagtatcca aaagcaacta aggcattatt    900

aaaaggcatc atggaggccc aacaatggtt ggacaacttt gacaatcgca aggaggcggc    960

acagattttg gctggccgca actactttaa cctcaacaac ccggaaatcc tggcggatcc   1020

ttacgtaggt aagtacgata tgggtgatgg tcgcaagatt gacgataaaa gcatggctgc   1080

gtattactgg aaggatgaaa aagggtcagt ttcttaccca tacaaatcgc acgacttatg   1140

gttcatcact gaaaacgtcc gttgggggtt tctgccgaag gattatctgg caaacggtgc   1200

agccaaagct aaggagttaa tcgacaaggt caatcgggag gacatctgga aagaagcagc   1260

taaagaagcc ggtattgcag cggccgacat tccaaccagc acgtcccgtg ggtagaaga   1320

gttcttcgac ggcaccaaat tcgacccaga aaagccagac gaatatctga aatcgctcaa   1380

aatcaaaaaa gtcagcgtag gcggcagcac cggcgaaaaa ccgtataaat gcccggaatg   1440

cggcaaaagc tttagccgca gcggtggttc acatcatcat catcatcatt aatgaaaggg   1500

cgatatccag cacactggcg gccgttacta gtggatccgg ctgctaacaa agcccgaaag   1560

gaagctgagt tggctgctgc caccgctgag caataactag cataacccct tggggcctct   1620

aaacgggtct tgaggggttt tttgctgaaa ggaggaacta tatccggagc gactcccacg   1680

gcacgttggc aagctcggaa ttcggcgtaa tc                                  1712
```

<210> SEQ ID NO 146
<211> LENGTH: 1712
<212> TYPE: DNA
<213> ORGANISM: Artificial Sequence
<220> FEATURE:
<223> OTHER INFORMATION: Exemplary Expression Construct for avBicarbBP5_18C_16W_bZif

<400> SEQUENCE: 146

```
gccagtaagc ttcggtcacg cttgggactg ccataggctg gcccggtgat gccggccacg     60

atgcgtccgg cgtagaggat cgagatctcg atcccgcgaa attaatacga ctcactatag    120

ggagaccaca acggtttccc tctagaaata attttgttta actttaagaa ggagatatac    180

catggctgaa caagcaccag aagttacaac agtaaagctc gggtattggc cgtgcgtcga    240

atccgctcct ctcatcattg ctaaagaaaa ggggtttttc gccaagtatg gtctgacaaa    300

tgtagaatta tcgaaacagg catcgtgggg cagtgcccgg gataatgtag agatcggtag    360

cgccgggggc gggatcgacg gtggtcaatg gcagatgcct atgccacatc tcatcactga    420

aggcttaatt acgaagggca atcagaaaat cccaatgtac gtcttagcac agttgatcac    480

ccacgggaac gggattgcca ttgcaaacaa acatcaaggg aaggggatca gtttgaagct    540

cgagggtgct aagagcctgt tcagtcagct caagagctcc acgccattca cagccgcttt    600

cacttttcct catgtaaatc aagacttatg gattcgctac tggttggctg caggggggtat    660

tgaccctgat gcagatgtaa aattgttaac ggtcccagca gcccaaaccg tagccaatat    720

gaagaccggc acaatggacg cattttccac gggcgaccca tggccattcc gtctcgtaaa    780
```

```
cgacaaaatc ggttacatgg cggccttgac agcggagatc tggaaaaacc accctgagga    840

atacctcgca atgcgtgcag attgggtcga caagtatcca aaagcaacta aggcattatt    900

aaaaggcatc atggaggccc aacaatggtt ggacaacttt gacaatcgca aggaggcggc    960

acagattttg gctggccgca actactttaa cctcaacaac ccggaaatcc tggcggatcc   1020

ttacgtaggt aagtacgata tgggtgatgg tcgcaagatt gacgataaaa gcatggctgc   1080

gtattactgg aaggatgaaa aagggtcagt ttcttaccca tacaaatcgc acgacttatg   1140

gttcatcact gaaaacgtcc gttggggggtt tctgccgaag gattatctgg caaacggtgc   1200

agccaaagct aaggagttaa tcgacaaggt caatcgggag gacatctgga aagaagcagc   1260

taaagaagcc ggtattgcag cggccgacat tccaaccagc acgtcccgtg gggtagaaga   1320

gttcttcgac ggcaccaaat tcgacccaga aaagccagac gaatatctga aatcgctcaa   1380

aatcaaaaaa gtcagcgtag gcggcagcac cggcgaaaaa ccgtataaat gcccggaatg   1440

cggcaaaagc tttagccgca gcggtggttc acatcatcat catcatcatt aatgaaaggg   1500

cgatatccag cacactggcg gccgttacta gtggatccgg ctgctaacaa agcccgaaag   1560

gaagctgagt tggctgctgc caccgctgag caataactag cataacccct tggggcctct   1620

aaacgggtct tgaggggttt tttgctgaaa ggaggaacta tatccggagc gactcccacg   1680

gcacgttggc aagctcggaa ttcggcgtaa tc                                 1712
```

<210> SEQ ID NO 147
<211> LENGTH: 1712
<212> TYPE: DNA
<213> ORGANISM: Artificial Sequence
<220> FEATURE:
<223> OTHER INFORMATION: Exemplary Expression Construct for avBicarbBP5_18C_16E_bZif

<400> SEQUENCE: 147

```
gccagtaagc ttcggtcacg cttgggactg ccataggctg gcccggtgat gccggccacg     60

atgcgtccgg cgtagaggat cgagatctcg atcccgcgaa attaatacga ctcactatag    120

ggagaccaca acggtttccc tctagaaata attttgttta actttaagaa ggagatatac    180

catggctgaa caagcaccag aagttacaac agtaaagctc gggtatgaac cgtgcgtcga    240

atccgctcct ctcatcattg ctaaagaaaa ggggtttttc gccaagtatg gtctgacaaa    300

tgtagaatta tcgaaacagg catcgtgggg cagtgcccgg gataatgtag agatcggtag    360

cgccgggggc gggatcgacg gtggtcaatg gcagatgcct atgccacatc tcatcactga    420

aggcttaatt acgaagggca atcagaaaat cccaatgtac gtcttagcac agttgatcac    480

ccacgggaac gggattgcca ttgcaaacaa acatcaaggg aaggggatca gtttgaagct    540

cgagggtgct aagagcctgt tcagtcagct caagagctcc acgccattca cagccgcttt    600

cacttttcct catgtaaatc aagacttatg gattcgctac tggttggctg caggggggtat    660

tgaccctgat gcagatgtaa aattgttaac ggtcccagca gcccaaaccg tagccaatat    720

gaagaccggc acaatggacg cattttccac gggcgaccca tggccattcc gtctcgtaaa    780

cgacaaaatc ggttacatgg cggccttgac agcggagatc tggaaaaacc accctgagga    840

atacctcgca atgcgtgcag attgggtcga caagtatcca aaagcaacta aggcattatt    900

aaaaggcatc atggaggccc aacaatggtt ggacaacttt gacaatcgca aggaggcggc    960

acagattttg gctggccgca actactttaa cctcaacaac ccggaaatcc tggcggatcc   1020

ttacgtaggt aagtacgata tgggtgatgg tcgcaagatt gacgataaaa gcatggctgc   1080
```

gtattactgg aaggatgaaa aagggtcagt ttcttaccca tacaaatcgc acgacttatg 1140
gttcatcact gaaaacgtcc gttgggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg ggtagaaga 1320 gttcttcgac ggcaccaaat tcgacccaga aaagccagac gaatatctga aatcgctcaa 1380
aatcaaaaaa gtcagcgtag gcggcagcac cggcgaaaaa ccgtataaat gcccggaatg 1440
cggcaaaagc tttagccgca gcggtggttc acatcatcat catcatcatt aatgaaaggg 1500
cgatatccag cacactggcg gccgttacta gtggatccgg ctgctaacaa agcccgaaag 1560
gaagctgagt tggctgctgc caccgctgag caataactag cataacccct tggggcctct 1620
aaacgggtct tgaggggttt tttgctgaaa ggaggaacta tatccggagc gactcccacg 1680
gcacgttggc aagctcggaa ttcggcgtaa tc 1712

<210> SEQ ID NO 148
<211> LENGTH: 1712
<212> TYPE: DNA
<213> ORGANISM: Artificial Sequence
<220> FEATURE:
<223> OTHER INFORMATION: Exemplary Expression Construct for avBicarbBP5_18C_49F_bZif

<400> SEQUENCE: 148
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catggctgaa caagcaccag aagttacaac agtaaagctc gggtatatcc cgtgcgtcga 240
atccgctcct ctcatcattg ctaaagaaaa ggggtttttc gccaagtatg gtctgacaaa 300
tgtagaatta tcgaaacagg catcgtttgg cagtgcccgg gataatgtag agatcggtag 360
cgccgggggc gggatcgacg gtggtcaatg gcagatgcct atgccacatc tcatcactga 420
aggcttaatt acgaagggca atcagaaaat cccaatgtac gtcttagcac agttgatcac 480
ccacgggaac gggattgcca ttgcaaacaa acatcaaggg aaggggatca gtttgaagct 540
cgagggtgct aagagcctgt tcagtcagct caagagctcc acgccattca cagccgcttt 600
cacttttcct catgtaaatc aagacttatg gattcgctac tggttggctg caggggggtat 660 tgaccctgat gcagatgtaa aattgttaac ggtcccagca gcccaaaccg tagccaatat 720
gaagaccggc acaatggacg cattttccac gggcgaccca tggccattcc gtctcgtaaa 780
cgacaaaatc ggttacatgg cggccttgac agcggagatc tggaaaaacc accctgagga 840
atacctcgca atgcgtgcag attgggtcga caagtatcca aaagcaacta aggcattatt 900
aaaaggcatc atggaggccc aacaatggtt ggacaacttt gacaatcgca aggaggcggc 960
acagattttg gctggccgca actactttaa cctcaacaac ccggaaatcc tggcggatcc 1020
ttacgtaggt aagtacgata tgggtgatgg tcgcaagatt gacgataaaa gcatggctgc 1080
gtattactgg aaggatgaaa aagggtcagt ttcttaccca tacaaatcgc acgacttatg 1140
gttcatcact gaaaacgtcc gttgggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg ggtagaaga 1320 gttcttcgac ggcaccaaat tcgacccaga aaagccagac gaatatctga aatcgctcaa 1380
aatcaaaaaa gtcagcgtag gcggcagcac cggcgaaaaa ccgtataaat gcccggaatg 1440
cggcaaaagc tttagccgca gcggtggttc acatcatcat catcatcatt aatgaaaggg 1500
cgatatccag cacactggcg gccgttacta gtggatccgg ctgctaacaa agcccgaaag 1560
gaagctgagt tggctgctgc caccgctgag caataactag cataacccct tggggcctct 1620
aaacgggtct tgaggggttt tttgctgaaa ggaggaacta tatccggagc gactcccacg 1680
gcacgttggc aagctcggaa ttcggcgtaa tc 1712

<210> SEQ ID NO 149
<211> LENGTH: 1712
<212> TYPE: DNA
<213> ORGANISM: Artificial Sequence
<220> FEATURE:
<223> OTHER INFORMATION: Exemplary Expression Construct for avBicarbBP5_18C_49Y_bZif

<400> SEQUENCE: 149
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catggctgaa caagcaccag aagttacaac agtaaagctc gggtatatcc cgtgcgtcga 240
atccgctcct ctcatcattg ctaaagaaaa ggggtttttc gccaagtatg gtctgacaaa 300
tgtagaatta tcgaaacagg catcgtatgg cagtgcccgg gataatgtag agatcggtag 360
cgccgggggc gggatcgacg gtggtcaatg gcagatgcct atgccacatc tcatcactga 420
aggcttaatt acgaagggca atcagaaaat cccaatgtac gtcttagcac agttgatcac 480
ccacgggaac gggattgcca ttgcaaacaa acatcaaggg aaggggatca gtttgaagct 540
cgagggtgct aagagcctgt tcagtcagct caagagctcc acgccattca cagccgcttt 600
cacttttcct catgtaaatc aagacttatg gattcgctac tggttggctg caggggggtat 660 tgaccctgat gcagatgtaa aattgttaac ggtcccagca gcccaaaccg tagccaatat 720
gaagaccggc acaatggacg cattttccac gggcgaccca tggccattcc gtctcgtaaa 780
cgacaaaatc ggttacatgg cggccttgac agcggagatc tggaaaaacc accctgagga 840
atacctcgca atgcgtgcag attgggtcga caagtatcca aaagcaacta aggcattatt 900
aaaaggcatc atggaggccc aacaatggtt ggacaacttt gacaatcgca aggaggcggc 960
acagattttg gctggccgca actactttaa cctcaacaac ccggaaatcc tggcggatcc 1020
ttacgtaggt aagtacgata tgggtgatgg tcgcaagatt gacgataaaa gcatggctgc 1080
gtattactgg aaggatgaaa aagggtcagt ttcttaccca tacaaatcgc acgacttatg 1140
gttcatcact gaaaacgtcc gttgggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg ggtagaaga 1320 gttcttcgac ggcaccaaat tcgacccaga aaagccagac gaatatctga aatcgctcaa 1380
aatcaaaaaa gtcagcgtag gcggcagcac cggcgaaaaa ccgtataaat gcccggaatg 1440
cggcaaaagc tttagccgca gcggtggttc acatcatcat catcatcatt aatgaaaggg 1500
cgatatccag cacactggcg gccgttacta gtggatccgg ctgctaacaa agcccgaaag 1560
gaagctgagt tggctgctgc caccgctgag caataactag cataacccct tggggcctct 1620
aaacgggtct tgaggggttt tttgctgaaa ggaggaacta tatccggagc gactcccacg 1680
gcacgttggc aagctcggaa ttcggcgtaa tc 1712

<210> SEQ ID NO 150
<211> LENGTH: 1712
<212> TYPE: DNA
<213> ORGANISM: Artificial Sequence
<220> FEATURE:
<223> OTHER INFORMATION: Exemplary Expression Construct for
avBicarbBP5_18C_141V_bZif

<400> SEQUENCE: 150
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catggctgaa caagcaccag aagttacaac agtaaagctc gggtatatcc cgtgcgtcga 240
atccgctcct ctcatcattg ctaaagaaaa ggggtttttc gccaagtatg gtctgacaaa 300
tgtagaatta tcgaaacagg catcgtgggg cagtgcccgg gataatgtag agatcggtag 360
cgccgggggc gggatcgacg gtggtcaatg gcagatgcct atgccacatc tcatcactga 420
aggcttaatt acgaagggca atcagaaaat cccaatgtac gtcttagcac agttgatcac 480
ccacgggaac gggattgcca ttgcaaacaa acatcaaggg aaggggatca gtttgaagct 540
cgagggtgct aagagcctgt tcagtcagct caagagctcc acgccattca cagccgcttt 600
cgtgtttcct catgtaaatc aagacttatg gattcgctac tggttggctg caggggggtat 660 tgaccctgat gcagatgtaa aattgttaac ggtcccagca gcccaaaccg tagccaatat 720
gaagaccggc acaatggacg cattttccac gggcgaccca tggccattcc gtctcgtaaa 780
cgacaaaatc ggttacatgg cggccttgac agcggagatc tggaaaaacc accctgagga 840
atacctcgca atgcgtgcag attgggtcga caagtatcca aaagcaacta aggcattatt 900
aaaaggcatc atggaggccc aacaatggtt ggacaacttt gacaatcgca aggaggcggc 960
acagattttg gctggccgca actactttaa cctcaacaac ccggaaatcc tggcggatcc 1020
ttacgtaggt aagtacgata tgggtgatgg tcgcaagatt gacgataaaa gcatggctgc 1080
gtattactgg aaggatgaaa aagggtcagt ttcttaccca tacaaatcgc acgacttatg 1140
gttcatcact gaaaacgtcc gttgggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg ggtagaaga 1320 gttcttcgac ggcaccaaat tcgacccaga aaagccagac gaatatctga aatcgctcaa 1380
aatcaaaaaa gtcagcgtag gcggcagcac cggcgaaaaa ccgtataaat gcccggaatg 1440
cggcaaaagc tttagccgca gcggtggttc acatcatcat catcatcatt aatgaaaggg 1500
cgatatccag cacactggcg gccgttacta gtggatccgg ctgctaacaa agcccgaaag 1560
gaagctgagt tggctgctgc caccgctgag caataactag cataacccct tggggcctct 1620
aaacgggtct tgaggggttt tttgctgaaa ggaggaacta tatccggagc gactcccacg 1680
gcacgttggc aagctcggaa ttcggcgtaa tc 1712

<210> SEQ ID NO 151
<211> LENGTH: 1712
<212> TYPE: DNA
<213> ORGANISM: Artificial Sequence
<220> FEATURE:
<223> OTHER INFORMATION: Exemplary Expression Construct for
avBicarbBP5_18C_141F_bZif

<400> SEQUENCE: 151
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catggctgaa caagcaccag aagttacaac agtaaagctc gggtatatcc cgtgcgtcga 240
atccgctcct ctcatcattg ctaaagaaaa ggggtttttc gccaagtatg gtctgacaaa 300
tgtagaatta tcgaaacagg catcgtgggg cagtgcccgg gataatgtag agatcggtag 360
cgccgggggc gggatcgacg gtggtcaatg gcagatgcct atgccacatc tcatcactga 420
aggcttaatt acgaagggca atcagaaaat cccaatgtac gtcttagcac agttgatcac 480
ccacgggaac gggattgcca ttgcaaacaa acatcaaggg aaggggatca gtttgaagct 540
cgagggtgct aagagcctgt tcagtcagct caagagctcc acgccattca cagccgcttt 600
ctttttcct catgtaaatc aagacttatg gattcgctac tggttggctg caggggggtat 660
tgaccctgat gcagatgtaa aattgttaac ggtcccagca gcccaaaccg tagccaatat 720
gaagaccggc acaatggacg cattttccac gggcgaccca tggccattcc gtctcgtaaa 780
cgacaaaatc ggttacatgg cggccttgac agcggagatc tggaaaaacc accctgagga 840
atacctcgca atgcgtgcag attgggtcga caagtatcca aaagcaacta aggcattatt 900
aaaaggcatc atggaggccc aacaatggtt ggacaacttt gacaatcgca aggaggcggc 960
acagattttg gctggccgca actactttaa cctcaacaac ccggaaatcc tggcggatcc 1020
ttacgtaggt aagtacgata tgggtgatgg tcgcaagatt gacgataaaa gcatggctgc 1080
gtattactgg aaggatgaaa aagggtcagt ttcttaccca tacaaatcgc acgacttatg 1140
gttcatcact gaaaacgtcc gttgggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg gggtagaaga 1320
gttcttcgac ggcaccaaat tcgacccaga aaagccagac gaatatctga aatcgctcaa 1380
aatcaaaaaa gtcagcgtag gcggcagcac cggcgaaaaa ccgtataaat gcccggaatg 1440
cggcaaaagc tttagccgca gcggtggttc acatcatcat catcatcatt aatgaaaggg 1500
cgatatccag cacactggcg gccgttacta gtggatccgg ctgctaacaa agcccgaaag 1560
gaagctgagt tggctgctgc caccgctgag caataactag cataacccct tggggcctct 1620
aaacgggtct tgaggggttt tttgctgaaa ggaggaacta tatccggagc gactcccacg 1680
gcacgttggc aagctcggaa ttcggcgtaa tc 1712

<210> SEQ ID NO 152
<211> LENGTH: 1712
<212> TYPE: DNA
<213> ORGANISM: Artificial Sequence
<220> FEATURE:
<223> OTHER INFORMATION: Exemplary Expression Construct for avBicarbBP5_18C_141Y_bZif

<400> SEQUENCE: 152
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catggctgaa caagcaccag aagttacaac agtaaagctc gggtatatcc cgtgcgtcga 240
atccgctcct ctcatcattg ctaaagaaaa ggggtttttc gccaagtatg gtctgacaaa 300
tgtagaatta tcgaaacagg catcgtgggg cagtgcccgg gataatgtag agatcggtag 360
cgccgggggc gggatcgacg gtggtcaatg gcagatgcct atgccacatc tcatcactga 420
aggcttaatt acgaagggca atcagaaaat cccaatgtac gtcttagcac agttgatcac 480
ccacgggaac gggattgcca ttgcaaacaa acatcaaggg aaggggatca gtttgaagct 540
cgagggtgct aagagcctgt tcagtcagct caagagctcc acgccattca cagccgcttt 600
ctattttcct catgtaaatc aagacttatg gattcgctac tggttggctg caggggggtat 660 tgaccctgat gcagatgtaa aattgttaac ggtcccagca gcccaaaccg tagccaatat 720
gaagaccggc acaatggacg cattttccac gggcgaccca tggccattcc gtctcgtaaa 780
cgacaaaatc ggttacatgg cggccttgac agcggagatc tggaaaaacc accctgagga 840
atacctcgca atgcgtgcag attgggtcga caagtatcca aaagcaacta aggcattatt 900
aaaaggcatc atggaggccc aacaatggtt ggacaacttt gacaatcgca aggaggcggc 960
acagattttg gctggccgca actactttaa cctcaacaac ccggaaatcc tggcggatcc 1020
ttacgtaggt aagtacgata tgggtgatgg tcgcaagatt gacgataaaa gcatggctgc 1080
gtattactgg aaggatgaaa aagggtcagt ttcttaccca tacaaatcgc acgacttatg 1140
gttcatcact gaaaacgtcc gttgggggtt tctgccgaag gattatctgg caaacggtgc 1200
agccaaagct aaggagttaa tcgacaaggt caatcgggag gacatctgga aagaagcagc 1260
taaagaagcc ggtattgcag cggccgacat tccaaccagc acgtcccgtg gggtagaaga 1320
gttcttcgac ggcaccaaat tcgacccaga aaagccagac gaatatctga aatcgctcaa 1380
aatcaaaaaa gtcagcgtag gcggcagcac cggcgaaaaa ccgtataaat gcccggaatg 1440
cggcaaaagc tttagccgca gcggtggttc acatcatcat catcatcatt aatgaaaggg 1500
cgatatccag cacactggcg gccgttacta gtggatccgg ctgctaacaa agcccgaaag 1560
gaagctgagt tggctgctgc caccgctgag caataactag cataacccct tggggcctct 1620
aaacgggtct tgaggggttt tttgctgaaa ggaggaacta tatccggagc gactcccacg 1680
gcacgttggc aagctcggaa ttcggcgtaa tc 1712

<210> SEQ ID NO 153
<211> LENGTH: 1712
<212> TYPE: DNA
<213> ORGANISM: Artificial Sequence
<220> FEATURE:
<223> OTHER INFORMATION: Exemplary Expression Construct for
avBicarbBP5_18C_141W_bZif

<400> SEQUENCE: 153
gccagtaagc ttcggtcacg cttgggactg ccataggctg gcccggtgat gccggccacg 60
atgcgtccgg cgtagaggat cgagatctcg atcccgcgaa attaatacga ctcactatag 120
ggagaccaca acggtttccc tctagaaata attttgttta actttaagaa ggagatatac 180
catggctgaa caagcaccag aagttacaac agtaaagctc gggtatatcc cgtgcgtcga 240
atccgctcct ctcatcattg ctaaagaaaa ggggtttttc gccaagtatg gtctgacaaa 300
tgtagaatta tcgaaacagg catcgtgggg cagtgcccgg gataatgtag agatcggtag 360
cgccgggggc gggatcgacg gtggtcaatg gcagatgcct atgccacatc tcatcactga 420
aggcttaatt acgaagggca atcagaaaat cccaatgtac gtcttagcac agttgatcac 480
ccacgggaac gggattgcca ttgcaaacaa acatcaaggg aaggggatca gtttgaagct 540

```
cgagggtgct aagagcctgt tcagtcagct caagagctcc acgccattca cagccgcttt    600

ctggtttcct catgtaaatc aagacttatg gattcgctac tggttggctg caggggggtat   660

tgaccctgat gcagatgtaa aattgttaac ggtcccagca gcccaaaccg tagccaatat    720

gaagaccggc acaatggacg cattttccac gggcgaccca tggccattcc gtctcgtaaa    780

cgacaaaatc ggttacatgg cggccttgac agcggagatc tggaaaaacc accctgagga    840

atacctcgca atgcgtgcag attgggtcga caagtatcca aaagcaacta aggcattatt    900

aaaaggcatc atggaggccc aacaatggtt ggacaacttt gacaatcgca aggaggcggc    960

acagattttg gctggccgca actactttaa cctcaacaac ccggaaatcc tggcggatcc   1020

ttacgtaggt aagtacgata tgggtgatgg tcgcaagatt gacgataaaa gcatggctgc   1080

gtattactgg aaggatgaaa aagggtcagt ttcttaccca tacaaatcgc acgacttatg   1140

gttcatcact gaaaacgtcc gttgggggtt tctgccgaag gattatctgg caaacggtgc   1200

agccaaagct aaggagttaa tcgacaaggt caatcgggag gacatctgga aagaagcagc   1260

taaagaagcc ggtattgcag cggccgacat tccaaccagc acgtcccgtg gggtagaaga   1320

gttcttcgac ggcaccaaat tcgacccaga aaagccagac gaatatctga aatcgctcaa   1380

aatcaaaaaa gtcagcgtag gcggcagcac cggcgaaaaa ccgtataaat gcccggaatg   1440

cggcaaaagc tttagccgca gcggtggttc acatcatcat catcatcatt aatgaaaggg   1500

cgatatccag cacactggcg gccgttacta gtggatccgg ctgctaacaa agcccgaaag   1560

gaagctgagt tggctgctgc caccgctgag caataactag cataacccct tggggcctct   1620

aaacgggtct tgaggggttt tttgctgaaa ggaggaacta tatccggagc gactcccacg   1680

gcacgttggc aagctcggaa ttcggcgtaa tc                                 1712
```

<210> SEQ ID NO 154
<211> LENGTH: 1712
<212> TYPE: DNA
<213> ORGANISM: Artificial Sequence
<220> FEATURE:
<223> OTHER INFORMATION: Exemplary Expression Construct for avBicarbBP5_18C_141Q_bZif

<400> SEQUENCE: 154

```
gccagtaagc ttcggtcacg cttgggactg ccataggctg gcccggtgat gccggccacg     60

atgcgtccgg cgtagaggat cgagatctcg atcccgcgaa attaatacga ctcactatag    120

ggagaccaca acggtttccc tctagaaata attttgttta actttaagaa ggagatatac    180

catggctgaa caagcaccag aagttacaac agtaaagctc gggtatatcc cgtgcgtcga    240

atccgctcct ctcatcattg ctaaagaaaa ggggtttttc gccaagtatg gtctgacaaa    300

tgtagaatta tcgaaacagg catcgtgggg cagtgcccgg gataatgtag agatcggtag    360

cgccgggggc gggatcgacg gtggtcaatg gcagatgcct atgccacatc tcatcactga    420

aggcttaatt acgaagggca atcagaaaat cccaatgtac gtcttagcac agttgatcac    480

ccacgggaac gggattgcca ttgcaaacaa acatcaaggg aaggggatca gtttgaagct    540

cgagggtgct aagagcctgt tcagtcagct caagagctcc acgccattca cagccgcttt    600

ccagtttcct catgtaaatc aagacttatg gattcgctac tggttggctg caggggggtat   660

tgaccctgat gcagatgtaa aattgttaac ggtcccagca gcccaaaccg tagccaatat    720

gaagaccggc acaatggacg cattttccac gggcgaccca tggccattcc gtctcgtaaa    780

cgacaaaatc ggttacatgg cggccttgac agcggagatc tggaaaaacc accctgagga    840
```

```
atacctcgca atgcgtgcag attgggtcga caagtatcca aaagcaacta aggcattatt    900

aaaaggcatc atggaggccc aacaatggtt ggacaacttt gacaatcgca aggaggcggc    960

acagattttg gctggccgca actactttaa cctcaacaac ccggaaatcc tggcggatcc   1020

ttacgtaggt aagtacgata tgggtgatgg tcgcaagatt gacgataaaa gcatggctgc   1080

gtattactgg aaggatgaaa aagggtcagt ttcttaccca tacaaatcgc acgacttatg   1140

gttcatcact gaaaacgtcc gttgggggtt tctgccgaag gattatctgg caaacggtgc   1200

agccaaagct aaggagttaa tcgacaaggt caatcgggag gacatctgga aagaagcagc   1260

taaagaagcc ggtattgcag cggccgacat tccaaccagc acgtcccgtg ggtagaaga   1320

gttcttcgac ggcaccaaat tcgacccaga aaagccagac gaatatctga aatcgctcaa   1380

aatcaaaaaa gtcagcgtag gcggcagcac cggcgaaaaa ccgtataaat gcccggaatg   1440

cggcaaaagc tttagccgca gcggtggttc acatcatcat catcatcatt aatgaaaggg   1500

cgatatccag cacactggcg gccgttacta gtggatccgg ctgctaacaa agcccgaaag   1560

gaagctgagt tggctgctgc caccgctgag caataactag cataacccct tggggcctct   1620

aaacgggtct tgaggggttt tttgctgaaa ggaggaacta tatccggagc gactcccacg   1680

gcacgttggc aagctcggaa ttcggcgtaa tc                                 1712
```

```
<210> SEQ ID NO 155
<211> LENGTH: 12
<212> TYPE: PRT
<213> ORGANISM: Artificial Sequence
<220> FEATURE:
<223> OTHER INFORMATION: KLGXIXIXEXAP (conserved sequence)
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 155

Lys Leu Gly Xaa Ile Xaa Ile Xaa Glu Xaa Ala Pro
1               5                   10


<210> SEQ ID NO 156
<211> LENGTH: 10
<212> TYPE: PRT
<213> ORGANISM: Artificial Sequence
<220> FEATURE:
<223> OTHER INFORMATION: DGGQXQMPMP (conserved sequence)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 156

Asp Gly Gly Gln Xaa Gln Met Pro Met Pro
1               5                   10


<210> SEQ ID NO 157
```

<211> LENGTH: 5
<212> TYPE: PRT
<213> ORGANISM: Artificial Sequence
<220> FEATURE:
<223> OTHER INFORMATION: GNGIA (conserved sequence)

<400> SEQUENCE: 157

Gly Asn Gly Ile Ala
1 5

<210> SEQ ID NO 158
<211> LENGTH: 8
<212> TYPE: PRT
<213> ORGANISM: Artificial Sequence
<220> FEATURE:
<223> OTHER INFORMATION: TFXXVNQD (conserved sequence)
<220> FEATURE:
<221> NAME/KEY: misc_feature
<222> LOCATION: (3)..(4)
<223> OTHER INFORMATION: Xaa can be any naturally occurring amino acid

<400> SEQUENCE: 158

Thr Phe Xaa Xaa Val Asn Gln Asp
1 5

<210> SEQ ID NO 159
<211> LENGTH: 5
<212> TYPE: PRT
<213> ORGANISM: Artificial Sequence
<220> FEATURE:
<223> OTHER INFORMATION: HPEEY (conserved sequence)

<400> SEQUENCE: 159

His Pro Glu Glu Tyr
1 5

<210> SEQ ID NO 160
<211> LENGTH: 5
<212> TYPE: PRT
<213> ORGANISM: Artificial Sequence
<220> FEATURE:
<223> OTHER INFORMATION: VYSXR (conserved sequence)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 160

Val Tyr Ser Xaa Arg
1 5

<210> SEQ ID NO 161
<211> LENGTH: 5
<212> TYPE: PRT
<213> ORGANISM: Artificial Sequence
<220> FEATURE:
<223> OTHER INFORMATION: GLXXR (conserved sequence)
<220> FEATURE:
<221> NAME/KEY: misc_feature
<222> LOCATION: (3)..(4)
<223> OTHER INFORMATION: Xaa can be any naturally occurring amino acid

<400> SEQUENCE: 161

Gly Leu Xaa Xaa Arg
1 5

<210> SEQ ID NO 162
<211> LENGTH: 4
<212> TYPE: PRT

<213> ORGANISM: Artificial Sequence
<220> FEATURE:
<223> OTHER INFORMATION: YYXX (conserved sequence)
<220> FEATURE:
<221> NAME/KEY: misc_feature
<222> LOCATION: (3)..(4)
<223> OTHER INFORMATION: Xaa can be any naturally occurring amino acid

<400> SEQUENCE: 162

Tyr Tyr Xaa Xaa
1

<210> SEQ ID NO 163
<211> LENGTH: 4
<212> TYPE: PRT
<213> ORGANISM: Artificial Sequence
<220> FEATURE:
<223> OTHER INFORMATION: YXGR (conserved sequence)
<220> FEATURE:
<221> NAME/KEY: misc_feature
<222> LOCATION: (2)..(2)
<223> OTHER INFORMATION: Xaa can be any naturally occurring amino acid

<400> SEQUENCE: 163

Tyr Xaa Gly Arg
1

<210> SEQ ID NO 164
<211> LENGTH: 4
<212> TYPE: PRT
<213> ORGANISM: Artificial Sequence
<220> FEATURE:
<223> OTHER INFORMATION: SPAD (conserved sequence)

<400> SEQUENCE: 164

Ser Pro Ala Asp
1

<210> SEQ ID NO 165
<211> LENGTH: 6
<212> TYPE: PRT
<213> ORGANISM: Artificial Sequence
<220> FEATURE:
<223> OTHER INFORMATION: GWXPXY (conserved sequence)
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 165

```
Gly Trp Xaa Pro Xaa Tyr
1               5
```

<210> SEQ ID NO 166
<211> LENGTH: 401
<212> TYPE: PRT
<213> ORGANISM: Artificial Sequence
<220> FEATURE:
<223> OTHER INFORMATION: 2I4C seed sequence (synBicarbBP1)

<400> SEQUENCE: 166

```
Pro Glu Met Met Pro Glu Thr Ala Asn Ile Lys Leu Gly Tyr Ile Pro
1               5                   10                  15

Ile Val Glu Ala Ala Pro Leu Ile Ile Ala Gln Glu Lys Gly Phe Phe
            20                  25                  30
```

Ala Lys Tyr Gly Met Thr Gly Val Glu Val Ser Lys Gln Ala Asn Trp
35 40 45

Ala Ser Ala Arg Asp Asn Val Thr Ile Gly Ser Gln Gly Gly Gly Ile
50 55 60

Asp Gly Gly Gln Trp Gln Met Pro Met Pro His Leu Ile Thr Glu Gly
65 70 75 80

Ile Ile Thr Asn Gly Asn Lys Val Pro Met Tyr Val Leu Ala Gln Leu
85 90 95

Ile Thr Gln Gly Asn Gly Ile Ala Val Ala Pro Met His Glu Gly Lys
100 105 110

Gly Val Asn Leu Asp Ile Thr Lys Ala Ala Asp Tyr Ile Lys Gly Phe
115 120 125

Asn Lys Thr Asn Gly Arg Lys Phe Lys Ala Ala His Thr Phe Pro Asn
130 135 140

Val Asn Gln Asp Phe Trp Ile Arg Tyr Trp Phe Ala Ala Gly Gly Val
145 150 155 160

Asp Pro Asp Thr Asp Ile Asp Leu Leu Ala Val Pro Pro Ala Glu Thr
165 170 175

Val Gln Gly Met Arg Asn Gly Thr Met Asp Ala Phe Ser Thr Gly Asp
180 185 190

Pro Trp Pro Tyr Arg Ile Val Thr Glu Asn Ile Gly Tyr Met Ala Gly
195 200 205

Leu Thr Ala Gln Ile Trp Pro Tyr His Pro Glu Glu Tyr Leu Ala Ile
210 215 220

Arg Ala Asp Trp Val Asp Lys Asn Pro Lys Ala Thr Lys Ala Leu Leu
225 230 235 240

Lys Gly Ile Met Glu Ala Gln Gln Trp Ile Asp Asp Pro Lys Asn Arg
245 250 255

Pro Glu Val Val Gln Ile Val Ser Gly Arg Asn Tyr Phe Asn Val Pro
260 265 270

Thr Thr Ile Leu Glu Ser Pro Phe Lys Gly Gln Tyr Thr Met Gly Asp
275 280 285

Gly Gln Pro Ala Ile Asp Asp Phe Gln Lys Gly Pro Leu Tyr Trp Lys
290 295 300

Asp Gly Ile Gly Asn Val Ser Tyr Pro Tyr Lys Ser His Asp Leu Trp
305 310 315 320

Phe Leu Thr Glu Ser Ile Arg Trp Gly Phe His Lys Asn Ala Ile Pro
325 330 335

Asp Leu Asp Thr Ala Gln Lys Ile Ile Asp Lys Val Asn Arg Glu Asp
340 345 350

Leu Trp Arg Glu Ala Ala Thr Glu Ala Gly Phe Thr Ala Asp Ile Pro
355 360 365

Ser Ser Thr Ser Arg Gly Val Glu Thr Phe Phe Asp Gly Ile Thr Phe
370 375 380

Asp Pro Ala Asn Pro Ser Ala Tyr Leu Gln Ser Leu Ala Ile Lys Lys
385 390 395 400

Val

<210> SEQ ID NO 167
<211> LENGTH: 316
<212> TYPE: PRT
<213> ORGANISM: Artificial Sequence
<220> FEATURE:
<223> OTHER INFORMATION: 1SI0 seed sequence (mhFeBP1)

<400> SEQUENCE: 167

Ala Asn Glu Val Asn Val Tyr Ser Tyr Arg Gln Pro Tyr Leu Ile Glu
1               5                   10                  15

Pro Met Leu Lys Asn Phe Glu Lys Asp Thr Gly Ile Lys Val Asn Ile
            20                  25                  30

Ile Phe Ala Asp Lys Gly Leu Val Asp Arg Val Lys Gln Glu Gly Glu
        35                  40                  45

Leu Ser Pro Ala Asp Val Leu Leu Thr Val Asp Ile Ser Arg Val Met
    50                  55                  60

Glu Ile Val Asn Ala Asp Leu Ala Gln Lys Ile Asp Ser Lys Val Leu
65                  70                  75                  80

Glu Lys Asn Ile Pro Ala Gln Phe Arg Asp Ser Asn Asp Gln Trp Phe
                85                  90                  95

Gly Leu Thr Thr Arg Ala Arg Val Ile Tyr Thr Ser Lys Asp Arg Val
            100                 105                 110

Gly Lys Leu Pro Ala Gly Phe Asp Tyr Leu Asp Leu Ala Lys Pro Glu
        115                 120                 125

Tyr Lys Gly Lys Val Cys Val Arg Ser Gly Lys Asn Ser Tyr Asn Val
    130                 135                 140

Ser Leu Phe Ala Ala Met Ile Glu His Tyr Gly Ile Glu Lys Thr Lys
145                 150                 155                 160

Ala Phe Leu Glu Gly Leu Lys Ala Asn Leu Ala Arg Lys Pro Gln Gly
                165                 170                 175

Gly Asp Arg Asp Gln Val Lys Ala Ile Lys Glu Gly Ile Cys Asp Tyr
            180                 185                 190

Ser Ile Gly Asn Ser Tyr Tyr Tyr Gly Lys Met Leu Asp Asp Glu Lys
        195                 200                 205

Gln Lys Ser Trp Ala Glu Ala Ala Ile Ile Asn Phe Pro Ser Gly Glu
    210                 215                 220

His Gly Thr His Lys Asn Ile Ser Gly Val Val Ile Ala Lys His Ser
225                 230                 235                 240

Pro Asn Lys Ala Asn Ala Val Lys Leu Ile Glu Tyr Leu Ser Gly Glu
                245                 250                 255

Lys Ala Gln Gly Leu Tyr Ala Glu Leu Asn His Glu Tyr Pro Val Lys
            260                 265                 270

Glu Gly Ile Glu Pro Ser Ala Ile Val Lys Gly Trp Gly Thr Phe Lys
        275                 280                 285

Ser Asp Thr Ile Lys Leu Glu Asp Ile Ala Lys Asn Tyr Glu Ala Ala
    290                 295                 300

Leu Lys Leu Val Asp Glu Val Lys Phe Asp Asp Phe
305                 310                 315

<210> SEQ ID NO 168
<211> LENGTH: 310
<212> TYPE: PRT
<213> ORGANISM: Artificial Sequence
<220> FEATURE:
<223> OTHER INFORMATION: 4ELR seed sequence (ttFeBP5)

<400> SEQUENCE: 168

Ser Pro Thr Leu Thr Ile Tyr Ser Gly Arg Gly Gln Ser Leu Val Glu
1               5                   10                  15

Pro Leu Val Lys Gln Phe Glu Ala Glu Thr Gly Ile Arg Val Gln Val
            20                  25                  30

```
Arg Tyr Ser Thr Asp Ala Gln Ile Leu Ala Ala Leu Gln Glu Glu Gly
        35                  40                  45

Ser Arg Ser Pro Ala Asp Leu Phe Trp Ala Asn Thr Ala Gly Ala Leu
    50                  55                  60

Gly Gln Ala Ser Ala Lys Gly Leu Leu Arg Pro Leu Gly Glu Thr Leu
65                  70                  75                  80

Leu Glu Lys Pro Ile Ala Phe Val Pro Ala Ser Arg Thr Trp Val Pro
                85                  90                  95

Val Thr Val Arg Leu Arg Val Leu Ala Tyr Asn Pro Asp Arg Ile Lys
            100                 105                 110

Ala Glu Glu Leu Pro Glu Ser Leu Leu Asp Leu Pro Arg Phe Ala Arg
        115                 120                 125

Glu Lys Gly Leu Val Gly Arg Val Gly Trp Thr Pro Thr Tyr Ser Ser
    130                 135                 140

Phe Gln Asp Met Val Ala Gly Met Ile Ala Leu Tyr Gly Glu Glu Lys
145                 150                 155                 160

Thr Arg Glu Trp Leu Leu Ala Met Lys Ala Leu Ala Pro Lys Ala Tyr
                165                 170                 175

Pro Ser Asn Pro Ala Met Leu Asp Ala Ile Arg Ala Gly Glu Val Asp
            180                 185                 190

Leu Gly Ser Thr Asn His Tyr Tyr Val Val Arg Phe Arg Arg Ala Gly
        195                 200                 205

Tyr Arg Leu Gly Met His His Phe Arg Asp Gly Asp Ala Gly Asn Leu
    210                 215                 220

Ala Leu Val Thr Gly Ala Gly Leu Leu Lys Thr Ser Lys Asn Leu Ala
225                 230                 235                 240

Ala Ala Thr Arg Phe Leu Thr Tyr Leu Leu Ser Pro Gln Ala Gln Gln
                245                 250                 255

Tyr Phe Val Gly Asn Ile Gly Glu Tyr Pro Leu Val Lys Gly Val Ala
            260                 265                 270

Leu Asp Pro Asn Leu Leu Pro Leu Glu Glu Ala Leu Ala Lys Ser Pro
        275                 280                 285

Lys Leu Asp Leu Glu Lys Leu Pro Leu Asp Arg Ala Leu Arg Leu Leu
    290                 295                 300

Arg Glu Thr Gly Val Leu
305                 310


<210> SEQ ID NO 169
<211> LENGTH: 109
<212> TYPE: PRT
<213> ORGANISM: Escherichia coli

<400> SEQUENCE: 169

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95
```

```
Lys Gly Gln Leu Lys Glu Phe Leu Asp Ala Asn Leu Ala
            100                 105


<210> SEQ ID NO 170
<211> LENGTH: 118
<212> TYPE: PRT
<213> ORGANISM: Artificial Sequence
<220> FEATURE:
<223> OTHER INFORMATION: Adaptor0

<400> SEQUENCE: 170

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 171
<211> LENGTH: 118
<212> TYPE: PRT
<213> ORGANISM: Artificial Sequence
<220> FEATURE:
<223> OTHER INFORMATION: Adaptor1.0

<400> SEQUENCE: 171

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Cys Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 172
<211> LENGTH: 118
<212> TYPE: PRT
<213> ORGANISM: Artificial Sequence
<220> FEATURE:
<223> OTHER INFORMATION: Adaptor2.0a
```

<400> SEQUENCE: 172

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Cys Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115

<210> SEQ ID NO 173
<211> LENGTH: 118
<212> TYPE: PRT
<213> ORGANISM: Artificial Sequence
<220> FEATURE:
<223> OTHER INFORMATION: Adaptor2.0b

<400> SEQUENCE: 173

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Cys Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115

<210> SEQ ID NO 174
<211> LENGTH: 118
<212> TYPE: PRT
<213> ORGANISM: Artificial Sequence
<220> FEATURE:
<223> OTHER INFORMATION: Adaptor3.0

<400> SEQUENCE: 174

Met Ser Ala Lys Ile Ile His Leu Thr Asp Cys Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

```
Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 175
<211> LENGTH: 118
<212> TYPE: PRT
<213> ORGANISM: Artificial Sequence
<220> FEATURE:
<223> OTHER INFORMATION: Adaptor4.0

<400> SEQUENCE: 175

Met Ser Ala Lys Ile Ile His Leu Thr Asp Asp Ser Phe Asp Cys Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 176
<211> LENGTH: 118
<212> TYPE: PRT
<213> ORGANISM: Artificial Sequence
<220> FEATURE:
<223> OTHER INFORMATION: Adaptor5.0

<400> SEQUENCE: 176

Met Ser Ala Lys Ile Ile His Leu Thr Asp Asp Ser Phe Asp Thr Asp
1               5                   10                  15

Val Leu Lys Ala Cys Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
```

```
            100                 105                 110

His His His His His His
        115


<210> SEQ ID NO 177
<211> LENGTH: 118
<212> TYPE: PRT
<213> ORGANISM: Artificial Sequence
<220> FEATURE:
<223> OTHER INFORMATION: Adaptor6.0

<400> SEQUENCE: 177

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Cys
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 178
<211> LENGTH: 118
<212> TYPE: PRT
<213> ORGANISM: Artificial Sequence
<220> FEATURE:
<223> OTHER INFORMATION: Adaptor7.0

<400> SEQUENCE: 178

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Cys Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 179
<211> LENGTH: 118
<212> TYPE: PRT
<213> ORGANISM: Artificial Sequence
<220> FEATURE:
```

<223> OTHER INFORMATION: Adaptor8.0

<400> SEQUENCE: 179

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Cys Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115

<210> SEQ ID NO 180
<211> LENGTH: 118
<212> TYPE: PRT
<213> ORGANISM: Artificial Sequence
<220> FEATURE:
<223> OTHER INFORMATION: Adaptor9.0

<400> SEQUENCE: 180

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Cys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115

<210> SEQ ID NO 181
<211> LENGTH: 118
<212> TYPE: PRT
<213> ORGANISM: Artificial Sequence
<220> FEATURE:
<223> OTHER INFORMATION: Adaptor10.0

<400> SEQUENCE: 181

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp

```
        35                  40                  45

Glu Tyr Gln Gly Lys Leu Thr Val Ala Met Leu Asn Ile Asp Cys Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 182
<211> LENGTH: 118
<212> TYPE: PRT
<213> ORGANISM: Artificial Sequence
<220> FEATURE:
<223> OTHER INFORMATION: Adaptor11.0

<400> SEQUENCE: 182

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Cys Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Ser
            100                 105                 110

His His His His His His
        115


<210> SEQ ID NO 183
<211> LENGTH: 118
<212> TYPE: PRT
<213> ORGANISM: Artificial Sequence
<220> FEATURE:
<223> OTHER INFORMATION: Adaptor12.0

<400> SEQUENCE: 183

Met Ser Ala Lys Ile Ile His Leu Thr Asp Asp Ser Phe Asp Thr Asp
1               5                   10                  15

Val Leu Lys Ala Asp Gly Ala Ile Leu Val Ala Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Met Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Cys Ala Ala Thr Lys Val Gly Ala Leu Ser
                85                  90                  95
```

Lys Gly Gln Leu Lys Glu Phe Leu Asp Ala Asn Leu Ala Gly Gly Ser
100 105 110

His His His His His His
115

<210> SEQ ID NO 184
<211> LENGTH: 118
<212> TYPE: PRT
<213> ORGANISM: Artificial Sequence
<220> FEATURE:
<223> OTHER INFORMATION: Adaptor13.0

<400> SEQUENCE: 184

Met Ser Ala Lys Ile Ile His Leu Thr Asp Asp Ser Phe Asp Thr Asp
1 5 10 15

Val Leu Lys Ala Asp Gly Ala Ile Leu Val Ala Phe Trp Ala Glu Trp
20 25 30

Cys Gly Pro Cys Lys Met Ile Ala Pro Ile Leu Asp Glu Ile Ala Asp
35 40 45

Glu Tyr Gln Gly Lys Leu Thr Val Ala Met Leu Asn Ile Asp Gln Asn
50 55 60

Pro Gly Thr Ala Pro Lys Tyr Gly Ile Arg Gly Ile Pro Thr Leu Leu
65 70 75 80

Leu Phe Lys Asn Gly Glu Val Ala Ala Thr Lys Cys Gly Ala Leu Ser
85 90 95

Lys Gly Gln Leu Lys Glu Phe Leu Asp Ala Asn Leu Ala Gly Gly Ser
100 105 110

His His His His His His
115

<210> SEQ ID NO 185
<211> LENGTH: 118
<212> TYPE: PRT
<213> ORGANISM: Artificial Sequence
<220> FEATURE:
<223> OTHER INFORMATION: Adaptor14.0

<400> SEQUENCE: 185

Met Ser Ala Lys Ile Ile His Leu Thr Asp Asp Ser Phe Asp Thr Asp
1 5 10 15

Val Leu Lys Ala Asp Gly Ala Ile Leu Val Ala Phe Trp Ala Glu Trp
20 25 30

Cys Gly Pro Cys Lys Met Ile Ala Pro Ile Leu Asp Glu Ile Ala Asp
35 40 45

Glu Tyr Gln Gly Lys Leu Thr Val Ala Met Leu Asn Ile Asp Gln Asn
50 55 60

Pro Gly Thr Ala Pro Lys Tyr Gly Ile Arg Gly Ile Pro Thr Leu Leu
65 70 75 80

Leu Phe Lys Asn Gly Glu Val Ala Ala Thr Lys Val Gly Ala Leu Ser
85 90 95

Cys Gly Gln Leu Lys Glu Phe Leu Asp Ala Asn Leu Ala Gly Gly Ser
100 105 110

His His His His His His
115

<210> SEQ ID NO 186
<211> LENGTH: 118
<212> TYPE: PRT
<213> ORGANISM: Artificial Sequence
<220> FEATURE:
<223> OTHER INFORMATION: Adaptor15.0

<400> SEQUENCE: 186

Met Ser Ala Lys Ile Ile His Leu Thr Asp Asp Ser Phe Asp Thr Asp
1 5 10 15

Val Leu Lys Ala Asp Gly Ala Ile Leu Val Ala Phe Trp Ala Glu Trp
20 25 30

Cys Gly Pro Cys Lys Met Ile Ala Pro Ile Leu Asp Glu Ile Ala Asp
35 40 45

Glu Tyr Gln Gly Lys Leu Thr Val Ala Met Leu Asn Ile Asp Gln Asn
50 55 60

Pro Gly Thr Ala Pro Lys Tyr Gly Ile Arg Gly Ile Pro Thr Leu Leu
65 70 75 80

Leu Phe Lys Asn Gly Glu Val Ala Ala Thr Lys Val Gly Ala Leu Ser
85 90 95

Lys Gly Cys Leu Lys Glu Phe Leu Asp Ala Asn Leu Ala Gly Gly Ser
100 105 110

His His His His His His
115

<210> SEQ ID NO 187
<211> LENGTH: 118
<212> TYPE: PRT
<213> ORGANISM: Artificial Sequence
<220> FEATURE:
<223> OTHER INFORMATION: Adaptor16.0

<400> SEQUENCE: 187

Met Ser Ala Lys Ile Ile His Leu Thr Asp Asp Ser Phe Asp Thr Asp
1 5 10 15

Val Leu Lys Ala Asp Gly Ala Ile Leu Val Ala Phe Trp Ala Glu Trp
20 25 30

Cys Gly Pro Cys Lys Met Ile Ala Pro Ile Leu Asp Glu Ile Ala Asp
35 40 45

Glu Tyr Gln Gly Lys Leu Thr Val Ala Met Leu Asn Ile Asp Gln Asn
50 55 60

Pro Gly Thr Ala Pro Lys Tyr Gly Ile Arg Gly Ile Pro Thr Leu Leu
65 70 75 80

Leu Phe Lys Asn Gly Glu Val Ala Ala Thr Lys Val Gly Ala Leu Ser
85 90 95

Lys Gly Gln Leu Lys Glu Phe Leu Asp Cys Asn Leu Ala Gly Gly Ser
100 105 110

His His His His His His
115

<210> SEQ ID NO 188
<211> LENGTH: 441
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:

<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (38)..(44)
<223> OTHER INFORMATION: Xaa can be any naturally occurring amino acid
<220> FEATURE:
<221> NAME/KEY: misc_feature
<222> LOCATION: (46)..(50)
<223> OTHER INFORMATION: Xaa can be any naturally occurring amino acid
<220> FEATURE:
<221> NAME/KEY: misc_feature
<222> LOCATION: (52)..(53)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(59)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (157)..(158)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: misc_feature
<222> LOCATION: (164)..(165)
<223> OTHER INFORMATION: Xaa can be any naturally occurring amino acid
<220> FEATURE:
<221> NAME/KEY: misc_feature
<222> LOCATION: (167)..(171)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (175)..(176)
<223> OTHER INFORMATION: Xaa can be any naturally occurring amino acid
<220> FEATURE:
<221> NAME/KEY: misc_feature
<222> LOCATION: (178)..(179)
<223> OTHER INFORMATION: Xaa can be any naturally occurring amino acid
<220> FEATURE:
<221> NAME/KEY: misc_feature
<222> LOCATION: (181)..(182)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (190)..(190)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (246)..(248)
<223> OTHER INFORMATION: Xaa can be any naturally occurring amino acid
<220> FEATURE:
<221> NAME/KEY: misc_feature
<222> LOCATION: (253)..(253)
<223> OTHER INFORMATION: Xaa can be any naturally occurring amino acid
<220> FEATURE:
<221> NAME/KEY: misc_feature
<222> LOCATION: (260)..(260)
<223> OTHER INFORMATION: Xaa can be any naturally occurring amino acid
<220> FEATURE:
<221> NAME/KEY: misc_feature
<222> LOCATION: (268)..(268)
<223> OTHER INFORMATION: Xaa can be any naturally occurring amino acid
<220> FEATURE:
<221> NAME/KEY: misc_feature
<222> LOCATION: (292)..(292)
<223> OTHER INFORMATION: Xaa can be any naturally occurring amino acid
<220> FEATURE:
<221> NAME/KEY: misc_feature
<222> LOCATION: (294)..(295)
<223> OTHER INFORMATION: Xaa can be any naturally occurring amino acid
<220> FEATURE:
<221> NAME/KEY: misc_feature
<222> LOCATION: (298)..(298)
<223> OTHER INFORMATION: Xaa can be any naturally occurring amino acid
<220> FEATURE:
<221> NAME/KEY: misc_feature
<222> LOCATION: (300)..(300)
<223> OTHER INFORMATION: Xaa can be any naturally occurring amino acid
<220> FEATURE:
<221> NAME/KEY: misc_feature
<222> LOCATION: (302)..(302)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (308)..(308)
<223> OTHER INFORMATION: Xaa can be any naturally occurring amino acid
<220> FEATURE:
<221> NAME/KEY: misc_feature
<222> LOCATION: (311)..(311)

<223> OTHER INFORMATION: Xaa can be any naturally occurring amino acid
<220> FEATURE:
<221> NAME/KEY: misc_feature
<222> LOCATION: (313)..(315)
<223> OTHER INFORMATION: Xaa can be any naturally occurring amino acid
<220> FEATURE:
<221> NAME/KEY: misc_feature
<222> LOCATION: (318)..(319)
<223> OTHER INFORMATION: Xaa can be any naturally occurring amino acid
<220> FEATURE:
<221> NAME/KEY: misc_feature
<222> LOCATION: (321)..(321)
<223> OTHER INFORMATION: Xaa can be any naturally occurring amino acid
<220> FEATURE:
<221> NAME/KEY: misc_feature
<222> LOCATION: (323)..(323)
<223> OTHER INFORMATION: Xaa can be any naturally occurring amino acid
<220> FEATURE:
<221> NAME/KEY: misc_feature
<222> LOCATION: (325)..(325)
<223> OTHER INFORMATION: Xaa can be any naturally occurring amino acid
<220> FEATURE:
<221> NAME/KEY: misc_feature
<222> LOCATION: (330)..(332)
<223> OTHER INFORMATION: Xaa can be any naturally occurring amino acid
<220> FEATURE:
<221> NAME/KEY: misc_feature
<222> LOCATION: (335)..(337)
<223> OTHER INFORMATION: Xaa can be any naturally occurring amino acid
<220> FEATURE:
<221> NAME/KEY: misc_feature
<222> LOCATION: (339)..(339)
<223> OTHER INFORMATION: Xaa can be any naturally occurring amino acid
<220> FEATURE:
<221> NAME/KEY: misc_feature
<222> LOCATION: (345)..(346)
<223> OTHER INFORMATION: Xaa can be any naturally occurring amino acid
<220> FEATURE:
<221> NAME/KEY: misc_feature
<222> LOCATION: (349)..(349)
<223> OTHER INFORMATION: Xaa can be any naturally occurring amino acid
<220> FEATURE:
<221> NAME/KEY: misc_feature
<222> LOCATION: (372)..(372)
<223> OTHER INFORMATION: Xaa can be any naturally occurring amino acid
<220> FEATURE:
<221> NAME/KEY: misc_feature
<222> LOCATION: (374)..(374)
<223> OTHER INFORMATION: Xaa can be any naturally occurring amino acid
<220> FEATURE:
<221> NAME/KEY: misc_feature
<222> LOCATION: (376)..(381)
<223> OTHER INFORMATION: Xaa can be any naturally occurring amino acid
<220> FEATURE:
<221> NAME/KEY: misc_feature
<222> LOCATION: (383)..(385)
<223> OTHER INFORMATION: Xaa can be any naturally occurring amino acid
<220> FEATURE:
<221> NAME/KEY: misc_feature
<222> LOCATION: (387)..(387)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
<222> LOCATION: (421)..(421)
<223> OTHER INFORMATION: Xaa can be any naturally occurring amino acid
<220> FEATURE:
<221> NAME/KEY: misc_feature
<222> LOCATION: (428)..(428)
<223> OTHER INFORMATION: Xaa can be any naturally occurring amino acid
<220> FEATURE:
<221> NAME/KEY: misc_feature
<222> LOCATION: (432)..(432)
<223> OTHER INFORMATION: Xaa can be any naturally occurring amino acid
<220> FEATURE:
<221> NAME/KEY: misc_feature

```
<222> LOCATION: (439)..(441)
<223> OTHER INFORMATION: Xaa can be any naturally occurring amino acid

<400> SEQUENCE: 188

Xaa Xaa Xaa Xaa Met Xaa Xaa Xaa Ser Arg Arg Lys Phe Leu Leu Thr
1               5                   10                  15

Ala Gly Ala Xaa Ala Xaa Gly Ala Xaa Phe Leu Lys Gly Cys Ala Gly
            20                  25                  30

Asn Pro Pro Xaa Pro Xaa Xaa Xaa Xaa Xaa Xaa Xaa Gln Xaa Xaa Xaa
        35                  40                  45

Xaa Xaa Ala Xaa Xaa Leu Ser Xaa Glu Xaa Xaa Pro Glu Thr Thr Xaa
    50                  55                  60

Lys Leu Gly Ile Pro Ile Val Glu Ser Ala Pro Leu Ile Ile Ala Lys
65                  70                  75                  80

Glu Lys Gly Phe Phe Ala Lys Tyr Gly Thr Xaa Val Val Ser Lys Gln
                85                  90                  95

Ala Ser Trp Gly Ser Ala Arg Asp Asn Val Glu Ile Gly Ser Ala Gly
            100                 105                 110

Gly Gly Asp Gly Gly Gln Trp Gln Met Pro Met Pro His Leu Ile Thr
        115                 120                 125

Glu Gly Ile Ile Thr Lys Gly Asn Xaa Lys Ile Pro Met Tyr Val Leu
    130                 135                 140

Ala Gln Leu Xaa Thr Gln Gly Asn Gly Ile Ala Ala Xaa Xaa His Xaa
145                 150                 155                 160

Gly Lys Gly Xaa Xaa Leu Xaa Xaa Xaa Xaa Xaa Ala Xaa Tyr Xaa Xaa
                165                 170                 175

Gly Xaa Xaa Lys Xaa Xaa Gly Xaa Pro Phe Lys Ala Ala Xaa Thr Phe
            180                 185                 190

Pro Xaa Val Asn Gln Asp Phe Trp Ile Arg Tyr Trp Leu Ala Ala Gly
        195                 200                 205

Gly Ile Pro Xaa Asp Xaa Leu Leu Ala Val Pro Ala Ala Thr Val Ala
    210                 215                 220

Xaa Met Arg Thr Gly Thr Met Asp Ala Phe Ser Thr Gly Asp Pro Trp
225                 230                 235                 240

Pro Xaa Arg Ile Val Xaa Xaa Xaa Lys Ile Gly Ala Xaa Leu Thr Ala
                245                 250                 255

Ile Trp Pro Xaa His Pro Glu Glu Tyr Leu Ala Xaa Arg Ala Trp Val
            260                 265                 270

Asp Lys His Pro Lys Ala Thr Lys Ala Leu Leu Lys Gly Met Glu Ala
        275                 280                 285

Gln Gln Trp Xaa Asp Xaa Xaa Asn Arg Xaa Glu Xaa Ala Xaa Ile Leu
    290                 295                 300

Xaa Gly Arg Xaa Tyr Phe Xaa Pro Xaa Xaa Xaa Ile Leu Xaa Xaa Pro
305                 310                 315                 320

Xaa Gly Xaa Tyr Xaa Gly Asp Gly Arg Xaa Xaa Xaa Asp Asp Xaa Xaa
                325                 330                 335

Xaa Ala Xaa Leu Tyr Trp Lys Asp Xaa Xaa Gly Asn Xaa Ser Tyr Pro
            340                 345                 350

Tyr Lys Ser His Asp Leu Trp Phe Leu Thr Glu Ser Val Arg Trp Gly
        355                 360                 365

Phe Leu Pro Xaa Asp Xaa Leu Xaa Xaa Xaa Xaa Xaa Xaa Ala Xaa Xaa
    370                 375                 380

Xaa Ile Xaa Lys Val Asn Arg Glu Asp Leu Trp Xaa Glu Ala Ala Lys
385                 390                 395                 400
```

```
Leu Gly Ile Ala Ala Ala Ile Pro Thr Ser Thr Ser Arg Gly Glu Thr
                405                 410                 415

Phe Phe Asp Gly Xaa Lys Phe Pro Glu Asn Pro Xaa Ala Tyr Leu Xaa
            420                 425                 430

Ser Leu Lys Ile Lys Lys Xaa Xaa Xaa
        435                 440
```

<210> SEQ ID NO 189
<211> LENGTH: 301
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (24)..(26)
<223> OTHER INFORMATION: Xaa can be any naturally occurring amino acid
<220> FEATURE:
<221> NAME/KEY: misc_feature
<222> LOCATION: (30)..(37)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid
<220> FEATURE:
<221> NAME/KEY: misc_feature
<222> LOCATION: (47)..(48)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (63)..(64)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (78)..(79)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (85)..(86)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (110)..(113)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (124)..(124)
<223> OTHER INFORMATION: Xaa can be any naturally occurring amino acid
<220> FEATURE:
<221> NAME/KEY: misc_feature
<222> LOCATION: (129)..(129)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (133)..(133)
<223> OTHER INFORMATION: Xaa can be any naturally occurring amino acid
<220> FEATURE:
<221> NAME/KEY: misc_feature
<222> LOCATION: (139)..(143)
<223> OTHER INFORMATION: Xaa can be any naturally occurring amino acid
<220> FEATURE:
<221> NAME/KEY: misc_feature
<222> LOCATION: (145)..(146)
<223> OTHER INFORMATION: Xaa can be any naturally occurring amino acid
<220> FEATURE:
<221> NAME/KEY: misc_feature
<222> LOCATION: (148)..(149)
<223> OTHER INFORMATION: Xaa can be any naturally occurring amino acid
<220> FEATURE:

<221> NAME/KEY: misc_feature
<222> LOCATION: (155)..(155)
<223> OTHER INFORMATION: Xaa can be any naturally occurring amino acid
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (168)..(168)
<223> OTHER INFORMATION: Xaa can be any naturally occurring amino acid
<220> FEATURE:
<221> NAME/KEY: misc_feature
<222> LOCATION: (170)..(171)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (178)..(178)
<223> OTHER INFORMATION: Xaa can be any naturally occurring amino acid
<220> FEATURE:
<221> NAME/KEY: misc_feature
<222> LOCATION: (180)..(184)
<223> OTHER INFORMATION: Xaa can be any naturally occurring amino acid
<220> FEATURE:
<221> NAME/KEY: misc_feature
<222> LOCATION: (186)..(186)
<223> OTHER INFORMATION: Xaa can be any naturally occurring amino acid
<220> FEATURE:
<221> NAME/KEY: misc_feature
<222> LOCATION: (191)..(192)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: misc_feature
<222> LOCATION: (196)..(199)
<223> OTHER INFORMATION: Xaa can be any naturally occurring amino acid
<220> FEATURE:
<221> NAME/KEY: misc_feature
<222> LOCATION: (201)..(204)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (209)..(211)
<223> OTHER INFORMATION: Xaa can be any naturally occurring amino acid
<220> FEATURE:
<221> NAME/KEY: misc_feature
<222> LOCATION: (214)..(218)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (230)..(230)
<223> OTHER INFORMATION: Xaa can be any naturally occurring amino acid
<220> FEATURE:
<221> NAME/KEY: misc_feature
<222> LOCATION: (235)..(235)
<223> OTHER INFORMATION: Xaa can be any naturally occurring amino acid
<220> FEATURE:
<221> NAME/KEY: misc_feature
<222> LOCATION: (237)..(237)
<223> OTHER INFORMATION: Xaa can be any naturally occurring amino acid
<220> FEATURE:
<221> NAME/KEY: misc_feature
<222> LOCATION: (239)..(240)
<223> OTHER INFORMATION: Xaa can be any naturally occurring amino acid
<220> FEATURE:
<221> NAME/KEY: misc_feature
<222> LOCATION: (245)..(247)
<223> OTHER INFORMATION: Xaa can be any naturally occurring amino acid
<220> FEATURE:
<221> NAME/KEY: misc_feature
<222> LOCATION: (250)..(250)
<223> OTHER INFORMATION: Xaa can be any naturally occurring amino acid
<220> FEATURE:
<221> NAME/KEY: misc_feature
<222> LOCATION: (253)..(253)
<223> OTHER INFORMATION: Xaa can be any naturally occurring amino acid
<220> FEATURE:
<221> NAME/KEY: misc_feature
<222> LOCATION: (255)..(255)
<223> OTHER INFORMATION: Xaa can be any naturally occurring amino acid
<220> FEATURE:
<221> NAME/KEY: misc_feature
<222> LOCATION: (260)..(265)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
<222> LOCATION: (269)..(271)
<223> OTHER INFORMATION: Xaa can be any naturally occurring amino acid
<220> FEATURE:
<221> NAME/KEY: misc_feature
<222> LOCATION: (276)..(279)
<223> OTHER INFORMATION: Xaa can be any naturally occurring amino acid
<220> FEATURE:
<221> NAME/KEY: misc_feature
<222> LOCATION: (282)..(282)
<223> OTHER INFORMATION: Xaa can be any naturally occurring amino acid
<220> FEATURE:
<221> NAME/KEY: misc_feature
<222> LOCATION: (287)..(287)
<223> OTHER INFORMATION: Xaa can be any naturally occurring amino acid
<220> FEATURE:
<221> NAME/KEY: misc_feature
<222> LOCATION: (292)..(292)
<223> OTHER INFORMATION: Xaa can be any naturally occurring amino acid
<220> FEATURE:
<221> NAME/KEY: misc_feature
<222> LOCATION: (294)..(295)
<223> OTHER INFORMATION: Xaa can be any naturally occurring amino acid
<220> FEATURE:
<221> NAME/KEY: misc_feature
<222> LOCATION: (298)..(298)
<223> OTHER INFORMATION: Xaa can be any naturally occurring amino acid
<220> FEATURE:
<221> NAME/KEY: misc_feature
<222> LOCATION: (300)..(301)
<223> OTHER INFORMATION: Xaa can be any naturally occurring amino acid

<400> SEQUENCE: 189

```
Xaa Xaa Met Xaa Xaa Asn Val Tyr Ser Xaa Arg Xaa Xaa Xaa Leu Ile
1               5                   10                  15

Lys Pro Xaa Leu Xaa Xaa Phe Xaa Xaa Xaa Thr Gly Ile Xaa Xaa Xaa
            20                  25                  30

Xaa Xaa Xaa Xaa Xaa Glu Leu Val Arg Leu Xaa Xaa Glu Gly Xaa Xaa
        35                  40                  45

Thr Pro Ala Asp Val Phe Leu Thr Xaa Asp Ala Gly Xaa Leu Xaa Xaa
    50                  55                  60
```

```
Ala Xaa Ala Xaa Leu Leu Gln Pro Xaa Ser Arg Glu Leu Xaa Xaa Pro
65                  70                  75                  80

Xaa Gln Phe Arg Xaa Xaa Asn Xaa Trp Phe Gly Leu Ser Xaa Arg Xaa
                85                  90                  95

Arg Xaa Val Tyr Asn Lys Xaa Arg Val Lys Pro Xaa Gln Xaa Xaa Xaa
            100                 105                 110

Xaa Tyr Xaa Asp Leu Thr Xaa Pro Gln Trp Lys Xaa Lys Ala Val Arg
        115                 120                 125

Xaa Ser Xaa Asn Xaa Tyr Asn Gln Ser Leu Xaa Xaa Xaa Xaa Xaa Ala
    130                 135                 140

Xaa Xaa Gly Xaa Xaa Thr Lys Gln Phe Leu Xaa Gly Leu Lys Ala Asn
145                 150                 155                 160

Xaa Ala Arg Xaa Pro Xaa Gly Xaa Asp Xaa Xaa Gln Val Xaa Ala Val
                165                 170                 175

Ala Xaa Gly Xaa Xaa Xaa Xaa Xaa Ile Xaa Asn His Tyr Tyr Xaa Xaa
            180                 185                 190

Arg Xaa Leu Xaa Xaa Xaa Xaa Glu Xaa Xaa Xaa Xaa Ala Xaa Ala Ala
        195                 200                 205

Xaa Xaa Xaa Phe Pro Xaa Xaa Xaa Xaa Xaa Gly Ala His Xaa Asn Ser
    210                 215                 220

Gly Ile Gly Val Thr Xaa Ala Ser Lys Asn Xaa Glu Xaa Ala Xaa Xaa
225                 230                 235                 240

Leu Ile Glu Val Xaa Xaa Xaa Ala Gln Xaa Met Ala Xaa Leu Xaa Glu
                245                 250                 255

Tyr Pro Val Xaa Xaa Xaa Xaa Xaa Xaa Pro Xaa Leu Xaa Xaa Xaa Gly
            260                 265                 270

Thr Phe Arg Xaa Xaa Xaa Xaa Leu Ala Xaa Leu Ala Glu Asn Xaa Glu
        275                 280                 285

Ala Ala Leu Xaa Leu Xaa Xaa Val Gly Xaa Arg Xaa Xaa
    290                 295                 300
```

<210> SEQ ID NO 190
<211> LENGTH: 323
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(27)

<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (36)..(37)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (67)..(69)
<223> OTHER INFORMATION: Xaa can be any naturally occurring amino acid
<220> FEATURE:
<221> NAME/KEY: misc_feature
<222> LOCATION: (73)..(74)
<223> OTHER INFORMATION: Xaa can be any naturally occurring amino acid
<220> FEATURE:
<221> NAME/KEY: misc_feature
<222> LOCATION: (76)..(78)
<223> OTHER INFORMATION: Xaa can be any naturally occurring amino acid
<220> FEATURE:
<221> NAME/KEY: misc_feature
<222> LOCATION: (81)..(84)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (89)..(92)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (107)..(110)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (118)..(118)
<223> OTHER INFORMATION: Xaa can be any naturally occurring amino acid
<220> FEATURE:
<221> NAME/KEY: misc_feature
<222> LOCATION: (123)..(124)
<223> OTHER INFORMATION: Xaa can be any naturally occurring amino acid
<220> FEATURE:
<221> NAME/KEY: misc_feature
<222> LOCATION: (127)..(127)
<223> OTHER INFORMATION: Xaa can be any naturally occurring amino acid
<220> FEATURE:
<221> NAME/KEY: misc_feature
<222> LOCATION: (129)..(131)
<223> OTHER INFORMATION: Xaa can be any naturally occurring amino acid
<220> FEATURE:
<221> NAME/KEY: misc_feature
<222> LOCATION: (133)..(133)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (149)..(150)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (161)..(162)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (168)..(169)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (180)..(180)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (195)..(195)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (199)..(225)
<223> OTHER INFORMATION: Xaa can be any naturally occurring amino acid
<220> FEATURE:
<221> NAME/KEY: misc_feature
<222> LOCATION: (227)..(227)
<223> OTHER INFORMATION: Xaa can be any naturally occurring amino acid
<220> FEATURE:
<221> NAME/KEY: misc_feature
<222> LOCATION: (229)..(230)
<223> OTHER INFORMATION: Xaa can be any naturally occurring amino acid
<220> FEATURE:

<221> NAME/KEY: misc_feature
<222> LOCATION: (233)..(234)
<223> OTHER INFORMATION: Xaa can be any naturally occurring amino acid
<220> FEATURE:
<221> NAME/KEY: misc_feature
<222> LOCATION: (236)..(237)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (251)..(251)
<223> OTHER INFORMATION: Xaa can be any naturally occurring amino acid
<220> FEATURE:
<221> NAME/KEY: misc_feature
<222> LOCATION: (253)..(253)
<223> OTHER INFORMATION: Xaa can be any naturally occurring amino acid
<220> FEATURE:
<221> NAME/KEY: misc_feature
<222> LOCATION: (256)..(258)
<223> OTHER INFORMATION: Xaa can be any naturally occurring amino acid
<220> FEATURE:
<221> NAME/KEY: misc_feature
<222> LOCATION: (260)..(260)
<223> OTHER INFORMATION: Xaa can be any naturally occurring amino acid
<220> FEATURE:
<221> NAME/KEY: misc_feature
<222> LOCATION: (262)..(262)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
<222> LOCATION: (271)..(272)
<223> OTHER INFORMATION: Xaa can be any naturally occurring amino acid
<220> FEATURE:
<221> NAME/KEY: misc_feature
<222> LOCATION: (275)..(275)
<223> OTHER INFORMATION: Xaa can be any naturally occurring amino acid
<220> FEATURE:
<221> NAME/KEY: misc_feature
<222> LOCATION: (278)..(281)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (289)..(294)
<223> OTHER INFORMATION: Xaa can be any naturally occurring amino acid
<220> FEATURE:
<221> NAME/KEY: misc_feature
<222> LOCATION: (296)..(296)
<223> OTHER INFORMATION: Xaa can be any naturally occurring amino acid
<220> FEATURE:
<221> NAME/KEY: misc_feature
<222> LOCATION: (299)..(301)
<223> OTHER INFORMATION: Xaa can be any naturally occurring amino acid
<220> FEATURE:
<221> NAME/KEY: misc_feature
<222> LOCATION: (304)..(304)
<223> OTHER INFORMATION: Xaa can be any naturally occurring amino acid
<220> FEATURE:
<221> NAME/KEY: misc_feature
<222> LOCATION: (308)..(308)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: misc_feature
<222> LOCATION: (322)..(322)
<223> OTHER INFORMATION: Xaa can be any naturally occurring amino acid

<400> SEQUENCE: 190

Xaa Xaa Xaa Met Leu Thr Xaa Tyr Ser Gly Arg Gly Xaa Xaa Leu Val
1 5 10 15

Xaa Xaa Leu Val Xaa Gln Xaa Glu Xaa Xaa Xaa Asp Xaa Xaa Val Xaa
20 25 30

Val Arg Tyr Xaa Xaa Asp Xaa Leu Leu Ala Ala Leu Gln Glu Gly Asp
35 40 45

Xaa Ser Pro Ala Asp Val Phe Trp Ala Asn Thr Ala Gly Ala Leu Gly
50 55 60

Xaa Ala Xaa Xaa Xaa Gly Leu Leu Xaa Xaa Leu Xaa Xaa Xaa Leu Thr
65 70 75 80

Xaa Xaa Xaa Xaa Arg Phe Xaa Pro Xaa Xaa Xaa Xaa Trp Xaa Pro Val
85 90 95

Ser Xaa Arg Xaa Arg Val Xaa Ala Tyr Asn Xaa Xaa Xaa Xaa Ser Asp
100 105 110

Xaa Leu Pro Asp Ser Xaa Asp Leu Pro Glu Xaa Xaa Glu Phe Xaa Gly
115 120 125

Xaa Xaa Xaa Arg Xaa Gly Trp Thr Pro Xaa Tyr Ser Ser Phe Gln Asp
130 135 140

Phe Thr Ala Arg Xaa Xaa Glu Gly Glu Glu Ala Thr Xaa Ala Trp Leu
145 150 155 160

Xaa Xaa Met Xaa Ala Ala Gly Xaa Xaa Ser Tyr Pro Ser Xaa Ala Met
165 170 175

Xaa Ala Ile Xaa Ala Gly Glu Asp Xaa Ala Xaa Thr Asn His Tyr Tyr
180 185 190

Gln Arg Xaa Leu Xaa Gly Xaa Xaa Xaa Xaa Xaa Xaa Xaa Xaa Xaa Xaa
195 200 205

Xaa Xaa Xaa Xaa Xaa Xaa Xaa Xaa Xaa Xaa Xaa Xaa Xaa Xaa Xaa Xaa
210 215 220

Xaa Ala Xaa Ala Xaa Xaa Gly Thr Xaa Xaa Phe Xaa Xaa Gly Asp Ala
225 230 235 240

Gly Xaa Leu Ala Leu Val Thr Gly Ala Gly Xaa Leu Xaa Thr Ser Xaa
245 250 255

Xaa Xaa Thr Xaa Ala Xaa Arg Phe Leu Arg Xaa Leu Leu Ser Xaa Xaa
260 265 270

Ala Gln Xaa Phe Ala Xaa Xaa Xaa Xaa Glu Tyr Pro Leu Xaa Gly Val
275 280 285

Xaa Xaa Xaa Xaa Xaa Xaa Pro Xaa Asp Ala Xaa Xaa Xaa Ser Pro Xaa
290 295 300

Ile Asp Leu Xaa Lys Leu Xaa Asp Pro Thr Leu Asp Leu Arg Ala Gly
305 310 315 320

Val Xaa Leu

<210> SEQ ID NO 191
<211> LENGTH: 452
<212> TYPE: PRT
<213> ORGANISM: Artificial Sequence
<220> FEATURE:
<223> OTHER INFORMATION: synBicarbBP1

<400> SEQUENCE: 191

Met Gly Ser Phe Asn Arg Arg Lys Phe Leu Leu Thr Ser Ala Ala Thr
1 5 10 15

Ala Thr Gly Ala Leu Phe Leu Lys Gly Cys Ala Gly Asn Pro Pro Asp

```
            20                  25                  30

Pro Asn Ala Ala Ser Thr Gly Thr Asn Pro Ser Pro Gln Ala Ala Gly
        35                  40                  45

Asp Ile Ser Pro Glu Met Met Pro Glu Thr Ala Asn Ile Lys Leu Gly
    50                  55                  60

Tyr Ile Pro Ile Val Glu Ala Ala Pro Leu Ile Ile Ala Gln Glu Lys
65                  70                  75                  80

Gly Phe Phe Ala Lys Tyr Gly Met Thr Gly Val Glu Val Ser Lys Gln
                85                  90                  95

Ala Asn Trp Ala Ser Ala Arg Asp Asn Val Thr Ile Gly Ser Gln Gly
            100                 105                 110

Gly Gly Ile Asp Gly Gly Gln Trp Gln Met Pro Met Pro His Leu Ile
        115                 120                 125

Thr Glu Gly Ile Ile Thr Asn Gly Asn Lys Val Pro Met Tyr Val Leu
    130                 135                 140

Ala Gln Leu Ile Thr Gln Gly Asn Gly Ile Ala Val Ala Pro Met His
145                 150                 155                 160

Glu Gly Lys Gly Val Asn Leu Asp Ile Thr Lys Ala Ala Asp Tyr Ile
                165                 170                 175

Lys Gly Phe Asn Lys Thr Asn Gly Arg Lys Phe Lys Ala Ala His Thr
            180                 185                 190

Phe Pro Asn Val Asn Gln Asp Phe Trp Ile Arg Tyr Trp Phe Ala Ala
        195                 200                 205

Gly Gly Val Asp Pro Asp Thr Asp Ile Asp Leu Leu Ala Val Pro Pro
    210                 215                 220

Ala Glu Thr Val Gln Gly Met Arg Asn Gly Thr Met Asp Ala Phe Ser
225                 230                 235                 240

Thr Gly Asp Pro Trp Pro Tyr Arg Ile Val Thr Glu Asn Ile Gly Tyr
                245                 250                 255

Met Ala Gly Leu Thr Ala Gln Ile Trp Pro Tyr His Pro Glu Glu Tyr
            260                 265                 270

Leu Ala Ile Arg Ala Asp Trp Val Asp Lys Asn Pro Lys Ala Thr Lys
        275                 280                 285

Ala Leu Leu Lys Gly Ile Met Glu Ala Gln Gln Trp Ile Asp Asp Pro
    290                 295                 300

Lys Asn Arg Pro Glu Val Val Gln Ile Val Ser Gly Arg Asn Tyr Phe
305                 310                 315                 320

Asn Val Pro Thr Thr Ile Leu Glu Ser Pro Phe Lys Gly Gln Tyr Thr
                325                 330                 335

Met Gly Asp Gly Gln Pro Ala Ile Asp Asp Phe Gln Lys Gly Pro Leu
            340                 345                 350

Tyr Trp Lys Asp Gly Ile Gly Asn Val Ser Tyr Pro Tyr Lys Ser His
        355                 360                 365

Asp Leu Trp Phe Leu Thr Glu Ser Ile Arg Trp Gly Phe His Lys Asn
    370                 375                 380

Ala Ile Pro Asp Leu Asp Thr Ala Gln Lys Ile Ile Asp Lys Val Asn
385                 390                 395                 400

Arg Glu Asp Leu Trp Arg Glu Ala Ala Thr Glu Ala Gly Phe Thr Ala
                405                 410                 415

Asp Ile Pro Ser Ser Thr Ser Arg Gly Val Glu Thr Phe Phe Asp Gly
            420                 425                 430

Ile Thr Phe Asp Pro Ala Asn Pro Ser Ala Tyr Leu Gln Ser Leu Ala
        435                 440                 445
```

Ile Lys Lys Val
    450

<210> SEQ ID NO 192
<211> LENGTH: 444
<212> TYPE: PRT
<213> ORGANISM: Artificial Sequence
<220> FEATURE:
<223> OTHER INFORMATION: teBicarbBP2

<400> SEQUENCE: 192

```
Met Ser Gln Leu Ser Arg Arg Arg Phe Leu Met Thr Ala Thr Ala Thr
1               5                   10                  15

Ala Val Gly Ala Ile Ala Leu Lys Gly Cys Ala Pro Ala Glu Thr Pro
            20                  25                  30

Gln Gly Gln Gln Gln Gly Gly Thr Thr Thr Gly Gly Leu Glu Thr Asp
        35                  40                  45

Thr Ile Lys Leu Gly Phe Ile Pro Ile Val Glu Ser Ala Pro Leu Ile
    50                  55                  60

Ile Ala Lys Glu Lys Gly Phe Phe Ala Lys His Gly Leu Thr Asn Ala
65                  70                  75                  80

Glu Leu Ser Lys Gln Ala Asn Trp Ala Ser Ala Arg Asp Asn Val Val
                85                  90                  95

Ile Gly Ser Ala Gly Gly Gly Ile Asp Gly Gly Gln Trp Gln Met Pro
            100                 105                 110

Met Pro Tyr Leu Ile Ser Glu Gly Ile Ile Thr Leu Asn Asn Gln Lys
        115                 120                 125

Leu Pro Met Tyr Val Leu Ala Gln Leu Asn Thr Gln Gly Asn Gly Ile
    130                 135                 140

Ala Ile Ser Gly Ala Asn Lys Gly Lys Gly Leu His Leu Lys Ile Ala
145                 150                 155                 160

Asp Pro Asp Tyr Ile Lys Gly Phe Ala Ala Lys Asn Gly Arg Lys Phe
                165                 170                 175

Lys Ala Ala His Thr Phe Pro His Val Asn Gln Asp Leu Trp Ile Arg
            180                 185                 190

Tyr Trp Phe Ala Ala Asn Gly Ile Asp Pro Asp Arg Asp Ile Glu Leu
        195                 200                 205

Leu Ala Val Pro Pro Ala Glu Thr Val Ala Gly Met Arg Asn Gly Thr
    210                 215                 220

Met Asp Ala Phe Ser Thr Gly Asp Pro Trp Pro Phe Arg Ile Val Ser
225                 230                 235                 240

Asp Asp Ile Gly Tyr Met Ala Thr Leu Thr Ala Gln Ile Trp Pro Tyr
                245                 250                 255

His Pro Glu Glu Tyr Leu Ala Val Arg Ala Asp Trp Val Asp Lys His
            260                 265                 270

Pro Lys Ala Thr Lys Ala Leu Leu Lys Ala Val Met Glu Ala Gln Gln
        275                 280                 285

Trp Ala Asp Asp Lys Ala Asn Arg Pro Glu Leu Ile Gln Ile Ala Ser
    290                 295                 300

Arg Arg Glu Tyr Phe Asn Ile Pro Gly Asn Ile Leu Thr Pro Pro Tyr
305                 310                 315                 320

Glu Gly Thr Tyr Thr Met Gly Asp Gly Gln Pro Asn Phe Asn Asp Phe
                325                 330                 335

Asn Ile Gly Pro Leu Tyr Trp Arg Asp Pro Asn Gly Asn Ser Ile Ser
            340                 345                 350
```

Tyr Pro Tyr Lys Ser His Asp Leu Trp Phe Leu Thr Glu Asn Leu Arg
355 360 365

Trp Gly Phe Asn Ala Asp Lys Leu Lys Asp Phe Asp Asn Ile Lys Gln
370 375 380

Met Ile Gly Arg Val Asn Arg Ser Asp Leu Trp Gln Glu Ala Ala Lys
385 390 395 400

Glu Leu Gly Ile Pro Ala Ala Glu Ile Pro Thr Thr Glu Ser Arg Gly
405 410 415

Val Glu Thr Phe Phe Asp Gly Ile Lys Phe Asp Pro Asp Asn Pro Gln
420 425 430

Ala Tyr Leu Asp Ser Leu Lys Ile Lys Val Lys Ser
435 440

<210> SEQ ID NO 193
<211> LENGTH: 448
<212> TYPE: PRT
<213> ORGANISM: Artificial Sequence
<220> FEATURE:
<223> OTHER INFORMATION: ctBicarbBP3

<400> SEQUENCE: 193

Met Thr Glu Phe Ser Arg Arg Lys Phe Ile Ile Thr Ala Gly Ala Ser
1 5 10 15

Ala Val Gly Ser Val Phe Leu Lys Gly Cys Leu Gly Asn Pro Pro Asp
20 25 30

Ser Val Thr Gly Thr Gln Thr Gln Gln Val Ala Ala Val Asn Val Ser
35 40 45

Pro Glu Gln Ala Pro Glu Thr Thr Arg Val Lys Leu Gly Tyr Ile Pro
50 55 60

Ile Val Glu Ala Ala Pro Ile Ile Ile Ala Lys Glu Lys Gly Phe Phe
65 70 75 80

Ala Lys Tyr Gly Met Thr Asp Val Asp Val Ser Lys Gln Ala Ser Trp
85 90 95

Gly Ser Met Arg Asp Asn Thr Glu Ile Gly Ala Ala Gly Gly Gly Val
100 105 110

Asp Gly Gly Gln Tyr Gln Met Pro Met Pro His Leu Ile Thr Glu Gly
115 120 125

Arg Ile Thr Lys Gly Asn Lys Pro Ile Pro Met Tyr Val Leu Ala Gln
130 135 140

Leu Asn Thr Gln Gly Asn Gly Ile Ala Ile Ala Glu Lys His Arg Gly
145 150 155 160

Lys Gly Ile Glu Leu Glu Leu Ala Lys Gly Gly Lys Asn Leu Phe Gly
165 170 175

Gln Leu Lys Ser Ala Asn Thr Pro Phe Thr Ala Ala Tyr Thr Phe Ala
180 185 190

Gln Val Asn Gln Asp Phe Trp Ile Arg Tyr Trp Leu Ala Ala Gly Gly
195 200 205

Val Asn Pro Asp Ala Asp Val Lys Leu Ile Pro Val Pro Ala Ala Gln
210 215 220

Thr Val Ala Asn Met Lys Thr Gly Thr Met Asp Ala Phe Ser Thr Gly
225 230 235 240

Asp Pro Trp Pro Tyr Arg Ile Val Lys Asp Lys Ile Gly Phe Leu Ala
245 250 255

Met Leu Thr Ala Asp Met Trp Glu Phe His Pro Glu Glu Tyr Leu Ala
260 265 270

Leu Arg Ala Glu Trp Val Asp Lys His Pro Lys Ala Thr Lys Ala Leu
275 280 285

Leu Lys Gly Ile Met Glu Ala Gln Gln Trp Leu Asp Asn Phe Asp Asn
290 295 300

Arg Glu Glu Ala Ala Lys Ile Leu Gly Gly Arg Asn Tyr Phe Asn Leu
305 310 315 320

Pro Ala Glu Ile Leu Ala Gly Pro Phe Ala Gly Lys Tyr Asp Met Gly
325 330 335

Glu Gly Arg Thr Val Asp Asp Arg Asn Lys Ala Val Leu Tyr Trp Lys
340 345 350

Asp Pro Arg Gly Ser Val Ser Tyr Pro Tyr Lys Ser His Asp Leu Trp
355 360 365

Phe Leu Thr Glu Ser Val Arg Trp Gly Phe Leu Pro Pro Asp Ser Leu
370 375 380

Thr Lys Ala Gln Ala Leu Ile Asp Lys Val Asn Arg Glu Asp Leu Trp
385 390 395 400

Lys Glu Ala Ala Lys Glu Leu Gly Val Ala Ala Ala Asp Ile Pro Thr
405 410 415

Ser Thr Ser Arg Gly Val Glu Thr Phe Phe Asp Gly Val Lys Phe Asp
420 425 430

Pro Glu Asn Pro Ala Ala Tyr Leu Lys Ser Leu Lys Ile Lys Lys Ala
435 440 445

<210> SEQ ID NO 194
<211> LENGTH: 458
<212> TYPE: PRT
<213> ORGANISM: Artificial Sequence
<220> FEATURE:
<223> OTHER INFORMATION: avBicarbBP5

<400> SEQUENCE: 194

Met Thr Glu Phe Phe Asn Gln Phe Ser Arg Arg Lys Phe Ile Val Thr
1 5 10 15

Ala Gly Ala Ser Ala Gly Ala Val Phe Leu Lys Gly Cys Leu Gly Asn
20 25 30

Pro Pro Glu Thr Thr Gly Gly Thr Gln Ser Ala Pro Thr Ala Gln Pro
35 40 45

Ala Ala Asn Val Ser Ala Glu Gln Ala Pro Glu Val Thr Thr Val Lys
50 55 60

Leu Gly Tyr Ile Pro Ile Val Glu Ser Ala Pro Leu Ile Ile Ala Lys
65 70 75 80

Glu Lys Gly Phe Phe Ala Lys Tyr Gly Leu Thr Asn Val Glu Leu Ser
85 90 95

Lys Gln Ala Ser Trp Gly Ser Ala Arg Asp Asn Val Glu Ile Gly Ser
100 105 110

Ala Gly Gly Gly Ile Asp Gly Gly Gln Trp Gln Met Pro Met Pro His
115 120 125

Leu Ile Thr Glu Gly Leu Ile Thr Lys Gly Asn Gln Lys Ile Pro Met
130 135 140

Tyr Val Leu Ala Gln Leu Ile Thr His Gly Asn Gly Ile Ala Ile Ala
145 150 155 160

Asn Lys His Gln Gly Lys Gly Ile Ser Leu Lys Leu Glu Gly Ala Lys
165 170 175

Ser Leu Phe Ser Gln Leu Lys Ser Ser Thr Pro Phe Thr Ala Ala Phe
180 185 190

Thr Phe Pro His Val Asn Gln Asp Leu Trp Ile Arg Tyr Trp Leu Ala
        195                 200                 205

Ala Gly Gly Ile Asp Pro Asp Ala Asp Val Lys Leu Leu Thr Val Pro
    210                 215                 220

Ala Ala Gln Thr Val Ala Asn Met Lys Thr Gly Thr Met Asp Ala Phe
225                 230                 235                 240

Ser Thr Gly Asp Pro Trp Pro Phe Arg Leu Val Asn Asp Lys Ile Gly
                245                 250                 255

Tyr Met Ala Ala Leu Thr Ala Glu Ile Trp Lys Asn His Pro Glu Glu
            260                 265                 270

Tyr Leu Ala Met Arg Ala Asp Trp Val Asp Lys Tyr Pro Lys Ala Thr
        275                 280                 285

Lys Ala Leu Leu Lys Gly Ile Met Glu Ala Gln Gln Trp Leu Asp Asn
    290                 295                 300

Phe Asp Asn Arg Lys Glu Ala Ala Gln Ile Leu Ala Gly Arg Asn Tyr
305                 310                 315                 320

Phe Asn Leu Asn Asn Pro Glu Ile Leu Ala Asp Pro Tyr Val Gly Lys
                325                 330                 335

Tyr Asp Met Gly Asp Gly Arg Lys Ile Asp Asp Lys Ser Met Ala Ala
            340                 345                 350

Tyr Tyr Trp Lys Asp Glu Lys Gly Ser Val Ser Tyr Pro Tyr Lys Ser
        355                 360                 365

His Asp Leu Trp Phe Ile Thr Glu Asn Val Arg Trp Gly Phe Leu Pro
    370                 375                 380

Lys Asp Tyr Leu Ala Asn Gly Ala Ala Lys Ala Lys Glu Leu Ile Asp
385                 390                 395                 400

Lys Val Asn Arg Glu Asp Ile Trp Lys Glu Ala Ala Lys Glu Ala Gly
                405                 410                 415

Ile Ala Ala Ala Asp Ile Pro Thr Ser Thr Ser Arg Gly Val Glu Glu
            420                 425                 430

Phe Phe Asp Gly Thr Lys Phe Asp Pro Glu Lys Pro Asp Glu Tyr Leu
        435                 440                 445

Lys Ser Leu Lys Ile Lys Lys Val Ser Val
    450                 455

<210> SEQ ID NO 195
<211> LENGTH: 459
<212> TYPE: PRT
<213> ORGANISM: Artificial Sequence
<220> FEATURE:
<223> OTHER INFORMATION: calBicarbBP4

<400> SEQUENCE: 195

Met Ser Asp Phe Leu Asn Gln Ile Asn Arg Arg Lys Phe Ile Leu Thr
1               5                   10                  15

Ala Gly Ala Ser Ala Gly Ala Ile Phe Leu Lys Gly Cys Leu Gly Asn
            20                  25                  30

Pro Pro Asp Ser Thr Gly Gly Asn Ser Gln Ala Ile Pro Thr Ala Gln
        35                  40                  45

Gln Val Ala Asn Leu Thr Pro Glu Gln Lys Pro Glu Thr Glu Thr Val
    50                  55                  60

Lys Leu Gly Tyr Ile Pro Ile Val Glu Ser Ala Pro Leu Ile Ile Ala
65                  70                  75                  80

Lys Glu Lys Gly Leu Phe Ala Lys Tyr Gly Met Thr Lys Val Glu Leu
                85                  90                  95

```
Ala Lys Gln Ala Ser Trp Gly Ala Ala Arg Asp Asn Val Glu Ile Gly
            100                 105                 110

Ser Ala Gly Gly Gly Ile Asp Gly Gly Gln Trp Gln Met Pro Met Pro
        115                 120                 125

His Leu Ile Thr Ala Gly Leu Ile Thr Lys Gly Asn Lys Glu Ile Pro
    130                 135                 140

Met Tyr Val Leu Ala Gln Leu Val Thr His Gly Asn Gly Ile Ala Ile
145                 150                 155                 160

Ala Asp Lys His Lys Gly Lys Gly Leu Gly Leu Lys Leu Asp Gly Ala
                165                 170                 175

Lys Ser Leu Phe Lys Glu Leu Lys Ser Ser Thr Pro Phe Thr Ala Ala
            180                 185                 190

Phe Thr Phe Pro His Val Asn Gln Asp Leu Trp Ile Arg Tyr Trp Leu
        195                 200                 205

Ala Ala Ser Gly Leu Asp Pro Asp Ala Asp Val Lys Leu Leu Thr Val
    210                 215                 220

Pro Ala Ala Gln Thr Val Ala Asn Met Lys Thr Gly Thr Met Asp Ala
225                 230                 235                 240

Phe Ser Thr Gly Asp Pro Trp Pro Phe Arg Ile Val Asn Asp Lys Ile
                245                 250                 255

Gly Phe Met Ala Leu Leu Thr Ala Glu Met Trp Lys Asn His Pro Glu
            260                 265                 270

Glu Tyr Leu Ala Met Arg Gly Asp Trp Val Asp Lys His Pro Lys Ala
        275                 280                 285

Thr Lys Ala Ile Leu Lys Ala Val Met Glu Ala Gln Gln Trp Leu Asp
    290                 295                 300

Asn Phe Glu Asn Arg Lys Glu Ala Ala Thr Ile Leu Ala Gly Arg Lys
305                 310                 315                 320

Tyr Phe Asp Leu Ser Ser Pro Glu Ile Leu Leu Asp Pro Tyr Gln Gly
                325                 330                 335

Lys Tyr Asp Met Gly Asp Gly Arg Lys Ile Asp Asp Lys Leu Met Ala
            340                 345                 350

Pro Tyr Tyr Trp Lys Asp Glu Lys Gly Ser Val Ser Tyr Pro Tyr Lys
        355                 360                 365

Ser His Asp Leu Trp Phe Ile Thr Glu Asn Val Arg Trp Gly Phe Leu
    370                 375                 380

Pro Lys Asp Tyr Leu Ala Asn Asn Ala Ala Lys Ala Lys Glu Leu Ile
385                 390                 395                 400

Asn Lys Val Asn Arg Glu Asp Ile Trp Lys Glu Ala Ala Lys Asp Leu
                405                 410                 415

Gly Ile Ala Ala Ala Asp Ile Pro Thr Ser Thr Ser Arg Gly Val Glu
            420                 425                 430

Glu Phe Phe Asp Gly Val Lys Phe Asp Pro Glu Lys Pro Glu Glu Tyr
        435                 440                 445

Leu Lys Ser Leu Lys Ile Lys Lys Ala Gly Val
    450                 455
```

<210> SEQ ID NO 196
<211> LENGTH: 449
<212> TYPE: PRT
<213> ORGANISM: Artificial Sequence
<220> FEATURE:
<223> OTHER INFORMATION: cmBicarbBP6

<400> SEQUENCE: 196

Met Gln His Leu Ser Arg Arg His Phe Leu Leu Ala Ala Gly Ala Ala
1 5 10 15

Gly Gly Ala Thr Leu Leu Lys Gly Cys Ala Ile Asn Pro Pro Ser Pro
20 25 30

Asp Ala Leu Ser Pro Lys Ala Gln Ala Leu Thr Leu Ser Ser Ala Thr
35 40 45

Thr Pro Glu Thr Thr Ala Val Lys Leu Gly Tyr Ile Ala Ile Ala Glu
50 55 60

Ser Ala Pro Leu Ile Ile Ala Arg Glu Lys Gly Phe Phe Ala Arg His
65 70 75 80

Gly Met Thr Asp Val Asp Val Ser Lys Gln Ala Ser Trp Gly Ser Ala
85 90 95

Arg Asp Asn Ile Glu Ile Gly Ser Ser Asn Gly Gly Ile Asp Gly Gly
100 105 110

Gln Trp Gln Met Pro Met Pro Gln Leu Ile Ser Glu Gly Ile Ile Thr
115 120 125

Lys Gly Asn Arg Lys Ile Pro Met Leu Ser Leu Ala Gln Leu Ser Thr
130 135 140

Gln Gly Asn Gly Ile Ala Ile Ser Thr Gln His Ala Gly Lys Gly Phe
145 150 155 160

Gly Leu Asp Val Ser Gly Ala Ala Glu Tyr Val Arg Asp Met Lys Ala
165 170 175

Asp Gly Lys Pro Phe Lys Ala Ala Tyr Thr Phe Pro Arg Val Asn Gln
180 185 190

Asp Phe Trp Ile Arg Tyr Trp Leu Ala Ala Gly Gly Ile Asp Pro Asn
195 200 205

Lys Asp Ile Asp Leu Ile Ala Val Pro Ala Ala Gln Thr Val Ala Ser
210 215 220

Met Arg Thr Gly Ser Met Asp Gly Phe Ser Thr Gly Asp Pro Trp Pro
225 230 235 240

Ser Arg Ile Leu Arg Asp Arg Arg Lys Tyr Gly Phe Leu Ala Val Leu
245 250 255

Thr Ala Gln Ile Trp Pro Ala His Pro Glu Glu Tyr Phe Ala Met Arg
260 265 270

Glu Asp Trp Val Arg Lys His Pro Lys Ala Ala Lys Ala Ile Leu Lys
275 280 285

Gly Ile Met Glu Ala Gln Met Trp Ala Asp Asp Pro Lys Asn Arg Ala
290 295 300

Glu Met Ala Ala Ile Leu Ala Gln Arg Lys Tyr Phe Asn Val Pro Ser
305 310 315 320

Asp Leu Leu Ile Gly Pro Tyr Val Gly Glu Tyr Ile Leu Gly Ala Asp
325 330 335

Arg Lys Thr Val Lys Asp Glu Lys Leu Ala Ile Arg Tyr Trp Lys Asp
340 345 350

Ala Arg Gly Asn Val Ser Tyr Pro Tyr Lys Ser His Asp Leu Trp Phe
355 360 365

Leu Thr Glu Ser Val Arg Trp Gly Phe Leu Pro Gln Gly Ala Leu Gly
370 375 380

Glu Ala Asp Arg Ile Ile Asn Ala Val Ser Gly Glu Lys Tyr Trp Arg
385 390 395 400

Glu Ala Ala Gln Glu Leu Gly Ile Ala Ser Ala Asp Ile Pro Pro Ser
405 410 415

```
Thr Ser Arg Gly Ile Glu Lys Phe Phe Asp Gly Ala Glu Phe Asn Pro
            420                 425                 430

Glu Lys Pro Lys Ala Tyr Leu Asp Ser Leu Lys Ile Lys Asn Leu Lys
        435                 440                 445

Ala


<210> SEQ ID NO 197
<211> LENGTH: 342
<212> TYPE: PRT
<213> ORGANISM: Artificial Sequence
<220> FEATURE:
<223> OTHER INFORMATION: mhFeBP1

<400> SEQUENCE: 197

Met Lys Lys Thr Leu Ser Ala Leu Ala Ile Ala Ala Ala Thr Phe Thr
1               5                   10                  15

Ser Thr Ser Thr Leu Ala Ala Asn Glu Val Asn Val Tyr Ser Tyr Arg
            20                  25                  30

Gln Pro Tyr Leu Ile Glu Pro Met Leu Lys Asn Phe Glu Lys Asp Thr
        35                  40                  45

Gly Ile Lys Val Asn Ile Ile Phe Ala Asp Lys Gly Leu Val Asp Arg
    50                  55                  60

Val Lys Gln Glu Gly Glu Leu Ser Pro Ala Asp Val Leu Leu Thr Val
65                  70                  75                  80

Asp Ile Ser Arg Val Met Glu Ile Val Asn Ala Asp Leu Ala Gln Lys
                85                  90                  95

Ile Asp Ser Lys Val Leu Glu Lys Asn Ile Pro Ala Gln Phe Arg Asp
            100                 105                 110

Ser Asn Asp Gln Trp Phe Gly Leu Thr Thr Arg Ala Arg Val Ile Tyr
        115                 120                 125

Thr Ser Lys Asp Arg Val Gly Lys Leu Pro Ala Gly Phe Asp Tyr Leu
    130                 135                 140

Asp Leu Ala Lys Pro Glu Tyr Lys Gly Lys Val Ala Val Arg Ser Gly
145                 150                 155                 160

Lys Asn Ser Tyr Asn Val Ser Leu Phe Ala Ala Met Ile Glu His Tyr
                165                 170                 175

Gly Ile Glu Lys Thr Lys Ala Phe Leu Glu Gly Leu Lys Ala Asn Leu
            180                 185                 190

Ala Arg Lys Pro Gln Gly Gly Asp Arg Asp Gln Val Lys Ala Ile Lys
        195                 200                 205

Glu Gly Ile Ala Asp Tyr Ser Ile Gly Asn Ser Tyr Tyr Tyr Gly Lys
    210                 215                 220

Met Leu Asp Asp Glu Lys Gln Lys Ser Trp Ala Glu Ala Ala Ile Ile
225                 230                 235                 240

Asn Phe Pro Ser Gly Glu His Gly Thr His Lys Asn Ile Ser Gly Val
                245                 250                 255

Val Ile Ala Lys His Ser Pro Asn Lys Ala Asn Ala Val Lys Leu Ile
            260                 265                 270

Glu Tyr Leu Ser Gly Glu Lys Ala Gln Gly Leu Tyr Ala Glu Leu Asn
        275                 280                 285

His Glu Tyr Pro Val Lys Glu Gly Ile Glu Pro Ser Ala Ile Val Lys
    290                 295                 300

Gly Trp Gly Thr Phe Lys Ser Asp Thr Ile Lys Leu Glu Asp Ile Ala
305                 310                 315                 320

Lys Asn Tyr Glu Ala Ala Leu Lys Leu Val Asp Glu Val Lys Phe Asp
```

```
                325                 330                 335

Asp Phe Ser Glu Lys Lys
            340


<210> SEQ ID NO 198
<211> LENGTH: 353
<212> TYPE: PRT
<213> ORGANISM: Artificial Sequence
<220> FEATURE:
<223> OTHER INFORMATION: exiFeBP2

<400> SEQUENCE: 198

Met Asn Lys Lys Tyr Ala Ala Leu Gly Ile Ser Ala Ala Leu Thr Thr
1               5                   10                  15

Ser Leu Leu Ala Ala Cys Ala Ser Thr Asp Glu Thr Thr Ser Asn Glu
            20                  25                  30

Gly Ser Asp Asp Ser Asn Val Val Asn Val Tyr Ser Ser Arg His Tyr
        35                  40                  45

Asp Val Asp Gln Gln Leu Tyr Lys Gln Phe Glu Glu Glu Thr Gly Ile
    50                  55                  60

Lys Val Asn Val Val Glu Gly Lys Ser Asp Glu Leu Leu Glu Arg Leu
65                  70                  75                  80

Asn Thr Glu Gly Glu Asn Thr Glu Ala Asp Leu Phe Ile Thr Ala Asp
                85                  90                  95

Ala Gly Asn Leu Tyr Gln Ala Lys Glu Ala Gly His Leu Gln Ala Val
            100                 105                 110

Asp Ser Asp Glu Leu Glu Ser Asn Ile Pro Glu Lys Tyr Arg Asp Thr
        115                 120                 125

Asp Asn Glu Trp Phe Gly Leu Thr Lys Arg Ala Arg Val Ile Val Tyr
    130                 135                 140

Ser Lys Asp Arg Val Lys Pro Glu Asp Leu Ser Thr Tyr Glu Ala Leu
145                 150                 155                 160

Thr Glu Glu Gln Trp Asn Gly Lys Val Leu Val Arg Pro Ser Glu Asn
                165                 170                 175

Met Tyr Asn Ile Ser Leu Leu Ala Ser Phe Ile Glu Val Asn Gly Val
            180                 185                 190

Asp Glu Ala Lys Glu Trp Ala Lys Gly Leu Val Asn Asn Met Ala Arg
        195                 200                 205

Asp Pro Gln Gly Asn Asp Arg Asp Gln Ala Lys Ala Val Val Ala Gly
    210                 215                 220

Glu Gly Asp Val Ala Ile Met Asn Thr Tyr Tyr Met Gly Leu Met Leu
225                 230                 235                 240

Asn Ser Glu Asp Glu Glu Glu Lys Lys Val Ala Glu Gln Leu Gly Val
                245                 250                 255

Phe Phe Pro Asn Gln Asp Thr Thr Gly Thr His Val Asn Ile Ser Gly
            260                 265                 270

Ile Ala Met Thr Lys Ala Ser Lys Asn Thr Glu Asn Ala Gln Lys Leu
        275                 280                 285

Met Glu Phe Met Ser Glu Pro Ser Ala Gln Glu Lys Phe Ala Ser Val
    290                 295                 300

Asn Tyr Glu Tyr Pro Val Asn Glu Ser Val Glu Pro Asn Glu Leu Leu
305                 310                 315                 320

Gln Ser Trp Gly Glu Phe Lys Glu Gln Asp Ile Asn Leu Ser Ala Leu
                325                 330                 335

Gly Glu Asn Gln Gln Glu Ala Ile Arg Ile Phe Asn Glu Val Gly Trp
```

```
        340                 345                 350

Lys


<210> SEQ ID NO 199
<211> LENGTH: 355
<212> TYPE: PRT
<213> ORGANISM: Artificial Sequence
<220> FEATURE:
<223> OTHER INFORMATION: teFeBP3

<400> SEQUENCE: 199

Met Glu Lys Val Gly Arg Arg Val Phe Leu Gly Met Gly Ala Ala Ala
1               5                   10                  15

Thr Ala Tyr Val Thr His His Leu Trp Asn Gln Asn Ala Glu Ser Ser
            20                  25                  30

Tyr Ala Gln Gln Ser Ser Gly Gly Val Ile Asn Val Tyr Ser Ala Arg
        35                  40                  45

His Tyr Asp Thr Asp Lys Ala Leu Tyr Asn Thr Phe Thr Gln Gln Thr
    50                  55                  60

Gly Ile Arg Val Asn Ile Ile Glu Ala Glu Ala Asp Ala Leu Ile Glu
65                  70                  75                  80

Arg Ile Arg Ser Glu Gly Ser Arg Thr Pro Ala Asp Val Leu Ile Thr
                85                  90                  95

Val Asp Ala Gly Arg Leu Trp Arg Ala Gln Glu Ala Gly Ile Leu Gln
            100                 105                 110

Pro Ile Gln Ser Arg Val Leu Asn Ser Val Val Pro Ala Asn Leu Arg
        115                 120                 125

Glu Pro Gln Gly His Trp Phe Gly Leu Ser Arg Arg Val Arg Val Leu
    130                 135                 140

Ile Tyr Asn Lys Ser Arg Val Asn Pro Ser Gln Leu Ser Thr Tyr Glu
145                 150                 155                 160

Asp Leu Ala Asn Pro Lys Trp Arg Arg Gln Ile Leu Thr Arg Ser Ser
                165                 170                 175

Ser Asn Ile Tyr Asn Gln Ser Leu Thr Gly Ser Leu Leu Ala Ile His
            180                 185                 190

Gly Ala Gln Lys Thr Glu Gln Trp Ala Arg Gly Leu Val Gln Asn Phe
        195                 200                 205

Ala Arg Pro Pro Glu Gly Asn Asp Thr Ala Gln Ile Arg Ala Ser Ala
    210                 215                 220

Glu Gly Val Gly Ser Val Ala Ile Ala Asn His Tyr Tyr Leu Ala Arg
225                 230                 235                 240

Leu Ile Ala Ser Asp Lys Glu Gln Asp Arg Ala Val Ala Ala Lys Val
                245                 250                 255

Gly Leu Phe Phe Pro Asn Gln Arg Asp Arg Gly Ala His Val Asn Ile
            260                 265                 270

Ser Gly Ala Gly Val Val Ala Gly Ala Pro Asn Arg Gln Gly Ala Ile
        275                 280                 285

Arg Phe Leu Glu Tyr Leu Val Ser Pro Lys Ala Gln Glu Met Phe Ala
    290                 295                 300

Met Ala Asn Phe Glu Tyr Pro Val Arg Ala Gly Val Pro Val His Pro
305                 310                 315                 320

Ile Val Lys Gln Phe Gly Asn Phe Arg Gly Gln Asn Val Asn Ala Ala
                325                 330                 335

Val Phe Gly Arg Asn Asn Ala Glu Ala Leu Arg Ile Met Asp Arg Ala
            340                 345                 350
```

```
Gly Trp Arg
        355


<210> SEQ ID NO 200
<211> LENGTH: 343
<212> TYPE: PRT
<213> ORGANISM: Artificial Sequence
<220> FEATURE:
<223> OTHER INFORMATION: cnFeBP4

<400> SEQUENCE: 200

Met Ala Ser Ser Cys Arg Thr Phe Leu Ala Leu Thr Leu Leu Leu Gly
1               5                   10                  15

Ala Leu Thr Leu Pro Gln Trp Ala Ala Gly Thr Ala Glu Ala Ala Glu
            20                  25                  30

Lys Leu Val Val Tyr Ser Gly Arg Ala Glu Arg Leu Ile Lys Pro Val
        35                  40                  45

Leu Asp Glu Phe Gln Ala Lys Ser Gly Ile Gln Ile Glu Leu Leu Ser
    50                  55                  60

Ser Gly Thr Thr Glu Leu Val Asn Arg Leu Gln Ala Glu Gly Asp His
65                  70                  75                  80

Thr Pro Ala Asp Val Phe Leu Thr Asn Asp Ala Gly Ser Leu Glu His
                85                  90                  95

Ala Arg Glu Leu Lys Leu Leu Arg Pro Met Asn Met Arg Glu Val Glu
            100                 105                 110

Arg Ala Ile Pro Ser Gln Phe Arg Ala Ala Asp Asn Ser Trp Ile Gly
        115                 120                 125

Leu Ser Gly Arg Phe Trp Ile Val Val Tyr Asn Thr Asn Leu Val Lys
    130                 135                 140

Pro Asp Gln Ile Lys Ser Leu Phe Asp Leu Thr Gln Pro Gln Trp Lys
145                 150                 155                 160

Asp Lys Ile Ala Val Pro Asn Ser Gly Ser Glu Tyr Leu Gln Ala Gly
                165                 170                 175

Val Ser Val Ile Lys Ala Thr Phe Gly Asp Glu Arg Thr Lys Gln Phe
            180                 185                 190

Leu Gln Gly Leu Lys Ala Asn Ala Gly Thr Gln Val Tyr Gln Lys Ser
        195                 200                 205

Ser Gln Ile Val Glu Ala Val Ala Lys Gly Gln Val Ala Ala Gly Ile
    210                 215                 220

Val Asn His Tyr Tyr Ile Tyr Arg His Leu Ala Thr Gln Pro Thr Ala
225                 230                 235                 240

Pro Ile Ala Ala Val Met Thr Asp Gln Gln Glu Gly Gly Met Gly Ala
                245                 250                 255

Ile Met Asn Val Thr Gly Ile Gly Val Thr Arg Ala Ser Lys His Val
            260                 265                 270

Glu Ser Ala Lys Leu Leu Ile Glu Phe Leu Val Ala Gln Ala Gly Gln
        275                 280                 285

Lys Met Phe Ala Asp Leu Asp Lys Glu Tyr Pro Leu His Pro Asp Val
    290                 295                 300

Lys Ala Asp Pro Thr Leu Ile Asp Arg Arg Thr Phe Arg Ala Ala Gln
305                 310                 315                 320

Val Pro Leu Ala Arg Leu Ala Glu Leu Arg Glu Ala Thr Leu Thr Leu
                325                 330                 335

Ile Glu Gln Val Gly Leu Arg
            340
```

<210> SEQ ID NO 201
<211> LENGTH: 330
<212> TYPE: PRT
<213> ORGANISM: Artificial Sequence
<220> FEATURE:
<223> OTHER INFORMATION: ttFeBP5

<400> SEQUENCE: 201

```
Met Met Lys Arg Tyr Leu Leu Thr Leu Ala Ala Phe Ala Ala Leu Gly
1               5                   10                  15

Ala Leu Ala Gln Ser Pro Thr Leu Thr Ile Tyr Ser Gly Arg Gly Gln
            20                  25                  30

Ser Leu Val Glu Pro Leu Val Lys Gln Phe Glu Ala Glu Thr Gly Ile
        35                  40                  45

Arg Val Gln Val Arg Tyr Ser Thr Asp Ala Gln Ile Leu Ala Ala Leu
    50                  55                  60

Gln Glu Glu Gly Ser Arg Ser Pro Ala Asp Leu Phe Trp Ala Asn Thr
65                  70                  75                  80

Ala Gly Ala Leu Gly Gln Ala Ser Ala Lys Gly Leu Leu Arg Pro Leu
                85                  90                  95

Gly Glu Thr Leu Leu Glu Lys Pro Ile Ala Phe Val Pro Ala Ser Arg
            100                 105                 110

Thr Trp Val Pro Val Thr Val Arg Leu Arg Val Leu Ala Tyr Asn Pro
        115                 120                 125

Asp Arg Ile Lys Ala Glu Glu Leu Pro Glu Ser Leu Leu Asp Leu Pro
    130                 135                 140

Arg Phe Ala Arg Glu Lys Gly Leu Val Gly Arg Val Gly Trp Thr Pro
145                 150                 155                 160

Thr Tyr Ser Ser Phe Gln Asp Met Val Ala Gly Met Ile Ala Leu Tyr
                165                 170                 175

Gly Glu Glu Lys Thr Arg Glu Trp Leu Leu Ala Met Lys Ala Leu Ala
            180                 185                 190

Pro Lys Ala Tyr Pro Ser Asn Pro Ala Met Leu Asp Ala Ile Arg Ala
        195                 200                 205

Gly Glu Val Asp Leu Gly Ser Thr Asn His Tyr Tyr Val Val Arg Phe
    210                 215                 220

Arg Arg Ala Gly Tyr Arg Leu Gly Met His His Phe Arg Asp Gly Asp
225                 230                 235                 240

Ala Gly Asn Leu Ala Leu Val Thr Gly Ala Gly Leu Leu Lys Thr Ser
                245                 250                 255

Lys Asn Leu Ala Ala Ala Thr Arg Phe Leu Thr Tyr Leu Leu Ser Pro
            260                 265                 270

Gln Ala Gln Gln Tyr Phe Val Gly Asn Ile Gly Glu Tyr Pro Leu Val
        275                 280                 285

Lys Gly Val Ala Leu Asp Pro Asn Leu Leu Pro Leu Glu Glu Ala Leu
    290                 295                 300

Ala Lys Ser Pro Lys Leu Asp Leu Glu Lys Leu Pro Leu Asp Arg Ala
305                 310                 315                 320

Leu Arg Leu Leu Arg Glu Thr Gly Val Leu
                325                 330
```

<210> SEQ ID NO 202
<211> LENGTH: 353
<212> TYPE: PRT
<213> ORGANISM: Artificial Sequence
<220> FEATURE:
<223> OTHER INFORMATION: msFeBP6

<400> SEQUENCE: 202

Met Lys Lys Val Phe Ser Val Leu Leu Ala Ser Ala Leu Ala Leu Gly
1 5 10 15

Val Ala Gln Ala Gln Gln Ser Leu Thr Leu Tyr Thr Gly Arg Ser Gln
20 25 30

Ala Leu Val Asp Lys Leu Val Gln Gln Phe Gln Lys Asp Thr Gly Ile
35 40 45

Lys Val Asn Val Arg Tyr Gly Arg Asp Ala Glu Ile Leu Ala Ala Leu
50 55 60

Gln Glu Glu Gly Ser Arg Ser Pro Ala Asp Val Phe Trp Ala Asn Thr
65 70 75 80

Ser Gly Ala Leu Glu Glu Ala Val Lys Arg Asn Leu Leu Val Gln Leu
85 90 95

Pro Ala Ser Leu Thr Arg Gln Pro Gln Glu Phe Val Pro Ser His Gly
100 105 110

Arg Trp Val Pro Val Ser Val Arg Phe Arg Val Ala Ala Tyr Asn Pro
115 120 125

Thr Lys Val Lys Asp Ser Asp Phe Pro Ala Ser Val Met Asp Leu Pro
130 135 140

Lys Val Ala Lys Phe Lys Gly Arg Ile Gly Trp Thr Pro Thr Tyr Ser
145 150 155 160

Ser Phe Gln Asp Phe Ile Thr Ala Met Arg Val Val Lys Gly Glu Ala
165 170 175

Ala Thr Lys Ala Trp Leu Gln Ala Met Ile Ala Ala Gly Ala Lys Ala
180 185 190

Tyr Pro Ser Asn Pro Pro Met Leu Glu Ala Met Gln Ala Gly Glu Ile
195 200 205

Asp Val Ala Leu Thr Asn His Tyr Tyr Ile Gln Arg Ile Leu Ala Gly
210 215 220

Val Gly Glu Gly Glu Tyr Glu Gly Lys Glu Glu Ser Glu Glu Glu Glu
225 230 235 240

Lys Lys Glu Leu Ala Ala Arg Glu Ala Lys Ala Gly Val Ala Thr His
245 250 255

Tyr Phe Ala Pro Gly Asp Val Gly Gly Leu Ala Leu Val Thr Gly Ala
260 265 270

Gly Ile Leu Ala Thr Ser Lys His Gln Thr Asn Ala Thr Arg Phe Leu
275 280 285

Asn Tyr Leu Leu Ser Lys Lys Ala Gln Pro Tyr Phe Val Asp Glu Val
290 295 300

Arg Glu Tyr Pro Val Ile Ala Gly Val Arg Val Ala Lys Gly Met Leu
305 310 315 320

Pro Phe Ala Asn Ala Ile Arg Leu Ser Pro Lys Ile Asp Phe Ala Lys
325 330 335

Leu Thr Asp Leu Glu Gly Thr Leu Lys Leu Leu Arg Glu Val Gly Leu
340 345 350

Leu

<210> SEQ ID NO 203
<211> LENGTH: 360
<212> TYPE: PRT
<213> ORGANISM: Artificial Sequence
<220> FEATURE:

<223> OTHER INFORMATION: srFeBP7

<400> SEQUENCE: 203

```
Met Lys Arg Leu Leu Ser Leu Ser Leu Val Val Thr Leu Val Leu Ser
1               5                   10                  15

Leu Leu Gly Cys Gly Gly Glu Gln Gln Asp Glu Leu Val Ile Tyr Ser
            20                  25                  30

Gly Arg Ser Lys Ala Leu Val Asp Ser Leu Val Gln Gln Tyr Arg Gln
        35                  40                  45

Gln Ala Asp Val Pro Val Arg Val Arg Tyr Gly Thr Asp Ser Gln Leu
    50                  55                  60

Leu Ala Ala Leu Gln Glu Glu Gly Asp Gln Ser Pro Ala Asp Val Phe
65                  70                  75                  80

Trp Ala Asn Thr Thr Gly Ala Leu Gly Asn Ala Val Asn Asn Gly Leu
                85                  90                  95

Leu Thr Glu Leu Pro Asp Thr Leu Ala Asn Arg Ala Ala Arg Phe Thr
            100                 105                 110

Pro Ser Asn Gln Arg Trp Thr Pro Val Thr Thr Arg Phe Arg Val Leu
        115                 120                 125

Ala Tyr Asn Ser Asp Ala Val Ser Pro Glu Asp Leu Pro Asp Ser Val
    130                 135                 140

Leu Asp Leu Pro Glu His Glu Glu Phe Glu Gly Arg Val Gly Trp Thr
145                 150                 155                 160

Pro Ala Tyr Ser Ser Phe Gln Asp Phe Val Thr Ala Leu Arg Val Thr
                165                 170                 175

Glu Gly Ala Glu Thr Ala Arg Thr Trp Leu Ser Asp Met Gln Ala Leu
            180                 185                 190

Asn Pro Asn Ser Tyr Thr Ser Asn Thr Pro Met Val Gln Ala Leu Glu
        195                 200                 205

Ala Gly Glu Ile Asp Val Ala Leu Thr Asn His Tyr Tyr Val Leu Arg
    210                 215                 220

Leu Lys His Gly Gly Ala Glu Gly Glu Tyr Glu Gly Glu Glu Glu Glu
225                 230                 235                 240

Gly Glu Glu His Glu Glu Glu His Glu Glu Glu Ala Thr Pro Arg Ala
                245                 250                 255

Ser Ala Pro Val Glu Met Tyr His Phe Ala Asp Gly Asp Leu Gly Asn
            260                 265                 270

Leu Ala Leu Val Thr Gly Ala Gly Ala Leu Gln Thr Ser Asn Gln Pro
        275                 280                 285

Asp Ala Ala Asn Arg Phe Leu Arg Phe Leu Leu Ser Glu Gln Ala Gln
    290                 295                 300

Ser Phe Ala Ala Thr Arg Val Asn Glu Tyr Pro Val Val Ser Gly Ala
305                 310                 315                 320

Ser Val Pro Asp Tyr Leu Met Pro Ala Asp Glu Ala Leu Lys Met Ser
                325                 330                 335

Pro Glu Phe Asp Leu Gln Lys Leu Gln Asn Met Glu Pro Thr Leu Asp
            340                 345                 350

Leu Leu Arg Asp Ala Gly Ala Leu
        355                 360
```

<210> SEQ ID NO 204
<211> LENGTH: 385
<212> TYPE: PRT
<213> ORGANISM: Artificial Sequence
<220> FEATURE:

<223> OTHER INFORMATION: hlFeBP8

<400> SEQUENCE: 204

```
Met Thr Asn Tyr Leu Pro Asp Gly Val Asp Arg Arg Gln Phe Leu Ala
1               5                   10                  15

Ala Thr Gly Ala Leu Gly Val Ala Gly Leu Ala Gly Cys Thr Gly Asp
            20                  25                  30

Asp Thr Asp Gly Gly Ser Gly Asn Ser Ser Asp Gly Gly Asp Gly Gly
        35                  40                  45

Asp Gly Gly Asp Gly Ser Ile Gly Gln Ile Gly Ser Gly Arg Glu Gly
    50                  55                  60

Arg Gly Ala Pro Gly Gly Ile Pro Met Ala Glu Met Pro Asp Leu Glu
65                  70                  75                  80

Gly Glu Leu Thr Val Tyr Ser Gly Arg Gly Glu Phe Leu Val Gly Glu
                85                  90                  95

Leu Val Glu Tyr Ile Glu Asp Gln Tyr Asp Asp Phe Asp Leu Thr Val
            100                 105                 110

Arg Tyr Ala Gly Ser Thr Asp Leu Val Asn Gln Ile Leu Asn Glu Gly
        115                 120                 125

Asp Gly Ser Pro Ala Asp Val Phe Tyr Ser Val Asn Ala Gly Ser Leu
    130                 135                 140

Gly Thr Leu Ala Gly Glu Gly Arg Ser Gln Ala Leu Ser Ser Glu Ile
145                 150                 155                 160

Thr Asp Met Val Arg Ser Glu Phe Arg Thr Glu Gln Trp Ile Gly Thr
                165                 170                 175

Ser Gly Arg Ala Arg Thr Val Pro Tyr Asn Thr Gly Glu Phe Ser Asp
            180                 185                 190

Asp Asp Leu Pro Asp Asp Ile Met Ala Tyr Pro Glu Glu Phe Ala Gly
        195                 200                 205

Ser Leu Gly Trp Ala Pro Ser Tyr Gly Ser Ala Gln Ala Phe Ile Thr
    210                 215                 220

Ala Met Arg Leu Ile Glu Gly Glu Glu Ala Thr Leu Ala Trp Leu Glu
225                 230                 235                 240

Ser Val Val Glu Ala Gly Ile Ser Ser Tyr Pro Asp Glu Phe Ala Ala
                245                 250                 255

Ala Gln Ala Ile Ala Asp Gly Glu Ile Asp Ala Ala Phe Thr Asn His
            260                 265                 270

Tyr Tyr Ile Gln Arg Val Leu Asp Gly Asn Pro Asp Ala Ser Ile Gly
        275                 280                 285

Thr Ala Phe Thr Ser Gly Asp Ala Gly Ala Val Phe Asn Val Ala Gly
    290                 295                 300

Ala Ala Val Val Asp Thr Ala Ser Asp Ala Thr Leu Ala Glu Asn Phe
305                 310                 315                 320

Ile Arg His Leu Leu Ser Ala Glu Ala Gln Asp Tyr Phe Ala Arg Ser
                325                 330                 335

Thr Phe Glu Tyr Pro Leu Ile Pro Asp Val Glu Pro Ile Gly Asp Leu
            340                 345                 350

Pro Thr Ile Asp Glu Leu Asp Val Pro Asp Ile Asp Leu Thr Glu Leu
        355                 360                 365

Ser Asp Leu Glu Pro Thr Ile Asp Leu Met Arg Glu Ala Gly Val Glu
    370                 375                 380

Val
385
```

BICARBONATE BIOSENSORS, CALCIUM BIOSENSORS, AND USES THEREOF

RELATED APPLICATIONS

This application is a national stage application, filed under 35 U.S.C. § 371, of International Application No. PCT/US2016/062963 filed Nov. 19, 2016, which claims benefit of priority to U.S. Provisional Application No. 62/257,792, filed Nov. 20, 2015, U.S. Provisional Application No. 62/257,817, filed Nov. 20, 2015, and U.S. Provisional Application No. 62/257,796, filed Nov. 20, 2015, the entire contents of each of which are incorporated herein by reference.

INCORPORATION-BY-REFERENCE OF SEQUENCE LISTING

The contents of the text file named "123658-11601_Sequence_Listing_ST25.txt", which was created on Jun. 20, 2023 and is 543 KB in size, is hereby incorporated by reference in its entirety.

FIELD OF THE INVENTION

The present invention relates to compositions and methods for detecting and determining the concentrations of bicarbonate and calcium.

BACKGROUND

Bicarbonate levels are currently measured using either sample acidification in combination with a $CO_2$-selective electrode, or alkalinization followed by a colorimetric coupled enzyme assay (Burtis 2012). Reagents and the modification of test samples is required in such methods.

Many fluorescent indicators have been developed to measure calcium levels within cells (Valeur 2012). However, these indicators are tuned for the micromolar range and therefore are not appropriate for measuring extracellular levels.

Improved sensors for bicarbonate and calcium are needed.

SUMMARY OF THE INVENTION

Aspects of the present subject matter provide improved biosensors that rapidly, reliably, and accurately detect and quantify ligands such as bicarbonate and calcium (i.e., $Ca^{2+}$) with significant advantages over previous systems.

The present disclosure also provides a biosensor for bicarbonate, comprising a reporter group that is attached to a bicarbonate-binding protein. The bicarbonate-binding protein includes a domain or region(s) that binds the bicarbonate. The domain or region involved in ligand binding is comprised of a plurality of residues, e.g., non-contiguous amino acids of the ligand-binding protein, which are contact points or sites of contact between the ligand and its cognate ligand-binding protein. The binding of bicarbonate to the bicarbonate-binding domain of the bicarbonate-binding protein causes a change in signaling by the reporter group. In various implementations, the biosensor may produce a signal when a bicarbonate is bound to the bicarbonate-binding domain that is not produced (and/or that is different from a signal that is produced) when the bicarbonate is absent from the bicarbonate-binding domain.

Also included are biosensors for calcium (i.e. $Ca^{2+}$) comprising a calcium-binding protein and an attached reporter group. Upon $Ca^{2+}$ binding to a calcium-binding domain of the calcium-binding protein, signaling of the reporter group changes. In various embodiments, the calcium-binding protein comprises a variant or mutant of a naturally occurring bicarbonate-binding protein. In certain embodiments, the calcium-binding protein comprises 1, 2, 3, 4, 5, 6, 7, 8, 9, or 10 substitutions compared to a naturally occurring bicarbonate-binding protein. In some embodiments, the calcium-binding protein is at least about 75%, 80%, 85%, 90%, 95%, 96%, 97%, 98%, or 99% identical to a bicarbonate-binding protein. In various embodiments, the calcium-binding protein has a Kd for bicarbonate that is at least about 5 mM, 10 mM, 25 mM, 50 mM, 75 mM, 100 mM, 500 mM, or 1000 mM higher than a corresponding naturally occurring bicarbonate-binding protein and/or $Ca^{2+}$.

These biosensors have widespread utility including in clinical, industrial, food and beverage production and storage, and environmental settings.

A reporter group that transduces a detectable signal may be attached to the ligand-binding proteins (biosensors) described herein. The reporter group is attached to the ligand-binding protein so that a signal transduced by the reporter group when the ligand-binding protein is bound to ligand differs from a signal transduced by the reporter group when the ligand-binding protein is not bound to ligand. The proteins may be engineered to include a single cysteine to which the detectable label, e.g., a fluorophore is covalently attached. The biosensors are reagentless in that their monitoring mechanism requires neither additional substrates for a signal to develop, nor measurement of substrate consumption or product generation rates to determine ligand concentrations.

In some embodiments, the biosensor proteins include a second fluorophore, thereby permitting ratiometric sensing/detection of an analyte using establishing non-geometrically modulated Forster resonance energy transfer (ngmFRET).

Among the advantages of these fluorophore-containing protein constructs is their high durability. The constructs retain their ability to bind ligand, change shape and thus detect the analyte (such as bicarbonate or $Ca^{2+}$) (a) even when immobilized (directly or indirectly) onto a solid surface such as a bead, plate, or sheet; (b) even after desiccation (and subsequent reconstitution in a physiological buffer solution); (c) even when subjected to ambient conditions, e.g., conditions that can be encountered in storage and/or transportation; and (d) even when aged/stored for extended periods of time, e.g., weeks, months, or even years. Thus, the biosensors do not require refrigeration or a cold chain for distribution, permitting a wider range of applicability such as in-the-field use and reducing the cost of the sensor product.

For clinical applications, microliter volumes (e.g., less than 0.1, 0.5, 1, 2, 3, 4, 5, 6, 7, 8, 9, or 10, or less than 10 μl) of a bodily fluid such as blood may be used. Moreover compared to conventional enzyme-based or antibody based assay systems, the results are achieved virtually instantaneously, e.g., 0.1-5 minutes, e.g., 0.1-1 minutes, or within 30-60 seconds. A further advantage is that the sensors consistently and reliably bind to and detect the analyte (bicarbonate or a $Ca^{2+}$) in complex fluids such as whole blood, plasma, serum, saliva, urine, and environmental fluids. Thus in a clinical setting, whole blood need not be processed, thereby reducing time and cost of the diagnostic procedure. Alternatively or in addition, the biosensors provided herein may be used to monitor ligand levels continuously. In a non-limiting example, one or more biosensors is immobilized at the tip of a thin optical fiber to construct a ligand-responsive optode. Such an optode can be introduced into the body (e.g., subcutaneously). The sensor may be in continuous contact with the sample, and excitation and emission light are passed to and from the immobilized sensor, respectively. Fluctuations in the ligand sample alter the dynamic equilibrium between the open and closed states of the ligand-binding protein, which is transduced into fluctuations of the fluorescent emission signal, by virtue of the sensing mechanism of the conjugated fluorophore. The emitted light intensities may be read by a reader connected to the optode.

In non-clinical situations, e.g., food and beverage composition (e.g., meat, canned food, dairy, nondairy, a fermented food, a fruit, a vegetable, a tuber, a starch, a grain, pasta, yogurt, soup, ice cream, a broth, a puree, a shake, a smoothie, a batter, a condiment, a sauce, a soft drink, a fountain beverage, water, coffee, tea, milk, a dairy-based beverages, soy-based beverage, an almond-based beverage, vegetable juice, fruit juice, a fruit juice-flavored drink, an energy drink, or an alcoholic beverage) production and/or storage, industrial, environmental (e.g., wetlands, rivers, streams, ponds, marine environments, wells, aquariums, pools, lakes, rivers, brooks, reservoirs, ground water, residential land, commercial/industrial land, agricultural land, or land abutting agricultural land), or commercial settings such as analysis of waste water, food or beverage production, or bioreactor/fermentation monitoring, the samples to be analyzed can be used directly upon sampling without further purification or processing, similarly reducing time and expense of the test. Moreover, the immobilized sensors need not be washed to remove unbound material following contacting the test sample with the sensors, because the unbound material ("contaminants") do not materially affect the production of a precise, reliable detectable assay signal.

Included herein are bicarbonate and $Ca^{2+}$ biosensors that produce a dichromatic, ratiometric signal, i.e., the signal is defined as the quotient of the intensities at two independent wavelengths. The advantage of such a signal is that it provides an internally consistent reference. The self-calibrating nature of a ratiometric measurement removes the necessity for carrying out on-board calibration tests prior to each measurement.

Thus, reagentless, fluorescently responsive biosensors present a number of advantages over enzyme-based biosensors, including elimination of chemical transformations, elimination of substrate requirements, and self-calibration, which together lead to rapid response times, continuous monitoring capabilities, simple sample-handling, and lower cost due to simplified manufacturing and distribution processes.

Ligand-Binding Proteins

Aspects of the present subject matter provide biosensors comprising a ligand-binding protein that binds bicarbonate (i.e., a bicarbonate-binding protein). Variants of bicarbonate-binding proteins that have been selected, designed, or engineered to specifically bind $Ca^{2+}$ (i.e., calcium-binding proteins) are also included. The biosensors provided herein may have an affinity for ligand that falls within a range that is relevant for commercial, industrial, research, food and beverage, cell culture, environmental, and/or physiological (e.g., clinical or veterinarial) applications.

Typically, a natural bicarbonate-binding protein has a bicarbonate dissociation constant ($K_d$) of about 10 μM or less at room temperature. However, bicarbonate-binding proteins may be selected, designed, or engineered (e.g., via mutation) to have a different affinity for bicarbonate (e.g., to detect higher or lower levels of bicarbonate). In embodiments, a bicarbonate-binding protein has a $K_d$ for bicarbonate in the micromolar, nanomolar, picomolar, or femtomolar range. In various embodiments, the bicarbonate-binding protein binds bicarbonate as a metal complex, e.g., as calcium ($Ca^{II}$)-bicarbonate, or as iron ($Fe^{III}$)-bicarbonate. In some embodiments, the bicarbonate-binding protein has a $K_d$ for calcium ($Ca^{II}$)-bicarbonate or iron ($Fe^{III}$)-bicarbonate in the micromolar, nanomolar, picomolar, or femtomolar range. For example, a bicarbonate-binding protein may have a $K_d$ for bicarbonate of at least about 0.00001 mM, 0.0001 mM, 0.001 mM, 0.1 mM, 0.2 mM, 0.3 mM, 0.4 mM, 0.5 mM, 0.6 mM, 0.7 mM, 0.8 mM, 0.9 mM, 1 mM, 1.1 mM, 1.2 mM, 1.3 mM, 1.4 mM, 1.5 mM, 1.6 mM, 1.7 mM, 1.8 mM, 1.9 mM, 2 mM, 2.5 mM, 3 mM, 3.5 mM, 4 mM, 4.5 mM, 5 mM, 5.5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 34 mM, 35 mM, 36 mM, 37 mM, 38 mM, 39 mM, 40 mM, 41 mM, 42 mM, 43 mM, 44 mM, 45 mM, 46 mM, 47 mM, 48 mM, 49 mM, 50 mM, 75 mM, 100 mM, 200 mM, 300 mM, 400 mM, 500 mM, 600 mM, 700 mM, 800 mM, 900 mM, or 1000 mM, and/or less than about 0.00001 mM, 0.0001 mM, 0.001 mM, 0.1 mM, 0.2 mM, 0.3 mM, 0.4 mM, 0.5 mM, 0.6 mM, 0.7 mM, 0.8 mM, 0.9 mM, 1 mM, 1.1 mM, 1.2 mM, 1.3 mM, 1.4 mM, 1.5 mM, 1.6 mM, 1.7 mM, 1.8 mM, 1.9 mM, 2 mM, 2.5 mM, 3 mM, 3.5 mM, 4 mM, 4.5 mM, 5 mM, 5.5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 34 mM, 35 mM, 36 mM, 37 mM, 38 mM, 39 mM, 40 mM, 41 mM, 42 mM, 43 mM, 44 mM, 45 mM, 46 mM, 47 mM, 48 mM, 49 mM, 50 mM, 75 mM, 100 mM, 200 mM, 300 mM, 400 mM, 500 mM, 600 mM, 700 mM, 800 mM, 900 mM, or 1000 mM. In various embodiments, the $K_d$ for bicarbonate is as measured in a solution comprising 1 mM $Ca^{2+}$ or 10 μM $Fe^{3+}$. In some embodiments, a bicarbonate-binding protein has a $K_d$ for bicarbonate below, within, or above the normal range of bicarbonate in human blood. The normal blood bicarbonate concentration in humans is typically referred to as 22-29 mM but may vary by sex and age. Exemplary normal bicarbonate levels are as follows:

Males
12-24 months: 17-25 mM
3 years: 18-26 mM
4-5 years: 19-27 mM
6-7 years: 20-28 mM
8-17 years: 21-29 mM
> or =18 years: 22-29 mM
Females
1-3 years: 18-25 mM
4-5 years: 19-26 mM
6-7 years: 20-27 mM
8-9 years: 21-28 mM
> or =10 years: 22-29 mM Aspects provide bicarbonate biosensors comprising bicarbonate-binding proteins with a $K_d$ for bicarbonate within one of more of the ranges disclosed herein.

In various embodiments, a calcium-binding protein has a $K_d$ for $Ca^{2+}$ in the millimolar, micromolar, nanomolar, picomolar, or femtomolar range. The normal physiological concentration of $Ca^{2+}$ in human blood is between 1.2-1.3 mM. The detection of much higher amounts/ranges is useful in e.g., environmental, food and beverage, and industrial applications For example, a calcium-binding protein may have a $K_d$ for $Ca^{2+}$ of at least about 0.00001 mM, 0.0001 mM, 0.001 mM, 0.1 mM, 0.2 mM, 0.3 mM, 0.4 mM, 0.5 mM, 0.6 mM, 0.7 mM, 0.8 mM, 0.9 mM, 1 mM, 1.1 mM, 1.2 mM, 1.3 mM, 1.4 mM, 1.5 mM, 1.6 mM, 1.7 mM, 1.8 mM, 1.9 mM, 2 mM, 2.1 mM, 2.2 mM, 2.3 mM, 2.4 mM, 2.5 mM, 2.6 mM, 2.7 mM, 2.8 mM, 2.9 mM, 3 mM, 3.1 mM, 3.2 mM, 3.3 mM, 3.4 mM, 3.5 mM, 3.6 mM, 3.7 mM, 3.8 mM, 3.9 mM, 4 mM, 4.1 mM, 4.2 mM, 4.3 mM, 4.4 mM, 4.5 mM, 4.6 mM, 4.7 mM, 4.8 mM, 4.9 mM, 5 mM, 5.1 mM, 5.2 mM, 5.3 mM, 5.4 mM, 5.5 mM, 5.6 mM, 5.7 mM, 5.8 mM, 5.9 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 34 mM, 35 mM, 36 mM, 37 mM, 38 mM, 39 mM, 40 mM, 41 mM, 42 mM, 43 mM, 44 mM, 45 mM, 46 mM, 47 mM, 48 mM, 49 mM, 50 mM, 75 mM, 100 mM, 125 mM, 150 mM, 200 mM, 300 mM, 400 mM, 500 mM, 600 mM, 700 mM, 800 mM, 900 mM, or 1000 mM, and/or less than about 0.00001 mM, 0.0001 mM, 0.001 mM, 0.1 mM, 0.2 mM, 0.3 mM, 0.4 mM, 0.5 mM, 0.6 mM, 0.7 mM, 0.8 mM, 0.9 mM, 1 mM, 1.1 mM, 1.2 mM, 1.3 mM, 1.4 mM, 1.5 mM, 1.6 mM, 1.7 mM, 1.8 mM, 1.9 mM, 2 mM, 2.1 mM, 2.2 mM, 2.3 mM, 2.4 mM, 2.5 mM, 2.6 mM, 2.7 mM, 2.8 mM, 2.9 mM, 3 mM, 3.1 mM, 3.2 mM, 3.3 mM, 3.4 mM, 3.5 mM, 3.6 mM, 3.7 mM, 3.8 mM, 3.9 mM, 4 mM, 4.1 mM, 4.2 mM, 4.3 mM, 4.4 mM, 4.5 mM, 4.6 mM, 4.7 mM, 4.8 mM, 4.9 mM, 5 mM, 5.1 mM, 5.2 mM, 5.3 mM, 5.4 mM, 5.5 mM, 5.6 mM, 5.7 mM, 5.8 mM, 5.9 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 34 mM, 35 mM, 36 mM, 37 mM, 38 mM, 39 mM, 40 mM, 41 mM, 42 mM, 43 mM, 44 mM, 45 mM, 46 mM, 47 mM, 48 mM, 49 mM, 50 mM, 75 mM, 100 mM, 125 mM, 150 mM, 200 mM, 300 mM, 400 mM, 500 mM, 600 mM, 700 mM, 800 mM, 900 mM, or 1000 mM. Aspects provide cation biosensors comprising calcium-binding proteins with a $K_d$ for $Ca^{2+}$ within one of more of the ranges disclosed herein.

With respect to the present subject matter, $K_d$ is the equilibrium dissociation constant between a ligand-binding protein and its ligand. $K_d$ decreases with increasing affinity, and $K_d$ may be used as an expression of affinity (the lower the value, the higher the affinity). The $K_d$ value relates to the concentration of ligand required for detectable ligand-binding to occur and so the lower the $K_d$ value (lower concentration required), the higher the affinity of the ligand-binding protein for the ligand. The $K_d$ value corresponds to the ligand concentration at which the binding protein is 50% saturated.

| $K_d$ value | Molar concentration |
|---|---|
| $10^{-1}$ to $10^{-3}$ | Millimolar (mM) |
| $10^{-4}$ to $10^{-6}$ | Micromolar (μM) |
| $10^{-7}$ to $10^{-9}$ | Nanomolar (nM) |
| $10^{-10}$ to $10^{-12}$ | Picomolar (pM) |
| $10^{-13}$ to $10^{-15}$ | Femtomolar (fM) |

The ligand-binding proteins (as well as biosensors comprising the ligand-binding proteins) provided herein lack enzymatic activity and are not enzymes. As used herein, an "enzyme" is a protein that catalyzes a specific biochemical reaction. The ligand is not chemically altered (i.e., no chemical bond or atom of the ligand is added or removed) by the ligand-binding protein. Thus, when ligand dissociates from a ligand-binding protein described herein, the ligand contains the same chemical structure it had before it became bound to the ligand-binding protein.

The ligand-binding protein may comprise a naturally occurring protein or a protein that is modified compared to a naturally occurring protein. For example, the ligand-binding protein may comprise one or more mutations compared to a naturally occurring protein. In some embodiments, the naturally occurring protein is a naturally occurring counterpart of the ligand-binding protein (e.g., the ligand-binding protein is a mutant of the naturally occurring counterpart).

A "naturally occurring counterpart" of a mutant polypeptide is a polypeptide produced in nature from which the mutant polypeptide has been or may be derived (e.g., by one or more mutations). For example, the naturally occurring counterpart is an endogenous polypeptide produced by an organism in nature, wherein the endogenous polypeptide typically does not have one or more of the mutations present in the mutant polypeptide. For convenience and depending on context, a naturally occurring counterpart may be referred to herein for the purpose of comparison and to illustrate the location and/or presence of one or more mutations, binding activities, and/or structural features.

As used herein, a "mutation" is a difference between the amino acid sequence of a modified polypeptide/protein and a naturally occurring counterpart. A polypeptide having a mutation may be referred to as a "mutant." Non-limiting examples of mutations include insertions, deletions, and substitutions. However, the term "mutation" excludes (i) the addition of amino acids to the N-terminus or C-terminus of a polypeptide, and (ii) the omission/deletion/replacement of a polypeptide's signal peptide (e.g., replacement with another signal peptide or with a methionine).

The addition of amino acids to the N-terminus or C-terminus of a protein via a peptide bond may be referred to herein as a "fusion" of the amino acids to the protein. Similarly, an exogenous protein fused to amino acids (e.g., another protein, a fragment, a tag, or a polypeptide moiety) at its N-terminus or C-terminus may be referred to as a "fusion protein." The added amino acids may comprise a heterologous polypeptide, e.g., a polypeptide reporter group such as a fluorescent protein, a moiety that facilitates the isolation or modification of a polypeptide, or a moiety that facilitates the attachment of a polypeptide to a substrate or surface. As used herein, "heterologous" when referring to the added amino acids (e.g., a "polypeptide") of a fusion protein indicates that the polypeptide is not naturally part of the protein to which it is fused in the fusion protein. For example, the sequence of a heterologous polypeptide ("added amino acids") that is fused to a protein is encoded by an organism other than the organism from which the protein is derived, is not known to be naturally encoded by any organism, or is encoded by a gene other than the wild-type gene that encodes an endogenous version of the protein.

As used herein the term "signal peptide" refers to a short (e.g., 5-30 or 10-60 amino acids long) stretch of amino acids at the N-terminus of a protein that directs the transport of the protein. In various embodiments, the signal peptide is cleaved off during the post-translational modification of a protein by a cell. Signal peptides may also be referred to as "targeting signals," "leader sequences," "signal sequences," "transit peptides," or "localization signals." In instances where a signal peptide is not defined for a ligand-binding protein discussed herein, the signal peptide may optionally be considered to be, e.g., the first 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus of the translated protein (compared to a protein that has not had the signal peptide removed, e.g., compared to a naturally occurring protein).

In some embodiments, the ligand-binding protein comprises 1, 2, 3, 4, 5, 6, 7, 8, 9, 10, 15, 20, 25, 30, 40, 50, 60, 70, 80, 90, 100, 1-10, 1-15, 1-20, 5-15, 5-20, 10-25, 10-50, 20-50, 25-75, 25-100 or more mutations compared to a naturally occurring protein while retaining at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.5%, or about 100% of the activity of the naturally occurring protein. Mutations include but are not limited to substitutions, insertions, and deletions. Non-limiting examples of ligand-binding proteins may have 1, 2, 3, 4, 5, 6, 7, 8, 9, 10, 15, 20, 25, 30, 40, 50, 60, 70, 80, 90, 100, 1-10, 1-15, 1-20, 5-15, 5-20, 10-25, 10-50, 20-50, 25-75, 25-100, or more substitution mutations compared to a naturally occurring protein while retaining at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.5%, or about 100% of the activity of the naturally occurring protein. In embodiments, at least one amino acid of the ligand-binding protein has been substituted with a cysteine. Alternatively or in addition, a ligand-binding protein may include one or more mutations that remove a cysteine, e.g., 1, 2, 3, 4, 5, 6, 7, 8, 9, 10 or more substitutions or deletions of a cysteine compared to a naturally occurring protein.

Alternatively, the ligand-binding protein is not a mutant. For example, a reporter group is fused to the N-terminus or the C-terminus of the ligand-binding protein.

In some embodiments, the reporter group is conjugated to an amino acid that is no more than about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein. In some embodiments, the reporter group is conjugated to an amino acid that is at least about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein. In some embodiments, about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids (including or not including the signal peptide) have been deleted (e.g. are absent) from the N-terminus of the protein compared to its naturally occurring counterpart. In some embodiments, less than 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids (including or not including the signal peptide) have been deleted (e.g. are absent) from the N-terminus of the protein compared to its naturally occurring counterpart. In some embodiments, about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids have been deleted (e.g. are absent) from the C-terminus of the protein compared to its naturally occurring counterpart. In some embodiments, less than 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids have been deleted (e.g. are absent) from the C-terminus of the protein compared to its naturally occurring counterpart.

In various embodiments, a ligand-binding protein may comprise a stretch of amino acids (e.g., the entire length of the ligand-binding protein or a portion comprising at least about 50, 100, 200, 250, 300, 350, 400, or 450 amino acids) in a sequence that is at least about 90%, 91%, 92%, 93%, 94%, 95%, 96%, 97%, 98%, 99%, 99.1%, 99.2%, 99.3%, 99.4%, or 99.5% identical to an amino acid sequence of a naturally occurring protein.

In some embodiments, the mutations are conservative, and the present subject matter includes many ligand-binding proteins in which the only mutations are substitution mutations. In non-limiting examples, a ligand-binding protein has no deletions or insertions compared to a naturally occurring protein (e.g., a naturally occurring counterpart). In non-limiting examples, the ligand-binding protein does not comprise a deletion or insertion compared to its naturally occurring counterpart. Alternatively, a ligand-binding protein may have (i) less than about 5, 4, 3, 2, or 1 inserted amino acids, and/or (ii) less than about 5, 4, 3, 2, or 1 deleted amino acids compared to a naturally occurring protein.

In various embodiments, a naturally occurring protein to which a ligand-binding protein is compared or has been derived (e.g., by mutation, fusion, or other modification) from a prokaryotic ligand-binding protein such as a bacterial ligand-binding protein. For example, the prokaryotic ligand-binding protein is a mutant, fragment, or variant of a natural (i.e., wild-type) bacterial protein. In various embodiments, the bacterial ligand-binding protein is from a thermophilic, mesophilic, or cryophilic prokaryotic microorganism (e.g., a thermophilic, mesophilic, or cryophilic bacterium).

A microorganism is "thermophilic" if it is capable of surviving, growing, and reproducing at temperatures between 41 and 140° C. (106 and 284° F.), inclusive. In various embodiments, a thermophilic organism has an optimal growth temperature between 41 and 140° C., or that is at least about 45, 50, 55, 60, 65, 70, 75, 80, 85, 90, 95, 100, 105, 110, 115, 120, 125, 130, 135, or 140° C. Many thermophiles are archaea. Thermophilic eubacteria are suggested to have been among the earliest bacteria. Thermophiles are found in various geothermally heated regions of the Earth, such as hot springs and deep sea hydrothermal vents, as well as decaying plant matter, such as peat bogs and compost. Unlike other types of microorganisms, thermophiles can survive at much hotter temperatures, whereas other bacteria would be damaged and sometimes killed if exposed to the same temperatures. Thermophiles may be classified into three groups: (1) obligate thermophiles; (2) facultative thermophiles; and (3) hyperthermophiles. Obligate thermophiles (also called extreme thermophiles) require such high temperatures for growth, whereas facultative thermophiles (also called moderate thermophiles) can thrive at high temperatures, but also at lower temperatures (e.g. below 50° C.). Hyperthermophiles are particularly extreme thermophiles for which the optimal temperatures are above 80° C. Some microorganisms can live at temperatures higher than 100° C. at large depths in the ocean where water does not boil because of high pressure. Many hyperthermophiles are also able to withstand other environmental extremes such as high acidity or radiation levels. A compound (e.g., a protein or biosensor) is "thermotolerant" if it is capable of surviving exposure to temperatures above 41° C. For example, in some embodiments a thermotolerant biosensor retains its function and does not become denatured when exposed to a temperature of about 45, 50, 55, 60, 65, 70, 75, 80, 85, 90, 95, 100, 105, 110, 115, 120, 125, 130, 135, or 140° C. for at least about 1, 2, 3, 4, 5, 6, 7, 8, 9, 10, 15, 20, 25, 30 or more minutes. In some embodiments, the thermotolerant compound survives exposure to 45, 50, 55, 60, 65, 70, 75, 80, 85, 90, 95, 100, 105, 110, 115, 120, 125, 130, 135, or 140° C. under pressure.

A microorganism is "mesophilic" if it is capable of surviving, growing, and reproducing at temperatures between 20 and 40° C. (68 and 104° F.), inclusive. "Psychrophiles" or "cryophiles" are microorganisms that are capable of growth and reproduction in cold temperatures. In various embodiments, a psychrophile is capable of growth and reproduction at a temperature of 10° C. or less, e.g., between −20° C. and +10° C.

In some embodiments, the microbial protein is produced by a bacterial microorganism, an archaean microorganism, an algal microorganism, a protozoan microorganism, or a fungal microorganism. In non-limiting examples, the microbial protein is produced by a Gram-positive bacterium or a Gram-negative bacterium. In various embodiments, a biosensor comprises a modified (e.g., mutated, fused, and/or conjugated) periplasmic binding protein or a cytoplasmic binding protein.

Aspects of the present subject matter provide a ligand-binding protein with a mutation that alters the interaction of the ligand-binding protein with a ligand (i.e. bicarbonate or $Ca^{2+}$). For example, the ligand-binding protein comprises a mutation that alters the interaction of the ligand-binding protein with the ligand compared to a naturally occurring counterpart. In some embodiments, the ligand-binding protein comprises a mutation that alters the interaction of an amino acid of the ligand-binding protein with a water molecule compared to a naturally occurring counterpart.

In some embodiments, the ligand-binding protein does not comprise a signal peptide. For example, the signal peptide (e.g., that is present in a naturally occurring counterpart) may be replaced with a methionine.

Exemplary implementations relate to a ligand such as bicarbonate or $Ca^{2+}$, wherein the ligand-binding protein comprises a bicarbonate-binding protein or a calcium-binding protein. For example, the ligand-binding protein may comprise a mutant of, a fragment of, or a fusion protein comprising a microbial bicarbonate-binding protein. In embodiments, the ligand-binding protein is not a mutant or fragment to which a heterologous polypeptide has been attached or added. In some embodiments, the ligand-binding protein has an affinity ($K_d$) for a ligand within the concentration range of the ligand in a subject. In certain embodiments, the ligand-binding protein has an affinity ($K_d$) for ligand in the range of about 0.01 mM to about 50 mM, about 0.01 mM to about 25 mM, about 0.01 mM to about 0.1 mM, about 0.01 mM to about 0.5 mM, about 0.1 mM to about 2 mM, about 0.2 mM to about 2 mM, about 0.3 mM to about 2 mM, about 0.4 mM to about 2 mM, about 0.5 mM to about 2 mM, about 0.6 mM to about 2 mM, about 0.7 mM to about 2 mM, about 0.8 mM to about 2 mM, about 0.9 mM to about 2 mM, about 1 mM to about 2 mM, about 1.25 mM to about 2 mM, about 1.5 mM to about 2 mM, about 0.01 mM to about 10 mM, about 0.01 mM to about 5 mM, about 0.1 mM to about 50 mM, about 0.1 mM to about 25 mM, about 0.1 mM to about 10 mM, about 0.1 mM to about 5 mM, about 1 mM to about 50 mM, about 0.5 mM to about 10 mM, about 0.1 mM to about 15 mM, about 1 mM to about 25 mM, about 1 mM to about 10 mM, about 1 mM to about 5 mM, about 0.5 mM to about 1 mM, about 2 mM to about 4 mM, about 15 mM to about 35 mM, about 20 mM to about 30 mM, about 100 mM to about 150 mM, about 100 mM to about 200 mM, about 150 mM to about 250 mM, about 250 mM to about 500 mM, about 500 mM to about 750 mM, or about 750 mM to about 1000 mM. In various embodiments, the biosensor is capable of detecting ligand when ligand is present at a concentration of at least about 0.001 mM, 0.1 mM, 0.5 mM, 1 mM, 2 mM, 3 mM, 4 mM, 5 mM, 6 mM, 7 mM, 8 mM, 9 mM, 10 mM, 15 mM, 20 mM, 25 mM, 50 mM, 75 mM, 100 mM, 125 mM, 150 mM, 200 mM, 300 mM, 400 mM, 500 mM, 600 mM, 700 mM, 800 mM, 900 mM, or 1000 mM. The ratiometric reagentless biosensors produce precise measurements over an extended concentration ranges, as noted above, as well as in sample volumes of less than about, e.g., 10 μl, 9 μl, 8 μl, 7 μl, 6 μl, 5 μl, 4 μl, 3 μl, 2 μl, or 1 μl. In some embodiments, the volume of sample that is applied to a biosensor or a device comprising a biosensor is less than 0.1, 0.5, 1, 2, 3, 4, 5, 6, 7, 8, 9, 10, 25, 50, 75, 100, 150, 300, 500, or 1000 μl. In some embodiments, the volume is about 0.1 μl to about 1000 μl, about 0.1 μl to about 100 μl, about 1 μl to about 1000 μl, about 1 μl to about 10 μl, about 1 μl to about 100 μl, about 1 μl to about 50 μl, about 10 μl to about 50 μl, or about 5 μl to about 50 μl. In some embodiments, the ligand-binding protein comprises a mutation that alters (e.g., increases or decreases) the interaction of the mutant with bound ligand compared to a naturally occurring protein (e.g., a microbial bicarbonate-binding protein). In non-limiting examples, the ligand-binding protein comprises a mutation that alters (e.g., increases or decreases) the mutant's affinity and/or specificity for ligand compared to an unmutated ligand-binding protein (e.g., a microbial bicarbonate-binding protein). In non-limiting examples, the mutant's $K_d$ for the ligand is at least 0.001, 0.01, 0.1, 1, 2, 3, 4, 5, 6, 7, 8, 9, 10, 20, 30, 40, 50, 60, 70, 80, 90, 100, 150, 200, 300, 400, 500, 600, 700, 800, 900, or 1000 mM higher or lower for bicarbonate and/or $Ca^{2+}$ compared to the unmutated ligand-binding protein.

In certain embodiments, the ligand-binding protein comprises a mutation that alters the interaction between the protein and bound ligand, a mutation that alters the equilibrium between the open and closed states of the ligand-binding protein, a mutation that alters the interaction between the ligand-binding protein and a reporter group (such as a fluorescent conjugate, e.g., the interaction with a carbonyl group or a naphthalene ring of a prodan-derived fluorophore such as Acrylodan or Badan), and/or a mutation that impacts indirect interactions that alter the geometry of the ligand binding site. In various embodiments, the mutation does not reduce, or negligibly impacts, the thermostability of the ligand-binding protein. In some embodiments, the mutation alters the thermostability of the ligand-binding protein by less than about 1, 2, 3, 4, 5, or 10° C.

In some embodiments, the interaction of a bicarbonate-binding protein with a portion of bicarbonate selected from an —OH group, an oxygen atom (e.g., —O—), or a —C(═O)O— group, or any combination thereof, is different than that of a naturally occurring counterpart of the bicarbonate-binding protein.

In various embodiments, the ligand-binding protein is purified. In some embodiments, the naturally occurring counterpart of the ligand-binding protein is from a Gram-positive bacterium or a Gram-negative bacterium.

In some embodiments, the ligand-binding protein comprises or comprises a mutant of a microbial calcium-bicarbonate binding protein.

The present subject matter provides a ligand-binding protein that is or is a mutant of: a *Synechocystis* sp. (e.g., *S.* sp. PCC6803) bicarbonate-binding protein, a *Thermosynechococcus* sp. (e.g., *T. vulcanus*, *T. elongatus*, or *T. elongatus* BP-1) bicarbonate-binding protein, a *Chroococcidiopsis* sp. (e.g., *C. thermalis*, *C. gigantea*, *C. cubana*, or *C. codiicola*) bicarbonate-binding protein, a *Calothrix* sp. (e.g., *C. aberrans, C. adscencens, C. aeruginea, C. africana, C. allorgei, C. australiensis, C. baileyi, C. bharadwajae, C. borealis, C. braunii, C. breviarticulata, C. calida, C. castellii, C. capitularis, C. cavernarum Copeland, C. charicola, C. clavata, C. clavatoides, C. codicola, C. columbiana, C. compacta, C. confervicola, C. contarenii, C. coriacea, C. crustacea, C. cylindrica, C. desertica, C. elsteri, C. epiphytica, C. evanescens, C. estonica, C. fasciculata, C. feldmannii, C. flahaultii, C. floccosa, C. fritschii, C. fuellebornii, C. fusca, C. fusco-violacea, C. geilterii, C. geitonos, C. ghosei, C. gigas, C. gloeocola, C. goetzei, C. hunanica, C. inaequabilis, C. inserta, C. javanica, C. karnatakensis, C. kawraiskyi, C. kossinskajae, C. kuntzei, C. linearis, C. minima, C. nidulans, C. parasitica, C. parietina, C. parva, C. pilosa, C. prolfera, C. pulvinata, C. rectangularis, C. reptans, C. rodriguezii, C. santapaui, C. scopulorum, C. scytonemicola, C. simplex, C. simulans, C. stagnalis, C. subantarctica, C. subsimplex, C. tenella, C. thermalis, C. turfosa, C. viguieri, C. vivipara, C. violacea, C. weberi, C. wembaerensis, C. aeruginosa, C. aestuarii, C. antarctica, C. atricha, C. bossei, C. brevissima, C. clausa, C. conica, C. dnieprensis, C. elenkinii, C. fonticola, C. galpinii, C. gelatinosa, C. gracilis, C. intricata, C. litoralis, C. marchica, C. nodulosa, C. obtusa, C. rhizosoleniae*, or *C. schweickertii*) bicarbonate-binding protein, a mutant of a *Anabaena* sp. (e.g., *A. aequalis, A. affinis, A. angstumalis angstumalis, A. angstumalis marchita, A. aphanizomendoides, A. azollae, A. bornetiana, A. catenula, A. cedrorum, A. circinalis, A. confervoides, A. constricta, A. cyanobacterium, A. cycadeae, A. cylindrica, A. echinispora, A. felisii, A. flos-aquae flos-aquae, A. flos-aquae minor, A. flos-aquae treleasei, A. helicoidea, A. inaequalis, A. lapponica, A. laxa, A. lemmermannii, A. levanderi, A. limnetica, A. macrospora macrospora, A. macrospora robusta, A. monticulosa, A. nostoc, A. oscillarioides, A. planctonica, A. raciborskii, A. scheremetievi, A. sphaerica, A. spiroides crassa, A. spiroides spiroides, A. subcylindrica, A. torulosa, A. unispora, A. variabilis, A. verrucosa, A. viguieri, A. wisconsinense*, or *A. zierlingii*) bicarbonate-binding protein, or a *Chamaesiphon* sp. (e.g., *C. africanus, C. amethystinus, C. britannicus, C. carpaticus, C. confervicola, C. cylindricus, C. cylindrosporus, C. halophilus, C. incrustans, C. investiens, C. jaoi, C. komarekii, C. longus, C. macer, C. major, C. minimus, C. minutus, C. portoricensis, C. rostafinskii, C. sideriphilus, C. tibeticus, C. aggregatus, C. fallax, C. fuscus, C. geitleri, C. mollis, C. niger, C. ocobyrsiodes, C. polonicus, C. polymorphus, C. starmachii, C. stratosus*, or *C. subglobosus*) bicarbonate-binding protein.

In various embodiments, a biosensor comprises a ligand-binding protein that is or is a mutant of: a bicarbonate-binding protein from *Synechocystis* sp. (synBicarbBP1; SEQ ID NO: 1, 15, or 75); a bicarbonate-binding protein from *Thermosyneochococcus elongatus* (teBicarbBP2; SEQ ID NO: 2, 16, or 76); a bicarbonate-binding protein from *Chroococcidiopsis thermalis* (ctBicarbBP3; SEQ ID NO: 3, 17, or 77); a bicarbonate-binding protein from *Calothrix* sp. (calBicarbBP4; SEQ ID NO: 4, 18, or 78); a bicarbonate-binding protein from *Anabaena variabilis* (avBicarbBP5; SEQ ID NO: 5, 19, or 79); or a bicarbonate-binding protein from *Chamaesiphon minutus* (cmBicarbBP6; SEQ ID NO: 6, 20, or 80).

Aspects of the present subject matter include a ligand-binding protein that is or is a mutant of a protein listed in Table 1, e.g., the protein numbered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 in Table 1.

In some embodiments, the ligand-binding protein comprises or comprises a mutant of a microbial iron-binding protein.

The present subject matter provides a ligand-binding protein that is or is a mutant of: a *Mannheimia* sp. (e.g., *M. caviae, M. glucosida, M. granulomatis, M. haemolytica, M. ruminalis*, or *M. varigena*) bicarbonate and iron binding protein, an *Exiguobacterium* sp. (e.g., *E. acetylicum, E. aestuarii, E. alkaliphilum, E. antarcticum, E. aquaticum, E. artemiae, E. aurantiacum, E. enclense, E. indicum, E. marinum, E. mexicanum, E. oxidotolerans, E. profundum, E. sibiricum, E. soli*, or *E. undae*) bicarbonate and iron binding protein, a *Thermosynechococcus* sp. (e.g., *T. vulcanus, T. elongatus*, or *T. elongatus* BP-1) bicarbonate and iron binding protein, a *Candidatus nitrospira* sp. (e.g., *Candidatus nitrospira defluvii, Candidatus nitrospira nitrificans, Candidatus nitrospira nitrosa, Candidatus nitrospira inopinata, Candidatus Magnetobacterium casensis, Candidatus Magnetobacterium bavaricum, Candidatus Magnetoovum chiemensis*) bicarbonate and iron binding protein, a *Thermus* sp. (e.g., *T. caldophilus, T. eggertssonii, T. kawarayensis, T. murrieta, T. nonproteolyticus, T. parvatiensis, T rehai, T. yunnanensis, T. amyloliquefaciens, T antranikianii, T aquaticus, T. arciformis, T. brockianus, T. caliditerrae, T. chliarophilus, T. composti, T. filiformis, T. igniterrae, T. islandicus, T oshimai, T. profundus, T. scotoductus, T. tengchongensis*, or *T. thermophilus*) bicarbonate and iron binding protein, a *Meiothermus* sp. (*M. chiliarophilus, M. cerbereus, M. granaticius, M. rosaceus, M. ruber, M. rufus, M. silvanus, M. taiwanensis*, or *M. timidus*) bicarbonate and iron binding protein, a *Salinibacter* sp. (e.g., *S. ruber, S. iranicus*, or *S. luteus*) bicarbonate and iron binding protein, or a *Halorubrum* sp. (e.g., *H. aidingense, H. alkaliphilum, H. arcis, H. calforniensis, H. coriense, H. distributum, H. ejinorense, H. ezzemoulense, H. kocurii, H. lacusprofundi, H. lipolyticum, H. litoreum, H. luteum, H. orientalis, H. saccharovorum, H. salsolis, H. sodomense, H. tebenquichense, H. terrestre, H. tibetense, H. trapanicum, H. vacuolatum*, or *H. xinjiangense*) bicarbonate and iron binding protein.

In various embodiments, a biosensor comprises a ligand-binding protein that is or is a mutant of: a bicarbonate and iron binding protein from *Mannheimia haemolytica* (mhFeBP1; SEQ ID NO: 7, 21, or 81); a bicarbonate and iron binding protein from *Exiguobacterium* sp. (exiFeBP2; SEQ ID NO: 8, 22, or 82); a bicarbonate and iron binding protein from *Thermosynechoccus elongatus* (teFeBP3; SEQ ID NO: 9, 23, or 83); a bicarbonate and iron binding protein from *Candidatus nitrospira* (cnFeBP4; SEQ ID NO: 10, 24, or 84); a bicarbonate and iron binding protein from *Thermus thermophilus* (ttFeBP5; SEQ ID NO: 11, 25, or 85); a bicarbonate and iron binding protein from *Meiothermus silvanus* (msFeBP6; SEQ ID NO: 12, 26, or 86); a bicarbonate and iron binding protein from *Salinibacter ruber* (srFeBP7; SEQ ID NO: 13, 27, or 87); or a bicarbonate and iron binding protein from *Halorubrum lacusprofundi* (hlFeBP8; SEQ ID NO: 14, 28, or 88).

Aspects of the present subject matter include a ligand-binding protein that is or is a mutant of a protein listed in Table 2, e.g., the protein numbered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 270, 271, 272, 273, 274, 275, 276, 277, 278, 279, 280, 281, 282, 283, 284, 285, 286, 287, 288, 289, 290, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, or 523 in Table 2.

Aspects of the present subject matter also include a ligand-binding protein that is or is a mutant of a protein listed in Table 3, e.g., the protein numbered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, or 71 in Table 3.

With regard to a defined polypeptide, % identity figures higher or lower than those provided herein will encompass various embodiments. Thus, where applicable, in light of a minimum % identity figure, a polypeptide may comprise an amino acid sequence which is at least 60%, 65%, 70%, 75%, 76%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the reference SEQ ID NO or to each of the reference SEQ ID NOs. In embodiments, the polypeptide comprises an amino acid sequence that is 100% identical to the reference SEQ ID NO. Where applicable, in light of a maximum % identity to a reference sequence, a polypeptide may comprise an amino acid sequence which is less than 75%, 70%, 65%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, or 15% identical to the reference SEQ ID NO or to each of the reference SEQ ID NOs. In certain embodiments, a polypeptide comprises amino acids in a sequence that is preferably at least about 10%, 11%, 12%, 13%, 14%, 15%, 16%, 17%, 18%, 19%, 20%, 21%, 22%, 23%, 24%, 25%, 26%, 27%, 28%, 29%, or 30% and less than about 75%, 70%, 65%, 60%, 55%, 50%, 45%, 44%, 43%, 42%, 41%, 40%, 39%, 38%, 37%, 36%, 35%, 34%, 33%, 32%, 31%, or 30% identical to the reference SEQ ID NO or to each of the reference SEQ ID NOs. In certain embodiments, a polypeptide comprises amino acids in a sequence that is between about 10% and about 60%, 11% and about 60%, 12% and about 60%, 13% and about 60%, 14% and about 60%, 15% and about 60%, 16% and about 60%, 17% and about 60%, 18% and about 60%, 19% and about 60%, 20% and about 60%, 21% and about 60%, 22% and about 60%, 23% and about 60%, 24% and about 60%, 25% and about 60%, 26% and about 60%, 27% and about 60%, 28% and about 60%, 29% and about 60%, 30% and about 60%, about 25% and about 100%, about 25% and about 95%, about 25% and about 85%, about 25% and about 75%, about 25% and about 70%, about 25% and about 65%, 60%, about 25% and about 55%, about 25% and about 50%, about 25% and about 45%, about 25% and about 44%, about 25% and about 43%, about 25% and about 42%, about 25% and about 41%, about 25% and about 40%, about 25% and about 39%, about 25% and about 38%, about 25% and about 37%, about 25% and about 36%, about 25% and about 35%, about 25% and about 34%, about 25% and about 33%, about 25% and about 32%, about 25% and about 31%, or about 25% and about 30% identical to the reference SEQ ID NO or to each of the reference SEQ ID NOs. Non-limiting examples of reference proteins and amino acid sequences disclosed herein include:

(i) a bicarbonate-binding protein from *Synechocystis* sp. (synBicarbBP1; genome, NC_017052, protein YP_005410477.1; SEQ ID NO: 1);

(ii) a bicarbonate-binding protein from *Thermosynechococcus elongatus* (teBicarbBP2; genome, NC_004113, protein NP_682790.1; SEQ ID NO: 2);

(iii) a bicarbonate-binding protein from *Chroococcidiopsis thermalis* (ctBicarbBP3; genome, NC_019695, protein YP_007090308.1; SEQ ID NO: 3);

(iv) a bicarbonate-binding protein from *Calothrix* sp. (calBicarbBP4; genome, NC_019751, protein YP_007137061.1; SEQ ID NO: 4);

(v) a bicarbonate-binding protein from *Anabaena variabilis* (avBicarbBP5; genome, NC_007413, protein YP_321546.1; SEQ ID NO: 5);

(vi) a bicarbonate-binding protein from *Chamaesiphon minutus* (cmBicarbBP6; genome, NC_019697, protein YP_007099445.1; SEQ ID NO: 6);

(vii) a bicarbonate and iron binding protein from *Mannheimia haemolytica* (mhFeBP 1; genome, NC_0121082, protein, YP_007884192.1; SEQ ID NO: 7);

(viii) a bicarbonate and iron binding protein from *Exiguobacterium* sp. (exiFeBP2; genome, NC_012673, protein, YP_002886303.1; SEQ ID NO: 8);

(ix) a bicarbonate and iron binding protein from *Thermosynechoccus elongatus* (teFeBP3; genome, NC_004113, protein, NP_681303.1; SEQ ID NO: 9);

(x) a bicarbonate and iron binding protein from *Candidatus nitrospira* (cnFeBP4; genome, NC_014355, protein, YP_003796723.1; SEQ ID NO: 10);

(xi) a bicarbonate and iron binding protein from *Thermus thermophilus* (ttFeBP5; genome, NC_006461, protein, YP_144894.1; SEQ ID NO: 11);

(xii) a bicarbonate and iron binding protein from *Meiothermus silvanus* (msFeBP6; genome, NC_014212, protein, YP_003686074.1; SEQ ID NO: 12);

(xiii) a bicarbonate and iron binding protein from *Salinibacter ruber* (srFeBP7; genome, NC_014032, protein, YP_003572493.1; SEQ ID NO: 13); and (xiv) a bicarbonate and iron binding protein from *Halorubrum lacusprofundi* (hlFeBP8; genome, NC_012029, protein, YP_002564837.1; SEQ ID NO: 14).

In some embodiments, the ligand-binding protein comprises an amino acid sequence with at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100% identity to 1, 2, 3, 4, 5, 6, 7, 8, 9, 10 or more ligand-binding proteins disclosed herein.

The ligand-binding proteins disclosed herein may optionally be fused (e.g., at their N-terminal and/or C-terminal ends) to a motif comprising a stretch of amino acids that facilitates the isolation or other manipulation such as conjugation to a moiety or immobilization on a substrate such as a plastic, a cellulose product such as paper, polymer, metal, noble metal, semiconductor, or quantum dot (e.g., a fluorescent quantum dot). A non-limiting example of such a stretch of amino acids has the sequence: GGSHHHHHH (SEQ ID NO: 89). This motif is not required for, is not believed to influence or affect ligand-binding activity or signal transduction, and may be omitted from any ligand-binding protein or biosensor disclosed herein. Additionally, for every sequence disclosed herein that includes GGSHHHHHH (SEQ ID NO: 89), a corresponding sequence that is identical except that it lacks GGSHHHHHH (SEQ ID NO: 89) is also provided and intended to be disclosed. For example, each of SEQ ID NOs: 1-74 (and the non-limiting examples of other proteins used in the experiments disclosed herein) comprises this motif (SEQ ID NO: 89). Alternatively or in addition, a ligand-binding protein may be fused to a heterologous polypeptide or "added amino acids" that facilitates the attachment thereof to a surface, such as the surface of a device.

In some embodiments, a polypeptide comprises 1, 2, 3, 4, 5, or more substitutions or deletions of a cysteine compared to the naturally occurring counterpart of the polypeptide (i.e., 1, 2, 3, 4, 5, or more native cysteines have been removed), e.g., 1, 2, 3, 4, 5, or more cysteine to alanine substitutions compared to the naturally occurring counterpart of the polypeptide. In some embodiments, all of the cysteines of a polypeptide have been deleted and/or substituted compared to its natural counterpart. In some embodiments, one or more cysteines of a polypeptide have been substituted with an alanine, a serine, or a threonine.

In embodiments, the amino acid sequence of a protein comprises no more than 1, 2, 3, 4, 5, 6, 7, 8, 9, 10, 15, 20, 25, 30, 35, 40, 45, or 50 mutations compared to its naturally occurring counterpart. In some embodiments, less than 50, 45, 40, 35, 30, 25, 20, 15, 10, 9, 8, 7, 6, 5, 4, 3, or 2 of the mutations is a deletion or insertion of 1, 2, 3, 4, or 5 or no more than 1, 2, 3, 4, or 5 amino acids. In some embodiments, 1, 2, 3, 4, 5, 6, 7, 8, 9, 10, 15, 20, 25, 30, 35, 40, 45, 50 or more of the mutations is a substitution mutation. In certain embodiments, every mutation to a protein compared to its naturally occurring counterpart is a substitution mutation. In various embodiments, 1, 2, 3, 4, 5, 6, 7, 8, 9, 10, 15, 20, 25, 30, 35, 40, 45, 50 or more or all of the mutations to a protein compared to its naturally occurring counterpart is a conservative substitution mutation.

In various embodiments, a polypeptide does not have any insertion or deletion compared to its natural counterpart, other than (optionally) the removal of the signal peptide and/or the fusion of compounds such as another polypeptide at the N-terminus or C-terminus thereof.

Ligand-Binding Proteins Comprising a Primary Complementary Surface (PCS)

The following BLAST parameters are used to identify sequence homologues of a bicarbonate-binding protein (such as synBicarbBP1, mhFeBP1, or ttFeBP5): (1) Expect threshold is 10.0; (2) Gap cost is Existence: 11 and Extension: 1; (3) The Matrix employed is BLOSUM62; (4) The filter for low complexity regions is "on." Such an alignment may be generated using the ProteinHunter program. The ProteinHunter package always executes BLAST searches, with the following command "blastall-p blastp-m 8-b 50000-d % s-i<INPUT FILE>-o<OUTPUT FILE>"

where <INPUT FILE> and <OUTPUT FILE> specify the input and output files, respectively for a given calculation. This command executes the BLAST alignment program for protein sequences with default parameters, intrinsically set by the program. The BLAST program version is 2.2.24.

Sequence homologues of synBicarbBP1, mhFeBP1, or ttFeBP5 identified using BLAST may be aligned with synBicarbBP1, mhFeBP1, or ttFeBP5 using ClustalW to identify homologues that share a PCS with synBicarbBP1, mhFeBP1, or ttFeBP5 as discussed below.

Aspects of the present subject matter provide ligand-binding proteins that share a PCS with a bicarbonate-binding protein disclosed herein.

In embodiments, the PCS comprises at least about 3, 4, 5, 6, 7, or 8 amino acid positions used to identify a bicarbonate-binding protein. For example, the PCS of synBicarbBP1 may comprise positions 20, 49, 71, 102, 142, 148, 220, and 221, wherein each position is counted as in SEQ ID NO: 15 or 75. In various embodiments, a protein shares a PCS with synBicarbBP1 if the amino acid sequence of the protein has (i) E at the position that aligns with position 20 of synBicarbBP1;

(ii) W at the position that aligns with position 49 of synBicarbBP1;

(iii) Q at the position that aligns with position 71 of synBicarbBP1;

(iv) N at the position that aligns with position 102 of synBicarbBP1;

(v) T at the position that aligns with position 142 of synBicarbBP1;

(vi) Q at the position that aligns with position 148 of synBicarbBP1;

(vii) E at the position that aligns with position 220 of synBicarbBP1; and (viii) E at the position that aligns with position 221 of synBicarbBP1, wherein the alignment between synBicarbBP1 (SEQ ID NO: 15 or 75) and the protein is constructed using the ClustalW alignment program.

In embodiments, the PCS comprises at least about 3, 4, or 5 amino acid positions used to identify a bicarbonate-binding protein. For example, the PCS of mhFeBP1 may comprise positions 11, 102, 143, 199, and 200 wherein each position is counted as in SEQ ID NO: 21 or 81. In various embodiments, a protein shares a PCS with mhFeBP1 if the amino acid sequence of the protein has (i) R at the position that aligns with position 11 of mhFeBP1;
(ii) R at the position that aligns with position 102 of mhFeBP1;
(iii) Y at the position that aligns with position 143 of mhFeBP1;
(iv) Y at the position that aligns with position 199 of mhFeBP1; and
(v) Y at the position that aligns with position 200 of mhFeBP1, wherein the alignment between mhFeBP1 (SEQ ID NO: 21 or 81) and the protein is constructed using the ClustalW alignment program.

In embodiments, the PCS comprises at least about 3, 4, or 5 amino acid positions used to identify a bicarbonate-binding protein. For example, the PCS of ttFeBP5 may comprise positions 11, 101, 143, 200, and 201 wherein each position is counted as in SEQ ID NO: 25 or 85. In various embodiments, a protein shares a PCS with ttFeBP5 if the amino acid sequence of the protein has (i) R at the position that aligns with position 11 of ttFeBP5;
(ii) R at the position that aligns with position 101 of ttFeBP5;
(iii) Y at the position that aligns with position 143 of ttFeBP5;
(iv) Y at the position that aligns with position 200 of ttFeBP5; and
(v) Y at the position that aligns with position 201 of ttFeBP5, wherein the alignment between ttFeBP5 (SEQ ID NO: 25 or 85) and the protein is constructed using the ClustalW alignment program.

The ProteinHunter package always executes multiple sequence alignments with the following command "clustalw-infile=<INPUT FILE>-outfile=<OUTPUT-FILE>-align-quiet"

This command executes the CLUSTALW multi-sequence alignment program for protein sequences. There are no user-specified parameter settings that alter the alignment behavior of the program. The CLUSTALW program version is 2.1.

For convenience and depending on context, a position that aligns with a stated position of synBicarbBP1, mhFeBP1, or ttFeBP5 may be referred to herein as "equivalent" to the stated position.

Exemplary Ligand-Binding Proteins

Various biosensors provided herein comprise ligand-binding proteins, such as ligand-binding proteins that have altered amino acid sequences compared to their naturally occurring counterparts. In embodiments, such proteins are conjugated to reporter groups.

In various embodiments, the Ca root-mean-square deviation (RMSD) between the backbone of the ligand-binding polypeptide and synBicarbBP1, teBicarbBP2, ctBicarbBP3, calBicarbBP4, avBicarbBP5, cmBicarbBP6, mhFeBP1, exiFeBP2, teFeBP3, cnFeBP4, ttFeBP5, msFeBP6, srFeBP7, and/or hlFeBP8 is, e.g., between about 0-3 Å, 0-1 Å, 0-1.5 Å, 0-2 Å, 0.1-3 Å, 0.5-1 Å, 0.5-1.5 Å, or 0.5-2 Å, or less than about 0.1 Å, 0.2 Å, 0.3 Å, 0.4 Å, 0.5 Å, 0.6 Å, 0.7 Å, 0.8 Å, 0.9 Å, 1.0 Å, 1.5 Å, 1.6 Å, 1.7 Å, 1.8 Å, 1.9 Å, 2.0 Å, 2.5 Å, or 3 Å. In some embodiments, the C, RMSD between the N-terminal domain (i.e., the portion of the protein at the N-terminal side of the binding domain hinge) backbone of the ligand-binding polypeptide and the corresponding domain of synBicarbBP1, teBicarbBP2, ctBicarbBP3, calBicarbBP4, avBicarbBP5, cmBicarbBP6, mhFeBP1, exiFeBP2, teFeBP3, cnFeBP4, ttFeBP5, msFeBP6, srFeBP7, and/or hlFeBP8 is, e.g., between about 0-3 Å, 0-1 Å, 0-1.5 Å, 0-2 Å, 0.1-3 Å, 0.5-1 Å, 0.5-1.5 Å, or 0.5-2 Å, or less than about 0.1 Å, 0.2 Å, 0.3 Å, 0.4 Å, 0.5 Å, 0.6 Å, 0.7 Å, 0.8 Å, 0.9 Å, 1.0 Å, 1.5 Å, 1.6 Å, 1.7 Å, 1.8 Å, 1.9 Å, 2.0 Å, 2.5 Å, or 3 Å. In certain embodiments, the C, RMSD between the C-terminal domain (i.e., the portion of the protein at the C-terminal side of the binding domain hinge) backbone of the ligand-binding polypeptide and the corresponding domain of synBicarbBP1, teBicarbBP2, ctBicarbBP3, calBicarbBP4, avBicarbBP5, cmBicarbBP6, mhFeBP1, exiFeBP2, teFeBP3, cnFeBP4, ttFeBP5, msFeBP6, srFeBP7, and/or hlFeBP8 is, e.g., between about 0-3 Å, 0-1 Å, 0-1.5 Å, 0-2 Å, 0.1-3 Å, 0.5-1 Å, 0.5-1.5 Å, or 0.5-2 Å, or less than about 0.1 Å, 0.2 Å, 0.3 Å, 0.4 Å, 0.5 Å, 0.6 Å, 0.7 Å, 0.8 Å, 0.9 Å, 1.0 Å, 1.5 Å, 1.6 Å, 1.7 Å, 1.8 Å, 1.9 Å, 2.0 Å, 2.5 Å, or 3 Å. Non-limiting considerations relating to the sequence and structural differences between homologous proteins are discussed in Chothia and Lesk (1986) *The EMBO Journal,* 5(4):823-826, the entire content of which is incorporated herein by reference.

Non-limiting examples of ligand-binding polypeptides that are useful in biosensors provided herein include synBicarbBP1, teBicarbBP2, ctBicarbBP3, calBicarbBP4, avBicarbBP5, cmBicarbBP6, mhFeBP1, exiFeBP2, teFeBP3, cnFeBP4, ttFeBP5, msFeBP6, srFeBP7, and hlFeBP8. In embodiments, a biosensor comprises a modified synBicarbBP1, teBicarbBP2, ctBicarbBP3, calBicarbBP4, avBicarbBP5, cmBicarbBP6, mhFeBP1, exiFeBP2, teFeBP3, cnFeBP4, ttFeBP5, msFeBP6, srFeBP7, or hlFeBP8 polypeptide having an amino acid substitution compared to its naturally occurring counterpart, such that the polypeptide has a cysteine at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 270, 271, 272, 273, 274, 275, 276, 277, 278, 279, 280, 281, 282, 283, 284, 285, 286, 287, 288, 289, 290, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, or 460 or any combination of 1, 2, 3, 4, or 5 thereof, wherein the position corresponds a SEQ ID NO disclosed herein for synBicarbBP1, teBicarbBP2, ctBicarbBP3, calBicarbBP4, avBicarbBP5, cmBicarbBP6, mhFeBP1, exiFeBP2, teFeBP3, cnFeBP4, ttFeBP5, msFeBP6, srFeBP7, or hlFeBP8. In embodiments, the cysteine is conjugated to a reporter group.

In various embodiments, the disassociation constant of the mutant ligand-binding polypeptide differs by at least about 1 μM, 5 μM, 10 μM, 20 μM, 25 μM, 30 μM, 35 μM, 40 μM, 45 μM, 50 μM, 75 μM, 100 μM, 200 μM, 300 μM, 400 μM, 500 μM, 600 μM, 700 μM, 800 μM, 900 μM, 1 mM, 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, or 100 mM (increase or decrease) compared to its naturally occurring counterpart.

The biosensors and ligand-binding proteins provided herein are robust and useful at a wide range of physical conditions, e.g., pressure, temperature, salinity, osmolality, and pH conditions. For example, biosensors and ligand-binding proteins provided herein may survive substantial periods of time after being dried or exposed to high temperatures. In some embodiments, the biosensor maintains at least about 75%, 80%, 85%, 90%, 95%, 96%, 97%, 98%, 99%, 99.5%, 99.9%, or more of its signal transduction activity after exposure to a temperature of about 40, 45, 50, 55, 60, 65, 70, 75, 80, 85, 90, 95, 100, 105, 110, 115, 120, or 125, or 40-125° C. for about 1, 2, 3, 4, 5, 6, 15, 30, 60, 120, 180, 240, or 360 minutes. In certain embodiments, the biosensor maintains at least about 75%, 80%, 85%, 90%, 95%, 96%, 97%, 98%, 99%, 99.5%, 99.9%, or more of its signal transduction activity after 1, 2, 3, 4, or 5 freeze-thaw cycles in an aqueous solution. In various embodiments, the biosensor maintains at least about 75%, 80%, 85%, 90%, 95%, 96%, 97%, 98%, 99%, 99.5%, 99.9%, or more of its signal transduction activity after storage at a temperature of between 20-37° C. for about 1, 2, 3, 4, 5, 6, 7, 8, 9, 10, 11, 12, 18, 24, or 1-24 months in dry form. In some embodiments, the optimal functional temperature of the biosensor is between 41 and 122° C., between 20 and 40° C., or less than about 10° C. (e.g., between −20 and +10° C.). Devices, compositions, and biosensors provided herein may be stored, e.g., with or without protection from exposure to light. In some embodiments, the devices, compositions, and biosensors are stored in the dark, e.g., with protection from light. synBicarbBP1 is a non-limiting reference protein respect to bicarbonate-binding proteins and calcium-binding proteins. An alignment of synBicarbBP1 with other polypeptides (SEQ ID NO: 191-196) is provided in FIG. 5.

In various embodiments, a ligand-binding protein (or its naturally occurring counterpart) comprises (a) an amino acid sequence that is preferably (i) at least about 10%, 11%, 12%, 13%, 14%, 15%, 16%, 17%, 18%, 19%, 20%, 21%, 22%, 23%, 24%, 25%, 26%, 27%, 28%, 29%, or 30%, and (ii) less than about 75%, 70%, 65%, 60%, 55%, 50%, 45%, 44%, 43%, 42%, 41%, 40%, 39%, 38%, 37%, 36%, or 35% identical to synBicarbBP1;

(b) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 18 of synBicarbBP1;

(c) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 18 of synBicarbBP1; (d) a stretch of amino acids in the sequence KLGX$_1$IX$_2$IX$_3$EX$_4$AP (where $X_1$ is any amino acid, or where $X_1$ is F or Y; where $X_2$ is any amino acid, or where $X_2$ is P or A; where $X_3$ is any amino acid, or where $X_3$ is V or A; and where $X_4$ is any amino acid, or where $X_4$ is S or A) (SEQ ID NO: 155);

(e) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 70 of synBicarbBP1;

(f) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 70 of synBicarbBP1;

(g) a stretch of amino acids in the sequence DGGQXQMPMP (where X is any amino acid, or where X is W or Y) (SEQ ID NO: 156);

(h) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 103 of synBicarbBP1;

(i) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 103 of synBicarbBP1;

(j) a stretch of amino acids in the sequence GNGIA (SEQ ID NO: 157);

(k) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 144 of synBicarbBP1;

(l) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 144 of synBicarbBP1;

(m) a stretch of amino acids in the sequence TFX$_1$X$_2$VNQD (where $X_1$ is any amino acid, or where $X_1$ is P or A; and where $X_2$ is any amino acid, or where $X_2$ is N, H, Q, or R) (SEQ ID NO: 158);

(n) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 220 of synBicarbBP1;

(o) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 220 of synBicarbBP1;

(p) a stretch of amino acids in the sequence HPEEY (SEQ ID NO: 159);

(q) no more than 1, 2, 3, 4, 5, 6, 7, 8, 9, 10, or 15 deleted or inserted amino acids compared to synBicarbBP1, not including amino acids added to the N-terminus or C-terminus of the polypeptide compared to its natural counterpart, and including or not including the signal peptide of the natural counterpart of the polypeptide;

(r) at least 10, 11, 12, 13, or 14, or exactly 10, 11, 12, 13, or 14 α-helices; and/or (s) at 10, 11, 12, 13, or 14 β-strands or exactly 10, 11, 12, 13, or 14 β-strands.

In embodiments, two or more or each of features (b)-(p) above occurs in the polypeptide in the order listed above as the amino acid sequence of the polypeptide is viewed or read from the N-terminus to the C-terminus (with additional features and/or amino acid sequences therebetween). For example, the polypeptide may have an N-terminus, followed by feature (b), (c), or (d), followed by feature (e), (f), or (g), followed by feature (h), (i), or (j), followed by feature (k), (1), or (m), followed by feature (n), (o), or (p), followed by the C-terminus.

As used herein when referring to the order of features in an amino acid read from the N terminus to the C-terminus, a first feature is "followed by" a second feature when the second feature occurs after the first feature in the amino acid sequence. The words "followed by" do not require that the second feature immediately follow or be close to the first feature. For example, the N-terminus is followed by the C-terminus.

The features listed above are not limiting and may be combined with any other relevant features disclosed herein, including those listed below.

In some embodiments the polypeptide comprises the following sequence (SEQ ID NO: 188):

```
XXXXMXXXSRRKFLLTAGAXAXGAXFLKGCAGNPPXPXXXXXXXQXXXXX

AXXLSXEXXPETTX!KLG%IPIVESAPLIIAKEKGFFAKYG$TXV#VSKQ

ASWGSARDNVEIGSAGGG!DGGQWQMPMPHLITEGIITKGNXKIPMYVLA

QLXTQGNGIA!AXXHXGKGXXLXXXXXAXYXXGXXKXXGXPFKAAXTFPX

VNQDFWIRYWLAAGGI#P#XD!XLLAVPAA#TVAXMRTGTMDAFSTGDPW

PXRIVX#XXKIG%$AXLTA#IWPXHPEEYLAXRA#WVDKHPKATKALLKG

!MEAQQWXD#XXNRXEXAXILXGRXYF#XPXXXILXXP%XGXYX$GDGRX

XXDDXXXAXLYWKDXXGNX!SYPYKSHDLWFLTESVRWGFLPXDXLXXXX

XXAXXXIXKVNREDLWXEAAK#LGIAAA#IPTSTSRG!ETFFDGXKF#PE

NPXAYLXSLKIKKXXX
```

wherein each

X is, individually, any amino acid or is absent,

! is, individually, I or V, $ is, individually, L or M,

% is, individually, F or Y, and

#is, individually, N, D, Q, or E.

In a non-limiting example, the ligand-binding protein comprises an N-terminal domain and a C-terminal domain connected by a flexible hinge, with the ligand-binding site (the ligand binding domain) located in the cleft between the N-terminal and the C-terminal domain.

In some embodiments, the ligand-binding protein comprises, from the N-terminus to the C-terminus, a first β-strand (β1), followed by a first α-helix (α1), followed by a second β-strand (β2), followed by a second α-helix (α2), followed by a third β-strand (β3), followed by a third α-helix (α3), followed by a fourth β-strand (β4), followed by a fifth β-strand (β5), followed by a fourth α-helix (α4), followed by a sixth β-strand (β6), followed by a fifth α-helix (α5), followed by a sixth α-helix (α6), followed by a seventh β-strand (β7), followed by a seventh α-helix (α7), followed by an eighth β-strand (β8), followed by a ninth β-strand (β9), followed by an eighth α-helix (α8), followed by a ninth α-helix (α9), followed by a tenth β-strand (β10), followed by a tenth α-helix (α10), followed by an eleventh β-strand (β11), followed by a twelfth β-strand (β12), followed by a thirteenth β-strand (β13), followed by an eleventh α-helix (α11), followed by a twelfth α-helix (α12), followed by a thirteenth α-helix (α13), followed by a fourteenth 1-strand (β14), followed by a fourteenth α-helix (α14). In some embodiments, the polypeptide comprises (i) 1, 2, or 3 amino acid substitutions between β1 and α1; (ii) 1, 2, or 3 amino acid substitutions between α1 and β2; (iii) 1, 2, or 3 amino acid substitutions between β2 and α2; (iv) 1, 2, or 3 amino acid substitutions between α2 and β3; (v) 1, 2, or 3 amino acid substitutions between the β3 and α3; (vi) 1, 2, or 3 amino acid substitutions between α3 and β4; (vii) 1, 2, or 3 amino acid substitutions between β4 and β5; (viii) 1, 2, or 3 amino acid substitutions between β5 and α4; (ix) 1, 2, or 3 amino acid substitutions between α4 and β6; (x) 1, 2, or 3 amino acid substitutions between β6 and α5; (xi) 1, 2, or 3 amino acid substitutions between α5 and α6; (xii) 1, 2, or 3 amino acid substitutions between α6 and β7; (xiii) 1, 2, or 3 amino acid substitutions between β7 and α7; (xiv) 1, 2, or 3 amino acid substitutions between α7 and β8; (xv) 1, 2, or 3 amino acid substitutions between β8 and β9; (xvi) 1, 2, or 3 amino acid substitutions between β9 and α8; (xvii) 1, 2, or 3 amino acid substitutions between α8 and α9; (xviii) 1, 2, or 3 amino acid substitutions between α9 and β10; (xix) 1, 2, or 3 amino acid substitutions between β10 and α10; (xx) 1, 2, or 3 amino acid substitutions between α10 and β11; (xxi) 1, 2, or 3 amino acid substitutions between β11 and β12; (xxii) 1, 2, or 3 amino acid substitutions between β12 and β13; (xxiii) 1, 2, or 3 amino acid substitutions between β13 and α11; (xxiv) 1, 2, or 3 amino acid substitutions between α11 and α12; (xxv) 1, 2, or 3 amino acid substitutions between α12 and α13; (xxvi) 1, 2, or 3 amino acid substitutions between α13 and β14; (xxvii) 1, 2, or 3 amino acid substitutions between β14 and α14; (xxviii) 1, 2, or 3 amino acid substitutions in α1, α2, α3, α4, α5, α6, α7, α8, α9, α10, α1 1, α12, α13, or α14; and/or (xxix) 1, 2, or 3 amino acid substitutions in β1, β2, β3, β4, β5, β6, β7, β8, β9, β10, β11, β12, β13, or β14. In some embodiments, the substitutions are conservative substitutions. In various embodiments, the polypeptide comprises a cysteine substitution within α2, α5, α7, 01, or β7, or between β1 and α1, β3 and α3, or β6 and α5.

The ligand-binding polypeptide may further comprise 1, 2, or more $Ca^{2+}$ binding sites.

Beta sheets consist of beta strands (also β-strand) connected laterally by at least two or three backbone hydrogen bonds, forming a generally twisted, pleated sheet. A β-strand is a stretch of polypeptide chain, e.g. 3 to 20 amino acids long, with backbone in an extended conformation.

Alpha-helical and β-strand segments assignments are calculated from a three-dimensional protein structure as follows, and as described in C. A. F. Andersen, B. Rost, 2003, Structural Bioinformatics, 341-363, P. E. Bourne, ed., Wiley, the entire content of which is incorporated herein by reference. First for a given residue, i, the backbone trace angle, τ, is calculated, defined as the dihedral angle between the four successive Ca atom positions of residues in the linear protein sequence i, i+1, i+2, i+3. These values are calculated for all residues. Second, the residues that form backbone hydrogen bonds with each other are recorded. A hydrogen bond is scored if the distance between the backbone amide nitrogen and carbonyl oxygen of two different residues in the protein is calculated to be 2.5 Å or less, and if the calculated angle between the nitrogen, its amide proton, and the carbonyl is greater than 120°. A residue is deemed to be in an α-helix, if 35≤τ≤K 65, and it makes a backbone hydrogen bond with its $i+_4$th neighbor in the linear amino acid sequence. It is deemed to be in a β-strand, if the absolute t value falls in the interval 120≤|τ|≤180 and if it makes at least one hydrogen bond with another residue with the same τ value range. Alpha-helical segments comprise at least four residues; β-strand residues comprise at least three residues.

In embodiments, a biosensor comprises a modified synBicarbBP1. In non-limiting examples, the modified synBicarbBP1 may comprise one or more, or any combination of the following substitutions compared to its naturally occurring counterpart: 116X, P17X, 118X, W49X, Q71X, H141X, T142X, F143X, P144X, N147X, T191X, and W195X, where X is any amino acid, an amino acid that results in a conservative substitution, or a cysteine, and where each position is counted in synBicarbBP1 with the signal peptide replaced with a methionine (SEQ ID NO: 15 or 75). In some embodiments, the modified synBicarbBP1 comprises 1, 2, 3, 4, 5, 6, 7, 8, 9, 10, 11, or 12 of the following substitutions: 116 Å, 116C, 116M, 116F, 116Y, 116E, I16W, P17C, I18C, W49 A, W49C, W49F, W49Y, Q71C, H141C, T142 A, T142C, T142F, T142Y, T142W, T142Q, T142E, T142V, F143C, P144C, N147C, T191C, and W195C.

In various embodiments, the ligand-binding protein comprises a mutation that decreases bicarbonate binding compared to a naturally occurring counterpart. In non-limiting examples, the modified synBicarbBP1 may comprise one or more, or any combination of the following substitutions compared to its naturally occurring counterpart: I16X, W49X, Q71X, and T142X, where X is any amino acid, an amino acid that results in a conservative substitution, or an alanine, and where each position is counted in synBicarbBP1 with the signal peptide replaced with a methionine (SEQ ID NO: 15 or 75). In some embodiments, the modified synBicarbBP1 comprises 1 or 2 of the following substitutions: I16A, I16C, I16M, I16F, I16Y, 116E, I16W, W49A, W49C, W49C, W49F, W49Y, Q71C, T142A, T142C, T142F, T142Y, T142W, T142Q, T142E, and T142V.

In embodiments, a biosensor comprises a modified teBicarbBP2. In non-limiting examples, the modified teBicarbBP2 may comprise one or more, or any combination of the following substitutions compared to its naturally occurring counterpart: I12X, P13X, I14X, W45X, Q67X, H137X, T138X, F139X, P140X, N143X, T187X, W191X, C247X, and C260X, where X is any amino acid, an amino acid that results in a conservative substitution, or a cysteine, and where each position is counted in teBicarbBP2 with the signal peptide replaced with a methionine (SEQ ID NO: 16 or 76). The sequence for teBicarbBP2 (SEQ ID NO: 16 or 76) comprises C247A and C260A mutations. In some embodiments, the modified teBicarbBP2 comprises 1, 2, 3, 4, 5, 6, 7, 8, 9, 10, 11, 12, 13, or 14 of the following substitutions: I12A, I12C, I12M, I12F, I12Y, 112E, I12W, P13C, I14C, W45A, W45C, W45F, W45Y, Q67C, H137C, T138A, T138C, T138F, T138Y, T138W, T138Q, T138E, T138V, F139C, P140C, N143C, T187C, W191C, C247A, and C260A.

In various embodiments, the ligand-binding protein comprises a mutation that decreases bicarbonate binding compared to a naturally occurring counterpart. In non-limiting examples, the modified teBicarbBP2 may comprise one or more, or any combination of the following substitutions compared to its naturally occurring counterpart: I12X, W45X, Q67X, and T138X, where X is any amino acid, an amino acid that results in a conservative substitution, or an alanine, and where each position is counted in teBicarbBP2 with the signal peptide replaced with a methionine (SEQ ID NO: 16 or 76). In some embodiments, the modified teBicarbBP2 comprises 1 or 2 of the following substitutions: I12A, I12C, I12M, I12F, I12Y, 112E, I12W, W45A, W45C, W45F, W45Y, Q67C, T138A, T138C, T138F, T138Y, T138W, T138Q, T138E, and T138V.

In embodiments, a biosensor comprises a modified ctBicarbBP3. In non-limiting examples, the modified ctBicarbBP3 may comprise one or more, or any combination of the following substitutions compared to its naturally occurring counterpart: 116X, P17X, 118X, W49X, Q71X, Y142X, T143X, F144X, A145X, N148X, T192X, and W196X, where X is any amino acid, an amino acid that results in a conservative substitution, or a cysteine, and where each position is counted in ctBicarbBP3 with the signal peptide replaced with a methionine (SEQ ID NO: 17 or 77). In some embodiments, the modified ctBicarbBP3 comprises 1, 2, 3, 4, 5, 6, 7, 8, 9, 10, 11, or 12 of the following substitutions: 116 Å, 116C, 116M, 116F, 116Y, 116E, 116W, P17C, I18C, W49 A, W49C, W49F, W49Y, Q71C, Y142C, T143 Å, T143C, T143F, T143Y, T143W, T143Q, T143E, T143V, F144C, A145C, N148C, T192C, and W196C.

In various embodiments, the ligand-binding protein comprises a mutation that decreases bicarbonate binding compared to a naturally occurring counterpart. In non-limiting examples, the modified ctBicarbBP3 may comprise one or more, or any combination of the following substitutions compared to its naturally occurring counterpart: I16X, W49X, Q71X, and T143X, where X is any amino acid, an amino acid that results in a conservative substitution, or an alanine, and where each position is counted in ctBicarbBP3 with the signal peptide replaced with a methionine (SEQ ID NO: 17 or 77). In some embodiments, the modified ctBicarbBP3 comprises 1 or 2 of the following substitutions: I16A, I16C, I16M, I16F, I16Y, I16E, I16E, W49A, W49C, W49F, W49Y, Q71C, T143A, T143C, T143F, T143Y, T143W, T143Q, T143E, and T143V.

In embodiments, a biosensor comprises a modified calBicarbBP4. In non-limiting examples, the modified calBicarbBP4 may comprise one or more, or any combination of the following substitutions compared to its naturally occurring counterpart: I16X, P17X, I18X, W49X, Q71X, F140X, T141X, F142X, P143X, N146X, T190X, and W194X, where X is any amino acid, an amino acid that results in a conservative substitution, or a cysteine, and where each position is counted in calBicarbBP4 with the signal peptide replaced with a methionine (SEQ ID NO: 18 or 78). In some embodiments, the modified calBicarbBP4 comprises 1, 2, 3, 4, 5, 6, 7, 8, 9, 10, 11, or 12 of the following substitutions: I16A, I16C, I16M, I16F, I16Y, I16E, I16W, P17C, I18C, W49A, W49C, W49F, W49Y, Q71C, F140C, T141A, T141C, T141F, T141Y, T141W, T141Q, T141E, T141V, F142C, P143C, N146C, T190C, and W196C.

In various embodiments, the ligand-binding protein comprises a mutation that decreases bicarbonate binding compared to a naturally occurring counterpart. In non-limiting examples, the modified calBicarbBP4 may comprise one or more, or any combination of the following substitutions compared to its naturally occurring counterpart: I16X, W49X, Q71X, and T141X, where X is any amino acid, an amino acid that results in a conservative substitution, or an alanine, and where each position is counted in calBicarbBP4 with the signal peptide replaced with a methionine (SEQ ID NO: 18 or 78). In some embodiments, the modified calBicarbBP4 comprises 1, 2, 3, 4, 5, 6, 7, 8, 9, 10, 11, or 12 of the following substitutions: 116A, 116C, 116M, I16F, I16Y, 116E, I16W, W49A, W49C, W49F, W49Y, Q71C, T141A, T141C, T141F, T141Y, T141W, T141Q, T141E, and T141V.

In embodiments, a biosensor comprises a modified avBicarbBP5. In non-limiting examples, the modified avBicarbBP5 may comprise one or more, or any combination of the following substitutions compared to its naturally occurring counterpart: 116X, P17X, 118X, W49X, Q71X, C96X, F140X, T141X, F142X, P143X, N146X, T190X, and W194X, where X is any amino acid, an amino acid that results in a conservative substitution, or a cysteine, and where each position is counted in avBicarbBP5 with the signal peptide replaced with a methionine (SEQ ID NO: 19 or 79). The sequence for avBicarbBP5 (SEQ ID NO: 19 or 79) comprises a C96A mutation. In some embodiments, the modified avBicarbBP5 comprises 1, 2, 3, 4, 5, 6, 7, 8, 9, 10, 11, 12, or 13 of the following substitutions: I16A, I16C, I16M, I16F, I16Y, 116E, I16W, P17C, I18C, W49A, W49C, W49F, W49Y, Q71C, Q71D, Q71N, Q71E, Q71M, C96A, F140C, T141A, T141C, T141F, T141Y, T141W, T141Q, T141E, T141V, F142C, P143C, N146C, T190C, and W194C.

In various embodiments, the ligand-binding protein comprises a mutation that decreases bicarbonate binding compared to a naturally occurring counterpart. In non-limiting examples, the modified avBicarbBP5 may comprise one or more, or any combination of the following substitutions compared to its naturally occurring counterpart: I16X, W49X, Q71X, and T141X, where X is any amino acid, an amino acid that results in a conservative substitution, or an alanine, and where each position is counted in avBicarbBP5 with the signal peptide replaced with a methionine (SEQ ID NO: 19 or 79). In some embodiments, the modified avBicarbBP5 comprises 1, 2, 3, 4, 5, 6, 7, 8, 9, 10, 11, or 12 of the following substitutions: 116A, 116C, 116M, I16F, I16Y, 116E, I16W, W49A, W49C, W49F, W49Y, Q71C, T141A, T141C, T141F, T141Y, T141W, T141Q, T141E, and T141V.

In embodiments, a biosensor comprises a modified cmBicarbBP6. In non-limiting examples, the modified cmBicarbBP6 may comprise one or more, or any combination of the following substitutions compared to its naturally occurring counterpart: I17X, A18X, I19X, W50X, Q72X, Y142X, T143X, F144X, P145X, N148X, T192X, W196X, and C254X, where X is any amino acid, an amino acid that results in a conservative substitution, or a cysteine, and where each position is counted in cmBicarbBP6 with the signal peptide replaced with a methionine (SEQ ID NO: 20 or 80). The sequence for cmBicarbBP6 (SEQ ID NO: 20 or 80) comprises a C254A mutation. In some embodiments, the modified cmBicarbBP6 comprises 1, 2, 3, 4, 5, 6, 7, 8, 9, 10, 11, 12, or 13 of the following substitutions: 117A, 117C, 117M, 117F, I17Y, 117E, I17W, A18C, I19C, W50A, W50C, W50F, W50Y, Q72C, Y142C, T143A, T143C, T143F, T143Y, T143W, T143Q, T143E, T143V, F144C, P145C, N148C, T192C, W196C, and C254A.

In various embodiments, the ligand-binding protein comprises a mutation that decreases bicarbonate binding compared to a naturally occurring counterpart. In non-limiting examples, the modified cmBicarbBP6 may comprise one or more, or any combination of the following substitutions compared to its naturally occurring counterpart: I17X, W50X, Q72X, and T141X, where X is any amino acid, an amino acid that results in a conservative substitution, or an alanine, and where each position is counted in cmBicarbBP6 with the signal peptide replaced with a methionine (SEQ ID NO: 20 or 80). In some embodiments, the modified cmBicarbBP6 comprises 1, 2, 3, 4, 5, 6, 7, 8, 9, 10, 11, or 12 of the following substitutions: 117A, 117C, 117M, I17F, I17Y, 117E, I17W, W50A, W50C, W50F, W50Y, Q72C, T143A, T143C, T143F, T143Y, T143W, T143Q, T143E, and T143V.

mhFeBP1 is a non-limiting reference protein respect to bicarbonate-binding proteins. An alignment of mhFeBP1 with other polypeptides (SEQ ID NO: 197-200) is provided in FIG. 6A.

In various embodiments, a ligand-binding protein (or its naturally occurring counterpart) comprises (a) an amino acid sequence that is preferably (i) at least about 10%, 11%, 12%, 13%, 14%, 15%, 16%, 17%, 18%, 19%, 20%, 21%, 22%, 23%, 24%, 25%, 26%, 27%, 28%, 29%, or 30%, and (ii) less than about 75%, 70%, 65%, 60%, 55%, 50%, 45%, 44%, 43%, 42%, 41%, 40%, 39%, 38%, 37%, 36%, or 35% identical to mhFeBP1;

(b) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 9 of mhFeBP1;

(c) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 9 of mhFeBP1;

(d) a stretch of amino acids in the sequence VYSXR (where X is any amino acid, or where X is Y, S, A or G) (SEQ ID NO: 160);

(e) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 100 of mhFeBP1;

(f) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 100 of mhFeBP1;

(g) a stretch of amino acids in the sequence $GLX_1X_2R$ (where $X_1$ is any amino acid, or where $X_1$ is T or S; and where $X_2$ is any amino acid, or where $X_2$ is T, K, R or G) (SEQ ID NO: 161);

(h) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 200 of mhFeBP1;

(i) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 200 of mhFeBP1;

(j) a stretch of amino acids in the sequence $YYX_1X_2$ (where $X_1$ is any amino acid, or where $X_1$ is Y, M, L, or I; and where $X_2$ is any amino acid, or where $X_2$ is G, A or Y) (SEQ ID NO: 162);

(k) no more than 1, 2, 3, 4, 5, 6, 7, 8, 9, 10, or 15 deleted or inserted amino acids compared to mhFeBP1, not including amino acids added to the N-terminus or C-terminus of the polypeptide compared to its natural counterpart, and including or not including the signal peptide of the natural counterpart of the polypeptide;

(l) at least 7, 8, 9, or 10, or exactly 7, 8, 9, or 10 $\alpha$-helices; and/or (m) at least 4, 5, 6, or 7 $\beta$-strands or exactly 4, 5, 6, or 7 $\beta$-strands.

In embodiments, two or more or each of features (b)-(j) above occurs in the polypeptide in the order listed above as the amino acid sequence of the polypeptide is viewed or read from the N-terminus to the C-terminus (with additional features and/or amino acid sequences therebetween). For example, the polypeptide may have an N-terminus, followed by feature (b), (c), or (d), followed by feature (e), (f), or (g), followed by feature (h), (i), or (j), followed by the C-terminus.

The features listed above are not limiting and may be combined with any other relevant features disclosed herein, including those listed below.

In some embodiments the polypeptide comprises the following sequence (SEQ ID NO: 189):

```
XXmXXnVYSXEXXXlikpXlXXFXXXtGIX!#XXXXXXXeLv#RlXXEGX

XtpADvflTXDagXlXXaX#aXllqpX#srel#XX!PXqfRXX#nXWfGL

sXRXr!XvynkXrVkpXqXXXXyXdLtXpqwkXk!avrXsXnXYnqslXX

XXXaXXGX#XtkqflXGLkaNXarXpXgXdXXqvXAvaXGXXXXXIXNhY

YXXrXlXXXXeX#XXXaXaaXXXfpXXXXXGahXN!sGigvtXasknXeX

AXXliE%$vXXXaQXm%AXl#XEYPvXXX!XXXpXlXXXgtFrXXX!Xla

XlaenXeaalXlX#XvgXrXX
```

wherein each

X is, individually, any amino acid or is absent,

! is, individually, I or V, $ is, individually, L or M,

% is, individually, F or Y, and

#is, individually, N, D, Q, or E.

In a non-limiting example, the ligand-binding protein comprises an N-terminal domain and a C-terminal domain connected by a flexible hinge, with the ligand-binding site (the ligand binding domain) located in the cleft between the N-terminal and the C-terminal domain.

In some embodiments, the ligand-binding protein comprises, from the N-terminus to the C-terminus, a first $\beta$-strand ($\beta$1), followed by a first $\alpha$-helix ($\alpha$1), followed by a second $\beta$-strand ($\beta$-2), followed by a second $\alpha$-helix ($\alpha$2), followed by a third $\beta$-strand ($\beta$3), followed by a third $\alpha$-helix ($\alpha$3), followed by a fourth $\alpha$-helix ($\alpha$4), followed by a fourth $\beta$-strand ($\beta$4), followed by a fifth $\alpha$-helix ($\alpha$5), followed by a sixth $\alpha$-helix ($\alpha$6), followed by a fifth $\beta$-strand ($\beta$5), followed by a seventh $\alpha$-helix ($\alpha$7), followed by a sixth $\beta$-strand ($\beta$6), followed by a seventh $\beta$-strand ($\beta$7), followed by an eighth $\alpha$-helix ($\alpha$8), followed by a ninth $\alpha$-helix ($\alpha$9), followed by a tenth $\alpha$-helix ($\alpha$10). In some embodiments, the polypeptide comprises (i) 1, 2, or 3 amino acid substitutions between $\beta$31 and $\alpha$1; (ii) 1, 2, or 3 amino acid substitutions between $\alpha$1 and $\beta$2; (iii) 1, 2, or 3 amino acid substitutions between $\beta$2 and $\alpha$2; (iv) 1, 2, or 3 amino acid substitutions between $\alpha$2 and $\beta$3; (v) 1, 2, or 3 amino acid substitutions between the $\beta$3 and $\alpha$3; (vi) 1, 2, or 3 amino acid substitutions between $\alpha$3 and $\alpha$4; (vii) 1, 2, or 3 amino acid substitutions between $\alpha$4 and $\beta$4; (viii) 1, 2, or 3 amino acid substitutions between $\beta$4 and $\alpha$5; (ix) 1, 2, or 3 amino acid substitutions between $\alpha$5 and $\alpha$6; (x) 1, 2, or 3 amino acid substitutions between $\alpha$6 and $\beta$5; (xi) 1, 2, or 3 amino acid substitutions between $\beta$5 and $\alpha$7; (xii) 1, 2, or 3 amino acid substitutions between $\alpha$7 and $\beta$6; (xiii) 1, 2, or 3 amino acid substitutions between $\beta$6 and $\beta$7; (xiv) 1, 2, or 3 amino acid substitutions between $\beta$7 and $\alpha$8; (xv) 1, 2, or 3 amino acid substitutions between $\alpha$8 and $\alpha$9; (xvi) 1, 2, or 3 amino acid substitutions between $\alpha$9 and $\alpha$10; (xvii) 1, 2, or 3, amino acid substitutions in $\alpha$1, $\alpha$2, $\alpha$3, $\alpha$4, $\alpha$5, $\alpha$6, $\alpha$7, $\alpha$8, $\alpha$9, or $\alpha$10; and/or (xviii) 1, 2, or 3 amino acid substitutions in $\beta$1, $\beta$2, $\beta$3, $\beta$4, $\beta$5, $\beta$6, or $\beta$7. In some embodiments, the substitutions are conservative substitutions. In various embodiments, the polypeptide comprises a cysteine substitution within $\beta$1, between 31 and $\alpha$1, within $\alpha$1, between 32 and $\alpha$2, between $\beta$32 and $\alpha$3, within $\beta$4, within $\alpha$5, within $\alpha$6, within $\beta$5, within $\alpha$7, or between $\alpha$8 and $\alpha$9.

The ligand-binding polypeptide may further comprise 1, 2, or more iron binding sites. In some embodiments, said iron comprises Fe(I), Fe(II), or Fe(III).

In embodiments, a biosensor comprises a modified mhFeBP1. In non-limiting examples, the modified mhFeBP1 may comprise one or more, or any combination of the following substitutions compared to its naturally occurring counterpart: Y10X, Q12X, Y14X, L15X, A36X, D37X, V59X, C135X, R137X, N141X, S142X, G178X, C191X, N197X, N267X, and E269X, where X is any amino acid, an amino acid that results in a conservative substitution, or a cysteine, and where each position is counted in mhFeBP1 with the signal peptide replaced with a methionine (SEQ ID NO: 21 or 81). The sequence for mhFeBP1 (SEQ ID NO: 21 or 81) comprises C135A and C191A mutations. In some embodiments, the modified mhFeBP1 comprises 1, 2, 3, 4, 5, 6, 7, 8, 9, 10, 11, 12, 13, 14, 15, or 16 of the following substitutions: Y10C, Y10A, Y10M, Y10F, Y10I, Y10E, Y10W, Q12C, Y14C, L15C, A36C, D37A, D37F, D37Y, D37C, V59C, C135A, R137C, N141C, N141A, N141F, N141Y, N141W, N141Q, N141E, N141V, S142C, G178C, C191A, N197C, N267C, and E269C.

In embodiments, a biosensor comprises a modified exiFeBP2. In non-limiting examples, the modified exiFeBP2 may comprise one or more, or any combination of the following substitutions compared to its naturally occurring counterpart: S9X, H11X, D13X, V14X, G35X, K36X, A59X, R136X, N140X, M141X, N177X, N196X, N269X, and E271X, where X is any amino acid, an amino acid that results in a conservative substitution, or a cysteine, and where each position is counted in exiFeBP2 with the signal peptide replaced with a methionine (SEQ ID NO: 22 or 82). In some embodiments, the modified exiFeBP2 comprises 1, 2, 3, 4, 5, 6, 7, 8, 9, 10, 11, 12, 13 or 14 of the following substitutions: S9C, S9A, S9M, S9F, S9I, S9E, S9W, H11C, D13C, V14C, G35C, K36C, K36A, K36F, K36Y, A59C, R136C, N140C, N140A, N140F, N140Y, N140W, N140Q, N140E, N140V, M141C, N177C, N196C, N269C, and E271C.

In embodiments, a biosensor comprises a modified teFeBP3. In non-limiting examples, the modified teFeBP3 may comprise one or more, or any combination of the following substitutions compared to its naturally occurring counterpart: A8X, H10X, D12X, T13X, E35X, A36X, V58X, R135X, N139X, I140X, N176X, C184X, N195X, N268X, and E270X, where X is any amino acid, an amino acid that results in a conservative substitution, or a cysteine, and where each position is counted in teFeBP3 with the signal peptide replaced with a methionine (SEQ ID NO: 23 or 83). The sequence for teFeBP3 (SEQ ID NO: 23 or 83) comprises a C184S mutation.

In some embodiments, the modified teFeBP3 comprises 1, 2, 3, 4, 5, 6, 7, 8, 9, 10, 11, 12, 13, 14, or 15 of the following substitutions: A8C, A8S, A8M, A8F, A81, A8E, A8W, H10C, D12C, T13C, E35C, A36C, A36K, A36F, A36Y, V58C, R135C, N139C, N139A, N139F, N139Y, N139W, N139Q, N139E, N139V, I140C, N176C, C184A, C184S, N195C, N268C, and E270C.

In embodiments, a biosensor comprises a modified cnFeBP4. In non-limiting examples, the modified cnFeBP4 may comprise one or more, or any combination of the following substitutions compared to its naturally occurring counterpart: G8X, A10X, R12X, L13X, S34X, G35X, N58X, P135X, S139X, E140X, K176X, N195X, D264X, and E266X, where X is any amino acid, an amino acid that results in a conservative substitution, or a cysteine, and where each position is counted in cnFeBP4 with the signal peptide replaced with a methionine (SEQ ID NO: 24 or 84). In some embodiments, the modified cnFeBP4 comprises 1, 2, 3, 4, 5, 6, 7, 8, 9, 10, 11, 12, 13, or 14 of the following substitutions: G8C, G8A, G8M, G8F, G81, G8E, G8W, A10C, R12C, L13C, S34C, G35C, G35K, G35F, G35Y, N58C, P135C, S139C, S139A, S139F, S139Y, S139W, S139Q, S139E, S139V, E140C, K176C, N195C, D264C, and E266C. ttFeBP5 is a non-limiting reference protein respect to bicarbonate-binding proteins. An alignment of ttFeBP5 with other polypeptides (SEQ ID NO: 201-204) is provided in FIG. 6B.

In various embodiments, a ligand-binding protein (or its naturally occurring counterpart) comprises

- (a) an amino acid sequence that is preferably (i) at least about 10%, 11%, 12%, 13%, 14%, 15%, 16%, 17%, 18%, 19%, 20%, 21%, 22%, 23%, 24%, 25%, 26%, 27%, 28%, 29%, or 30%, and (ii) less than about 75%, 70%, 65%, 60%, 55%, 50%, 45%, 44%, 43%, 42%, 41%, 40%, 39%, 38%, 37%, 36%, or 35% identical to ttFeBP5;
- (b) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 9 of ttFeBP5;
- (c) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 9 of ttFeBP5;
- (d) a stretch of amino acids in the sequence YXGR (where X is any amino acid, or where X is S or T) (SEQ ID NO: 163);
- (e) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 53 of ttFeBP5;
- (f) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 53 of ttFeBP5;
- (g) a stretch of amino acids in the sequence SPAD (SEQ ID NO: 164);
- (h) a cysteine substitution (compared to its naturally occurring counterpart) within a stretch of at least 5, 10, or 20 amino acids having at least about 50%, 55%, 60%, 65%, 75%, 80%, 85%, 90%, or 95% identity to a stretch of consecutive amino acids including position 135 of ttFeBP5;
- (i) a stretch of at least 4, 5, 6, 7, 8, 9, 10, 11, 12, 13, 14, 15, 20, 25, or 30 amino acids having at least about 50%, 55%, 60%, 65%, 75%, 80%, 85%, 90%, or 95% identity to a stretch of consecutive amino acids including position 135 of ttFeBP5;
- (j) a stretch of amino acids in the sequence $GWX_1PX_2Y$ (where $X_1$ is any amino acid, or where $X_1$ is T or A; and where $X_2$ is any amino acid, or where $X_2$ is T, A, or S) (SEQ ID NO: 165);
- (k) no more than 1, 2, 3, 4, 5, 6, 7, 8, 9, 10, or 15 deleted or inserted amino acids compared to ttFeBP5, not including amino acids added to the N-terminus or C-terminus of the polypeptide compared to its natural counterpart, and including or not including the signal peptide of the natural counterpart of the polypeptide;
- (l) at least 9, 10, 11, 12, or 13, or exactly 9, 10, 11, 12, or 13 α-helices; and/or
- (m) at least 5, 6, 7, 8, or 9, β-strands or exactly 5, 6, 7, 8, or 9 β-strands.

In embodiments, two or more or each of features (b)-(j) above occurs in the polypeptide in the order listed above as the amino acid sequence of the polypeptide is viewed or read from the N-terminus to the C-terminus (with additional features and/or amino acid sequences therebetween). For example, the polypeptide may have an N-terminus, followed by feature (b), (c), or (d), followed by feature (e), (f), or (g), followed by feature (h), (i), or (j), followed by the C-terminus.

The features listed above are not limiting and may be combined with any other relevant features disclosed herein, including those listed below.

In some embodiments the polypeptide comprises the following sequence (SEQ ID NO: 190):

```
XXXMLTXYSGRGXXLVXXLVXQXEX#XXDXXVXVRYXXDX#LLAALQ#EG
DXSPADVFWANTAGALGXAXXXGLLXXLXXXLTXXXXRFXPXXXXWXPVS
XRXRVXAYNXXXXSDX#LPDSX$DLPEXXEEXGXXXRXGWTPXYSSFQDF
!TA$RXXEGEEATXAWLXXMXAAGXXSYPS#XAMX#AIXAGE!DXAXTNH
YY!QRXLGXXXXXXXXXXXXXXXXXXXXXXXXXXXXAXAXXGTXXFXXGD
AGXLALVTGAGXLXTSXXXTXAXRFLRXLLSXXAQX%FAXXXXEYPL!XG
VXXXXX$XPXD#AXXXSPXIDLXKLXD$#PTLDL$R#AGVXL
```

wherein each

X is, individually, any amino acid or is absent,

! is, individually, I or V, $ is, individually, L or M,

% is, individually, F or Y, and

#is, individually, N, D, Q, or E.

In a non-limiting example, the ligand-binding protein comprises an N-terminal domain and a C-terminal domain connected by a flexible hinge, with the ligand-binding site (the ligand binding domain) located in the cleft between the N-terminal and the C-terminal domain.

In some embodiments, the ligand-binding protein comprises, from the N-terminus to the C-terminus: a first β-strand (β1), followed by a first α-helix (α1), followed by a second β-strand (β2), followed by a second α-helix (α2), followed by a third β-strand (β3), followed by a third α-helix (α3), followed by a fourth α-helix (α4), followed by a fourth β-strand (β4), followed by a fifth α-helix (α5), followed by a sixth α-helix (α6), followed by a fifth β-strand (β5), followed by a seventh α-helix (α7), followed by a eighth α-helix (α8), followed by a sixth β-strand (β6), followed by a ninth α-helix (α9), followed by a seventh β-strand (β7), followed by a tenth α-helix (α10), followed by an eleventh α-helix (α1 l), followed by an eighth β-strand (β8), followed by a ninth β-strand (β9), followed by a twelfth α-helix (α12), followed by a thirteenth α-helix (α13). In some embodiments, the polypeptide comprises (i) 1, 2, or 3 amino acid substitutions between 31 and α1; (ii) 1, 2, or 3 amino acid substitutions between α1 and β2; (iii) 1, 2, or 3 amino acid substitutions between 32 and α2; (iv) 1, 2, or 3 amino acid substitutions between α2 and β3; (v) 1, 2, or 3 amino acid substitutions between the 33 and α3; (vi) 1, 2, or 3 amino acid substitutions between α3 and α4; (vii) 1, 2, or 3 amino acid substitutions between α4 and β4; (viii) 1, 2, or 3 amino acid substitutions between β4 and α5; (ix) 1, 2, or 3 amino acid substitutions between α5 and α6; (x) 1, 2, or 3 amino acid substitutions between α6 and β5; (xi) 1, 2, or 3 amino acid substitutions between 35 and α7; (xii) 1, 2, or 3 amino acid substitutions between α7 and α8; (xiii) 1, 2, or 3 amino acid substitutions between α8 and β6; (xiv) 1, 2, or 3 amino acid substitutions between 36 and α9; (xv) 1, 2, or 3 amino acid substitutions between α9 and β7; (xvi) 1, 2, or 3 amino acid substitutions between 37 and α10; (xvii) 1, 2, or 3 amino acid substitutions between α10 and α11; (xviii) 1, 2, or 3 amino acid substitutions between α11 and β8; (xix) 1, 2, or 3 amino acid substitutions between 38 and β9; (xx) 1, 2, or 3 amino acid substitutions between β9 and α12; (xxi) 1, 2, or 3 amino acid substitutions between α12 and α13; (xxii) 1, 2, or 3, amino acid substitutions in α1, α2, α3, α4, α5, α6, α7, α8, α9, α10, α11, α12, or α13; and/or (xxiii) 1, 2, or 3 amino acid substitutions in β1, β2, β3, β4, β5, β6, β7, β8, or β9. In some embodiments, the substitutions are conservative substitutions. In various embodiments, the polypeptide comprises a cysteine substitution within β1, between β1 and α1, within α1, within β2, within β4, within β5, between 34 and α7, within α7, within β6, within α9, or between α11 and β8.

The ligand-binding polypeptide may further comprise 1, 2, or more iron binding sites. In some embodiments, said iron comprises Fe(I), Fe(II), or Fe(III).

In embodiments, a biosensor comprises a modified ttFeBP5. In non-limiting examples, the modified ttFeBP5 may comprise one or more, or any combination of the following substitutions compared to its naturally occurring counterpart: G10X, G12X, S14X, L15X, S36X, T37X, N60X, V137X, P141X, T142X, S179X, N198X, I263X, and E265X, where X is any amino acid, an amino acid that results in a conservative substitution, or a cysteine, and where each position is counted in ttFeBP5 with the signal peptide replaced with a methionine (SEQ ID NO: 25 or 85). In some embodiments, the modified ttFeBP5 comprises 1, 2, 3, 4, 5, 6, 7, 8, 9, 10, 11, 12 or 13 of the following substitutions: G10C, G10A, G10M, G10F, G10I, G10E, G10W, G12C, S14C, L15C, S36C, T37C, T37K, T37F, T37Y, N60C, V137C, P141C, P141A, P141F, P141Y, P141W, P141Q, P141E, P141V, T142C, S179C, N198C, 1263C, and E265C.

In embodiments, a biosensor comprises a modified msFeBP6. In non-limiting examples, the modified msFeBP6 may comprise one or more, or any combination of the following substitutions compared to its naturally occurring counterpart: G8X, S10X, A12X, L13X, G34X, R35X, N58X, I132X, P136X, T137X, S174X, N193X, V283X, and E285X, where X is any amino acid, an amino acid that results in a conservative substitution, or a cysteine, and where each position is counted in msFeBP6 with the signal peptide replaced with a methionine (SEQ ID NO: 26 or 86). In some embodiments, the modified msFeBP6 comprises 1, 2, 3, 4, 5, 6, 7, 8, 9, 10, 11, 12 or 13 of the following substitutions: G8C, G8A, G8M, G8F, G81, G8E, G8W, S10C, A12C, L13C, G34C, R35C, R35K, R35F, R35Y, N58C, I132C, P136C, P136A, P136F, P136Y, P136W, P136Q, P136E, P136V, T137C, S174C, N193C, V283C, and E285C.

In embodiments, a biosensor comprises a modified srFeBP7. In non-limiting examples, the modified srFeBP7 may comprise one or more, or any combination of the following substitutions compared to its naturally occurring counterpart: G7X, S9X, A11X, L12X, G33X, T34X, N57X, V131X, P135X, A136X, S174X, N192X, V285X, and E287X, where X is any amino acid, an amino acid that results in a conservative substitution, or a cysteine, and where each position is counted in srFeBP7 with the signal peptide replaced with a methionine (SEQ ID NO: 27 or 87). In some embodiments, the modified srFeBP7 comprises 1, 2, 3, 4, 5, 6, 7, 8, 9, 10, 11, 12 or 13 of the following substitutions: G7C, G7A, G7M, G7F, G7I, G7E, G7W, S9C, A11C, L11C, G33C, T34C, T34K, T34F, T34Y, N57C, V131C, P135C, P135A, P135F, P135Y, P135W, P135Q, P135E, P135V, A136C, S174C, N192C, V285C, and E287C.

In embodiments, a biosensor comprises a modified hlFeBP8. In non-limiting examples, the modified hlFeBP8 may comprise one or more, or any combination of the following substitutions compared to its naturally occurring counterpart: G7X, G9X, F11X, L12X, A34X, G35X, V58X, L129X, P133X, S134X, C138X, D171X, C176C, N190X, T256X, and E258X, where X is any amino acid, an amino acid that results in a conservative substitution, or a cysteine, and where each position is counted in hlFeBP8 with the signal peptide replaced with a methionine (SEQ ID NO: 28 or 88). The sequence for hlFeBP8 (SEQ ID NO: 28 or 88) comprises C138A and C176A mutations. In some embodiments, the modified hlFeBP8 comprises 1, 2, 3, 4, 5, 6, 7, 8, 9, 10, 11, 12, 13, 14, or 15 of the following substitutions: G7C, G7A, G7M, G7F, G7I, G7E, G7W, G9C, F11C, L12C, A34X, G35C, G35K, G35F, G35Y, V58C, L129C, P133C, P133A, P133F, P133Y, P133W, P133Q, P133E, P133V, S134C, C138A, D171C, C176A, N190C, T256C, and E258C.

Reporter Group Attachment

Aspects of the present subject matter provide a biosensor that comprises a one or more reporter groups attached to a ligand-binding protein, wherein binding of a ligand to a ligand-binding domain of the ligand-binding protein causes a change in signaling by the reporter group. In various embodiments, the reporter group is attached to an endosteric site, an allosteric site, or a peristeric site of the ligand-binding protein. In embodiments, the reporter group is covalently or noncovalently attached to the ligand-binding protein.

As used herein, "signaling" refers to the emission of energy (which may be referred to as a "signal") by one or more reporter groups. In various implementations, the signal comprises electromagnetic radiation such as a light. In some embodiments, the signal is detected as a complete emission spectrum (or spectrums) or a portion (or portions) thereof. For example, a signal may comprise emitted light at a particular wavelength or wavelengths, or range(s) of wavelengths. In some embodiments, a change in signaling comprises a spectral change (e.g., a spectral shift and/or change in intensity). In some embodiments, a change in signaling comprises a dichromatic shift or a monochromatic fluorescence intensity change.

For convenience and depending on context, a reporter group may be referred to by a name of an unattached form of the reporter group regardless of whether the reporter group is attached to a ligand-binding protein. For example, a compound known as "Compound A" when in an unconjugated form may be referred to herein as "Compound A" when in a form that is attached to a ligand-binding protein. In a specific example, the term "Acrylodan" is used to refer to unreacted/unconjugated Acrylodan, as well as Acrylodan that is conjugated to a ligand-binding protein.

In certain embodiments, a biosensor comprises a reporter group that is conjugated to a ligand-binding protein, and the reporter group is conjugated to an amino acid of the protein that is at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 angstroms (Å) from the ligand when the ligand is bound to the protein. In embodiments, the reporter group is conjugated to an amino acid of the protein that is about 0.1 Å to about 100 Å, about 0.1 Å to about 5 Å, about 5 Å to about 10 Å, about 10 Å to about 20 Å, about 20 Å to about 50 Å, about 50 Å to about 75 Å, or about 75 Å to about 100 Å from the ligand when the ligand is bound to the protein. In some embodiments, the reporter group is conjugated to an amino acid of the protein that is within an α-helix or a β-strand. In some embodiments, the reporter group is conjugated to an amino acid that (i) is not within an α-helix or a β-strand, but is within about 10, 9, 8, 7, 6, 5, 4, 3, 2, or 1 amino acids of an amino acid of the protein's amino acid sequence that is within an α-helix or a β-strand. In some embodiments, the reporter group is conjugated to an amino acid that is in an inter-domain hinge amino acid region between two domains of a protein. In some embodiments, the reporter group is conjugated to an amino acid that is between (i) an α-helix and a β-strand; (ii) two α-helixes; or (iii) two β-strands of a protein. In some embodiments, the reporter group is conjugated to an amino acid (e.g., a cysteine such as a cysteine added by substitution compared to a naturally corresponding polypeptide) between positions 1-25, 25-50, 50-75, 75-100, 100-125, 125-150, 150-175, 175-200, 200-225, 225-250, 250-275, 275-350, 275-300, 275-325, 300-325, 300-350, 300-400, 350-400, 350-400, or 400-450 (inclusive) of a polypeptide (e.g., not including N-terminal fusion proteins compared to the polypeptide's naturally occurring counterpart).

Periplasmic binding proteins are characterized by two lobes connected by a hinge region; ligand bind at a location at the interface between the two domains. Such proteins or engineered versions thereof (as described herein) can adopt two different conformations: a ligand-free open form and a ligand-bound closed form, which interconvert through a relatively large bending motion around the hinge (FIG. 1A; Dwyer et al., 2004, Current Opinion in Structural Biology 12:495-504).

The remarkable adaptability of this superfamily of ligand-binding proteins is likely to have arisen from positioning the location of binding of the ligand at the interface between the lobes and from the large ligand-mediated conformational change. In this arrangement, ligands are placed within an environment that resembles a protein interior, but the residues forming the contact points or contact sites with the ligand are positioned at the surface of the lobes.

Direct signaling relationships between proteins and reporter groups are readily designed by replacing a residue known to form a ligand contact with a cysteine to which the fluorophore is attached ("endosteric" attachment site). Other, indirect signaling relationships can be established in two ways. The first relies on visual inspection of the ligand complex structure, and identifying residues that are located in the vicinity of the binding site, but do not interact directly with the ligand, and that are likely to be involved in conformational changes. Typically, such "peristeric" sites are located adjacent to the residues that form direct contacts with the bound ligand. In the case of the bPBPs, such residues are located at the perimeter of the inter-domain cleft that forms the ligand binding site location. The environment of these peristeric sites changes significantly upon formation of the closed state. These are examples of positions which are proximal to the ligand-binding pocket/domain. The second, most general, approach identifies sites in the protein structure that are located anywhere in the protein, including locations at some distance away from the ligand-binding site (i.e., distal to the ligand-binding pocket/domain), and undergo a local conformational change in concert with ligand binding. If the structures of both the open and closed states are known, then such "allosteric" sites can be identified using a computational method that analyzes the conformational changes that accompany ligand binding (Marvin et al., Proc. Natl. Acad. Sci. USA 94:4366-4371, 1997). Alternatively, once allosteric sites have been identified in one bPBP, modeling and structural homology arguments can be invoked to identify such sites in other bPBPs in which only one state has been characterized (Marvin & Hellinga, J. Am. Chem. Soc. 120:7-11, 1998). This generalized conformational analysis also may identify peristeric and endosteric sites, which were identified and classified by visual inspection.

In non-limiting implementations, the reporter group is attached to the ligand-binding protein via a biotin-avidin interaction. The reporter group may be, e.g., conjugated to biotin and the ligand-binding protein is conjugated to avidin. In an example, the avidin is bound to four biotin molecules wherein each biotin molecule is individually conjugated to a reporter group. Alternatively, the reporter group is conjugated to avidin and the ligand-binding protein is conjugated to biotin. For example, the avidin is bound to four biotin molecules, wherein each biotin molecule is individually conjugated to a ligand-binding protein.

As used herein, "conjugated" means covalently attached. One compound may be directly conjugated to another compound, or indirectly conjugated, e.g., via a linker.

In some embodiments, the reporter group is directly attached to the ligand-binding protein. In various embodiments, the reporter group is attached to an amino acid of the ligand-binding protein that is at least about 2, 4, 6, 8, 10, 11, 12, 13, 14, 15, 16, 17, 18, 19, 20, 25, 30, 35, 40, 45, 50, 55, 60, 65, 70, 75, 80, 85, 90, 95, or 100 angstroms (Å) from the ligand when the ligand is bound to the ligand-binding protein. In certain embodiments, the reporter group is conjugated to an amino acid having a position within positions 1-25, 25-50, 50-75, 75-100, 100-125, 125-150, 150-175, 175-200, 200-225, 225-250, 250-275, or 275-300 of the ligand-binding protein, wherein position 1 is the N-terminal amino acid of the ligand-binding protein. In non-limiting examples, the reporter group is conjugated to an amino acid of the ligand-binding protein that is (a) within an α-helix or a β-strand of the ligand-binding protein; (b) not within an α-helix; (c) not within a β-strand; (d) within about 5 or 10 amino acids of an amino acid that is within an α-helix or β-strand; (e) within a stretch of consecutive amino acids that links two domains of the ligand-binding protein; (f) within a stretch of consecutive amino acids that links an α-helix and a β-strand; (g) within a stretch of consecutive amino acids that links two α-helices; or (h) within a stretch of consecutive amino acids that links two β-strands. In some embodiments, the reporter group is directly attached to the N-terminus or the C-terminus of the ligand-binding protein.

The reporter group may be conjugated to the ligand-binding protein a variety of linkers or bonds, including (but not limited to) a disulfide bond, an ester bond, a thioester bond, an amide bond, or a bond that has been formed by a click reaction. In some embodiments, the click reaction is a reaction between (a) an azide and an alkyne; (b) an azide and an alkyne in the presence of Cu(I); (c) an azide and a strained cyclooctyne; (d) an azide and a dibenzylcyclooctyne, a difluorooctyne, or a biarylazacyclooctynone; (e) a diaryl-strained-cyclooctyne and a 1,3-nitrone; (f) an azide, a tetrazine, or a tetrazole and a strained alkene; (g) an azide, a tetrazine, or a tretrazole and a oxanorbornadiene, a cyclooctene, or a trans-cycloalkene; (h) a tetrazole and an alkene; or (i) a tetrazole with an amino or styryl group that is activated by ultraviolet light and an alkene. These exemplary click chemistry reactions have high specificity, efficient kinetics, and occur in vivo under physiological conditions. See, e.g., Baskin et al. Proc. Natl. Acad. Sci. USA 104(2007):16793; Oneto et al. Acta biomaterilia (2014); Neves et al. Bioconjugate chemistry 24(2013):934; Koo et al. Angewandte Chemie 51(2012):11836; Rossin et al. Angewandte Chemie 49(2010):3375, and U.S. Patent Application Publication No. 20160220686, published Aug. 4, 2016, the entire content of each of which is incorporated herein by reference. For a review of a wide variety of click chemistry reactions and their methodologies, see e.g., Nwe K and Brechbiel M W, 2009 Cancer Biotherapy and Radiopharmaceuticals, 24(3): 289-302; Kolb H C et al., 2001 Angew. Chem. Int. Ed. 40: 2004-2021. The entire contents of each of the foregoing references are incorporated herein by reference.

As used herein, the term "linker" refers to a molecule or sequence (such as an amino acid sequence), that attaches, as in a bridge, one molecule or sequence to another molecule or sequence. "Linked" means attached or bound by covalent bonds, or non-covalent bonds, or other bonds, such as van der Waals forces. In some embodiments, a linker comprises a chemical structure that has resulted from a reaction used to attach one molecule to another.

In various implementations of the present subject matter, the reporter group is conjugated to a cysteine of the ligand-binding protein. The cysteine may be present in the amino acid sequence of a natural counterpart or version of the ligand-binding protein or added to the ligand-binding protein by a substitution mutation in a coding sequence or by altering the sequence synthetically using known chemical means. In some embodiments, the cysteine is at the N-terminus or the C-terminus of the ligand-binding protein. In some embodiments, the cysteine is no more than about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein. In some embodiments, the cysteine is at least about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein.

Non-limiting examples relate to the conjugation of a reporter group to a primary amine of the ligand-binding protein. In certain embodiments, the primary amine is present in a lysine of the ligand-binding protein. The lysine may be present in the amino acid sequence of a natural counterpart or version of the ligand-binding protein or added to the ligand-binding protein by a substitution mutation in a coding sequence or by altering the sequence synthetically using known chemical means. In some embodiments, the lysine is at the N-terminus or the C-terminus of the ligand-binding protein. In some embodiments, the lysine is no more than about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein. In some embodiments, the lysine is at least about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 5-15, 5-20, 5-25, 5-100, 10-15, 10-20, 10-25, 10-50, 10-100, 25-50, 25-75, or 25-100 amino acids from the N-terminus or the C-terminus of the ligand-binding protein.

Aspects of the present subject matter provide a biosensor in which the reporter group is attached to the ligand-binding protein via a linker. In some embodiments, the linker comprises an organic compound that is less than about 30, 20, 15, or 10 Å long. Non-limiting examples of linkers include O, S, NH, PH, and alkyl linkers.

"Alkyl," as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The ranges provided above are inclusive of all values between the minimum value and the maximum value. The term "alkyl" includes both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety. Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. The alkyl groups may also contain one or more heteroatoms within the carbon backbone. Preferably the heteroatoms incorporated into the carbon backbone are oxygen, nitrogen, sulfur, and combinations thereof. In certain embodiments, the alkyl group contains between one and four heteroatoms.

In some embodiments, the linker comprises a bond formed by a chemical reaction involving a reactive group such as a maleimide group. Alternatively or in addition, the linker comprises a stretch of amino acids. In a non-limiting example, the linker comprises a polyglycine linker. In embodiments, the polyglycine linker comprises 2, 3, 4, 5, or more glycines. Optionally, the polyglycine linker further comprises a serine.

In various implementations, the reporter group is attached to a linker via a covalent bond and the linker is attached to a ligand-binding protein via a covalent bond. In embodiments, the covalent bond between the linker and the reporter group and/or the covalent bond between the linker and the ligand-binding protein is a disulfide bond, an ester bond, a thioester bond, an amide bond, a carbamate bond, or a bond that has been formed by a click reaction. Non-limiting examples of click reactions include reactions between an azide and an alkyne; an azide and an alkyne in the presence of Cu(I); an azide and a strained cyclooctyne; an azide and a dibenzylcyclooctyne, a difluorooctyne, or a biarylazacyclooctynone; a diaryl-strained-cyclooctyne and a 1,3-nitrone; an azide, a tetrazine, or a tetrazole and a strained alkene; an azide, a tetrazine, or a tretrazole and a oxanorbornadiene, a cyclooctene, or a trans-cycloalkene; a tetrazole and an alkene; or a tetrazole with an amino or styryl group that is activated by ultraviolet light and an alkene.

Reporter Groups

Various types of reporter groups may be used in embodiments of the present subject matter. For example, the reporter group may comprise a fluorophore that produces a fluorescent signal. Biosensors comprising a fluorophore may be referred to herein as fluorescently responsive sensors (FRSs).

Preferably, the binding of ligand to an FRS results in a change in ratiometric ΔR in the signal from a reporter group. A ratiometric signal ($R_{1,2}$) is defined as the quotient of two intensities, $I_{\lambda 1}$ and $I_{\lambda 2}$, measured at two independent wavelengths, $\lambda_1$ and $\lambda_2$ and may be calculated according to the following equation:

$$R_{1,2}=I_{\lambda 1}/I_{\lambda 2}$$

In some embodiments, intensities are, e.g., integrated, filtered, assessed, detected, or evaluated over a range of wavelengths. In some embodiments, intensities are integrated over a range of wavelengths in a recorded emission spectrum. In some embodiments, a range of wavelengths is selected using a filter. In some embodiments, $\lambda_1$ is the intensity over a 1 nm to 60 nm interval centered between 400 and 1000 nm, and $\lambda_2$ is the intensity over a 1 nm to 60 nm interval centered between 400 nm and 1000 nm. In some embodiments, intensities are integrated, filtered, assessed, detected, or evaluated over a 1 nm, 2 nm, 10 nm, 15 nm, 20 nm, 25 nm, 30 nm, 35 nm, 40 nm, 45 nm, 50 nm, 55 nm, 60 nm, 75 nm, 100 nm, 10-40 nm, 10-50 nm, 20-50 nm, or 10-100 nm regions, centered between 400-1000 nm, e.g. between 420 nm and 520 nm for $\lambda_1$, and 400-1000 nm, e.g. between 500 nm to 600 nm for $\lambda_2$. In some embodiments, intensities are recorded through a bandpass filter. A non-limiting example of a bandpass filter is a 10 nm, 15 nm, 20 nm, 25 nm, 30 nm, 35 nm, 40 nm, 45 nm, 50 nm, 75 nm, 100 nm, 10-40 nm, 10-50 nm, 20-50 nm, or 10-100 nm bandpass filter, centered between 400-1000 nm, e.g. at 452 nm for $\lambda_1$ and at 400-1000 nm, e.g. at 528 nm ($\lambda_2$).

Aspects of the present subject matter provide FRSs whose emission spectra change (e.g., the shape of the emission spectra change) in response to ligand binding. In various embodiments, the ratio of intensities at two chosen wavelengths of an FRS's emission spectrum changes upon ligand binding. In some embodiments, the emission spectral shape and/or intensity of the fluorophore changes when the position of atoms within the fluorophore changes with respect to each other (e.g., due to the rotation of bound atoms with respect to each other or a change in the angle of a bond). In non-limiting examples, the emission spectral shape and/or intensity of the fluorophore changes when (i) one portion of the fluorophore rotates around a bond axis compared to another portion of the fluorophore and/or (ii) when the angle of a bond between two atoms of the fluorophore changes. In a non-limiting example, the fluorophore is a prodan-derived fluorophore (e.g., Acrylodan or Badan) and binding of ligand alters the orientation of a dimethylamino group, a naphthalene ring, and/or a carbonyl with respect to the ligand-binding protein and/or each other. In a non-limiting example, the degree of polarization of a dipole on the fluorophore changes in response to ligand binding. In various embodiments, the emission spectral shape and/or intensity of the fluorophore changes when an atom electrostatically interacts with the fluorophore. For example, the emission spectral shape and/or intensity of the fluorophore changes when the source of a positive or negative charge changes its distance with respect to the fluorophore within about 1, 2, 3, 4, 5, or 10 Å of the fluorophore. In some embodiments, the fluorophore exhibits hypsochromicity or bathochromicity upon ligand binding to the ligand-binding domain of the ligand-binding protein. In certain embodiments, the fluorophore has an emission spectrum comprising radiation with a wavelength (e.g., a peak emission wavelength) of about 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm, 800 nm, 850 nm, 900 nm, 950 nm, or 1000 nm, or about 400 nm to about 450 nm, about 450 nm to about 500 nm, about 500 nm to about 550 nm, about 550 nm to about 600 nm, about 600 nm to about 650 nm, about 650 to about 700 nm, about 700 nm to about 750 nm, about 750 nm to about 800 nm, or about 800 nm to about 1000 nm.

In some embodiments, the signal comprises the emission intensity of the fluorophore recorded at a single wavelength or range of wavelengths. The change in signal may be a shift in the single wavelength or range of wavelengths. In some embodiments, the shift in the wavelength is at least about 1 nm, at least about 2 nm, at least about 3 nm, at least about 4 nm, at least about 5 nm, at least about 6 nm, at least about 7 nm, at least about 8 nm, at least about 9 nm, at least about 10 nm, at least about 11 nm, at least about 12 nm, at least about 13 nm, at least about 14 nm, at least about 15 nm, at least about 16 nm, at least about 17 nm, at least about 18 nm, at least about 19 nm, at least about 20 nm, at least about 25 nm, at least about 30 nm, at least about 35 nm, at least about 40 nm, at least about 45 nm, at least about 50 nm, at least about 55 nm, at least about 60 nm, at least about 65 nm, at least about 70 nm, at least about 75 nm, at least about 80 nm, at least about 85 nm, at least about 90 nm, at least about 95 nm, at least about 100 nm, at least about 105 nm, at least about 110 nm, at least about 115 nm, at least about 120 nm, at least about 125 nm, or at least about 130 nm. In some embodiments, the shift in the wavelength is about 1 nm to about 20 nm, about 2 nm to about 20 nm, about 3 nm to about 20 nm, about 4 nm to about 20 nm, about 5 nm to about 20 nm, about 1 nm to about 19 nm, about 1 nm to about 18 nm, about 1 nm to about 17 nm, 1 nm to about 16 nm, about 1 nm to about 15 nm, about 1 nm to about 14 nm, about 1 nm to about 13 nm, about 1 nm to about 12 nm, about 1 nm to about 11 nm, or about 1 nm to about 10 nm. In some embodiments, the shift in the wavelength is about 1 nm to about 20 nm. In some embodiments, the shift in the wavelength is about 1 nm to about 130 nm.

In certain embodiments, the signal comprises the ratio or quotient of the emission intensities recorded at two distinct wavelengths or ranges of wavelengths, i.e., a ratiometric signal. For example, as shown in FIGS. 1A-D, ligand binding may be determined by measuring the ratio of blue to green emission intensities. The change in signal may be decreased emission intensity at one wavelength, and no change in emission intensity at the other wavelength. The change in signal may be increased emission intensity at one wavelength, and no change in emission intensity at the other wavelength. The change in signal may be increased emission intensity at one wavelength, and increased emission intensity at the other wavelength. The change in signal may be decreased emission intensity at one wavelength, and decreased emission intensity at the other wavelength. The change in signal may be increased emission intensity at one wavelength, and decreased emission intensity at the other wavelength. In some embodiments, the change in ratio of the emission intensities recorded at two distinct wavelengths or ranges of wavelengths may be at least about 1.1-fold, at least about 1.2-fold, at least about 1.4-fold, at least about 1.6-fold, at least about 1.8-fold, at least about 2.0-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 12-fold, at least about 14-fold, at least about 16-fold, at least about 18-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, or at least about 100-fold. In some embodiments, the change in ratio of the emission intensities recorded at two distinct wavelengths or ranges of wavelengths may be a decrease of at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%, or of 5-25%, 25-50%, 25-75%, 50-75%, 50-90%, or 75-99% or the reciprocal thereof.

The change in signal may be a change in the ratio of the two distinct wavelengths or ranges of wavelengths. The change in signal may be a shift in the two distinct wavelengths or ranges of wavelengths. In some embodiments, one wavelength shifts. In some embodiments, both wavelengths shift. In some embodiments, the shift in the wavelength is at least about 1 nm, at least about 2 nm, at least about 3 nm, at least about 4 nm, at least about 5 nm, at least about 6 nm, at least about 7 nm, at least about 8 nm, at least about 9 nm, at least about 10 nm, at least about 11 nm, at least about 12 nm, at least about 13 nm, at least about 14 nm, at least about 15 nm, at least about 16 nm, at least about 17 nm, at least about 18 nm, at least about 19 nm, at least about 20 nm, at least about 25 nm, at least about 30 nm, at least about 35 nm, at least about 40 nm, at least about 45 nm, at least about 50 nm, at least about 55 nm, at least about 60 nm, at least about 65 nm, at least about 70 nm, at least about 75 nm, at least about 80 nm, at least about 85 nm, at least about 90 nm, at least about 95 nm, at least about 100 nm, at least about 105 nm, at least about 110 nm, at least about 115 nm, at least about 120 nm, at least about 125 nm, or at least about 130 nm. In some embodiments, the shift in the wavelength is about 1 nm to about 20 nm, about 2 nm to about 20 nm, about 3 nm to about 20 nm, about 4 nm to about 20 nm, about 5 nm to about 20 nm, about 1 nm to about 19 nm, about 1 nm to about 18 nm, about 1 nm to about 17 nm, 1 nm to about 16 nm, about 1 nm to about 15 nm, about 1 nm to about 14 nm, about 1 nm to about 13 nm, about 1 nm to about 12 nm, about 1 nm to about 11 nm, or about 1 nm to about 10 nm. In some embodiments, the shift in the wavelength is about 1 nm to about 20 nm. In some embodiments, the shift in the wavelength is about 1 nm to about 130 nm.

A fluorophore may comprise, e.g., a fluorescent protein or an organic compound having a molecular weight less than about 2000 Daltons (Da). Non-limiting examples of commercially available fluorophores include such as 5-iodoacetamidofluorescein (5-IAF) or 6-iodoacetamidofluorescein (6-IAF), rhodamine, Oregon Green, eosin, Texas Red, indocarbocyanine, oxacarbocyanine, thiacarbocyanine, merocyanine, Badan, Acrylodan, IAEDANS, comprising 3-cyano-7-hydroxycoumarin, 7-hydroxycoumarin-3-carboxylic acid, 6,8-difluoro-7-hydroxy-4-methylcoumarin, or 7-amino-4-methylcoumarin, pyridyloxazole, nitrobenzoxadiazole, benzoxadiazole, DRAQ5, DRAQ7, or CyTRAK Orange, cascade blue, Nile red, Nile blue, cresyl violet, oxazine 170, proflavin, acridine orange, acridine yellow, auramine, crystal violet, malachite green, porphin, phthalocyanine, bilirubin, pyrene, N,N'-dimethyl-N-(iodoacetyl)-N'-(7-nitrobenz-2-ox-a-1,3-diazol-4-yl)ethylenediamide (NBD), N-((2-(iodoacetoxy)ethyl)-N-methy-1)amino-7-nitrobenz-2-oxa-1,3-diazole (NBDE), JPW4039, JPW4042, JPW4045, Pacific Blue, CPM, N,N'-Dimethyl-N-(Iodoacetyl)-N'-(7-Nitrobenz-2-Oxa-1,3-Diazol-4-yl)Ethylenediamine (IANBD), 7-diethylamino-3-(4'-maleimidylphenyl)-4-methylcoumarin (CPM), BODIPY 499, BODIPY 507/545, BODIPY 499/508, Alexa 432, Alexa488, Alexa532, Alexa546, Cy5, or 1-(2-maleimidylethyl)-4-(5-(4-methoxyphenyl)oxazol-2-yl)pyridinium methanesulfonate (PyMPO maleimide) (PyMPO). In various embodiments, the reporter group was thiol-reactive prior to being conjugated to a polypeptide disclosed herein. In embodiments, the reporter group is linked to a polypeptide disclosed herein via a disulfide bond. Additional non-limiting examples of commercially available fluorophores include fluorescent proteins such as Blue Fluorescent Protein (BFP), TagBFP, mTagBFP2, Azurite, Enhanced Blue Florescent Protein 2 (EBFP2), mKalamal, Sirius, Sapphire, T-Sapphire, Cyan Fluorescent Protein (CFP); Enhanced Cyan Fluorescent Protein (ECFP), Cerulean, SCFP3A, mTurquoise, mTurquoise2, monomeric Midoriishi-Cyan, TagCFP, mTFP1, AmCyan1, Green Fluorescent Protein (GFP), Enhanced Green Fluorescent Protein (EGFP), Emerald, Superfolder GFP, AcGFP1, ZsGreenl, Monomeric Azami Green, TagGFP2, mUKG, mWasabi, Clover, mNeonGreen, Yellow Fluorescent Protein (YFP), Enhanced Yellow Fluorescent Protein (EYFP), Citrine, Venus, Super Yellow Fluorescent Protein 2 (SYFP2), TagYFP, ZsYellowl, mBanana, Orange Fluorescent Protein (OFP), Monomeric Kusabira-Orange (mKO), mKOκ, mKO2, mOrange, mOrange2, Red Fluorescent Protein (RFP), DsRed-Express, DsRed-Express2, DsRed2, AsRed2, mRaspberry, mCherry, mStrawberry, mTangerine, tdTomato, TagRFP, TagRFP-T, mApple, mRuby, mRuby2, mPlum, HcRed-Tandem, mKate2, mNeptune, HcRedl, E2-Crimson, NirFP, TagRFP657, IFP1.4, or iRFP.

In some embodiments, the fluorophore comprises xanthene, a xanthene derivative, cyanine, a cyanine derivative, squaraine, a squaraine derivative, naphthalene, a naphthalene derivative, coumarin, a coumarin derivative, oxadiazole, an oxadiazole derivative, anthracene, an anthracene derivative, a boradiazaindacine (BODIPY) family fluorophore, pyrene, a pyrene derivative, acridine, an acridine derivative, arylmethine, an arylmethine derivative, tetrapyrrole, or a tetrapyrrole derivative. For example, the fluorophore may comprise a xanthene derivative comprising fluorescein or a fluorescein derivative, rhodamine, Oregon Green, eosin, or Texas Red. Non-limiting examples of fluorescein derivatives include 5-fluorescein, 6-carboxyfluorescein, 3'6-carboxyfluorescein, 5(6)-carboxyfluorescein, 6-hexachlorofluorescein, 6-tetrachlorofluorescein, or isothiocyanate. In some embodiments, the fluorophore comprises a cyanine derivative comprising indocarbocyanine, oxacarbocyanine, thiacarbocyanine, or merocyanine. In certain embodiments, the fluorophore comprises a squaraine derivative comprising a ring-substituted squaraine. In various embodiments, the fluorophore comprises a naphthalene derivative comprising a dansyl or prodan naphthalene derivative. In a non-limiting example, the fluorophore comprises prodan or a derivative thereof. In certain embodiments, the fluorophore comprises Badan, Acrylodan, or N-(Iodoacetaminoethyl)-1-naphthylamine-5-sulfonic acid (IAEDANS). In some embodiments, the fluorophore comprises a coumarin derivative such as 3-cyano-7-hydroxycoumarin, 7-hydroxycoumarin-3-carboxylic acid, 6,8-difluoro-7-hydroxy-4-methylcoumarin (DiFMU), or 7-amino-4-methylcoumarin. In various embodiments, the fluorophore comprises an oxadiazole derivative such as pyridyloxazole, nitrobenzoxadiazole, or benzoxadiazole. In certain embodiments, the fluorophore comprises an anthracene derivative comprising an anthraquinone such as DRAQ5, DRAQ7, or CyTRAK Orange. In various embodiments, the fluorophore comprises a pyrene derivative comprising cascade blue. In non-limiting examples the fluorophore comprises an oxazine derivative such as Nile red, Nile blue, cresyl violet, or oxazine 170. In some embodiments, the fluorophore comprises an acridine derivative such as proflavin, acridine orange, or acridine yellow. In certain embodiments, the fluorophore comprises an arylmethine derivative such as auramine, crystal violet, or malachite green. In various embodiments, the fluorophore comprises a tetrapyrrole derivative comprising porphin, phthalocyanine, or bilirubin.

Aspects of the present subject matter relate to the use of fluorophores that may readily be attached to a ligand-binding protein disclosed herein, e.g., at a cysteine residue. For example, a fluorophore may comprise a sulfhydryl group prior to attachment to a ligand-binding protein that is reacted with a moiety of the ligand-binding protein to attach the fluorophore to the ligand-binding protein. In some embodiments, the fluorophore comprised a thiol group prior to attachment to the ligand-binding protein. For example, the fluorophore was thiol reactive prior to attachment to the ligand-binding protein. Non-limiting examples of fluorophores that may readily be attached to ligand-binding proteins using thiol reactions include fluorescein, pyrene, NBD, NBDE, Acrylodan (6-acryloyl 1-2-dimethylaminonaphthalene), Badan (6-bromo-acetyl-2-dimethylamino-naphthalene), JPW4039, JPW4042, or JPW4045.

In certain embodiments, the fluorophore comprises a derivative of a Prodan-based fluorophore such as Acrylodan or Badan. The excitation and emission properties of the Prodan-based fluorophores Acrylodan and Badan can be altered by manipulating the fluorescent ring system, while preserving the dimethylamino donor group, and the twistable carbonyl acceptor (Klymchenko 2013 *Progress in Molecular Biology and Translational Science,* 35-58). Replacement of the two-ring naphthalene with a three-ring anthracene (Lu 2006 *J. Org. Chem.,* 71, 9651-9657), fluorene (Kucherak 2010 *J. Phys. Chem. Lett.,* 1, 616-620), pyrene (Niko 2013 *Chem. Eur. J.,* 19, 9760-9765), or styrene (Benedetti 2012 *J. Am. Chem. Soc.,* 134, 12418-12421) cores significantly red-shift the excitation and emission properties, and in the case of the latter two, improve brightness through improvements in their excitation peak extinction coefficients. The entire content of each of the references cited above (as well as all other references referred to herein including the contents of nucleic acid and amino acid sequence accession number references) are incorporated herein by reference. Non-limiting examples of prodan analogues include 2-cyano-6-dihexylaminoanthracene and 2-propionyl-6-dihexylaminoanthracene, as well as fluorophores comprising the following structures:

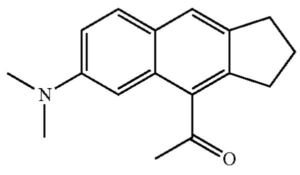
,
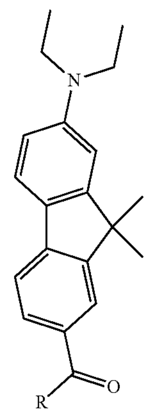
, or
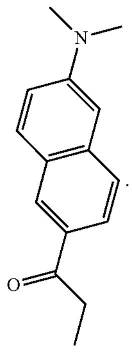
.

In some embodiments, the fluorophore comprises a fluorescent protein. Fluorescent proteins that emit blue, cyan, green, yellow, orange, red, far-red, or near infrared radiation when contacted with excitation radiation are known in the art and commercially available as proteins and via the expression of vectors that encode the fluorescent protein. Non-limiting examples of fluorescent proteins include Blue Fluorescent Protein (BFP), TagBFP, mTagBFP2, Azurite, Enhanced Blue Florescent Protein 2 (EBFP2), mKalamal, Sirius, Sapphire, T-Sapphire, Cyan Fluorescent Protein (CFP); Enhanced Cyan Fluorescent Protein (ECFP), Cerulean, SCFP3 Å, mTurquoise, mTurquoise2, monomeric Midoriishi-Cyan, TagCFP, mTFP1, AmCyan1, Green Fluorescent Protein (GFP), Enhanced Green Fluorescent Protein (EGFP), Emerald, Superfolder GFP, AcGFP1, ZsGreenl, Monomeric Azami Green, TagGFP2, mUKG, mWasabi, Clover, mNeonGreen, Yellow Fluorescent Protein (YFP), Enhanced Yellow Fluorescent Protein (EYFP), Citrine, Venus, Super Yellow Fluorescent Protein 2 (SYFP2), TagYFP, ZsYellowl, mBanana, Orange Fluorescetn Protein (OFP), Monomeric Kusabira-Orange (mKO), mKOκ, mKO2, mOrange, mOrange2, Red Fluorescent Protein (RFP), DsRed-Express, DsRed-Express2, DsRed2, AsRed2, mRaspberry, mCherry, mStrawberry, mTangerine, tdTomato, TagRFP, TagRFP-T, mApple, mRuby, mRuby2, mPlum, HcRed-Tandem, mKate2, mNeptune, HcRedl, E2-Crimson, NirFP, TagRFP657, IFP1.4, or iRFP.

In some embodiments, the fluorophore comprises a quantum dot (Medintz et al. 2005) (Sapsford, Berti and Medintz 2006 Angew Chem Int Ed Engl, 45, 4562-89; Resch-Genger et al. 2008 Nat Methods, 5, 763-75). In some embodiments the emission properties of the conjugated protein are enhanced by immobilization on or near metallic nanoparticles (Zeng et al. 2014 *Chem Soc Rev,* 43, 3426-52; Shen et al. 2015 Nanoscale, 7, 20132-41).

In various embodiments, the peak emission wavelength and/or the emission intensity of the biosensor change when the ligand binds to the ligand-binding protein. In some embodiments, the biosensor exhibits a dichromatic signaling change when the ligand binds to the ligand-binding protein. In various embodiments, the peak emission wavelength of the biosensor shifts by at least about 5, 10, 15, 20, 30, 40, 50, or by about 5-50 nm when the biosensor binds to ligand. In certain embodiments, the emission intensity of the biosensor increases by at least about 5%, 10%, 20%, 30%, 40%, 50%, 60%, 70%, 80%, 90%, 100%, 150%, 200%, or 300% when the biosensor binds to ligand. In various embodiments, the signal produced by the reporter group persists for at least 1 nanoseconds (ns), 5 ns, 10 ns, 25 ns, 50 ns, 75 ns, 100 ns, 200 ns, 300 ns, 400 ns, 500 ns, 600 ns, 700 ns, 800 ns, 900 ns, 0.001 milliseconds (ms), 0.01 ms, 0.1 ms, 1 ms, 5 ms, 10 ms, 20 ms, 25 ms, 50 ms, 100 ms, or 500 ms when the ligand binds to the ligand-binding protein.

Ratiometric Sensing with Fluorescence Energy Transfer

The present subject matter provides methods for converting monochromatic responses into dichromatic responses that enable ratiometric sensing. If the fluorescence emission spectrum changes shape in response to analyte binding such that the ratio of emission intensities at two appropriately chosen wavelengths reports on analyte concentration (dichromatic response), then ratiometric measurements can be used to monitor analyte concentrations. In embodiments, these methods are based on establishing non-geometrically modulated Forster resonance energy transfer (ngmFRET) between a fluorophore (a directly responsive partner), and a second fluorophore that neither interacts directly with the ligand, nor is sensitive to ligand-mediated changes in its environment (an indirectly responsive partner). Biosensors that undergo ngmFRET (or altered ngmFRET) upon ligand binding are also provided herein, as well as compositions and devices comprising such biosensors.

Methods, compounds, and compositions provided herein overcome challenges regarding the design of biosensors that produce a ratiometric signal. For example, a biosensor that exhibits a monochromatic response (which does not produce a ratiometric signal) to ligand binding may be converted into a biosensor that produces a dichromatic/ratiometric signal. Moreover, the number of fluorophores that may be utilized in ratiometric biosensors is dramatically increased by the present subject matter. For example, fluorophores that typically do not show a dichromatic response to ligand binding (such as fluorescein and derivatives thereof) may be used together with an additional reporter group (such as another fluorophore) to produce a ratiometric signal. Also included are methods, compounds, and compositions relating to biosensors with multiple reporter groups that have improved ratiometric signals compared to other ratiometric biosensors (e.g., ratiometric biosensors having a single reporter group).

Traditional/conventional geometrically-modulated Fluorescence Resonance Energy Transfer (tgmFRET) is a physical phenomenon that was first described over 50 years ago. In tgmFRET, the transfer of excited state energy from a donor fluorophore to an acceptor fluorophore (i.e. energy transfer) is modulated by a ligand-binding event through changes in the distance and/or angle between the donor and acceptor fluorophores. tgmFRET is manifested by opposing changes in the fluorescence emission intensities of the donor and acceptor fluorophores, respectively, in response to ligand binding. For instance, a decrease in distance results in a decrease of the donor fluorescence emission intensity and an increase in the acceptor fluorescence intensity, as energy is transferred from the former to the latter. A ligand-mediated increase in the distance between the partners has the opposite effect (the fluorescence emission intensity of the donor increases, whereas that of the acceptor decreases). In tgmFRET, ligand-mediated modulation of fluorescence intensity arises from global changes in the entire system, and can occur only if both partners are present.

By contrast, in ngmFRET ligand-mediated modulation of fluorescence intensity arises from changes that are localized to the photophysics of the directly responsive fluorophore. Unlike tgmFRET, ligand-mediated changes in fluorescence therefore occur also if only the directly responsive partner is present in isolation by itself. Although the entire ngmFRET system comprising two partners is not required for evincing ligand-mediated changes in fluorescence emission intensity, the response of such a system is qualitatively changed or quantitatively enhanced over the responses of the isolated directly responsive partner (e.g. converting a monochromatic into a dichromatic response, thereby enabling ratiometry). Furthermore, unlike tgmFRET, the pattern of fluorescence intensity changes manifested by ligand binding in ngmFRET systems are not limited to opposing changes only. Instead, in ngmFRET almost all combinations of emission intensity changes are possible: opposing changes in the two partners, both partners increase, both decrease, one partner remains unchanged whereas the other increases or decreases. The majority of these responses evince changes that are unequal in magnitude and/or direction (i.e. increase, decrease), and accordingly are manifested as ligand-mediated changes in the ratio of the two fluorescence emission intensities. This versatility of ngmFRET system response patterns has great utility in the field of fluorescent biosensors.

The ligand-mediated alteration of the photophysics of the directly responsive partner includes changes to its spectral properties such as the shape of the excitation or emission spectra, and the ratio of radiative to non-radiative emission rates. The fluorescence emission intensity of the indirectly responsive partner in isolation does not change in response to ligand binding; its intensity changes only in the presence of a directly responsive partner in the complete ngmFRET system. In the field fluorescence spectroscopy, the term "quenching" has often been used loosely to refer to a decrease fluorescence emission intensity. However, as used herein, the term "quenching" strictly means a "change in the ratio of radiative to non-radiative emission rates" of a fluorophore.

Aspects of the present subject matter provide biosensors in which ngmFRET occurs between two or more reporter groups (e.g., a donor fluorophore and an acceptor fluorophore) of the biosensor. For example, ngmFRET may change (e.g., increase or decrease) when ligand is bound to the biosensor and a donor fluorophore is contacted with radiation within its excitation wavelength. Effects from tgmFRET and ngmFRET may occur together and be combined into an overall ligand-mediated change in fluorescence emission intensity. In preferred embodiments, less than half or none of the change in overall ligand-mediated change in fluorescence emission intensity is due to tgmFRET. In embodiments, most of the overall ligand-mediated change in fluorescence emission intensity change is not due to a change in the distance between the donor and acceptor fluorophore or as a result of a change in the orientation between the donor and acceptor fluorophore. In non-limiting examples, less than about 25%, 20%, 15%, 10%, 5%, 4%, 3%, 2%, 1%, or 0.5% of the change in overall ligand-mediated change in fluorescence emission intensity is due to tgmFRET. In various embodiments, at least about 70%, 75%, 80%, 85%, 90%, 95%, 96%, 97%, 98%, 99%, 99.5%, 99.9%, or 99.99% of the ligand-mediated change in fluorescence emission intensity is due to ngmFRET. For example, the change in overall ligand-mediated change in fluorescence emission intensity comprises a spectral change (e.g., in the excitation or emission spectrum) and/or a change in the ratio of the radiative to non-radiative decay rates of one of the fluorophores (by itself and regardless of the presence of any other fluorophore/partner) upon ligand binding.

In some embodiments, ligand binding mediates spectral shifts in the absorption or emission spectrum of the directly responsive partner. In certain embodiments such changes are due at least in part to a switch between different excited states in the ligand-free and ligand-bound biosensor. The two excited states are associated with different transition dipoles. This class of changes is termed "dipole switching" herein.

In embodiments, the reporter groups include a directly responsive partner (which may be a donor fluorophore or an acceptor fluorophore) and an indirectly responsive partner (which may be a donor fluorophore or an acceptor fluorophore). Depending on context, a "directly responsive" partner is a fluorophore that responds to (i) ligand-induced protein conformational changes upon ligand binding to a ligand-binding protein; or (ii) ligand binding to the directly responsive partner itself. In some embodiments, the directly responsive partner comprises a fluorophore (i.e., it is a directly responsive fluorophore). In various embodiments, the directly responsive fluorophore exhibits a monochromatic or dichromatic spectral change, and/or a change in the ratio of radiative to non-radiative emission rates, upon ligand binding. In certain embodiments relating to ligand binding to the directly responsive partner itself, the directly responsive partner may be a fluorophore such as a fluorescent protein or a small molecule fluorescent compound. An "indirectly responsive" partner is a fluorophore for which no change in emission spectra, excitation spectra, or change in the ratio of radiative to non-radiative emission rates is caused by ligand binding in the absence of a directly responsive partner. In some embodiments, the indirectly responsive partner comprises a fluorophore (i.e., it is an indirectly responsive fluorophore). When paired with a directly responsive partner with which the indirectly responsive partner is a ngmFRET donor or acceptor, the emission fluorescence intensity of the indirectly responsive partner changes due to a change in energy flow in the ngmFRET pathway upon ligand binding. See, e.g., FIG. 74.

ngmFRET Biosensors

Provided herein are methods, compositions, biosensors, and devices comprising multiple reporter groups, e.g. a directly responsive fluorophore and an indirectly responsive fluorophore, between which ngmFRET occurs.

Aspects include a method of detecting a ligand in a sample, comprising contacting a biosensor with a ligand. In various embodiments, the ligand comprises bicarbonate or $Ca^{2+}$. The biosensor comprises a ligand-binding protein, a directly responsive fluorophore and an indirectly responsive fluorophore. The directly responsive and the indirectly responsive fluorophores are located at two distinct sites of the ligand-binding-protein. In some embodiments, the directly responsive fluorophore is a donor fluorophore and the indirectly responsive fluorophore is an acceptor fluorophore. Alternatively, the directly responsive fluorophore is an acceptor fluorophore and the indirectly responsive fluorophore is a donor fluorophore. The method includes contacting the biosensor with radiation comprising a wavelength within the excitation spectrum of the donor fluorophore. When the biosensor is contacted with such radiation, a fluorescence property of the directly responsive fluorophore changes in response to ligand binding. This change in fluorescent property is independent of the indirectly responsive fluorophore, and occurs regardless of whether the indirectly responsive fluorophore is absent or present. The fluorescence properties of the indirectly responsive fluorophore do not change in response to ligand binding in the absence of the directly responsive fluorophore. When the biosensor is contacted with radiation comprising a wavelength within the excitation spectrum of the donor fluorophore, then (i) ngmFRET occurs between the directly responsive fluorophore and the indirectly responsive fluorophore; (ii) fluorescent light is emitted from the biosensor, and the light emitted from the biosensor comprises a combination of light emitted from the directly responsive fluorophore and light emitted from the indirectly responsive fluorophore; and (iii) the ratio of the fluorescence emission intensity emitted from the biosensor at each of two distinct wavelengths changes in response to ligand binding. In various embodiments, the method further comprises measuring fluorescent light that is emitted from the directly responsive fluorophore and the indirectly responsive fluorophore, and calculating a ratiometric signal to detect the ligand in the sample.

The ratiometric signal (R1,2) comprises a quotient of two intensities, $I_{\lambda1}$ and $I_{\lambda2}$, measured at two independent wavelengths, $\lambda_1$ and $\lambda_2$ and is calculated according to the following equation:

$$R1,2=I_{\lambda1}/I_{\lambda2}.$$

The two independent wavelengths $\lambda_1$ and $\lambda_2$ may be from a single fluorophore or from a combination of two or more fluorophores (e.g., a pair of fluorophores between which ngmFRET occurs). In some embodiments, $\lambda_1$ falls within the emission spectrum of a directly responsive fluorophore and $\lambda_2$ falls within the emission spectrum of an indirectly responsive fluorophore. In certain embodiments, $\lambda_1$ falls within the emission spectrum of an indirectly responsive fluorophore and $\lambda_2$ falls within the emission spectrum of a directly responsive fluorophore. In various embodiments, $\lambda_1$ falls within the emission spectrum of both a directly responsive fluorophore and an indirectly responsive fluorophore. In various embodiments, $\lambda_2$ falls within the emission spectrum of both a directly responsive fluorophore and an indirectly responsive fluorophore.

Aspects of the present subject matter provide FRSs whose emission spectra change (e.g., the shape of the emission spectra change) in response to ligand binding. In various embodiments, the ratio of intensities at two chosen wavelengths of an FRS's emission spectrum changes upon ligand binding.

In various embodiments, the emission spectra of two or more fluorophores contributes to $I_{\lambda 1}$ and/or $I_{\lambda 2}$. In some embodiments, the emission spectrum of a directly responsive fluorophore contributes to $I_{\lambda 1}$ and/or $I_{\lambda 2}$ and the emission spectrum of an indirectly responsive fluorophore contributes to $I_{\lambda 1}$ and/or $I_{\lambda 2}$. In certain embodiments, a directly responsive fluorophore contributes to $I_{\lambda 1}$ and the emission spectrum of an indirectly responsive fluorophore contributes to $I_{\lambda 2}$. In some embodiments, a directly responsive fluorophore contributes to $I_{\lambda 2}$ and the emission spectrum of an indirectly responsive fluorophore contributes to $I_{\lambda 1}$. In various embodiments, both the emission spectrum of a directly responsive fluorophore and the emission spectrum of an indirectly responsive fluorophore contributes to $I_{\lambda 1}$. In some embodiments, both the emission spectrum of a directly responsive fluorophore and the emission spectrum of an indirectly responsive fluorophore contributes to $I_{\lambda 2}$.

In some embodiments, the directly responsive fluorophore is Pacific Blue and emission intensity is measured at a wavelength or range of wavelengths between about 400 nm and 1000 nm (e.g., including a wavelength of about 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, or 460 nm), and wherein the indirectly responsive fluorophore is Oregon Green and emission intensity is measured at a wavelength or range of wavelengths between about 400 nm and 1000 nm (e.g., including a wavelength of about 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, or 540 nm). In some embodiments, the directly responsive fluorophore is Pacific Blue and emission intensity is measured at a wavelength or range of wavelengths between about 400 nm and 1000 nm (e.g., including a wavelength of about 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, or 470 nm), and wherein the indirectly responsive fluorophore is 5-IAF and emission intensity is measured at a wavelength or range of wavelengths between about 400 nm and 1000 nm (e.g., including a wavelength of about 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, or 540 nm). In some embodiments, the directly responsive fluorophore is Badan and emission intensity is measured at a wavelength or range of wavelengths between about 400 nm and 1000 nm (e.g., including a wavelength of about 470, 471, 472, 473, 474, 475, 476, 478, 479, 480, 481, 482, 483, 484, 485, 486, 487, 488, 489, 490, 491, 492, 493, 494, 495, 496, 497, 498, 499, 500, 501, 502, 503, 504, or 505 nm), and wherein the indirectly responsive fluorophore is Alexa532 and emission intensity is measured at a wavelength or range of wavelengths between about 400 nm and 1000 nm (e.g., including a wavelength of about 540, 541, 542, 543, 544, 545, 546, 547, 548, 549, 550, 551, 552, 553, 554, 556, 557, 558, 559, 560, 561, 562, 563, 564, 565, 566, 567, 568, 569, or 570 nm). In some embodiments, the directly responsive fluorophore is Badan and emission intensity is measured at a wavelength or range of wavelengths between about 400 nm and 1000 nm (e.g., including a wavelength of about 540, 541, 542, 543, 544, 545, 546, 547, 548, 549, 550, 551, 552, 553, 554, 556, 557, 558, 559, 560, 561, 562, 563, 564, 565, 566, 567, 568, 569, or 570 nm), and wherein the indirectly responsive fluorophore is Alexa532 and emission intensity is measured at a wavelength or range of wavelengths between about 400 nm and 1000 nm (e.g., including a wavelength of about 450, 451, 452, 453, 454, 455, 456, 457, 458, 459, 500, 501, 502, 503, 504, 505, 506, 507, 508, 509, or 510 nm). In some embodiments, the directly responsive fluorophore is Badan and emission intensity is measured at a wavelength or range of wavelengths between about 400 nm and 1000 nm (e.g., including a wavelength of about 540, 541, 542, 543, 544, 545, 546, 547, 548, 549, 550, 551, 552, 553, 554, 556, 557, 558, 559, 560, 561, 562, 563, 564, 565, 566, 567, 568, 569, or 570 nm), and wherein the indirectly responsive fluorophore is Alexa532 and emission intensity is measured at a wavelength or range of wavelengths between about 400 nm and 1000 nm (e.g., including a wavelength of about 470, 471, 472, 473, 474, 475, 476, 478, 479, 480, 481, 482, 483, 484, 485, 486, 487, 488, 489, 490, 491, 492, 493, 494, 495, 496, 497, 498, 499, 500, 501, 502, 503, 504, or 505 nm). In some embodiments, the directly responsive fluorophore is Badan and emission intensity is measured at a wavelength or range of wavelengths between about 400 nm and 1000 nm (e.g., including a wavelength of about 450, 451, 452, 453, 454, 454, 456, 457, 458, 459, 460, 461, 462, 463, 464, 465, 466, 467, 468, 469, 470, 471, 472, 473, 474, or 475 nm), and wherein the indirectly responsive fluorophore is Alexa532 and emission intensity is measured at a wavelength or range of wavelengths between about 400 nm and 1000 nm (e.g., including a wavelength of about 540, 541, 542, 543, 544, 545, 546, 547, 548, 549, 550, 551, 552, 553, 554, 556, 557, 558, 559, 560, 561, 562, 563, 564, 565, 566, 567, 568, 569, or 570 nm). In some embodiments, the directly responsive fluorophore is Pacific Blue and emission intensity is measured at a wavelength or range of wavelengths between about 400 nm and 1000 nm (e.g., including a wavelength of about 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, or 460 nm), and wherein the indirectly responsive fluorophore is Texas Red and emission intensity is measured at a wavelength or range of wavelengths between about 400 nm and 1000 nm (e.g., including a wavelength of about 610, 611, 612, 613, 614, 615, 616, 617, 618, 619, 620, 621, 622, 623, 624, 625, 626, 627, 628, 629, or 670 nm). In some embodiments, the directly responsive fluorophore is Pacific Blue and emission intensity is measured at a wavelength or range of wavelengths between about 400 nm and 1000 nm (e.g., including a wavelength of about 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, or 460 nm), and wherein the indirectly responsive fluorophore is Texas Red and emission intensity is measured at a wavelength or range of wavelengths between about 400 nm and 1000 nm (e.g., including a wavelength of about 610, 611, 612, 613, 614, 615, 616, 617, 618, 619, 620, 621, 622, 623, 624, 625, 626, 627, 628, 629, or 670 nm). In some embodiments, the directly responsive fluorophore is Pacific Blue and emission intensity is measured at a wavelength or range of wavelengths between about 400 nm and 1000 nm (e.g., including a wavelength of about 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, or 460 nm), and wherein the indirectly responsive fluorophore is Texas Red and emission intensity is measured at a wavelength or range of wavelengths between about 400 nm and 1000 nm (e.g., including a wavelength of about 430, 431, 432, 433, 434, 435, 436, 437, 438, 439, 440, 441, 442, 443, 444, 445, 446, 447, 448, 449, 450, 451, 452, 453, 454, or 455 nm). In some embodiments, the directly responsive fluorophore is Acrylodan and emission intensity is measured at a wavelength or range of wavelengths between about 400 nm and 1000 nm (e.g., including a wavelength of about 470, 471, 472, 473, 474, 475, 476, 478, 479, 480, 481, 482, 483, 484, 485, 486, 487, 488, 489, 490, 491, 492, 493, 494, 495, 496, 497, 498, 499, 500, 501, 502, 503, 504, or 505) nm, and wherein the indirectly responsive fluorophore is 5-IAF and emission intensity is measured at a wavelength or range of wavelengths between about 400 nm and 1000 nm (e.g., including a wavelength of about 450, 451, 452, 453, 454, 454, 456, 457, 458, 459, 460, 461, 462, 463, 464, 465, 466, 467, 468, 469, 470, 471, 472, 473, 474, or 475 nm). In some embodiments, the directly responsive fluorophore is Acrylodan and emission intensity is measured at a wavelength or range of wavelengths between about 400 nm and 1000 nm (e.g., including a wavelength of about 470, 471, 472, 473, 474, 475, 476, 478, 479, 480, 481, 482, 483, 484, 485, 486, 487, 488, 489, 490, 491, 492, 493, 494, 495, 496, 497, 498, 499, 500, 501, 502, 503, 504, or 505 nm), and wherein the indirectly responsive fluorophore is Alexa532 and emission intensity is measured at a wavelength or range of wavelengths between about 400 nm and 1000 nm (e.g., including a wavelength of about 450, 451, 452, 453, 454, 454, 456, 457, 458, 459, 460, 461, 462, 463, 464, 465, 466, 467, 468, 469, 470, 471, 472, 473, 474, or 475 nm). In some embodiments, the directly responsive fluorophore is Alexa532 and emission intensity is measured at a wavelength or range of wavelengths between about 400 nm and 1000 nm (e.g., including a wavelength of about 540, 541, 542, 543, 544, 545, 546, 547, 548, 549, 550, 551, 552, 553, 554, 556, 557, 558, 559, 560, 561, 562, 563, 564, 565, 566, 567, 568, 569, or 570) nm, and wherein the indirectly responsive fluorophore is 5-IAF and emission intensity is measured at a wavelength or range of wavelengths between about 400 nm and 1000 nm (e.g., including a wavelength of about 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, or 540 nm). In some embodiments, the directly responsive fluorophore is Alexa532 and emission intensity is measured at a wavelength or range of wavelengths between about 400 nm and 1000 nm (e.g., including a wavelength of about 540, 541, 542, 543, 544, 545, 546, 547, 548, 549, 550, 551, 552, 553, 554, 556, 557, 558, 559, 560, 561, 562, 563, 564, 565, 566, 567, 568, 569, or 570) nm, and wherein the indirectly responsive fluorophore is Oregon Green and emission intensity is measured at a wavelength or range of wavelengths between about 400 nm and 1000 nm (e.g., including a wavelength of about 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, or 540 nm). In some embodiments, the directly responsive fluorophore is Badan and emission intensity is measured at a wavelength or range of wavelengths between about 400 nm and 1000 nm (e.g., including a wavelength of about 505,506,507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, or 540 nm), and wherein the indirectly responsive fluorophore is 5-IAF and emission intensity is measured at a wavelength or range of wavelengths between about 400 nm and 1000 nm (e.g., including a wavelength of about 450, 451, 452, 453, 454, 454, 456, 457, 458, 459, 460, 461, 462, 463, 464, 465, 466, 467, 468, 469, 470, 471, 472, 473, 474, or 475 nm). In some embodiments, the directly responsive fluorophore is Acrylodan and emission intensity is measured at a wavelength or range of wavelengths between about 400 nm and 1000 nm (e.g., including a wavelength of about 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, or 540) nm, and wherein the indirectly responsive fluorophore is 5-IAF and emission intensity is measured at a wavelength or range of wavelengths between about 400 nm and 1000 nm (e.g., including a wavelength of about 450, 451, 452, 453, 454, 454, 456, 457, 458, 459, 460, 461, 462, 463, 464, 465, 466, 467, 468, 469, 470, 471, 472, 473, 474, or 475 nm. In some embodiments, the directly responsive fluorophore is Acrylodan and emission intensity is measured at a wavelength or range of wavelengths between about 400 nm and 1000 nm (e.g., including a wavelength of about 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, or 540 nm), and wherein the indirectly responsive fluorophore is Alexa532 and emission intensity is measured at a wavelength or range of wavelengths between about 400 nm and 1000 nm (e.g., including a wavelength of about 450, 451, 452, 453, 454, 454, 456, 457, 458, 459, 460, 461, 462, 463, 464, 465, 466, 467, 468, 469, 470, 471, 472, 473, 474, or 475 nm).

In various embodiments, the ligand-binding protein comprises a cysteine at the position of its amino acid sequence that aligns with position 16, 17, 18, 190, or 194 of avBicarbBP5 (SEQ ID NO: 19 or 79) when the amino acid sequence of the ligand-binding protein is aligned with the amino acid sequence of avBicarbBP5 using the ClustalW alignment program, and wherein the Pacific Blue, the Alexa532, the Acrylodan, or the Badan is covalently attached to the cysteine. In some embodiments, the 5-IAF, the Alexa532, the Texas Red, the IANBD, or the Oregon Green is attached to the N-terminus or the C-terminus of the ligand-binding protein via a fluorophore attachment motif. In a non-limiting example, the ligand-binding protein comprises an amino acid sequence of SEQ ID NO: 64.

In various embodiments, the change in the fluorescent property of the directly responsive fluorophore comprises (i) a bathochromic or hypsochromic shift in the emission or excitation spectrum thereof; and/or (ii) a change in the ratio of radiative to non-radiative emission rates thereof.

In embodiments, the directly responsive fluorophore comprises a donor fluorophore and the indirectly responsive fluorophore comprises an acceptor fluorophore. In some embodiments, the emission intensity of the donor fluorophore decreases and the emission intensity of the acceptor fluorophore increases upon ligand binding to the ligand-binding protein when the donor fluorophore is contacted with radiation within the excitation spectrum of the donor fluorophore. In some embodiments, the emission intensity of the donor fluorophore increases and the emission intensity of the acceptor fluorophore decreases upon ligand binding to the ligand-binding protein when the donor fluorophore is contacted with radiation within the excitation spectrum of the donor fluorophore. In some embodiments, the emission intensities of the donor fluorophore and the acceptor fluorophore both decrease upon ligand binding to the ligand-binding protein when the donor fluorophore is contacted with radiation within the excitation spectrum of the donor fluorophore. In some embodiments, the emission intensity of the donor fluorophore decreases and the emission intensity of the acceptor fluorophore increases, decreases, or remains about the same upon ligand binding to the ligand-binding protein when the donor fluorophore is contacted with radiation within the excitation spectrum of the donor fluorophore. In some embodiments, the emission intensity of the donor fluorophore increases, decreases, or remains about the same and the emission intensity of the acceptor fluorophore decreases upon ligand binding to the ligand-binding protein when the donor fluorophore is contacted with radiation within the excitation spectrum of the donor fluorophore. In some embodiments, the emission intensities of the donor fluorophore and the acceptor fluorophore both increase upon ligand binding to the ligand-binding protein when the donor fluorophore is contacted with radiation within the excitation spectrum of the donor fluorophore. In some embodiments, the emission intensity of the donor fluorophore increases, decreases, or remains about the same and the emission intensity of the acceptor fluorophore increases upon ligand binding to the ligand-binding protein when the donor fluorophore is contacted with radiation within the excitation spectrum of the donor fluorophore. In some embodiments, the emission intensity of the donor fluorophore increases and the emission intensity of the acceptor fluorophore increases, decreases, or remains about the same upon ligand binding to the ligand-binding protein when the donor fluorophore is contacted with radiation within the excitation spectrum of the donor fluorophore.

In embodiments the directly responsive fluorophore comprises an acceptor fluorophore and the indirectly responsive fluorophore comprises a donor fluorophore. In some embodiments, the emission intensity of the donor fluorophore decreases and the emission intensity of the acceptor fluorophore increases, decreases, or remains about the same upon ligand binding to the ligand-binding protein when the donor fluorophore is contacted with radiation within the excitation spectrum of the donor fluorophore. In some embodiments, the emission intensity of the donor fluorophore increases and the emission intensity of the acceptor fluorophore increases, decreases, or remains about the same upon ligand binding to the ligand-binding protein when the donor fluorophore is contacted with radiation within the excitation spectrum of the donor fluorophore. In some embodiments, the emission intensity of the donor fluorophore remains about the same and the emission intensity of the acceptor fluorophore decreases upon ligand binding to the ligand-binding protein when the donor fluorophore is contacted with radiation within the excitation spectrum of the donor fluorophore. In some embodiments, the emission intensity of the donor fluorophore decreases and the emission intensity of the acceptor fluorophore increases, decreases, or remains about the same upon ligand binding to the ligand-binding protein when the donor fluorophore is contacted with radiation within the excitation spectrum of the donor fluorophore. In some embodiments, the emission intensity of the donor fluorophore increases and the emission intensity of the acceptor fluorophore increases, decreases, or remains about the same upon ligand binding to the ligand-binding protein when the donor fluorophore is contacted with radiation within the excitation spectrum of the donor fluorophore. In some embodiments, the emission intensity of the donor fluorophore remains about the same and the emission intensity of the acceptor fluorophore increases upon ligand binding to the ligand-binding protein when the donor fluorophore is contacted with radiation within the excitation spectrum of the donor fluorophore. In some embodiments, the emission intensity of the donor fluorophore decreases and the emission intensity of the acceptor fluorophore increases upon ligand binding to the ligand-binding protein when the donor fluorophore is contacted with radiation within the excitation spectrum of the donor fluorophore. In some embodiments, the emission intensity of the donor fluorophore increases and the emission intensity of the acceptor fluorophore remains about the same, increases, or decreases upon ligand binding to the ligand-binding protein when the donor fluorophore is contacted with radiation within the excitation spectrum of the donor fluorophore.

In instances in which an emission intensity increases, the increase may be, e.g., between about 0.1% to 10%, 10% to 50%, or 50% to 100%, or at least about 0.1%, 0.5%, 1%, 2%, 3%, 4%, 5%, 10%, 15%, 20%, 25%, 50%, 75%, 100%, 2-fold, 3-fold, 4-fold, 5-fold, 6-fold, 7-fold, 8-fold, 9-fold, or 10-fold. In instances in which an emission intensity decreases, the decrease may be, e.g., a decrease of between about at least about 0.1% to 10%, 10% to 50%, or 50% to 00%, or at least about 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, or 90%. In various embodiments in which both the emission intensity of the donor fluorophore and the acceptor fluorophore increases, then the increases are not equal. In certain embodiments in which both the emission intensity of the donor fluorophore and the acceptor fluorophore decreases, then the decreases are not equal.

In certain embodiments, the indirectly responsive fluorophore is attached to the ligand-binding protein via a covalent bond. Various approaches for attaching reporter groups such as directly and indirectly responsive fluorophores to a polypeptide such as a ligand-binding protein are described herein. In some embodiments, the covalent bond comprises a disulfide bond, a thioester bond, a thioether bond, an ester bond, an amide bond, or a bond that has been formed by a click reaction.

In some embodiments, the indirectly responsive fluorophore is attached to the ligand-binding protein via a non-covalent bond. In certain embodiments, the indirectly responsive fluorophore is attached to a cysteine or a lysine of the ligand-binding protein.

In various embodiments, the indirectly responsive fluorophore is attached to the N-terminus or the C-terminus of the protein. In some embodiments, the indirectly responsive fluorophore is attached to the N-terminus or the C-terminus of the protein via a fluorophore attachment motif.

In some embodiments, fluorophore attachment motif comprises a polypeptide. Various embodiments may be used to link a fluorophore with a ligand-binding protein. In some embodiments, the polypeptide comprises a stretch of at least 50, 60, 70, 80, 90, or 100 amino acids. In a non-limiting example, the polypeptide comprises amino acids in the sequence of PZif (SEQ ID NO: 90). In another non-limiting example, the polypeptide comprises a stretch of at least 50, 60, 70, 80, 90, or 100 amino acids in a sequence that is at least about 85%, 90%, 95%, or 99% identical to the amino acid sequence of *E. coli* thioredoxin (ecTRX; SEQ ID NO: 169).

In some embodiments, the directly responsive fluorophore is attached to the ligand-binding protein via a covalent bond. In various embodiments, the covalent bond comprises a disulfide bond, a thioester bond, a thioether bond, an ester bond, an amide bond, or a bond that has been formed by a click reaction. In directly responsive fluorophore is attached to a cysteine or a lysine of the protein.

In some embodiments, an overlap of the emission spectrum of the donor fluorophore and the excitation spectrum of the acceptor fluorophore increases upon ligand binding. In certain embodiments, the directly responsive fluorophore comprises the donor fluorophore, and the increase results from a bathochromic shift in the emission spectrum of the donor fluorophore. Alternatively, the directly responsive fluorophore comprises the acceptor fluorophore, and the increase results from a hypsochromic shift in the excitation spectrum of the acceptor fluorophore.

In various embodiments, an overlap of the emission spectrum of the donor fluorophore and the excitation spectrum of the acceptor fluorophore decreases upon ligand binding. In some embodiments, the directly responsive fluorophore comprises the donor fluorophore, and the decrease results from a hypsochromic shift in the emission spectrum of the donor fluorophore. In certain embodiments, the directly responsive fluorophore comprises the acceptor fluorophore, and the decrease results from a bathochromic shift in the excitation spectrum of the acceptor fluorophore.

In some embodiments, the directly responsive fluorophore has a monochromatic spectral change upon ligand binding. Alternatively, the directly responsive fluorophore has a dichromatic spectral change upon ligand binding.

In certain embodiments, the emission intensity of the donor fluorophore and/or the acceptor fluorophore increases in two phases as ligand concentration increases.

In various embodiments, the ratio of radiative to non-radiative emission or intensity of the directly responsive fluorophore increases by at least about 0.1%, 0.5%, 1%, 2%, 3%, 4%, 5%, 10%, 15%, 20%, 25%, 50%, 75%, 100%, 2-fold, 3-fold, 4-fold, 5-fold, 6-fold, 7-fold, 8-fold, 9-fold, or 10-fold upon ligand binding to the ligand-binding protein. Alternatively, the ratio of radiative to non-radiative emission or intensity of the directly responsive fluorophore decreases by at least about 0.1%, 0.5%, 1%, 2%, 3%, 4%, 5%, 10%, 15%, 20%, 25%, 50%, 75%, 90%, 95%, or 99% upon ligand binding to the ligand-binding protein.

In embodiments, the directly responsive fluorophore and the indirectly responsive fluorophore are not a naphthalene derivative. In some embodiments, the directly responsive fluorophore and the indirectly responsive fluorophore are not Prodan, Acrylodan, or Badan. In certain embodiments, the directly responsive fluorophore is not a naphthalene derivative. In some embodiments, the directly responsive fluorophore is not Prodan, Acrylodan, or Badan.

In various embodiments, the directly responsive fluorophore comprises xanthene, a xanthene derivative, fluorescein, a fluorescein derivative, coumarin, a coumarin derivative, cyanine, a cyanine derivative, rhodamine, a rhodamine derivative, phenoxazine, a phenoxazine derivative, squaraine, a squaraine derivative, coumarin, a coumarin derivative, oxadiazole, an oxadiazole derivative, anthracene, an anthracene derivative, a boradiazaindacine (BODIPY) family fluorophore, pyrene, a pyrene derivative, acridine, an acridine derivative, arylmethine, an arylmethine derivative, tetrapyrrole, or a tetrapyrrole derivative. In some embodiments, the directly responsive fluorophore comprises fluorescein or a derivative thereof.

In some embodiments, the directly responsive fluorophore and/or the indirectly responsive fluorophore comprises a fluorescent protein. In various embodiments, the directly responsive fluorophore and/or the indirectly responsive fluorophore comprises an organic compound having a molecular weight less than about 2000 Da (e.g., 5-iodoacetamidofluorescein (5-IAF) or 6-iodoacetamidofluorescein (6-IAF), rhodamine, Oregon Green, eosin, Texas Red, indocarbocyanine, oxacarbocyanine, thiacarbocyanine, merocyanine, Badan, Acrylodan, IAEDANS, comprising 3-cyano-7-hydroxycoumarin, 7-hydroxycoumarin-3-carboxylic acid, 6,8-difluoro-7-hydroxy-4-methylcoumarin, or 7-amino-4-methylcoumarin, pyridyloxazole, nitrobenzoxadiazole, benzoxadiazole, DRAQ5, DRAQ7, or CyTRAK Orange, cascade blue, Nile red, Nile blue, cresyl violet, oxazine 170, proflavin, acridine orange, acridine yellow, auramine, crystal violet, malachite green, porphin, phthalocyanine, bilirubin, pyrene, N,N'-dimethyl-N-(iodoacetyl)-N'-(7-nitrobenz-2-ox-a-1,3-diazol-4-yl)ethylenediamide (NBD), N-((2-(iodoacetoxy)ethyl)-N-methy-1)amino-7-nitrobenz-2-oxa-1,3-diazole (NBDE), JPW4039, JPW4042, JPW4045, Pacific Blue, CPM, N,N'-Dimethyl-N-(Iodoacetyl)-N'-(7-Nitrobenz-2-Oxa-1,3-Diazol-4-yl)Ethylenediamine (IANBD), 7-diethylamino-3-(4'-maleimidylphenyl)-4-methylcoumarin (CPM), BODIPY 499, BODIPY 507/545, BODIPY 499/508, Alexa 432, Alexa488, Alexa532, Alexa546, Cy5, or 1-(2-maleimidylethyl)-4-(5-(4-methoxyphenyl)oxazol-2-yl)pyridinium methanesulfonate (PyMPO maleimide) (PyMPO)). Numerous combinations of directly responsive fluorophores and indirectly responsive fluorophores are possible. For example, in various non-limiting examples, (a) the donor fluorophore comprises Pacific Blue and the acceptor fluorophore comprises 5-IAF or 6-iodoacetamidofluorescein (6-IAF); (b) the donor fluorophore comprises Pacific Blue and the acceptor fluorophore comprises Oregon Green; (c) the donor fluorophore comprises IAEDANS and the acceptor fluorophore comprises 5-IAF or 6-IAF; (d) the donor fluorophore comprises acrylodan and the acceptor fluorophore comprises Alexa532; (e) the donor fluorophore comprises acrylodan and the acceptor fluorophore comprises 5-IAF or 6-IAF; (f) the donor fluorophore comprises acrylodan and the acceptor fluorophore comprises Pacific Blue or YFP; (g) the donor fluorophore comprises 5-JAF or 6-JAF and the acceptor fluorophore comprises Pacific Blue; (h) the donor fluorophore comprises badan and the acceptor fluorophore comprises 5-JAF or 6-IAF; or (i) the donor fluorophore comprises badan and the acceptor fluorophore comprises Alexa532.

Aspects also include a biosensor for a ligand comprising a ligand-binding protein, a directly responsive fluorophore and an indirectly responsive fluorophore, the directly responsive and the indirectly responsive fluorophores being located at two distinct sites of the ligand-binding-protein, wherein (i) the directly responsive fluorophore is a donor fluorophore and the indirectly responsive fluorophore is an acceptor fluorophore; or (ii) the directly responsive fluorophore is an acceptor fluorophore and the indirectly responsive fluorophore is an donor fluorophore. In various embodiments, the ligand comprises bicarbonate or $Ca^{2+}$.

Any of the ligand-binding proteins disclosed herein, as well as others, may be included in the biosensors and methods that are provided.

Aspects of the present subject matter also provide a method for constructing a biosensor, comprising: (a) providing a ligand-binding protein; (b) identifying at least one putative allosteric, endosteric, or peristeric site of the ligand-binding based a structure of the ligand-binding protein; (c) mutating the ligand-binding protein to substitute an amino acid at the at least one putative allosteric, endosteric, or peristeric site of the second protein with a cysteine; (d) conjugating a donor fluorophore or an acceptor fluorophore to the cysteine to produce single labeled biosensor; (e) detecting whether there is a spectral shift or change in emission intensity of the single labeled biosensor upon ligand binding when the donor fluorophore or the acceptor fluorophore is fully excited; and (f) if a spectral shift or change in emission intensity is detected in (e), attaching a donor fluorophore to the second protein if an acceptor fluorophore is attached to the cysteine, and attaching an acceptor fluorophore to the second protein if an acceptor fluorophore is attached to the cysteine.

In various embodiments, the ligand-binding protein has been identified by (i) selecting a first protein having a known amino acid sequence (seed sequence), wherein the first protein is known to bind a ligand; (ii) identifying a second protein having an amino acid sequence (hit sequence) with at least 15% sequence identity to the seed sequence; (iii) aligning the seed amino acid sequence and the hit sequence, and comparing the hit sequence with the seed sequence at positions of the seed sequence that correspond to at least 5 primary complementary surface (PCS) amino acids, wherein each of the at least 5 PCS amino acids has a hydrogen bond interaction or a van der Waals interaction with ligand when ligand is bound to the first protein; and (iv) identifying the second protein to be a ligand-binding protein if the hit sequence comprises at least 5 amino acids that are consistent with the PCS.

In some embodiments, the spectral shift comprises a monochromatic fluorescence intensity change or a dichromatic spectral shift.

Also provided is a method of converting a biosensor that shows a monochromatic response upon ligand binding into a biosensor with a dichromatic response upon ligand binding, the method comprising (a) selecting a biosensor that exhibits a monochromatic response upon ligand binding, wherein the biosensor comprises a ligand-binding protein and a first reporter group; and (b) attaching a second reporter group to the biosensor, wherein the second reporter group has (i) an excitation spectrum that overlaps with the emission spectrum of the first reporter group; or (ii) an emission spectrum that overlaps with the excitation spectrum of the first reporter group.

Also provided is a method of increasing a dichromatic response of a biosensor to ligand binding, the method comprising (a) selecting a biosensor that exhibits a dichromatic response upon ligand binding, wherein the biosensor comprises a ligand-binding protein and a first reporter group; and (b) attaching a second reporter group to the biosensor, wherein the second reporter group has (i) an excitation spectrum that overlaps with the emission spectrum of the first reporter group; or (ii) an emission spectrum that overlaps with the excitation spectrum of the first reporter group.

In some embodiments, the second reporter group is within about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 4, 6, 8, 10, 11, 12, 13, 14, 15, 16, 17, 18, 19, 20, 25, 30, 35, 40, 45, 50, 55, 60, 65, 70, 75, 80, 85, 90, 95, 100, 125, 150, or 200 angstroms (Å) of the first reporter group regardless of whether ligand is bound to the biosensor. Suitable distances may be determined in part by the distance-dependence of the energy transfer between a given donor-acceptor pair (see, e.g, J. R. Lakowicz, 2006, Principles of Fluorescence Spectroscopy, Springer, incorporated herein by reference). In some embodiments, when the ligand is bound to the biosensor, the average distance between the first reporter group and the second reporter group changes by less than about 5, 4, 3, 2, 1, 0.9, 0.8, 0.7, 0.6, 0.5, 0.4, 0.3, 0.2, 0.1, 0.05, or 0.01 angstroms (Å) compared to when ligand is not bound to the ligand-binding protein.

In various embodiments, if the acceptor fluorophore comprises palladium, platinum, ruthenium, or osmium, then the acceptor fluorophore is not attached to the amino group of the N-terminus of the ligand-binding protein. In some embodiments, the acceptor fluorophore does not comprise $[Ru(bpy)_3]^{2+}$, $[Ru(Ph_2phen)_3]_{2+}$, $[Ru(bpy)_2(dcbpy)]^{2+}$, or $[Ru(bpy)_2(phen\text{-}ITC)]^{2+}$, where bpy is 2,2'-bipyridine, phen is 1,10-phenanthroline, dcbpy is 4,4'-dicarboxy-2,2'-bipyridine, and ITC is isothiocyanate. In certain embodiments, the biosensor does not comprise an *E. coli* glutamine-binding protein with Acrylodan attached to 179C. In some embodiments, the biosensor does not comprise *E. coli* ligand-binding protein with Acrylodan attached to 255C.

tgmFRET Biosensors

While ngmFRET is preferred to tgmFRET, tgmFRET may be used alternatively or in addition to ngmFRET in certain embodiments.

In various embodiments, the biosensor comprises multiple reporter groups, including a first reporter group and a second reporter group. For example, the first reporter group may comprise a donor fluorophore and the second reporter group may comprise an acceptor fluorophore. In certain embodiments, FRET is detectable by a change in the fluorescence of the acceptor fluorophore or by a decrease in of donor fluorophore fluorescence. In various embodiments, the donor fluorophore, and/or the acceptor fluorophore is fluorescent. In some embodiments, both the donor fluorophore and the acceptor fluorophore are fluorescent.

In various embodiments, the angle and/or distance between the donor fluorophore and the acceptor fluorophore changes upon ligand binding. In some embodiments, neither the donor fluorophore nor the acceptor fluorophore is directly responsive to ligand binding. In some embodiments the donor fluorophore and/or the acceptor fluorophore is attached to the N-terminus or the C-terminus of the ligand-binding protein (e.g., directly or via a fluorophore attachment motif). In certain embodiments, the donor fluorophore and/or the acceptor fluorophore is attached to a fluorophore attachment motif. For example, the fluorophore attachment motif may be conjugated to the N-terminus or the C-terminus of the ligand-binding protein.

In some embodiments, the donor fluorophore and/or the acceptor fluorophore comprises a fluorescent protein. In various embodiments, the donor fluorophore and/or the acceptor fluorophore comprises an organic compound having a molecular weight less than about 2000 Da (e.g., 5-iodoacetamidofluorescein (5-IAF) or 6-iodoacetamidofluorescein (6-IAF), rhodamine, Oregon Green, eosin, Texas Red, indocarbocyanine, oxacarbocyanine, thiacarbocyanine, merocyanine, Badan, Acrylodan, IAEDANS, comprising 3-cyano-7-hydroxycoumarin, 7-hydroxycoumarin-3-carboxylic acid, 6,8-difluoro-7-hydroxy-4-methylcoumarin, or 7-amino-4-methylcoumarin, pyridyloxazole, nitrobenzoxadiazole, benzoxadiazole, DRAQ5, DRAQ7, or CyTRAK Orange, cascade blue, Nile red, Nile blue, cresyl violet, oxazine 170, proflavin, acridine orange, acridine yellow, auramine, crystal violet, malachite green, porphin, phthalocyanine, bilirubin, pyrene, N,N'-dimethyl-N-(iodoacetyl)-N'-(7-nitrobenz-2-ox-a-1,3-diazol-4-yl)ethylenediamide (NBD), N-((2-(iodoacetoxy)ethyl)-N-methy-1)amino-7-nitrobenz-2-oxa-1,3-diazole (NBDE), Acrylodan, JPW4039, JPW4042, JPW4045, Oregon Green, Pacific Blue, CPM, N,N'-Dimethyl-N-(Iodoacetyl)-N'-(7-Nitrobenz-2-Oxa-1,3-Diazol-4-yl)Ethylenediamine (IANBD), 7-diethylamino-3-(4'-maleimidylphenyl)-4-methylcoumarin (CPM), BODIPY 499, BODIPY 507/545, BODIPY 499/508, Alexa 432, Alexa488, Alexa532, Alexa546, Cy5, or 1-(2-maleimidylethyl)-4-(5-(4-methoxyphenyl)oxazol-2-yl)pyridinium methanesulfonate (PyMPO maleimide) (PyMPO)). For example, the organic compound is a fluorophore. Numerous combinations of donor and acceptor fluorophores are possible.

Fluorophore Attachment Motifs

Aspects of the present subject matter include the use of one or more fluorophore attachment motifs to attach one or more reporter groups to a ligand-binding protein. For example, a reporter group may be attached to a fluorophore attachment motif that is attached to the N-terminus or the C-terminus of the ligand-binding protein.

In various implementations, the fluorophore attachment motif comprises a polypeptide. In some embodiments, the polypeptide comprises amino acids in the βZif amino acid sequence (SEQ ID NO: 90).

In some embodiments, the polypeptide comprises a stretch of at least 50, 60, 70, 80, 90, or 100 amino acids in a sequence that is at least about 85%, 90%, 95%, or 99% identical to the amino acid sequence of *E. coli* thioredoxin (ecTRX; SEQ ID NO: 169). In some embodiments, the polypeptide is a mutant of ecTRX comprising a D3X, K4X, K19X, D27X, K37X, K53X, K58X, K70X, R74X, K83X, K91X, K97X, or K101X mutation, or any combination thereof, wherein X is any amino acid, and wherein each ecTRX amino acid position is numbered as in SEQ ID NO: 169. In certain embodiments, the polypeptide is a mutant of ecTRX comprising a D3A, K4R, K4Q, K19R, K19Q, D27A, K37R, K53M, K53R, K58M, K70R, R74C, K83R, K91R, K97R, or K101R mutation, or any combination thereof, wherein each ecTRX amino acid position is numbered as in SEQ ID NO: 169.

In non-limiting examples, the polypeptide comprises amino acids in the sequence set forth as any one of SEQ ID NOS: 169-187.

In certain embodiments, the polypeptide comprises (a) at least 1, 2, or 3 thiol groups; (b) at least 1, 2, or 3 cysteines that each comprise a sulfhydryl group; (c) at least 1, 2, or 3 primary amine groups; and/or (d) at least 1, 2, or 3 lysines that each comprise a primary amine. In some embodiments there is no disulfide bond between cysteines within the amino acid sequence of the polypeptide.

In some embodiments, the polypeptide comprises a hexahistidine tag. In some embodiments, the hexahisidine tag is attached to another portion of the polypeptide via a GGS linker.

Exemplary Methods of Using Biosensors Provided Herein

Aspects of the present subject matter provide a method of assaying for a ligand in a sample. The method may include contacting the sample with a biosensor disclosed herein under conditions such that the ligand-binding protein of the biosensor binds to the ligand if ligand is present in the sample. The method also comprises detecting (i) whether a signal is produced by a reporter group of the biosensor; and/or (ii) the a signal produced by a reporter group of the biosensor. In a non-limiting example, a reporter group of the biosensor is fluorescent, and the method further comprises contacting the reporter group with electromagnetic radiation having a wavelength that comprises a wavelength within the band of excitation wavelengths of the reporter group.

In various embodiments, the method further comprises (i) comparing a signal produced by a reporter group of the biosensor when the biosensor is contacted with the sample with a signal produced by a control sample containing a known quantity of ligand (e.g., ligand at a concentration of about 0.5, 1, 2, 3, 4, 5, 6, 7, 8, 9, 10, 15, 20, 25, 30, 35, 40, 45, 50, 75, 100, 125, or 150 mM, or a series of control samples having concentrations within the range of about 0.5 mM to about 150 mM); and (ii) detecting the presence or absence of ligand in the sample based on this comparison. In embodiments the control sample lacks ligand (e.g., the concentration of ligand is 0 mM). Alternatively or in addition, the method further comprises (i) comparing a signal produced by a reporter group of the biosensor when the biosensor is contacted with the sample with signals produced by a series of control samples containing known quantities of ligand; and (ii) determining the quantity of ligand in the sample based on this comparison. In some embodiments, the series of control samples comprises at least 2, 3, 4, 5, 6, 7, 8, 9, or 10 control samples, and wherein each control sample comprises a different quantity of ligand. Alternatively or in addition, the method further comprises determining the concentration of a ligand in a sample, wherein determining the concentration of the ligand in the sample comprises comparing the signal to a standard hyperbolic ligand binding curve to determine the concentration of the ligand in the test sample, wherein the standard hyperbolic ligand binding curve is prepared by measuring the signal produced by the reporter group of the biosensor when the biosensor is contacted with control samples containing known concentrations of ligand. In various embodiments, the method comprises (i) measuring a ratiometric change (ΔR) and/or an intensity change (ΔI) of a signal produced by the reporter group. In some embodiments, the method includes quantitating the level of ligand present in the sample.

In embodiments, the ligand comprises bicarbonate and the ligand-binding protein comprises a bicarbonate-binding protein. In some embodiments, the bicarbonate-binding protein has an affinity for bicarbonate that is higher than its naturally occurring counterpart. In certain embodiments relating to the detection or measurement of bicarbonate, $Ca^{2+}$ and/or iron is added to a reaction composition, device, or sample before, at the same time as, or after a biosensor is contacted with $Ca^{2+}$ or with a sample that comprises or is being tested for $Ca^{2+}$. In some embodiments, the $Ca^{2+}$ and/or iron is added to a concentration of at least about 0.1 mM, 0.5 mM, 1 mM, 1.2 mM, 1.3 mM, 1.4 mM, 1.5 mM, 2 mM, 3 mM, 4 mM, 5 mM, 6 mM, 7 mM, 8 mM, 9 mM, 10 mM of $Ca^{2+}$ and/or iron, e.g., in the sample or reaction composition. In certain embodiments, $Ca^{2+}$ and/or iron is added to a device such that it is present at a concentration of at least about 0.1 mM, 0.5 mM, 1 mM, 1.2 mM, 1.3 mM, 1.4 mM, 1.5 mM, 2 mM, 3 mM, 4 mM, 5 mM, 6 mM, 7 mM, 8 mM, 9 mM, 10 mM when a sample or reaction mixture is added to the device, e.g., when a part/chamber of the device is filled with the sample or reaction composition.

In embodiments, the ligand comprises $Ca^{2+}$ and the ligand-binding protein comprises a calcium-binding protein. In some embodiments, the calcium-binding protein has an affinity for bicarbonate that is higher than its naturally occurring counterpart. In certain embodiments relating to the detection or measurement of $Ca^{2+}$, bicarbonate is added to a reaction composition, device, or sample before, at the same time as, or after a biosensor is contacted with $Ca^{2+}$ or with a sample that comprises or is being tested for $Ca^{2+}$. In some embodiments, the bicarbonate is added to a concentration of at least about 1 mM, 5 mM, 10 mM, 20 mM, 30 mM, 40 mM, 50 mM, 75 mM, 100 mM, 200 mM, 300 mM, 400 mM, 500 mM, 600 mM, 700 mM, 800 mM, 900 mM, or 1000 mM of bicarbonate, e.g., in the sample or reaction composition. In certain embodiments, bicarbonate is added to a device such that it is present at a concentration of at least about 1 mM, 5 mM, 10 mM, 20 mM, 30 mM, 40 mM, 50 mM, 75 mM, 100 mM, 200 mM, 300 mM, 400 mM, 500 mM, 600 mM, 700 mM, 800 mM, 900 mM, or 1000 mM when a sample or reaction mixture is added to the device, e.g., when a part/chamber of the device is filled with the sample or reaction composition.

Aspects of the present subject matter also provide a method of assaying for multiple ligands in a sample, wherein the multiple ligands comprise a first ligand and a second ligand. Such a method may include contacting the sample with (i) a first biosensor a first ligand provided herein and (ii) a second biosensor for the second ligand, under conditions such that the ligand-binding protein of the first biosensor binds to the first ligand, if the first ligand is present in the sample, and detecting (i) a signal, e.g. magnitude of the signal, produced by a reporter group of the first biosensor, or (ii) whether a signal is produced by a reporter group of the first biosensor. In some embodiments, the second biosensor is also a biosensor provided herein, and the second biosensor is contacted with the second ligand under conditions such that the ligand-binding protein of the second biosensor binds to the second ligand it is present in the sample. The method may further comprise detecting (i) a signal, e.g. magnitude of the signal, produced by a reporter group of the second biosensor, or (ii) whether a signal is produced by a reporter group of the second biosensor.

In some embodiments, the signal produced by the reporter group of the first biosensor is different than the signal produced by the reporter group of the second biosensor. In a non-limiting example, the reporter group of the first biosensor and the reporter group of the second biosensor are each fluorescent, and the peak emission wavelength of the reporter group of the first biosensor is at least about 10, 25, 50, 75, or 100 nm greater or lower than the peak emission wavelength of the reporter group of the second biosensor.

Non-limiting examples of biosensors that may be used as the second biosensor include biosensors with ligand-binding proteins comprising a GGBP (e.g., an *E. coli* GGBP) or a derivative or mutant thereof, (ii) an *E. coli* arabinose binding protein (e.g., an *E. coli* arabinose binding protein) or a derivative or mutant thereof; (iii) a dipeptide binding protein (e.g., an *E. coli* dipeptide binding protein) or a derivative or mutant thereof, (iv) a histidine binding protein (e.g., an *E. coli*, histidine binding protein) or a derivative or mutant thereof, (v) a ribose binding protein (e.g., an *E. coli* ribose binding protein) or a derivative or mutant thereof, (vi) a sulfate binding protein (e.g., an *E. coli* sulfate binding protein) or a derivative or mutant thereof; (vii) a maltose binding protein (e.g., an *E. coli* maltose binding protein) or a derivative or mutant thereof; (viii) a glutamine binding protein (e.g., an *E. coli* glutamine binding protein) or a derivative or mutant thereof, (ix) a glutamate/aspartate binding protein (e.g., an *E. coli* glutamate/aspartate binding protein) or a derivative or mutant thereof; (x) a phosphate binding protein (e.g., an *E. coli* phosphate binding protein) or a derivative or mutant thereof, or (xi) an iron binding protein [e.g., a *Haemophilus influenza* (*H. influenzae*) iron binding protein] or a derivative or mutant thereof. For example, the second biosensor comprises an *E. coli* GGBP having a Y10C, Y10A, D14A, D14Q, D14N, D14S, D14T, D14E, D14H, D14L, D14Y, D14F, D14C, N15C, F16L, F16A, F16Y, F16C, N91A, K92C, E93C, S112A, S115A, E149C, E149K, E149Q, E149S, H152A, H152F, H152Q, H152N, H152C, D154A, D154C, D154N, A155S, A155H, A155L, A155F, A155Y, A155N, A155K, A155M, A155W, A155Q, A155C, R158A, R158K, R158C, M182C, M182W, W183C, W183A, N211F, N211W, N211K, N211Q, N211S, N211H, N211M, N211C, D212C, D236A, D236N, L238C, L255C, N256A, N256D, D257C, V293C, P294C, or V296C mutation (e.g., comprising 1, 2, 3, 4, 5 or more of these mutations), wherein each amino acid position is numbered as in (SEQ ID NO: 94); (ii) an *E. coli* arabinose binding protein having a D257C, F23C, K301C, L253C, or L298C mutation (e.g., comprising 1, 2, 3, 4, or 5 of these mutations) (see, e.g., U.S. Patent Application Publication No. 2004/0118681, the entire contents of which are incorporated herein by reference) (see, e.g., U.S. Patent Application Publication No. 2004/0118681, the entire contents of which are incorporated herein by reference); (iii) an *E. coli* dipeptide binding protein having a D450C, K394C, R141C, S111C, T44C, or W315C mutation (e.g., comprising 1, 2, 3, 4, 5 or 6 of these mutations) (see, e.g., U.S. Patent Application Publication No. 2004/0118681, the entire contents of which are incorporated herein by reference); (iv) an *E. coli*, histidine binding protein having a E167C, K229C, V163C, Y230C, F231C, Y88C mutation (e.g., comprising 1, 2, 3, 4, 5 or 6 of these mutations) (see, e.g., U.S. Patent Application Publication No. 2004/0118681, the entire contents of which are incorporated herein by reference); (v) an *E. coli* ribose binding protein having a T135C, D165C, E192C, A234C, L236C, or L265C mutation (e.g., comprising 1, 2, 3, 4, 5 or 6 of these mutations) (see, e.g., U.S. Patent Application Publication No. 2004/0118681, the entire contents of which are incorporated herein by reference); (vi) an *E. coli* sulfate binding protein having a L65C, N70C, Q294C, R134C, W290C, or Y67C mutation (e.g., comprising 1, 2, 3, 4, 5 or 6 of these mutations) (see, e.g., U.S. Patent Application Publication No. 2004/0118681 the entire content of which is incorporated herein by reference); (vii) an *E. coli* maltose binding protein having a D95C, F92C, E163C, G174C, I329C, or S233C mutation (e.g., comprising 1, 2, 3, 4, 5 or 6 of these mutations) (see, e.g., U.S. Patent Application Publication No. 2004/0118681 the entire content of which is incorporated herein by reference); (viii) an *E. coli* glutamine binding protein having a N160C, F221C, K219C, L162C, W220C, Y163C, or Y86C mutation (e.g., comprising 1, 2, 3, 4, 5 or more of these mutations) (see, e.g., U.S. Patent Application Publication No. 2004/0118681 the entire content of which is incorporated herein by reference); (ix) an *E. coli* glutamate/aspartate binding protein having a A207C, A210C, E119C, F126C, F131C, F270C, G211C, K268C, Q123C, or T129C mutation (e.g., comprising 1, 2, 3, 4, 5 or more of these mutations) (see, e.g., U.S. Patent Application Publication No. 2004/0118681 the entire content of which is incorporated herein by reference); (x) an *E. coli* phosphate binding protein having a A225C, N223C, N226C, S164C, or S39C mutation (e.g., comprising 1, 2, 3, 4, or 5 of these mutations) (see, e.g., U.S. Patent Application Publication No. 2004/0118681 the entire content of which is incorporated herein by reference); or (xi) a *Haemophilus influenza* (*H. influenzae*) iron binding protein having a E203C, K202C, K85C, or V287C mutation (e.g., comprising 1, 2, 3, or 4 of these mutations) (see, e.g., U.S. Patent Application Publication No. 2004/0118681 the entire content of which is incorporated herein by reference). In various embodiments, the sample is suspected of comprising bicarbonate and/or $Ca^{2+}$.

References and PDB[a] files for bPBP structures, genes, and ligand binding crystal structure

| bPBP | open form | closed form | DNA sequence | ligand affinity |
|---|---|---|---|---|
| arabinose BP | | Quiocho and Vyas, 1984 1ABE | Scripture et al., 1987 | Clark et al., 1982; Miller et al., 1983 |

-continued

References and PDB[a] files for bPBP structures, genes, and ligand binding crystal structure

| bPBP | open form | closed form | DNA sequence | ligand affinity |
|---|---|---|---|---|
| dipeptide BP | Nickitenko et al., 1995 1DPE | Dunten & Mowbray, 1995 1DPP | Abouhamad et al., 1991 | Guyer et al., 1986; Smith et al., 1999 |
| Glu/Asp BP | | | | Barash Halpern, 1975; Willis Furlong, 1975 |
| Fe(III) BP | Bruns et al., 2001 1D9V | Bruns et. al., 1997 1MRP | Sanders et al., 1994 | Adhikari et al., 1995 |
| glucose BP | | Vyas et al., 1988; Vyas et al., 1994 1GLG | Scholle et al., 1987 | Anraku, 1968 |
| histidine BP | | Yao et al., 1994 1HSL | Joshi & Ames 1996 | Miller et al., 1983 |
| maltose BP | Sharff et al., 1992 1OMP | Spurlino et al., 1991; Quiocho et al., 1997 1ANF | Duplay et al., 1984 | Schwartz et al., 1976 |
| phosphate BP | Ledvina et al., 1996 1OIB | Luecke & Quiocho, 1990 1IXH | Magota et al., 1984 | Medveczky & Rosenberg, 1969 |
| glutamine BP | Hsiao et al., 1996 1GGG | Sun et al., 1998 1WDN | Nohno et al., 1986 | Weiner et al., 1971 |
| ribose BP | Bjorkman & Mowbray, 1998 1URP | Mowbray & Cole, 1992 2DRI | Groarke et al., 1983 | Willis & Furlong, 1974 |
| sulfate BP | | Pflugrath & Quiocho, 1985; He & Quiocho, 1993 1SBP | Hellinga & Evans, 1985 | Jacobson & Quiocho, 1988 |

[a]Protein Data Bank (Berman et al., 2000)

Abouhamad et al., Molec. Microbiol. 5: 1035-1047 (1991)
Adhikari et al., J. Biol. Chem. 270: 25142-25149 (1995)
Anraku, J. Biol. Chem. 243: 3116-3122 (1968)
Barash & Halpern, Biochim. Biophys. Acta 386: 168-180 (1975)
Bjorkman & Mowbray, J. Mol. Biol. 279: 651-664 (1998)
Bruns et al., Biochemistry 40: 15631-15637 (2001)
Bruns et al., Nat. Struct. Biol. 4: 919-924 (1997)
Clark et al., Biochemistry 21: 2227-2233 (1982)
Dunten & Mowbray, Protein Sci. 4: 2327-2334 (1995)
Duplay et al., J. Biol. Chem. 259: 10606-10613 (1984)
Groarke et al., J. Biol. Chem. 258: 12952-12956 (1983)
Guyer et al., J. Bacteriol. 168: 775-779 (1986)
He & Quiocho, Protein Sci. 2: 1643-1647 (1993)
Hellinga & Evans, Eur. J. Biochem. 149: 363-373 (1985)
Hsiao et al., J. Mol. Biol. 262: 225-242 (1996)
Jacobson & Quiocho, J. Mol. Biol. 204: 783-787 (1988)
Joshi & Ames, GenBank Accession Number U47027 (1996)
Ledvina et al., Proc. Natl. Acad. Sci. USA 93: 6786-6791 (1996)
Luecke & Quiocho, Nature 347: 402-406 (1990)
Magota et al., J. Bacteriol. 157: 909-917 (1984)
Medveczky & Rosenberg, Biochim. Biophys. Acta 192: 369-371 (1969)
Miller et al., J. Biol. Chem. 258: 13665-13672 (1983)
Mowbray & Cole, J. Mol. Biol. 225: 155-175 (1992)
Nickitenko et al., Biochemistry 34: 16585-16595 (1995)
Nohno et al., Molec. Gen. Genet. 205: 260-269 (1986)
Pflugrath & Quiocho, Nature 314: 257-260 (1985)
Quiocho et al., Structure 5: 997-1015 (1997)
Quiocho & Vyas, Nature 310: 381-386 (1984)
Sanders et al., Infect. Immun. 62: 4515-4525 (1994)
Scholle et al., Molec. Gen. Genet. 208: 247-253 (1987)
Scripture et al., J. Mol. Biol. 197: 37-46 (1987)
Schwartz et al., Eur. J. Biochem. 71: 167-170 (1976)
Sharff et al., Biochemistry 31: 10657-10663 (1992)
Smith et al., Microbiology 145: 2891-2901 (1999)
Spurlino et al., J. Biol. Chem. 266: 5202-5219 (1991)
Sun et al., J. Mol. Biol. 278: 219-229 (1998)
Vyas et al., Biochemistry 33: 4762-4768 (1994)
Vyas et al., Science 242: 1290-1295 (1988)
Weiner et al., Arch. Biochem. Biophys. 142: 715-717 (1971)
Willis & Furlong, J. Biol. Chem. 249: 6926-6929 (1974)
Willis & Furlong, J. Biol. Chem. 250: 2574-2580 (1975)
Yao et al., Biochemistry 33: 4769-4779 (1994)

Various types of samples may be used in methods provided herein. In non-limiting examples, a sample may comprise a reaction product, a buffer, and/or a solvent. In some embodiments, the solvent is an aqueous solvent. In some embodiments, the solvent comprises a non-polar solvent, a polar aprotic solvent, and/or a polar protic solvent. For example, a sample may comprise water, liquid ammonia, liquid sulfur dioxide, sulfuryl chloride, sulfuryl chloride fluoride, phosphoryl chloride, dinitrogen tetroxide, antimony trichloride, bromine pentafluoride, hydrogen fluoride, dimethyl sulfoxide, hexane, benzene, toluene, 1,4-dioxane, chloroform, diethyl ether, dichloromethane, N-methylpyrrolidone, tetrahydrofuran, ethyl acetate, acetone, dimethylformamide, acetonitrile, tormic acid, n-butanol, isopropanol, nitromethane, ethanol, methanol, and/or acetic acid.

In embodiments, a sample comprises a Newtonian liquid, a shear thickening liquid, a shear thinning liquid, a thixotropic liquid, a rheopectic liquid, or a Bingham plastic. In some implementations, a sample has a dynamic viscosity of at least about 0.5, 0.6, 0.7, 0.8, 0.9, 1, 1.1, 1.2, 1.3, 1.4, 1.5, or 2 pascal-seconds (Pa·s) or less than about 2, 1.5, 1.4, 1.3, 1.2, 1.1, 1, 0.9, 0.8, 0.7, 0.6, 0.5 Pa·s; and/or a kinematic viscosity of at least about 0.5, 0.6, 0.7, 0.8, 0.9, 1, 1.1, 1.2, 1.3, 1.4, 1.5, or 2 centistokes (cSt) or less than about 2, 1.5, 1.4, 1.3, 1.2, 1.1, 1, 0.9, 0.8, 0.7, 0.6, 0.5 cSt.

In various embodiments, the sample comprises a biological sample. The sample may comprise, e.g., a clinical sample (i.e., a sample collected in a clinical or veterinary setting, e.g., by or at the request or supervision or direction of a doctor, nurse, aid worker, or medic) and/or a physiological sample (a sample collected from an organism, e.g., a mammal such as a human). In certain embodiments, the biological sample comprises or has been provided or obtained from a skin surface or a mucosal surface. In some embodiments, the biological sample comprises a biological fluid. Non-limiting examples of biological fluids include sweat, tear fluid, blood, serum, plasma, interstitial fluid, amniotic fluid, sputum, gastric lavage, skin oil, milk, fecal matter, emesis, bile, saliva, urine, mucous, semen, lymph, spinal fluid, synovial fluid, a cell lysate, venom, hemolymph, and fluid obtained from plants such as the fluid transported in xylem cells or phloem sieve tube elements of a plant (e.g. sap).

The present subject matter also provides biosensors, methods, compositions, and devices useful for measuring the level of a ligand within a liquid solution or suspension or composition comprising cultured cells or tissue or a supernatant of such a solution or suspension, e.g., a sample of conditioned media or a sample of growth media in which a population of cells was cultured. In some embodiments, the sample is within a culture (e.g., inserted into a bioreactor) or provided from a media, culture, or reaction, e.g., in a bioreactor. For example, the sample may be within or provided from a fermenter such as a culture or culture supernatant from a fermentation reaction (e.g., an ongoing fermentation, the culture of cells in research settings, the production of a compound, etc.). Thus, the level of a ligand can be assayed at a timepoint of interest or at a series of timepoints over the duration of cell culture, e.g. continuously, in or from a reaction or culture. Bioreactors include devices or systems that support a biologically active environment. For example, a bioreactor may comprise a vessel in which a chemical process is carried out which involves organisms or biochemically active substances derived from such organisms. Such a process can either be aerobic or anaerobic. Organisms growing in bioreactors may be, e.g., submerged or suspended in liquid medium or may be attached to the surface of a solid medium. Submerged cultures may be suspended or immobilized. Suspension bioreactors can use a wider variety of organisms, since special attachment surfaces are not needed, and can operate at much larger scale than immobilized cultures. However, in a continuously operated process the organisms will be removed from the reactor with the effluent. Immobilization is a general term describing a wide variety of cell or particle attachment or entrapment. It can be applied to basically all types of biocatalysis including enzymes, cellular organelles, and cells (e.g., animal cells, plant cells, fungal cells, and bacterial cells). Immobilization is useful for continuously operated processes, since the organisms will not be removed with the reactor effluent, but is limited in scale because the cells are only present on the surfaces of the vessel. A bioreactor may also refer to a device or system meant to grow cells or tissues in the context of cell culture. The interrogation and/or monitoring of ligand levels in such samples permits the evaluation of the status of growth of the cells or production of secreted products by the cells to inform harvest or feeding or other modification of the culture.

Aspects of the present subject matter relate to the use of methods and biosensors provided herein to detect contamination.

In some embodiments, the sample comprises an environmental sample. Depending on context, there are instances in which a biological sample may also be, or may be within, an environmental sample. In certain embodiments, an environmental sample comprises a solute obtained from a biological composition, such as bone, nail, hair, shell, or cartilage. In various embodiments, an environmental sample comprises a solute obtained from an environmental substance and/or an environmental surface. For example, the solute may be dissolved/obtained from the environmental substance and/or an environmental surface using an aqueous or nonaqueous solution. In some embodiments, an aqueous may optionally comprise a nonaqueous solvent (e.g., mixed with an aqueous solvent). Non-limiting examples of environmental substances include rock, soil, clay, sand, meteorites, asteroids, dust, plastic, metal, mineral, fossils, sediment, and wood. Non-limiting examples of environmental surfaces include the surface of a vehicle such as a civilian vehicle (e.g., a satellite, a bike, a rocket, an automobile, a truck, a motorcycle, a yacht, a bus, or a plane) or a military vehicle (e.g., a tank, an armored personnel carrier, a transport truck, a jeep, a mobile artillery unit, a mobile antiaircraft unit, a minesweeper, a Mine-Resistant Ambush Protected (MRAP) vehicle, a lightweight tactical all-terrain vehicle, a high mobility multipurpose wheeled vehicle, a mobile multiple rocket launch system, an amphibious landing vehicle, a ship, a hovercraft, a submarine, a transport plane, a fighter jet, a helicopter, a rocket, or an Unmanned Arial Vehicle), a drone, a robot, a building, furniture, or an organism other than a human. In some embodiments, the sample comprises an environmental fluid. Non-limiting examples of environmental fluids include marine water, well water, drinking well water, water at the bottom of well dug for petroleum extraction or exploration, melted ice water, pond water, aquarium water, pool water, lake water, mud, stream water, river water, brook water, waste water, treated waste water, reservoir water, rain water, and ground water. In some embodiments, waste water comprises sewage water, septic tank water, agricultural runoff, water from an area in which chemical or oil spill has or is suspected of having occurred (e.g., an oil spill into a marine environment), water from an area where a radiation leak has or is suspected of having occurred (e.g., coolant from a nuclear reactor), water within the plumbing of a building, water within or exiting a research facility, and/or water within or exiting a manufacturing facility such as a factory.

As used herein, "suspected" with respect to an event means that there has been at least one test (e.g., a test other than a method or assay provided herein), occurrence (e.g., that is likely to or that may cause the event such as an emergency, leak, accident, flood, earthquake, storm, fire, malfunction, sunk vessel, or crash), or report (e.g., by a witness, informant, or observer) that is consistent with the event having occurred.

In certain embodiments, the sample comprises a food or beverage additive and/or a food or beverage composition. In some embodiments, the food or beverage composition comprises a fermented composition. In various embodiments, the sample comprises a fluid obtained from a food composition. Alternatively or in addition, the sample may comprise a solute dissolved from a food composition. In some examples, a solute is or has been dissolved from a food composition with an aqueous or nonaqueous solution. In various implementations, an aqueous solution may optionally comprise a nonaqueous solvent. In certain embodiments, a sample comprises a food composition in semisolid or liquid form. Non-limiting examples of such compositions include yogurt, soup, ice cream, a broth, a puree, a shake, a smoothie, a batter, a condiment, a sauce, and any combination thereof. In some implementations, a sample is a food engineering process (e.g., obtained from a food design, storage, transport, or production process or from equipment intended to process, transport, or store food). A food composition may comprise, e.g., a plant or a composition isolated from a plant, and/or an animal or a composition isolated from an animal. In various embodiments, a sample comprises a beverage composition. Non-limiting examples of beverage compositions include soft drinks, fountain beverages, water, coffee, tea, milk, dairy-based beverages, soy-based beverages (e.g., soy milk), almond-based beverages (e.g., almond milk), vegetable juice, fruit juice, fruit juice-flavored drinks, energy drinks, sports and fitness drinks, alcoholic products, and beverages comprising any combination thereof. Non-limiting examples of beverage compositions comprising water include purified water (e.g., filtered water, distilled water, or water purified by reverse osmosis), flavored water, mineral water, spring water, sparkling water, tonic water, and any combination thereof. In various embodiments, the sample comprises alcohol. Non-limiting examples of such samples include samples comprising or obtained/provided from beer, malt beverages, liqueur, wine, spirits, and any combination thereof.

In some embodiments, a sample comprises a nutritional or supplement composition. In certain implementations, the nutritional or supplement composition comprises an omega-3 fatty acid, a vitamin, a mineral, a protein powder, or a meal supplement.

In certain embodiments, a biosensor is implanted in a subject's body. For example, a biosensor may be implanted in a subject's blood vessel, vein, eye, natural or artificial pancreas, alimentary canal, stomach, intestine, esophagus, or skin (e.g., within the skin or under the skin). In various embodiments, the biosensor is configured within or on the surface of a contact lens. In some embodiments, the biosensor is configured to be implanted in or under the skin. In non-limiting examples, the biosensor is implanted in a subject with an optode and/or a microbead. In certain embodiments, the biosensor generates a signal transdermally.

The present subject matter includes a method for monitoring the level of a ligand, comprising periodically or continuously detecting the level of the ligand, wherein detecting the level of the ligand comprises (a) providing or obtaining a sample; (b) contacting the sample with a biosensor for the ligand under conditions such that the ligand-binding protein of the biosensor binds to the ligand, and (c) detecting a signal produced by the biosensor.

Aspects of the present subject matter also provide a method for monitoring the level of a ligand (e.g., bicarbonate or $Ca^{2+}$) in a subject, comprising periodically detecting the level of the ligand in the subject. Detecting the level of the ligand in the subject may comprise (a) providing or obtaining a biological sample from the subject; (b) contacting the biological sample with a biosensor for the ligand provided herein under conditions such that the ligand-binding protein of the biosensor binds to the ligand, if the ligand is present in the biological sample, and (c) detecting (i) a signal produced by a reporter group of the biosensor, or (ii) whether a signal is produced by a reporter group of the biosensor. The level of the ligand may be detected, e.g., at least once every 1, 2, 3, 6, or 12 hours, at least once every 1, 2, 3, or 4 days, at least once every 1, 2, or three weeks, or at least once every 1, 2, 3, 4, 6, or 12 months.

The present subject matter also provides a method for monitoring the level of a ligand in a subject. The method comprises (a) administering a biosensor provided herein or a device comprising a biosensor provided herein to the subject, wherein after administration the biosensor is in contact with a bodily fluid or surface that typically comprises the ligand, and (b) detecting (i) a signal produced by a reporter group of the biosensor continuously or repeatedly at intervals less than about 30 minutes (m), 15m, 10m, 5m, 1m, 30 seconds (s), 15s, 10s, 5s, Is, 0.1s, 0.001s, 0.0001s, or 0.00001 apart, and/or (ii) whether a signal is produced by a reporter group of the biosensor continuously or repeatedly at intervals less than about 30m, 15m, 10m, 5m, 1m, 30s, 15s, 10s, 5s, Is, 0.1s, 0.001s, 0.0001s, or 0.00001 apart.

Non-limiting aspects of continuously monitoring ligand levels are described in Weidemaier et al. (2011) Biosensors and Bioelectronics 26, 4117-4123 and Judge et al. (2011) Diabetes Technology & Therapeutics, 13(3):309-317, the entire contents of each of which are hereby incorporated herein by reference.

Also within various implementations is a composition comprising a purified ligand-binding fluorescently-responsive sensor protein and a solid substrate, e.g., a particle, a bead such as a magnetic bead, or a planar surface such as a chip or slide, wherein the sensor protein is immobilized onto the solid substrate. In some embodiments, the biosensor is immobilized on a patch. In some embodiments, the patch comprises a polymer or copolymer comprising hydroxyethyl (meth)acrylate, a polyolefin, polyurethane, polystyrene, an ethylene/methacrylic acid copolymer, an ethylene/methyl methacrylate copolymer, a polyester, and/or a polyurethane. In some embodiments, the patch comprises a woven fabric, a knitted fabric, or a nonwoven fabric of a synthetic fiber and/or natural fiber. In certain embodiments, the patch has an adhesive layer. An exemplary solid substrate solid substrate comprises a cyclic olefin copolymer. In some embodiments, the ligand-binding protein is thermostable.

A thermostable biosensor protein is one in which the activity (ligand binding) is retained after exposure to relatively high temperatures. For example, the urea sensor protein comprises a mid-point thermal melt transition greater than 30° C., greater than 40° C., greater than 50° C., greater than 60° C., greater than 70° C., greater than 80° C., greater than 90° C., or greater than 100° C., or about 30° C. to about 100° C., about 40° C. to about 100° C., about 50° C. to about 100° C., about 60° C. to about 100° C., about 70° C. to about 100° C., about 80° C. to about 100° C., or about 90° C. to about 100° C. In some embodiments, the sensor protein contains a single cysteine residue. In some embodiments, the single cysteine residue is located in a site of the ligand-binding protein, where it responds to ligand binding. In some examples, the protein comprises the amino acid sequence of SEQ ID NO: 64 (avBicarbBP5_18C_16F_bZif), 53 (teFeBP3_E270C), or 38 (avBicarBP5_18C), and in some examples, the single cysteine is conjugated to Badan, Acrylodan, or a derivative thereof, or Pacific Blue. For example, the derivative comprises a replacement of the two-ring naphthalene of Acrylodan or Badan with a three-ring anthracene, a fluorene, or a styrene. A reporter group is covalently bound to the single cysteine. In some situations, the solid substrate comprises a plurality of sensor proteins, each of which comprises a different dissociation constant ($K_d$) for ligand, e.g., for detecting and quantifying ligand levels across many ranges of concentrations.

The present subject matter also includes a composition comprising purified sensor protein with less than 65% identity and greater than 27% identity (e.g., 44-48% sequence identity) to any one of SEQ ID NOS: 1-28 or 75-88, wherein the sensor protein comprises a single cysteine residue, and a solid substrate, such that the sensor protein is immobilized onto the solid substrate.

In some embodiments, a method of detecting the presence of or the quantity of ligand in a test sample is carried out using the following steps: contacting the test sample with the biosensor or sensor protein/solid support construct to yield a complex of ligand and the ligand-binding protein or biosensor protein; contacting the complex with an excitation light; measuring an emission intensity of the reporter group from at least two wavelengths; computing a ratiometric signal from the two (or more) wavelengths; and comparing the signal to a known ligand binding curve of signals to identify the presence of or calculate the quantity of ligand in the test sample. The test sample may be obtained from a variety of sources. For example, the test sample may be selected from a bodily fluid, a food, a beverage, or a bioreactor culture broth. The testing method may be carried out in vivo, e.g., using an implantable device or dermal patch, or ex vivo.

In various embodiments, the subject to be tested is a mammal, e.g., a primate (such as a human, a monkey, a chimpanzee, or a gorilla), a fish, a bird, a reptile, an amphibian, or an arthropod. In some embodiments, the subject is a fish, a cow, a pig, a camel, a llama, a horse, a race horse, a work horse, a goat, a rabbit, a sheep, a hamster, a guinea pig, a cat, a wolf, a dog (e.g., a pet dog, a work dog, a police dog, or a military dog), a rat, a mouse, a seal, a whale, a manatee, a lizard, a snake, a chicken, a goose, a swan, a duck, or a penguin.

Exemplary Methods for Assaying the Level of Bicarbonate in Subjects

Aspects of the present subject matter provide a method for assaying the level of bicarbonate in a subject. The method may comprise contacting a biological sample from the subject with a biosensor for bicarbonate under conditions such that the biosensor binds to bicarbonate present in the biological sample. The biosensor comprises a reporter group attached to a bicarbonate-binding protein, and binding of bicarbonate to a bicarbonate-binding domain of the bicarbonate-binding protein causes a change in signaling by the reporter group. In various embodiments, the subject has, is suspected of having, has previously had, or is undergoing routine (e.g., during a physical) testing for a disease or an injury associated with abnormal bicarbonate levels (e.g., in a bodily fluid such as blood). Non-limiting examples of conditions and injuries that may lead to or involve high levels of bicarbonate include vomiting, dehydration, blood transfusions, overuse of medicines that contain bicarbonate (especially antacids), anorexia, chronic obstructive pulmonary disease (COPD), respiratory insufficiency, lung dysfunction, fluid in the lungs (pulmonary edema), heart disease, Cushing's disease, and Conn's syndrome. A high level of bicarbonate can be result from metabolic alkalosis, a condition that causes a pH increase in tissue. Metabolic alkalosis can happen from a loss of acid from the body, such as through vomiting and dehydration. It may also be related to conditions including anorexia and COPD.

As used herein, "suspected" with respect to a subject's condition (e.g., disease or injury) means that the subject has at least one symptom or test (e.g., a test other than an assay or method provided herein) that is consistent with the condition.

A wide range of conditions and injuries, including aspirin overdose, alcohol overdose, malnutrition, hyperthyroidism, diarrhea, kidney disease, and liver disease, uncontrolled diabetes, diabetic ketoacidosis, and a heart attack can lead to or involve low bicarbonate levels. A low level of bicarbonate may be caused by a condition called metabolic acidosis, or too much acid in the body. Metabolic acidosis is a condition that occurs when the body produces excessive quantities of acid or when the kidneys are not removing enough acid from the body. If unchecked, metabolic acidosis leads to acidemia, i.e., blood pH is low (less than 7.35) due to increased production of hydrogen ions by the body or the inability of the body to form bicarbonate in the kidney. Its causes are diverse, and its consequences can be serious, including coma and death. Together with respiratory acidosis, it is one of the two general causes of acidemia.

In some embodiments, the subject has a liver disease, a kidney disease (such as chronic kidney disease or an acute kidney injury), or diabetes. In some embodiments, the biological sample comprises blood, plasma, serum, sweat, tear fluid, or urine. In certain embodiments, the biological sample is present in or on the surface of the subject. In various implementations, the biosensor is applied onto or inserted into the subject. For example, the biosensor may be tattooed into the subject or is in or on a device that is implanted into the subject. In some embodiments, the biosensor may be present in or on a contact lens that is worn by the subject. Methods for determining the level of bicarbonate, e.g. in a subject who has, is suspected of having, has previously had, or is undergoing routine (e.g., during a physical) testing for a disease or an injury associated with abnormal bicarbonate levels, may be performed without other testing related to bicarbonate levels, or performed as part of a battery of clinical testing. In some embodiments, the subject has, has previously had, is suspected of having metabolic acidosis or metabolic alkalosis.

In some embodiments, the biological sample comprises blood, plasma, serum, sweat, tear fluid, or urine. In certain embodiments, the biological sample is present in or on the surface of the subject. In various implementations, the biosensor is applied onto or inserted into the subject. For example, the biosensor may be tattooed into the subject or is in or on a device that is implanted into the subject. In some embodiments, the biosensor may be present in or on a contact lens that is worn by the subject. Methods for determining the level of bicarbonate, e.g. in a subject who has, is suspected of having, has previously had, or is undergoing routine (e.g., during a physical) testing for a disease or an injury associated with abnormal bicarbonate levels, may be performed without other testing related to bicarbonate levels, or performed as part of a battery of clinical testing. In some embodiments, the subject is a human athlete, a soldier, a marine, a sailor, a pilot, an astronaut, a work animal (e.g., a work dog such as a sled dog, a military dog, a police dog, a rescue dog, a work horse, a police or military horse, or ox), or a performance animal (e.g., a race dog, a race camel, a race horse, a performance seal or sea lion, or a performance dolphin or porpoise).

Any type of abnormal bicarbonate level may be assessed, monitored or detected using the compounds, compositions, and methods provided herein. Additionally, any subject who has or is at risk of a disease or injury associated with an abnormal bicarbonate level may be assessed and/or monitored using the compounds, compositions, and methods provided herein.

Exemplary Methods for Assaying the Level of $Ca^{2+}$ in Subjects

Aspects of the present subject matter provide a method for assaying the level of a $Ca^{2+}$ in a subject. The method may comprise contacting a biological sample from the subject with a biosensor for $Ca^{2+}$ under conditions such that the biosensor binds to $Ca^{2+}$ present in the biological sample. The biosensor comprises a reporter group attached to a calcium-binding protein, and binding of the $Ca^{2+}$ to a calcium-binding domain of the calcium-binding protein causes a change in signaling by the reporter group.

In various embodiments, the subject has, is suspected of having, has previously had, or is undergoing routine (e.g., during a physical) testing for a disease or an injury associated with abnormal $Ca^{2+}$ levels (e.g., in a bodily fluid such as blood).

Non-limiting examples of diseases and injuries associated with abnormal $Ca^{2+}$ levels include hypercalcemia, pancreatitis, kidney dysfunction (e.g., kidney failure, acute kidney injury or chronic kidney disease), a parathyroid disease, abnormal parathyroid gland function, hyperparathyroidism, muscle cramps, muscle spasms, muscle twitching and/or tingling in the fingers and/or around the mouth, and cancer (such as kidney, lung, or ovary cancer). Abnormally high levels of $Ca^{2+}$ may be caused by consuming too much calcium or vitamin D, hyperparathyroidism, an infection that causes granulomas such as tuberculosis and certain fungal and mycobacterial infections, multiple myeloma, T cell lymphoma and certain other cancers, metastatic bone tumors, hyperthyroidism, excessive thyroid hormone replacement drugs/treatment, Paget's disease, abnormal bone destruction and regrowth, sarcoidosis, tumors that produce a parathyroid hormone, and the administration of certain drugs such as lithium, tamoxifen, or a thiazide.

In some embodiments, the biological sample comprises blood, plasma, serum, sweat, tear fluid, or urine. In certain embodiments, the biological sample is present in or on the surface of the subject. In various implementations, the biosensor is applied onto or inserted into the subject. For example, the biosensor may be tattooed into the subject or is in or on a device that is implanted into the subject. In some embodiments, the biosensor may be present in or on a contact lens that is worn by the subject. Methods for determining the level of $Ca^{2+}$, e.g. in a subject who has, is suspected of having, has previously had, or is undergoing routine (e.g., during a physical) testing for a disease or an injury associated with abnormal levels of $Ca^{2+}$, may be performed without other testing related to $Ca^{2+}$ levels, or performed as part of a battery of clinical testing. In some embodiments, the subject is a human athlete, a soldier, a marine, a sailor, a pilot, an astronaut, a work animal (e.g., a work dog such as a sled dog, a military dog, a police dog, a rescue dog, a work horse, a police or military horse, or ox), or a performance animal (e.g., a race dog, a race camel, a race horse, a performance seal or sea lion, or a performance dolphin or porpoise).

Any type of abnormal $Ca^{2+}$ level may be assessed, monitored or detected using the compounds, compositions, and methods provided herein. Additionally, any subject who has or is at risk of a disease or injury associated with an abnormal cation level may be assessed and/or monitored using the compounds, compositions, and methods provided herein.

Exemplary Devices and Compositions Comprising Biosensors

Aspects of the present subject matter provide a device comprising one or more biosensors provided herein. Such devices may be, e.g., wearable, implantable, portable, or fixed.

In some embodiments, the device is a nanoparticle or a microparticle comprising the biosensor. Non-limiting examples of devices include devices comprising a test strip, patch, plate, bead, or chip comprising a biosensor provided herein. In certain embodiments, a device may comprise a desiccated biosensor.

The present subject matter also provides a contact lens or a skin patch comprising a biosensor provided herein. In some embodiments, the biosensor is throughout the contact lens or skin patch or within a particular region or zone of a contact lens or skin patch (e.g., in one or more shapes (e.g., a square, circle, or star), dots, lines, or zones, located at the periphery or a portion of the periphery of a contact lens or patch). In some embodiments, the skin patch comprises an adhesive that facilitates attachment of the patch to the surface of skin.

Devices provided herein may include a variety of structural compositions. For example, many polymers (including copolymers), and plastics may be used. Non-limiting examples of compositions useful in certain devices include glass, polystyrene, polypropylene, cyclic olefin copolymers, ethylene-norbornene copolymers, polyethylene, dextran, nylon, amylase, paper, a natural cellulose, a modified cellulose, a polyacrylamide, gabbros, gold, and magnetite (as well as combinations thereof). In some embodiments, the device comprises a hydrogel, a cryogel, or a soluble gel. For example, the biosensor may be incorporated into or onto the hydrogel, cryogel, or soluble gel. In various embodiments, the device comprises a matrix comprising nanopores, micropores, and/or macropores. In certain embodiments, the surface of a device comprises a polymer. In an embodiment, the surface comprises the surface of a particle or a bead having a diameter of about 0.001-1, 0.001-0.1, 0.01-0.1, 0.001-0.01, 0.1-1, 0.1-0.5, or 0.01-0.5 centimeters (cm). For example, the particle comprises a nanoparticle or a microparticle.

Non-limiting examples of polymers include cyclic olefin copolymers, ethylene-norbornene copolymers, polylactic acid, polyglycolic acid, agarose, alginate, poly(lactide-co-glycolide), gelatin, collagen, agarose, natural and synthetic polysaccharides, polyamino acids, poly(lysine), polyesters, polyhydroxybutyrates, polyanhydrides, polyphosphazines, polyvinyl alcohol, polyalkylene oxide, polyethylene oxide, polyallylamines, polyacrylates, modified styrene polymers, poly(4-aminomethylstyrene), pluronic polyols, polyoxamers, polyuronic acid, polyvinylpyrrolidone, hydroxyethyl (meth)acrylate, polyolefins, polyurethane, polystyrene, ethylene/methacrylic acid copolymers, ethylene/methyl methacrylate copolymers, polyester, and polyurethane. In some embodiments, the patch comprises a woven fabric, a knitted fabric, or a nonwoven fabric of a synthetic fiber and/or natural fiber.

Non-limiting examples of temporary tattoo compositions for application to a subject's skin are discussed in U.S. Patent Application Publication No. 20090325221, published Dec. 31, 2009, and U.S. Pat. No. 6,428,797, the entire contents of each of which are incorporated herein by reference. Biosensor disclosed herein may be incorporated into any temporary tattoo or other composition for application to the skin. For example, a temporary tattoo decal for application to a subject's skin and configured to detect the presence of a ligand may comprise, e.g., a base paper or plastic; a water-soluble slip layer applied to the base paper or plastic; a temporary tattoo applied to the water-soluble release layer on the base paper, wherein the temporary tattoo comprises a biosensor disclosed herein; an adhesive layer overlying the temporary tattoo; and a protective sheet overlying the adhesive layer.

In some embodiments, the device comprises a plastic polymer comprising cyclic olefin copolymer (COC), such as e.g. TOPAS® COC. Several types of cyclic olefin copolymers are available based on different types of cyclic monomers and polymerization methods. Cyclic olefin copolymers are produced by chain copolymerization of cyclic monomers such as 8,9,10-trinorborn-2-ene (norbornene) or 1,2,3,4,4a,5,8,8a-octahydro-1,4:5,8-dimethanonaphthalene (tetracyclododecene) with ethene (such as TOPAS Advanced Polymer's TOPAS, Mitsui Chemical's APEL), or by ring-opening metathesis polymerization of various cyclic monomers followed by hydrogenation (Japan Synthetic Rubber's ΔRTON, Zeon Chemical's Zeonex and Zeonor). See, e.g., International Union of Pure and Applied Chemistry (2005) *Purr. Appl. Chem.* 77(5):801-814. These later materials using a single type of monomer may be referred to as cyclic olefin polymers (COPs). A CAS Registry number for COC is 26007-43-2.

In some embodiments, the biosensor is covalently or noncovalently (e.g., electrostatically) attached to a surface of a device. In certain embodiments, the biosensor is attached to a surface of a device or is not attached to a surface of the device (e.g., the biosensor is physically present within the device as a component of a solution or powder but not chemically immobilized onto or into a device surface). For example, the biosensor may move within the confines of a device chamber.

A biosensor may be attached to a device via a variety or means, e.g., via attachment motif. In some embodiments, the attachment motif is attached to the N-terminus or the C-terminus of the biosensor. In certain embodiments, the biosensor is linked to an attachment motif via a covalent bond. In various embodiments, the biosensor is linked to the attachment motif via a linker. A non-limiting example of a linker is a polyglycine comprising 2, 3, 4, 5, or more glycines and optionally further comprising a serine. In some embodiments, the attachment motif comprises a polypeptide. Non-limiting examples of polypeptides useful in attachment moieties include hexahistidine peptides, hexalysine peptides, zinc-finger domains (ZF-QNKs), and disulfide-containing truncated zinc fingers (βZifs). An example of a hexalysine peptide comprises amino acids in the sequence of SEQ ID NO: 93, an example of a ZF-QNK comprises amino acids in the sequence of SEQ ID NO: 91, and an example of a βZif comprises amino acids in the sequence of SEQ ID NO: 90. In some embodiments, the attachment motif comprises a polypeptide that binds to plastic or cellulose.

The hexahistidine, hexalysine, βZif and QNK-ZF fusions enable FRSs to be immobilized onto chemically functionalized surfaces. Non-limiting aspects of chemically functionalized surfaces are discussed in Biju, V. (2014) *Chem Soc Rev,* 43, 744-64 and McDonagh (2008) *Chem Rev,* 108, 400-422, the entire contents of which are incorporated herein by reference. Directed evolution methods have been used to develop peptides that bind directly to non-functionalized surfaces (Care, Bergquist and Sunna 2015 *Trends Biotechnol,* 33, 259-68; Baneyx 2007 *Curr. Opin. Biotechnol.,* 18, 312-317; Gunay and Klok 2015 *Bioconjug Chem,* 26, 2002-15), including various plastics (Adey et al. 1995 Gene, 156, 27-31; Serizawa et al. 2005 *J Am Chem Soc,* 127, 13780-1; Serizawa, Sawada and Kitayama 2007a *Angew Chem Int Ed Engl,* 46, 723-6; Serizawa, Sawada and Matsuno 2007b *Langmuir,* 23, 11127-33; Serizawa, Techawanitchai and Matsuno 2007c *Chembiochem,* 8, 989-93; Matsuno et al. 2008 *Langmuir,* 24, 6399-403; Chen, Serizawa and Komiyama 2011 *J Pept Sci,* 17, 163-8; Kumada 2010 J. *Biosci. and BioEng.,* 109, 583-587; Date et al. 2011 *ACS Appl Mater Interfaces,* 3, 351-9; Kumada 2012, Vodnik, Strukelj and Lunder 2012 *J. Biotech.,* 160, 222-228; Kumada 2014 *Biochem. et Biophys. Acta,* 1844, 1960-1969; Ejima, Matsuno and Serizawa 2010 *Langmuir,* 26, 17278-85), inorganic materials (Hnilova 2012 *Soft Matter,* 8, 4327-4334; Care et al. 2015 *Trends Biotechnol,* 33, 259-68), nanoparticles (Avvakumova et al. 2014 *Trends Biotechnol,* 32, 11-20), and cellulosic paper (Guo et al. 2013 *Biomacromolecules,* 14, 1795-805). Such peptides, or natural material-binding domains (Oliveira et al. 2015 *Biotechnol Adv,* 33, 358-69), also can be fused to FRSs to direct site-specific, oriented immobilization on their target materials while preserving FRS function. For instance, plastic-binding peptides have been developed that direct immobilization on polystyrene (Adey et al. 1995 *Gene,* 156, 27-31; Serizawa et al. 2007c *Chembiochem,* 8, 989-93; Kumada 2010 *Biochem. et Biophys. Acta,* 1844, 1960-1969; Vodnik et al. 2012 *Anal Biochem,* 424, 83-6), polymethyl acrylate (Serizawa et al. 2005 *JAm Chem Soc,* 127, 13780-1; Serizawa et al. 2007a *Angew Chem Int Ed Engl,* 46, 723-6; Serizawa et al. 2007b *Langmuir,* 23, 11127-33; Kumada 2014 *Biochem. et Biophys. Acta,* 1844, 1960-1969), polycarbonate (Kumada 2012 *J. Biotech.,* 160, 222-228), polylactide (Matsuno et al. 2008 *Langmuir,* 24, 6399-403), and polyphenylene vinylene (Ejima et al. 2010 *Langmuir,* 26, 17278-85). Cellulose-binding peptides (Guo et al. 2013 *Biomacromolecules,* 14, 1795-805) and natural domains (Oliveira et al. 2015 *Biotechnol Adv,* 33, 358-69; Shoseyov, Shani and Levy 2006 *Microbiol Mol Biol Rev,* 70, 283-95) can be used to immobilize fusion proteins on paper. Inorganic material include noble metals (Hnilova 2012 *Soft Matter,* 8, 4327-4334), semi-conductors (Care et al. 2015 *Trends Biotechnol,* 33, 259-68), and fluorescent quantum dots (Medintz et al. 2005 *Nat Mater,* 4, 435-46; Lee et al. 2002 *Science,* 296, 892-5). The entire contents of each of the references above (and all other references herein) is incorporated herein by reference.

In some embodiments, the attachment motif is attached to a device surface and/or within a matrix of the device. In some embodiments, a biosensor is attached to an attachment motif via a covalent bond and the attachment motif is attached to a device via a covalent bond. Non-limiting examples of covalent bonds include disulfide bonds, ester bonds, thioester bonds, amide bonds, and bonds that have been formed by click reactions. Non-limiting examples of a click reaction include a reaction between an azide and an alkyne; an azide and an alkyne in the presence of Cu(I); an azide and a strained cyclooctyne; an azide and a dibenzylcyclooctyne, a difluorooctyne, or a biarylazacyclooctynone; a diaryl-strained-cyclooctyne and a 1,3-nitrone; an azide, a tetrazine, or a tetrazole and a strained alkene; an azide, a tetrazine, or a tretrazole and a oxanorbornadiene, a cyclooctene, or a trans-cycloalkene; a tetrazole and an alkene; or a tetrazole with an amino or styryl group that is activated by ultraviolet light and an alkene.

Alternatively or in addition, a surface of a device may be modified to contain a moiety (e.g. a reactive group) what facilitates the attachment of a biosensor and/or binds to the biosensor. In some embodiments, the biosensor is attached to a surface via a biotin-avidin interaction.

In various implementations, the device comprises a first region or chamber for receiving a sample and a second region or chamber that comprises the biosensor, wherein the first region or chamber is separated from the second region or chamber by a filter. In some examples, the filter is impermeable to compounds greater than about 1, 2, 3, 4, 5, 10, 50, 200, or 250 kiloDalton (kDa) in size. The sample may comprise, e.g., a tube, such as a tube that is configured for centrifugation. When sample is placed into the first region and the device is centrifuged, then a portion of the sample comprising a ligand flows through the filter into the second region where the biosensor is contacted.

Non-limiting examples of devices provided herein include endoscopy probes and colonoscopy probes.

In some embodiments, the device comprises an optode. In non-limiting examples, the optode comprises an optical fiber and a single biosensor or composite biosensor. In certain embodiments, the single biosensor or composite biosensor is immobilized on the surface or at an end of the optical fiber. In some embodiments, the optode is configured for implantation into a subject. Alternatively or in addition, the optode is configured for insertion into a sample.

The devices provided herein may optionally comprise a biosensor panel, a composite sensor, a sensor array, and/or a composition comprising a plurality of biosensors. In various embodiments, a device comprises multiple biosensors that detect a range of different ligand concentrations in a single sample and/or assay run (i.e., each biosensor has a different affinity for the ligand). Devices may provide spatial localization of multiple biosensors to provide the necessary addressability of different elements in a multi-sensor array comprising sensors that differ in their engineered affinities for coverage of a wide range of ligand concentrations, or sensors that each detects distinct analytes.

Aspects of the present subject matter provide a biosensor panel comprising a plurality of biosensors, wherein the plurality of biosensors comprises at least one biosensor disclosed herein. In some embodiments, the plurality comprises at least about 2, 3, 4, 5, 10, 20, 30, 40, 50, 60, 70, 80, 90, or 100 biosensors.

The present subject matter also provides a composite sensor. The composite sensor may comprise a sensor element, wherein the sensor element comprises 2 or more biosensors, wherein at least 1 of the 2 or more biosensors is a biosensor disclosed herein. In some embodiments, the biosensors are not spatially separated in the sensor element, e.g., the biosensors are mixed within a solution, or immobilized on a surface of the sensor element. Alternatively, a mixture of different biosensors is physically present, e.g., loose, within a region or chamber of a sensor device/structure. In various embodiments, the composite sensor comprises a plurality of sensor elements, wherein each sensor element of the plurality of sensor elements comprises 2 or more biosensors, wherein at least 1 of the 2 or more biosensors is a biosensor provided herein. In some embodiments, the plurality of sensor elements comprises at least about 2, 3, 4, 5, 10, 20, 30, 40, 50, 60, 70, 80, 90, or 100 sensor elements.

Also included herein is a sensor array comprising a plurality of biosensors of the present subject matter. The sensor array may include, e.g., multichannel array or a multiplexed array. In some embodiments, the biosensors of the plurality of biosensors are spatially separated from each other. In certain embodiments, the biosensors are arranged linearly or in a grid on a surface of the array.

The present subject matter provides a composition comprising a plurality of biosensors including at least one biosensor disclosed herein. Also provided is a non-human mammal comprising a biosensor or device disclosed herein.

Exemplary Polypeptides and Polynucleotides

The present subject matter provides polynucleotides encoding any one of the polypeptides disclosed herein. The polypeptides are also provided. In various embodiments, the polynucleotides are codon-optimized for expression in a desired host cell, such as bacterial cells (e.g., *E. coli*), yeast, insect cells, plant cells, algal cells, or mammalian cells. The polypeptides provided herein include polypeptides comprising the amino acid sequence of any one of SEQ ID NOS: 1-88. The polynucleotides provided herein include polynucleotides encoding a polypeptide comprising the amino acid sequence of any one of SEQ ID NOS: 1-88.

The polypeptides and biosensors provided herein may be in a variety of forms, e.g., purified in solution, dried (e.g. lyophilized) such as in the form of a powder, and in the form of a crystal (e.g., a crystal suitable for x-ray crystallography). Thus, aspects of the present subject matter provide crystal structures and crystalized forms of the ligand-binding proteins and biosensors disclosed herein. Such crystal structures and crystalized proteins are useful for designing and optimizing biosensors using principles and methods discussed herein.

Also provided are expression vectors comprising a polynucleotide of the present subject matter and/or encoding a polypeptide disclosed herein. Non-limiting examples of expression vectors include viral vectors and plasmid vectors. In some embodiments, an expression vector comprises nucleotides in the sequence set forth as any one of SEQ ID NOS: 95-154. In various embodiments, a polynucleotide encoding a ligand-binding protein and/or biosensor is operably linked to a promoter. The promoter may be expressed, e.g., in a prokaryotic and/or a eukaryotic cell.

The subject matter further includes an isolated cell comprising an expression vector provided herein. The isolated cell may be, e.g., a bacterial cell, a yeast cell, an algal cell, a plant cell, an insect cell, or a mammalian cell. Also included is a non-human multicellular organism such as a plant or an animal (e.g., an insect, a mammal, a worm, a fish, a bird, or a reptile) comprising an expression vector disclosed herein.

Exemplary Methods for Designing Biosensors

Aspects of the present subject matter provide method of identifying a candidate ligand-binding protein for use in a biosensor, comprising: (a) selecting a first protein having a known amino acid sequence (seed sequence), wherein the first protein is known to bind bicarbonate; (b) identifying a second protein having an amino acid sequence (hit sequence) with at least 15% sequence identity to the seed sequence; (c) aligning the seed amino acid sequence and the hit sequence, and comparing the hit sequence with the seed sequence at positions of the seed sequence that correspond to at least 5 primary complementary surface (PCS) amino acids, wherein each of the at least 5 PCS amino acids has a hydrogen bond interaction or a van der Waals interaction with bicarbonate when bicarbonate is bound to the first protein; and (d) identifying the second protein to be a candidate ligand-binding protein if the hit sequence comprises at least 5 amino acids that are consistent with the PCS.

The present subject matter also includes a method for constructing a candidate biosensor, comprising: (a) providing a candidate ligand-binding protein; (b) generating a structure of the second protein; (c) identifying at least one putative allosteric, endosteric, or peristeric site of the second protein based on the structure; (d) mutating the second protein to substitute an amino acid at the at least one putative allosteric, endosteric, or peristeric site of the second protein with a cysteine; and (e) conjugating a fluorescent compound to the cysteine. In some embodiments, the structure comprises a homology model of the second protein generated using a structure of the first protein. In some embodiments, the structure comprises a structure experimentally determined by nuclear magnetic resonance spectroscopy or X-ray crystallography.

Aspects of the present subject matter further provide a method for constructing a biosensor comprising a desired dissociation constant ($K_d$) for a ligand, comprising: (a) providing an initial biosensor that does not comprise the desired $K_d$ for the ligand, wherein the initial biosensor is a biosensor provided herein; (b) mutating the initial biosensor to (i) alter a direct interaction in the PCS between the initial biosensor and bound ligand; (ii) manipulate the equilibrium between open and closed states of the initial biosensor; (iii) alter an interaction between the ligand-binding protein and the reporter group of the initial biosensor; or (iv) alter an indirect interaction that alters the geometry of the binding site of the biosensor, to produce a modified biosensor; and (c) selecting the modified biosensor if the modified biosensor comprises the desired $K_d$ for the ligand. In some embodiments, the reporter group comprises Acrylodan, Badan, or a derivative thereof, and mutating the initial biosensor in (b) comprises altering an interaction between the ligand-binding protein and a carbonyl group of the Acrylodan, Badan, or derivative thereof. In some embodiments, the reporter group comprises Acrylodan, Badan, or a derivative thereof, and mutating the initial biosensor in (b) comprises altering an interaction between the ligand-binding protein and a naphthalene ring of the Acrylodan, Badan, or derivative thereof. In some embodiments, mutating the initial biosensor comprises introducing a substitution mutation into the initial biosensor. In some embodiments, the method further comprises immobilizing the affinity-tuned biosensor on a substrate.

In some embodiments, the second protein comprises (i) amino acids in the sequence of any one of SEQ ID NOS: 1-88; (ii) a stretch of amino acids in a sequence that is least about 95, 96, 97, 98, or 99% identical to the sequence of any one of SEQ ID NOS: 1-88; (iii) a stretch of at least about 50, 100, 150, 200, 250, 300, 350, 400, or 450 amino acids in a sequence that is at least about 95, 96, 97, 98, or 99% identical to a sequence within any one of SEQ ID NOS: 1-88; or (iv) a stretch of at least about 50, 100, 150, 200, 250, 300, 350, 400, or 450 amino acids in a sequence that is identical to a sequence within any one of SEQ ID NOS: 1-88. In various embodiments, attaching the reporter group to the putative allosteric, endosteric, or peristeric site of the first protein comprises substituting a cysteine at the site with a cysteine. For example, the reporter group is conjugated to the cysteine. Preferably, attaching a reporter group to the corresponding amino acid of the second protein produces a functional biosensor.

The selected first protein (e.g., the amino acid sequence thereof) may be novel or known. However, in many instances, the function of the first protein will not be known. In a non-limiting example, identifying a protein not previously known to have bicarbonate binding activity may comprise a structurally assisted functional evaluation (SAFE) homolog search method comprising the following steps:

(1) Collecting a sequence homology set using a BLAST sequence alignment tool starting with a bicarbonate-binding protein sequence disclosed herein or a homologue thereof as a seed. Permissive settings are used, such that pairwise hits are required to have a minimum of only, e.g., 20%, 25%, 30%, 35% or 40% sequence identity with the seed sequence. The lengths of the hit and seed are mutually constrained such that the alignment covers at least, e.g., 60%, 65%, 70%, 85%, or 90% within each partner.

(2) Structure-based encoding of biological function: A primary complementary surface (PCS) comprising the protein residues that form hydrogen bonds and van der Waals contacts with a bound bicarbonate is defined using computer-assisted, visual inspection of the three-dimensional structure of the protein-bicarbonate complex. This definition specifies residue positions and their permitted amino acid identity. Multiple amino acid identities are permitted at each position to encode functionally equivalent residues. This definition establishes a search filter for the accurate prediction of bicarbonate-binding proteins within the universe of sequence homologs collected in (1). For example, a candidate's residue corresponding to position 20 of synBicarbBP1 may be E; a candidate's residue corresponding to position 49 of synBicarbBP1 may be W; a candidate's residue corresponding to position 71 of synBicarbBP1 may be Q; a candidate's residue corresponding to position 102 of synBicarbBP1 may be N; a candidate's residue corresponding to position 142 of synBicarbBP1 may be T; a candidate's residue corresponding to position 148 of synBicarbBP1 may be Q; a candidate's residue corresponding to position 220 of synBicarbBP1 may be E; a candidate's residue corresponding to position 221 of synBicarbBP1 may be E. In another example, a candidate's residue corresponding to position 11 of mhFeBP1 may be R; a candidate's residue corresponding to position 102 of mhFeBP1 may be R; a candidate's residue corresponding to position 143 of mhFeBP1 may be Y; a candidate's residue corresponding to position 199 of mhFeBP1 may be Y; and a candidate's residue corresponding to position 200 of mhFeBP1 may be Y. In another example, a candidate's residue corresponding to position 11 of ttFeBP5 may be R; a candidate's residue corresponding to position 101 of ttFeBP5 may be R; a candidate's residue corresponding to position 143 of ttFeBP5 may be Y; a candidate's residue corresponding to position 200 of ttFeBP5 may be Y; and a candidate's residue corresponding to position 201 of ttFeBP5 may be Y.

(3) Accurate sequence alignment: Tools such as ClustalW are used to construct an accurate alignment of all the sequence homologs. The seed sequence is included in the alignment. This multiple sequence alignment establishes the equivalent positions of the seed bicarbonate-binding protein (primary complementary surface) PCS in each sequence homolog.

(4) Function evaluation: The bicarbonate-binding properties of each of the aligned sequence homologs is determined by measuring their compliance with the PCS sequence filter.

A "Hamming distance", H, is assigned for each homolog, which specifies the degree of sequence identity of all the residues at the aligned PCS positions. A value of H=0 indicates that the identities of all the residues at the aligned PCS positions match the amino acid(s) allowed in the PCS search filter; H>0, indicates that one or more aligned positions have disallowed residues. Sequences for which H=0 are predicted to encode bicarbonate-binding proteins.

(5) Selection of representative SAFE homologs: The sequence homologs are ordered by (a) identity with the seed PCS, as measured by the Hamming distance, (b) fractional overall sequence identity with the seed sequence. A subset for sequences with H=0, sampling the fractional overall sequence identity is selected for experimental verification.

In a non-limiting example, identifying a protein not previously known to have bicarbonate-binding activity may comprise the following steps:

(1) performing a computational search of sequence databases to define a broad group of simple sequence or structural homologs of any known, bicarbonate-binding protein;
(2) using the list from step (1), deriving a search profile containing common sequence and/or structural motifs shared by the members of the list [e.g. by using computer programs such as MEME (Multiple Em for Motif Elicitation available at meme.sdsc.edu/meme/cgi-bin/meme.cgi) or BLAST];
(3) searching sequence/structural databases, using a derived search profile based on the common sequence or structural motif from step (2) as query (e.g., using computer programs such as BLAST, or MAST (Motif Alignment Search Tool available at meme.sdsc.edu/meme/cgi-bin/mast.cgi), and identifying a candidate sequence, wherein a sequence homology and/or structural similarity to a reference bicarbonate-binding protein is a predetermined percentage threshold;
(4) compiling a list of candidate sequences to generate a list of candidate bicarbonate-binding proteins;
(5) expressing the candidate bicarbonate-binding proteins in a host organism; and
(6) testing for bicarbonate binding activity, wherein detection of bicarbonate binding in the organism (or the media thereof) indicates that the candidate sequence comprises a novel bicarbonate-binding protein.

In non-limiting examples, the MEME suite of sequence analysis tools (meme.sdsc.edu/meme/cgi-bin/meme.cgi) can also be used as an alternative to BLAST. Sequence motifs are discovered using the program "MEME". These motifs can then be used to search sequence databases using the program "MAST." The BLAST search algorithm is well-known.

In various embodiments relating to alignments using a ClustalW alignment program, the ClustalW alignment program may be, e.g., ClustalW alignment program version 2.1.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DESCRIPTION OF THE DRAWINGS

FIG. 1A: FRSs can be constructed by site-specifically attaching a fluorophore to a protein that undergoes a conformational change upon binding ligand (triangle) in a location between the two lobes of the protein (periplasmic binding protein or engineered derivative thereof), such that the shape and intensities of the fluorescent conjugate emission spectra changes. FIG. 1B: In the absence of ligand, the emitted fluorescence color is predominantly blue, whereas the ligand complex fluoresces green. Arrows indicate the direction of change upon ligand addition. FIG. 1C: The ligand dependence of the absolute blue and green intensities.

FIG. 1D: The ratio of the blue and green emission intensities enables ligand binding to be determined.

FIG. 2 is a diagram of the bicarbonate buffering system establishes the equilibria between carbon dioxide ($CO_2$), carbonic acid ($H_2CO_3$), hydrogen ions and bicarbonate ($HCO_3^-$). This system is essential for maintaining the physiological acid-base balance.

FIG. 3A shows the structure of the bicarbonate-binding protein from *Synechocystis* PCC 6803, synBicarbBP1 [PDB identifier 2i4c (Koropatkin 2007)]. The three dimensional structure is shown. Arrows point to bicarbonate, and $Ca^{2+}$, and residues of the primary complementary surface; small gray spheres show the location of cysteine mutations. FIG. 3B: $Ca^{2+}$ coordination. The calcium coordination sphere forms a typical pentagonal bipyramid, with a bidentate contribution from the bound bicarbonate. FIG. 3C: Residues involved in binding of $HCO_3^-$ and $Ca^{2+}$. The PCS sequence filter used to identify the subset of bicarbonate-calcium binding proteins within a family of sequence synBicarbBP1 homologs. Residue numbering according to PDB accession 2i4c (SEQ ID NO: 166).

FIGS. 4A and B show the structures of the bicarbonate-binding proteins. Arrows point to $Fe^{III}$, bicarbonate, and residues of the primary complementary surface. FIG. 4A: structure of the *Mannheimia haemolytica* bicarbonate-binding protein. FIG. 4B: structure of the *Thermus thermophilus* bicarbonate-binding protein. FIG. 4C: The PCS sequence filter used to identify bicarbonate binding protein. The 1SI0 seed sequence (corresponding to mhFeBP1; SEQ ID NO: 167) and the 4ELR seed sequence (corresponding to ttFeBP5; SEQ ID NO: 168) were used.

FIGS. 6A and B show alignments of Fe—$HCO_3$ binding proteins. FIG. 6A (SEQ ID NO: 197-200): Seed is *Mannheimia haemolytica* Fe—$HCO_3$ binding protein (sequence numbering and secondary structure assignments according to PDB accession 1si0).

FIG. 7A: Corrected emission spectra (purple line, no bicarbonate; red line, 700 mM bicarbonate; black lines, intermediate bicarbonate concentrations). FIG. 7B: Dichromatic signal ($\lambda_1$=455 nm, $\lambda_2$=519 nm; black circles, experimental data points; gray lines, fit to binding isotherm, ${}^{app}K_d$=24 mM). FIG. 7C: Monochromatic signal (gray, 455 nm data points and fit; black, 519 nm data points and fit; ${}^{true}K_d$=61 mM).

FIG. 8A: Corrected emission spectra (purple line, no bicarbonate; red line, 700 mM bicarbonate; black lines, intermediate bicarbonate concentrations). FIG. 8B: Dichromatic signal ($\lambda_1$=455 nm, $\lambda_{2=489}$ nm; black circles, experimental data points; gray lines, fit to binding isotherm, ${}^{app}K_d$=48 mM). FIG. 8C: Monochromatic signal (blue, 455 nm data points and fit; black, 489 nm data points and fit; ${}^{true}K_d$=35 mM).

FIG. 9A: Corrected emission spectra. Arrows indicate direction of change with increased calcium concentration FIG. 9B: Monochromatic signal (green, 489 nm data points and fit; blue, 525 nm data points and fit; ${}^{true}K_d$=1.0 mM). FIG. 9C: Dichromatic signal ($\lambda_1$=489 nm, $\lambda_2$=525 nm; blue circles, experimental data points; red/green lines, fit to binding isotherm, ${}^{app}K_d$=0.62 mM).

FIG. 10A: Emission spectra. Arrows, change in intensity with increased bicarbonate concentration. FIG. 10B: Monochromatic signal (blue, 445 nm data points and fit; green, 517 nm data points and fit; ${}^{true}K_d$=20 mM). FIG. 10C: Dichromatic signal ($\lambda_1$=445 nm, $\lambda_2$=517 nm; blue circles, experimental data points; red/green lines, fit to binding isotherm, ${}^{app}K_d$=15 mM).

FIG. 11A: Emission spectra. Arrows, change in intensity with increased $CaCl_2$) concentration. FIG. 11B: Monochromatic signal (blue, 455 nm data points and fit; green, 520 nm data points and fit; ${}^{true}K_d$=1.1 mM). FIG. 11C: Dichromatic signal ($\lambda_1$=445 nm, $\lambda_2$=520 nm; blue circles, experimental data points; red/green lines, fit to binding isotherm, ${}^{app}K_d$=0.96 mM).

FIGS. 12A-D are diagrams showing three dominant factors that affect ngmFRET between donor and acceptors in which one partner responds to ligand binding. FIG. 12A: Simplified Jablonski diagram illustrating radiative and non-radiative pathways in the donor and acceptor. The donor excited state (D*) is formed through illumination by the excitation source (wavy arrow) whereas the acceptor excited state (A*) is formed by resonance energy transfer (dashed arrow). The fluorescence intensity is determined by the ratio of radiative decay (gray arrows) of the excited states (gray lines) to the ground state (black line) relative to all non-radiative processes (black arrows), and the resonance energy transfer rate, $k_t$, from donor to acceptor. FIG. 12B: Interdipole geometry. Top, FRET efficiency ($f=Q_r/(Q_0-Q_\infty)$, where the $Q_r$, $Q_0$, $Q_\infty$ are the quantum efficiencies at distances r, closest approach, and infinity, respectively) varies as the $6^{th}$ power of the distance between two dipoles. Bottom, FRET efficiency varies as the square of the orientation factor κ, where $\kappa=\sin\theta_D \sin\theta_A \cos\chi-2\cos\theta_D \cos\theta_A$ with $\theta_D$ and $\theta_A$ the angles of the donor (blue) and acceptor (red) electronic transition dipoles with the line connecting them, and χ the angle between the planes within which they lie. FIG. 12C: Spectral overlap (gray area) between the donor fluorescence emission (${}^{D}$I, blue) and acceptor fluorescence excitation (${}^{A}$A, black) spectra. This overlap increases with bathochromic or hypsochromic shifts of the donor emission (red arrow) and acceptor excitation (dotted blue arrow) spectra, respectively. Shifts in the opposite directions decreases spectral overlap. FIG. 12D shows the shift in spectral overlap between apo form and bound form upon ligand binding.

FIG. 13 shows the sequence of an exemplary synBicarbBP1 expression construct (SEQ ID NO: 95).

FIG. 14 shows the sequence of an exemplary teBicarbBP2 expression construct (SEQ ID NO: 96).

FIG. 15 shows the sequence of an exemplary ctBicarbBP3 expression construct (SEQ ID NO: 97).

FIG. 16 shows the sequence of an exemplary calBicarbBP4 expression construct (SEQ ID NO: 98).

FIG. 17 shows the sequence of an exemplary avBicarbBP5 expression construct (SEQ ID NO: 99).

FIG. 18 shows the sequence of an exemplary cmBicarbBP6 expression construct (SEQ ID NO: 100).

FIG. 19 shows the sequence of an exemplary mhFeBP1 expression construct (SEQ ID NO: 101).

FIG. 20 shows the sequence of an exemplary exiFeBP2 expression construct (SEQ ID NO: 102).

FIG. 21 shows the sequence of an exemplary teFeBP3 expression construct (SEQ ID NO: 103).

FIG. 22 shows the sequence of an exemplary cnFeBP4 expression construct (SEQ ID NO: 104).

FIG. 23 shows the sequence of an exemplary ttFeBP5 expression construct (SEQ ID NO: 105).

FIG. 24 shows the sequence of an exemplary msFeBP6 expression construct (SEQ ID NO: 106).

FIG. 25 shows the sequence of an exemplary srFeBP7 expression construct (SEQ ID NO: 107).

FIG. 26 shows the sequence of an exemplary hlFeBP8 expression construct (SEQ ID NO: 108).

FIG. 27 shows the sequence of an exemplary avBicarBP5_16C expression construct (SEQ ID NO: 109).

FIG. 28 shows the sequence of an exemplary avBicarBP5_17C expression construct (SEQ ID NO: 110).

FIG. 29 shows the sequence of an exemplary avBicarBP5_18C expression construct (SEQ ID NO: 111).

FIG. 30 shows the sequence of an exemplary avBicarBP5_49C expression construct (SEQ ID NO: 112).

FIG. 31 shows the sequence of an exemplary avBicarBP5_71C expression construct (SEQ ID NO: 113).

FIG. 32 shows the sequence of an exemplary avBicarBP5_140C expression construct (SEQ ID NO: 114).

FIG. 33 shows the sequence of an exemplary avBicarBP5_141C expression construct (SEQ ID NO: 115).

FIG. 34 shows the sequence of an exemplary avBicarBP5_142C expression construct (SEQ ID NO: 116).

FIG. 35 shows the sequence of an exemplary avBicarBP5_143C expression construct (SEQ ID NO: 117).

FIG. 36 shows the sequence of an exemplary avBicarBP5_146C expression construct (SEQ ID NO: 118).

FIG. 37 shows the sequence of an exemplary avBicarBP5_190C expression construct (SEQ ID NO: 119).

FIG. 38 shows the sequence of an exemplary avBicarBP5_194C expression construct (SEQ ID NO: 120).

FIG. 39 shows the sequence of an exemplary teFeBP3_A8C expression construct (SEQ ID NO: 121).

FIG. 40 shows the sequence of an exemplary teFeBP3_$H_{10}$C expression construct (SEQ ID NO: 122).

FIG. 41 shows the sequence of an exemplary teFeBP3_D12C expression construct (SEQ ID NO: 123).

FIG. 42 shows the sequence of an exemplary teFeBP3_T13C expression construct (SEQ ID NO: 124).

FIG. 43 shows the sequence of an exemplary teFeBP3_A36C expression construct (SEQ ID NO: 125).

FIG. 44 shows the sequence of an exemplary teFeBP3_V58C expression construct (SEQ ID NO: 126).

FIG. 45 shows the sequence of an exemplary teFeBP3_R135C expression construct (SEQ ID NO: 127).

FIG. 46 shows the sequence of an exemplary teFeBP3_N139C expression construct (SEQ ID NO: 128).

FIG. 47 shows the sequence of an exemplary teFeBP3_I140C expression construct (SEQ ID NO: 129).

FIG. 48 shows the sequence of an exemplary teFeBP3_N176C expression construct (SEQ ID NO: 130).

FIG. 49 shows the sequence of an exemplary teFeBP3_N195C expression construct (SEQ ID NO: 131).

FIG. 50 shows the sequence of an exemplary teFeBP3_N268C expression construct (SEQ ID NO: 132).

FIG. 51 shows the sequence of an exemplary teFeBP3_E270C expression construct (SEQ ID NO: 133).

FIG. 52 shows the sequence of an exemplary avBicarbBP5_16C_bZif expression construct (SEQ ID NO: 134).

FIG. 53 shows the sequence of an exemplary avBicarbBP5_17C_bZif expression construct (SEQ ID NO: 135).

FIG. 54 shows the sequence of an exemplary avBicarbBP5_18C_bZif expression construct (SEQ ID NO: 136).

FIG. 55 shows the sequence of an exemplary avBicarbBP5_190C_bZif expression construct (SEQ ID NO: 137).

FIG. 56 shows the sequence of an exemplary avBicarbBP5_194C_bZif expression construct (SEQ ID NO: 138).

FIG. 57 shows the sequence of an exemplary avBicarbBP5_16C_71D_bZif expression construct (SEQ ID NO: 139).

FIG. 58 shows the sequence of an exemplary avBicarbBP5_16C_71N_bZif expression construct (SEQ ID NO: 140).

FIG. 59 shows the sequence of an exemplary avBicarbBP5_16C_71E_bZif expression construct (SEQ ID NO: 141).

FIG. 60 shows the sequence of an exemplary avBicarbBP5_16C_71M_bZif expression construct (SEQ ID NO: 142).

FIG. 61 shows the sequence of an exemplary avBicarbBP5_18C_16M_bZif expression construct (SEQ ID NO: 143).

FIG. 62 shows the sequence of an exemplary avBicarbBP5_18C_16F_bZif expression construct (SEQ ID NO: 144).

FIG. 63 shows the sequence of an exemplary avBicarbBP5_18C_16Y_bZif expression construct (SEQ ID NO: 145).

FIG. 64 shows the sequence of an exemplary avBicarbBP5_18C_16W_bZif expression construct (SEQ ID NO: 146).

FIG. 65 shows the sequence of an exemplary avBicarbBP5_18C_16E_bZif expression construct (SEQ ID NO: 147).

FIG. 66 shows the sequence of an exemplary avBicarbBP5_18C_49F_bZif expression construct (SEQ ID NO: 148).

FIG. 67 shows the sequence of an exemplary avBicarbBP5_18C_49Y_bZif expression construct (SEQ ID NO: 149).

FIG. 68 shows the sequence of an exemplary avBicarbBP5_18C_141V_bZif expression construct (SEQ ID NO: 150).

FIG. 69 shows the sequence of an exemplary avBicarbBP5_18C_141F_bZif expression construct (SEQ ID NO: 151).

FIG. 70 shows the sequence of an exemplary avBicarbBP5_18C_141Y_bZif expression construct (SEQ ID NO: 152).

FIG. 71 shows the sequence of an exemplary avBicarbBP5_18C_141W_bZif expression construct (SEQ ID NO: 153).

FIG. 72 shows the sequence of an exemplary avBicarbBP5_18C_141Q_bZif expression construct (SEQ ID NO: 154).

FIG. 73 are illustrations of fluorophore structures. Naphthalene family (arrows indicate known or potential internal twists)

FIG. 74 is a diagram relating to directly responsive partners and indirectly responsive partners in ngmFRET pathways.

DETAILED DESCRIPTION

Figure 1A:
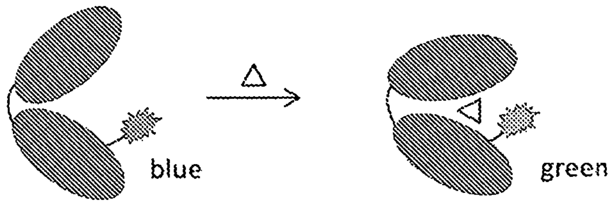
FIG. 1A is a cartoon and FIGS. 1B-D are graphs illustrating fluorescently responsive sensors.
Figure 1B:
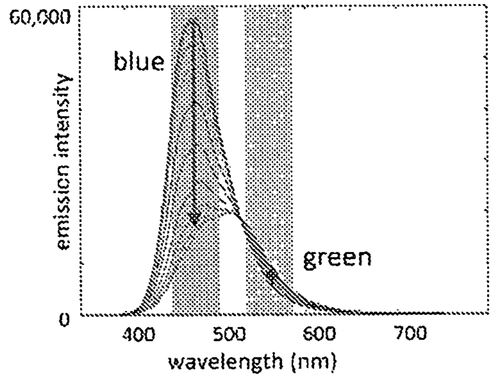
Figure 1C:
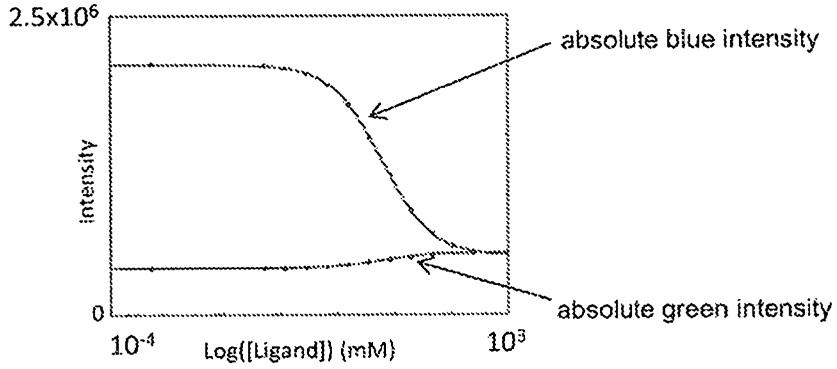
Figure 1D:
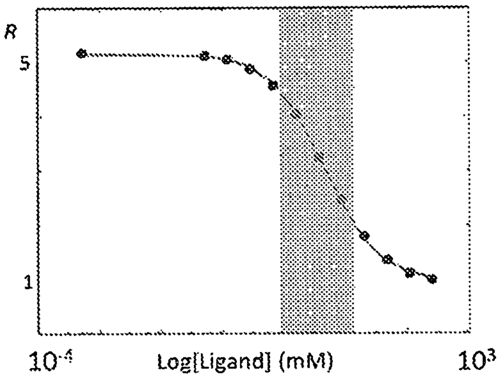

Fluorescently responsive sensors (FRSs) based on engineered proteins that couple ligand-binding events to changes in the emission properties of fluorophores (being fluorescent by themselves and regardless of the presence of any other fluorophore/partner) or semi-synthetically incorporated chromophores have wide-ranging applications in cell biology and analytical chemistry. If the fluorescence emission spectrum of an engineered FRS changes shape in response to ligand binding such that the ratio of intensities at two appropriately chosen wavelengths reports on ligand concentration (dichromatic response), then ratiometric measurements can be used to monitor analyte concentrations. Ratiometry is essential for devices that rely on changes in fluorescence emission intensities, because it provides an internally consistent reference. The self-calibrating nature of a ratiometric measurement removes the necessity for carrying out on-board calibration tests prior to each measurement, obviating the need for multiple components and fluidic circuitry. Accordingly, reagentless, ratiometric fluorescent sensors have many uses in process engineering, environmental or clinical chemistry, including single-use point-of-care applications, wearable devices, or implanted "tattoos" that are interrogated transdermally.

The periplasmic binding protein (PBP) superfamily provide a rich source of FRSs, because PBPs combine a large diversity of ligand specificities with a common structural mechanism that is well suited to the construction of fluorescence signal transduction schemes. The three-dimensional PBP monomer structure comprises two α/β domains linked by a β-strand hinge. Binding of ligand is accompanied by a large hinge-bending motion that transitions the protein from an open to a closed state in which the ligand is enveloped within a cleft between the two domains. Semisynthetic FRSs can be engineered with PBPs by site-specifically attaching single, thiol-reactive, environmentally sensitive fluorophores that respond to the ligand-mediated conformational change (FIGS. 1A-D). Semisynthetic, fluorescently labeled glucose-binding proteins in the periplasmic binding protein superfamily have been engineered successfully as reagentless, ratiometric glucose biosensors that can be used for point-of-care diagnostics and in vivo continuous glucose monitoring applications.

Here we present the construction of reagentless, ratiometric, fluorescent bicarbonate and calcium sensors based on engineered periplasmic binding proteins. There are two known classes of bicarbonate-binding proteins in the PBP superfamily. Both bind bicarbonate as a metal complex: either as calcium-bicarbonate, or as iron ($Fe^{III}$)-bicarbonate. The $Ca^{II}$—$HCO_3$ binding proteins typically are found in photosynthetic bacteria where they participate in $HCO_3^-$ uptake processes for conversion into and fixation of $CO_2$ in carboxysomes (Price 2008), whereas the $Fe^{III}$—$HCO_3$ binding proteins are more wide-spread and participate in bacterial iron uptake systems (Siburt 2012). We have converted and optimized a representative member of each class into bicarbonate sensors, and optimized their performance for sensing in the clinically relevant bicarbonate concentration range (20-30 mM): the $Ca^{II}$—$HCO_3$ binding protein from *Anabaena variabilis* (avBicarbBP5), and the $Fe^{III}$—$HCO_3$ binding protein from *Thermosynechococcus elongatus* (teFBP3). We further engineered the $Ca^{II}$—$HCO_3$ binding protein into a sensor for ionized calcium, $Ca^{2+}$, with optimal performance in the 1 mM concentration range, required for sensing $Ca^{2+}$ in clinical samples.

Bicarbonate is an essential component for maintaining acid-base homeostasis in blood (Warrel 2010) (FIG. 2). The clinical reference range for bicarbonate is 20-30 mM (Burtis 2012). Various acidosis and alkalosis conditions alter this concentration. Together with the blood pH, determination of the concentration of this important buffer therefore provides information on the pathogenesis of the imbalance (Warrel 2010). Clinical automation instrumentation uses either sample acidification in combination with a $CO_2$-selective electrode, or alkalinization followed by a colorimetric coupled enzyme assay (Burtis 2012). The fluorescent sensors presented here offer a significantly simpler measurement principle.

There are three major forms of extracellular calcium in blood: bound to protein (albumin), complexed to phosphate or citrate, and the free $Ca^{2+}$ ion (Warrel 2010). The concentration of free $Ca^{2+}$ is tightly regulated in the 1.2-1.3 mM range (Burtis 2012). Deviations from this range are indicative of various diseases; ionized $Ca^{2+}$ determination therefore is a common clinical chemistry test (Burtis 2012). Because of the importance of $Ca^{2+}$ in intracellular biochemical signaling mechanisms, many fluorescent indicators have been developed for measuring intracellular $Ca^{2+}$ levels (Valeur 2012). These are tuned for the micromolar range and therefore are not appropriate for measuring extracellular levels. By contrast, the construction of semi-synthetic $Ca^{2+}$ biosensors based on engineered avBicarbBP5, tuned for the 0.5-10 mM range provide fluorescent sensors that are appropriate for clinical chemistry applications.

Biosensors

Biosensors are molecular recognition elements that transduce ligand-binding events into physical signals. Biosensors as detailed herein bind at least one ligand and emit a signal. A ligand-bound biosensor results in a signal that is different from the unbound biosensor. This difference facilitates detection of the at least one ligand and/or determination of ligand concentration. The biosensors may be used without the assistance of other reagents.

Described herein are novel engineered biosensors. These biosensors may have altered ligand-binding affinities, tailored ligand-binding specificities, and/or temperature dependencies of ligand binding or stability. For example, the herein described engineered ligand biosensors provide high-accuracy information related to extended ligand concentration ranges.

Binding of ligand mediates conformational changes in the biosensor, such as hinge-bending motions of the polypeptide. The conformational changes affect the environment of the reporter such that a change in the reporter-generated signal occurs. That is, without ligand bound, the biosensor results in signal generated from the reporter, and when ligand is bound, the signal generated from the reporter changes. The ligand-bound biosensor results in a reporter-generated signal that is different from the unbound biosensor.

In some embodiments, the methods and compositions include a plurality of a single type of biosensor. The biosensors may be identical in structure and function. For example, the biosensors of a single type may have the same polypeptide, the same reporter, and the same ligand affinity.

In other embodiments, the methods and compositions include a plurality of different types of biosensors. A plurality of these different types of biosensors may be arranged or incorporated in a panel. As used herein, a "panel" refers to two or more biosensors. The two or more biosensors may be different from each other. The biosensors may differ in structure and/or function. Biosensors may differ in polypeptide sequence, reporter, ligand affinities, or a combination thereof. Accordingly, there may be different types of biosensors. In some embodiments, each biosensor in the panel comprises the same reporter group. In some embodiments, each biosensor in the panel comprises a different reporter group. The panel may include at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, or at least 100 biosensors.

The panel of biosensors includes at least one sensor element. "Sensor element" refers to a single spot, site, location, or well for the at least one biosensor, to which a sample or aliquot thereof may be applied. The panel may be a composite sensor or an array.

In some embodiments, the panel is a composite sensor. In a composite sensor, each sensor element includes a mixture of two or more different biosensors. In some embodiments, the composite sensor includes one sensor element. In some embodiments, the composite sensor includes two or more sensor elements. In some embodiments, signals are measured from a composite sensor in which the signals arise from one or more biosensors in the sensor element. For example, signals may be measured from a composite sensor in which the signals arise from a subset of the total number of biosensors in the sensor element. For example, signals may be measured from a composite sensor in which the signals arise from two of five biosensors in the sensor element.

In some embodiments, the panel is an array. In an array, each sensor element includes a single type of biosensor. An array comprises a plurality of individually and spatially localized sensor elements. Each sensor element includes a biosensor that is different than or the same as the biosensor of a different sensor element. In some embodiments, signals are measured from an array in which the signals arise separately from two or more selected biosensors in separate sensor elements. An array may comprise a plurality of sensor elements of a variety of sizes and configurations. An array may comprise a plurality of sensor elements arranged linearly. For example, an array may comprise a plurality of micrometer-sized sensor elements arranged in a single row. An array may comprise a plurality of sensor elements arranged in a grid. The grid may be two- or three-dimensional. In some embodiments, the grid is a spatially addressable grid. In some embodiments, the biosensors are incorporated into an array, such as a multichannel or multiplexed array.

The biosensors of the present disclosure can be used in any setting where ligand detection is required or desired, such a medical setting (e.g., determining the level of blood ligand in a subject), environmental setting (e.g., determining the level of ligand in an environmental sample), biological setting (e.g., determining the presence or amount of ligand in a reaction), or in process engineering, such as monitoring the amount of ligand in a fermentation reaction (e.g., a bacterial culture, a yeast culture, beer/wine production, etc.). Other examples include, but are not limited to, uses in the food industry (Suleiman et al, In: Biosensor Design and Application: Mathewson and Finley Eds; American Chemical Society, Washington, DC 1992, vol. 511); in clinical chemistry (Wilkins et al., Med. Eng. Phys. 1996, 18, 273-288; Pickup, Tr. Biotech. 1993, 11, 285-291; Meyerhoff et al., Endricon 1966, 6, 51-58; Riklin et al., Nature 1995, 376, 672-675); Willner et al., J. Am. Chem. Soc. 1996, 118, 10321-10322); as the basis for the construction of a fluorescent flow cell containing immobilized ligand binding protein-FAST conjugates (see, e.g., Wilkins et al., Med. Eng. Phys. 1966, 18, 273-288; Pickup, Tr. Biotech. 1993, 11, 285-291; Meyerhoff et al., Endricon. 1966, 6, 51; Group, New Engl. J. Med. 1993, 329, 977-986; Gough et al., Diabetes 1995, 44, 1005-1009); and in an implantable devices.

The biosensors as detailed herein may be administered in a variety of ways known by those of skill in the art, as appropriate for each application. Biosensors may be provided in a solution. The solution may be buffered. Biosensors may be provided in a solution and mixed directly with a sample. In some embodiments, a biosensor is immobilized onto a surface. Biosensors may be immobilized within a disposable cartridge into which a sample may be introduced or applied. Biosensors may be implanted or incorporated in a wearable device. The biosensor may be provided as an optode.

The biosensor may be attached to or incorporated in a wearable device. Wearable devices may include, for example, adhesive strips, patches, and contact lenses. The biosensor may be configured for placement in contact with a subject's skin or mucosal surface. In some embodiments, the biosensor is configured as an adhesive strip. In some embodiments, the biosensor is configured within or on the surface of a contact lens. In some embodiments, the contact lens is formed from a transparent substrate shaped to be worn directly over a subject's eye, as described in, for example, U.S. Pat. No. 8,608,310.

The biosensor may be implanted. The biosensor may be implanted in a subject's body. The biosensor may be implanted in a subject's blood vessel, vein, eye, natural or artificial pancreas, skin, or anywhere in the alimentary canal including the stomach, intestine and esophagus. The biosensor may be implanted in a subject with a microbead. In some embodiments, the biosensor is configured to be implanted in the skin. The biosensor may be implanted in a subject sub-dermally. The biosensor may generate the signal transdermally. In some embodiments, the biosensor may be implanted in a subject with transdermal microbeads, wherein the optical signals can be transmitted remotely between the biosensor and detecting device.

In some embodiments, the biosensor is administered as an optode. As used herein, "optode" refers to an optical fiber with a single biosensor, or a composite biosensor, immobilized at the surface or at the end. An "optode" may also be referred to as an "optrode." In some embodiments, the biosensor is implanted in a subject as an optode. The optode may be incorporated with or into a needle. The optode may be incorporated with a probe such as endoscopy or colonoscopy probes. The optode may be used in a tumor, near a tumor, or at the periphery of a tumor. In some embodiments, the biosensor may be implanted in a subject as an optode, wherein the optical signals can be transmitted between the biosensor and detecting device using physical links. In some embodiments, the biosensor is administered as an optode to a sample or reaction. The optode may be contacted with a sample or reaction. In some embodiments, an optode is used to continuously or episodically monitor a ligand in a sample or reaction.

Methods of Detecting the Presence of a Ligand

Provided herein is a method of detecting the presence of a ligand in a sample. The method may include contacting the biosensor with the sample; measuring a signal from the biosensor; and comparing the signal to a ligand-free control. A difference in signal indicates the presence of ligand in the sample.

Also provided herein is a method of detecting the presence of ligand in a sample. The method may include (a) providing a biosensor disclosed herein in which the reporter group is attached the ligand-binding protein so that a signal transduced by the reporter group when the ligand-binding protein is bound to ligand differs from a signal transduced by the reporter group when the ligand-binding protein is not bound to ligand; (b) contacting the biosensor with the test sample under conditions such that the biosensor can bind to ligand present in the test sample; and (c) comparing the signal transduced by the reporter group when the biosensor is contacted with the test sample with the signal transduced by the reporter group when the biosensor is contacted with a ligand-free control sample, wherein a difference in the signal transduced by the reporter group when the biosensor is contacted with the test sample, as compared to when the biosensor is contacted with the control sample, indicates that the test sample contains ligand.

Methods of Determining the Concentration of a Ligand

Provided herein is a method of determining the concentration of a ligand in a sample. The method may include contacting the biosensor with the sample; measuring a signal from the biosensor; and comparing the signal to a standard hyperbolic ligand binding curve to determine the concentration of ligand in the test sample. The standard hyperbolic ligand binding curve may be prepared by measuring the signal transduced by the biosensor when contacted with control samples containing known concentrations of ligand.

Another aspect of the present disclosure provides a method of determining the concentration of ligand in a test sample comprising, consisting of, or consisting essentially of: (a) providing a biosensor comprising a biosensor as described herein in which the reporter group is attached the ligand-binding protein so that a signal transduced by the reporter group when the ligand-binding protein is bound to ligand differs from a signal transduced by the reporter group when the ligand-binding protein is not bound to ligand; (b) contacting the biosensor with the test sample under conditions such that the biosensor can bind to ligand present in the test sample; and (c) comparing the signal transduced by the reporter group when the biosensor is contacted with the test sample with a standard hyperbolic binding curve prepared by measuring the signal transduced by the reporter group when the biosensor is contacted with control samples containing known quantities of ligand to determine the concentration of ligand in the test sample.

Methods of Monitoring the Presence of a Ligand

The present invention is directed to a method of episodically or continuously monitoring the presence of a ligand in a reaction. In certain embodiments, the biosensors may be used in the continuous monitoring of ligand in a reaction. In certain embodiments, the ligand sensors may be used in episodic monitoring of sample aliquots.

The method of episodically or continuously monitoring the presence of a ligand in a reaction may include contacting the biosensor with the reaction; maintaining the reaction under conditions such that the polypeptide is capable of binding ligand present in the reaction; and episodically or continuously monitoring the signal from the biosensor in the reaction.

The method of episodically or continuously monitoring the presence of a ligand in a reaction may include contacting the biosensor with the reaction; maintaining the reaction under conditions such that the polypeptide is capable of binding ligand present in the reaction; episodically or continuously monitoring the signal from the biosensor in the reaction; and comparing the signal to a standard hyperbolic ligand binding curve to determine the concentration of ligand in the test sample. The standard hyperbolic ligand binding curve may be prepared by measuring the signal transduced by the biosensor when contacted with control samples containing known concentrations of ligand.

In some embodiments, the method further includes comparing the signal to a ligand-free control, wherein a difference in signal indicates the presence of ligand in the reaction.

In some embodiments, the method further includes comparing the signal to a standard hyperbolic ligand binding curve to determine the concentration of ligand in the test sample. The standard hyperbolic ligand binding curve may be prepared by measuring the signal transduced by the biosensor when contacted with control samples containing known concentrations of ligand.

Another aspect of the present disclosure provides a method of continuously monitoring the presence of ligand in a reaction comprising, consisting of, or consisting essentially of: (a) providing a biosensor as described herein in which the reporter group is attached the ligand-binding protein so that a signal transduced by the reporter group when the ligand-binding protein is bound to ligand differs from a signal transduced by the reporter group when the ligand-binding protein is not bound to ligand (b) maintaining the biosensor within the reaction and under conditions such that the biosensor can bind to ligand present in the reaction; (c) continuously monitoring the signal transduced by the reporter group when the biosensor is contacted with the ligand present in the reaction; and optionally (d) comparing the signal transduced by the reporter group when the biosensor is contacted with the ligand present in the reaction with the signal transduced by the reporter group when the biosensor is contacted with a ligand-free control sample, wherein a difference in the signal transduced by the reporter group when the biosensor is contacted with the ligand present in the reaction, as compared to when the biosensor is contacted with the control sample, indicates ligand is present in the reaction.

Yet another aspect of the present disclosure provides a method of continuously monitoring the concentration of ligand in a reaction comprising, consisting of, or consisting essentially of: (a) providing a biosensor as described herein in which the reporter group is attached the ligand-binding protein so that a signal transduced by the reporter group when the ligand-binding protein is bound to ligand differs from a signal transduced by the reporter group when the ligand-binding protein is not bound to ligand; (b) maintaining the biosensor within the reaction under conditions such that the biosensor can bind to ligand present in the reaction; and (c) continuously monitoring the signal transduced by the reporter group when the biosensor is contacted with the ligand present in the reaction; and (d) comparing the signal transduced by the reporter group when the biosensor is contacted with the ligand present in the reaction with a standard hyperbolic ligand binding curve prepared by measuring the signal transduced by the reporter group when the biosensor is contacted with control samples containing known quantities of ligand to determine the concentration of ligand in the reaction.

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means ±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes/nucleic acids or sequences/amino acids that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

"Subject" as used herein refers to any organism from which a biological sample is obtained. For example, the sample is a biological fluid or tissue. For example, a subject is one who wants or is in need of detecting ligand or determining the concentration of ligand with the herein described biosensors. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant.

As used herein, an "expression vector" is a DNA or RNA vector that is capable of effecting expression of one or more polynucleotides. Preferably, the expression vector is also capable of replicating within the host cell. Expression vectors can be either prokaryotic or eukaryotic, and are typically include plasmids. Expression vectors of the present invention include any vectors that function (i.e., direct gene expression) in host cells of the present invention, including in one of the prokaryotic or eukaryotic cells described herein, e.g., gram-positive, gram-negative, pathogenic, non-pathogenic, commensal, cocci, *bacillus*, or spiral-shaped bacterial cells; archaeal cells; or protozoan, algal, fungi, yeast, plant, animal, vertebrate, invertebrate, arthropod, mammalian, rodent, primate, or human cells. Expression vectors of the present invention contain regulatory sequences such as transcription control sequences, translation control sequences, origins of replication, and other regulatory sequences that are compatible with the host cell and that control the expression of a polynucleotide. In particular, expression vectors of the present invention include transcription control sequences. Transcription control sequences are sequences which control the initiation, elongation, and termination of transcription. Particularly important transcription control sequences are those which control transcription initiation such as promoter, enhancer, operator and repressor sequences. Suitable transcription control sequences include any transcription control sequence that can function in at least one of the cells of the present invention. A variety of such transcription control sequences are known to those skilled in the art.

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

The term "diagnosis" refers to a determination that a disease is present in the subject. Similarly, the term "prognosis" refers to a relative probability that a certain future outcome may occur in the subject. For example, in the context of the present disclosure, prognosis can refer to the likelihood that an individual will develop a disease, or the likely severity of the disease (e.g., severity of symptoms, rate of functional decline, survival, etc.).

Unless required otherwise by context, the terms "polypeptide" and "protein" are used interchangeably herein.

A polypeptide or class of polypeptides may be defined by the extent of identity (% identity) of its amino acid sequence to a reference amino acid sequence, or by having a greater % identity to one reference amino acid sequence than to another. A variant of any of genes or gene products disclosed herein may have, e.g., 50%, 55%, 60%, 65%, 70%, 75%, 80%, 85%, 90%, 95%, 96%, 97%, 98%, or 99% sequence identity to the nucleic acid or amino acid sequences described herein. The term "% identity," in the context of two or more nucleic acid or polypeptide sequences, refers to two or more sequences or subsequences that are the same or have a specified percentage of amino acid residues or nucleotides that are the same, when compared and aligned for maximum correspondence, as measured using a sequence comparison algorithm or by visual inspection. For example, % identity is relative to the entire length of the coding regions of the sequences being compared, or the length of a particular fragment or functional domain thereof. Variants as disclosed herein also include homologs, orthologs, or paralogs of the genes or gene products described herein. In some embodiments, variants may demonstrate a percentage of homology or identity, for example, at least about 50%, 55%, 60%, 65%, 70%, 75%, 80%, 85%, 90%, 95%, 96%, 97%, 98%, or 99% identity conserved domains important for biological function, e.g., in a functional domain, e.g. a ligand-binding or catalytic domain.

For sequence comparison, one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Percent identity is determined using BLAST. For the BLAST searches, the following parameters were employed: (1) Expect threshold is 10; (2) Gap cost is Existence: 11 and Extension: 1; (3) The Matrix employed is BLOSUM62; (4) The filter for low complexity regions is "on."

The present invention also provides for functional fragments of the genes or gene products described herein. A fragment of a protein is characterized by a length (number of amino acids) that is less than the length of the full length mature form of the protein. A fragment, in the case of these sequences and all others provided herein, may be a part of the whole that is less than the whole. Moreover, a fragment ranges in size from a single nucleotide or amino acid within a polynucleotide or polypeptide sequence to one fewer nucleotide or amino acid than the entire polynucleotide or polypeptide sequence. Finally, a fragment is defined as any portion of a complete polynucleotide or polypeptide sequence that is intermediate between the extremes defined above.

For example, fragments of any of the proteins or enzymes disclosed herein or encoded by any of the genes disclosed herein can be 10 to 20 amino acids, 10 to 30 amino acids, 10 to 40 amino acids, 10 to 50 amino acids, 10 to 60 amino acids, 10 to 70 amino acids, 10 to 80 amino acids, 10 to 90 amino acids, 10 to 100 amino acids, 50 to 100 amino acids, 75 to 125 amino acids, 100 to 150 amino acids, 150 to 200 amino acids, 200 to 250 amino acids, 250 to 300 amino acids, 300 to 350, 350-400, or 350-450 amino acids. The fragments encompassed in the present subject matter comprise fragments that retain functional fragments. As such, the fragments preferably retain the binding domains that are required or are important for functional activity. Fragments can be determined or generated by using the sequence information herein, and the fragments can be tested for functional activity using standard methods known in the art. For example, the encoded protein can be expressed by any recombinant technology known in the art and the binding activity of the protein can be determined.

As used herein a "biologically active" fragment is a portion of a polypeptide which maintains an activity of a full-length reference polypeptide. Biologically active fragments as used herein exclude the full-length polypeptide. Biologically active fragments can be any size as long as they maintain the defined activity. Preferably, the biologically active fragment maintains at least 10%, at least 50%, at least 75% or at least 90%, of the activity of the full length protein.

Amino acid sequence variants/mutants of the polypeptides of the defined herein can be prepared by introducing appropriate nucleotide changes into a nucleic acid defined herein, or by in vitro synthesis of the desired polypeptide. Such variants/mutants include, for example, deletions, insertions or substitutions of residues within the amino acid sequence. A combination of deletion, insertion and substitution can be made to arrive at the final construct, provided that the final peptide product possesses the desired activity and/or specificity.

Mutant (altered) peptides can be prepared using any technique known in the art. For example, a polynucleotide defined herein can be subjected to in vitro mutagenesis or DNA shuffling techniques as broadly described by Harayama (1998). Products derived from mutated/altered DNA can readily be screened using techniques described herein to determine if they possess, for example, ligand binding activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues. In some embodiments, a mutated or modified protein does not comprise any deletions or insertions. In various embodiments, a mutated or modified protein has less than about 10, 9, 8, 7, 6, 5, 4, 3, or 2 deleted or inserted amino acids.

Substitution mutants have at least one amino acid residue in the polypeptide molecule removed and a different residue inserted in its place. Sites may be substituted in a relatively conservative manner in order to maintain activity and/or specificity. Such conservative substitutions are shown in the table below under the heading of "exemplary substitutions."

In certain embodiments, a mutant/variant polypeptide has only, or not more than, one or two or three or four conservative amino acid changes when compared to a naturally occurring polypeptide. Details of conservative amino acid changes are provided in the table below. As the skilled person would be aware, such minor changes can reasonably be predicted not to alter the activity of the polypeptide when expressed in a recombinant cell.

| Original Residue | Exemplary Substitutions |
|---|---|
| Alanine (Ala) | Val; Leu; Ile; Gly |
| Arginine (Arg) | Lys |
| Asparagine (Asn) | Gln; His |
| Cysteine (Cys) | Ser |
| Glutamine (Gln) | Asn; His |
| Glutamic Acid (Glu) | Asp |
| Glycine (Gly) | Pro; Ala |
| Histidine (His) | Asn; Gln |
| Isoleucine (Ile) | Leu; Val; Ala |
| Leucine (Leu) | Ile; Val; Met; Ala; Phe |
| Lysine (Lys) | Arg |
| Methionine (Met) | Leu; Phe |
| Phenylalanine (Phe) | Leu; Val; Ala |
| Proline (Pro) | Gly |
| Serine (Ser) | Thr |
| Threonine (Thr) | Ser |

-continued

| Original Residue | Exemplary Substitutions |
|---|---|
| Tryptophan (Trp) | Tyr |
| Tyrosine (Tyr) | Trp; Phe |
| Valine (Val) | Ile; Leu; Met; Phe; Ala |

Mutations can be introduced into a nucleic acid sequence such that the encoded amino acid sequence is altered by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. Certain amino acids have side chains with more than one classifiable characteristic. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, tryptophan, cysteine), nonpolar side chains (e.g., alanine, valine, leucine, isoleucine, proline, phenylalanine, methionine, tyrosine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a given polypeptide is replaced with another amino acid residue from the same side chain family. Alternatively, in another embodiment, mutations can be introduced randomly along all or part of a given coding sequence, such as by saturation mutagenesis, and the resultant mutants can be screened for given polypeptide biological activity to identify mutants that retain activity. Conversely, the invention also provides for variants with mutations that enhance or increase the endogenous biological activity. Following mutagenesis of the nucleic acid sequence, the encoded protein can be expressed by any recombinant technology known in the art and the activity/specificity of the protein can be determined. An increase, decrease, or elimination of a given biological activity of the variants disclosed herein can be readily measured by the ordinary person skilled in the art, i.e., by measuring the capability for binding a ligand and/or signal transduction.

In various embodiments, a polypeptide comprises mutations such that 1, 2, 3, 4, 5, 6, 7, 8, 9, or 10, or less than about 10, 9, 8, 7, 6, 5, 4, 3, or 2 amino acids is substituted with a cysteine and/or a lysine.

Polypeptides can be produced in a variety of ways, including production and recovery of natural polypeptides or recombinant polypeptides according to methods known in the art. In one embodiment, a recombinant polypeptide is produced by culturing a cell capable of expressing the polypeptide under conditions effective to produce the polypeptide, such as a host cell defined herein.

Key to the Sequence Listing

| SEQ ID NO | Sequence Name |
|---|---|
| 1 | synBicarbBP1 [U.S. National Center for Biotechnology Information (NCBI) Accession Nos. YP_005410477.1 and WP_010874027.1] |
| 2 | teBicarbBP2 [U.S. National Center for Biotechnology Information (NCB1) Accession No. NP_682790.1] |
| 3 | ctBicarbBP3 [U.S. National Center for Biotechnology Information (NCBI) Accession Nos. YP_007090308.1 and WP_015152989.1] |
| 4 | calBicarbBP4 [U.S. National Center for Biotechnology Information (NCBI) Accession Nos. YP_007137061.1 and WP_015197735.1] |
| 5 | avBicarbBP5 [U.S. National Center for Biotechnology Information (NCBI) Accession Nos. YP_321546.1 and WP_011317875.1] |
| 6 | cmBicarbBP6 [U.S. National Center for Biotechnology Information (NCBI) Accession Nos. YP_007099445.1 and WP_015162006.1] |
| 7 | mhFeBP1 [U.S. National Center for Biotechnology Information (NCBI) Accession Nos. YP_07884192.1 and WP_006253500.1] |
| 8 | exiFeBP2 [U.S. National Center for Biotechnology Information (NCBI) Accession Nos. YP_002886303.1 and WP_015880417.1] |
| 9 | teFeBP3 [U.S. National Center for Biotechnology Information (NCBI) Accession No., NP_681303.1] |
| 10 | cnFeBP4 [U.S. National Center for Biotechnology Information (NCBI) Accession Nos. YP_003796723.1 and WP_013247623.1] |
| 11 | ttFeBP5 [U.S. National Center for Biotechnology Information (NCBI) Accession No. YP_144894.1] |
| 12 | msFeBPG [U.S. National Center for Biotechnology Information (NCBI) Accession Nos. YP_003686074.1 and WP_013159102.1] |
| 13 | srFeBP7 [U.S. National Center for Biotechnology Information (NCBI) Accession Nos. YP_003572493.1 and WP_013062602.1] |
| 14 | hlFeBP8 [U.S. National Center for Biotechnology Information (NCBI) Accession Nos YP_2564837.1 and WP_012659409.1] |

-continued

| SEQ ID NO | Sequence Name |
|---|---|
| 15 | synBicarbBP1 (with signal peptide replaced with M and a GGSHHHHHH at C-terminus) |
| 16 | teBicarbBP2 (with C247A and C260A substitution mutations, the signal peptide replaced with M, and a GGSHHHHHH at C-terminus) |
| 17 | ctBicarbBP3 (with signal peptide replaced with M and a GGSHHHHHH at C-terminus) |
| 18 | calBicarbBP4 (with signal peptide replaced with M and a GGSHHHHHH at C-terminus) |
| 19 | avBicarbBP5 (with C96A substitution mutation, signal peptide replaced with M, and a GGSHHHHHH at C-terminus) |
| 20 | cmBicarbBP6 (with C254A substitution mutation, signal peptide replaced with M, and a GGSHHHHHH at C-terminus) |
| 21 | mhFeBP1 (with C135 A and C191A substitution mutations, the signal peptide replaced with M, and a GGSHHHHHH at C-terminus) |
| 22 | exiFeBP2 (with signal peptide replaced with M and a GGSHHHHHH at C-terminus) |
| 23 | teFeBP3 (with C184S substitution mutation, the signal peptide replaced with M, and a GGSHHHHHH at C-terminus) |
| 24 | cnFeBP4 (with signal peptide replaced with M and a GGSHHHHHH at C-terminus) |
| 25 | ttFeBPS (with signal peptide replaced with M and a GGSHHHHHH at C-terminus) |
| 26 | msFeBP6 (with signal peptide replaced with M and a GGSHHHHHH at C-terminus) |
| 27 | srFeBP7 (with signal peptide replaced with M and a GGSHHHHHH at C-terminus) |
| 28 | hlFeBP8 (with C138A and C176A substitution mutations, the signal peptide replaced w ith M, and a GGSHHHHHH at C-terminus) |
| 29 | avBicarBP5_16C (with I16C and C96A substitution mutations, signal peptide replaced with M, and a GGSHHHHHH at C-terminus) |
| 30 | avBicarBP5_17C (with P17C and C96A substitution mutations, signal peptide replaced with M, and a GGSHHHHHH at C-terminus) |
| 31 | avBicarBP5_18C (with I18C and C96A substitution mutations, signal peptide replaced with M, and a GGSHHHHHH at C-terminus) |
| 32 | avBicarBP5_49C (with W49C and C96A substitution mutations, signal peptide replaced with M, and a GGSHHHHHH at C-terminus) |
| 33 | avBicarBP5_71C (with Q71C and C96A substitution mutations, signal peptide replaced with M, and a GGSHHHHHH at C-terminus) |
| 34 | avBicarBP5_140C (with F140C and C96A substitution mutations, signal peptide replaced with M, and a GGSHHHHHH at C-terminus) |
| 35 | avBicarBP5_141C (with T141C and C96A substitution mutations, signal peptide replaced with M, and a GGSHHHHHH at C-terminus) |
| 36 | avBicarBP5_142C (with F142C and C96A substitution mutations, signal peptide replaced with M, and a GGSHHHHHH at C-terminus) |
| 37 | avBicarBP5_143C (with P143C and C96A substitution mutations, signal peptide replaced with M, and a GGSHHHHHH at C-terminus) |
| 38 | avBicarBP5_146C (with N146C and C96A substitution mutations, signal peptide replaced with M, and a GGSHHHHHH at C-terminus) |
| 39 | avBicarBP5_190C (with T190C and C96A substitution mutations, signal peptide replaced with M, and a GGSHHHHHH at C-terminus) |
| 40 | avBicarBP5_194C (with W194C and C96A substitution mutations, signal peptide replaced with M, and a GGSHHHHHH at C-terminus) |

-continued

| SEQ ID NO | Sequence Name |
|---|---|
| 41 | teFeBP3_A8C (with A8C and C184S substitution mutations, the signal peptide replaced with M, and a GGSHHHHHH at C-terminus) |
| 42 | teFeBP3_H10C (with H10C and C184S substitution mutations, the signal peptide replaced with M, and a GGSHHHMHH at C-terminus) |
| 43 | teFeBP3_D12C (with D12C and C184S substitution mutations, the signal peptide replaced with M, and a GGSHHHMHH at C-terminus) |
| 44 | teFeBP3_T13C (with T13C and C184S substitution mutations, the signal peptide replaced with M, and a GGSHHHHHH at C-terminus) |
| 45 | teFeBP3_A36C (with A36C and C184S substitution mutations, the signal peptide replaced with M, and a GGSHHHHHH at C-terminus) |
| 46 | teFeBP3_V58C (with V58C and C184S substitution mutations, the signal peptide replaced with M, and a GGSHHHHHH at C-terminus) |
| 47 | teFeBP3_R135C (with R135C and C184S substitution mutations, the signal peptide replaced with M, and a GGSHHHHHH at C-terminus) |
| 48 | teFeBP3_N139C (with N139C and C184S substitution mutations, the signal peptide replaced with M, and a GGSHHHHHH at C-terminus) |
| 49 | teFeBP3_I140C (with I140C and C184S substitution mutations, the signal peptide replaced with M, and a GGSHHHHHH at C-terminus) |
| 50 | teFeBP3_N176C (with N176C and C184S substitution mutations, the signal peptide replaced with M, and a GGSHHHHHH at C-terminus) |
| 51 | teFeBP3_N195C (with N195C and C184S substitution mutations, the signal peptide replaced with M, and a GGSHHHHHH at C-terminus) |
| 52 | teFeBP3_N268C (with N268C and C184S substitution mutations, the signal peptide replaced with M, and a GGSHHHHHH at C-terminus) |
| 53 | teFeBP3_E270C (with E270C and C184S substitution mutations, the signal peptide replaced with M, and a GGSHHHHHH at C-terminus) |
| 54 | avBicarbBP5_16C_bZif (with I16C substitution mutation, signal peptide replaced with M, a bZif fusion, and a GGSHHHHHH at C-terminus) |
| 55 | avBicarbBP5_17C_bZif (with P17C substitution mutation, signal peptide replaced with M, a bZif fusion, and a GGSHHHHHH at C-terminus) |
| 56 | avBicarbBP5_18C_bZif (with I18C substitution mutation, signal peptide replaced with M, a bZif fusion, and a GGSHHHHHH at C-terminus) |
| 57 | avBicarbBP5_190C_bZif (with T190C substitution mutation, signal peptide replaced with M, a bZif fusion, and a GGSHHHHHH at C-terminus) |
| 58 | avBicarbBP5_194C_bZif (with W194C substitution mutation, signal peptide replaced with M, a bZif fusion, and a GGSHHHHHH at C-terminus) |
| 59 | avBicarbBP5_16C_71D_bZif (with I16C and Q71D substitution mutations, signal peptide replaced with M, a bZif fusion, and a GGSHHHHHH at C-terminus) |
| 60 | avBicarbBP5_16C_71N_bZif (with I16C and Q71N substitution mutations, signal peptide replaced with M, a bZif fusion, and a GGSHHHHHH at C-terminus) |
| 61 | avBicarbBP5_16C_71E_bZif (with I16C and Q71E substitution mutations, signal peptide replaced with M, a bZif fusion, and a GGSHHHHHH at C-terminus) |
| 62 | avBicarbBP5_16C_71M_bZif (with I16C and Q71M substitution mutations, signal peptide replaced with M, a bZif fusion, and a GGSHHHHHH at C-terminus) |
| 63 | avBicarbBP5_18C_16M_bZif (with I18C and I16M substitution mutations, signal peptide replaced with M, a bZif fusion, and a GGSHHHHHH at C-terminus) |
| 64 | avBicarbBP5_18C_16F_bZif (with I18C and I16F substitution mutations, signal peptide replaced with M, a bZif fusion, and a GGSHHHHHH at C-terminus) |
| 65 | avBicarbBP5_18C_16Y_bZif (with I18C and I16Y substitution mutations, signal peptide replaced with M, a bZif fusion, and a GGSHHHHHH at C-terminus) |

-continued

| SEQ ID NO | Sequence Name |
|---|---|
| 66 | avBicarbBP5_18C_16W_bZif(with I18C and I16W substitution mutations, signal peptide replaced with M, a bZif fusion, and a GGSHHHHHH at C-terminus) |
| 67 | avBicarbBP5_18C_16E_bZif (with I18C and I16F substitution mutations, signal peptide replaced with M, a bZif fusion, and a GGSHHHHHH at C-terminus) |
| 68 | avBicarbBPS_18C_49F_bZif (with I18C and W49F substitution mutations, signal peptide replaced with M, a bZif fusion, and a GGSHHHHHH at C-terminus) |
| 69 | avBicarbBP5_18C_49Y_bZif (with I18C and W49Y substitution mutations, signal peptide replaced with M, a bZif fusion, and a GGSHHHHHH at C-terminus) |
| 70 | avBicarbBP5_18C_141V_bZif (with I18C and T141V substitution mutations, signal peptide replaced with M, a bZif fusion, and a GGSHHHHHH at C-terminus) |
| 71 | avBicarbBP5_18C_14IF_bZif (with I18C and T141F substitution mutations, signal peptide replaced with M, a bZif fusion, and a GGSHHHHHH at C-terminus) |
| 72 | avBicarbBP5_18C_141Y_bZif (with I18C and T141Y substitution mutations, signal peptide replaced with M, a bZif fusion, and a GGSHHHHHH at C-terminus) |
| 73 | avBicarbBP5_18C_141W_bZif (with I18C and T141W substitution mutations, signal peptide replaced with M, a bZif fusion, and a GGSHHHHHH at C-terminus) |
| 74 | avBicarbBP5_18C_141Q_bZif (with I18C and T141Q substitution mutations, signal peptide replaced with M, a bZif fusion, and a GGSHHHHHH at C-terminus) |
| 75 | synBicarbBP1 (with signal peptide replaced with M) |
| 76 | eBicarbBP2 (with C247A and C260A substitution mutations and signal peptide replaced with M) |
| 77 | tBicarbBP3 (with signal peptide replaced with M) |
| 78 | calBicarbBP4 (with signal peptide replaced with M) |
| 79 | avBicarbBP (with C96A substitution mutation and signal peptide replaced with M) |
| 80 | cmBicarbBP6 (with C254A substitution mutation and signal peptide replaced with M) |
| 81 | mhFeBP1 (with C135A and C191A substitution mutations and signal peptide replaced with M) |
| 82 | exiFeBP2 (with signal peptide replaced with M) |
| 83 | teFeBP3 (with C184S substitution mutation and signal peptide replaced with M) |
| 84 | cnFeBP4 (with signal peptide replaced with M) |
| 85 | ttFeBP5 (with signal peptide replaced with M) |
| 86 | msFeBP6 (with signal peptide replaced with M) |
| 87 | srFeBP7 (with signal peptide replaced with M) |
| 88 | hlFeBP8 (with C138A and C176A substitution mutations and signal peptide replaced with M) |
| 89 | GGSHHHHHH |
| 90 | βZif |
| 91 | ZF-QNK |
| 92 | Hexahistidine Tag |
| 93 | Hexalysine Tag |
| 94 | ecGGBP (with signal peptide removed) |

-continued

| SEQ ID NO | Sequence Name |
|---|---|
| 95 | Exemplary Expression Construct for synBicarbBP1 |
| 96 | Exemplary Expression Construct for teBicarbBP2 |
| 97 | Exemplary Expression Construct for ctBicarbBP3 |
| 98 | Exemplary Expression Construct for calBicarbBP4 |
| 99 | Exemplary Expression Construct for avBicarbBP5 |
| 100 | Exemplary Expression Construct for cmBicarbBP6 |
| 101 | Exemplary Expression Construct for mhFeBP1 |
| 102 | Exemplary Expression Construct for exiFeBP2 |
| 103 | Exemplary Expression Construct for teFeBP3 |
| 104 | Exemplary Expression Construct for cnFeBP4 |
| 105 | Exemplary Expression Construct for ttFeBP5 |
| 106 | Exemplary Expression Construct for msFeBP6 |
| 107 | Exemplary Expression Construct for srFeBP7 |
| 108 | Exemplary Expression Construct for hlFeBP8 |
| 109 | Exemplary Expression Construct for avBicarBP5_16C |
| 110 | Exemplary Expression Construct for avBicarBP5_17C |
| 111 | Exemplary Expression Construct for avBicarBP5_18C |
| 112 | Exemplary Expression Construct for avBicarBP5_49C |
| 113 | Exemplary Expression Construct for avBicarBP5_71C |
| 114 | Exemplary Expression Construct for avBicarBP5_140C |
| 115 | Exemplary Expression Construct for avBicarBP5_141C |
| 116 | Exemplary Expression Construct for avBicarBP5_142C |
| 117 | Exemplary Expression Construct for avBicarBP5_143C |
| 118 | Exemplary Expression Construct for avBicarBP5_146C |
| 119 | Exemplary Expression Construct for avBicarBP5_190C |
| 120 | Exemplary Expression Construct for avBicarBP5_194C |
| 121 | Exemplary Expression Construct for teFeBP3_A8C |
| 122 | Exemplary Expression Construct for teFeBP3_H10C |
| 123 | Exemplary Expression Construct for teFeBP3_D12C |
| 124 | Exemplary Expression Construct for teFeBP3_T13C |
| 125 | Exemplary Expression Construct for teFeBP3_A36C |
| 126 | Exemplary Expression Construct for teFeBP3_V58C |
| 127 | Exemplary Expression Construct for teFeBP3_R135C |
| 128 | Exemplary Expression Construct for teFeBP3_N139C |
| 129 | Exemplary Expression Construct for teFeBP3_I140C |
| 130 | Exemplary Expression Construct for teFeBP3_N176C |
| 131 | Exemplary Expression Construct for teFeBP3_N195C |
| 132 | Exemplary Expression Construct for teFeBP3_N268C |

-continued

| SEQ ID NO | Sequence Name |
|---|---|
| 133 | Exemplary Expression Construct for teFeBP3_E270C |
| 134 | Exemplary Expression Construct for avBicarbBP5_16C_bZif |
| 135 | Exemplary Expression Construct for avBicarbBP5_17C_bZif |
| 136 | Exemplary Expression Construct for avBicarbBP5_18C bZif |
| 137 | Exemplary Expression Construct for avBicarbBP5_190C_bZif |
| 138 | Exemplary Expression Construct for avBicarbBP5_194C_bZif |
| 139 | Exemplary Expression Construct for avBicarbBP5_16C_71D_bZif |
| 140 | Exemplary Expression Construct for avBicarbBP5_16C_71N_bZif |
| 141 | Exemplary Expression Construct for avBicarbBP5_16C_71E_bZif |
| 142 | Exemplaiy Expression Construct for avBicarbBP5_16C_71M_bZif |
| 143 | Exemplary Expression Construct for avBicarbBP5_18C_16M_bZif |
| 144 | Exemplary Expression Construct for avBicarbBP5_18C_16F_bZif |
| 145 | Exemplary Expression Construct for avBicarbBP5_18C_16Y_bZif |
| 146 | Exemplary Expression Construct for avBicarbBP5_18C_16W_bZif |
| 147 | Exemplary Expression Construct for avBicarbBP5_18C_16E_bZif |
| 148 | Exemplary Expression Construct for avBicarbBP5_18C_49F_bZif |
| 149 | Exemplary Expression Construct for avBicarbBP5_18C_49Y_bZif |
| 150 | Exemplary Expression Construct for avBicarbBP5_18C_141V_bZif |
| 151 | Exemplary Expression Construct for avBicarbBP5_18C_141F_bZif |
| 152 | Exemplary Expression Construct for avBicarbBP5_18C_141Y_bZif |
| 153 | Exemplary Expression Construct for avBicarbBP5_18C_141W_bZif |
| 154 | Exemplary Expression Construct for avBicarbBP5_18C_141Q_bZif |
| 155 | KLGXIXIXEXAP (conserved sequence) |
| 156 | DGGQXQMPMP (conserved sequence) |
| 157 | GNGIA (conserved sequence |
| 158 | TFXXVNQD (conserved sequence |
| 159 | HPEEY (conserved sequence) |
| 160 | VYSXR (conserved sequence) |
| 161 | GLXXR (conserved sequence) |
| 162 | YYXX (conserved sequence) |
| 163 | YXGR (conserved sequence |
| 164 | SPAD (conserved sequence) |
| 165 | GWXPXY (conserved sequence) |
| 166 | 2I4C seed sequence (synBicarbBP1) |
| 167 | 1SI0 seed sequence (mhFeBP1) |
| 168 | 4ELR seed sequence (ttFeBP5) |
| 169 | ecTrx |
| 170 | Adaptor0 |
| 171 | Adaptor1.0 |

-continued

| SEQ ID NO | Sequence Name |
|---|---|
| 172 | Adaptor2.0a |
| 173 | Adaptor2.0b |
| 174 | Adaptor3.0 |
| 175 | Adaptor4.0 |
| 176 | Adaptor5.0 |
| 177 | Adaptor6.0 |
| 178 | Adaptor7.0 |
| 179 | Adaptor8.0 |
| 180 | Adaptor9.0 |
| 181 | Adaptor10.0 |
| 182 | Adaptor11.0 |
| 183 | Adaptor12.0 |
| 184 | Adaptor13.0 |
| 185 | Adaptor14.0 |
| 186 | Adaptor15.0 |
| 187 | Adaptor16.0 |

The terms "bZif" and "βZif" are used synonymously herein. Exemplary amino acid sequences are listed below for convenience.

synBicarbBP1
SARDNVTIGSQGGGIDGGQWQMPMPHLITEGIITNGNKVPMYVLAQLITQ

GNGIAVAPMHEGKGVNLDITKAADYIKGFNKTNGRKFKAAHTFPNVNQDF

WIRYWFAAGGVDPDTDIDLLAVPPAETVQGMRNGTMDAFSTGDPWPYRIV

TENIGYMAGLTAQIWPYHPEEYLAIRADWVDKNPKATKALLKGIMEAQQW

IDDPKNRPEVVQFVSGRNYFNVPTTILESPFKGQYTMGDGQPAIDDFQKG

PLYWRDGIGNVSYPYRSHDLWFLTESIRWGFHRNAIPDLDTAQRIIDRVN

REDLWREAATEAGFTADIPSSTSRGVETFFDGITFDPANPSAYLQSLAfR

RVGGSHHHHHH** teBicarbBP2
MLETDTIRLGFIPIVESAPLIIAKERGFFARHGLTNAELSRQANWASARD

NVVIGSAGGGIDGGQWQMPMPYLISEGIITLNNQRLPMYVLAQLNTQGNG

IAISGANKGRGLHLRIADPDYIKGFAARNGRKFKAAHTFPHVNQDLWIRY

WFAANGIDPDRDIELLAVPPAETVAGMRNGTMDAFSTGDPWPFRIVSDDI

GYMATLTAQIWPYHPEEYLAVRADWVDKHPKATKALLKAVMEAQQWADDK

ANRPELIQIASRREYFNIPGNILTPPYEGTYTMGDGQPNFNDFNIGPLYW

RDPNGNSISYPYKSHDLWFLTENLRWGFNADKLKDFDNIKQMIGRVNRSD

LWQEAAKELGIPAAEIPTTESRGVETFFDGIKFDPDNPQAYLDSLKIKVK

SGGSHHHHHH**

-continued ctBicarbBP3
MPEQAPETTRVKLGYIPIVEAAPIIIAKEKGFFAKYGMTDVDVSKQASWG

SMRDNTEIGAAGGGVDGGQYQMPMPHLITEGRITKGNKPIPMYVLAQLNT

QGNGIAIAEKHRGKGIELELAKGGKNLFGQLKSANTPFTAAYTFAQVNQD

FWIRYWLAAGGVNPDADVKLIPVPAAQTVANMKTGTMDAFSTGDPWPYRI

VKDKIGFLAMLTADMWEFHPEEYLALRAEWVDKHPKATKALLKGIMEAQQ

WLDNFDNREEAAKILGGRNYFNLPAEILAGPFAGKYDMGEGRTVDDRNKA

VLYWRDPRGSVSYPYKSHDLWFLTESVRWGFLPPDSLTKAQALIDKVNRE

DLWKEAAKELGVAAADIPTSTSRGVETFFDGVKFDPENPAAYLRSLRIRR

AGGSHHHHHH** calBicarbBP4
MPEQRPETETVRLGYIPIVESAPLIIARERGLFARYGMTRVELARQASWG

AARDNVEIGSAGGGIDGGQWQMPMPHLITAGLITRGNREIPMYVLAQLVT

HGNGIAIADRHRGRGLGLRLDGARSLFRELRSSFPFTAAFTFPHVNQDLW

IRYWLAASGLDPDADVKLLTVPAAQTVANMRTGTMDAFSTGDPWPFRIVN

DRIGFMALLTAEMWKNHPEEYLAMRGDWVDRHPRATRAILRAVMEAQQWL

DNFENRREAATILAGRRYFDLSSPEILLDPYQGRYDMGDGRRIDDRLMAP

YYWKDERGSVSYPYRSHDLWFITENVRWGFLPRDYLANNAAKAKELrNKV

NREDIWREAARDLGIAAADIPTSTSRGVEEFFDGVRFDPERPEEYLRSLR

IRRAGVGGSHHHHHH**

-continued avBicarbBP5
MAEQAPEVTTVKLGYTPIVESAPLIIAKEKGFFAKYGLTNVELSRQASWG
SARDNVEIGSAGGGIDGGQWQMPMPHLITEGLITRGNQRIPMYVLAQLIT
HGNGIAIANRHQGRGISLRLEGARSLFSQLRSSTPFTAAFTFPHVNQDLW
IRYWLAAGGIDPDADVRLLTVPAAQTVANMRTGTMDAFSTGDPWPFRLVN
DRIGYMAALTAEIWRNHPEEYLAMRADWVDRYPRATRALLKGIMEAQQWL
DNFDNRREAAQILAGRNYFNLNNPEILADPYVGRYDMGDGRRIDDRSMAA
YYWKDEKGSVSYPYKSHDLWFITENVRWGFLPKDYLANGAAKAKELIDKV
NREDIWKEAAKEAGIAAADIPTSTSRGVEEFFDGFKFDPEKPDEYLKSLK
IKKVSVGGSHHHHHH** cmBicarbBP6
MSSATTPETTAVKLGYIAIAESAPLIIAREKGFFARHGMTDVDVSKQASW
GSARDNIEIGSSNGGIDGGQWQMPMPQLISEGIITKGNRKIPMLSLAQLS
TQGNGIAISTQHAGKGFGLDVSGAAEYVRDMKADGKPFKAAYTFPRVNQD
FWIRYWLAAGGIDPNKDIDLIAVPAAQTVASMRTGSMDGFSTGDPWPSRI
LRDRRKYGFLAVLTAQIWPAHPEEYFAMREDWVRKHPKAAKAILKGIMEA
QMWADDPKNRAEMAAILAQRKYFNVPSDLLIGPYVGEYILGADRKTVKDE
KLAIRYWKDARGNVSYPYKSHDLWFLTESVRWGFLPQGALGEADRIINAV
SGEKYWREAAQELGIASADIPPSTSRGIEKFFDGAEFNPEKPKAYLDSLK
IKNLKAGGSHHHHHH** mhFeBP1
MANEVNVYSYRQPYLIEPMLKNFEKDTGIKVNIIFADKGLVDRVKQEGEL
SPADVLLTVDISRVMEIVNADLAQKIDSKVLEKNIPAQFRDSNDQWFGLT
TRARVFYTSKDRVGKLPAGFDYLDLAKPEYKGKVAVRSGKNSYNVSLFAA
MIEHYGlEKTKAFLEGLKANLARKPQGGDRDQVKAIKEGIADYSIGNSYY
YGKMLDDEKQKSWAEAAIINFPSGEHGTHKNISGVVIAKHSPNKANAVKL
IEYLSGEKAQGLYAELNHEYPVKEGIEPSAIVKGWGTFKSDTIKLEDIAK
NYEAALKLVDEVKFDDFGGSHHHHHH** exiFeBP2
MNVVNVYSSRHYDVDQQLYKQFEEETGIKVNVVEGKSDELLERLNTEGEN
TEADLFITADAGNLYQAKEAGHLQAVDSDELESNIPEKYRDTDNEWFGLT
KRARVIVYSKDRVKPEDLSTYEALTEEQWNGKVLVRPSENMYNISLLASF
IEVNGVDEAKEWAKGLVNNMARDPQGNDRDQAKAVVAGEGDVAIMNTYYM
GLMLNSEDEEEKKVAEQLGVFFPNQDTTGTHVNISGIAMTKASKNTENAQ
KLMEFMSEPSAQEKFASVNYEYPVNESVEPNELLQSWGEFKEQDINLSAL
GENQQEAIRIFNEVGWKGGSHHHHHH** teFeBP3
MVINVYSARHYDTDKALYNTFTQQTGIRVNIIEAEADALIERIRSEGSRT
PADVLITVDAGRLWRAQEAGILQPIQSRVLNSVVPANLREPQGHWFGLSR
RVRVLIYNKSRVNPSQLSTYEDLANPKWRRQILTRSSSNIYNQSLTGSLL
AIHGAQKTEQWARGLVQNFARPPEGNDTAQIRASAEGVGSVAIANHYYLA
RLIASDKEQDRAVAAKVGLFFPNQRDRGAHVNISGAGVVAGAPNRQGAIR

-continued

FLEYLVSPKAQEMFAMANFEYPVRAGVPVHPIVKQFGNFRGQNVNAAVFG
RNNAEALRIMDRAGWRGGSHHHHHH** cnFeBP4
MKLVVYSGRAERLIKPVLDEFQAKSGIQIELLSSGTTELVNRLQAEGDHT
PADVFLTNDAGSLEHARELKLLRPMNMREVERAIPSQFRAADNSWIGLSG
RFWIVVYNTNLVKPDQIKSLFDLTQPQWKDKIAVPNSGSEYLQAGVSVIK
ATFGDERTKQFLQGLKANAGTQVYQKSSQIVEAVAKGQVAAGIVNHYYIY
RHLATQPTAPIAAVMTDQQEGGMGAIMNVTGIGVTRASKHVESAKLLIEF
LVAQAGQKMFADLDKEYPLHPDVKADPTLIDRRTFRAAQVPLARLAELRE
ATLTLIEQVGLRGGSHHHHHH** ttFeBP5
MSPTLTIYSGRGQSLVEPLVKQFEAETGIRVQVRYSTDAQILAALQEEGS
RSPADLFWANTAGALGQASAKGLLRPLGETLLEKPIAFVPASRTWVPVTV
RLRVLAYNPDRIKAEELPESLLDLPRFAREKGLVGRVGWTPTYSSFQDMV
AGMIALYGEEKTREWLLAMKALAPKAYPSNPAMLDAIRAGEVDLGSTNHY
YVVRFRRAGYRLGMHHFRDGDAGNLALVTGAGLLKTSKNLAAATRFLTYL
LSPQAQQYFVGNIGEYPLVKGVALDPNLLPLEEALAKSPKLDLEKLPLDR
ALRLLRETGVLGGSHHHHHH** msFeBP6
MSLTLYTGRSQALVDKLVQQFQKDTGIKVNVRYGRDAEILAALQEEGSRS
PADVFWANTSGALEEAVKRNLLVQLPASLTRQPQEFVPSHGRWVPVSVRF
RVAAYNPTKVKDSDFPASVMDLPKVAKFKGRIGWTPTYSSFQDFITAMRV
VKGEAATKAWLQAMIAAGAKAYPSNPPMLEAMQAGEIDVALTNHYYIQRI
LAGVGEGEYEGKEESEEEEKKELAAREAKAGVATHYFAPGDVGGLALVTG
AGILATSKHQTNATRFLNYLLSKKAQPYFVDEVREYPVIAGVRVAKGMLP
FANAIRLSPKIDFAKLTDLEGTLKLLREVGLLGGSHHHHHH** srFeBP7
MLVIYSGRSKALVDSLVQQYROQADVPVRVRYGTDSQLLAALQEEGDQSP
ADVFWANTTGALGNAVNNGLLTELPDTLANRAARFTPSNQRWTPVTTRFR
VLAYNSDAVSPEDLPDSVLDLPEHEEFEGRVGWTPAYSSFQDFVTALRVT
EGAETARTWLSDMQALNPNSYTSNTPMVQALEAGEIDVALTNHYYVLRLK
HGGAEGEYEGEEEEGEEHEEEHEEEATPRASAPVEMYHFADGDLGNLALV
TGAGALQTSNQPDAANRFLRFLLSEQAQSFAATRVNEYPVVSGASVPDYL
MPADEALKMSPEFDLQKLQNMEPTLDLLRDAGALGGSHHHHHH** hlFeBPX
MLTVYSGRGEFLVGELVEYIEDQYDDFDLTVRYAGSTDLVNQILNEGDGS
PADVFYSVNAGSLGTLAGEGRSQALSSEITDMVRSEFRTEQWIGTSGRAR
TVPYNTGEFSDDDLPDDIMAYPEEFAGSLGWAPSYGSAQAFITAMRLIEG
EEATLAWLESVVEAGISSYPDEFAAAQAIADGEIDAAFTNHYYIQRVLDG
NPDASIGTAFTSGDAGAVFNVAGAAVVDTASDATLAENFIRHLLSAEAQD
YFARSTFEYPLIPDVEPIGDLPTIDELDVPDIDLTELSDLEPTIDLMREA
GVEVGGSHHHHHH**

-continued avBicarBP5 Cysteine Scans avBicarBP5_16C

MAEQAPEVTTVKLGYCPIVESAPLIIAKEKGFFAKYGLTNVELSKQASWG

SARDNVEIGSAGGGIDGGQWQMPMPHLITEGLITKGNQKIPMYVLAQLIT

HGNGIAIANKHQGKGISLKLEGAKSLFSQLKSSTPFTAAFTFPHVNQDLW

IRYWLAAGGIDPDADVKLLTVPAAQTVANMKTGTMDAFSTGDPWPFRLVN

DKIGYMAALTAEIWKNHPEEYLAMRADWVDKYPKATKALLKGIMEAQQWL

DNFDNRKEAAQILAGRNYFNLNNPEILADPYVGKYDMGDGRKIDDKSMAA

YYWKDEKGSVSYPYKSHDLWFITENVRWGFLPKDYLANGAAKAKELIDKV

NREDIWKEAAKEAGIAAADIPTSTSRGVEEFFDGTKFDPEKPDEYLKSLK

IKKVSVGGSHHHHHH** avBicarBP5_17C

MAEQAPEVTTVKLGYICIVESAPLIIAKEKGFFAKYGLTNVELSKQASWG

SARDNVEIGSAGGGIDGGQWQMPMPHLITEGLITKGNQKIPMYVLAQLIT

HGNGIAIANKHQGKGISLKLEGAKSLFSQLKSSTPFTAAFTFPHVNQDLW

IRYWLAAGGIDPDADVKLLTVPAAQTVANMKTGTMDAFSTGDPWPFRLVN

DKIGYMAALTAEIWKNHPEEYLAMRADWVDKYPKATKALLKGIMEAQQWL

DNFDNRKEAAQILAGRNYFNLNNPEILADPYVGKYDMGDGRKIDDKSMAA

YYWKDEKGSVSYPYKSHDLWFITENVRWGFLPKDYLANGAAKAKELIDKV

NREDIWKEAAKEAGIAAADIPTSTSRGVEEFFDGTKFDPEKPDEYLKSLK

IKKVSVGGSHHHHHH** avBicarBP5_18C

MAEQAPEVTTVKLGYIPCVESAPLIIAKEKGFFAKYGLTNVELSKQASWG

SARDNVEIGSAGGGIDGGQWQMPMPHLITEGLITKGNQKIPMYVLAQLIT

HGNGIAIANKHQGKGISLKLEGAKSLFSQLKSSTPFTAAFTFPHVNQDLW

IRYWLAAGGIDPDADVKLLTVPAAQTVANMKTGTMDAFSTGDPWPFRLVN

DKIGYMAALTAEIWKNHPEEYLAMRADWVDKYPKATKALLKGIMEAQQWL

DNFDNRKEAAQILAGRNYFNLNNPEILADPYVGKYDMGDGRKIDDKSMAA

YYWKDEKGSVSYPYKSHDLWFITENVRWGFLPKDYLANGAAKAKELIDKV

NREDIWKEAAKEAGIAAADIPTSTSRGVEEFFDGTKFDPEKPDEYLKSLK

IKKVSVGGSHHHHHH** avBicarBP5_49C

MAEQAPEVTTVKLGYIPIVESAPLIIAKEKGFFAKYGLTNVELSKQASCG

SARDNVEIGSAGGGIDGGQWQMPMPHLITEGLITKGNQKIPMYVLAQLIT

HGNGIAIANKHQGKGISLKLEGAKSLFSQLKSSTPFTAAFTFPHVNQDLW

IRYWLAAGGIDPDADVKLLTVPAAQTVANMKTGTMDAFSTGDPWPFRLVN

DKIGYMAALTAEIWKNHPEEYLAMRADWVDKYPKATKALLKGIMEAQQWL

DNFDNRKEAAQILAGRNYFNLNNPEILADPYVGKYDMGDGRKIDDKSMAA

YYWKDEKGSVSYPYKSHDLWFFFENVRWGFLPKDYLANGAAKAKELIDKV

NREDIWKEAAKEAGIAAADIPTSTSRGVEEFFDGTKFDPEKPDEYLKSLK

IKKVSVGGSHHHHHH**

-continued avBicarBP5_71C

MAEQAPEVTTVKLGYIPIVESAPLIIAKEKGFFAKYGLTNVELSKQASWG

SARDNVEIGSAGGGIDGGQWCMPMPHLITEGLITKGNQKIPMYVLAQLIT

HGNGIAIANKHQGKGISLKLEGAKSLFSQLKSSTPFTAAFTFPHVNQDLW

IRYWLAAGGIDPDADVKLLTVPAAQTVANMKTGTMDAFSTGDPWPFRLVN

DKIGYMAALTAEIWKNHPEEYLAMRADWVDKYPKATKALLKGIMEAQQWL

DNFDNRKEAAQILAGRNYFNLNNPEILADPYVGKYDMGDGRKIDDKSMAA

YYWKDEKGSVSYPYKSHDLWFITENVRWGFLPKDYLANGAAKAKELIDKV

NREDIWKEAAKEAGIAAADIPTSTSRGVEEFFDGTKFDPEKPDEYLKSLK

IKKVSVGGSHHHHHH** avBicarBP5_140C

MAEQAPEVTTVKLGYIPIVESAPLIIAKEKGFFAKYGLTNVELSKQASWG

SARDNVEIGSAGGGIDGGQWQMPMPHLITEGLITKGNQKIPMYVLAQLIT

HGNGIAIANKHQGKGISLKLEGAKSLFSQLKSSTPFTAACTFPHVNQDLW

IRYWLAAGGIDPDADVKLLTVPAAQTVANMKTGTMDAFSTGDPWPFRLVN

DKIGYMAALTAEIWKNHPEEYLAMRADWVDKYPKATKALLKGIMEAQQWL

DNFDNRKEAAQILAGRNYFNLNNPEILADPYVGKYDMGDGRKIDDKSMAA

YYWKDEKGSVSYPYKSHDLWFITENVRWGFLPKDYLANGAAKAKELIDKV

NREDIWKEAAKEAGIAAADIPTSTSRGVEEFFDGTKFDPEKPDEYLKSLK

IKKVSVGGSHHHHHH** avBicarBP5_141C

MAEQAPEVTTVKLGYIPIVESAPLIIAKEKGFFAKYGLTNVELSKQASWG

SARDNVEIGSAGGGIDGGQWQMPMPHLITEGLITKGNQKIPMYVLAQLIT

HGNGIAIANKHQGKGISLKLEGAKSLFSQLKSSTPFTAAFCFPHVNQDLW

IRYWLAAGGIDPDADVKLLTVPAAQTVANMKTGTMDAFSTGDPWPFRLVN

DKIGYMAALTAEIWKNHPEEYLAMRADWVDKYPKATKALLKGIMEAQQWL

DNFDNRKEAAQILAGRNYFNLNNPEILADPYVGKYDMGDGRKIDDKSMAA

YYWKDEKGSVSYPYKSHDLWFITENVRWGFLPKDYLANGAAKAKELIDKV

NREDIWKEAAKEAGIAAADIPTSTSRGVEEFFDGTKFDPEKPDEYLKSLK

IKKVSVGGSHHHHHH** avBicarBP5_142C

MAEQAPEVTTVKLGYIPIVESAPLIIAKEKGFFAKYGLTNVELSKQASWG

SARDNVEIGSAGGGIDGGQWQMPMPHLITEGLITKGNQKIPMYVLAQLIT

HGNGIAIANKHQGKGISLKLEGAKSLFSQLKSSTPFTAAFTCPHVNQDLW

IRYWLAAGGIDPDADVKLLTVPAAQTVANMKTGTMDAFSTGDPWPFRLVN

DKIGYMAALTAEIWKNHPEEYLAMRADVWDKYPKATKALLKGIMEAQQWL

DNFDNRKEAAQILAGRNYFNLNNPEILADPYVGKYDMGDGRKIDDKSMAA

YYWKDEKGSVSYPYKSHDLWFITENVRWGFLPKDYLANGAAKAKELIDKV

NREDIWKEAAKEAGIAAADIPTSTSRGVEEFFDGTKFDPEKPDEYLKSLK

IKKVSVGGSHHHHHH** avBicarBP5_143C

MAEQAPEVTTVKLGYIPIVESAPLIIAKEKGFFAKYGLTNVELSKQASWG

SARDNVEIGSAGGGIDGGQWQMPMPHLITEGLITKGNQKIPMYVLAQLIT

HGNGIAIANKHQGKGISLKLEGAKSLFSQLKSSTPFTAAFTFCHVNQDLW
IRYWLAAGGIDPDADVKLLTVPAAQTVANMKTGTMDAFSTGDPWPFRLVN
DKIGYMAALTAEIWKNHPEEYLAMRADWVDKYPKATKALLKGIMEAQQWL
DNFDNRKEAAQILAGRNYFNLNNPEILADPYVGKYDMGDGRKIDDKSMAA
YYWKDEKGSVSYPYKSHDLWFITENVRWGFLPKDYLANGAAKAKELIDKV
NREDIWKEAAKEAGIAAADIPTSTSRGVEEFFDGTKFDPEKPDEYLKSLK
IKKVSVGGSHHHHHH** avBicarBP5_146C
MAEQAPEVTTVKLGYIPIVESAPLIIAKEKGFFAKYGLTNVELSKQASWG
SARDNVETGSAGGGIDGGQWQMPMPHLITEGLITKGNQKIPMYVLAQLIT
HGNGIAIANKHQGKGISLKLEGAKSLFSQLKSSTPFTAAFTFPHVCQDLW
IRYWLAAGGIDPDADVKLLTVPAAQTVANMKTGTMDAFSTGDPWPFRLVN
DKIGYMAALTAEIWKNHPEEYLAMRADWVDKYPKATKALLKGIMEAQQWL
DNFDNRKEAAQILAGRNYFNLNNPEILADPYVGKYDMGDGRKIDDKSMAA
YYWKDEKGSVSYPYKSHDLWFITENVRWGFLPKDYLANGAAKAKELIDKV
NREDIWKEAAKEAGIAAADIPTSTSRGVEEFFDGTKFDPEKPDEYLKSLK
IKKVSVGGSHHHHHH** avBicarBP5_190C
MAEQAPEVTTVKLGYIPIVESAPLIIAKEKGFFAKYGLTNVELSKQASWG
SARDNVEIGSAGGGIDGGQWQMPMPHLITEGLITKGNQKIPMYVLAQLIT
HGNGIAIANKHQGKGISLKLEGAKSLFSQLKSSTPFTAAFTFPHVNQDLW
IRYWLAAGGIDPDADVKLLTVPAAQTVANMKTGTMDAFSCGDPWPFRLVN
DKIGYMAALTAEIWKNHPEEYLAMRADWVDKYPKATKALLKGIMEAQQWL
DNFDNRKEAAQILAGRNYFNLNNPEILADPYVGKYDMGDGRKIDDKSMAA
YYWKDEKGSVSYPYKSHDLWFITENVRWGFLPKDYLANGAAKAKELIDKV
NREDIWKEAAKEAGIAAADIPTSTSRGVEEFFDGTKFDPEKPDEYLKSLK
IKKVSVGGSHHHHHH** avBicarBP5_194C
MAEQAPEVTTVKLGYIPIVESAPLIIAKEKGFFAKYGLTNVELSKQASWG
SARDNVEIGSAGGGIDGGQWQMPMPHLITEGLITKGNQKIPMYVLAQLIT
HGNGIAIANKHQGKGISLKLEGAKSLFSQLKSSTPFTAAFTFPHVNQDLW
IRYWLAAGGIDPDADVKLLTVPAAQTVANMKTGTMDAFSTGDPCPFRLVN
DKIGYMAALTAEIWKNHPEEYLAMRADWVDKYPKATKALLKGIMEAQQWL
DNFDNRKEAAQILAGRNYFNLNNPEILADPYVGKYDMGDGRKIDDKSMAA
YYWKDEKGSVSYPYKSHDLWFITENVRWGFLPKDYLANGAAKAKELIDKV
NREDIWKEAAKEAGIAAADIPTSTSRGVEEFFDGTKFDPEKPDEYLKSLK
IKKVSVGGSHHHHHH** teFeBP3 Cysteine Scans
teFeBP3_A8C
MVINVYSCRHYDTDKALYNTFTQQTGIRVNIIEAEADALIERIRSEGSRT
PADVLITVDAGRLWRAQEAGILQPIQSRVLNSVVPANLREPQGHWFGLSR
RVRVLIYNKSRVNPSQLSTYEDLANPKWRRQILTRSSSNIYNQSLTGSLL
AIHGAQKTEQWARGLVQNFARPPEGNDTAQIRASAEGVGSVAIANHYYLA
RLIASDKEQDRAVAAKVGLFFPNQRDRGAHVNISGAGVVAGAPNRQGAIR
FLEYLVSPKAQEMFAMANFEYPVRAGVPVHPIVKQFGNFRGQNVNAAVFG
RNNAEALRIMDRAGWRGGSHHHHHH** teFeBP3_H10C
MVINVYSARCYDTDKALYNTFTQQTGIRVNIIEAEADALIERIRSEGSRT
PADVLITVDAGRLWRAQEAGILQPIQSRVLNSVVPANLREPQGHWFGLSR
RVRVLIYNKSRVNPSQLSTYEDLANPKWRRQILTRSSSNIYNQSLTGSLL
AIHGAQKTEQWARGLVQNFARPPEGNDTAQIRASAEGVGSVAIANHYYLA
RLIASDKEQDRAVAAKVGLFFPNQRDRGAHVNISGAGVVAGAPNRQGAIR
FLEYLVSPKAQEMFAMANFEYPVRAGVPVHPIVKQFGNFRGQNVNAAVFG
RNNAEALRIMDRAGWRGGSHHHHHH** teFeBP3_D12C
MVINVYSARHYCTDKALYNTFTQQTGIRVNIIEAEADALIERIRSEGSRT
PADVLITVDAGRLWRAQEAGILQPIQSRVLNSVVPANLREPQGHWFGLSR
RVRVLIYNKSRVNPSQLSTYEDLANPKWRRQILTRSSSNIYNQSLTGSLL
AIHGAQKTEQWARGLVQNFARPPEGNDTAQIRASAEGVGSVAIANHYYLA
RLIASDKEQDRAVAAKVGLFFPNQRDRGAHVNISGAGVVAGAPNRQGAIR
FLEYLVSPKAQEMFAMANFEYPVRAGVPVHPIVKQFGNFRGQNVNAAVFG
RNNAEALRIMDRAGWRGGSHHHHHH** teFeBP3_T13C
MVINVYSARHYDCDKALYNTFTQQTGIRVNIIEAEADALIERIRSEGSRT
PADVLITVDAGRLWRAQEAGILQPIQSRVLNSVVPANLREPQGHWFGLSR
RVRVLIYNKSRVNPSQLSTYEDLANPKWRRQILTRSSSNIYNQSLTGSLL
AIHGAQKTEQWARGLVQNFARPPEGNDTAQIRASAEGVGSVAIANHYYLA
RLIASDKEQDRAVAAKVGLFFPNQRDRGAHVNISGAGVVAGAPNRQGAIR
FLEYLVSPKAQEMFAMANFEYPVRAGVPVHPIVKQFGNFRGQNVNAAVFG
RNNAEALRIMDRAGWRGGSHHHHHH** teFeBP3_A36C
MVINVYSARHYDTDKALYNTFTQQTGIRVNIIEAECDALIERIRSEGSRT
PADVLITVDAGRLWRAQEAGILQPIQSRVLNSVVPANLREPQGHWFGLSR
RVRVLIYNKSRVNPSQLSTYEDLANPKWRRQILTRSSSNIYNQSLTGSLL
AIHGAQKTEQWARGLVQNFARPPEGNDTAQIRASAEGVGSVAIANHYYLA
RLIASDKEQDRAVAAKVGLFFPNQRDRGAHVNISGAGVVAGAPNRQGAIR
FLEYLVSPKAQEMFAMANFEYPVRAGVPVHPIVKQFGNFRGQNVNAAVFG
RNNAEALRIMDRAGWRGGSHHHHHH** teFeBP3_V58C
MVINVYSARHYDTDKALYNTFTQQTGIRVNIIEAEADALIERIRSEGSRT
PADVLITCDAGRLWRAQEAGILQPIQSRVLNSVVPANLREPQGHWFGLSR
RVRVLIYNKSRVNPSQLSTYEDLANPKWRRQILTRSSSNIYNQSLTGSLL
AIHGAQKTEQWARGLVQNFARPPEGNDTAQIRASAEGVGSVAIANHYYLA
RLIASDKEQDRAVAAKVGLFFPNQRDRGAHVNISGAGVVAGAPNRQGAIR
FLEYLVSPKAQEMFAMANFEYPVRAGVPVHPIVKQFGNFRGQNVNAAVFG
RNNAEALRIMDRAGWRGGSHHHHHH**

-continued teFeBP3_R135C
MVINVYSARHYDTDKALYNTFTQQTGIRVNIIEAEADALIERIRSEGSRT
PADVLITVDAGRLWRAQEAGILQPIQSRVLNSVVPANLREPQGHWFGLSR
RVRVLIYNKSRVNPSQLSTYEDLANPKWRRQILTCSSSNIYNQSLTGSLL
AIHGAQKTEQWARGLVQNFARPPEGNDTAQIRASAEGVGSVAIANHYYLA
RLIASDKEQDRAVAAKVGLFFPNQRDRGAHVNISGAGVVAGAPNRQGAIR
FEEYLVSPKAQEMFAMANFEYPVRAGVPVHPIVKQFGNFRGQNVNAAVFG
RNNAEALRIMDRAGWRGGSHHHHHH** teFeBP3_N139C
MVINVYSARHYDTDKALYNTFTQQTGIRVNIIEAEADALIERIRSEGSRT
PADVLITVDAGRLWRAQEAGILQPIQSRVLNSVVPANLREPQGHWFGLSR
RVRVLIYNKSRVNPSQLSTYEDLANPKWRRQILTRSSSCIYNQSLTGSLL
AIHGAQKTEQWARGLVQNFARPPEGNDTAQIRASAEGVGSVAIANHYYLA
RLIASDKEQDRAVAAKVGLFFPNQRDRGAHVNISGAGVVAGAPNRQGAIR
FLEYLVSPKAQEMFAMANFEYPVRAGVPVHPIVKQFGNFRGQNVNAAVFG
RNNAEALRIMDRAGWRGGSHHHHHH** teFeBP3_I140C
MVINVYSARHYDTDKALYNTFTQQTGIRVNIIEAEADALIERIRSEGSRT
PADVLITVDAGRLWRAQEAGILQPIQSRVLNSVVPANLREPQGHWFGLSR
RVRVLIYNKSRVNPSQLSTYEDLANPKWRRQILTRSSSNCYNQSLTGSLL
AIHGAQKTEQWARGLVQNFARPPEGNDTAQIRASAEGVGSVAIANHVYLA
RLIASDKEQDRAVAAKVGLFFPNQRDRGAHVNISGAGVVAGAPNRQGAIR
FLEYLVSPKAQEMFAMANFEYPVRAGVPVHPIVRQFGNFRGQNVNAAVFG
RNNAEALRIMDRAGWRGGSHHHHHH** teFeBP3_N176C
MVINVYSARHYDTDKALYNTFTQQTGIRVNIIEAEADALIERIRSEGSRT
PADVLITVDAGRLWRAQEAGILQPIQSRVLNSVVPANLREPQGHWFGLSR
RVRVLIYNKSRVNPSQLSTYEDLANPKWRRQILTRSSSNIYNQSLTGSLL
AIHGAQKTEQWARGLVQNFARPPEGCDTAQIRASAEGVGSVAIANHYYLA
RLIASDKEQDRAVAAKVGLFFPNQRDRGAHVNISGAGVVAGAPNRQGAIR
FLEYLVSPKAQEMFAMANFEYPVRAGVPVHPIVKQFGNFRGQNVNAAVFG
RNNAEALRIMDRAGWRGGSHHHHHH** teFeBP3_N195C
MVINVYSARHYDTDKALYNTFTQQTGIRVNIIEAEADALIERIRSEGSRT
PADVLITVDAGRLWRAQEAGILQPIQSRVLNSVVPANLREPQGHWFGLSR
RVRVLIYNKSRVNPSQLSTYEDLANPKWRRQILTRSSSNIYNQSLTGSLL
AIHGAQKTEQWARGLVQNFARPPEGNDTAQIRASAEGVGSVAIACHYYLA
RLIASDKEQDRAVAAKVGLFFPNQRDRGAHVNISGAGVVAGAPNRQGAIR
FLEYLVSPKAQEMFAMANFEYPVRAGVPVHPIVKQFGNFRGQNVNAAVFG
RNNAEALRIMDRAGWRGGSHHHHHH** teFeBP3_N268C
MVINVYSARHYDTDKALYNTFTQQTGIRVNIIEAEADALIERIRSEGSRT
PADVLITVDAGRLWRAQEAGILQPIQSRVLNSVVPANLREPQGHWFGLSR

-continued

RVRVLIYNKSRVNPSQLSTYEDLANPKWRRQILTRSSSNIYNQSLTGSLL
AIHGAQKTEQWARGLVQNFARPPEGNDTAQIRASAEGVGSVAIANHYYLA
RLIASDKEQDRAVAAKVGLFFPNQRDRGAHVNISGAGVVAGAPNRQGAIR
FLEYLVSPKAQEMFAMACFEYPVRAGVPVHPIVKQFGNFRGQNVNAAVFG
RNNAEALRIMDRAGWRGGSHHHHHH** teFeBP3_E270C
MVINVYSARHYDTDKALYNTFTQQTGIRVNIIEAEADALIERIRSEGSRT
PADVLITVDAGRLWRAQEAGILQPIQSRVLNSVVPANLREPQGHWFGLSR
RVRVLIYNKSRVNPSQLSTYEDLANPKWRRQILTRSSSNIYNQSLTGSLL
AIHGAQKTEQWARGLVQNFARPPEGNDTAQIRASAEGVGSVAIANHYYLA
RLIASDKEQDRAVAAKVGLFFPNQRDRGAHVNISGAGVVAGAPNRQGAIR
FLEYLVSPKAQEMFAMANFCYPVRAGVPVHPIVKQFGNFRGQNVNAAVFG
RNNAEALRIMDRAGWRGGSHHHHHH** bZifs of Cys Scans in avBicarbP5
avBicarbBP5_16C_bZif
MAEQAPEVTTVKLGYCPIVESAPLIIAKEKGFFAKYGLTNVELSKQASWG
SARDNVEIGSAGGGIDGGQWQMPMPHLITEGLITKGNQKIPMYVLAQLIT
HGNGIAIANKHQGKGISLKLEGAKSLFSQLKSSTPFTAAFTFPHVNQDLW
IRYWLAAGGIDPDADVKLLTVPAAQTVANMKTGTMDAFSTGDPWPFRLVN
DKIGYMAALTAEIWKNHPEEYLAMRADWVDKYPKATKALLKGIMEAQQWL
DNFDNRKEAAQILAGRNYFNLNNPEILADPYVGKYDMGDGRKIDDKSMAA
YYWKDEKGSVSYPYKSHDLWFITENVRWGFLPKDYLANGAAKAKELIDKV
NREDIWKEAAKEAGIAAADIPTSTSRGVEEFFDGTKFDPEKPDEYLKSLK
IKKVSVGGSTGEKPYKCPECGKSFSRSGGSHHHHHH** avBicarbBP5_17C_bZif
MAEQAPEVTTVKLGYICIVESAPLIIAKEKGFFAKYGLTNVELSKQASWG
SARDNVEIGSAGGGIDGGQWQMPMPHLITEGLITKGNQKIPMYVLAQLIT
HGNGIAIANKHQGKGISLKLEGAKSLFSQLKSSTPFTAAFTFPHVNQDLW
IRYWLAAGGIDPDADVKLLTVPAAQTVANMKTGTMDAFSTGDPWPFRLVN
DKIGYMAALTAEIWKNHPEEYLAMRADWVDKYPKATKALLKGIMEAQQWL
DNFDNRKEAAQILAGRNYFNLNNPEILADPYVGKYDMGDGRKIDDKSMAA
YYWKDEKGSVSYPYKSHDLWFITENVRWGFLPKDYLANGAAKAKELIDKV
NREDIWKEAAKEAGIAAADIPTSTSRGVEEFFDGTKFDPEKPDEYLKSLK
IKKVSVGGSTGEKPYKCPECGKSFSRSGGSHHHHHH** avBicarbBP5_18C_bZif
MAEQAPEVTTVKLGYIPCVESAPLIIAKEKGFFAKYGLTNVELSKQASWG
SARDNVEIGSAGGGIDGGQWQMPMPHLITEGLITKGNQKIPMYVLAQLIT
HGNGIAIANKHQGKGISLKLEGAKSLFSQLKSSTPFTAAFTFPHVNQDLW
IRYWLAAGGIDPDADVKLLTVPAAQTVANMKTGTMDAFSTGDPWPFRLVN
DKIGYMAALTAEIWKNHPEEYLAMRADWVDKYPKATKALLKGIMEAQQWL
DNFDNRKEAAQILAGRNYFNLNNPEILADPYVGKYDMGDGRKIDDKSMAA
YYWKDEKGSVSYPYKSHDLWFITENVRWGFLPKDYLANGAAKAKELIDKV -continued

NREDIWKEAAKEAGIAAADIPTSTSRGVEEFFDGTKFDPEKPDEYLKSLK

IKKVSVGGSTGEKPYKCPECGKSFSRSGGSHHHHHH** avBicarbBP5_190C_bZif
MAEQAPEVTTVKLGYIPIVESAPLIIAKEKGFFAKYGLTNVELSKQASWG

SARDNVEIGSAGGGIDGGQWQMPMPHLITEGLITKGNQKIPMYVLAQLIT

HGNGIAIANKHQGKGISLKLEGAKSLFSQLKSSTPFTAAFTFPHVNQDLW

IRYWLAAGGIDPDADVKLLTVPAAQTVANMKTGTMDAFSCGDPWPFRLVN

DKIGYMAALTAEIWKNHPEEYLAMRADWVDKYPKATKALLKGIMEAQQWL

DNFDNRKEAAQILAGRNYFNLNNPEILADPYVGKYDMGDGRKIDDKSMAA

YYWKDEKGSVSYPYKSHDLWFITENVRWGFLPKDYLANGAAKAKELIDKV

NREDIWKEAAKEAGIAAADIPTSTSRGVEEFFDGTKFDPEKPDEYLKSLK

IKKVSVGGSTGEKPYKCPECGKSFSRSGGSHHHHHH** avBicarbBP5_194C_bZif
MAEQAPEVTTVKLGYIPIVESAPLIIAKEKGFFAKYGLTNVELSKQASWG

SARDNVEIGSAGGGIDGGQWQMPMPHLITEGLITKGNQKIPMYVLAQLIT

HGNGIAIANKHQGKGISLKLEGAKSLFSQLKSSTPFTAAFTFPHVNQDLW

IRYWLAAGGIDPDADVKLLTVPAAQTVANMKTGTMDAFSTGDPCPFRLVN

DKIGYMAALTAEIWKNHPEEYLAMRADWVDKYPKATKALLKGIMEAQQWL

DNFDNRKEAAQILAGRNYFNLNNPEILADPYVGKYDMGDGRKIDDKSMAA

YYWKDEKGSVSYPYKSHDLWFITENVRWGFLPKDYLANGAAKAKELIDKV

MIEDIWKEAAKEAGIAAADIPTSTSRGVEEFFDGTKFDPEKPDEYLKSLK

IKKVSVGGSTGEKPYKCPECGKSFSRSGGSHHHHHH**

Affinity Variants of avBicarbP5_16C-bZif
avBicarbBP5_16C_71D_bZif
MAEQAPEVTTVKLGYCPIVESAPLIIAKEKGFFAKYGLTNVELSKQASWG

SARDNVEIGSAGGGIDGGQWDMPMPHLITEGLITKGNQKIPMYVLAQLIT

HGNGIAIANKHQGKGISLKLEGAKSLFSQLKSSTPFTAAFTFPHVNQDLW

IRYWLAAGGIDPDADVKLLTVPAAQTVANMKTGTMDAFSTGDPWPFRLVN

DKIGYMAALTAEIWKNHPEEYLAMRADWVDKYPKATKALLKGIMEAQQWL

DNFDNRKEAAQILAGRNYFNLNNPEILADPYVGKYDMGDGRKIDDKSMAA

YYWKDEKGSVSYPYKSHDLWFITENVRWGFLPKDYLANGAAKAKELIDKV

NREDIWKEAAKEAGIAAADIPTSTSRGVEEFFDGTKFDPEKPDEYLKSLK

IKKVSVGGSTGEKPYKCPECGKSFSRSGGSHHHHHH** avBicarbBP5_116C_71N_bZif
MAEQAPEVTTVKLGYCPIVESAPLIIAKEKGFFAKYGLTNVELSKQASWG

SARDNVEIGSAGGGIDGGQWNMPMPHLITEGLITKGNQKIPMYVLAQLIT

HGNGIAIANKHQGKGISLKLEGAKSLFSQLKSSTPFTAAFTFPHVNQDLW

IRYWLAAGGIDPDADVKLLTVPAAQTVANMKTGTMDAFSTGDPWPFRLVN

DKIGYMAALTAEIWKNHPEEYLAMRADWVDKYPKATKALLKGIMEAQQWL

DNFDNRKEAAQILAGRNYFNLNNPEILADPYVGKYDMGDGRKIDDKSMAA

YYWKDEKGSVSYPYKSHDLWFITENVRWGFLPKDYLANGAAKAKELIDKV

NREDIWKEAAKEAGIAAADIPTSTSRGVEEFFDGTKFDPEKPDEYLKSLK

IKKVSVGGSTGEKPYKCPECGKSFSRSGGSHHHHHH**

-continued avBicarbBP5_16C_71E_bZif
MAEQAPEVTTVKLGYCPIVESAPLIIAKEKGFFAKYGLTNVELSKQASWG

SARDNVEIGSAGGGIDGGQWEMPMPHLITEGLITKGNQKIPMYVLAQLIT

HGNGIAIANKHQGKGISLKLEGAKSLFSQLKSSTPFTAAFTFPHVNQDLW

IRYWLAAGGIDPDADVKLLTVPAAQTVANMKTGTMDAFSTGDPWPFRLVN

DKIGYMAALTAEIWKNHPEEYLAMRADWVDKYPKATKALLKGIMEAQQWL

DNFDNRKEAAQILAGRNYFNLNNPEILADPYVGKYDMGDGRKIDDKSMAA

YYWKDEKGSVSYPYKSHDLWFITENVRWGFLPKDYLANGAAKAKELIDKV

NREDIWKEAAKEAGIAAADIPTSTSRGVEEFFDGTKFDPEKPDEYLKSLK

IKKVSVGGSTGEKPYKCPECGKSFSRSGGSHHHHHH** avBicarbBP5_16C_71M_bZif
MAEQAPEVTTVKLGYCPIVESAPLIIAKEKGFFAKYGLTNVELSKQASWG

SARDNVEIGSAGGGIDGGQWMMPMPHLITEGLITKGNQKIPMYVLAQLIT

HGNGIAIANKHQGKGISLKLEGAKSLFSQLKSSTPFTAAFTFPHVNQDLW

IRYWLAAGGIDPDADVKLLTVPAAQTVANMKTGTMDAFSTGDPWPFRLVN

DKIGYMAALTAEIWKNHPEEYLAMRADWVDKYPKATKALLKGIMEAQQWL

DNFDNRKEAAQILAGRNYFNLNNPEILADPYVGKYDMGDGRKIDDKSMAA

YYWKDEKGSVSYPYKSHDLWFITENVRWGFLPKDYLANGAAKAKELIDKV

NREDIWKEAAKEAGIAAADIPTSTSRGVEEFFDGTKFDPEKPDEYLKSLK

IKKVSVGGSTGEKPYKCPECGKSFSRSGGSHHHHHH**

Affinity Variants of avBicarbP5_18C-bZif
avBicarbBP5_18C_16M_bZif
MAEQAPEVTTVKLGYMPCVESAPLIIAKEKGFFAKYGLTNVELSKQASWG

SARDNVEIGSAGGGIDGGOWQMPMPHLITEGLITKGNQKIPMYVLAQLIT

HGNGIAIANKHQGKGISLKLEGAKSLFSQLKSSTPFTAAFTFPMVNQDLW

IRYWLAAGGIDPDADVKLLTVPAAQTVANMKTGTMDAFSTGDPWPFRLVN

DKIGYMAALTAEIWKNHPEEYLAMRADWVDKYPKATKALLKGIMEAQQWL

DNFDNRKEAAQILAGRNYFNLNNPEILADPYVGKYDMGDGRKIDDKSMAA

YYWKDEKGSVSYPYKSHDLWFITENVRWGFLPKDYLANGAAKAKELIDKV

NREDIWKEAAKEAGIAAADIPTSTSRGVEEFFDGTKFDPEKPDEYLKSLK

IKKVSVGGSTGEKPYKCPECGKSFSRSGGSHHHHHH** av BicarbBP5_ 18C_ 16F_bZif
MAEQAPEVTTVKLGYFPCVESAPLIIAKEKGFFAKYGLTNVELSKQASWG

SARDNVEIGSAGGGIDGGQWQMPMPHLITEGLITKGNQKIPMYVLAQLIT

HGNGIAIANKHQGKGISLKLEGAKSLFSQLKSSTPFTAAFTFPHVNQDLW

IRYWLAAGGIDPDADVKLLTVPAAQTVANMKTGTMDAFSTGDPWPFRLVN

DKIGYMAALTAEIWKNHPEEYLAMRADWVDKYPKATKALLKGIMEAQQWL

DNFDNRKEAAQILAGRNYFNLNNPEILADPYVGKYDMGDGRKIDDKSMAA

YYWKDEKGSVSYPYKSHDLWFITENVRWGFLPKDYLANGAAKAKELIDKV

NREDIWKEAAKEAGIAAADIPTSTSRGVEEFFDGTKFDPEKPDEYLKSLK

IKKVSVGGSTGEKPYKCPECGKSFSRSGGSHHHHHH**

-continued avBicarbBP5_18C_16Y_bZif
MAEQAPEVTTVkLGYYPCVESAPLIIAKEKGFFAKYGLTNVELSKQASWG
SARDNVEIGSAGGGIDGGQWQMPMPHLITEGLITKGNQKIPMYVLAQLIT
HGNGIAIANKHQGKGISLKLEGAKSLFSQLKSSTPFTAAFTFPHVNQDLW
IRYWLAAGGIDPDADVKLLTVPAAQTVANMKTGTMDAFSTGDPWPFRLVN
DKIGYMAALTAEIWKNHPEEYLAMRADWVDKYPKATKALLKGIMEAQQWL
DNFDNRKEAAQILAGRNYFNLNNPEILADPYVGKYDMGDGRKIDDKSMAA
YYWKDEKGSVSYPYKSHDLWFITENVRWGFLPKDYLANGAAKAKELIDKV
NREDIWKEAAKEAGIAAADIPTSTSRGVEEFFDGTKFDPEKPDEYLKSLK
IKKVSVGGSTGEKPYKCPECGKSFSRSGGSHHHHHH** avBicarbBP5_18C_16W_bZif
MAEQAPEVTTVKLGYWPCVESAPLIIAKEKGFFAKYGLTNVELSKQASWG
SARDNVEIGSAGGGIDGGQWOMPMPHLITEGLITKGNQKIPMYVLAQLIT
HGNGIAIANKHQGKGISLKLEGAKSLFSQLKSSTPFTAAFTFPHVNQDLW
IRYWLAAGGIDPDADVKLLTVPAAQTVANMKTGTMDAFSTGDPWPFRLVN
DKIGYMAALTAEIWKNHPEEYLAMRADWVDKYPKATKALLKGIMEAQQWL
DNFDNRKEAAQILAGRNYFNLNNPEILADPYVGKYDMGDGRKIDDKSMAA
YYWKDEKGSVSYPYKSHDLWFITENVRWGFLPKDYLANGAAKAKELIDKV
NREDIWKEAAKEAGIAAADIPTSTSRGVEEFFDGTKFDPEKPDEYLKSLK
IKKVSVGGSTGEKPYKCPECGKSFSRSGGSHHHHHH** avBicarbBP5_18C_16E_bZif
MAEQAPEVTTVKLGYEPCVESAPLIIAKEKGFFAKYGLTNVELSKQASWG
SARDNVEIGSAGGGIDGGQWQMPMPHLITEGLITKGNQKIPMYVLAQLIT
HGNGIAIANKHQGKGISLKLEGAKSLFSQLKSSTPFTAAFTFPHVNQDLW
IRYWLAAGGIDPDADVKLLTVPAAQTVANMKTGTMDAFSTGDPWPFRLVN
DKIGYMAALTAEIWKNHPEEYLAMRADWVDKYPKATKALLKGIMEAQQWL
DNFDNRKEAAQILAGRNYFNLNNPEILADPYVGKYDMGDGRKIDDKSMAA
YYWKDEKGSVSYPYKSHDLWFITENVRWGFLPKDYLANGAAKAKELIDKV
NREDIWKEAAKEAGIAAADIPTSTSRGVEEFFDGTKFDPEKPDEYLKSLK
IKKVSVGGSTGEKPYKCPECGKSFSRSGGSHHHHHH** avBicarbBP5_18C_49F_bZif
MAEQAPEVTTVKLGYIPCVESAPLIIAKEKGFFAKYGLTNVELSKQASFG
SARDNVEIGSAGGGIDGGQWQMPMPHLITEGLITKGNQKIPMYVLAQLIT
HGNGIAIANKHQGKGISLKLEGAKSLFSQLKSSTPFTAAFTFPHVNQDLW
IRYWLAAGGIDPDADVKLLTVPAAQTVANMKTGTMDAFSTGDPWPFRLVN
DKIGYMAALTAEIWKNHPEEYLAMRADWVDKYPKATKALLKGIMEAQQWL
DNFDNRKEAAQILAGRNYFNLNNPEILADPYVGKYDMGDGRKIDDKSMAA
YYWKDEKGSVSYPYKSHDLWFITENVRWGFLPKDYLANGAAKAKELIDKV
NREDIWKEAAKEAGIAAADIPTSTSRGVEEFFDGTKFDPEKPDEYLKSLK
IKKVSVGGSTGEKPYKCPECGKSFSRSGGSNHHHHFI** avBicarbBP5_18C_49Y_bZif
MAEQAPEVTTVKLGYIPCVESAPLIIAKEKGFFAKYGLTNVELSKQASYG
SARDNVEIGSAGGGIDGGQWQMPMPHLITEGLITKGNQKIPMYVLAQLIT
HGNGIAIANKHQGKGISLKLEGAKSLFSQLKSSTPFTAAFTFPHVNQDLW
IRYWLAAGGIDPDADVKLLTVPAAQTVANMKTGTMDAFSTGDPWPFRLVN
DKIGYMAALTAEIWKNHPEEYLAMRADWVDKYPKATKALLKGIMEAQQWL
DNFDNRKEAAQILAGRNYFNLNNPEILADPYVGKYDMGDGRKIDDKSMAA
YYWKDEKGSVSYPYKSHDLWFITENVRWGFLPKDYLANGAAKAKELIDKV
NREDIWKEAAKEAGIAAADIPTSTSRGVEEFFDGTKFDPEKPDEYLKSLK
IKKVSVGGSTGEKPYKCPECGKSFSRSGGSHHHHHH** avBicarbBP5_18C_141V_bZif
MAEQAPEVTTVKLGYIPCVESAPLIIAKEKGFFAKYGLTNVELSKQASWG
SARDNVEIGSAGGGIDGGQWQMPMPHLITEGLITKGNQKIPMYVLAQLIT
HGNGIAIANKHQGRGISLKLEGAKSLFSQLKSSTPFTAAFVFPHVNQDLW
IRYWLAAGGIDPDADVKLLTVPAAQTVANMKTGTMDAFSTGDPWPFRLVN
DKIGYMAALTAEIWKNHPEEYLAMRADWVDKYPKATKALLKGIMEAQQWL
DNFDNRKEAAQILAGRNYFNLNNPEILADPYVGKYDMGDGRKIDDKSMAA
YYWKDEKGSVSYPYKSHDLWFITENVRWGFLPKDYLANGAAKAKELIDKV
NREDIWKEAAKEAGIAAADIPTSTSRGVEEFFDGTKFDPEKPDEYLKSLK
IKKVSVGGSTGEKPYKCPECGKSFSRSGGSHHHHHH** avBicarbBP5_18C_141F_bZif
MAEQAPEVTTVKLGYIPCVESAPLIIAKEKGFFAKYGLTNVELSKQASWG
SARDNVEIGSAGGGIDGGQWQMPMPHLITEGLITKGNQKIPMYVLAQLIT
HGNGIAIANKHQGKGISLKLEGAKSLFSQLKSSTPFTAAFFFPHVNQDLW
IRYWLAAGGIDPDADVKLLTVPAAQTVANMKTGTMDAFSTGDPWPFRLVN
DKIGYMAALTAEIWKNHPEEYLAMRADWVDKYPKATKALLKGIMEAQQWL
DNFDNRKEAAQILAGRNYFNLNNPEILADPYVGKYDMGDGRKIDDKSMAA
YYWKDEKGSVSYPYKSHDLWFITENVRWGFLPKDYLANGAAKAKELIDKV
NREDIWKEAAKEAGIAAADIPTSTSRGVEEFFDGTKFDPEKPDEYLKSLK
IKKVSVGGSTGEKPYKCPECGKSFSRSGGSHHHHHH** avBicarbBP5_18C_141Y_bZif
MAEQAPEVTTVKLGYIPCVESAPLIIAKEKGFFAKYGLTNVELSKQASWG
SARDNVEIGSAGGGIDGGQWQMPMPHLITEGLITKGNQKIPMYVLAQLIT
HGNGIAIANKHQGKGISLKLEGAKSLFSQLKSSTPFTAAFYFPHVNQDLW
IRYWLAAGGIDPDADVKLLTVPAAQTVANMKTGTMDAFSTGDPWPFRLVN
DKIGYMAALTAEIWKNHPEEYLAMRADWVDKYPKATKALLKGIMEAQQWL
DNFDNRKEAAQILAGRNYFNLNNPEILADPYVGKYDMGDGRKIDDKSMAA
YYWKDEKGSVSYPYKSHDLWFITENVRWGFLPKDYLANGAAKAKELIDKV
NREDIWKEAAKEAGIAAADIPTSTSRGVEEFFDGTKFDPEKPDEYLKSLK
IKKVSVGGSTGEKPYKCPECGKSFSRSGGSHHHHHH** avBicarbBP5_18C_141W_bZif
MAEQAPEVTTVKLGYIPCVESAPLIIAKEKGFFAKYGLTNVELSKQASWG
SARDNVEIGSAGGGIDGGQWQMPMPHLITEGLITKGNQKIPMYVLAQLIT
HGNGIAIANKHQGKGISLKLEGAKSLFSQLKSSTPFTAAFWFPHVNQDLW
IRYWLAAGGIDPDADVKLLTVPAAQTVANMKTGTMDAFSTGDPWPFRLVN -continued

DKIGYMAALTAEIWKNHPEEYLAMRADWVDKYPKATKALLKGIMEAQQWL

DNFDNRKEAAQILAGRNYFNLNNPEILADPYVGKYDMGDGRKIDDKSMAA

YYWKDEKGSVSYPYKSHDLWFITENVRWGFLPKDYLANGAAKAKELIDKV

NREDIWKEAAREAGIAAADIPTSISRGVEEFFDGTKFDPEKPDEYLKSLK

IKKVSVGGSTGEKPYKCPECGKSFSRSGGSHHHHHH** avBicarbBP5_18C_141Q_bZif
MAEQAPEVTTVKLGYIPCVESAPLIIAKEKGFFAKYGLTNVELSKQASWG

SARDNVEIGSAGGGIDGGQWQMPMPHLITEGLITKGNQKIPMYVLAQLIT

HGNGIAIANKHQGKGISLKLEGAKSLFSQLKSSTPFTAAFQFPHVNQDLW

IRYWLAAGGIDPDADVKLLTVPAAQTVANMKTGTMDAFSTGDPWPFRLVN

DKIGYMAALTAEIWKNHPEEYLAMRADWVDKYPKATKALLKGIMEAQQWL

DNFDNRKEAAQILAGRNYFNLNNPEILADPYVGKYDMGDGRKIDDKSMAA

YYWKDEKGSVSYPYKSHDLWFITENVRWGFLPKDYLANGAAKAKELIDKV

NREDIWKEAAKEAGIAAADIPTSTSRGVEEFFDGTKFDPEKPDEYLKSLK

IKKVSVGGSTGEKPYKCPECGKSFSRSGGSHHHHHH**

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1. Fluorescently Responsive Sensor Engineering Phases

The engineering of FRSs can be divided into five phases:

1. Binding protein discovery. A set of binding protein sequence homologs is identified for the target ligand. Accurate assignment of their ligand-binding function requires application of a prediction method that incorporates information encoded in the experimentally determined three-dimensional structure of known periplasmic binding proteins for the target ligand.
2. Experimental lead validation. Synthetic genes are constructed, which are optimized for heterologous expression in *Escherichia coli* of one or more predicted binding protein sequences for the target ligand. The ligand binding properties and thermostabilities of the corresponding expressed, purified proteins are evaluated.
3. Engineering of fluorescent responses. Semisynthetic fluorescent conjugates of the experimentally validated leads are constructed by first attaching single fluorophores to single cysteine mutants. The effect of ligand binding on the fluorescence emission properties of those conjugates is evaluated. The spectral properties of a subset of responsive fluorophores is improved using a double-labeling strategy in which a second fluorophore is site-specifically attached to a small domain fused to the N- or C-terminus to establish ligand-modulated fluorescence resonance energy transfer. Those singly or doubly labeled conjugates that evince strong, ratiometric responses are selected as FRSs for use in sensing applications.
4. Affinity tuning. Single or multiple mutations are introduced by site-directed mutagenesis to alter the ligand-binding affinities of ligand-responsive FRSs. A set of FRS variants is selected that together cover the clinical ligand concentration range with high accuracy.

Example 2. Sensor Engineering Phase 1: Identification of a Family of Periplasmic Binding Proteins Homologs for the Target Ligand Using Structurally Assisted Function Evaluation As a first step in constructing robust sensor candidates for the target ligand, we examined bacterial genomic sequences to identify periplasmic binding protein sequences for bicarbonate and calcium in known thermophiles. Homologs from such organisms are likely to encode thermostable proteins (Urbieta et al. 2015). Analysis of enzyme families has shown that overall sequence identity below ~60% is a weak predictor of function conservation (Todd 2001, Tian 2003). Furthermore, functional assignments based on sequence homology alone are known to be particularly problematic in the PBP superfamily. For instance, PBPs that by overall sequence identity are predicted to bind oligopeptides were found to bind oligosaccharides (Cuneo, Beese and Hellinga 2009, Nanavati 2006). Enzyme functional assignments are improved greatly if a sequence selection filter based on conservation of catalytic residues identified from protein structures is included (George 2005). Such catalytic residues comprise a subset of all the residues that contact an enzyme substrate or inhibitor (George 2005). In the case of the PBPs, functional selection filters need to take into account all the protein-ligand contacts that encode the ligand-binding function. Accordingly, we have developed a structurally assisted functional evaluation (SAFE) method to identify PBP sequence homologs with accurately predicted function. The SAFE homolog search method consists of five steps:

1. Sequence homolog set is collected using the BLAST sequence alignment tool (Altschul et al. 1990), starting with a seed sequence. The following BLAST parameters: (1) Expect threshold is 10.0; (2) Gap cost is Existence: 11 and Extension: 1; (3) The Matrix employed is BLOSUM62; (4) The filter for low complexity regions is "on." Permissive settings are used, such that pairwise hits are required to have a minimum of only 20% sequence identity with the seed sequence. The lengths of the hit and seed are mutually constrained such that the alignment covers at least 70% within each partner. This set of sequences defines a universe of possible ligand-binding proteins for the target ligand without accurately assigning function.
2. Structure-based encoding of biological function. A primary complementary surface comprising the protein residues that form hydrogen bonds and van der Waals contacts with the bound complex is defined using computer-assisted, visual inspection of the three-dimensional structure of the ligand bound complex. This definition specifies residue positions and their permitted amino acid identity. Multiple amino acid identities are permitted at each position to encode functionally equivalent residues. This definition establishes a search filter for the accurate prediction of binding proteins for the target ligand within the universe of sequence homologs collected in (1).
3. Accurate sequence alignment. Tools such as ClustalW (Chenna et al. 2003) are used to construct an accurate alignment of all the sequence homologs. The seed sequence is included in this alignment. This multiple sequence alignment establishes the equivalent positions of the PCS in each sequence homolog.

4. Function evaluation. The ligand binding properties of each of the aligned sequence homologs is determined by measuring their compliance with the PCS sequence filter. A "Hamming distance", H, is assigned for each homolog, which specifies the degree of sequence identity of all the residues at the aligned PCS positions. A value of H=0 indicates that the identities of all the residues at the aligned PCS positions match the amino acid(s) allowed in the PCS search filter; H>0, indicates that one or more aligned positions have disallowed residues. Sequences for which H=0 are predicted to encode binding proteins of the target ligand.
5. Selection of representative SAFE homologs. The sequence homologs are ordered by (a) identity with the seed PCS, as measured by the Hamming distance, (b) fractional overall sequence identity with the seed sequence. A subset for sequences with H=0, sampling the fractional overall sequence identity is selected for experimental verification.

These steps are encoded in the ProteinHunter software tool, which encodes the flow of execution, applies the PCS search filter, and visualizes the results, and handles organism annotations such as thermophilicity, and Gram stain status.

The ProteinHunter package always executes BLAST searches, with the following command "blastall-p blastp-m 8-b 50000-d % s-i<INPUT FILE>-o<OUTPUT FILE>"

where <INPUT FILE> and <OUTPUT FILE> specify the input and output files, respectively for a given calculation. This command executes the BLAST alignment program for protein sequences with default parameters, intrinsically set by the program. The BLAST program version is 2.2.24.

The ProteinHunter package always executes multiple sequence alignments with the following command "clustalw-infile=<INPUT FILE>-outfile=<OUTPUT-FILE>-align-quiet"

This command executes the CLUSTALW multi-sequence alignment program for protein sequences. There are no user-specified parameter settings that alter the alignment behavior of the program. The CLUSTALW program version is 2.1.

Annotated genomic and plasmid sequences of 5062 prokaryotes were obtained from the National Center of Biotechnology Information (ftp.//ftp.ncbi.nih.gov/genomes/Bacteria/all.gbk.tar.gz).

Identification of $Ca^{II}$—$HCO_3$ Binding Proteins.

The cyanobacterium *Synechocystis* PCC 6803 has a bicarbonate PBP (synBicarbBP1) (Omata 1999) which is a component of an uptake system that builds up high cytoplasmic $CO_2$ concentrations for photosynthetic carbon fixation (Price 2008). The X-ray structure of this protein revealed that bicarbonate binds as a $Ca^{2+}$ complex (Koropatkin 2007) (FIGS. 3A and B). This structure was used to define a PCS encoding recognition of the $Ca^{II}$—$HCO_3$ complex (FIGS. 3B-C). Two of the bicarbonate oxygens participate in $Ca^{2+}$ coordination; the other oxygen forms hydrogen bonds with T192 and W99 (FIG. 3B). The $Ca^{2+}$ ion coordination sphere is a septa-coordinate pentagonal bipyramid. A PCS filter specifying the amino acid identity at each of these seven positions was used to predict $Ca^{II}$—$HCO_3$ binding proteins. The synBicarbBP1 sequence was used as a seed to identify 742 sequence homologs in 484 replicons, representing 289 different species. Of these 38 were predicted to be $Ca^{II}$—$HCO_3$ binding proteins based on their PCS (Table 1). The overall sequence identities of these homologs relative to the seed varied from 100% to 61%.

TABLE 1 synBicarbBP1 homologs.

| # | Name | 70 | 99 | 121 | 152 | 192 | 198 |
|---|---|---|---|---|---|---|---|
| 1 | 2I4C\| | E | W | Q | N | T | Q |
| 2 | NC_017052\|YP_005410477.1 | E | W | Q | N | T | Q |
| 3 | NC_017038\|YP_005384601.1 | E | W | Q | N | T | Q |
| 4 | NC_017039\|YP_005387770.1 | E | W | Q | N | T | Q |
| 5 | NC_000911\|NP_442732.1 | E | W | Q | N | T | Q |
| 6 | NC_010546\|YP_001801722.1 | E | W | Q | N | T | Q |
| 7 | NC_011729\|YP_002379906.1 | E | W | Q | N | T | Q |
| 8 | NC_019703\|YP_007108955.1 | E | W | Q | N | T | Q |
| 9 | NC_014501\|YP_003887015.1 | E | W | Q | N | T | Q |
| 10 | NC_019748\|YP_007133714.1 | E | W | Q | N | T | Q |
| 11 | NC_004113\|NP_682790.1 | E | W | Q | N | T | Q |
| 12 | NC_007776\|YP_476857.1 | E | W | Q | N | T | Q |
| 13 | NC_007775\|YP_474359.1 | E | W | Q | N | T | Q |
| 14 | NC_023033\|NK55_06690 | E | W | Q | N | T | Q |
| 15 | NC_010296\|YP_001657013.1 | E | W | Q | N | T | Q |
| 16 | NC_019745\|YP_007129075.1 | E | W | Q | N | T | Q |
| 17 | NC_019689\|YP_007080477.1 | E | W | Q | N | T | Q |
| 18 | NC_019680\|YP_007062720.1 | E | W | Q | N | T | Q |
| 19 | NC_019729\|YP_007115550.1 | E | W | Q | N | T | Q |
| 20 | NC_019676\|YP_007049841.1 | E | W | Q | N | T | Q |
| 21 | NC_013161\|YP_003138293.1 | E | W | Q | N | T | Q |
| 22 | NC_019695\|YP_007090308.1 | E | W | Q | N | T | Q |
| 23 | NC_010628\|YP_001865867.1 | E | W | Q | N | T | Q |
| 24 | NC_011726\|YP_002373642.1 | E | W | Q | N | T | Q |
| 25 | NC_007413\|YP_321546.1 | E | W | Q | N | T | Q |
| 26 | NC_019738\|YP_007123904.1 | E | W | Q | N | T | Q |
| 27 | NC_019684\|YP_007076410.1 | E | W | Q | N | T | Q |
| 28 | NC_003272\|NP_486917.1 | E | W | Q | N | T | Q |
| 29 | NC_019682\|YP_007066695.1 | E | W | Q | N | T | Q |
| 30 | NC_019757\|YP_007149519.1 | E | W | Q | N | T | Q |
| 31 | NC_019702\|YP_007104545.1 | E | W | Q | N | T | Q |
| 32 | NC_007604\|YP_400505.1 | E | W | Q | N | T | Q |
| 33 | NC_006576\|YP_173184.1 | E | W | Q | N | T | Q |
| 34 | NC_011884\|YP_002485585.1 | E | W | Q | N | T | Q |

TABLE 1-continued

| synBicarbBP1 homologs. | | | | | | | |
|---|---|---|---|---|---|---|---|
| 35 | NC_019771\|YP_007158727.1 | E | W | Q | N | T | Q |
| 36 | NC_019751\|YP_007137061.1 | E | W | Q | N | T | Q |
| 37 | NC_019675\|YP_007045476.1 | E | W | Q | N | T | Q |
| 38 | NC_019697\|YP_007099445.1 | E | W | Q | N | T | Q |
| 39 | NC_019439\|YP_007001023.1 | E | W | Q | N | T | Q |

| # | 270 | 271 | Identity | Gram | Temperature | Organism |
|---|---|---|---|---|---|---|
| 1 | E | E | | | | |
| 2 | E | E | 1 | − | Mesophilic | *Synechocystis* sp. |
| 3 | E | E | 1 | − | Mesophilic | *Synechocystis* sp. |
| 4 | E | E | 1 | − | Mesophilic | *Synechocystis* sp. |
| 5 | E | E | 1 | − | Mesophilic | *Synechocystis* sp. |
| 6 | E | E | 0.84 | − | Mesophilic | *Cyanothece* sp. |
| 7 | E | E | 0.83 | − | Mesophilic | *Cyanothece* sp. |
| 8 | E | E | 0.8 | + | Mesophilic | *Geitlerinema* sp. |
| 9 | E | E | 0.8 | − | Mesophilic | *Cyanothece* sp. |
| 10 | E | E | 0.73 | + | Mesophilic | *Stanieria cyanosphaera* |
| 11 | E | E | 0.72 | − | Thermophilic | *Thermosynechococcus elongatus* |
| 12 | E | E | 0.72 | − | Thermophilic | *Synechococcus* sp. |
| 13 | E | E | 0.71 | − | Thermophilic | *Synechococcus* sp. |
| 14 | E | E | 0.71 | − | Mesophilic | *Thermosynechococcus* sp. |
| 15 | E | E | 0.7 | − | Mesophilic | *Microcystis aeruginosa* |
| 16 | E | E | 0.69 | + | Mesophilic | *Gloeocapsa* sp. |
| 17 | E | E | 0.69 | + | Mesophilic | *Pleurocapsa* sp. |
| 18 | E | E | 0.69 | − | Thermophilic | *Synechococcus* sp. |
| 19 | E | E | 0.68 | + | Mesophilic | *Oscillatoria nigro-viridis* |
| 20 | E | E | 0.68 | − | Mesophilic | *Nostoc* sp. |
| 21 | E | E | 0.68 | − | Mesophilic | *Cyanothece* sp. |
| 22 | E | E | 0.67 | + | Mesophilic | *Chroococcidiopsis thermalis* |
| 23 | E | E | 0.67 | − | Mesophilic | *Nostoc punctiforme* |
| 24 | E | E | 0.66 | − | Mesophilic | *Cyanothece* sp. |
| 25 | E | E | 0.66 | + | Mesophilic | *Anabaena variabilis* |
| 26 | E | E | 0.66 | + | Mesophilic | *Microcoleus* sp. |
| 27 | E | E | 0.66 | − | Mesophilic | *Nostoc* sp. |
| 28 | E | E | 0.66 | − | Mesophilic | *Nostoc* sp. |
| 29 | E | E | 0.65 | + | Mesophilic | *Calothrix* sp. |
| 30 | E | E | 0.64 | + | Mesophilic | *Cylindrospermum stagnale* |
| 31 | E | E | 0.64 | − | Thermophilic | *Synechococcus* sp. |
| 32 | E | E | 0.64 | − | Mesophilic | *Synechococcus elongatus* |
| 33 | E | E | 0.64 | − | Mesophilic | *Synechococcus elongatus* |
| 34 | E | E | 0.63 | − | Mesophilic | *Cyanothece* sp. |
| 35 | E | E | 0.63 | + | Mesophilic | *Anabaena cylindrica* |
| 36 | E | E | 0.63 | + | Mesophilic | *Calothrix* sp. |
| 37 | E | E | 0.62 | + | Mesophilic | *Cyanobium gracile* |
| 38 | E | E | 0.61 | + | Mesophilic | *Chamaesiphon minutus* |
| 39 | E | E | 0.61 | + | Mesophilic | *Anabaena* sp. |

Identification of $Fe^{III}$—$HCO_3$ Binding Proteins.

Structures have been determined for $Fe^{III}$—$HCO_3$ binding proteins from *Mannheimia haemolytica* (mhFeBP1) and *Thermus thermophilus* (ttFeBP5) (FIG. 4). These revealed that two of the bicarbonate oxygens form a bidentate interaction with the bound iron. The other oxygen forms hydrogen bonds with an arginine. A second arginine also interacts with the bound bicarbonate. The $Fe^{III}$ coordination sphere is complete by the phenolic hydroxyls of three tyrosines. In both proteins two of the three tyrosines are located adjacent to each on a helix (helix A), and the third tyrosine is contributed by a second helix (helix B). The location of this tyrosine within the B helix differs by a ½-helical turn in the two proteins. Accordingly, the positional information is slightly different for the PCS filters of these proteins, even though the compositional information is identical (FIG. 4C).

The mhFeBP1 sequence was used as a seed to identify 1290 sequence homologs in 958 replicons, representing 601 different species. Of these 522 were predicted to be $Fe^{III}$—$HCO_3$ binding proteins based on their PCS (Table 2). Using the ttFeBP5 seed sequences, 1512 homologs (1172 replicons, 626 species) were identified, of which 70 satisfied the PCS filter (Table 3).

TABLE 2

| mhFeBP1 homologs. | | | | | | | | | | |
|---|---|---|---|---|---|---|---|---|---|---|
| # | Name | 10 | 101 | 142 | 198 | 199 | Identity | Gram | Temperature | Organism |
| 1 | 1SI0\| | R | R | Y | Y | Y | | | | |
| 2 | NC_020834\|YP_007669069.1 | R | R | Y | Y | Y | 1 | + | Mesophilic | *Mannheimia haemolytica* |
| 3 | NC_020833\|YP_007666187.1 | R | R | Y | Y | Y | 1 | + | Mesophilic | *Mannheimia haemolytica* |
| 4 | NC_021082\|YP_007884192.1 | R | R | Y | Y | Y | 1 | + | Mesophilic | *Mannheimia haemolytica* |
| 5 | NC_021743\|F382_02715 | R | R | Y | Y | Y | 1 | + | Mesophilic | *Mannheimia haemolytica* |
| 6 | NC_021883\|N220_08810 | R | R | Y | Y | Y | 1 | + | Mesophilic | *Mannheimia haemolytica* |

TABLE 2-continued mhFeBP1 homologs.

| # | Name | 10 | 101 | 142 | 198 | 199 | Identity | Gram | Temperature | Organism |
|---|---|---|---|---|---|---|---|---|---|---|
| 7 | NC_021739\|J451_03020 | R | R | Y | Y | Y | 1 | + | Mesophilic | *Mannheimia haemolytica* |
| 8 | NC_021738\|J450_02175 | R | R | Y | Y | Y | 0.98 | + | Mesophilic | *Mannheimia haemolytica* |
| 9 | NC_011852\|YP_002475690.1 | R | R | Y | Y | Y | 0.86 | − | Mesophilic | *Haemophilus parasuis* |
| 10 | NC_020515\|YP_007547693.1 | R | R | Y | Y | Y | 0.84 | + | Mesophilic | *Bibersteinia trehalosi* |
| 11 | NC_017027\|YP_005363665.1 | R | R | Y | Y | Y | 0.8 | − | Mesophilic | *Pasteurella multocida* |
| 12 | NC_002663\|NP_244988.1 | R | R | Y | Y | Y | 0.8 | − | Mesophilic | *Pasteurella multocida* |
| 13 | NC_017764\|YP_006240219.1 | R | R | Y | Y | Y | 0.8 | − | Mesophilic | *Pasteurella multocida* |
| 14 | NC_016808\|YP_005177128.1 | R | R | Y | Y | Y | 0.8 | − | Mesophilic | *Pasteurella multocida* |
| 15 | NC_010519\|YP_001784574.1 | R | R | Y | Y | Y | 0.78 | − | Mesophilic | *Haemophilus somnus* |
| 16 | NC_015460\|YP_004419395.1 | R | R | Y | Y | Y | 0.78 | − | Mesophilic | *Gallibacterium anatis* |
| 17 | NC_008309\|YP_718993.1 | R | R | Y | Y | Y | 0.78 | − | Mesophilic | *Haemophilus somnus* |
| 18 | NC_022528\|YP_008621989.1 | R | R | Y | Y | Y | 0.64 | − | Mesophilic | *Vibrio nigripulchritudo* |
| 19 | NC_022349\|YP_008535958.1 | R | R | Y | Y | Y | 0.64 | − | Mesophilic | *Vibrio alginolyticus* |
| 20 | NC_013456\|YP_003285201.1 | R | R | Y | Y | Y | 0.64 | − | Mesophilic | *Vibrio* sp. |
| 21 | NC_006370\|YP_131292.1 | R | R | Y | Y | Y | 0.64 | − | Psychrophilic | *Photobacterium profundum* |
| 22 | NC_011312\|YP_002263934.1 | R | R | Y | Y | Y | 0.63 | − | Psychrophilic | *Aliivibrio salmonicida* |
| 23 | NC_009783\|YP_001446607.1 | R | R | Y | Y | Y | 0.63 | − | Mesophilic | *Vibrio campbellii* |
| 24 | NC_022223\|N175_12595 | R | R | Y | Y | Y | 0.63 | + | Mesophilic | *Listonella anguillarum* |
| 25 | NC_019955\|YP_007275951.1 | R | R | Y | Y | Y | 0.63 | − | Mesophilic | *Vibrio parahaemolyticus* |
| 26 | NC_020802\|YP_007640830.1 | R | R | Y | Y | Y | 0.63 | + | Mesophilic | *Psychromonas* sp. |
| 27 | NC_015633\|YP_004567100.1 | R | R | Y | Y | Y | 0.63 | − | Mesophilic | *Vibrio anguillarum* |
| 28 | NC_021848\|M636_09480 | R | R | Y | Y | Y | 0.63 | − | Mesophilic | *Vibrio parahaemolyticus* |
| 29 | NC_021847\|M634_4850 | R | R | Y | Y | Y | 0.63 | − | Mesophilic | *Vibrio parahaemolyticus* |
| 30 | NC_004603\|NP_798870.1 | R | R | Y | Y | Y | 0.63 | − | Mesophilic | *Vibrio parahaemolyticus* |
| 31 | NC_011753\|YP_002418100.1 | R | R | Y | Y | Y | 0.63 | − | Mesophilic | *Vibrio splendidus* |
| 32 | NC_011184\|YP_002156950.1 | R | R | Y | Y | Y | 0.62 | − | Mesophilic | *Vibrio fischeri* |
| 33 | NC_006840\|VF2151 | R | R | Y | Y | Y | 0.62 | − | Mesophilic | *Vibrio fischeri* |
| 34 | NC_016613\|YP_005024030.1 | R | R | Y | Y | Y | 0.62 | − | Mesophilic | *Vibrio* sp. |
| 35 | NC_017270\|YP_005633217.1 | R | R | Y | Y | Y | 0.62 | − | Mesophilic | *Vibrio cholerae* |
| 36 | NC_012578\|YP_002809340.1 | R | R | Y | Y | Y | 0.62 | − | Mesophilic | *Vibrio cholerae* |
| 37 | NC_012668\|YP_002879527.1 | R | R | Y | Y | Y | 0.62 | − | Mesophilic | *Vibrio cholerae* |
| 38 | NC_016445\|YP_004936187.1 | R | R | Y | Y | Y | 0.62 | − | Mesophilic | *Vibrio cholerae* |
| 39 | NC_016944\|YP_005332437.1 | R | R | Y | Y | Y | 0.62 | − | Mesophilic | *Vibrio cholerae* |
| 40 | NC_002505\|NP_230257.1 | R | R | Y | Y | Y | 0.62 | − | Mesophilic | *Vibrio cholerae* |
| 41 | NC_009457\|YP_001216102.1 | R | R | Y | Y | Y | 0.62 | − | Mesophilic | *Vibrio cholerae* |
| 42 | NC_014965\|YP_004187783.1 | R | R | Y | Y | Y | 0.61 | − | Mesophilic | *Vibrio vulnificus* |
| 43 | NC_005139\|NP_935539.1 | R | R | Y | Y | Y | 0.61 | − | Mesophilic | *Vibrio vulnificus* |
| 44 | NC_004459\|NP_760550.2 | R | R | Y | Y | Y | 0.61 | − | Mesophilic | *Vibrio vulnificus* |
| 45 | NC_016602\|YP_004992111.1 | R | R | Y | Y | Y | 0.6 | − | Mesophilic | *Vibrio furnissii* |
| 46 | NC_008709\|YP_944308.1 | R | R | Y | Y | Y | 0.6 | + | Psychrophilic | *Psychromonas ingrahamii* |
| 47 | NC_015424\|YP_004394158.1 | R | R | Y | Y | Y | 0.6 | − | Mesophilic | *Aeromonas veronii* |
| 48 | NC_012691\|YP_002893739.1 | R | R | Y | Y | Y | 0.59 | − | Mesophilic | *Tolumonas auensis* |
| 49 | NC_021290\|YP_008041799.1 | R | R | Y | Y | Y | 0.59 | − | Mesophilic | *Aeromonas hydrophila* |
| 50 | NC_008570\|YP_855192.1 | R | R | Y | Y | Y | 0.59 | − | Mesophilic | *Aeromonas hydrophila* |
| 51 | NC_016745\|YP_005093558.1 | R | R | Y | Y | Y | 0.59 | + | Mesophilic | *Oceanimonas* sp. |
| 52 | NC_009348\|YP_001140561.1 | R | R | Y | Y | Y | 0.59 | − | Mesophilic. | *Aeromonas salmonicida* |
| 53 | NC_014541\|YP_003914651.1 | R | R | Y | Y | Y | 0.57 | − | Mesophilic | *Ferrimonas balearica* |
| 54 | NC_010334\|YP_001673131.1 | R | R | Y | Y | Y | 0.57 | − | Psychrophilic | *Shewanella halifaxensis* |
| 55 | NC_008345\|YP_749334.1 | R | R | Y | Y | Y | 0.57 | − | Mesophilic | *Shewanella frigidimarina* |
| 56 | NC_010506\|YP_001759384.1 | R | R | Y | Y | Y | 0.56 | − | Mesophilic | *Shewanelia woodyi* |
| 57 | NC_009901\|YP_001500706.1 | R | R | Y | Y | Y | 0.56 | − | Mesophilic | *Shewanella pealeana* |
| 58 | NC_008700\|YP_926544.1 | R | R | Y | Y | Y | 0.56 | − | Mesophilic | *Shewaneiia amazonensis* |
| 59 | NC_014012\|YP_003555527.1 | R | R | Y | Y | Y | 0.55 | − | Psychrophilic | *Shewanella violacea* |
| 60 | NC_009092\|YP_001092992.1 | R | R | Y | Y | Y | 0.55 | − | Mesophilic | *Shewaneiia loihica* |
| 61 | NC_009831\|YP_001472684.1 | R | R | Y | Y | Y | 0.55 | − | Psychrophilic | *Shewanella sediminis* |
| 62 | NC_007645\|YP_435624.1 | R | R | Y | Y | Y | 0.55 | − | Mesophilic | *Hahella chejuensis* |
| 63 | NC_007481\|YP_341153.1 | R | R | Y | Y | Y | 0.55 | − | Psychrophilic | *Pseudoalteromonas haloplanktis* |
| 64 | NC_008321\|YP_735470.1 | R | R | Y | Y | Y | 0.55 | − | Mesophilic | *Shewanella* sp. |
| 65 | NC_007643\|Rru_A0769 | R | R | Y | Y | Y | 0.55 | − | Mesophilic | *Rhodospirillum rubrum* |
| 66 | NC_008322\|YP_736666.1 | R | R | Y | Y | Y | 0.55 | − | Mesophilic | *Shewanella* sp. |
| 67 | NC_017584\|YP_006047056.1 | R | R | Y | Y | Y | 0.55 | − | Mesophilic | *Rhodospirillum rubrum* |
| 68 | NC_004347\|SO_0744 | R | R | Y | Y | Y | 0.54 | − | Mesophilic | *Shewanella oneidensis* |
| 69 | NC_008577\|YP_871146.1 | R | R | Y | Y | Y | 0.54 | − | Mesophilic | *Shewanella* sp. |
| 70 | NC_014803\|YP_004069765.1 | R | R | Y | Y | Y | 0.54 | − | Psychrophilic | *Pseudoalteromonas* sp. |
| 71 | NC_009997\|YP_001556237.1 | R | R | Y | Y | Y | 0.54 | − | Mesophilic | *Shewanella baltica* |
| 72 | NC_016901\|YP_005275030.1 | R | R | Y | Y | Y | 0.54 | − | Mesophilic | *Shewanella baltica* |
| 73 | NC_003910\|YP_267761.1 | R | R | Y | Y | Y | 0.53 | − | Psychrophilic | *Colwellia psychrerythraea* |
| 74 | NC_017571\|YP_006022146.1 | R | R | Y | Y | Y | 0.53 | − | Mesophilic | *Shewanella baltica* |
| 75 | NC_011663\|YP_002359536.1 | R | R | Y | Y | Y | 0.53 | − | Mesophilic | *Shewanella baltica* |
| 76 | NC_012587\|YP_002824894.1 | R | R | Y | Y | Y | 0.53 | − | Mesophilic | *Sinorhizobium fredii* |
| 77 | NC_016812\|YP_005187712.1 | R | R | Y | Y | Y | 0.53 | − | Mesophilic | *Sinorhizobium fredii* |
| 78 | NC_009665\|YP_001367881.1 | R | R | Y | Y | Y | 0.53 | − | Mesophilic | *Shewanella baltica* |
| 79 | NC_009636\|YP_001326020.1 | R | R | Y | Y | Y | 0.53 | − | Mesophilic | *Sinorhizobium medicae* |
| 80 | NC_017506\|YP_005885148.1 | R | R | Y | Y | Y | 0.53 | − | ? | *Marinobacter adhaerens* |
| 81 | NC_017322\|YP_005712524.1 | R | R | Y | Y | Y | 0.53 | − | Mesophilic | *Sinorhizobium meliloti* |
| 82 | NC_020528\|SM2011_c00784 | R | R | Y | Y | Y | 0.53 | − | Mesophilic | *Sinorhizobium meliloti* |

TABLE 2-continued mhFeBP1 homologs.

| # | Name | 10 | 101 | 142 | 198 | 199 | Identity | Gram | Temperature | Organism |
|---|---|---|---|---|---|---|---|---|---|---|
| 83 | NC_018000|YP_006395735.1 | R | R | Y | Y | Y | 0.53 | − | Mesophilic | *Sinorhizobium fredii* |
| 84 | NC_018700|YP_006839225.1 | R | R | Y | Y | Y | 0.53 | − | Mesophilic | *Sinorhizobium meliloti* |
| 85 | NC_018268|YP_006557993.1 | R | R | Y | Y | Y | 0.53 | − | Mesophilic | *Marinobacter* sp. |
| 86 | NC_011566|VP_002313357.1 | R | R | Y | Y | Y | 0.52 | − | Mesophilic | *Shewanella piezotolerans* |
| 87 | NC_017325|YP_005718919.1 | R | R | Y | Y | Y | 0.52 | − | Mesophilic | *Sinorhizobium meliloti* |
| 88 | NC_015590|YP_004547809.1 | R | R | Y | Y | Y | 0.52 | − | Mesophilic | *Sinorhizobium meliloti* |
| 89 | NC_019845|C770_GR4Chr0719 | R | R | Y | Y | Y | 0.52 | − | Mesophilic | *Sinorhizobium meliloti* |
| 90 | NC_017964|YP_006379465.1 | R | R | Y | Y | Y | 0.52 | + | Mesophilic | *Advenella kashmirensis* |
| 91 | NC_003047|NP_384835.1 | R | R | Y | Y | Y | 0.52 | − | Mesophilic | *Sinorhizobium meliloti* |
| 92 | NC_008750|YP_962119.1 | R | R | Y | Y | Y | 0.52 | − | Mesophilic | *Shewanella* sp. |
| 93 | NC_017566|YP_006011216.1 | R | R | Y | Y | Y | 0.52 | − | Mesophilic | *Shewanella putrefaciens* |
| 94 | NC_009438|YP_001184738.1 | R | R | Y | Y | Y | 0.52 | − | Mesophilic | *Shewanella putrefaciens* |
| 95 | NC_015259|YP_004305240.1 | R | R | Y | Y | Y | 0.52 | − | Mesophilic | *Polymorphum gilvum* |
| 96 | NC_008740|YP_958371.1 | R | R | Y | Y | Y | 0.52 | − | Mesophilic | *Marinobacter aquaeolei* |
| 97 | NC_016642|YP_005079787.1 | R | R | Y | Y | Y | 0.52 | + | Mesophilic | *Pseudovibrio* sp. |
| 98 | NC_017067|YP_005430089.1 | R | R | Y | Y | Y | 0.52 | − | Mesophilic | *Marinobacter hydrocarbonoclast* |
| 99 | NC_008254|YP_672740.1 | R | R | Y | Y | Y | 0.52 | − | Mesophilic | *Chelativorans* sp. |
| 100 | NC_005296|NP_949488.1 | R | R | Y | Y | Y | 0.52 | − | Mesophilic | *Rhodopseudomonas palustris* |
| 101 | NC_022535|YP_008631147.1 | R | R | Y | Y | Y | 0.51 | + | Mesophilic | *Rhizobium* sp. |
| 102 | NC_011004|YP_001993597.1 | R | R | Y | Y | Y | 0.51 | − | Mesophilic | *Rhodopseudomonas palustris* |
| 103 | NC_015183|YP_004277506.1 | R | R | Y | Y | Y | 0.51 | + | Mesophilic | *Agrobacterium* sp. |
| 104 | NC_007493|RSP_2913 | R | R | Y | Y | Y | 0.51 | − | Mesophilic | *Rhodobacter sphaeroides* |
| 105 | NC_003062|NP_353236.2 | R | R | Y | Y | Y | 0.51 | + | Mesophilic | *Agrobacterium fabrum* |
| 106 | NC_009049|YP_001043439.1 | R | R | Y | Y | Y | 0.51 | − | Mesophilic | *Rhodobacter sphaeroides* |
| 107 | NC_011963|YP_002525591.1 | R | R | Y | Y | Y | 0.51 | − | Mesophilic | *Rhodobacter sphaeroides* |
| 108 | NC_021033|YP_007821259.1 | R | R | Y | Y | Y | 0.51 | − | Mesophilic | *Taylorella asinigenitalis* |
| 109 | NC_021036|YP_007825629.1 | R | R | Y | Y | Y | 0.51 | − | Mesophilic | *Taylorella equigenitalis* |
| 110 | NC_014914|YP_004129165.1 | R | R | Y | Y | Y | 0.51 | − | Mesophilic | *Taylorella equigenitalis* |
| 111 | NC_018108|YP_006502736.1 | R | R | Y | Y | Y | 0.51 | − | Mesophilic | *Taylorella equigenitalis* |
| 112 | NC_009428|YP_001167314.1 | R | R | Y | Y | Y | 0.51 | − | Mesophilic | *Rhodobacter sphaeroides* |
| 113 | NC_011386|YP_002288119.1 | R | R | Y | Y | Y | 0.5 | − | Mesophilic | *Oligotropha carboxidovorans* |
| 114 | NC_017538|YP_005951842.1 | R | R | Y | Y | Y | 0.5 | − | Mesophilic | *Oligotropha carboxidovorans* |
| 115 | NC_016043|YP_004874880.1 | R | R | Y | Y | Y | 0.5 | − | Mesophilic | *Taylorella asinigenitalis* |
| 116 | NC_010511|YP_001772582.1 | R | R | Y | Y | Y | 0.49 | − | Mesophilic | *Methylobacterium* sp. |
| 117 | NC_007778|YP_485084.1 | R | R | Y | Y | Y | 0.49 | − | Mesophilic | *Rhodopseudomonas palustris* |
| 118 | NC_014834|YP_004110640.1 | R | R | Y | Y | Y | 0.49 | − | Mesophilic | *Rhodopseudomonas palustris* |
| 119 | NC_002927|NP_889482.1 | R | R | Y | Y | Y | 0.49 | − | Mesophilic | *Bordetella bronchiseptica* |
| 120 | NC_018828|YP_006896532.1 | R | R | Y | Y | Y | 0.49 | − | Mesophilic | *Bordetella parapertussis* |
| 121 | NC_017223|YP_005589733.1 | R | R | Y | Y | Y | 0.48 | − | Mesophilic | *Bordetella pertussis* |
| 122 | NC_007958|YP_568577.1 | R | R | Y | Y | Y | 0.48 | − | Mesophilic | *Rhodopseudomonas palustris* |
| 123 | NC_018518|YP_006626426.1 | R | R | Y | Y | Y | 0.48 | − | Mesophilic | *Bordetella pertussis* |
| 124 | NC_002929|NP_880337.1 | R | R | Y | Y | Y | 0.48 | − | Mesophilic | *Bordetella pertussis* |
| 125 | NC_002928|NP_885167.1 | R | R | Y | Y | Y | 0.48 | − | Mesophilic | *Bordetella parapertussis* |
| 126 | NC_019382|YP_006966829.1 | R | R | Y | Y | Y | 0.48 | − | Mesophilic | *Bordetella bronchiseptica* |
| 127 | NC_018829|YP_006900438.1 | R | R | Y | Y | Y | 0.48 | − | Mesophilic | *Bordetella bronchiseptica* |
| 128 | NC_007925|YP_533792.1 | R | R | Y | Y | Y | 0.48 | − | Mesophilic | *Rhodopseudomonas palustris* |
| 129 | NC_008435|YP_782979.1 | R | R | Y | Y | Y | 0.48 | − | Mesophilic | *Rhodopseudomonas palustris* |
| 130 | NC_011894|YP_002501458.1 | R | R | Y | Y | Y | 0.48 | − | Mesophilic | *Methylobacterium nodulans* |
| 131 | NC_017283|YP_005661039.1 | R | R | Y | Y | Y | 0.48 | − | Mesophilic | *Brucella melitensis* |
| 132 | NC_010551|YP_001807800.1 | R | R | Y | Y | Y | 0.48 | − | Mesophilic | *Burkholderia ambifaria* |
| 133 | NC_015858|YP_004757945.1 | R | R | Y | Y | Y | 0.48 | − | Mesophilic | *Brucella pinnipedialis* |
| 134 | NC_014034|YP_003578715.1 | R | R | Y | Y | Y | 0.48 | − | Mesophilic | *Rhodobacter capsulatus* |
| 135 | NC_018513|YP_006616387.1 | R | R | Y | Y | Y | 0.48 | − | Mesophilic | *Burkholderia cepacia* |
| 136 | NC_009504|YP_001257663.1 | R | R | Y | Y | Y | 0.48 | − | Mesophilic | *Brucella ovis* |
| 137 | NC_008390|YP_772986.1 | R | R | Y | Y | Y | 0.48 | − | Mesophilic | *Burkholderia ambifaria* |
| 138 | NC_009668|YP_001372359.1 | R | R | Y | Y | Y | 0.48 | − | Mesophilic | *Ochrobactrum anthropi* |
| 139 | NC_012442|YP_002734445.1 | R | R | Y | Y | Y | 0.47 | − | Mesophilic | *Brucella melitensis* |
| 140 | NC_022535|YP_008631357.1 | R | R | Y | Y | Y | 0.47 | + | Mesophilic | *Rhizobium* sp. |
| 141 | NC_017247|YP_005602286.1 | R | R | Y | Y | Y | 0.47 | − | Mesophilic | *Brucella melitensis* |
| 142 | NC_013118|YP_003105477.1 | R | R | Y | Y | Y | 0.47 | − | Mesophilic | *Brucella microti* |
| 143 | NC_017245|YP_005598924.1 | R | R | Y | Y | Y | 0.47 | − | Mesophilic | *Brucella melitensis* |
| 144 | NC_010104|YP_001594643.1 | R | R | Y | Y | Y | 0.47 | − | Mesophilic | *Brucella canis* |
| 145 | NC_010167|YP_001622484.1 | R | R | Y | Y | Y | 0.47 | − | Mesophilic | *Brucella suis* |
| 146 | NC_010740|YP_001932452.1 | R | R | Y | Y | Y | 0.47 | − | Mesophilic | *Brucella abortus* |
| 147 | NC_022906|V910_200569 | R | R | Y | Y | Y | 0.47 | − | Mesophilic | *Brucella ceti* |
| 148 | NC_016777|YP_005114137.1 | R | R | Y | Y | Y | 0.47 | − | Mesophilic | *Brucella abortus* |
| 149 | NC_016796|YP_005152703.1 | R | R | Y | Y | Y | 0.47 | − | Mesophilic | *Brucella canis* |
| 150 | NC_007624|YP_418727.1 | R | R | Y | Y | Y | 0.47 | − | Mesophilic | *Brucella abortus* |
| 151 | NC_006933|YP_223309.1 | R | R | Y | Y | Y | 0.47 | − | Mesophilic | *Brucella abortus* |
| 152 | NC_003318|NP_541562.1 | R | R | Y | Y | Y | 0.47 | − | Mesophilic | *Brucella melitensis* |
| 153 | NC_008687|YP_918207.1 | R | R | Y | Y | Y | 0.47 | + | Mesophilic | *Paracoccus denitrificans* |
| 154 | NC_010084|YP_001580275.1 | R | R | Y | Y | Y | 0.47 | − | Mesophilic | *Burkholderia multivorans* |
| 155 | NC_009937|YP_001525161.1 | R | R | Y | Y | Y | 0.47 | − | Mesophilic | *Azorhizobium caulinodans* |
| 156 | NC_010508|YP_001764480.1 | R | R | Y | Y | Y | 0.47 | − | Mesophilic | *Burkholderia cenocepacia* |
| 157 | NC_015458|YP_004416353.1 | R | R | Y | Y | Y | 0.47 | − | ? | *Pusillimonas* sp. |
| 158 | NC_016775|YP_005108693.1 | R | R | Y | Y | Y | 0.47 | − | Mesophilic | *Brucella suis* |

TABLE 2-continued mhFeBP1 homologs.

| # | Name | 10 | 101 | 142 | 198 | 199 | Identity | Gram | Temperature | Organism |
|---|---|---|---|---|---|---|---|---|---|---|
| 159 | NC_014217\|YP_003692549.1 | R | R | Y | Y | Y | 0.47 | − | Mesophilic | *Starkeya novella* |
| 160 | NC_007510\|YP_368558.1 | R | R | Y | Y | Y | 0.47 | − | Mesophilic | *Burkholderia lata* |
| 161 | NC_004311\|NP_699880.1 | R | R | Y | Y | Y | 0.47 | − | Mesophilic | *Brucella suis* |
| 162 | NC_011000\|YP_002230239.1 | R | R | Y | Y | Y | 0.47 | − | Mesophilic | *Burkholderia cenocepacia* |
| 163 | NC_022043\|YP_008406497.1 | R | R | Y | Y | Y | 0.47 | + | Mesophilic | *Paracoccus aminophilus* |
| 164 | NC_008060\|YP_620613.1 | R | R | Y | Y | Y | 0.47 | − | Mesophilic | *Burkholderia cenocepacia* |
| 165 | NC_003062\|NP_353437.2 | R | R | Y | Y | Y | 0.47 | + | Mesophilic | *Agrobacterium fabrum* |
| 166 | NC_008542\|YP_834855.1 | R | R | Y | Y | Y | 0.47 | − | Mesophilic | *Burkholderia cenocepacia* |
| 167 | NC_015183\|YP_004277705.1 | R | R | Y | Y | Y | 0.47 | + | Mesophilic | *Agrobacterium* sp. |
| 168 | NC_014640\|YP_003979373.1 | R | R | Y | Y | Y | 0.47 | − | Mesophilic | *Achromobacter xylosoxidans* |
| 169 | NC_023061\|AX27061_2729 | R | R | Y | Y | Y | 0.46 | − | Mesophilic | *Achromobacter xylosoxidans* |
| 170 | NC_021285\|YP_008031617.1 | R | R | Y | Y | Y | 0.46 | − | Mesophilic | *Achromobacter xylosoxidans* |
| 171 | NC_022659\|BBK_250 | R | R | Y | Y | Y | 0.46 | − | Mesophilic | *Burkholderia pseudomallei* |
| 172 | NC_014931\|YP_004156555.1 | R | R | Y | Y | Y | 0.46 | − | Mesophilic | *Variovorax paradoxus* |
| 173 | NC_014010\|YP_003552419.1 | R | R | Y | Y | Y | 0.46 | − | Mesophilic | *Candidatus Puniceispirillum* |
| 174 | NC_013446\|CtCNB1_0418 | R | R | Y | Y | Y | 0.46 | − | Mesophilic | *Comamonas testosteroni* |
| 175 | NC_021884\|BDL_744 | R | R | Y | Y | Y | 0.46 | − | Mesophilic | *Burkholderia pseudomallei* |
| 176 | NC_018527\|YP_006652216.1 | R | R | Y | Y | Y | 0.46 | − | Mesophilic | *Burkholderia pseudomallei* |
| 177 | NC_006348\|YP_103391.1 | R | R | Y | Y | Y | 0.46 | − | Mesophilic | *Burkholderia mallei* |
| 178 | NC_008785\|YP_992517.1 | R | R | Y | Y | Y | 0.46 | − | Mesophilic | *Burkholderia mallei* |
| 179 | NC_008836\|YP_001026683.1 | R | R | Y | Y | Y | 0.46 | − | Mesophilic | *Burkholderia mallei* |
| 180 | NC_009080\|YP_001080034.1 | R | R | Y | Y | Y | 0.46 | − | Mesophilic | *Burkholderia mallei* |
| 181 | NC_009076\|YP_001065655.1 | R | R | Y | Y | Y | 0.46 | − | Mesophilic | *Burkholderia pseudomallei* |
| 182 | NC_012695\|YP_002896116.1 | R | R | Y | Y | Y | 0.46 | − | Mesophilic | *Burkholderia pseudomallei* |
| 183 | NC_010170\|YP_001630893.1 | R | R | Y | Y | Y | 0.46 | − | Mesophilic | *Bordetella petrii* |
| 184 | NC_010645\|YP_786440.1 | R | R | Y | Y | Y | 0.46 | − | Mesophilic | *Bordetella avium* |
| 185 | NC_021173\|YP_007919037.1 | R | R | Y | Y | Y | 0.46 | − | Mesophilic | *Burkholderia thailandensis* |
| 186 | NC_016078\|YP_004898234.1 | R | R | Y | Y | Y | 0.46 | + | Mesophilic | *Pelagibacterium halotolerans* |
| 187 | NC_007651\|YP_443368.1 | R | R | Y | Y | Y | 0.46 | − | Mesophilic | *Burkholderia thailandensis* |
| 188 | NC_007434\|YP_332916.1 | R | R | Y | Y | Y | 0.46 | − | Mesophilic | *Burkholderia pseudomallei* |
| 189 | NC_009074\|YP_001058421.1 | R | R | Y | Y | Y | 0.46 | − | Mesophilic | *Burkholderia pseudomallei* |
| 190 | NC_017831\|YP_006275273.1 | R | R | Y | Y | Y | 0.46 | − | Mesophilic | *Burkholderia pseudomallei* |
| 191 | NC_022247\|VAPA_1c38240 | R | R | Y | Y | Y | 0.45 | − | Mesophilic | *Variovorax paradoxus* |
| 192 | NC_012791\|YP_002945581.1 | R | R | Y | Y | Y | 0.45 | − | Mesophilic | *Variovorax paradoxus* |
| 193 | NC_010510\|YP_001767013.1 | R | R | Y | Y | Y | 0.45 | − | Mesophilic | *Methylobacterium radiotolerans* |
| 194 | NC_009720\|YP_001418646.1 | R | R | Y | Y | Y | 0.45 | − | Mesophilic | *Xanthobacter autotrophicus* |
| 195 | NC_017956\|YP_006370956.1 | R | R | Y | Y | Y | 0.45 | + | Mesophilic | *Tistrella mobilis* |
| 196 | NC_006350\|YP_107899.1 | R | R | Y | Y | Y | 0.45 | − | Mesophilic | *Burkholderia pseudomallei* |
| 197 | NC_010725\|YP_001923256.1 | R | R | Y | Y | Y | 0.45 | − | Mesophilic | *Methylobacterium populi* |
| 198 | NC_018525\|YP_006646037.1 | R | R | Y | Y | Y | 0.45 | − | Mesophilic | *Pectobacterium carotovorum* |
| 199 | NC_012917\|YP_003016929.1 | R | R | Y | Y | Y | 0.45 | − | Mesophilic | *Pectobacterium carotovorum* |
| 200 | NC_004547\|YP_049576.1 | R | R | Y | Y | Y | 0.45 | − | Mesophilic | *Pectobacterium atrosepticum* |
| 201 | NC_012988\|YP_003066252.1 | R | R | Y | Y | Y | 0.44 | − | Mesophilic | *Methylobacterium extorquens* |
| 202 | NC_012808\|YP_002961615.1 | R | R | Y | Y | Y | 0.44 | − | Mesophilic | *Methylobacterium extorquens* |
| 203 | NC_010172\|YP_001638056.1 | R | R | Y | Y | Y | 0.44 | − | Mesophilic | *Methylobacterium extorquens* |
| 204 | NC_010995\|YP_001984073.1 | R | R | Y | Y | Y | 0.44 | − | Mesophilic | *Cellvibrio japonicus* |
| 205 | NC_014166\|YP_003656801.1 | R | R | Y | Y | Y | 0.44 | − | Mesophilic | *Arcobacter nitrofigilis* |
| 206 | NC_011757\|YP_002419429.1 | R | R | Y | Y | Y | 0.44 | − | Mesophilic | *Methylobacterium extorquens* |
| 207 | NC_015061\|YP_004212396.1 | R | R | Y | Y | Y | 0.44 | + | Mesophilic | *Rahnella* sp. |
| 208 | NC_017047\|YP_005401406.1 | R | R | Y | Y | Y | 0.44 | + | Mesophilic | *Rahnella aquatilis* |
| 209 | NC_017845\|YP_006283928.1 | R | R | Y | Y | Y | 0.44 | − | Mesophilic | *Pectobacterium* sp. |
| 210 | NC_020418\|YP_007504644.1 | R | R | Y | Y | Y | 0.43 | + | Mesophilic | *Morganella morganii* |
| 211 | NC_022997\|W911_04275 | R | R | Y | Y | Y | 0.43 | + | Mesophilic | *Hyphomicrobium nitrativorans* |
| 212 | NC_017309\|YP_005700102.1 | R | R | Y | Y | Y | 0.43 | − | Mesophilic | *Edwardsiella tarda* |
| 213 | NC_020796\|ETAC_3335 | R | R | Y | Y | Y | 0.43 | − | Mesophilic | *Edwardsiella piscicida* |
| 214 | NC_013889\|YP_003459550.1 | R | R | Y | Y | Y | 0.43 | + | Mesophilic | *Thioalkalivibrio* sp. |
| 215 | NC_013421\|YP_003260342.1 | R | R | Y | Y | Y | 0.43 | − | Mesophilic | *Pectobacterium wasabiae* |
| 216 | NC_018002\|YP_006405228.1 | R | R | Y | Y | Y | 0.43 | + | Mesophilic | *Sulfurospirillum barnesii* |
| 217 | NC_012779\|YP_002934481.1 | R | R | Y | Y | Y | 0.43 | − | Mesophilic | *Edwardsiella ictaluri* |
| 218 | NC_013508\|YP_003296812.1 | R | R | Y | Y | Y | 0.43 | − | Mesophilic | *Edwardsiella tarda* |
| 219 | NC_018644\|YP_006757561.1 | R | R | Y | Y | Y | 0.43 | + | Mesophilic | alpha proteobacterium |
| 220 | NC_017192\|YP_005554689.1 | R | R | Y | Y | Y | 0.42 | − | Mesophilic | *Arcobacter* sp. |
| 221 | NC_003911\|SPO3287 | R | R | Y | Y | Y | 0.42 | − | Mesophilic | *Ruegeria pomeroyi* |
| 222 | NC_015726\|YP_004684614.1 | R | R | Y | Y | Y | 0.42 | − | Mesophilic | *Cupriavidus necator* |
| 223 | NC_008044\|YP_612119.1 | R | R | Y | Y | Y | 0.42 | − | Mesophilic | *Ruegeria* sp. |
| 224 | NC_006513\|YP_159824.1 | R | R | Y | Y | Y | 0.42 | − | Mesophilic | *Aromatoleum aromaticum* |
| 225 | NC_022513\|N234_0870 | R | R | Y | Y | Y | 0.42 | − | Mesophilic | *Ralstonia pickettii* |
| 226 | NC_012673\|YP_002886303.1 | R | R | Y | Y | Y | 0.42 | + | Thermophilic | *Exiguobacterium* sp. |
| 227 | NC_014759\|YP_004053760.1 | R | R | Y | Y | Y | 0.42 | − | Mesophilic | *Marivirga tractuosa* |
| 228 | NC_019902\|YP_007215684.1 | R | R | Y | Y | Y | 0.42 | + | Mesophilic | *Thioalkalivibrio nitratireduce* |
| 229 | NC_014216\|YP_003691508.1 | R | R | Y | Y | Y | 0.42 | − | Mesophilic | *Desulfurivibrio alkaliphilus* |
| 230 | NC_018018\|YP_006433889.1 | R | R | Y | Y | Y | 0.42 | + | Mesophilic | *Flexibacter litoralis* |
| 231 | NC_017668\|YP_006182380.1 | R | R | Y | Y | Y | 0.42 | + | Mesophilic | *Halobacillus halophilus* |
| 232 | NC_013854\|YP_003448425.1 | R | R | Y | Y | Y | 0.41 | + | Mesophilic | *Azospirillum* sp. |
| 233 | NC_007908\|Rfer_2758 | R | R | Y | Y | Y | 0.41 | + | Mesophilic | *Albidiferax ferrireducens* |
| 234 | NC_006512\|YP_155448.1 | R | R | Y | Y | Y | 0.41 | − | Mesophilic | *Idiomarina loihiensis* |

TABLE 2-continued mhFeBP1 homologs.

| # | Name | 10 | 101 | 142 | 198 | 199 | Identity | Gram | Temperature | Organism |
|---|---|---|---|---|---|---|---|---|---|---|
| 235 | NC_008781\|YP_981845.1 | R | R | Y | Y | Y | 0.41 | − | Mesophilic | *Polaromonas naphthalenivorans* |
| 236 | NC_009253\|YP_001112883.1 | R | R | Y | Y | Y | 0.41 | + | Mesophilic | *Desulfotomaculum reducens* |
| 237 | NC_016622\|YP _005038613.1 | R | R | Y | Y | Y | 0.41 | + | Mesophilic | *Azospirillum lipoferum* |
| 238 | NC_021286\|YP_008034563.1 | R | R | Y | Y | Y | 0.41 | − | Mesophilic | *Idiomarina loihiensis* |
| 239 | NC_018010\|YP_006406798.1 | R | R | Y | Y | Y | 0.41 | + | Mesophilic | *Belliella baltica* |
| 240 | NC_008313\|YP_725275.1 | R | R | Y | Y | Y | 0.41 | − | Mesophilic | *Ralstonia eutropha* |
| 241 | NC_008702\|YP_933709.1 | R | R | Y | Y | Y | 0.41 | − | Mesophilic | *Azoarcus* sp. |
| 242 | NC_019738\|YP_007124478.1 | R | R | Y | Y | Y | 0.41 | + | Mesophilic | *Microcoleus* sp. |
| 243 | NC_010528\|YP_002004788.1 | R | R | Y | Y | Y | 0.41 | − | Mesophilic | *Cupriavidus taiwanensis* |
| 244 | NC_015276\|YP_004311821.1 | R | R | Y | Y | Y | 0.41 | − | Mesophilic | *Marinomonas mediterranea* |
| 245 | NC_320908\|YP_007698507.1 | R | R | Y | Y | Y | 0.41 | + | Mesophilic | *Octadecabacter arcticus* |
| 246 | NC_007953\|YP_556393.1 | R | R | Y | Y | Y | 0.41 | − | Mesophilic | *Burkholderia xenovorans* |
| 247 | NC_023135\|METH_00275 | R | R | Y | Y | Y | 0.41 | + | Mesophilic | *Leisingera methylohalidivorans* |
| 248 | NC_017187\|YP_005539339.1 | R | R | Y | Y | Y | 0.41 | − | Mesophilic | *Arcobacter butzleri* |
| 249 | NC_009850\|YP_001490892.1 | R | R | Y | Y | Y | 0.41 | − | Mesophilic | *Arcobacter butzleri* |
| 250 | NC_022759\|CFT03427_0122 | R | R | Y | Y | Y | 0.41 | − | Mesophilic | *Campylobacter fetus* |
| 251 | NC_020514\|YP_007544802.1 | R | R | Y | Y | Y | 0.41 | + | Mesophilic | *Glaciecola psychrophila* |
| 252 | NC_021878\|YP_00833.1820.1 | R | R | Y | Y | Y | 0.41 | − | Mesophilic | *Arcobacter butzleri* |
| 253 | NC_014366\|YP_003811659.1 | R | R | Y | Y | Y | 0.41 | + | Mesophilic | gamma proteobacterium |
| 254 | NC_007775\|YP_475512.1 | R | R | Y | Y | Y | 0.41 | − | Thermophilic | *Synechococcus* sp. |
| 255 | NC_007776\|YP_478858.1 | R | R | Y | Y | Y | 0.41 | − | Thermophilic | *Synechococcus* sp. |
| 256 | NC_018708\|YP_006855088.1 | R | R | Y | Y | Y | 0.41 | − | Mesophilic | *Acidovorax* sp. |
| 257 | NC_005295\|YP_179998.1 | R | R | Y | Y | Y | 0.41 | − | Mesophilic | *Ehrlichia ruminantium* |
| 258 | NC_004842\|YP_153489.1 | R | R | Y | Y | Y | 0.41 | − | Mesophilic | *Anaplasma marginale* |
| 259 | NC_008752\|YP_971208.1 | R | R | Y | Y | Y | 0.41 | − | Mesophilic | *Acidovorax citrulli* |
| 260 | NC_023065\|YP_008937446.1 | R | R | Y | Y | Y | 0.41 | + | Mesophilic | *Magnetospirillum gryphiswalden* |
| 261 | NC_011992\|YP_002553562.1 | R | R | Y | Y | Y | 0.4 | − | Mesophilic | *Acidovorax ebreus* |
| 262 | NC_012026\|YP_002563199.1 | R | R | Y | Y | Y | 0.4 | − | Mesophilic | *Anaplasma marginale* |
| 263 | NC_022760\|U370_00265 | R | R | Y | Y | Y | 0.4 | − | Mesophilic | *Anaplasma marginale* |
| 264 | NC_015422\|YP_004389134.1 | R | R | Y | Y | Y | 0.4 | − | Mesophilic | *Alicycliphilus denitrificans* |
| 265 | NC_016041\|YP_004871348.1 | R | R | Y | Y | Y | 0.4 | + | Mesophilic | *Glaciecola nitratireducens* |
| 266 | NC_014910\|YP_004126179.1 | R | R | Y | Y | Y | 0.4 | − | Mesophilic | *Alicycliphilus denitrificans* |
| 267 | NC_018012\|YP_006413475.1 | R | R | Y | Y | Y | 0.4 | + | Mesophilic | *Thiocystis violascens* |
| 268 | NC_017856\|YP_006293166.1 | R | R | Y | Y | Y | 0.4 | + | Mesophilic | *Methylophaga frappieri* |
| 269 | NC_007799\|YP_507013.1 | R | R | Y | Y | Y | 0.4 | − | Mesophilic | *Ehrlichia chaffeensis* |
| 270 | NC_002978\|NP_966643.1 | R | R | Y | Y | Y | 0.4 | − | Mesophilic | *Wolbachia endosymbiont* |
| 271 | NC_006831\|YP_196049.1 | R | R | Y | Y | Y | 0.4 | − | Mesophilic | *Ehrlichia ruminantium* |
| 272 | NC_008825\|YP_001020568.1 | R | R | Y | Y | Y | 0.4 | − | Mesophilic | *Methylibium petroleiphilum* |
| 273 | NC_008786\|YP_997316.1 | R | R | Y | Y | Y | 0.4 | − | Mesophilic | *Verminephrobacter eiseniae* |
| 274 | NC_008782\|YP_985876.1 | R | R | Y | Y | Y | 0.4 | − | Mesophilic | *Acidovorax* sp. |
| 275 | NC_009654\|YP_001342590.1 | R | R | Y | Y | Y | 0.4 | − | Mesophilic | *Martnomonas* sp. |
| 276 | NC_012039\|Cla_1526 | R | R | Y | Y | Y | 0.4 | − | Mesophilic | *Campylobacter lari* |
| 277 | NC_011901\|YP_002512540.1 | R | R | Y | Y | Y | 0.4 | + | Mesophilic | *Thioalkalivibrio sulfidiphilus* |
| 278 | NC_010002\|YP_001565757.1 | R | R | Y | Y | Y | 0.4 | − | Mesophilic | *Delftia acidovorans* |
| 279 | NC_022784\|U128_00245 | R | R | Y | Y | Y | 0.4 | − | Mesophilic | *Anaplasma marginale* |
| 280 | NC_015138\|YP_004234852.1 | R | R | Y | Y | Y | 0.4 | − | Mesophilic | *Acidovorax avenae* |
| 281 | NC_015677\|YP_004619583.1 | R | R | Y | Y | Y | 0.4 | − | Mesophilic | *Ramlibacter tataouinensis* |
| 282 | NC_015563\|YP_004487487.1 | R | R | Y | Y | Y | 0.4 | − | Mesophilic | *Delftia* sp. |
| 283 | NC_016616\|YP_005029105.1 | R | R | Y | Y | Y | 0.4 | + | Mesophilic | *Dechlorosoma suillim* |
| 284 | NC_017857\|YP_006297460.1 | R | R | Y | Y | Y | 0.4 | + | Mesophilic. | *Methylophaga nitratireducentic* |
| 285 | NC_018721\|YP_006868342.1 | R | R | Y | Y | Y | 0.4 | + | Mesophilic | *Psychroflexus torquis* |
| 286 | NC_023137\|Gal_03312 | R | R | Y | Y | Y | 0.4 | + | Mesophilic | *Phaeobacter gallaeciensis* |
| 287 | NC_012416\|YP_002727371.1 | R | R | Y | Y | Y | 0.4 | − | Mesophilic | *Wolbachia* sp. |
| 288 | NC_019748\|YP_007133065.1 | R | R | Y | Y | Y | 0.4 | + | Mesophilic | *Stanieria cyanosphaera* |
| 289 | NC_023035\|L21SP2_0743 | R | R | Y | Y | Y | 0.4 | − | Hyperthermophilic | *Spirochaeta* sp. |
| 290 | NC_020911\|YP_007702830.1 | R | R | Y | Y | Y | 0.4 | + | Mesophilic | *Octadecabacter antarcticus* |
| 291 | NC_021089\|YP_007889339.1 | R | R | Y | Y | Y | 0.4 | − | Mesophilic | *Wolbachia endosymbiont* |
| 292 | NC_017039\|YP_005385198.1 | R | R | Y | Y | Y | 0.4 | − | Mesophilic | *Synechocystis* sp. |
| 293 | NC_017075\|YP_005437539.1 | R | R | Y | Y | Y | 0.4 | + | Mesophilic | *Rubrivivax gelatinosus* |
| 294 | NC_014836\|YP_004113366.1 | R | R | Y | Y | Y | 0.4 | − | Mesophilic | *Desulfurispirillum indicum* |
| 295 | NC_014323\|YP_003775309.1 | R | R | Y | Y | Y | 0.4 | − | Mesophilic | *Herbaspirillum seropedicae* |
| 296 | NC_007354\|YP_302777.1 | R | R | Y | Y | Y | 0.4 | − | Mesophilic | *Ehrlichia canis* |
| 297 | NC_007204\|YP_264829.1 | R | R | Y | Y | Y | 0.4 | − | Psychrophilic | *Psychrobacter arcticus* |
| 298 | NC_018286\|YP_006564286.1 | R | R | Y | Y | Y | 0.4 | + | Mesophilic | *Phaeobacter gallaeciensis* |
| 299 | NC_018290\|YP_006574608.1 | R | R | Y | Y | Y | 0.4 | + | Mesophilic | *Phaeobacter inhibens* |
| 300 | NC_000911\|NP_440162.1 | R | R | Y | Y | Y | 0.4 | − | Mesophilic | *Synechocystis* sp. |
| 301 | NC_009138\|YP_001099462.1 | R | R | Y | Y | Y | 0.4 | − | Mesophilic | *Herminiimonas arsenicoxydans* |
| 302 | NC_012491\|YP_002770441.1 | R | R | Y | Y | Y | 0.39 | + | Mesophilic | *Brevibacillus brevis* |
| 303 | NC_010981\|YP_001975438.1 | R | R | Y | Y | Y | 0.39 | − | Mesophilic | *Wolbachia endosymbiont* |
| 304 | NC_020908\|YP_007697819.1 | R | R | Y | Y | Y | 0.39 | + | Mesophilic | *Octadecabacter arcticus* |
| 305 | NC_017052\|YP_005407905.1 | R | R | Y | Y | Y | 0.39 | − | Mesophilic | *Synechocystis* sp. |
| 306 | NC_013532\|YP_003328084.1 | R | R | Y | Y | Y | 0.39 | − | Mesophilic | *Anaplasma centrale* |
| 307 | NC_008599\|YP_891325.1 | R | R | Y | Y | Y | 0.39 | − | Mesophilic | *Campylobacter fetus* |
| 308 | NC_023063\|EMUR_00615 | R | R | Y | Y | Y | 0.39 | − | Mesophilic | *Ehrlichia muris* |
| 309 | NC_009952\|YP_001533361.1 | R | R | Y | Y | Y | 0.39 | − | Mesophilic | *Dinoroseobacter shibae* |
| 310 | NC_011726\|YP_002371657.1 | R | R | Y | Y | Y | 0.39 | − | Mesophilic | *Cyanothece* sp. |

TABLE 2-continued mhFeBP1 homologs.

| # | Name | 10 | 101 | 142 | 198 | 199 | Identity | Gram | Temperature | Organism |
|---|---|---|---|---|---|---|---|---|---|---|
| 311 | NC_017038\|YP_005382028.1 | R | R | Y | Y | Y | 0.39 | – | Mesophilic | *Synechocystis* sp. |
| 312 | NC_021661\|PSYCG_08920 | R | R | Y | Y | Y | 0.39 | – | Mesophilic | *Psychrobacter* sp. |
| 313 | NC_014414\|YP_003855886.1 | R | R | Y | Y | Y | 0.39 | – | Mesophilic | *Parvularcula bermudensis* |
| 314 | NC_008209\|RD1_0916 | R | R | Y | Y | Y | 0.39 | – | Mesophilic | *Roseobacter denitrificans* |
| 315 | NC_007948\|YP_549904.1 | R | R | Y | Y | Y | 0.39 | – | Mesophilic | *Polaromonas* sp. |
| 316 | NC_007969\|YP_580989.1 | R | R | Y | Y | Y | 0.39 | – | Psychrophilic | *Psychrobacter cryohalolentis* |
| 317 | NC_009659\|YP_001353939.1 | R | R | Y | Y | Y | 0.39 | – | Mesophilic | *Janthinobacterium* sp. |
| 318 | NC_013161\|YP_003137220.1 | R | R | Y | Y | Y | 0.39 | – | Mesophilic | *Cyanothece* sp. |
| 319 | NC_019729\|YP_007113899.1 | R | R | Y | Y | Y | 0.39 | + | Mesophilic | *Oscillatoria nigro-viridis* |
| 320 | NC_022132\|YP_008472938.1 | R | R | Y | Y | Y | 0.39 | – | Mesophilic | *Campylobacter coli* |
| 321 | NC_023018\|X636_20130 | R | R | Y | Y | Y | 0.39 | + | Mesophilic | *Pandoraea* sp. |
| 322 | NC_011726\|YP_002371656.1 | R | R | Y | Y | Y | 0.39 | – | Mesophilic | *Cyanothece* sp. |
| 323 | NC_022904\|U875_14655 | R | R | Y | Y | Y | 0.39 | + | Mesophilic | *Pandoraea pnomenusa* |
| 324 | NC_015497\|YP_004434941.1 | R | R | Y | Y | Y | 0.39 | + | Mesophilic | *Glaciecola* sp. |
| 325 | NC_015559\|YP_004480592.1 | R | R | Y | Y | Y | 0.39 | – | Mesophilic | *Marinomonas posidonica* |
| 326 | NC_020516\|YP_007551100.1 | R | R | Y | Y | Y | 0.39 | – | Mesophilic | *Azoarcus* sp. |
| 327 | NC_020417\|YP_007501864.1 | R | R | Y | Y | Y | 0.39 | + | Mesophilic | beta proteobacterium |
| 328 | NC_021881\|YYY_00245 | R | R | Y | Y | Y | 0.39 | – | Mesophilic | *Anaplasma phagocytophilum* |
| 329 | NC_022529\|YP_008623108.1 | R | R | Y | Y | Y | 0.38 | – | Mesophilic | *Campylobacter jejuni* |
| 330 | NC_022362\|YP_008561568.1 | R | R | Y | Y | Y | 0.38 | – | Mesophilic | *Campylobacter jejuni* |
| 331 | NC_013161\|YP_003137221.1 | R | R | Y | Y | Y | 0.38 | – | Mesophilic | *Cyanothece* sp. |
| 332 | NC_019738\|YP_007124477.1 | R | R | Y | Y | Y | 0.38 | + | Mesophilic | *Microcoleus* sp. |
| 333 | NC_009839\|YP_001481745.1 | R | R | Y | Y | Y | 0.38 | – | Mesophilic | *Campylobacter jejuni* |
| 334 | NC_020911\|YP_007706474.1 | R | R | Y | Y | Y | 0.38 | + | Mesophilic | *Octadecabacter antarcticus* |
| 335 | NC_019936\|YP_007238420.1 | R | R | Y | Y | Y | 0.38 | – | Mesophilic | *Pseudomonas stutzeri* |
| 336 | NC_016617\|YP_005030415.1 | R | R | Y | Y | Y | 0.38 | + | Mesophilic | *Azospirillum brasilense* |
| 337 | NC_021879\|YYU_00250 | R | R | Y | Y | Y | 0.38 | – | Mesophilic | *Anaplasma phagocytophilum* |
| 338 | NC_021880\|WSQ_00245 | R | R | Y | Y | Y | 0.38 | – | Mesophilic | *Anaplasma phagocytophilum* |
| 339 | NC_014634\|YP_003968941.1 | R | R | Y | Y | Y | 0.38 | – | Mesophilic | *Ilyobacter polytropus* |
| 340 | NC_007298\|YP_284282.1 | R | R | Y | Y | Y | 0.38 | – | Mesophilic | *Dechloromonas aromatica* |
| 341 | NC_007797\|YP_504684.1 | R | R | Y | Y | Y | 0.38 | – | Mesophilic | *Anaplasma phagocytophilum* |
| 342 | NC_018709\|YP_006857279.1 | R | R | Y | Y | Y | 0.38 | – | Mesophilic | *Campylobacter jejuni* |
| 343 | NC_007798\|YP_505908.1 | R | R | Y | Y | Y | 0.38 | – | Mesophilic | *Neorickettsia sennetsu* |
| 344 | NC_002163\|YP_002343633.1 | R | R | Y | Y | Y | 0.38 | – | Mesophilic | *Campylobacter jejuni* |
| 345 | NC_013166\|YP_003147637.1 | R | R | Y | Y | Y | 0.38 | – | Mesophilic | *Kangiella koreensis* |
| 346 | NC_009925\|YP_001514473.1 | R | R | Y | Y | Y | 0.38 | – | Mesophilic | *Acaryochloris marina* |
| 347 | NC_011662\|YP_002889566.1 | R | R | Y | Y | Y | 0.38 | – | Mesophilic | *Thauera* sp. |
| 348 | NC_019683\|YP_007069953.1 | R | R | Y | Y | Y | 0.38 | + | Mesophilic | *Leptolyngbya* sp. |
| 349 | NC_021084\|YP_007885545.1 | R | R | Y | Y | Y | 0.38 | – | Mesophilic | *Wolbachia endosymbiont* |
| 350 | NC_015730\|YP_004692622.1 | R | R | Y | Y | Y | 0.38 | – | Mesophilic | *Roseobacter litoralis* |
| 351 | NC_015672\|YP_004603167.1 | R | R | Y | Y | Y | 0.38 | – | Thermophilic | *Flexistipes sinusarabici* |
| 352 | NC_018267\|YP_006555929.1 | R | R | Y | Y | Y | 0.38 | – | Mesophilic | *Wolbachia endosymbiont* |
| 353 | NC_008340\|YP_743404.1 | R | R | Y | Y | Y | 0.38 | – | Mesophilic | *Alkalilimnicola ehrlichii* |
| 354 | NC_009524\|YP_001279771.1 | R | R | Y | Y | Y | 0.38 | – | Mesophilic | *Psychrobacter* sp. |
| 355 | NC_019567\|YP_007024115.1 | R | R | Y | Y | Y | 0.38 | + | Mesophilic | *Bdellovibrio bacteriovorus* |
| 356 | NC_017506\|YP_005887535.1 | R | R | Y | Y | Y | 0.38 | – | ? | *Marinobacter adhaerens* |
| 357 | NC_019776\|YP_007162494.1 | R | R | Y | Y | Y | 0.38 | + | Mesophilic | *Cyanobacterium aponinum* |
| 358 | NC_015740\|YP_004716401.1 | R | R | Y | Y | Y | 0.38 | – | Mesophilic | *Pseudomonas stutzeri* |
| 359 | NC_007802\|YP_508060.1 | R | R | Y | Y | Y | 0.38 | – | Mesophilic | *Jannaschia* sp. |
| 360 | NC_006576\|YP_172630.1 | R | R | Y | Y | Y | 0.38 | – | Mesophilic | *Synechococcus elongatus* |
| 361 | NC_006833\|YP_198228.1 | R | R | Y | Y | Y | 0.38 | – | Mesophilic | *Wolbachia endosymbiont* |
| 362 | NC_008789\|YP_001002765.1 | R | R | Y | Y | Y | 0.38 | – | Mesophilic | *Halorhodospira halophila* |
| 363 | NC_010475\|YP_001735740.1 | R | R | Y | Y | Y | 0.37 | – | Thermophilic | *Synechococcus* sp. |
| 364 | NC_009719\|YP_001411459.1 | R | R | Y | Y | Y | 0.37 | – | Mesophilic | *Parvibaculum lavamentivorans* |
| 365 | NC_013515\|YP_003306318.1 | R | R | Y | Y | Y | 0.37 | – | Mesophilic | *Streptobacillus moniliformis* |
| 366 | NC_014532\|YP_003899070.1 | R | R | Y | Y | Y | 0.37 | – | Mesophilic | *Halomonas elongata* |
| 367 | NC_007404\|YP_314748.1 | R | R | Y | Y | Y | 0.37 | – | Mesophilic | *Thiobacillus denitrificans* |
| 368 | NC_008228\|YP_661172.1 | R | R | Y | Y | Y | 0.37 | – | Mesophilic | *Pseudoalteromonas atlantica* |
| 369 | NC_009434\|PST_4066 | R | R | Y | Y | Y | 0.37 | – | Mesophilic | *Pseudomonas stutzeri* |
| 370 | NC_009654\|YP_001342678.1 | R | R | Y | Y | Y | 0.37 | – | Mesophilic | *Marinomonas* sp. |
| 371 | NC_022660\|N149_1535 | R | R | Y | Y | Y | 0.37 | – | Mesophilic | *Campylobacter coli* |
| 372 | NC_017280\|YP_005657152.1 | R | R | Y | Y | Y | 0.37 | – | Mesophilic | *Campylobacter jejuni* |
| 373 | NC_017279\|YP_005655535.1 | R | R | Y | Y | Y | 0.37 | – | Mesophilic | *Campylobacter jejuni* |
| 374 | NC_019695\|YP_007092604.1 | R | R | Y | Y | Y | 0.37 | + | Mesophilic | *Chroococcidiopsis thermalis* |
| 375 | NC_022351\|YP_008538079.1 | R | R | Y | Y | Y | 0.37 | – | Mesophilic | *Campylobacter jejuni* |
| 376 | NC_022352\|YP_008539796.1 | R | R | Y | Y | Y | 0.37 | – | Mesophilic | *Campylobacter jejuni* |
| 377 | NC_019978\|YP_007314869.1 | R | R | Y | Y | Y | 0.37 | + | Mesophilic | *Halobacteroides halobius* |
| 378 | NC_007614\|YP_4U431.1 | R | R | Y | Y | Y | 0.37 | – | Mesophilic | *Nitrosospira multiformis* |
| 379 | NC_008312\|YP_722952.1 | R | R | Y | Y | Y | 0.37 | – | Mesophilic | *Trichodesmium erythraeum* |
| 380 | NC_003912\|YP_178192.1 | R | R | Y | Y | Y | 0.37 | – | Mesophilic | *Campylobacter jejuni* |
| 381 | NC_018028\|YP_006455879.1 | R | R | Y | Y | Y | 0.37 | – | Mesophilic | *Pseudomonas stutzeri* |
| 382 | NC_017281\|YP_005658777.1 | R | R | Y | Y | Y | 0.37 | – | Mesophilic | *Campylobacter jejuni* |
| 383 | NC_022347\|YP_008534235.1 | R | R | Y | Y | Y | 0.37 | – | Mesophilic | *Campylobacter coli* |
| 384 | NC_013009\|YP_003081241.1 | R | R | Y | Y | Y | 0.37 | – | Mesophilic | *Neorickettsia risticii* |
| 385 | NC_022353\|YP_008541533.1 | R | R | Y | Y | Y | 0.37 | – | Mesophilic | *Campylobacter jejuni* |
| 386 | NC_019566\|YP_007020209.1 | R | R | Y | Y | Y | 0.37 | – | Mesophilic | *Candidatus Endolissoclinum* |

TABLE 2-continued mhFeBP1 homologs.

| # | Name | 10 | 101 | 142 | 198 | 199 | Identity | Gram | Temperature | Organism |
|---|---|---|---|---|---|---|---|---|---|---|
| 387 | NC_010524\|YP_001791320.1 | R | R | Y | Y | Y | 0.37 | − | Mesophilic | *Leptothrix cholodnii* |
| 388 | NC_015380\|YP_004358590.1 | R | R | Y | Y | Y | 0.37 | − | Mesophilic | *Candidatus Pelagibacter* |
| 389 | NC_021834\|M635_05205 | R | R | Y | Y | Y | 0.37 | − | Mesophilic | *Vibrio parahaemolyticus* |
| 390 | NC_019779\|YP_007169582.1 | R | R | Y | Y | Y | 0.37 | + | Mesophilic | *Halothece* sp. |
| 391 | NC_007604\|YP_401192.1 | R | R | Y | Y | Y | 0.37 | − | Mesophilic | *Synechococcus elongatus* |
| 392 | NC_009707\|YP_001397430.1 | R | R | Y | Y | Y | 0.37 | − | Mesophilic | *Campylobacter jejuni* |
| 393 | NC_008261\|YP_694897.1 | R | R | Y | Y | Y | 0.37 | + | Mesophilic | *Clostridium perfringens* |
| 394 | NC_013177\|YP_006526031.1 | R | R | Y | Y | Y | 0.37 | − | Mesophilic | *Pseudomonas stutzeri* |
| 395 | NC_018521\|YP_006632382.1 | R | R | Y | Y | Y | 0.37 | − | Mesophilic | *Campylobacter jejuni* |
| 396 | NC_017532\|YP_005940813.1 | R | R | Y | Y | Y | 0.37 | − | Mesophilic | *Pseudomonas stutzeri* |
| 397 | NC_014147\|YP_003626460.1 | R | R | Y | Y | Y | 0.36 | − | Mesophilic | *Moraxella catarrhalis* |
| 398 | NC_007298\|YP_284426.1 | R | R | Y | Y | Y | 0.36 | − | Mesophilic | *Dechloromonas aromatica* |
| 399 | NC_003366\|NP_561354.1 | R | R | Y | Y | Y | 0.36 | + | Mesophilic | *Clostridium perfringens* |
| 400 | NC_015410\|YP_004378171.1 | R | R | Y | Y | Y | 0.36 | − | Mesophilic | *Pseudomonas mendocina* |
| 401 | NC_015581\|YP_004537902.1 | R | R | Y | Y | Y | 0.36 | − | Mesophilic | *Thioalkalimicrobium cyclicum* |
| 402 | NC_007205\|YP_266646.1 | R | R | Y | Y | Y | 0.36 | − | Mesophilic | *Candidatus Pelagibacter* |
| 403 | NC_007963\|YP_572610.1 | R | R | Y | Y | Y | 0.36 | − | Mesophilic | *Chromohalobacter salexigens* |
| 404 | NC_008787\|YP_999899.1 | R | R | Y | Y | Y | 0.36 | − | Mesophilic | *Campylobacter jejuni* |
| 405 | NC_008347\|YP_756198.1 | R | R | Y | Y | Y | 0.36 | − | Mesophilic | *Maricaulis maris* |
| 406 | NC_012559\|LHK_02634 | R | R | Y | Y | Y | 0.36 | − | Mesophilic | *Laribacter hongkongensis* |
| 407 | NC_022360\|M802.5393 | R | R | Y | Y | Y | 0.36 | − | Mesophilic | *Pseudomonas aeruginosa* |
| 408 | NC_019701\|YP_007102660.1 | R | R | Y | Y | Y | 0.36 | + | Mesophilic | *Pseudanabaena* sp. |
| 409 | NC_019702\|YP_007105817.1 | R | R | Y | Y | Y | 0.36 | − | Thermophilic | *Synechococcus* sp. |
| 410 | NC_010546\|YP_001804046.1 | R | R | Y | Y | Y | 0.36 | − | Mesophilic | *Cyanothece* sp. |
| 411 | NC_022806\|PA1R_gp3150 | R | R | Y | Y | Y | 0.36 | − | Mesophilic | *Pseudomonas aeruginosa* |
| 412 | NC_015379\|YP_004356944.1 | R | R | Y | Y | Y | 0.36 | − | Mesophilic | *Pseudomonas brassicacearum* |
| 413 | NC_019905\|YP_007231935.1 | R | R | Y | Y | Y | 0.36 | − | Mesophilic | *Pseudomonas putida* |
| 414 | NC_020829\|YP_007655716.1 | R | R | Y | Y | Y | 0.36 | − | Mesophilic | *Pseudomonas denitrificans* |
| 415 | NC_013771\|UCYN_05550 | R | R | Y | Y | Y | 0.36 | − | Mesophilic | *Candidatas Atelocyanobacterium* |
| 416 | NC_018691\|YP_006818918.1 | R | R | Y | Y | Y | 0.36 | + | Mesophilic | *Alcanivorax dieselolei* |
| 417 | NC_007604\|YP_400426.1 | R | R | Y | Y | Y | 0.36 | − | Mesophilic | *Synechococcus elongatus* |
| 418 | NC_018220\|YP_006535054.1 | R | R | Y | Y | Y | 0.36 | − | Mesophilic | *Pseudomonas putida* |
| 419 | NC_002516\|PA5217 | R | R | Y | Y | Y | 0.36 | − | Mesophilic | *Pseudomonas aeruginosa* |
| 420 | NC_006138\|YP_065132.1 | R | R | Y | Y | Y | 0.36 | − | Psychrophilic | *Desulfotalea psychrophila* |
| 421 | NC_005085\|CV1902 | R | R | Y | Y | Y | 0.36 | − | Mesophilic | *Chromobacterium violaceum* |
| 422 | NC_006576\|YP_170856.1 | R | R | Y | Y | Y | 0.36 | − | Mesophilic | *Synechococcus elongatus* |
| 423 | NC_018080\|YP_006485484.1 | R | R | Y | Y | Y | 0.36 | − | Mesophilic | *Pseudomonas aeruginosa* |
| 424 | NC_009512\|YP_001270405.1 | R | R | Y | Y | Y | 0.36 | − | Mesophilic | *Pseudomonas putida* |
| 425 | NC_023076\|X970_24575 | R | R | Y | Y | Y | 0.36 | − | Mesophilic | *Pseudomonas monteilii* |
| 426 | NC_008463\|YP_793689.1 | R | R | Y | Y | Y | 0.36 | − | Mesophilic | *Pseudomonas aeruginosa* |
| 427 | NC_023066\|T223_28685 | R | R | Y | Y | Y | 0.36 | − | Mesophilic | *Pseudomonas aeruginosa* |
| 428 | NC_011770\|YP_002443189.1 | R | R | Y | Y | Y | 0.35 | − | Mesophilic | *Pseudomonas aeruginosa* |
| 429 | NC_022594\|N297_5395 | R | R | Y | Y | Y | 0.35 | − | Mesophilic | *Pseudomonas aeruginosa* |
| 430 | NC_017080\|YP_005446529.1 | R | R | Y | Y | Y | 0.35 | + | Mesophilic | *Phycisphaera mikurensis* |
| 431 | NC_013194\|YP_003167150.1 | R | R | Y | Y | Y | 0.35 | − | Mesophilic | *Candidatas Accumulibacter* |
| 432 | NC_023019\|U769_28730 | R | R | Y | Y | Y | 0.35 | − | Mesophilic | *Pseudomonas aeruginosa* |
| 433 | NC_010501\|YP_001751866.1 | R | R | Y | Y | Y | 0.35 | − | Mesophilic | *Pseudomonas putida* |
| 434 | NC_020813\|YP_007644977.1 | R | R | Y | Y | Y | 0.35 | + | Mesophilic | *Bdellovibrio exovorus* |
| 435 | NC_021577\|M062_27505 | R | R | Y | Y | Y | 0.35 | − | Mesophilic | *Pseudomonas aeruginosa* |
| 436 | NC_007577\|YP_397756.1 | R | R | Y | Y | Y | 0.35 | − | Mesophilic | *Prochlorococcus marinus* |
| 437 | NC_008260\|YP_694317.1 | R | R | Y | Y | Y | 0.35 | + | Mesophilic | *Alcanivorax borkumensis* |
| 438 | NC_017548\|YP_005977914.1 | R | R | Y | Y | Y | 0.35 | − | Mesophilic | *Pseudomonas aeruginosa* |
| 439 | NC_017530\|YP_005932744.1 | R | R | Y | Y | Y | 0.35 | − | Mesophilic | *Pseudomonas putida* |
| 440 | NC_012560\|YP_002801810.1 | R | R | Y | Y | Y | 0.35 | − | Mesophilic | *Azotobacter vinelandii* |
| 441 | NC_011884\|YP_002484191.1 | R | R | Y | Y | Y | 0.35 | − | Mesophilic | *Cyanothece* sp. |
| 442 | NC_012660\|YP_002875363.1 | R | R | Y | Y | Y | 0.35 | − | Mesophilic | *Pseudomonas fluorescens* |
| 443 | NC_022738\|PVLB_24670 | R | R | Y | Y | Y | 0.35 | − | Mesophilic | *Pseudomonas* sp. |
| 444 | NC_019670\|YP_007032226.1 | R | R | Y | Y | Y | 0.35 | − | Mesophilic | *Pseudomonas* sp. |
| 445 | NC_019680\|YP_007060009.1 | R | R | Y | Y | Y | 0.35 | − | Thermophilic | *Synechococcus* sp. |
| 446 | NC_015222\|YP_004294728.1 | R | R | Y | Y | Y | 0.35 | − | Mesophilic | *Nitrosomonas* sp. |
| 447 | NC_021150\|YP_007900667.1 | R | R | Y | Y | Y | 0.35 | − | Mesophilic | *Azotobacter vinelandii* |
| 448 | NC_015733\|YP_004704456.1 | R | R | Y | Y | Y | 0.35 | − | Mesophilic | *Pseudomonas putida* |
| 449 | NC_017038\|YP_005384390.1 | R | R | Y | Y | Y | 0.35 | − | Mesophilic | *Synechocystis* sp. |
| 450 | NC_017039\|YP_005387559.1 | R | R | Y | Y | Y | 0.35 | − | Mesophilic | *Synechocystis* sp. |
| 451 | NC_021237\|YP_008003151.1 | R | R | Y | Y | Y | 0.35 | − | Mesophilic | *Pseudomonas protegens* |
| 452 | NC_021499\|YP_008105776.1 | R | R | Y | Y | Y | 0.35 | − | Mesophilic | *Pseudomonas resinovorans* |
| 453 | NC_016002\|YP_004846419.1 | R | R | Y | Y | Y | 0.35 | + | Mesophilic | *Pseudogulbenkiania* sp. |
| 454 | NC_017986\|YP_006386336.1 | R | R | Y | Y | Y | 0.35 | − | Mesophilic | *Pseudomonas putida* |
| 455 | NC_002947\|NP_747297.1 | R | R | Y | Y | Y | 0.35 | − | Mesophilic | *Pseudomonas putida* |
| 456 | NC_005773\|YP_272537.1 | R | R | Y | Y | Y | 0.35 | − | Mesophilic | *Pseudomonas syringae* |
| 457 | NC_004129\|YP_263022.1 | R | R | Y | Y | Y | 0.35 | − | Mesophilic | *Pseudomonas protegens* |
| 458 | NC_009656\|YP_001351278.1 | R | R | Y | Y | Y | 0.35 | − | Mesophilic | *Pseudomonas aeruginosa* |
| 459 | NC_009465\|YP_001219493.1 | R | R | Y | Y | Y | 0.35 | − | Mesophilic | *Candidatus Vesicomyosocius* |
| 460 | NC_023075\|χ969_24940 | R | R | Y | Y | Y | 0.35 | − | Mesophilic | *Pseudomonas monteilii* |
| 461 | NC_022591\|N296_5395 | R | R | Y | Y | Y | 0.35 | − | Mesophilic | *Pseudomonas aeruginosa* |
| 462 | NC_022361\|M801_5260 | R | R | Y | Y | Y | 0.35 | − | Mesophilic | *Pseudomonas aeruginosa* |

TABLE 2-continued mhFeBP1 homologs.

| # | Name | 10 | 101 | 142 | 198 | 199 | Identity | Gram | Temperature | Organism |
|---|---|---|---|---|---|---|---|---|---|---|
| 463 | NC_010322\|YP_001671474.1 | R | R | Y | Y | Y | 0.35 | – | Mesophilic | *Pseudomonas putida* |
| 464 | NC_022808\|PA1S_gp3150 | R | R | Y | Y | Y | 0.35 | – | Mesophilic | *Pseudomonas aeruginosa* |
| 465 | NC_020912\|YP_007712322.1 | R | R | Y | Y | Y | 0.35 | – | Mesophilic | *Pseudomonas aeruginosa* |
| 466 | NC_017052\|YP_005410266.1 | R | R | Y | Y | Y | 0.35 | – | Mesophilic | *Synechocystis* sp. |
| 467 | NC_021291\|YP_008046709.1 | R | R | Y | Y | Y | 0.35 | + | Mesophilic | *Spiribacter salinus* |
| 468 | NC_021491\|L483_31150 | R | R | Y | Y | Y | 0.35 | – | Mesophilic | *Pseudomonas putida* |
| 469 | NC_016830\|YP_005211024.1 | R | R | Y | Y | Y | 0.35 | – | Mesophilic | *Pseudomonas fluorescens* |
| 470 | NC_014501\|YP_003887996.1 | R | R | Y | Y | Y | 0.35 | – | Mesophilic | *Cyanothece* sp. |
| 471 | NC_021505\|YP_008116305.1 | R | R | Y | Y | Y | 0.35 | – | Mesophilic | *Pseudomonas putida* |
| 472 | NC_008027\|YP_610714.1 | R | R | Y | Y | Y | 0.35 | – | Mesophilic | *Pseudomonas entomophila* |
| 473 | NC_000911\|NP_442521.1 | R | R | Y | Y | Y | 0.35 | – | Mesophilic | *Synechocystis* sp. |
| 474 | NC_004757\|NP_841102.1 | R | R | Y | Y | Y | 0.35 | – | Mesophilic | *Nitrosomonas europaea* |
| 475 | NC_017549\|YP_005984172.1 | R | R | Y | Y | Y | 0.35 | – | Mesophilic | *Pseudomonas aeruginosa* |
| 476 | NC_023149\|SCV20265_5937 | R | R | Y | Y | Y | 0.35 | – | Mesophilic | *Pseudomonas aeruginosa* |
| 477 | NC_010296\|YP_001660682.1 | R | R | Y | Y | Y | 0.34 | – | Mesophilic | *Microcystis aeruginosa* |
| 478 | NC_021149\|YP_007895619.1 | R | R | Y | Y | Y | 0.34 | – | Mesophilic | *Azotobacter vinelandii* |
| 479 | NC_015731\|YP_004694426.1 | R | R | Y | Y | Y | 0.34 | – | Mesophilic | *Nitrosomonas* sp. |
| 480 | NC_015556\|YP_004472575.1 | R | R | Y | Y | Y | 0.34 | – | Mesophilic | *Pseudomonas fulva* |
| 481 | NC_004578\|NP_790164.1 | R | R | Y | Y | Y | 0.34 | – | Mesophilic | *Pseudomonas syringae* |
| 482 | NC_008816\|YP_001009743.1 | R | R | Y | Y | Y | 0.34 | – | Mesophilic | *Prochlorococcus marinus* |
| 483 | NC_008817\|YP_001011645.1 | R | R | Y | Y | Y | 0.34 | – | Mesophilic | *Prochlorococcus marinus* |
| 484 | NC_022664\|SPICUR_06490 | R | R | Y | Y | Y | 0.34 | + | Mesophilic | *Spiribacter* sp. |
| 485 | NC_007492\|YP_351158.1 | R | R | Y | Y | Y | 0.34 | – | Mesophilic | *Pseudomonas fluorescens* |
| 486 | NC_017911\|YP_006326554.1 | R | R | Y | Y | Y | 0.34 | – | Mesophilic | *Pseudomonas fluorescens* |
| 487 | NC_018643\|YP_006756812.1 | R | R | Y | Y | Y | 0.34 | + | Mesophilic | alpha proteobacterium |
| 488 | NC_009482\|YP_001227890.1 | R | R | Y | Y | Y | 0.34 | – | Thermophilic | *Synechococcus* sp. |
| 489 | NC_012032\|Chy400_0349 | R | R | Y | Y | Y | 0.34 | – | Mesophilic | *Chloroflexus* sp. |
| 490 | NC_007005\|YP_233355.1 | R | R | Y | Y | Y | 0.34 | – | Mesophilic | *Pseudomonas syringae* |
| 491 | NC_004113\|NP_681303.1 | R | R | Y | Y | Y | 0.34 | + | Thermophilic | *Thermosynechococcus elongatus* |
| 492 | NC_008319\|YP_730750.1 | R | R | Y | Y | Y | 0.34 | – | Thermophilic | *Synechococcus* sp. |
| 493 | NC_023064\|U771_3037S | R | R | Y | Y | Y | 0.34 | – | Mesophilic | *Pseudomonas* sp. |
| 494 | NC_012881\|YP_002993137.1 | R | R | Y | Y | Y | 0.34 | + | Mesophilic | *Desulfovibrio salexigens* |
| 495 | NC_023033\|NK55_11575 | R | R | Y | Y | Y | 0.34 | + | Mesophilic | *Thermosynechococcus* sp. |
| 496 | NC_019780\|YP_007173026.1 | R | R | Y | Y | Y | 0.34 | + | Mesophilic | *Dactylococcopsis salina* |
| 497 | NC_005072\|NP_893281.1 | R | R | Y | Y | Y | 0.34 | – | Mesophilic | *Prochlorococcus marinus* |
| 498 | NC_009482\|YP_001227889.1 | R | R | Y | Y | Y | 0.34 | – | Thermophilic | *Synechococcus* sp. |
| 499 | NC_008610\|YP_903912.1 | R | R | Y | Y | Y | 0.34 | – | Mesophilic | *Candidatus Ruthia* |
| 500 | NC_011729\|YP_002376116.1 | R | R | Y | Y | Y | 0.33 | – | Mesophilic | *Cyanothece* sp. |
| 501 | NC_010175\|Caur_0325 | R | R | Y | Y | Y | 0.33 | – | Thermophilic | *Chloroflexus aurantiacus* |
| 502 | NC_019689\|YP_007080757.1 | R | R | Y | Y | Y | 0.33 | + | Mesophilic | *Pleurocapsa* sp. |
| 503 | NC_020209\|YP_007399509.1 | R | R | Y | Y | Y | 0.33 | – | Mesophilic | *Pseudomonas poae* |
| 504 | NC_019778\|YP_007165071.1 | R | R | Y | Y | Y | 0.33 | + | Mesophilic | *Cyanobacterium stanieri* |
| 505 | NC_009840\|YP_001484574.1 | R | R | Y | Y | Y | 0.33 | – | Mesophilic | *Prochlorococcus marinus* |
| 506 | NC_009976\|YP_001551140.1 | R | R | Y | Y | Y | 0.33 | – | Mesophilic | *Prochlorococcus marinus* |
| 507 | NC_005070\|NP_897888.1 | R | R | Y | Y | Y | 0.33 | – | Thermophilic | *Synechococcus* sp. |
| 508 | NC_013173\|YP_003157279.1 | R | R | Y | Y | Y | 0.33 | – | Mesophilic | *Desulfomicrobium baculatum* |
| 509 | NC_007516\|YP_381882.1 | R | R | Y | Y | Y | 0.33 | – | Thermophilic | *Synechococcus* sp. |
| 510 | NC_022579\|YP_008685335.1 | R | R | Y | Y | Y | 0.32 | + | Mesophilic | *Desulfovibrio hydrothermalis* |
| 511 | NC_020055\|YP_007326536.1 | R | R | Y | Y | Y | 0.32 | + | Mesophilic | *Desulfovibrio hydrothermalis* |
| 512 | NC_007498\|YP_006716608.1 | R | R | Y | Y | Y | 0.32 | – | Mesophilic | *Pelobacter carbinolicus* |
| 513 | NC_008819\|YP_001015440.1 | R | R | Y | Y | Y | 0.32 | – | Mesophilic | *Prochlorococcus marinus* |
| 514 | NC_009091\|YP_001091585.1 | R | R | Y | Y | Y | 0.32 | – | Mesophilic | *Prochlorococcus marinus* |
| 515 | NC_007513\|YP_378003.1 | R | R | Y | Y | Y | 0.32 | – | Thermophilic | *Synechococcus* sp. |
| 516 | NC_007335\|YP_291968.1 | R | R | Y | Y | Y | 0.32 | – | Mesophilic | *Prochlorococcus marinus* |
| 517 | NC_008820\|YP_001018048.1 | R | R | Y | Y | Y | 0.32 | – | Mesophilic | *Prochlorococcus marinus* |
| 518 | NC_008358\|YP_761373.1 | R | R | Y | Y | Y | 0.32 | – | Mesophilic | *Hyphomonas neptunium* |
| 519 | NC_019675\|YP_007047725.1 | R | R | Y | Y | Y | 0.32 | + | Mesophilic | *Cyanobium gracile* |
| 520 | NC_005071\|NP_894120.1 | R | R | Y | Y | Y | 0.31 | – | Mesophilic | *Prochlorococcus marinus* |
| 521 | NC_009481\|YP_001225531.1 | R | R | Y | Y | Y | 0.3 | – | Thermophilic | *Synechococcus* sp. |
| 522 | NC_005042\|Pro1272 | R | R | Y | Y | Y | 0.3 | – | Mesophilic | *Prochlorococcus marinus* |
| 523 | NC_014355\|YP_003796723.1 | R | R | Y | Y | Y | 0.27 | – | Mesophilic | *Candidatus Nitrospira* |

The ttFeBP5 sequence homologs contained 626 hits for which the PCS was off by one residue (H=1). Of these, 522 corresponded to all the hits predicted to be $Fe^{III}$—$HCO_3$ binding proteins in the mhFeBP1 homolog family (i.e. H=0). Similarly, of the 142 hits identified in hmFeBP1 sequence homologs with one PCS residue missing (H=1), 70 were identified as H=0 sequences in the ttFeBP5 homolog family. These observations clearly supports that there are two subtly different schemes for coordinating $Fe^{III}$, which can both be identified using a PCS filter with the appropriate positional information.

TABLE 3 ttFeBP5 homologs.

| # | Name | 30 | 120 | 162 | 219 | 220 | Identity | Gram | Temperature | Organism |
|---|---|---|---|---|---|---|---|---|---|---|
| 1 | 4ELR\| | R | R | Y | Y | Y | | | | |
| 2 | NC_006461\|YP_144894.1 | R | R | Y | Y | Y | 1 | – | Thermophilic | *Thermus thermophilus* |
| 3 | NC_005835\|YP_005233.1 | R | R | Y | Y | Y | 0.99 | – | Thermophilic | *Thermus thermophilus* |
| 4 | NC_017587\|YP_006058112.1 | R | R | Y | Y | Y | 0.95 | – | Thermophilic | *Thermus thermophilus* |
| 5 | NC_017272\|YP_005641170.1 | R | R | Y | Y | Y | 0.93 | – | Thermophilic | *Thermus thermophilus* |
| 6 | NC_014974\|YP_004203468.1 | R | R | Y | Y | Y | 0.84 | – | Thermophilic | *Thermus scotoductus* |
| 7 | NC_017278\|YP_005653498.1 | R | R | Y | Y | Y | 0.83 | – | Mesophilic | *Thermus* sp. |
| 8 | NC_019386\|YP_006971576.1 | R | R | Y | Y | Y | 0.82 | – | Mesophilic | *Thermus oshimai* |
| 9 | NC_013946\|YP_003507791.1 | R | R | Y | Y | Y | 0.67 | + | Thermophilic | *Meiothermus ruber* |
| 10 | NC_015387\|YP_004366938.1 | R | R | Y | Y | Y | 0.57 | – | Thermophilic | *Marinithermus hydrothermalis* |
| 11 | NC_019793\|YP_007180090.1 | R | R | Y | Y | Y | 0.55 | + | Mesophilic | *Deinococcus peraridilitoris* |
| 12 | NC_014212\|YP_003686074.1 | R | R | Y | Y | Y | 0.54 | + | Thermophilic | *Meiothermus silvanus* |
| 13 | NC_014032\|YP_003572493.1 | R | R | Y | Y | Y | 0.52 | – | Mesophilic | *Salinibacter ruber* |
| 14 | NC_007677\|YP_446499.1 | R | R | Y | Y | Y | 0.52 | – | Mesophilic | *Salinibacter ruber* |
| 15 | NC_015161\|YP_004256093.1 | R | R | Y | Y | Y | 0.5 | + | Mesophilic | *Deinococcus proteolyticus* |
| 16 | NC_012526\|YP_002786654.1 | R | R | Y | Y | Y | 0.49 | + | Mesophilic | *Deinococcus deserti* |
| 17 | NZ_AOLM00000000\|WP_007274470.1 | R | R | Y | Y | Y | 0.34 | + | Mesophilic | *Haloferax sulfurifontis* |
| 18 | NZ_AOLP00000000\|WP_004970546.1 | R | R | Y | Y | Y | 0.34 | + | Mesophilic | *Haloferax denitrificans* |
| 19 | NC_014729\|YP_004036524.1 | R | R | Y | Y | Y | 0.34 | – | Mesophilic | *Halogeometricum borinquense* |
| 20 | NC_013967\|YP_003535749.1 | R | R | Y | Y | Y | 0.33 | + | Mesophilic | *Haloferax volcanii* |
| 21 | NZ_AOLL00000000\|WP_006600212.1 | R | R | Y | Y | Y | 0.33 | + | Mesophilic | *Haloferax alexandrinus* |
| 22 | NZ_AOLI00000000\|WP_004976562.1 | R | R | Y | Y | Y | 0.33 | + | Mesophilic | *Haloferax gibbonsii* |
| 23 | NZ_AOLH00000000\|WP_004063130.1 | R | R | Y | Y | Y | 0.33 | + | Mesophilic | *Haloferax lucentense* |
| 24 | NZ_AOLE00000000\|WP_008574569.1 | R | R | Y | Y | Y | 0.33 | + | Mesophilic | *Haloferax* sp. |
| 25 | NC_017941\|HFX_1795 | R | R | Y | Y | Y | 0.33 | + | Mesophilic | *Haloferax mediterranei* |
| 26 | NZ_AOLF00000000\|WP_008574569.1 | R | R | Y | Y | Y | 0.33 | + | Mesophilic | *Haloferax* sp. |
| 27 | NZ_AOLD00000000\|WP_008574569.1 | R | R | Y | Y | Y | 0.33 | + | Mesophilic | *Haloferax* sp. |
| 28 | NZ_ARPY01000000\|WP_021054224.1 | R | R | Y | Y | Y | 0.33 | – | Mesophilic | *Haloquadratum walsbyi* |
| 29 | NZ_AOLG00000000\|WP_008093701.1 | R | R | Y | Y | Y | 0.33 | + | Mesophilic | *Haloferax prahovense* |
| 30 | NZ_AOLI00000000\|WP_007540595.1 | R | R | Y | Y | Y | 0.32 | + | Mesophilic | *Haloferax larsenii* |
| 31 | NZ_AOLK00000000\|WP_008324506.1 | R | R | Y | Y | Y | 0.32 | + | Mesophilic | *Haloferax elongans* |
| 32 | NZ_AOLN00000000\|WP_008317080.1 | R | R | Y | Y | Y | 0.32 | + | Mesophilic | *Haloferax mucosum* |
| 33 | NC_021716\|YP_008191219.1 | R | R | Y | Y | Y | 0.32 | – | Mesophilic | *Alteromonas macleodii* |
| 34 | NC_021710\|YP_008170211.1 | R | R | Y | Y | Y | 0.32 | – | Mesophilic | *Alteromonas macleodii* |
| 35 | NC_021712\|YP_008174294.1 | R | R | Y | Y | Y | 0.32 | – | Mesophilic | *Alteromonas macleodii* |
| 36 | NC_021717\|YP_008194574.1 | R | R | Y | Y | Y | 0.32 | – | Mesophilic | *Alteromonas macleodii* |
| 37 | NC_023045\|I533_00730 | R | R | Y | Y | Y | 0.32 | – | Mesophilic | *Alteromonas macleodii* |
| 38 | NC_021713\|YP_008178099.1 | R | R | Y | Y | Y | 0.32 | – | Mesophilic | *Alteromonas macleodii* |
| 39 | NC_021714\|YP_008182148.1 | R | R | Y | Y | Y | 0.32 | – | Mesophilic | *Alteromonas macleodii* |
| 40 | NC_019393\|YP_006975038.1 | R | R | Y | Y | Y | 0.32 | – | Mesophilic | *Alteromonas macleodii* |
| 41 | NC_011138\|MADE_1000805 | R | R | Y | Y | Y | 0.32 | – | Mesophilic | *Alteromonas macleodii* |
| 42 | NC_008212\|YP_658265.1 | R | R | Y | Y | Y | 0.32 | – | Mesophilic | *Haloquadratum walsbyi* |
| 43 | NC_018679\|YP_006801087.1 | R | R | Y | Y | Y | 0.32 | – | Mesophilic | *Alteromonas macleodii* |
| 44 | NC_018692\|YP_006823164.1 | R | R | Y | Y | Y | 0.32 | – | Mesophilic | *Alteromonas macleodii* |
| 45 | NC_018632\|YP_006746238.1 | R | R | Y | Y | Y | 0.31 | – | Mesophilic | *Alteromonas macleodii* |
| 46 | NC_018678\|YP_006797203.1 | R | R | Y | Y | Y | 0.31 | – | Mesophilic | *Alteromonas macleodii* |
| 47 | NZ_AOLZ00000000\|WP_007140174.1 | R | R | Y | Y | Y | 0.31 | + | Mesophilic | *Halobiforma lacisalsi* |
| 48 | NC_017857\|YP_006294772.1 | R | R | Y | Y | Y | 0.31 | + | Mesophilic | *Methylophaga* nitratireducentic |
| 49 | NC_015554\|YP_004468950.1 | R | R | Y | Y | Y | 0.31 | – | Mesophilic | *Alteromonas* sp. |
| 50 | NZ_AOID00000000\|WP_006430814.1 | R | R | Y | Y | Y | 0.31 | + | Mesophilic | *Natrinema versiforme* |
| 51 | NC_020388\|YP_007488351.1 | R | R | Y | Y | Y | 0.31 | + | Mesophilic | *Natronomonas moolapensis* |
| 52 | NC_014297\|YP_003737103.1 | R | R | Y | Y | Y | 0.3 | N/a | Mesophilic | *Halalkalicoccus jeotgali* |
| 53 | NZ_AOJH00000000\|WP_008848743.1 | R | R | Y | Y | Y | 0.3 | + | Mesophilic | *Halorubrum kocurii* |
| 54 | NZ_AOJK00000000\|WP_008444444.1 | R | R | Y | Y | Y | 0.3 | + | Mesophilic | *Halorubrum californiensis* |
| 55 | NZ_AOJ100000000\|WP_006111552.1 | R | R | Y | Y | Y | 0.3 | + | Mesophilic | *Halorubrum coriense* |
| 56 | NC_021313\|YP_008054586.1 | R | R | Y | Y | Y | 0.3 | + | Mesophilic | *Salinarchaeum* sp. |
| 57 | NC_007481\|YP_340128.1 | R | R | Y | Y | Y | 0.3 | – | Psychrophilic | *Pseudoalteromonas haloplanktis* |
| 58 | NZ_AOJF00000000\|WP_004598669.1 | R | R | Y | Y | Y | 0.3 | + | Mesophilic | *Halorubrum litoreum* |
| 59 | NZ_AOIW00000000\|WP_004598669.1 | R | R | Y | Y | Y | 0.3 | + | Mesophilic | *Halorubrum terrestre* |
| 60 | NZ_AOJN00000000\|WP_004598669.1 | R | R | Y | Y | Y | 0.3 | + | Mesophilic | *Halorubrum distributum* |
| 61 | NZ_AOJJ00000000\|WP_004598669.1 | R | R | Y | Y | Y | 0.3 | + | Mesophilic | *Halorubrum arcis* |
| 62 | NC_014803\|YP_004068662.1 | R | R | Y | Y | Y | 0.3 | – | Psychrophilic | *Pseudoalteromonas* sp. |
| 63 | NZ_AOJI00000000\|WP_008002218.1 | R | R | Y | Y | Y | 0.29 | + | Mesophilic | *Halorubrum aidingense* |
| 64 | NZ_AGCY01000000\|WP_021043411.1 | R | R | Y | Y | Y | 0.29 | + | Mesophilic | *halophilic archaeon* |
| 65 | NC_012029\|YP_002564837.1 | R | R | Y | Y | Y | 0.29 | + | Mesophilic | *Halorubrum lacusprofundi* |
| 66 | NZ_AOJD00000000\|WP_006629340.1 | R | R | Y | Y | Y | 0.29 | + | Mesophilic | *Halorubrum tebenquichense* |
| 67 | NZ_AOIQ00000000\|WP_007702269.1 | R | R | Y | Y | Y | 0.29 | + | Mesophilic | *Halovivax asiaticus* |
| 68 | NC_019964\|YP_007285378.1 | R | R | Y | Y | Y | 0.29 | + | Mesophilic | *Halovivax ruber* |
| 69 | NZ_AOJG00000000\|WP_008005399.1 | R | R | Y | Y | Y | 0.29 | + | Mesophilic | *Halorubrum lipolyticum* |
| 70 | NZ_AOJO00000000\|WP_008582685.1 | R | R | Y | Y | Y | 0.29 | + | Mesophilic | *Halorubrum hochstenium* |
| 71 | NZ_AOIA00000000\|WP_008420339.1 | R | R | Y | Y | Y | 0.29 | + | Mesophilic | *Natronococcus jeotgali* |

Example 3. Sensor Engineering Phase 2: Lead Protein Validation Using Ligand-Mediated Thermostability Shifts The ligand-binding properties of the proteins selected were determined experimentally. These experiments comprise four successive steps:

1. Synthetic gene construction. The amino acid sequence of the homology leads are backtranslated into DNA sequences. These are optimized for directing heterologous cytoplasmic expression of the protein homologues in *E. coli*, using either the OrfOpt or OrfMorph programs. These programs predict mRNA sequences that direct high-level protein expression in *E. coli*. The predicted gene sequences are assembled de novo from synthetic oligonucleotides.
2. Heterologous protein expression of the homologues in *E. coli*. Plasmids carrying the synthetic expression constructs (see above) were transformed into KRX *E. coli* K12 derivative strain) competent cells (Promega, Technical Bulletin TB352). Protein production was induced in bacterial cultures of these cultures, as described in the Materials and Methods.
3. Purification of successfully expressed protein using immobilized metal affinity chromatography, as described in Materials and Methods.
4. Verification of ligand binding. Determination of the ligand-binding properties of the purified proteins using a thermal stability shift assay, as described in Materials and Methods.

Lead Verification by Thermal Shift Analysis of Bicarbonate-Calcium Binding Proteins.

Figure 5:
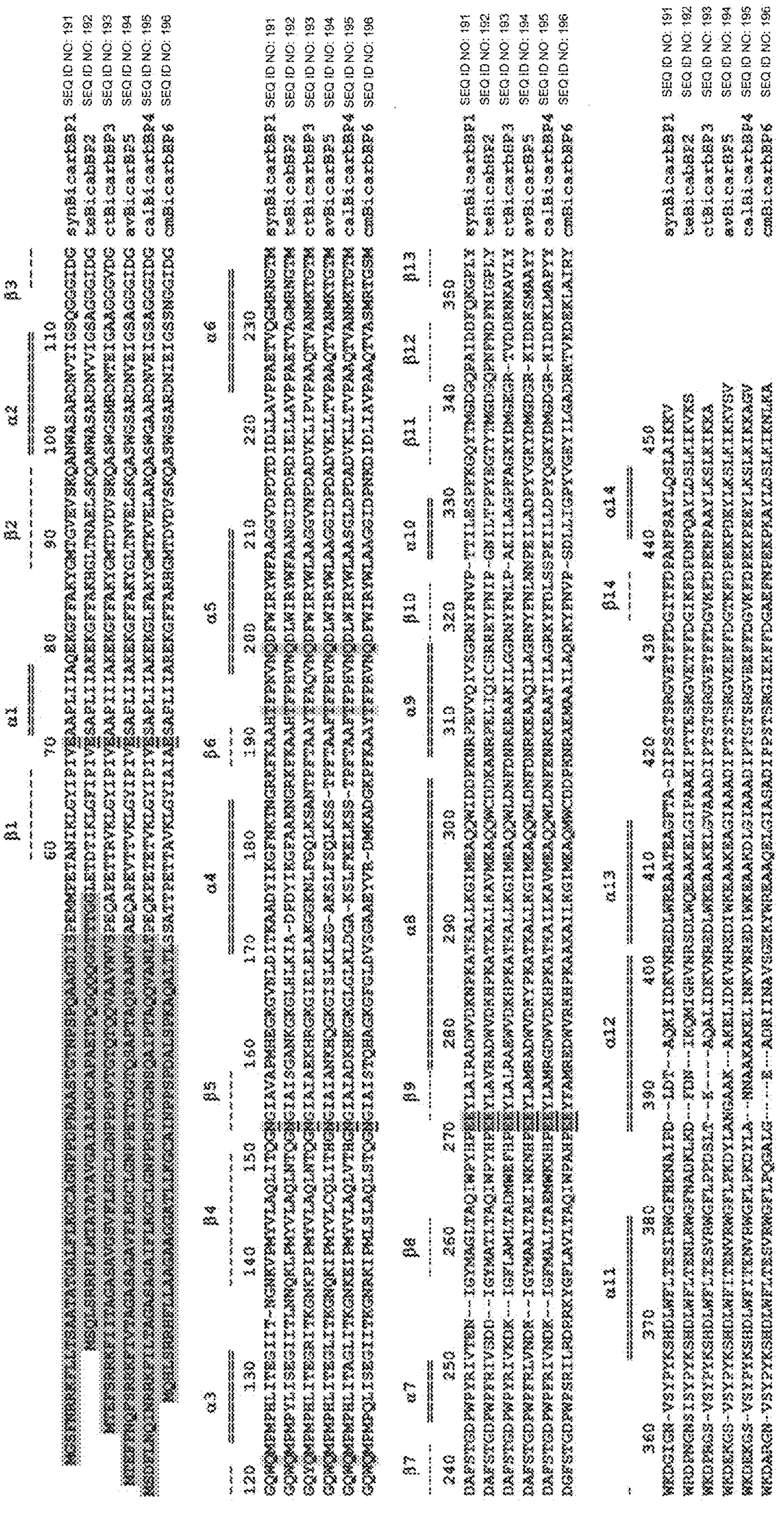
FIG. 5 shows an alignment of selected sequence hits (SEQ ID NO: 191-196) using Synechocystic PCC 6803 as seed, with a PCS defined by its structure (PDB accession 2i4c; sequence numbering according to PDB file). Leader peptide and PCS positions indicated in gray. $Ca^{2+}$-coordinating residues underlined.

The lead sequence and five additional homologs with identical PCS sequences (i.e. H=0) were selected, probing different degrees of sequence identity with the seed (FIG. 5). Synthetic genes with open reading frames optimized for heterologous protein over-expression in *Escherichia coli* using OrfOpt (Allert, Cox and Hellinga 2010) were synthesized for each lead. Three of the six leads produced soluble protein in a T7 expression system in sufficient quantity for functional analysis. The proteins were purified by immobilized metal affinity chromatography via a hexa-histidine tag fused to their carboxy-terminus. Bicarbonate binding was tested in a thermal stability shift assay (Layton and Hellinga 2010). All leads bound bicarbonate, and not nitrate (Table 4). The bicarbonate-binding protein from *Anabaena variabilis* (avBicarbBP5) was selected for further engineering.

TABLE 4

Ligand-binding and thermostability properties of synBicarbBP homologs.

| | | NCBI Accession codes | | | Soluble | Thermo-stability[c] | Ligand binding[d] | |
|---|---|---|---|---|---|---|---|---|
| Name | Organism | Genome | Protein | Identity[a] | Expression[b] | $^{apo}T_m$ (C.) | Bicarbonate | Nitrate |
| synBicarbBP1 | *Synechocystis* sp. | NC_017052 | YP_005410477.1 | 1 | n | | | |
| teBicarbBP2 | *Thermosynechococcus elongatus* | NC_004113 | NP_682790.1 | 0.83 | n | | | |
| ctBicarbBP3 | *Chroococcidiopsis thermalis* | NC_019695 | YP_007090308.1 | 0.67 | y | 86 | y | n |
| calBicarbBP4 | *Calothrix* sp. | NC_019751 | YP_007137061.1 | 0.65 | y | 89 | y | n |
| avBicarbBP5 | *Anabaena variabilis* | NC_007413 | YP_321546.1 | 0.66 | y | 82 | y | n |
| cmBicarbBP6 | *Chamaesiphon minutus* | NC_019697 | YP_007099445.1 | 0.63 | n | | | |

[a]Number of identical residues shared with the probe sequence.
[b]Judged by SDS gel electrophoresis of the soluble fraction of a total lysate.
[c]Determined in a Roche LightCycler, using SYPRO Orange to monitor the appearance of unfolded protein.
[d]Determined by monitoring an increase in the thermostability of the protein in the presence of ligand.

Lead Verification by Thermal Shift Analysis of Ferric-Bicarbonate Binding Proteins.

Figure 6B:
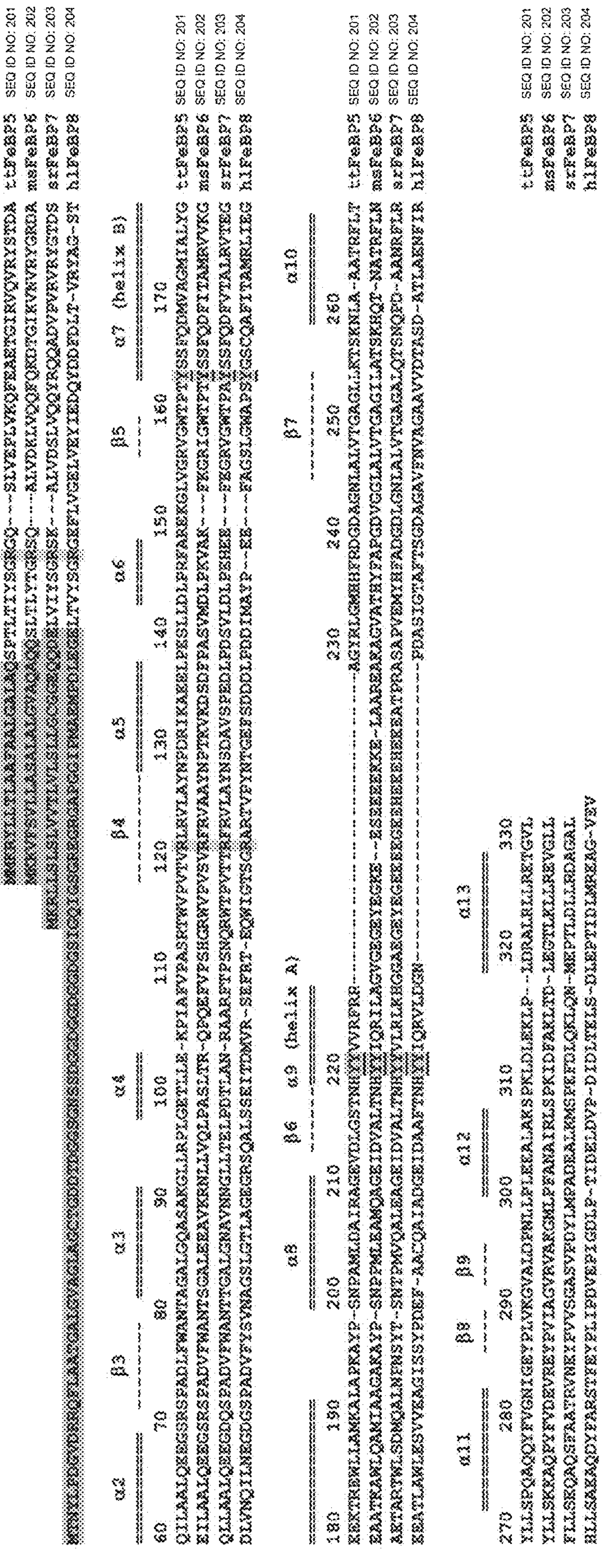
FIG. 6B (SEQ ID NO: 201-204): Seed is *Thermus thermophilus* Fe—$HCO_3$ binding protein (sequence numbering and secondary structure assignments according to PDB accession 4elr). Leader peptide sequences removed in expression constructs and PCS residues are highlighted. Tyrosine residues participating in iron coordination are underlined. Note the difference in the location of the tyrosine in helix B. In the mhFeBP1 homologs it is located at the N-terminus of that helix; in the tthFeBP5 homologs it is located two residues (~½ helical turn) in from the N-terminus.

For each of the two leads, the lead and three sequence homologs with identical PCS sequences were selected (FIG. 6). Synthetic genes with open reading frames optimized for heterologous protein over-expression in *Escherichia coli* using OrfMorph (see Materials and Methods) were synthesized for each lead. Six of the eight leads produced soluble protein in a T7 expression system in sufficient quantity for functional analysis (FIG. 6). The two leads from the ttFeBP5-seeded search precipitated upon storage. The proteins were purified by immobilized metal affinity chromatography via a hexa-histidine tag fused to their carboxy-terminus. Bicarbonate binding was tested in a thermal stability shift assay (Layton and Hellinga 2010). All four soluble leads bound bicarbonate (Table 5). The bicarbonate-binding protein from *Thermosynechococcus elongatus* (teFeBP3) was selected for further engineering. It is noteworthy that function was predicted accurately for homologs of considerably less than 60% sequence identity (the lowest is 26%), which is considered the lower limit for predicted function conservation on overall homology alone (Todd 2001, Tian 2003). The PCS-based method therefore is a powerful for the prediction of functional conservation in distantly related proteins.

TABLE 5

Ligand-binding and thermostability properties of FeBP homologs.

| Probe[a] | Name | Organism | NCBI Accession codes Genome | Protein | Identity[b] | Soluble Expression[c] | Thermo-stability[d] $^{apo}T_m$ (C) | Bicarbonate binding[e] |
|---|---|---|---|---|---|---|---|---|
| lsiO | mhFeBP1 | *Mannheimia haemolytica* | NC_0121082 | YP_007884192.1 | 1 | y | ~50[f] | y |
| | exiFeBP2 | *Exiguobacterium* sp. | NC_012673 | YP_002886303.1 | 0.41 | y | 37 | y |
| | teFeBP3 | *Thermosynechoccus elongatus* | NC_004113 | NP_681303.1 | 0.34 | y | 67 | y |
| | cnFeBP4 | *Candidatus nitrospira* | NC_014355 | YP_003796723.1 | 0.26 | y | ~50[g] | y[g] |
| 4elr | ttFeBP5 | *Thermus thermophilus* | NC_006461 | YP_144894.1 | 1 | y[h] | | |
| | msFeBP6 | *Meiothermus silvanus* | NC_014212 | YP_003686074.1 | 0.54 | y[h] | | |
| | srFeBP7 | *Salinibacter ruber* | NC_014032 | YP_003572493.1 | 0.52 | n | | |
| | hlFeBP8 | *Halorubrum lacusprofundi* | NC_012029 | YP_002564837.1 | 0.31 | n | | |

[a]PDB accession of the probe sequence and PCS definition (see Table 2-3).
[b]Number of identical residues shared with the probe sequence.
[c]Judged by SDS gel electrophoresis of the soluble fraction of a total lysate.
[d]Determined in a Roche LightCycler, using SYPRO Orange to monitor the appearance of unfolded protein.
[e]Determined by monitoring an increase in the thermostability of the protein in the presence of ligand.
[f]Estimate: multi-state unfolding.
[g]Estimated from incomplete data
[h]Precipitated during dialysis.

Example 4. Sensor Engineering Phase 3: Cysteine Mutant Scans and Fluorophore Screening to Identify Fluorescently Responsive Sensors for Target Ligand Semi-synthetic FRSs can be engineered by site-specifically attaching thiol-reactive, environmentally sensitive fluorophores that respond to ligand-mediated conformational changes. Identification of FRS candidates that can be used for sensing applications comprises three steps:

1. Cysteine scan. Mutant ligand-binding proteins containing single cysteines are constructed for site-specific attachment of thiol-reactive fluorophores. General structural principles have been established to identify positions in PBPs where attached single fluorophores are likely to exhibit ligand-dependent responses (de Lorimier et al. 2002). Candidate positions fall into three classes: endosteric, replacing a residue that contacts the ligand directly; peristeric, located at the rim of the binding site; allosteric (Marvin et al. 1997, Marvin 1998), located outside the binding site at sites that undergo local structural changes in concert with the hinge-bending motion.
2. Fluorophore screening. Thiol-reactive, environmentally sensitive fluorophores are attached to each cysteine mutant prepared in step 1.
3. Evaluation of the ligand-mediated change of all the fluorescent conjugates prepared in step 2. Responses to ligand binding in which there is both a change in fluorescence emission intensity and spectral shape are essential for chemometric applications, because such changes enable ratiometric measurements. Changes in spectral shape typically are accompanied by a shift in the wavelength of the emission intensity maxima. Three classes of fluorescent responses are possible:
   i. No response.
   ii. Monochromatic response (emission intensity increases or decreases without a change in spectral shape)
   iii. Dichromatic response (both intensity and spectral shape changes) which can be classified into two sub-classes:
      i. Hypsochromatic: emission intensity shifts to shorter wavelengths upon binding ligand ("blue shift").
      ii. Bathochromatic: emission intensity shifts to longer wavelengths upon binding ligand ("red shift").
4. Double labeling strategies to convert monochromatic responses into dichromatic signals, or to improve upon weak dichromatic responses.

Of particular interest are ligand-mediated responses that change both the shape and intensity of the emission spectra such that the ratio of the emission intensities at two appropriately chosen wavelengths reports on analyte concentration (dichromatic response). Such ratiometric measurements provide an internally consistent, self-calibrating reference, which removes the necessity for carrying out on-board calibration in conjunction with each measurement, obviating the need for multiple components and fluidic circuitry (Demchenko 2010, Demchenko 2014). The naphthalene derivatives Acrylodan and Badan have been particularly effective in establishing dichromatic responses in singly labeled proteins, because ligand-mediated protein conformational changes can be coupled to an exchange between two different fluorophore conformations (twists) that emit at different wavelengths. Initial screens therefore employ these fluorophores to identify locations where fluorescent conjugates respond to ligand binding. Two dominant electronic transitions give rise to fluorescence emission in these fluorophores with maxima in the blue (<500 nm) and green (>500 nm) regions, respectively.

Cysteine Scans to Identify Semisynthetic Fluorescent Bicarbonate Sensors in avBicarbBP5.

We tested the bicarbonate responses of Acrylodan conjugates attached to cysteine mutations at peristeric and endosteric positions of avBicarbBP (FIG. 3). With the exception of N146C, all positions exhibited monochromatic or no responses (Table 6). In the case of 146C, there was only a small shift in emission wavelengths, and no significant change in intensity. Several conjugates were predominantly in the green state (18C, 49C, 71C), or blue (141C, 190C) states, whereas others had a mixture of the two forms (16C, 17C, 140C, 143C, 146C, 194C). Acrylodan therefore could adopt both states in avBicarbBP5, but these did not alter in response to bicarbonate binding, with the exception of 146C. These results suggest that ligand binding is not accompanied by a large conformational change that couples to a redistribution of internal conjugate conformations. The structure of the hinge region in avBicarbBP5 clearly is not flexible, but resembles a small protein domain with a significant hydrophobic core (FIG. 3). The observed absence of conformational coupling between bicarbonate binding and Acrylodan twisting therefore is consistent with the avBicarbBP5.

TABLE 6

Bicarbonate response of Acrylodan conjugates in a cysteine scan of the avBicarbBPS scaffold.

| Position[a] | | | Response | | | Thermo- |
|---|---|---|---|---|---|---|
| | | | | | Excited | stability[f] |
| avBicarbBP6 | synBicarbBP1 | Class[b] | Shape[c] | Intensity[d] | states[e] | $^{apo}T_m$ (K) |
| I16C | 66 | p | 0 | | b/g | 334 |
| P17C | 67 | p | m | + | b/g | 326 |
| I18C | 68 | e | 0 | | g | 336 |
| W49C | 99 | e | 0 | | g | 322 |
| Q71C | 121 | e | 0 | | g | 343 |
| F140C | H191 | p | m | + | b/g | 338 |
| T141C | 192 | e | m | + | b | 331 |
| F142C | 193 | p | m | + | g | 331 |
| P143C | 194 | p | 0 | | b/g | 325 |
| N146C | 197 | p | d | 0 | b/g | 333 |
| T190C | 241 | p | m | + | b | 329 |
| W194C | 245 | p | m | + | b/g | 329 |

[a]Aligned position in the synBicarbBP1 numbering of the 2i4c PDB file is given.

[b]e, endosteric; p, peristeric.

[c]m, monochromatic; d, dichromatic (i.e. spectral shape changes); 0, no change.

[d]+, increases in response to bicarbonate; decreases; 0, no change.

[e]The dominant population of the excited states in the absence of bicarbonate is determined from the emission band intensities: b, blue (maxima < 500 nm); g, green (maxima > 500 nm); b/g, mixed population of blue and green.

[f]Determined by thermal melts based on Acrylodan fluorescence. The wild-type protein $^{apo}T_m$ = 355 K.

In the absence of conformational coupling between ligand binding and fluorophore twisting as a mechanism to obtain fluorescently responsive sensors, we tested Pacific Blue conjugates. We found that at positions 18C, 190C and 194C, Pacific Blue exhibited monochromatic changes in emission intensity in response to bicarbonate binding. Pacific Blue is a hydroxycoumarin derivative, the phenolate of which corresponds to the excited state (Sun 1998). It is therefore likely that binding of $Ca^{2+}$ stabilizes the excited state, with a concomitant increase in quantum yield.

Introducing Ratiometric Bicarbonate Responses in avBicarbBP5 Using Non-Geometrically Modulated FRET.

We have shown previously that fluorescence resonance energy transfer can be used to report on binding events by pairing an environmentally sensitive, ligand-responsive donor or acceptor with an insensitive partner. Ratiometric measurements are based on changes in donor and acceptor intensities in such non-geometric modulated FRET (ngmFRET) systems. The dichromatic response arises from ligand-mediated effects on the spectral overlap between the partners or the non-radiative decay rates of the sensitive fluorophore, either singly or in combination.

Figure 7A:
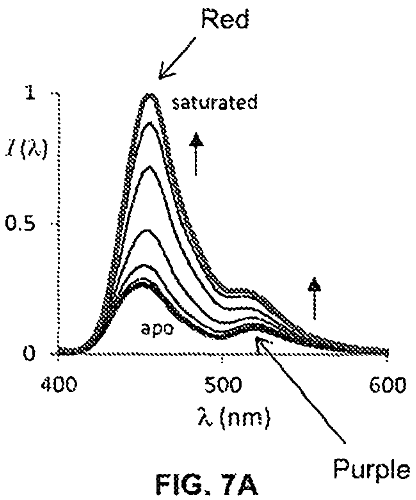
FIGS. 7A-C are graphs showing the fluorescent response of avBicarbBP5 194C·Pacific Blue, βZif Oregon Green to bicarbonate in the presence of $CaCl_2$) (1 mM).
Figure 7B:
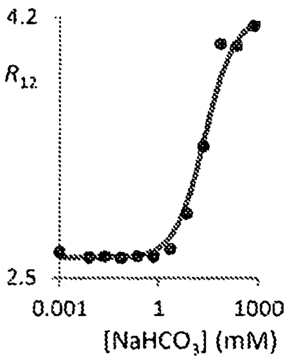
Figure 7C:
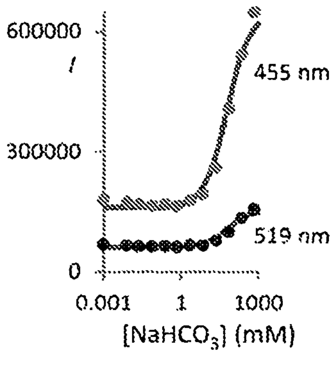

To convert the monochromatic Pacific Blue responses of the 18C and 194C conjugates into dichromatic signals, we constructed an ngmFRET system by fusing a C-terminal βZif domain which enables site-specific attachment a second fluorophore using orthogonal thiol chemistries (Smith et al. 2005). This avBicarbBP5 fusion protein was doubly labelled with Pacific Blue ngmFRET donor in the binding site and IANBD or the Fluorescein derivatives 5-IAF and Oregon Green as the ngmFRET acceptor at the C-terminal βZif. These conjugates exhibited strong dichromatic responses to bicarbonate binding (FIG. 7). Both donor and acceptor emissions increased in response to bicarbonate binding, which is the expected ngmFRET pattern for ligand-mediated changes in the non-radiative decay rates of a responsive donor (Allert 2015).

Cysteine Scans to Identify Semisynthetic Fluorescent Bicarbonate Sensors in teFeBP3.

Figure 8A:
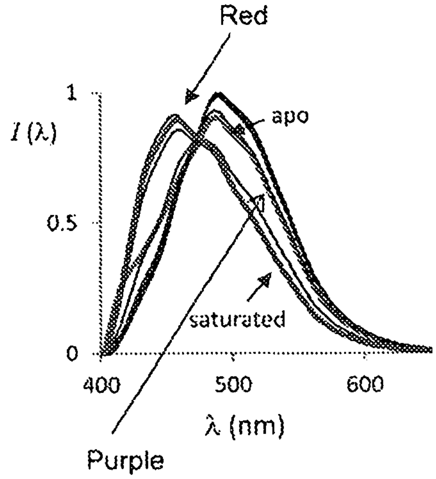
FIGS. 8A-C are graphs showing the fluorescent response of teFeBP3 270C·Badan to bicarbonate.
Figure 8B:
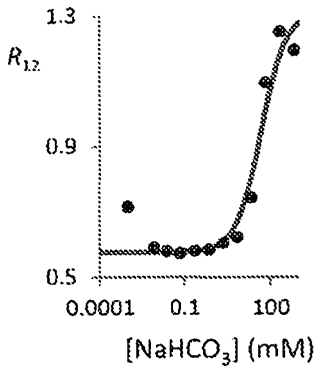
Figure 8C:
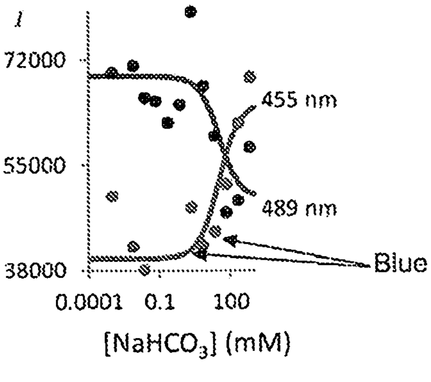

Several Acrylodan and Badan conjugates exhibited dichromatic responses to bicarbonate binding (Table 7). It is therefore possible to establish coupling between ligand-mediated protein conformational changes and conjugate twisting. The largest response was observed for the teFeBP3 E270C·Badan conjugate (FIG. 8). The apparent affinity for bicarbonate, based on the ratiometric signal, is 48 mM, which is suitable for measurements in the clinical reference concentration range.

TABLE 7

Bicarbonate response of Acrylodan conjugates in a cysteine scan of peristeric sites in the teFeBP3 scaffold.

| Position[a] | | Response: Acrylodan | | | Response: Badan | | |
|---|---|---|---|---|---|---|---|
| teFeBP3 | mhFeBP1 | Shape[b] | Intensity[c] | Excited states[d] | Shape[b] | Inten-sity[c] | Excited states[d] |
| A8C | Y9 | 0 | | b/g | m | + | b/g |
| H10C | Q11 | 0 | | b/g | d | − | b/g |
| D12C | Y13 | 0 | | b/g | 0 | | g |
| T13C | L14 | 0 | | b/g | d | − | g |
| A36C | 36 | m | − | b/g | d | − | b |
| V58C | 58 | d | + | b/g | d | + | b/g |
| R135C | 136 | m | + | g | 0 | | g |
| N139C | 140 | m | − | g | 0 | | b |
| I140C | S141 | 0 | | g | m | − | g |
| N176C | G177 | 0 | | g | m | − | g |
| N195C | 196 | 0 | | g | 0 | | b |
| N268C | 266 | 0 | | b | m | − | b/g |
| E270C | 268 | d | − | g | d | − | g |

[a]Aligned position in the mhFeBP1 numbering of the 1si0 PDB file is given.

[b]m, monochromatic; d, dichromatic (i.e. spectral shape changes); 0, no change.

[c]+, increases in response to bicarbonate; decreases; 0, no change. In the presence of $FeCl_3$ (10 μM).

[d]The dominant population of the excited states in the absence of bicarbonate is determined from the emission band intensities: b, blue (maxima < 500 nm); g, green (maxima > 500 nm); b/g, mixed population of blue and green.

Semisynthetic Fluorescent Calcium Sensors in avBicarbBP5.

Figure 9A:
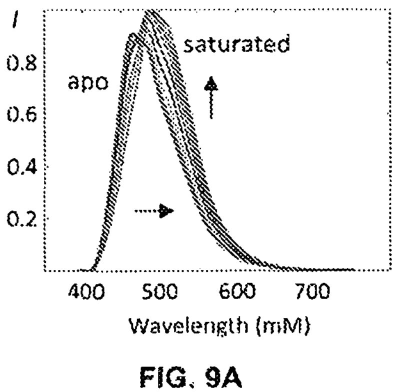
FIGS. 9A-C are graphs showing the fluorescent response of avBicarbBP5 18C·Badan to calcium.
Figure 9B:
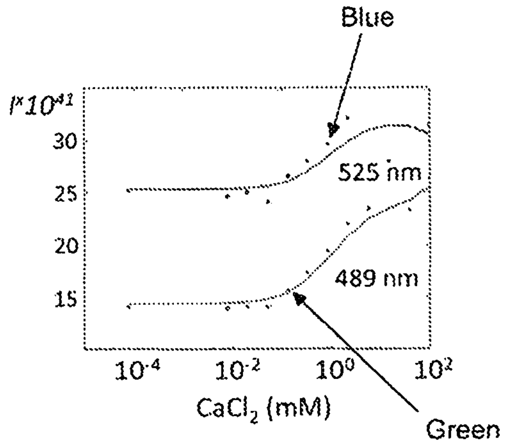
Figure 9C:
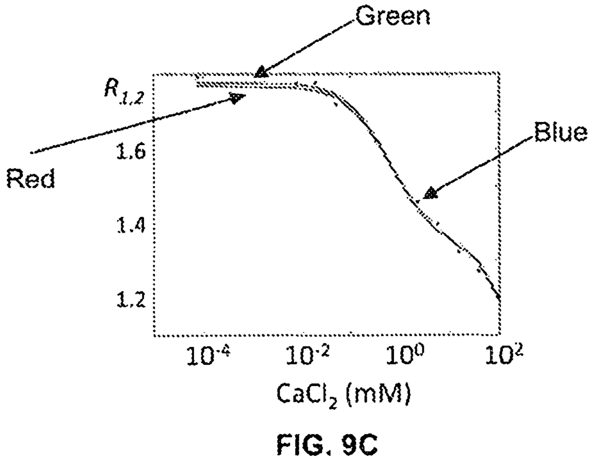

We tested fluorescent conjugates for response to $Ca^{2+}$ in the absence of bicarbonate (Table 8). Pacific Blue conjugates exhibited excellent responses at two sites (16C and 18C) and showed responses at 17C, 49C, 140C and 142C. Badan exhibited dichromatic response to $Ca^{2+}$ at 17C, 18C, 140C, 142C and 194C (FIG. 9). The 17C and 18C conjugates bind $Ca^{2+}$ with 1-2 mM affinities. Accordingly, these conjugates are well-suited for measuring $Ca^{2+}$ concentrations in the clinical reference range.

The cysteine scans also demonstrate that $Ca^{2+}$ and bicarbonate binding functions can be separated. The $Ca^{2+}$ affinities of the five 16C, 17C, 18C, 140C, and 142C conjugates change little, if at all, in the presence of 50 mM bicarbonate (Table 9). The avBicarbBP5 protein therefore can be engineered to function as either a $Ca^{II}$—$HCO_3$ or a $Ca^{2+}$ sensor.

TABLE 8

Calcium response in a cysteine scan of the avBicarbBP5 scaffold[a].

| Position[b] | | Class | Conjugate | Shape | Emission wavelength (nm) | | $K_d$ (mM) | |
|---|---|---|---|---|---|---|---|---|
| avBicarbBP5 | synBicarbBP1 | [c] | [d] | [e] | $\lambda_1$ | $\lambda_2$ | $^{app}K_d$ | $^{true}K_d$ |
| I16C | 66 | p | A | m | 481 | 526 | 22 | 22 |
| | | | B | 0 | | | | |
| | | | PB | m/d | 445 | 475 | 0.30 | 0.64 |
| | | | A532 | m/d | 540 | 582 | 0.30 | 0.71 |
| P17C | 67 | p | A | d | 443 | 548 | 1.9 | 2.5 |
| | | | B | d | 488 | 553 | 2.0 | 2.4 |
| | | | PB | m/d | 436 | 479 | 3.1 | 14 |
| | | | A532 | nt | 555 | 540 | 24 | 68 |
| I18C | 68 | e | A | d | 461 | 544 | 2.0 | 2.7 |
| | | | B | d | 441 | 548 | 1.1[f] | 2.2[f] |
| | | | PB | m/d | 444 | 479 | 2.7 | 5.3 |
| | | | A532 | m | 559 | 540 | 2.4 | 3.2 |
| W49C | 99 | e | A | 0 | | | | |
| | | | B | 0 | | | | |
| | | | PB | m | 442 | 477 | 41 | 33 |
| Q71C | 121 | e | A | 0 | | | | |
| | | | B | 0 | | | | |
| | | | PB | 0 | | | | |
| F140C | H191 | p | A | d | 483 | 520 | 0.35 | 0.41 |
| | | | B | d | 440 | 552 | 0.19 | 0.22 |
| | | | PB | m | 451 | 481 | 0.28 | 0.34 |
| | | | A532 | m | 549 | 579 | 2.0 | 2.5 |
| T141C | 192 | e | A | d | 440 | 531 | 0.46 | 0.53 |
| | | | B | 0 | | | | |
| | | | PB | 0 | | | | |
| | | | A532 | m/d | 555 | 540 | 0.6 | 0.7 |

TABLE 8-continued

Calcium response in a cysteine scan of the avBicarbBP5 scaffold[a].

| Position[b] | | Class | Conjugate | Shape | Emission wavelength (nm) | | $K_d$ (mM) | |
|---|---|---|---|---|---|---|---|---|
| avBicarbBP5 | synBicarbBP1 | [c] | [d] | [e] | $\lambda_1$ | $\lambda_2$ | ${}^{app}K_d$ | ${}^{true}K_d$ |
| F142C | 193 | p | A | d | 487 | 518 | 0.23 | 0.22 |
| | | | B | d | 483 | 515 | 0.2 | 0.2 |
| | | | PB | m | 460 | 435 | 0.04 | 0.04 |
| | | | A532 | m/d | 555 | 540 | 0.31 | 0.68 |
| P143C | 194 | p | A | m | 462 | 522 | 0.43 | 0.42 |
| | | | B | m | 488 | 568 | 0.92 | 0.98 |
| | | | PB | 0 | | | | |
| N146C | 197 | p | A | 0 | | | | |
| | | | B | 0 | | | | |
| | | | PB | 0 | | | | |
| T190C | 241 | p | A | d | 491 | 451 | 0.54 | 0.64 |
| | | | B | 0 | | | | |
| | | | PB | 0 | | | | |
| W194C | 245 | p | A | d | 483 | 510 | 20[f] | 10[f] |
| | | | B | m/d | 487 | 515 | 1.2 | 0.94 |
| | | | PB | 0 | | | | |

[a]Determined by fitting the ratiometric signal of the intensities measured at λ1 and λ2 to equations 1-5.
[b]Aligned position in the synBicarbBP numbering of the 2i4c PDB file is given.
[c] e, endosteric; p, peristeric.
[d] A, Acrylodan; B, Badan; PB, Pacific Blue, A532, Alexa532.
[e] m, monochromatic; d, dichromatic (i.e. spectral shape changes); 0, no or very small change.
[f]Approximate value.

TABLE 9

Calcium affinities for various avBicarbBP5 conjugates in the presence and absence of $NaHCO_3$[a].

| Mutation | Conjugate[b] | Wavelengths (nm) | | Affinity (mM) Calcium | | Affinity (mM) Calcium ($NaHCO_3$)[c] | |
|---|---|---|---|---|---|---|---|
| | | $\lambda_1$ | $\lambda_2$ | ${}^{app}K_d$ | ${}^{true}K_d$ | ${}^{app}K_d$ | ${}^{true}K_d$ |
| 16C | PB | 445 | 475 | 0.30 | 0.64 | 0.27 | 0.64 |
| 17C | B | 488 | 553 | 2.0 | 2.4 | 1.9 | 2.2 |
| 18C | PB | 444 | 479 | 2.7 | 5.3 | 2.1 | 4.2 |
| 140C | B | 440 | 552 | 0.19 | 0.22 | 0.1 | 0.12 |
| 142C | B | 483 | 515 | 0.2 | 0.2 | 0.12 | 0.11 |

[a]Determined by fitting the ratiometric signal of the intensities measured at λ1 and λ2 to equations 1-5.
[b]B, Badan; PB, Pacific Blue.
[c]Calcium titration in the presence of 50 mM $NaHCO_3$.

Example 5. Sensor Engineering Phase 4: Affinity Tuning

The response of biosensors based on *Langmuir* binding isotherms is most sensitive at analyte concentrations that match the apparent $K_d$ value of the protein (de Lorimier et al. 2002, Marvin et al. 1997). Accordingly sensor performance frequently needs to be optimized by "tuning" ligand affinity. The mutations that alter ligand affinities in PBPs generally fall into two classes:

1. Alteration of direct interactions in the PCS between the protein and the bound bicarbonate.
2. Manipulation of the equilibrium between the open and closed states (Marvin and Hellinga 2001).
3. Indirect interactions that alter the geometry of the binding site.

Tuning of Bicarbonate Affinity in avBicarBP5.

Figure 10A:
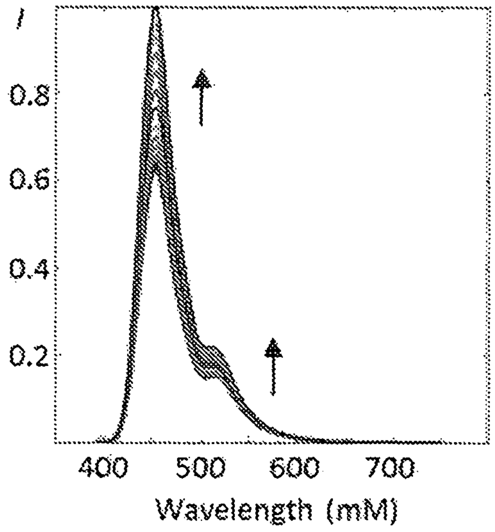
FIGS. 10A-C are graphs showing that the avBicarb5 18C, 16F·Pacific Blue, βZif·5-IAF conjugate exhibits a dichromatic response to bicarbonate in the presence of $CaCl_2$) (1 mM).
Figure 10B:
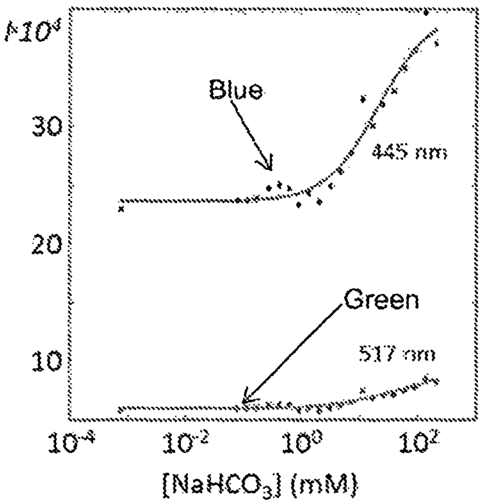
Figure 10C:
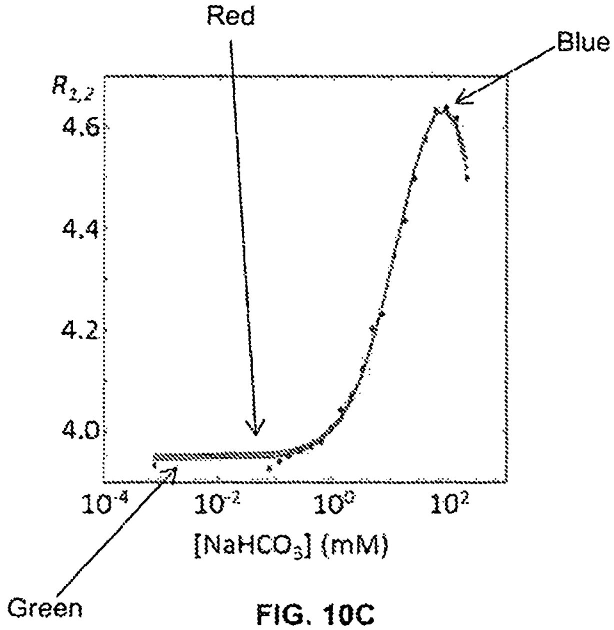

Physiological blood bicarbonate levels for a healthy individual are typically between ~20 mM to ~30 mM (Burtis 2012). A series of mutations were introduced at positions 16 and 141, respectively, to obtain variants with $K_d$ values near that concentration range (Table 10). Position 16 is located adjacent to the binding site, but does not interact directly with the bound complex. Mutations at this location therefore fall into the 3rd category. The threonine at position 141 (T192 in synBicarbBP1) forms a hydrogen bond with the bound bicarbonate (FIG. 3C). Mutations at this position therefore fall into the 1st category. The effects of these mutations were evaluated using ngmFRET in the doubly labeled C-terminal βZif fusions (Table 10). The I16F mutation in the 18C Pacific Blue background, combined with a Fluorescein acceptor, gives a response with a near-optimally tuned bicarbonate affinity (FIG. 10).

TABLE 10

Bicarbonate response of βZif conjugates of the avBicarbBP5 scaffold[a].

| Conjugate | | | Emission wavelength (nm) | | $K_d$[b] (mM) | | $K_d$[c,e] (mM) | |
|---|---|---|---|---|---|---|---|---|
| Mutant | avBicarbBP5 | βZif | λ1 | λ2 | ${}^{app}K_d$ | ${}^{true}K_d$ | ${}^{app}K_d$ | ${}^{true}K_d$ |
| 18C, 16M | Pacific Blue | 5-IAF | 455 | 520 | 6[d] | 6[d] | 160 | 170 |
| 18C, 16M | Badan | Alexa532 | 488 | 555 | | | 273 | 243 |
| 18C, 16F | Pacific Blue | 5-IAF | 455 | 517 | 15 | 20 | 12[d] | 13[d] |
| 18C, 16F | Badan | Alexa532 | 488 | 555 | | | 480 | 700 |

TABLE 10-continued

Bicarbonate response of βZif conjugates of the avBicarbBP5 scaffold[a].

| Conjugate | | | Emission wavelength (nm) | | $K_d$[b] (mM) | | $K_d$[c,e] (mM) | |
|---|---|---|---|---|---|---|---|---|
| Mutant | avBicarbBP5 | βZif | λ1 | λ2 | $^{app}K_d$ | $^{true}K_d$ | $^{app}K_d$ | $^{true}K_d$ |
| 18C, 16F | Pacific Blue | Texas Red | 455 | 620 | 31 | 25 | | |
| 18C, 16Y | Pacific Blue | 5-IAF | 455 | 515 | 10 | 12 | 34 | 46 |
| 18C, 16Y | Badan | Alexa532 | 488 | 555 | | | nb | nb |
| 18C, 16W | Pacific Blue | 5-IAF | 455 | 520 | 61 | 64 | 90[d] | 70[d] |
| 18C, 16W | Badan | Alexa532 | 488 | 555 | | | 580 | 780 |
| 18C, 16E | Pacific Blue | 5-IAF | 455 | 520 | 160 | 130 | | |
| 18C, 141F | Pacific Blue | 5-IAF | 455 | 520 | 58 | 69 | | |
| 18C, 141F | Badan | Alexa532 | 479 | 555 | | | 440 | 430 |
| 18C, 141Y | Pacific Blue | 5-IAF | 455 | 518 | 5.4 | 7.3 | nb | nb |
| 18C, 141W | Balan | Alexa532 | 483 | 555 | | | nb | nb |
| 18C, 141W | Pacific Blue | 5-IAF | 455 | 520 | 35 | 43 | 2.6 | 3.0 |
| 18C, 141Q | Pacific Blue | 5-IAF | 455 | 520 | 76 | 96 | 8.2 | 9.3 |
| 18C, 141Q | Badan | Alexa532 | 488 | 555 | | | 770 | 700 |
| 18C, 141E | Pacific Blue | 5-IAF | 455 | 520 | 196 | 238 | 138 | 216 |
| 190C | Acrylodan | 5-IAF | 586 | 460 | 3.0 | 3.4 | | |
| 190C | Acrylodan | Alexa532 | 487 | 460 | 5.5 | 6.1 | | |
| 194C | Pacific Blue | 5-IAF | 455 | 519 | 24 | 60 | | |
| 194C | Pacific Blue | IANBD | 455 | 519 | 14 | 61 | | |
| 194C | Pacific Blue | Oregon Green | 455 | 519 | 24 | 65 | | |

[a]Determined by fitting the ratiometric signal of the intensities measured at λ1 and λ2 to equation 1-5.
[b]In the presence of 1 mM $CaCl_2$.
[c]In the presence of 1 mM EGTA.
[d]Approximate value.
[e]nb, no binding.

Figure 11A:
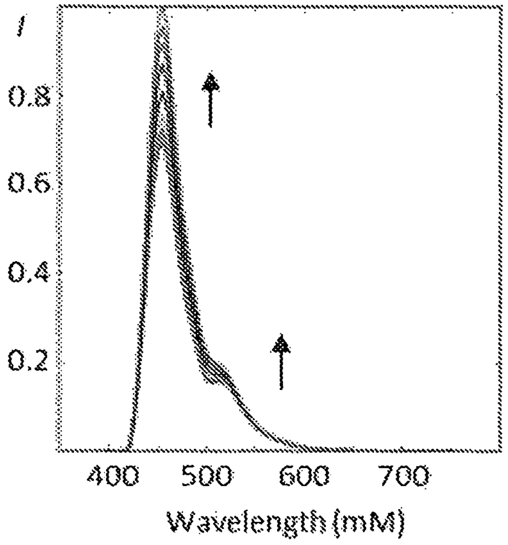
FIGS. 11A-C are graphs showing that the avBicarb5 16F 18C·Pacific Blue-βZif·5-IAF doubly labeled conjugate exhibits a dichromatic response to $Ca^{2+}$.
Figure 11B:
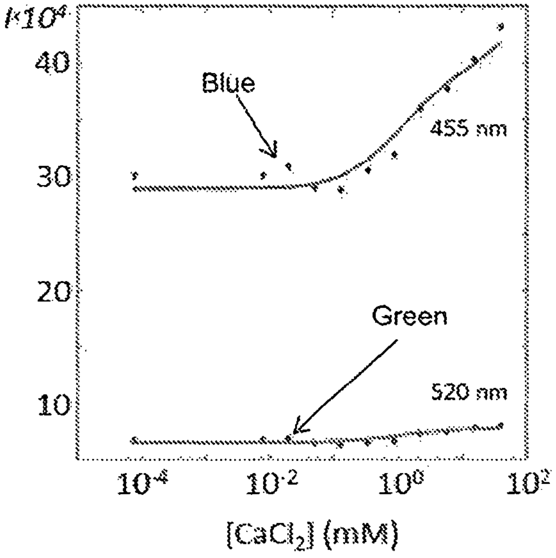
Figure 11C:
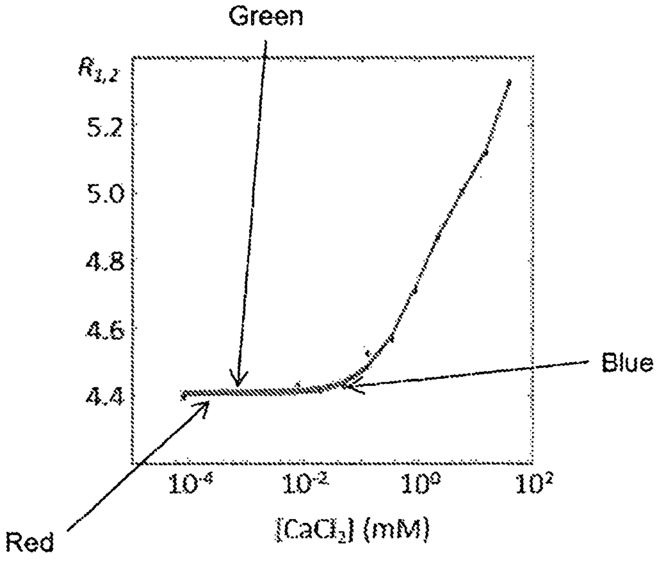
Figure 73A:
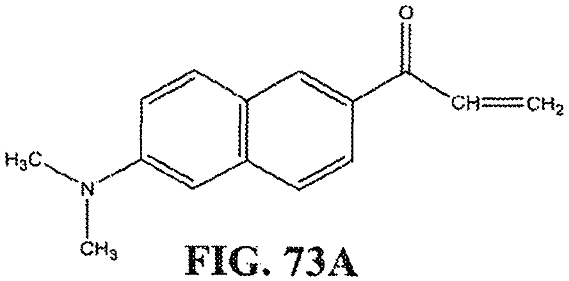
FIG. 73A shows Acrylodan.
Figure 73B:
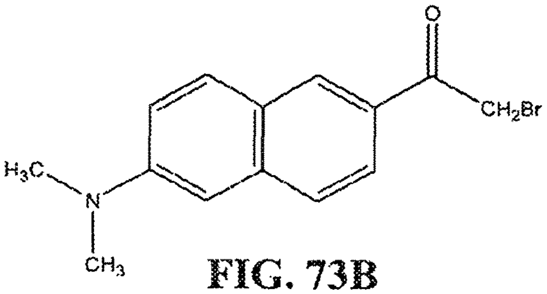
FIG. 73B shows Badan.
Figure 73C:
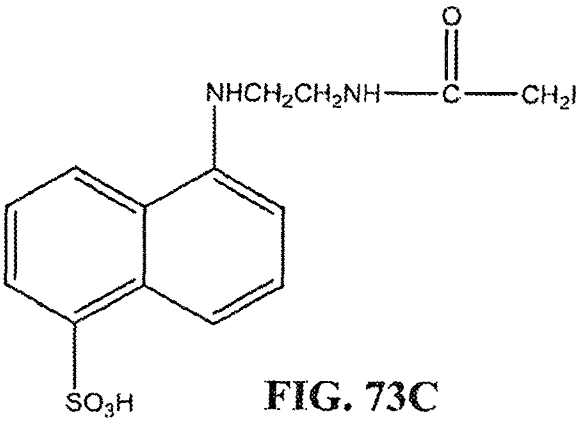
FIG. 73C shows IAEDANS. Xanthene family.
Figure 73D:
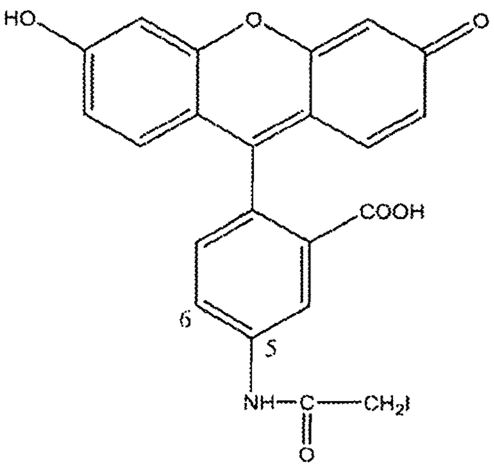
FIG. 73D shows Fluorescein (5-IAF and 6-IAF)
Figure 73E:
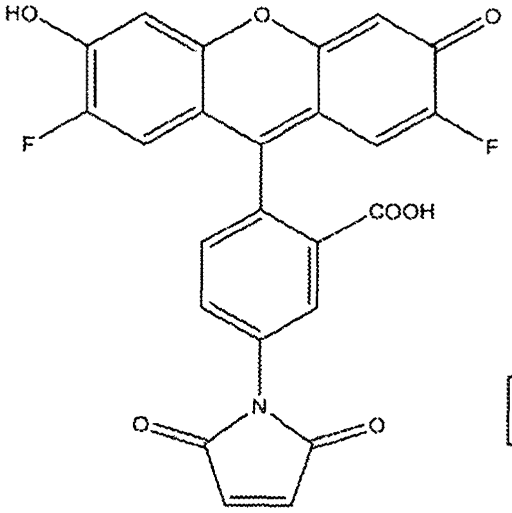
FIG. 73E shows Oregon Green.
Figure 73F:
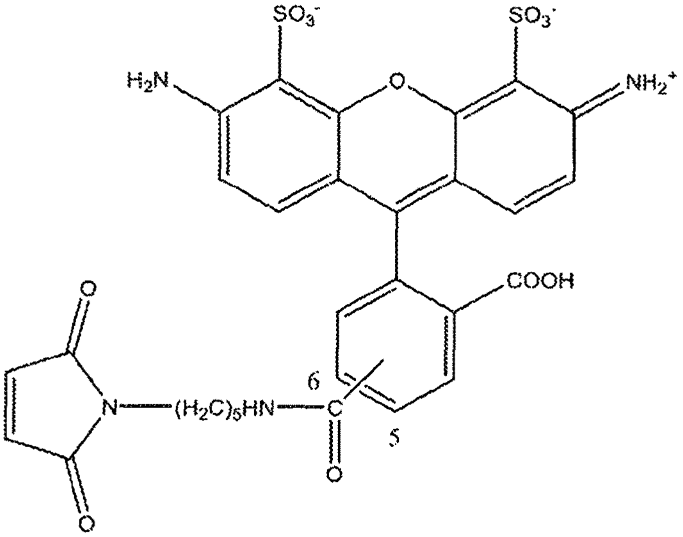
FIG. 73F shows Alexa 432.
Figure 73G:
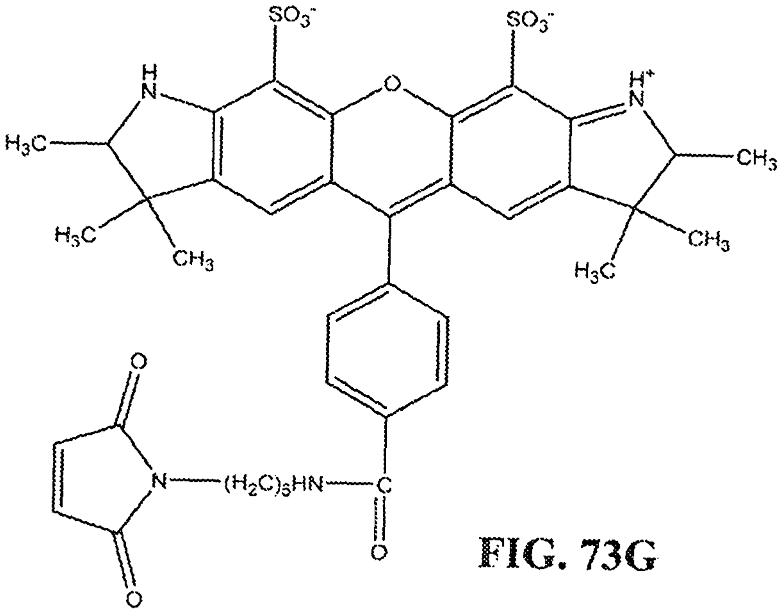
FIG. 73G shows Alexa532.
Figure 73H:
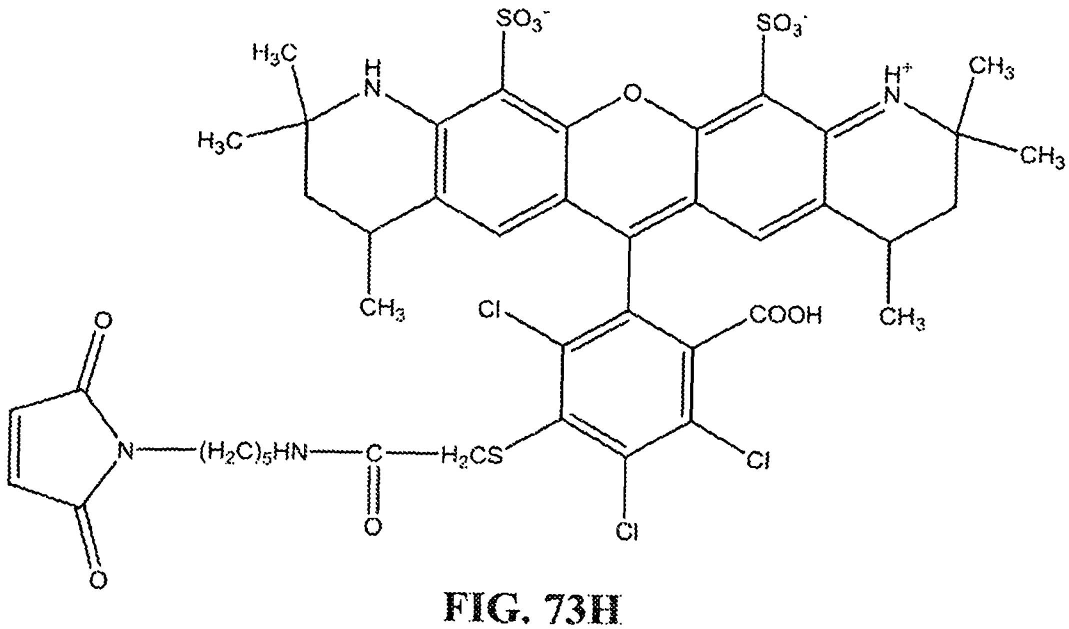
FIG. 73H shows Alexa 546.
Figure 73I:
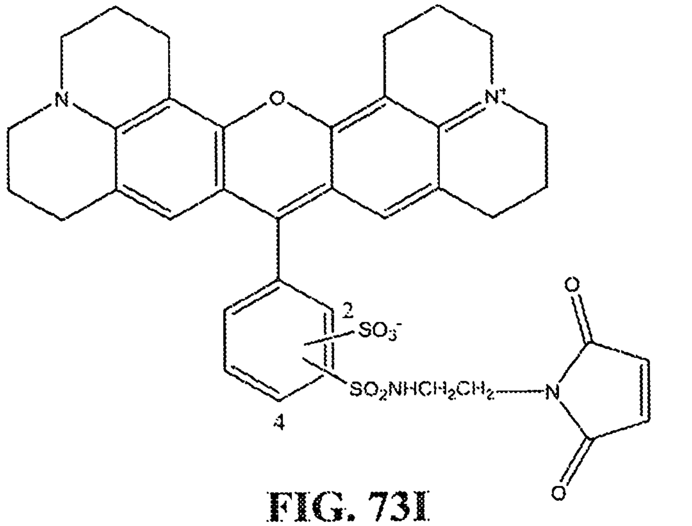
FIG. 73I shows Texas Red. Coumarin family.
Figure 73J:
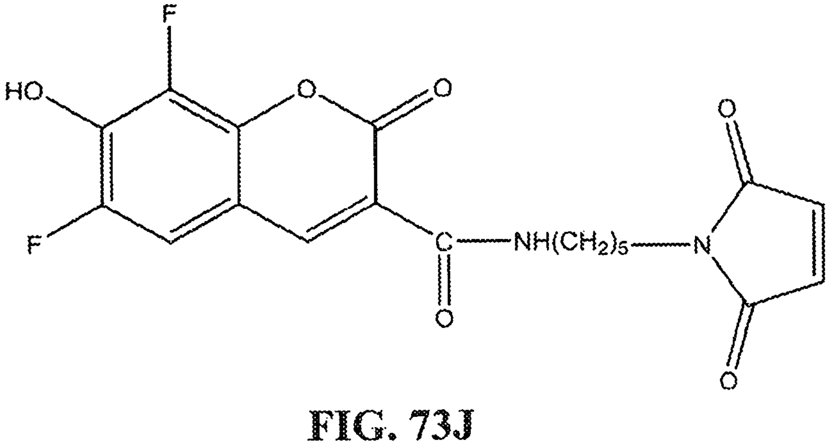
FIG. 73J shows Pacific Blue.
Figure 73K:
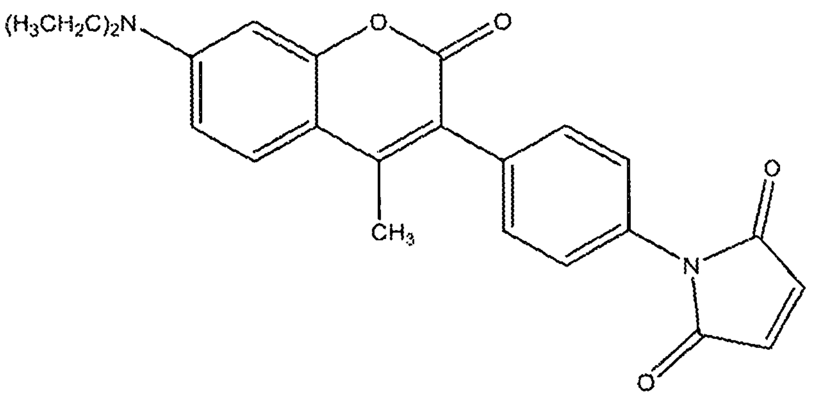
FIG. 73K shows CPM. Benzoxadiazole family.
Figure 73L:
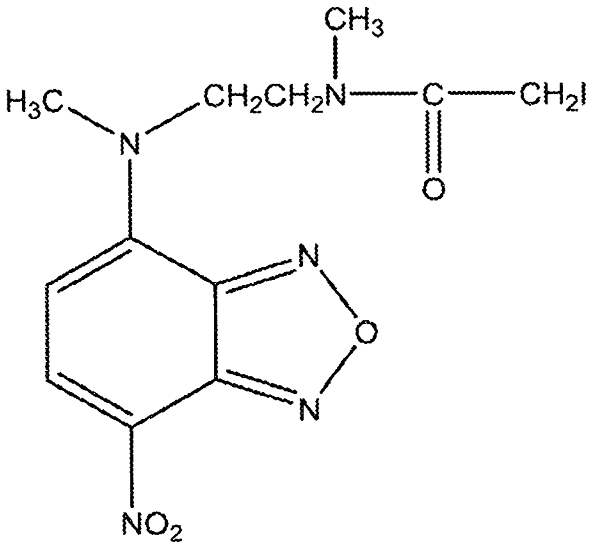
FIG. 73L shows IANBD. Boradiazaindacine (BODIPY) family.
Figure 73M:
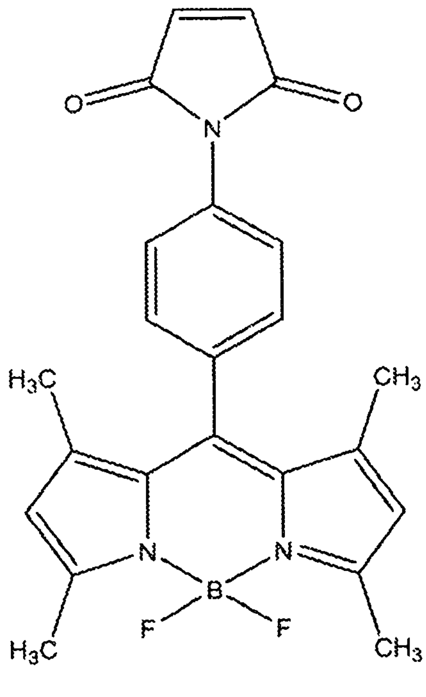
FIG. 73M shows BODIPY 499/508.
Figure 73N:
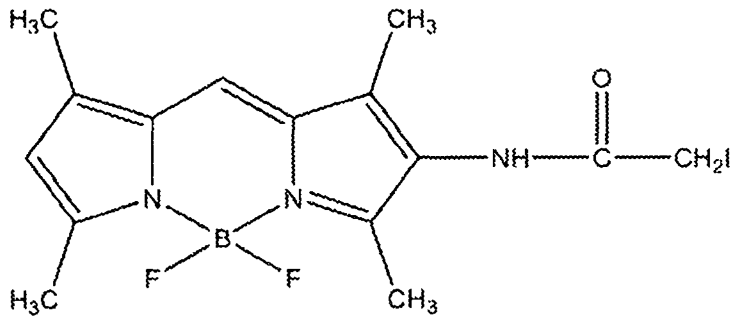
FIG. 73N shows BODIPY 507/545. Cyanine family.
Figure 73O:
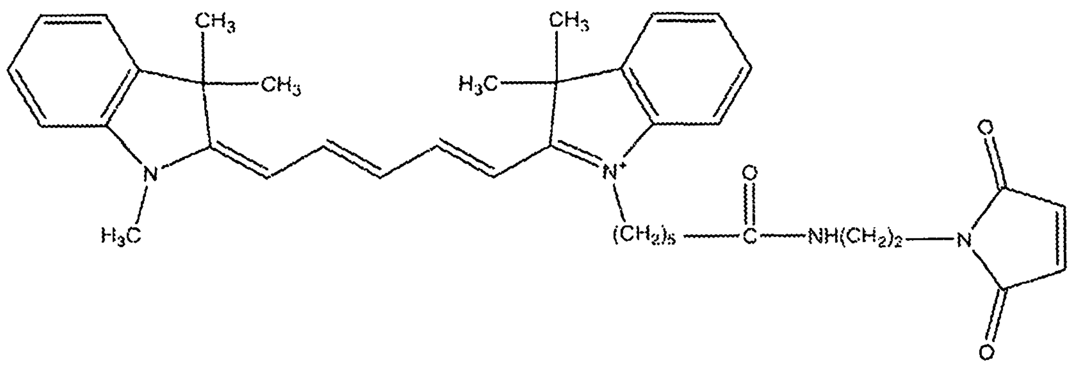
FIG. 73O shows Cy5. Miscellaneous.
Figure 73P:
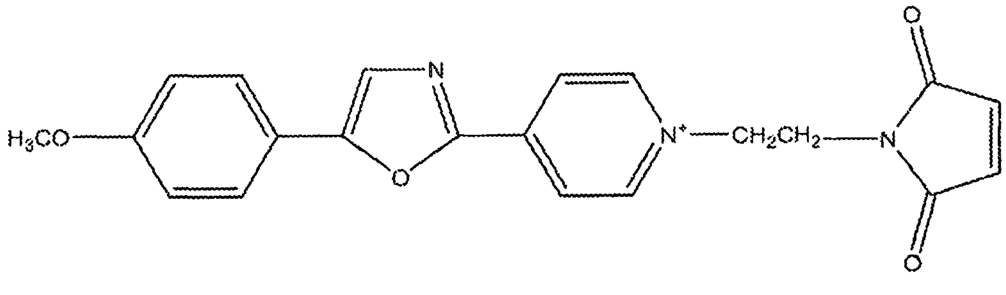
FIG. 73P shows PyMPO.

Tuning of $Ca^{2+}$ affinity in avBicarbBP5. The concentration of free $Ca^{2+}$ in blood is tightly regulated in the 1.2-1.3 mM range (Burtis 2012). The effect of mutations were studied at two labeled positions: 16C and 18C. Tuning mutations were introduced at positions 16 (in the 18C background), 49, 71, and 141, corresponding to positions 66, 99, 121, and 192, respectively in synBicarbBP1. Each of affinity tuning positions therefore corresponds to position in the PCS (FIG. 3C). The effects of these mutations were evaluated using ngmFRET in the doubly labeled C-terminal βZif fusions (Table 11). The range of obtained $Ca^{2+}$ affinities spanned approximately five orders of magnitude, ranging from 20 μM to 360 mM, with each decade represented at least once. Several mutants exhibit $K_d$ values appropriate for clinical sensing of ionized calcium (FIG. 11).

TABLE 11

Calcium response of βZif conjugates of the avBicarbBP5 scaffold[a].

| Conjugate | | | Emission wavelength (nm) | | $K_d$ (mM) | |
|---|---|---|---|---|---|---|
| Mutant | avBicarbBP5 | βZif | λ1 | λ2 | $^{app}K_d$ | $^{true}K_d$ |
| 16C | Pacific Blue | Oregon Green | 455 | 520 | 0.22 | 0.26 |
| 16C | Pacific Blue | 5-IAF | 455 | 517 | 0.02 | 0.02 |
| 16C | Alexa532 | 5-IAF | 555 | 515 | 0.5[b] | 0.5[b] |
| 16C | Alexa532 | Oregon Green | 551 | 524 | 13[b] | 14[b] |
| 16C, 71D | Pacific Blue | 5-IAF | 455 | 519 | 19[b] | 17[b] |
| 16C, 71N | Pacific Blue | 5-IAF | 455 | 515 | 0.21 | 0.18 |
| 16C, 71E | Pacific Blue | 5-IAF | 455 | 520 | 380 | 360 |
| 16C, 71M | Pacific Blue | 5-IAF | 455 | 519 | 20 | 20 |
| 17C | Acrylodan | 5-IAF | 514 | 465 | 4.2 | 1.8 |
| 17C | Badan | 5-IAF | 523 | 465 | 1.3 | 0.51 |
| 17C | Acrylodan | Alexa532 | 483 | 546 | 2.6 | 2.9 |
| 17C | Badan | Alexa532 | 491 | 545 | 0.85 | 0.96 |

TABLE 11-continued

Calcium response of βZif conjugates of the avBicarbBP5 scaffold[a].

| Conjugate | | | Emission wavelength (nm) | | $K_d$ (mM) | |
|---|---|---|---|---|---|---|
| Mutant | avBicarbBP5 | βZif | λ1 | λ2 | $^{app}K_d$ | $^{true}K_d$ |
| 17C | Pacific Blue | IANBD | 455 | 483 | 7.2 | 18 |
| 18C | Pacific Blue | 5-IAF | 455 | 523 | 3.0 | 3.1 |
| 18C | Pacific Blue | Oregon Green | 455 | 523 | 3.3 | 3.3 |
| 18C | Pacific Blue | IANBD | 455 | 480 | 1.1 | 1.7 |
| 18C | Acrylodan | 5-IAF | 523 | 484 | 8.9 | 12 |
| 18C | Acrylodan | Alexa532 | 495 | 470 | 3.9 | 4.1 |
| 18C | Badan | Alexa532 | 555 | 500 | 0.15 | 0.20 |
| 18C, 16M | Pacific Blue | 5-IAF | 455 | 517 | 1.0 | 0.91 |
| 18C, 16M | Badan | Alexa532 | 559 | 491 | 0.043 | 0.076 |
| 18C, 16F | Pacific Blue | 5-IAF | 455 | 520 | 0.96 | 1.1 |
| 18C, 16F | Badan | Alexa532 | 492 | 555 | 0.17 | 0.18 |
| 18C, 16F | Pacific Blue | Texas Red | 455 | 620 | 3.1 | 3.0 |
| 18C, 16Y | Pacific Blue | 5-IAF | 455 | 517 | 0.77 | 0.96 |
| 18C, 16Y | Badan | Alexa532 | 555 | 490 | 0.01 | 0.02 |
| 18C, 16Y | Pacific Blue | Texas Red | 455 | 440 | 16 | 17 |
| 18C, 16W | Pacific Blue | 5-IAF | 455 | 517 | 0.76 | 0.90 |
| 18C, 16W | Badan | Alexa532 | 487 | 555 | 0.02[b] | 0.02[b] |
| 18C, 16E | Pacific Blue | 5-IAF | 455 | 520 | 0.20 | 0.20 |
| 18C, 49F | Acrylodan | Alexa532 | 491 | 547 | 0.69 | 0.84 |
| 18C, 49F | Pacific Blue | Oregon Green | 455 | 516 | 19 | 26 |
| 18C, 49Y | Pacific Blue | Oregon Green | 455 | 515 | 15 | 19 |
| 18C, 49Y | Badan | Alexa532 | 486 | 555 | 1.2 | 1.4 |
| 18C, 141V | Acrylodan | Alexa532 | 487 | 545 | 9.7 | 9.3 |
| 18C, 141V | Pacific Blue | Oreon Green | 455 | 518 | 41 | 40 |
| 18C, 141F | Pacific Blue | 5-IAF | 455 | 522 | 2.0 | 2.1 |
| 18C, 141F | Badan | Alexa532 | 466 | 555 | 3.8 | 4.0 |
| 18C, 141Y | Badan | Alexa532 | 467 | 555 | 2.0 | 2.1 |
| 18C, 141Y | Pacific Blue | 5-IAF | 455 | 520 | 4.1 | 4.5 |
| 18C, 141W | Badan | Alexa532 | 464 | 555 | 1.2 | 1.3 |

TABLE 11-continued

Calcium response of βZif conjugates of the avBicarbBP5 scaffold[a].

| Conjugate | | | Emission wavelength (nm) | | $K_d$ (mM) | |
|---|---|---|---|---|---|---|
| Mutant | avBicarbBP5 | βZif | λ1 | λ2 | ${}^{app}K_d$ | ${}^{true}K_d$ |
| 18C, 141W | Pacific Blue | 5-IAF | 455 | 522 | 2.2 | 2.0 |
| 18C, 141Q | Pacific Blue | 5-IAF | 455 | 517 | 1.7 | 2.0 |
| 18C, 141Q | Badan | Alexa532 | 559 | 490 | 0.72 | 0.57 |
| 18C,141E | Pacific Blue | 5-IAF | 455 | 517 | 1.4 | 1.8 |

[a]Determined by fitting the ratiometric signal of the intensities measured at λ1 and λ2 to equation 1-5.
[b]Approximate value.

Example 6. Materials and Methods

Bioinformatic searches. Annotated genomic and plasmid sequences of 5062 prokaryotes were obtained from the National Center of Biotechnology Information (ftp.//ftp.ncbi.nih.gov/genomes/Bacteria/all.gbk.tar.gz), together with annotations recording prokaryotic lifestyles ( . . . /ProkaryotesOrganismInfo.txt). The Protein Databank (PDB) was obtained from www.rcsb.org. The downloaded genomic and structural data files were organized into pre-processed two databases (PG, prokaryotic genomes; PDB). The 'ProteinHunter' program provides an interface and methods for organizing, querying, and analyzing these databases. ProteinHunter comprises a graphical user interface, set of computer scripts, and a parallel computing environment. Together these set up the calculations, manage the flow of information and execution in each of the calculation phases, control other programs that carry out specific calculations such as BLAST (Altschul et al. 1990) and ClustalW (Chenna et al. 2003), and visualize the results.

To construct homolog sequence sets, single sequence seeds were extracted from either preprocessed PDB or PG databases. Homolog sets were then identified in the PDB or PG by using a seed sequence for a uni-directional BLAST search with the following parameters: expect threshold, 10.0; gap costs for existence, 11, and extension, 1; BLOSUM matrix; low complexity filter is on (the ProteinHunter package always executes BLAST searches with the following command "blastall-p blastp-m 8-b 50000-d<database file>-i<input file>-o <output file>, where <database file> specifies the name of the prebuilt search sequence file and <input file> and <output file> the seed sequence input and hit output files respectively. A pairwise BLAST alignment was scored in ProteinHunter as a homolog hit if it exceeded a minimum fraction of identical residues and if the alignment covered at least 70% of the probe and target sequences.

Function was inferred using the sequence of primary complementary surface (PCS) residues. A non-contiguous sequence comprising the PCS between the protein and the bound bicarbonate was identified using ProteinHunter, PCS residues were selected as members of the PCS if the calculated distance between any of their atoms and any bicarbonate atom was less than 5 Å, and the distances between their backbone $C_\alpha$ and any atom in bicarbonate-metal complex was greater than that of their $C_\beta$ atom and any atom in the ligand complex. Secondary shell residues that do not form hydrogen bonds or van der Waals contacts were removed by inspection from the resulting set. To determine the PCS sequence of members in the homolog set identified in ProteinHunter, their sequences were aligned using ClustalW (Chenna et al. 2003). This alignment identifies the positions of the PCS residues in each homolog, from which the corresponding PCS sequence in that homology is then read. For each homolog, the number of PCS mutations relative to the bicarbonate-binding PCS (Hamming distance, $H_{PCS}$) was counted. Homologs with $H_{PCS}=0$ were inferred to be bicarbonate-binding proteins. The PCS sequences were displayed sorted by their $H_{PCS}$ values, and within each $H_{PCS}$ value sorted by their fraction identical residues, indicating the replicon within which they reside (chromosome or plasmid), whether this replicon contains paralogs, and the temperature tolerance (hyperthermophile, thermophile, mesophile, psychrophile, unknown), their Gram stain classification (if known), and the percentage genomic AT content. Duplicate hits were removed automatically from this list if the organism name (genus and species), fractional identity and paralogs were the same. From this list representative, unique homologs with $H_{PCS}=0$ were chosen by inspection.

Gene synthesis and mutagenesis. The amino acid sequences for the predicted homologs identified in the bioinformatic search (see above) were extracted from the PG database. The putative leader peptide that mediates anchoring of the periplasmic-binding protein on the outside of the membrane (Gram positive bacteria) or directs secretion into the periplasm (Gram negative bacteria) was deleted by examining the multiple sequence alignment and removing the sequences N-terminal to the start of the mature seed protein amino acid sequence. Endogenous cysteines were changed to alanine. A hexahistidine tag was placed behind a GGS linker at the C-terminus of the mature protein to enable metal-mediated affinity purification (Hengen 1995). The final amino acid sequences were backtranslated into a DNA sequence encoding the open reading frame (ORF), which was placed in a construct behind an efficient Shine-Dalgarno ribosome-binding site, and flanked by a T7 promoter and terminator at the 5' and 3' ends respectively, using the GeneFab program (Cox et al. 2007). The resulting ORF sequences were optimized in context by OrfOpt or OrfMorph programs designed to predict highly expressed mRNA sequences in *E. coli* (see below). The resulting DNA sequences were synthesized by oligonucleotide assembly and cloned into pUC57 by GeneWiz, Inc. (South Plainfield, New Jersey).

Subsequent single and multiple point mutations were designed by preparing mutant sequences of the synthetic ORF sequences using the GfMutagenesis program that introduces point mutations into an ORF using the most prevalent codon in *E. coli* for an amino acid. Constructs for site-specific double labeling were designed by inserting the βZif domain sequence (Smith et al. 2005) before the hexahistidine C-terminal purification tag. All variants also were constructed by total gene synthesis.

Synthetic gene optimization. The OrfOpt program (U.S. Patent Publication No. 2011/0171737, incorporated by reference) uses stochastic optimization algorithms that choose different codons within an ORF without altering the amino acid sequence to optimize a target function designed to identify mRNA sequences that express proteins at high levels in *E. coli*. The OrfOpt simultaneously imposes AU-rich nucleotide composition at the 5' and 3' ends of the ORF, low RNA secondary structure content and favorable codon usage (Allert et al. 2010). The OrfMorph program reproduces the pattern of codon usage and RNA secondary structure observed in the parent genome of a protein, but using *E. coli* codon preferences and nucleotide composition.

Codon usage is calculated using the codon adaptation index (CAI), as described for OrfOpt, using codon frequency tables calculated for the genome under examination. The mean CAI value for a genome, $\mu_c$, and its standard deviation, $\sigma_c$, are calculated over all the codons in a genome. A codon usage score, c, is calculated for each codon in an open reading frame (ORF) by averaging the CAI over a 9-codon window, centered on the codon for which this score is calculated. A normalized codon usage score, $z_c$, is calculated for each codon as Z-score: $z_c=(c-\mu_c)/\sigma_c$. A plot of $z_c$ along an ORF establishes the codon usage pattern of that ORF. Rare codons ($z_c<0$) are hypothesized to slow down the elongation rate of ribosome translation, introducing "pause" sites at extreme values. Such pause sites are hypothesized to direct kinetics of co-translational folding, allowing a newly synthesized segment to fold before more protein is made. An RNA secondary structure score, s, is determined for each nucleotide by summing its participation in all possible hairpins that can form in its vicinity (settings: minimum duplex length 4 basepairs; maximum loop length, 30 bases; vicinity length, 100 bases), as described for OrfOpt. The average secondary structure energy, $\mu_s$, and its standard deviations, $\sigma_s$, are calculated over all the nucleotides in a genome. A normalized secondary structure energy score, $z_s$, is calculated for codon as the Z-score: $z_s=(c-\mu_s)/\sigma_s$. A plot of $z_s$ along an ORF establishes the secondary structure pattern of that ORF. Regions of above-average secondary structure ($z_s>0$) are hypothesized to slow down the elongation rate of ribose translation, introducing "pause" sites at extremes. As with CAI-mediated pause sites, secondary structure-driven pause sites are hypothesized to direct the kinetics of co-translational folding.

To mimic these patterns for heterologous expression of an ORF in *E. coli*, first the $z_c$ and $z_s$ scores are calculated using the parent organism codon table, $\mu_c$, $\sigma_c$, $\mu_s$, and $\sigma_s$ values. Second, a stochastic search algorithm is used that randomly chooses between degenerate codons to construct trial mRNA nucleotide sequences, calculating $z_c$ and $z_s$ scores for each trial sequence, but using the *E. coli* codon table, and *E. coli* $\mu_c$, $\sigma_c$, $\mu_s$, and $\sigma_s$ values. For each trial, the absolute differences between the *E. coli* trial scores, and the wild-type scores are summed over the entire ORF. The OrfMorph program searches for a minimum of these differences. The stochastic search algorithm operates by first choosing a codon position, second choosing a degenerate codon within the allowed codons at that position. If the choice results in an improved score, the sequence is kept, otherwise it is rejected. After a position has been selected, it is removed from the pool of allowed positions, and the next is chosen from the remainder. The algorithm terminates when two successive sweeps do not yield further improvements in the score. The resulting RNA nucleotide sequence that has codon usage patterns and secondary structure patterns that closely match those of the wild-type mRNA sequence in its parental genomic context. The hypothesis is that such matching improves production of soluble protein by mimicking co-translational folding contributions that minimize mis-folded protein intermediate aggregation.

Protein expression, purification, and fluorescent conjugate preparation. Plasmids carrying the expression constructs (see above) were transformed into KRX competent cells (Promega), and grown overnight at 37° C. on LB agar plates (100 mg/mL ampicillin). For expression and purification of homologs of cyanobacterium *Synechocystis* PCC 6803 $CaCl_2$) (1 mM) was added. For expression and purification of homologs of *Mannheimia haemolytica* $FeCl_3$ (10 μM) was added. A single colony was picked and grown overnight at 37° C. in Terrific Broth (TB; Research Products International). The overnight cultures were diluted 1:20 in 500 mL TB (100 mg/mL ampicillin), grown to an optical density of $A_{600}$=0.5 at 37° C. in vigorously aerated shaker flasks, induced by the addition of 2.5 mL rhamnose (20% w/v), and grown for a further 3-4 hrs. The cells were harvested by centrifugation (5,000 rpm, 10 min). After decanting the supernatant, the cell pellets were stored −80° C. The cell pellets were thawed, resuspended in 8 mL binding buffer (10 mM imadozole, 20 mM MOPS, 500 mM NaCl, pH 7.8). Following resuspension, 3 mL of BugBuster HT (EMD Millipore) was added. After incubation (20 mins, 25° C.), the cells were lysed on ice by sonication (2 minutes of one-second on/off pulses, 20-30% power). A clarified lysate was prepared by centrifugation (15,000 rpm, 20 min, 4° C.) from which recombinant protein was purified by batch immobilized metal affinity chromatography (IMAC). Resuspended IMAC agarose beads (5 mL; Sigma-Aldrich, P6611) were added to the lysate. After incubation at 4° C. in a Mini LabRoller (Labnet International) for 1 hr, the beads were washed at least five times with binding buffer. The immobilized protein beads were resuspended in labeling buffer (20 mM MOPS, 100 mM NaCl, pH 6.9) and labeled overnight (4° C., rotating end-over-end) with a thiol-reactive fluorophore (5-fold stoichiometric excess over protein). Following two rinses with labeling buffer to remove unincorporated label. For double labeling of βZif fusions, a second thiol-reactive label was added following reduction of the disulfide with 5 mM TCEP. To elute labeled protein from the IMAC beads, 6 mL of elution buffer (400 mM imidazole, 500 mM NaCl, 20 mM MOPS, pH 7.8) was added, incubated for 30 min (4° C., rotating end-over-end), and the beads removed by centrifugation. Following dialysis of the eluate against three changes of assay buffer (20 mM MOPS, 20 mM KCl, pH 7.4), using 10 kDa semi-perimeable membrane (Snakeskin tubing, Thermo Scientific), the fluorescent conjugates were concentrated in a 10 kDa cutoff spin concentrator (Vivaspin, GE Healthcare). Protein purity was assessed by SDS/PAGE. Protein concentrations were determined by (Nanodrop1000) at 280 nm (using extinction coefficients calculated from their sequence (Gill and von Hippel 1989, Artimo et al. 2012)), or at the fluorophore absorbance peak (Acrylodan, 391 nm and Badan, 387 nm).

Preparation of titration series to measure ligand-binding. 12-, 24-, or 48-point logarithmic titration series were prepared on a Tecan Freedom liquid-handling robot, using an in-house program, 'TitrationPlate', that compiles an abstract description of a multi-component titration series into machine instructions for operating the robot. For bicarbonate titrations in homologs of cyanobacterium *Synechocystis* PCC 6803, concentrations were varied from 0-1 M in 20 mM KCl, 20 mM MOPS (pH 7.4) supplemented with either 1 mM EGTA or 1 mM $CaCl_2$). For bicarbonate titrations in homologs of *Mannheimia haemolytica*, concentrations were varied from 0-1 M in 20 mM KCl, 20 mM MOPS (pH 7.4) in the presence of 10 μM $FeCl_3$. For calcium titrations in homologs of cyanobacterium *Synechocystis* PCC 6803, concentrations were varied from 0-1 M in 20 mM KCl, 20 mM MOPS (pH 7.4), and for some experiments supplemented with 50 mM $NaHCO_3$.

Determination of temperature- and ligand-dependent fluorescence landscapes. 12-, 24-, or 48-point logarithmic titration series were prepared on a Tecan Freedom liquid-handling robot (see above). Temperature-dependent fluorescence emission intensities of 20 μL aliquots, each containing 10 μM protein, were measured in 384-well microtiter plates in a LightCycler 480 II (Roche) using excitation and emission wavelengths available for this instrument that most closely matched the optical characteristics of the fluorescent conjugate. Temperatures were advanced in 1K steps. At each temperature, data was collected at 1-second intervals for 60 seconds at which point the signal had relaxed to a steady value associated with the new temperature. Under these experimental photobleaching was not observed. The in-house program 'TitrationMeltPlate' was used to convert these observations into time-independent datasets that record fluorescence as a function of temperature for each well and associate wells with their concentration of titrant and additive. Management tools were developed to maintain a database of titrations and their analyses.

Determination of emission intensity spectra. Ligand- and wavelength-dependent emission intensities were recorded on a Nanodrop3300 (Thermo Scientific) at room temperature. Using the LED closest to the optimal excitation wavelength of the fluorophore (UV, 365 nm; blue, 470 nm; 'white', 460-550 nm).

Ratiometric analysis of ligand binding. Isothermal ligand titrations were extracted from the fluorescent landscape or emission spectra datasets obtained as described above. Monochromatic emission intensities I (these intensities correspond to a bandpass intensity, recorded either with a physical filter in the case of the Roche LightCycler, or by integrating in the interval $\lambda-\delta$, $\lambda+\delta$ in the case of an emission spectrum), were fit to $$I_\lambda = {}^{apo}\beta_\lambda(1-\bar{y}_{true}) + {}^{sat}\alpha_\lambda\bar{y}_{true} \quad 1$$

where ${}^{apo}\beta_\lambda$, and ${}^{sat}\beta_\lambda$ are the fluorescence baselines associated with the ligand-free and ligand-bound states of the protein, respectively, and $\bar{y}_{true}$ the fractional saturation of the protein (Layton and Hellinga 2010). Baseline functions can be constant, linear, or a second-order polynomial. For the ligand- and temperature-dependent fluorescence landscapes, we use a constant value for ${}^{apo}\beta_x$, but ${}^{sat}\beta_x$ is described by a linear dependence on ligand concentration, [L]:

$$^{sat}\beta_x = a_x + b_x[L] \quad 2$$

For a single ligand-binding site, the fractional saturation is given by $$\bar{y} = \frac{[L]}{[L]+K_d} \quad 3$$

where [L] is the ligand (bicarbonate or calcium) concentration and $K_d$ the dissociation constant, ${}^{true}K_d$ for $\bar{y}_{true}$.

A ratiometric signal at a given point in a titration series, $R_{12}(t)$, is given by the ratio of intensities at two wavelengths, ${}^{obs}I(\lambda_1,t)$, ${}^{obs}I(\lambda_2,t)$ in the emission spectrum measured at that point:

$$R_{12}(t) = \frac{a_t{}^{obs}I(\lambda_1,t)}{a_t{}^{obs}I(\lambda_2,t)} \quad 4$$

where $a_t$ is an attenuation factor that describes the effect of variations in sample size (i.e. the amount of observable fluorophore) in the $t^{th}$ sample on the wavelength-independent intensity of the entire emission spectrum. This signal removes wavelength-independent emission intensity attenuation effects due to variations in conjugate concentration, photobleaching, fluctuations in excitation source intensities, and detection efficiency (Demchenko 2010, Demchenko 2014). It is a key aspect for high-precision sensing using the reagentless fluorescently-responsive sensors described here. The ratiometric signal also can be fit to a binding isotherm:

$$R_{1,2} = \beta_R(1-\bar{y}_R) + {}^{sat}\beta_R\bar{y}_R \quad 5$$

where ${}^{apo}\beta_R$ and ${}^{sat}\beta_K$ are the baselines, and $\bar{y}_R$ the apparent fractional saturation of the protein (with ${}^{app}K_d$). In general, ${}^{true}K_d \neq {}^{app}K_d$; if both baselines are constant, a simple relationship can be derived relating ${}^{app}K_d$ to ${}^{true}K_d$ (Grimley et al. 2013):

$$^{app}K_d = {}^{true}K_d\frac{^{apo}I_{\lambda 2}}{^{sat}I_{\lambda 2}} \quad 6$$

where ${}^{apo}\beta_{\lambda 2}$ and ${}^{sat}\beta_{\lambda 2}$ are the emission intensities of the monochromatic signal at wavelength $\lambda_2$ of the ligand-free and ligand-bound protein, respectively.

Following a fit of the titration series using equations 4 and 5, $a_t$ values can be recovered by taking the average comparison of the observed and calculated intensities at the two wavelengths:

$$a_t = \frac{1}{2}\left(\frac{^{calc}I(\lambda_1,t)}{^{obs}I(\lambda_1,t)} + \frac{^{calc}I(\lambda_2,t)}{^{obs}I(\lambda_2,t)}\right) \quad 7$$

The $a_t$ value can then be applied to all wavelengths to obtain an emission spectrum or integrated intensity of the $t^{th}$ titration point corrected for variations in sample size:

$$^{corr}I(\lambda) = a_t{}^{obs}I(\lambda) \quad 8$$

where ${}^{corr}I(\lambda)$ and ${}^{obs}I(\lambda)$ are the wavelength-dependent intensities of the corrected and observed emission spectra, respectively.

The fractional error in the chemometric concentration measurement, depends on the first derivative of the binding isotherm as follows (Marvin et al. 1997):

$$\frac{\partial S}{S} = \frac{\varepsilon_{1,2}}{S} \times \left(\frac{dR_{1,2}}{dS}\right)^{-1} \quad 9$$

Where $R_{1,2}$ is the ratiometric signal (equation 5), $\varepsilon_{1,2}$ its experimental error, and $\delta S$ is the resulting chemometric error in the concentration. We can then define a relative precision function $$P(S) = \frac{S}{\delta S} \times \frac{1}{P_{max}} \quad 10$$

where P(S) is the relative precision at concentration S, which reaches a maximum value (i.e. lowest error), $P_{max}$, at the $K_d$.

For a given isothermal titration, values for ${}^{app}K_d$ and ${}^{true}K_d$ were obtained using a non-linear fitting algorithm in which these two parameters were simultaneously fit to the three experimental binding isotherms using equations 1 and 5, with the two monochromatic isotherms sharing the same ${}^{true}K_d$ value. Three separate pairs of ${}^{apo}\beta$ and ${}^{sat}\beta$ were fit in this procedure, corresponding to the two monochromatic and the ratiometric signals, respectively. Two distinct ratiometric response models can be used: coupled (both wavelengths respond to ligand); uncoupled (the second wavelength is non-responsive; i.e. remains constant). Optionally, an attenuation vector, a(t) containing at values for each titration point (equation 7), can be refined by iterative fit cycles in which the a(t) vector of a previous cycle is used to adjust the integrated intensities of the next cycle. Programs 'Nanodrop3300' and'TitrationMeltAnalysis' were developed to analyze wavelength- or temperature-dependent ligand-binding datasets respectively.

Analysis of ligand-binding properties using thermal melts. The thermal stability of purified candidate proteins was determined by measuring the temperature-dependence of the fluorescence signal of an extrinsically added dye, SYPRO, using a Roche LightCycler (Layton and Hellinga 2010). The total fluorescence intensity, S, is given by $$S=\beta_F f_F+\beta_U f_U \quad (11)$$

where $f_F$ and $f_U$ are the fractions of protein in the folded and unfolded states, respectively, and $\beta_F$ and $\beta_U$ the fluorescence baselines of these two states. To get the fractions of the two states, we have $$f_N = \frac{1}{1+K_U(T)} \text{ and } f_U = 1 - f_N \quad (12)$$

where $K_U(T)$ is the temperature-dependent unfolding equilibrium constant, which by the van't Hoff approximation is given by $$K_U = e^{-\Delta H_U\left(\frac{1}{T}-\frac{1}{T_m}\right)/R} \quad (13)$$

Where T is the temperature, $T_m$, the unfolding reaction transition mid-point temperature, and $\Delta H_U$ the enthalpy of unfolding.

To obtain the temperature dependence of the binding reaction, the $K_d$ values of all the individually determined isotherms were fit the Gibbs-Hemholtz equation (Layton and Hellinga 2010):

$$\Delta G_b^{\circ}(T) = \Delta^{ref} H_b^{\circ} + \Delta C_{p,b}(T - T_{ref}) - T\left(\Delta^{ref} S_b^{\circ} + \Delta C_{p,b} \ln\frac{T}{T_{ref}}\right) \quad (14)$$

where $\Delta G_b^{\circ}(T)$ is the standard free energy of binding at 1 M ligand at temperature T, $$\Delta G_b^{\circ}(T) = -RT \ln\left(1 + \frac{1}{K_d(T)}\right) \quad (15)$$

$\Delta^{ref}H_b^{\circ}$ and $\Delta^{ref}S_b^{\circ}$ the molar enthalpy and entropy of binding, respectively, at the reference temperature, $T_{ref}$, and $\Delta C_{p,b}$ the heat capacity of the binding reaction. This data analysis was carried out using 'TitrationMeltAnalysis'.

Mechanisms for Chemical Sensing Based on Non-Geometric Modulation of FRET.

The subject matter disclosed herein is not limited to or bound by any particular scientific theory. However, discussions regarding ngmFRET are provided to facilitate the understanding of possible mechanisms involved with ngmFRET signaling in various embodiments described herein. Equations for calculating various values mentioned herein are also provided. ngmFRET is also described in PCT International Patent Application No. PCT/US16/62958, filed Nov. 19, 2016, the entire content of which is incorporated herein by reference.

The total signal, S, of a fluorescent sensor (either single-wavelength emission intensities, IA, or ratios of intensities at two wavelengths, $R_{12}$) is the sum of the fluorescence due to the ligand-free (apo) and ligand-bound states:

$$S=\alpha(1-\bar{y})+\beta\bar{y} \quad (16)$$

where α and β are the fluorescent baselines in the ligand-free and -bound states, respectively, and $\bar{y}$ is the fractional occupancy of the binding sites (equation 3).

Fluorescence quantum yields are the fractions of photons emitted by the excited state relative to the total absorbed, and correspond to the ratio of the radiative decay rate relative to the sum of the rates of all possible decay pathways (FIG. 12). For a single fluorophore:

$$Q = \frac{k_r}{k_r + k_{nr}} \quad (17)$$

where $k_r$ and $k_{nr}$ are the radiative and non-radiative decay rates of the excited state, respectively. If we define q as the ratio between the radiative and non-radiative decay rates, $$q = \frac{k_{nr}}{k_r} \quad (18)$$

then the quantum yield can be written as $$Q = \frac{1}{q+1} \quad (19)$$

Chemical sensors exploit the ligand-mediated shift of a fluorescent system between the ligand-free and ligand-bound states which each exhibit distinct quantum yields:

$$Q_{obs}=Q_{apo}(1-\bar{y})+Q_{sat}\bar{y} \quad (20)$$

where $Q_{obs}$, $Q_{apo}$ and $Q_{sat}$ are the quantum yield of the total system, the apo-protein, and the ligand-bound complex, respectively. In a system involving ngmFRET between a donor and acceptor fluorophore, the $Q_{apo}$ and $Q_{sat}$ quantum yields each are combinations of their respective donor and acceptor quantum yields:

$$Q_{apo}={}^{D}Q_{apo}+{}^{A}Q_{apo} \text{ and } Q_{sat}={}^{D}Q_{sat}+{}^{A}Q_{sat} \quad (21)$$

where the superscripts D and A indicate donor and acceptor fluorophores respectively. To understand ngmFRET-based sensors, we therefore need to examine the factors that affect each of these four quantum yields.

The intensity of the light emitted by a donor or its acceptor is determined by the rate of photon emission from their respective excited states (FIG. 12A). The excited state of a donor is formed by the incident light from the excitation source, and there are three pathways by which this state decays: radiative and non-radiative decay and resonance transfer (by itself and regardless of the presence of any other fluorophore/parter). By contrast, the rate of formation of the acceptor excited state is determined by the resonance transfer rate from the donor, and there are only two processes that determine its decay rate: the radiative and non-radiative pathways (by itself and regardless of the presence of any other fluorophore/parter). In an ngmFRET system, the patterns of ligand-mediated fluorescence intensity changes therefore depend on whether the fluorophore that responds directly to ligand binding functions as a donor or acceptor. To understand these relationships, we analyze the factors that determine the rates of formation and decay of the donor and acceptor excited states.

The rate of resonance energy transfer, $k_t$, along a non-radiative pathway between donor and acceptor (FIG. 12A) is a fraction of the donor radiative emission pathway rate (by itself and regardless of the presence of any other fluorophore/parter), $^{D}k_r$ (the emission rate in the absence of an acceptor) multiplied by the energy transfer coupling factor, $\varphi$, (Lakowicz 2006, Valeur 2012):

$$k_t = \varphi Q_D {}^{D}k_r \quad (22)$$

where $Q_D$ is the donor quantum yield in the absence of an acceptor.

According to the Forster model of weakly coupled oscillators (Lakowicz 2006, Valeur 2012), the energy transfer coupling factor is dependent on the spectral overlap, J, of the donor emission, $^{D}\lambda_{em}$, and acceptor excitation spectrum, $^{A}\lambda_{ex}$, and the variation of the geometry, G, between the donor and acceptor excited state transition dipoles with distance, r, and orientation factor, $\kappa$:

$$\varphi = G(r, \kappa) J({}^{D}\lambda_{em}, {}^{A}\lambda_{ex}) \frac{9000 \ln 10}{128\pi^5 N_A n^4} \quad (23)$$

where $$G(r, \kappa) = \frac{\kappa^2}{r^6} \quad (24)$$

and $$J({}^{D}\lambda_{em}, {}^{A}\lambda_{ex}) = \int F({}^{D}\lambda_{em}) \varepsilon({}^{A}\lambda_{ex}) \lambda^4 d\lambda \quad (25)$$

with n the refractive index of medium, $N_A$ Avogrado's number, $F({}^{D}\lambda_{em})$ the normalized donor emission spectrum, and $\varepsilon({}^{A}\lambda_{ex})$ the absorption coefficient of the acceptor excitation spectrum [this analysis is a re-arrangement of the traditional presentation of the equations describing traditional geometrically-modulated FRET (tgmFRET), separating the different contributions (geometry, spectral overlap, quenching)]. Ligand-mediated modulation of r, K and J therefore affects $k_t$ (FIG. 12B-D), leading to changes in donor and acceptor emission intensities (see below).

At steady state, the concentration of the donor excited state, [D*], is given by the following rate balance equation (see FIG. 12A):

$$N_0 \alpha k_{ex} - [D^*]({}^{D}k_{nr} + {}^{D}k_r + k_t) = 0 \quad (26)$$

where $N_0$ is the population of ground state fluorophores, $k_{ex}$ the rate of excitation photon absorption, $\alpha$ the effective illumination, $k_t$, the resonance energy transfer rate, $^{D}k_{nr}$ and $^{D}k_r$ the radiative and non-radiative decay rates of the donor (by itself and regardless of the presence of any other fluorophore/parter) in the absence of acceptor, respectively. Substituting $^{D}k_r$ (d+1) for $^{D}k_r + {}^{D}k_{nr}$ (using equation 18, with d≡q, the ratio of non-radiative to radiative decay rates in the donor), and replacing $k_t$ with equation 22 (with $Q_D = 1/(1+d)$, according to equation 23), we obtain $$N_0 \alpha k_{ex} - [D^*]^{D}k_r\left(1 + d + \frac{\varphi}{1+d}\right) = 0 \quad (27)$$

Hense $$[D^*] = \frac{N_0 \alpha k_{ex}}{{}^{D}k_r\left(1 + d + \frac{\varphi}{1+d}\right)} \quad (28)$$

The intensity of the emitted donor light, $I_D$, is $$I_D = [D^*]^{D}k_r = \frac{N_0 \alpha k_{ex}}{\left(1 + d + \frac{\varphi}{1+d}\right)} \quad (29)$$

The donor quantum yield, $Q_D$, is this emission intensity relative to the intensity of the excitation, $k_{ex}\alpha N_0$ $$Q_D = \frac{1}{\left(1 + d + \frac{\varphi}{1+d}\right)} \quad (30)$$

The rate balance equation for the acceptor excited state concentration, [A*], is given by $$[D^*]k_t - [A^*]({}^{A}k_r + {}^{A}k_{nr}) \quad (31)$$

Consequently, by applying equations 19, 22 and 30, the acceptor quantum yield, $Q_A$, is $$Q_A = \frac{\varphi}{(1+a)(1+d)\left(1 + d + \frac{\varphi}{1+d}\right)} \quad (32)$$

where a is the ratio of the radiative and non-radiative pathways in the acceptor.

The ratio of the acceptor and donor quantum yields therefore is $$\frac{Q_A}{Q_B} = \frac{\varphi}{(1+d)(1+a)} \quad (33)$$

This equation clearly shows that any ligand-mediated change in ngmFRET transfer ($\varphi$) or quenching of either the donor (d) or acceptor (a) leads to a change in the ratio of donor and acceptor emission intensities, thereby enabling ratiometry.

Classical ligand-mediated modulation of tgmFRET is concerned only with ligand-mediated changes in the distance between the donor and acceptor (Clegg 1995, Cheung 1991), and does not take advantage of effects that alter the photophysics of individual chromophores. By contrast, in ngmFRET systems, the directly responsive partner (DRP) responds to ligand binding through ligand mediated changes that alter the ratio of its radiative and non-radiative pathways (quenching, d or a) or its spectral properties (J), whereas the indirectly responsive partner (IRP) changes only as a consequence of the effect that such change have on the resonance energy transfer rate ($k_t$). It is important to realize that the DRP can function either as a ngmFRET donor an acceptor, depending on how the spectral overlap is set up with the IRP. Regardless of whether the DRP is a donor or acceptor, ligand-mediated alteration of its non-radiative to radiative decay rate ratio (parameter d for a DRP donor; a for an acceptor; by itself and regardless of the presence of any other fluorophore/parter) changes its emission intensity. In DRP donors quenching also alters the ngmFRET transfer rate (see equations 22 and 27), thereby changing the emission intensities of not only itself but also its TRP. By contrast, in DPR acceptors quenching does not alter ngmFRET, and hence do not affect its IRP donor intensity. A DRP acceptor therefore can alter intensities of its donor IRP only if ligand binding changes $\phi$. If the DRP is a donor, then manipulation of the energy transfer coupling factor, $\phi$, changes the rate of excited state decay; if it is an acceptor, the rate of excited state formation is altered.

Regardless of whether the DRP is a donor or acceptor, a change in any of the two parameters ($\phi$ and d or a) alters the ratio of the donor and acceptor quantum yields (equation 33), thereby enabling ratiometry. Ligand-mediated donor DRP quenching affects the quantum yields of both the donor, $Q_D$, and acceptor, $Q_A$, quantum yields (equations 30, 32). Quenching of an acceptor DRP alters only $Q_A$ (equation 30). Changes in $\phi$ affect quantum yields of both fluorophores, regardless whether the DRP functions as the donor or acceptor (equations 23-25, 30, 32). For systems in which there is no ligand-mediated change in the (average) distance between the two fluorophores, $\phi$ changes only if the DRP switches between two different excited state populations ("dipole switching") in response to ligand binding and if the two excited states differ in their spectral properties (emission for donor DRPs; absorption for acceptor DRPs). Excited state dipoles usually also differ in their dipole orientations, so it is likely that changes in spectral overlap involve (re-)orientation effects. They are also likely to differ in the relative rates of their radiative and non-radiative decay rates. Dipole switching therefore is likely to involve a combination of changes in ngmFRET and quenching effects.

There are eight possible combinations of ligand-mediated changes in quenching and ngmFRET parameters, which have different outcomes on the two emission intensities and their ratio, depending on whether the DRP is the donor or acceptor. The qualitative behavior of the resulting sixteen possibilities in ngmFRET systems are shown in Table 12. Twelve of these have a predictable outcome on the direction of change in the ratio of the two emission intensities. The effect on the direction of change for both donor and acceptor emission intensities can be predicted for seven models. For the other models, the direction of change of one or both peaks depends on the size of the change in the underlying parameters. Purely geometric effects (changes in inter-dipole distance or orientation) always result in anti-correlated changes in emission intensity changes (i.e. one increases and the other decreases, or vice versa). Correlated (i.e. both intensities increase or decrease) or uncorrelated (one changes, the other remains constant) intensity changes therefore are primafacie evidence for an ngmFRET effect.

TABLE 12

Qualitative analysis of the patterns of donor and acceptor emission intensity changes in ngmFRET[a]

| Directly responsive partner | Model | $Q_A/Q_D$ | $Q_D$ | $Q_A$ |
|---|---|---|---|---|
| Donor | $d^0\ \phi^+$ | ↑ | ↓ | ↑ |
| | $d^0\ \phi^-$ | ↓ | ↑ | ↓ |
| | $d^+\ \phi^0$ | ↓ | ↓ | ↓ |
| | $d^+\ \phi^+$ | * | ↓ | * |
| | $d^+\ \phi^-$ | ↓ | * | ↓ |
| | $d^-\ \phi^0$ | ↑ | ↑ | ↑ |
| | $d^-\ \phi^+$ | ↑ | * | ↑ |
| | $d^-\ \phi^-$ | * | ↑ | * |
| Acceptor | $\alpha^0\ \phi^+$ | ↑ | ↓ | * |
| | $\alpha^0\ \phi^-$ | ↓ | ↑ | * |
| | $\alpha^+\ \phi^0$ | ↓ | 0 | ↓ |
| | $\alpha^+\ \phi^+$ | * | ↓ | * |
| | $\alpha^+\ \phi^-$ | ↓ | ↑ | * |
| | $\alpha^-\ \phi^0$ | ↑ | 0 | ↑ |
| | $\alpha^-\ \phi^+$ | ↑ | ↓ | ↑ |
| | $\alpha^-\ \phi^-$ | * | ↑ | * |

[a]The effects of increasing or decreasing quenching in the directly responsive ngmFRET partner (d for donors, a for acceptors) or the energy transfer coupling ($\phi$) between the donor and acceptor are tabulated. The consequences of using a directly responsive donor or acceptor are examined. Changes in quenching and ngmFRET coupling parameters can occur singly or in combination, leading to 16 possible models. The models examine the effects of the direction of change in quenching parameters (no change, $d_0$ or $a^0$; increase $d^+$ or $a^+$; decrease, $d^-$ or $a^-$) and the energy transfer coupling factor (no change, $\phi^0$; increase, $\phi^0$; decrease, $\phi^-$) on the patterns in the direction of change of the donor, $Q_D$ (equation 16) or acceptor, $Q_A$ (equation 18) quantum yields, and their ratio, $Q_A/Q_D$ (equation 19): ↑, increase; ↓, decrease; 0, no change; *, response is dependent on precise quantitation rather than direction of change in the underlying parameter values.

Example 7. Bicarbonate Biosensors, Calcium Biosensors, and Uses Thereof

We report the construction of robust, thermostable, reagentless, fluorescently responsive biosensors for bicarbonate and calcium, derived from engineered periplasmic binding proteins. These proteins potentially can be used for high-precision chemometric measurements in the clinical concentration ranges for bicarbonate and ionized calcium, using fluorescence ratiometry measured with straightforward, inexpensive instrumentation.

Thermostable homologs of the bicarbonate-binding protein were identified using a bioinformatics search strategy that applied a structure-based sequence filter to identify the subset of sequences that retain the original function within the larger collection of aligned sequence homologs. The homologs tested appeared at sequence identities from 100% to 26% of the probe sequence. At level below 60%, overall identities are weak predictors of biological function (Todd 2001, Tian 2003, George 2005), application of the structure-based filter therefore was essential for accurate identification. The bicarbonate-binding properties of the predicted hits were tested experimentally by constructing synthetic genes optimized for heterologous protein expression in *E. coli* (Allert et al. 2010) and determining the bicarbonate-binding properties of the expressed proteins. This search resulted in the identification of two thermostable proteins, avBicarbBP5 and teFeBP3, which bind $Ca^{II}$- or $Fe^{III}$-bicarbonate complexes, respectively.

In avBicarbBP5, Pacific Blue conjugates were particularly effective for the construction of bicarbonate sensors. Pacific Blue is a hydroxycoumarin derivative, the phenolate of which corresponds to the excited state (Sun 1998). Without being bound by any scientific theory, it is therefore likely that binding of $Ca^{2+}$ stabilizes the excited state, with a concomitant increase in quantum yield. We also found that $Ca^{2+}$ and bicarbonate binding functions can be separated. The avBicarbBP5 protein therefore can be engineered to function as either a $Ca^{II}$—$HCO_3$ or a $Ca^{2+}$ sensor. The Pacific Blue conjugates exhibited monochromatic responses to ligand binding. These were converted into dichromatic responses that enable ratiometric measurements, using a double labeling strategy in which a second fluorophore was attached site-specifically to a small C-terminal βZif domain. Additional mutations further altered the affinities for either $Ca^{II}$—$HCO_3$ or $Ca^{2+}$ to match the clinical concentration ranges of these two analytes. The resulting sensors are well-suited for applications in point-of-care clinical chemistry or continuous monitoring of analyte concentrations.

In teFeBP3, several singly labeled Acrylodan and Badan conjugates exhibited good dichromatic responses to $Fe^{III}$—$HCO_3$ binding. Of these, the teFeBP3 270C·Badan conjugate evinced the largest response, with an apparent $K_d$ value of 48 mM. This sensor is suitable for measurements in the clinical reference concentration range.

The biosensors can be incorporated into point-of-care clinical devices to measure ligand (e.g., bicarbonate or $Ca^{2+}$) concentrations accurately, and rapidly at the patient bedside. In such a device, a small blood sample (<10 μL) is obtained by means of a finger stick using a lancet. This sample droplet is then placed on the aperture of a disposable cartridge containing desiccated, immobilized biosensors inside a small measurement chamber. The sample enters the chamber by virtue of passive capillary action, wetting the sensors upon contact. As soon as the sensors have been wetted, they bind ligand, and report on its concentration by virtue of the engineered fluorescent sensor mechanism. The cartridge is placed inside a small reader (handheld or on a desktop), and their fluorescence signal is measured by the (inexpensive) optoelectronic components of the reader. Excitation light is provided by a light-emitting diode (LED). In the case of Acrylodan or Badan, a commercially available 400 nm blue LED is used, and the emitted light is measured through two bandpass filters. Cartridges can contain multiple sensors, spanning the entire clinical range of possible ligand concentrations. Each sensor is immobilized at a particular, known location inside the cartridge, providing "spatial addressability". The intensity at a particular wavelength is then recorded by imagining these sensors using an inexpensive camera, such as a Complementary metal-oxide semiconductor (CMOS) device commonly found in consumer electronics such as cell phones. Each pixel in the camera records the emitted light on a gray scale. Integration of that signal imaged through the two signals, is analyzed by an on-board computer to calculate the ratiometric signal for each immobilized sensor. Pre-recorded hyperbolic binding curves are then used to calculate the ligand concentration in the sample. Recording through multiple sensors, tuned for accurate detection at different ligand concentrations provides a high-accuracy reading. This process is completed in less than a minute.

Similar instrumentation can be used for any type of episodic measurements, for instance, using other bodily fluids, or samples obtained from animals, or non-biological samples such as foods and beverages.

The FRS biosensors also can be used to monitor ligand levels continuously. For instance, sensors can be immobilized at the tip of a thin optical fiber to construct a ligand-responsive optode. Such an optode can be introduced into the body subcutaneously, using a small needle. Excitation and emission light are passed to and from the immobilized sensor, respectively. The sensor is in continuous contact with the sample. Fluctuations in the ligand sample alter the dynamic equilibrium between the open and closed states of the ligand-binding protein, which is transduced into fluctuations of the fluorescent emission signal, by virtue of the sensing mechanism of the conjugated fluorophore. The emitted light intensities are read through filters by a reader connected to the optode. This reader continuously displays the change in signal, and the corresponding calculated ligand concentrations.

Continuous ligand monitoring may be accomplished using a device containing the immobilized biosensor(s), e.g., a fiber optic biosensor, introduced into the subject intradermally or subcutaneously (Judge et al., 2011, *Diabetes Technology & Therapeutics* 13 (3):309-317; Weidemaier et al., 2011, *Biosensors and Bioelectronics* 26:4117-4123; hereby incorporated by reference).

As was discussed above, the features that distinguish the described constructs, devices, and methods from earlier bicarbonate and $Ca^{2+}$ assay systems include:

Self-calibration

Rapid response time

Simple sample-handling fluidic circuitry

No additional components/substrates ("reagentless")

No incubation time to develop signal. Reading is near-instantaneous and continuous Stability (simplifies manufacturing, distribution, storage)

Small sample volume (<10 μL).

Capable of precise measurements over extended ligand concentration ranges (e.g., from low to high ranges)

Multiple sensors also provides redundancy, lowering error

Large scope of uses: episodic, continuous, ex vivo, in vivo, optodes, implants.

REFERENCES

Ahmed, M. U., I. Saaem, P. C. Wu & A. S. Brown (2014) Personalized diagnostics and biosensors: a review of the biology and technology needed for personalized medicine. *Crit Rev Biotechnol,* 34, 180-96.

Allert, M., J. C. Cox & H. W. Hellinga (2010) Multifactorial determinants of protein expression in prokaryotic open reading frames. *J Mol Biol,* 402, 905-18.

Allert, M. J., Miriyala, J., Bergeron, A., Hellinga, H. W. (2015) Construction of ratiometric biosensors by exploiting ligand-mediated non-geometrical fluorescence Forster resonance energy transfer. In preparation.

Altschul, S. F., W. Gish, W. Miller, E. W. Myers & D. J. Lipman (1990) Basic local alignment search tool. *J Mol Biol,* 215, 403-10.

Arora, A., G. Simone, G. B. Salieb-Beugelaar, J. T. Kim & A. Manz (2010) Latest developments in micro total analysis systems. *Anal Chem,* 82, 4830-47.

Artimo, P., M. Jonnalagedda, K. Arnold, D. Baratin, G. Csardi, E. de Castro, S. Duvaud, V. Flegel, A. Fortier, E. Gasteiger, A. Grosdidier, C. Hernandez, V. Ioannidis, D. Kuznetsov, R. Liechti, S. Moretti, K. Mostaguir, N. Redaschi, G. Rossier, I. Xenarios & H. Stockinger (2012) ExPASy: SIB bioinformatics resource portal. *Nucleic Acids Res,* 40, W597-603.

Badugu, R., J. R. Lakowicz & C. D. Geddes (2005) A glucose-sensing contact lens: from bench top to patient. *Curr Opin Biotechnol,* 16, 100-7.

Bandodkar, A. J., W. Jia, C. Yardimci, X. Wang, J. Ramirez & J. Wang (2015) Tattoo-Based Noninvasive Glucose Monitoring: A Proof-of-Concept Study. *Anal. Chem.* (Washington, DC, U. S.), 87, 394-398.

Berntsson, R. P., S. H. Smits, L. Schmitt, D. J. Slotboom & B. Poolman (2010) A structural classification of substrate-binding proteins. *FEBS Lett,* 584, 2606-17.

Borisov, S. M. & O. S. Wolfbeis (2008) *Optical biosensors. Chem Rev,* 108, 423-61.

Burtis, C. A., Ashwood, E. R., Bruns, D. E. 2012. *Tietz Textbook of Clinical Chemistry and Molecular Diagnostics*. Elsevier.

Chenna, R., H. Sugawara, T. Koike, R. Lopez, T. J. Gibson, D. G. Higgins & J. D. Thompson (2003) Multiple sequence alignment with the Clustal series of programs. *Nucleic Acids Res,* 31, 3497-500.

Cheung, H. C. (1991) Resonance energy transfer. *Topics in Fluorescence Spectroscopy,* 2, 127-176.

Choleau, C., J. C. Klein, G. Reach, B. Aussedat, V. Demaria-Pesce, G. S. Wilson, R. Gifford & W. K. Ward (2002) Calibration of a subcutaneous amperometric glucose sensor. Part 1. Effect of measurement uncertainties on the determination of sensor sensitivity and background current. *Biosens Bioelectron,* 17, 641-6.

Clegg, R. M. (1995) Fluorescence resonance energy transfer. *Curr. Opin. Biotechnol.,* 6, 103-110.

Cox, J. C., J. Lape, M. A. Sayed & H. W. Hellinga (2007) Protein fabrication automation. *Protein Sci,* 16, 379-90.

Cuneo, M. J., L. S. Beese & H. W. Hellinga (2009) Structural analysis of semi-specific oligosaccharide recognition by a cellulose-binding protein of *Thermotoga maritima* reveals adaptations for functional diversification of the oligopeptide periplasmic binding protein fold. *J Biol Chem,* 284, 33217-23.

de Lorimier, R. M., J. J. Smith, M. A. Dwyer, L. L. Looger, K. M. Sali, C. D. Paavola, S. S. Rizk, S. Sadigov, D. W. Conrad, L. Loew & H. W. Hellinga (2002) Construction of a fluorescent biosensor family. *Protein Sci,* 11, 2655-75.

Demchenko, A. P. (2010) The concept of lambda-ratiometry in fluorescence sensing and imaging. *J Fluoresc,* 20, 1099-128.

Demchenko, A. P. (2014) Practical aspects of wavelength ratiometry in the studies of intermolecular interactions. *Journal of Molecular Structure,* 1077, 51-67.

George, R. A., Spriggs, R. V., Bartlett, G. J., Gutteridge, A., MacArthur, M. W., Porter, C. T., Al-Lazikani, B., Thornton, J. M., Swindells, M. B. (2005) Effective function annotation through catalytic residue conservation. *Proc Natl Acad Sci USA,* 102, 12299-12304.

Gill, S. C. & P. H. von Hippel (1989) Calculation of protein extinction coefficients from amino acid sequence data. *Anal Biochem,* 182, 319-26.

Grimley, J. S., L. Li, W. Wang, L. Wen, L. S. Beese, H. W. Hellinga & G. J. Augustine (2013) Visualization of synaptic inhibition with an optogenetic sensor developed by cell-free protein engineering automation. *J Neurosci,* 33, 16297-309.

Grunewald, F. S. 2014. Periplasmic binding proteins in biosensing applications. In *BIOREV,* 205-236. Springer Int., Switzerland.

Gubala, V., L. F. Harris, A. J. Ricco, M. X. Tan & D. E. Williams (2012) Point of care diagnostics: status and future. *Anal Chem,* 84, 487-515.

Hengen, P. N. (1995) Purification of His-Tag fusion proteins from *Escherichia coli. Trends Biochem Sci,* 20.

Heo, Y. J. & S. Takeuchi (2013) Towards smart tattoos: implantable biosensors for continuous glucose monitoring. *Adv Healthc Mater,* 2, 43-56.

Ispas, C. R. C., G.; Andreescu, S. (2012) Review: Recent Developments in Enzyme-Based Biosensors for Biomedical Analysis. *Anal. Lett.,* 45, 168-186.

Judge, K., L. Morrow, A. G. Lastovich, D. Kurisko, S. C. Keith, J. Hartsell, B. Roberts, E. McVey, K. Weidemaier, K. Win & M. Hompesch (2011) Continuous glucose monitoring using a novel glucose/galactose binding protein: results of a 12-hour feasibility study with the becton dickinson glucose/galactose binding protein sensor. *Diabetes Technol Ther,* 13, 309-17.

Koropatkin, N. M., Koppenaal, D. W., Pakrasi, H. B., Smith, T. J. (2007) The structure of a cyanobacterial bicarbonate transport protein, Cmp A. *J. Biol. Chem.,* 282, 2606-2614.

Kozma, P., A. Lehmann, K. Wunderlich, D. Michel, S. Schumacher, E. Ehrentreich-Forster & F. F. Bier (2013) A novel handheld fluorescent microarray reader for point-of-care diagnostic. *Biosens Bioelectron,* 47, 415-20.

Lakowicz, J. R. 2006. *Principles of fluorescence spectroscopy*. Springer, New York.

Layton, C. J. & H. W. Hellinga (2010) Thermodynamic analysis of ligand-induced changes in protein thermal unfolding applied to high-throughput determination of ligand affinities with extrinsic fluorescent dyes. *Biochemistry,* 49, 10831-41.

Liu, D., Evans, T., Zhang, F. (2015) Applications and advances of metabolite biosensors for metabolic engineering. *Metabolic Engin.,* 31, 35-43.

Marvin, J. S., E. E. Corcoran, N. A. Hattangadi, J. V. Zhang, S. A. Gere & H. W. Hellinga (1997) The rational design of allosteric interactions in a monomeric protein and its applications to the construction of biosensors. *Proc Natl Acad Sci USA,* 94, 4366-71.

Marvin, J. S. & H. W. Hellinga (2001) Manipulation of ligand binding affinity by exploitation of conformational coupling. *Nat Struct Biol,* 8, 795-8.

Marvin, J. S. H., H. W. (1998) Engineering biosensors by introducing fluorescent allosteric signal transducers: construction of a novel glucose sensor. *J Am Chem Soc,* 120, 7-11.

Matzeu, G., Florea, L., Diamond, D. (2015) Advances in wearable chemical sensor design for monitoring biological fluids. *Sens Actuators B Chem,* 211, 403-418.

Mohammed, M. D., M. P. Y. (2011) Lab-on-a-chip based immunosensor principles and technologies for the detection of cardiac biomarkers: a review. *Lab. Chip.,* 11, 569-595.

Nanavati, D. M., Thirangoon, T., Noll, K. M. (2006) Several archaeal homologs to putative oligopeptide-binding proteins encoded by *Thermotoga maritima* bind sugards. *Appl. Environ. Microbiol.,* 72, 1336-1345.

Okumoto, S., Jones, A., Frommer, W. B. (2012) Quantitative imaging with fluorescent biosensors. *Annu. Rev. Plant Biol.,* 63, 663-706.

Omata, T., Price, G. D., Badger, M. R., Okamura, M., Gohta, M., Ogawa, T. (1999) Identification of an ATP-binding cassette transporter involved in bicarbonate uptake in cyanobacterium Synechococcus sp. strain PCC 7942. Proc NatlAcad Sci USA, 96, 13751-13576.

Price, G. D., Badger, M. R., Wooddger, F. J., Long, B. M. (2008) Advances in understanding the cyanobacterial $CO_2$-concentrating-mechanism (CCM): functional components, Ci transporters, diversity, genetic regulation and prospects for engineering into plants. *J. Exp. Botany,* 59, 1441-1461.

Robinson, T. & P. S. Dittrich (2013) Microfluidic technology for molecular diagnostics. *Adv Biochem Eng Biotechnol,* 133, 89-114.

Rogers, M. L. & M. G. Boutelle (2013) Real-time clinical monitoring of biomolecules. *Annu Rev Anal Chem* (Palo Alto Calif), 6, 427-53.

Siburt, C. J. P., Mietzner, T. A., Crumbliss, A. L. (2012) FbpA—a bacterial transferrin with more to offer. *Biochim Biophys Acta,* 1820, 379-392.

Smith, J. J., D. W. Conrad, M. J. Cuneo & H. W. Hellinga (2005) Orthogonal site-specific protein modification by engineering reversible thiol protection mechanisms. *Protein Sci,* 14, 64-73.

Sun, W. C., Gee, K. R., Haugland, R. P. (1998) Synthesis of novel fluorinated coumarins: excellent UV-light excitable fluorescent dyes. *Bioorg Med Chem Lett,* 8, 3107-3110.

Tian, W., Skolnick, J. (2003) How well is enzyme function conserved as a function of pairwise sequence identity? *J. Mol. Biol.,* 333, 863-882.

Todd, A. E., Orengo, C. A., Thornton, J. M. (2001) Evolution of function in protein superfamilies, from a structural perspective. *J. Mol. Biol.,* 307, 1113-1143.

Urbieta, M. S., E. R. Donati, K. G. Chan, S. Shahar, L. L. Sin & K. M. Goh (2015) Thermophiles in the genomic era: Biodiversity, science, and applications. *Biotechnol Adv.*

Valeur, B., Berberan-Santos, M. N. 2012. Molecular Fluorescence. *Principles and Applications*. Weinheim: Wiley.

Wang, H., Nakata, E., Hamachi, I. (2009) Recent progress in strategies for the creation of protein-based fluorescent biosensors. *Chembiochem,* 10, 2560-2577.

Warrel, D. A., Cox, T. M., Firth, J. D. 2010. *Oxford Textbook of Medicine*. Oxford University Press.

Weidemaier, K., A. Lastovich, S. Keith, J. B. Pitner, M. Sistare, R. Jacobson & D. Kurisko (2011) Multi-day pre-clinical demonstration of glucose/galactose binding protein-based fiber optic sensor. *Biosens Bioelectron,* 26, 4117-23.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A biosensor for a ligand, comprising an *Anabaena variabilis* ligand-binding protein (avBicarbBP5) and a reporter group that transduces a detectable signal, wherein the reporter group is attached to the ligand-binding protein so that a signal transduced by the reporter group when the ligand-binding protein is bound to ligand differs from a signal transduced by the reporter group when the ligand-binding protein is not bound to ligand, wherein the ligand comprises a calcium ($Ca^{II}$)-bicarbonate complex ($Ca^{II}$—$HCO_3$) or free calcium ion ($Ca^{2+}$), and wherein the ligand-binding protein does not comprise an enzyme, wherein the ligand-binding protein comprises a mutation comprising one or more of the following substitutions: I16X, P17X, I18X, W49X, Q71X, C96X, F140X, T141X, F142X, P143X, N146X, T190X, and W194X, wherein X is an amino acid that results in a conservative substitution or a cysteine, of the protein avBicarbBP5 (SEQ ID NO: 5), and where each position is counted in avBicarbBP5 with the signal peptide replaced with a methionine (SEQ ID NO: 79).

2. The biosensor of claim 1, wherein the ligand-binding protein comprises amino acid sequence of SEQ ID NO: 64 or 38, and wherein said reporter group is selected from the group consisting of

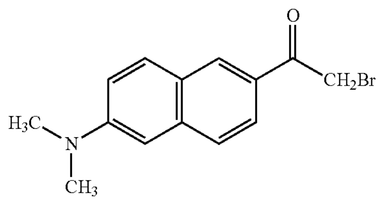

6-bromo-acetyl-2-dimethylamino-naphthalene and

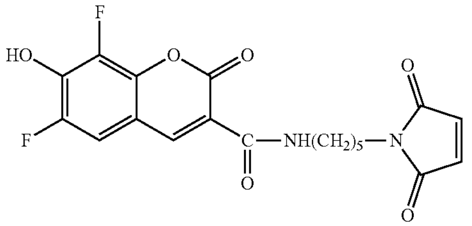

N-(5-(2,5-dioxo-2,5-dihydro-1H-pyrrol-1-yl)pentyl)-5,7-difluoro-6-hydroxy-3-oxo-3,4-dihydronaphthalene-2-carboxamide, and is attached to a cysteine of said ligand-binding protein.

3. The biosensor of claim 1, wherein the ligand-binding protein comprises a mutation compared to a naturally occurring avBicarbBP5 ligand-binding protein, wherein at least one amino acid of the naturally occurring avBicarbBP5 ligand-binding protein has been substituted with a cysteine.

4. The biosensor of claim 1, wherein the ligand-binding protein comprises a mutation compared to a naturally occurring avBicarbBP5 ligand-binding protein, wherein the ligand-binding protein has no deletions or insertions compared to the naturally occurring avBicarbBP5 ligand-binding protein.

5. The biosensor of claim 1, wherein the ligand-binding protein comprises a mutation compared to a naturally occurring avBicarbBP5 ligand-binding protein, wherein the ligand-binding protein comprises (i) less than about 5, 4, 3, 2, or 1 inserted amino acids, and/or (ii) less than about 5, 4, 3, 2, or 1 deleted amino acids compared to the naturally occurring avBicarbBP5 ligand-binding protein.

6. The biosensor of claim 1, wherein the ligand-binding protein comprises a calcium ($Ca^{II}$)-bicarbonate complex ($Ca^{II}$—$HCO_3$) ligand-binding protein.

7. The biosensor of claim 6, wherein the mutant comprises a mutation that alters the mutant's affinity and/or specificity for bicarbonate or $Ca^{2+}$ compared to the microbial bicarbonate-binding protein.

8. The biosensor of claim 1, wherein the ligand-binding protein further comprises or comprises a mutant of: a *Synechocystis* sp. bicarbonate-binding protein, a mutant of a *Thermosynechococcus* sp. bicarbonate-binding protein, a mutant of a *Chroococcidiopsis* sp. bicarbonate-binding protein, a mutant of a *Calothrix* sp. bicarbonate-binding protein, a mutant of a *Anabaena* sp. bicarbonate-binding protein, or a mutant of a *Chamaesiphon* sp. bicarbonate-binding protein, wherein the ligand-binding protein comprises or comprises a mutant of: a bicarbonate-binding protein from *Synechocystis* sp. (synBicarbBP1) comprising the amino acid sequence of SEQ ID NO: 1, 15, or 75; a bicarbonate-binding protein from *Thermosyneochococcus elongatus* (teBicarbBP2) comprising the amino acid sequence of one of SEQ ID NO: 2, 16, or 76; a bicarbonate-binding protein from *Chroococcidiopsis thermalis* (ctBicarbBP3) comprising the amino acid sequence of one of SEQ ID NO: 3, 17, or 77; a bicarbonate-binding protein from *Calothrix* sp. (calBicarbBP4) comprising the amino acid sequence of one of SEQ ID NO: 4, 18, or 78; or a bicarbonate-binding protein from *Chamaesiphon minutus* (cmBicarbBP6) comprising the amino acid sequence of one of SEQ ID NO: 6, 20, or 80.

9. The biosensor of claim 1, wherein the ligand-binding protein comprises an amino acid sequence that is between 10% and 100% identical to the amino acid sequence of ctBicarbBP3, calBicarbBP4, avBicarbBP5.

10. The biosensor of claim 1, wherein the reporter group is covalently attached to the ligand-binding protein.

11. The biosensor of claim 1, wherein the reporter group is conjugated to a cysteine of the ligand-binding protein.

12. The biosensor of claim 1, wherein the reporter group comprises a fluorophore.

13. A method of detecting the presence or concentration of a ligand in a sample, the method comprising:

(a) contacting the biosensor of claim 1 with the sample;

(b) measuring a signal from the biosensor; and (c) comparing the signal from step (b) to a signal produced by a control sample containing a known quantity of ligand, wherein a difference in signal indicates the presence of ligand in the sample.

14. A method for monitoring the level of a ligand in a subject, comprising (a) administering a biosensor according to claim 1 or a device comprising a biosensor according to claim 1 to the subject, wherein after administration the biosensor is in contact with a bodily fluid or surface of the subject, and (b) detecting (i) a signal produced by a reporter group of the biosensor continuously or repeatedly at intervals less than about 30 minutes apart, and/or (ii) whether a signal is produced by a reporter group of the biosensor continuously or repeatedly at intervals less than about 30 minutes apart.

15. The biosensor of claim 1, wherein the ligand-binding protein shares a primary complementary surface (PCS) with a bicarbonate-binding protein from *Synechocystis* sp. (synBicarbBP1), wherein the PCS of synBicarbBP1 comprises positions 20, 49, 71, 102, 142, 148, 220, and 221, wherein each position is counted as in SEQ ID NO: 15 or 75.

16. The biosensor of claim 15, wherein when the amino acid sequence of the ligand-binding protein is aligned with said synBicarbBP1 amino acid sequence, the ligand-binding protein comprises an amino acid sequence comprising (i) E at the position that aligns with position 20 of synBicarbBP1;

(ii) W at the position that aligns with position 49 of synBicarbBP1;

(iii) Q at the position that aligns with position 71 of synBicarbBP1;

(iv) N at the position that aligns with position 102 of synBicarbBP1;

(v) T at the position that aligns with position 142 of synBicarbBP1;

(vi) Q at the position that aligns with position 148 of synBicarbBP1;

(vii) E at the position that aligns with position 220 of synBicarbBP1; and (viii) E at the position that aligns with position 221 of synBicarbBP1.

17. The biosensor of claim 1, wherein the ligand-binding protein comprises a mutant of a bicarbonate-binding protein from *Anabaena variabilis* (avBicarbBP5), comprising a sequence from one of SEQ ID NO: 5, 19, or 79.

18. The biosensor of claim 17, wherein the ligand-binding protein comprises a mutant of avBicarbBP5 comprising an I18C mutation, an I16F mutation, or an I18C and I16F double mutation.

19. The biosensor of claim 18, wherein the ligand-binding protein further comprises a βZif peptide conjugated to the avBicarbBP5 mutant.

20. The biosensor of claim 19, comprising a first fluorophore conjugated to the 18C residue and a second fluorophore conjugated to the βZif peptide, wherein non-geometrically modulated Forster resonance energy transfer (ngmFRET) occurs between the two fluorophores.

21. The biosensor of claim 20, wherein the first fluorophore comprises

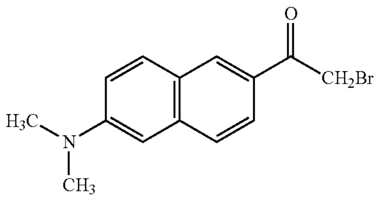

6-bromo-acetyl-2-dimethylamino-naphthalene,

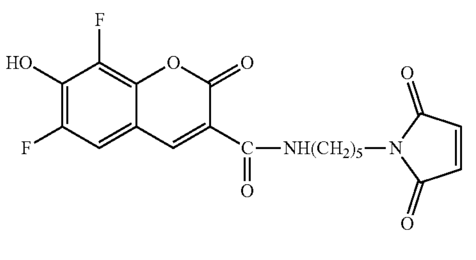

N-(5-(2,5-dioxo-2,5-dihydro-1H-pyrrol-1-yl)pentyl)-5,7-difluoro-6-hydroxy-3-oxo-3,4-dihydronaphthalene-2-carboxamide, or

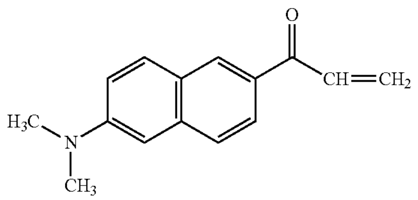 [SMILES: C=CC(=O)c1ccc2cc(N(C)C)ccc2c1]

6-Acryloyl-2-Dimethylaminonaphthalene and the second fluorophore comprises 5-iodoacetamidofluorescein (5-IAF),

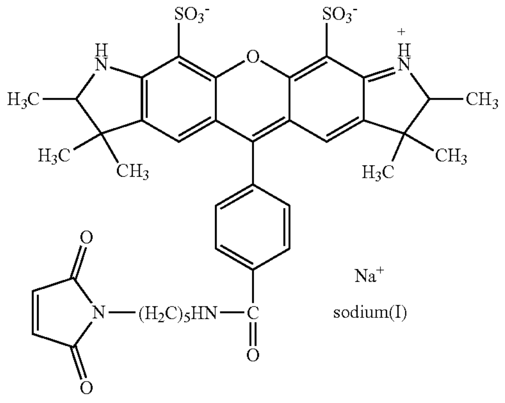

5-(4-((5-(2,5-dioxo-2,5-dihydro-1H-pyrrol-1-yl)pentyl)carbomoyl)phenyl)-2,3,3,7,7,8-hexamethyl-2,3,7,8-tetrahydro-1H-pyrano[3,2-f:5,6-f']diindol-9ium-10,12-disfulfonate,

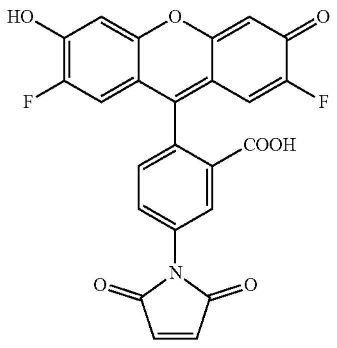 [SMILES: O=C(O)c1cc(N2C(=O)C=CC2=O)ccc1-c1c2cc(F)c(=O)cc-2oc2cc(O)c(F)cc12]

2-(2,7-difluoro-6-hydroxy-3-oxo-3H-xanthen-9-yl)-5-(2,5-dioxo-2,5-dihydro-1H-pyrrol-1-yl) benzoic acid

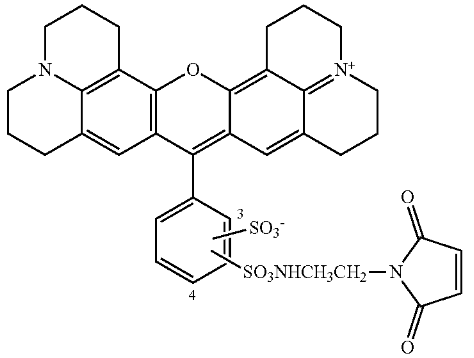

sulforhodamine 101-C2 maleimide or N,N'-Dimethyl-N-(Iodoacetyl)-N'-(7-Nitrobenz-2-Oxa-1,3-Diazol-4-yl)Ethyle-nediamine (IANBD).

22. The biosensor of claim 17, wherein the ligand-binding protein comprises an amino acid sequence having at least 70% sequence identity to SEQ ID NO: 5, 19, or 79.

23. The biosensor of claim 17, wherein the ligand-binding protein comprises an amino acid sequence having at least 90% sequence identity to SEQ ID NO: 5, 19, or 79.

24. The biosensor of claim 1, wherein the ligand-binding protein comprises an amino acid sequence having at least 90% sequence identity to SEQ ID NO: 64, and wherein said reporter group is attached to a cysteine of said ligand-binding protein.

25. The biosensor of claim 1, wherein the ligand-binding protein comprises the amino acid sequence of SEQ ID NO: 64, and wherein said reporter group is attached to a cysteine of said ligand-binding protein.

26. The biosensor of claim 24 or 25, wherein said reporter group is selected from the group consisting of:

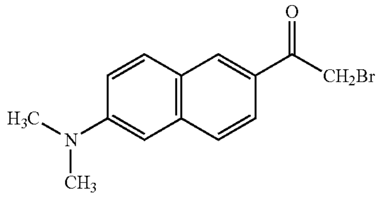

6-bromo-acetyl-2-dimethylamino-naphthalene and

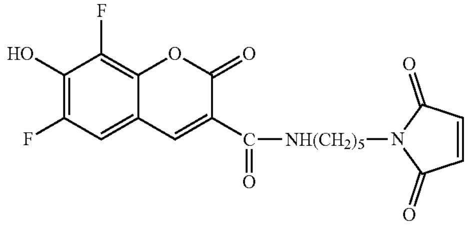

N-(5-(2,5-dioxo-2,5-dihydro-1H-pyrrol-1-yl)pentyl)-5,7-difluoro-6-hydroxy-3-oxo-3,4-dihydronaphthalene-2-carboxamide.

* * * * *

UNITED STATES PATENT AND TRADEMARK OFFICE

CERTIFICATE OF CORRECTION

PATENT NO. : 11,852,637 B2
APPLICATION NO. : 15/776871
DATED : December 26, 2023
INVENTOR(S) : Homme W. Hellinga et al.

It is certified that error appears in the above-identified patent and that said Letters Patent is hereby corrected as shown below:

In the Claims

At Column 546, Claim number 21, Line number 67, please insert --,-- after “acid”

At Column 547, Claim number 21, Line number 17, please insert --,-- after “maleimide”

Signed and Sealed this
Thirteenth Day of February, 2024

Katherine Kelly Vidal

Katherine Kelly Vidal
*Director of the United States Patent and Trademark Office*